United States Patent
Perkins et al.

(10) Patent No.: US 12,016,449 B2
(45) Date of Patent: Jun. 25, 2024

(54) HOLDING ACCESSORY FOR A WIRELESSLY LOCATABLE TAG

(71) Applicant: Apple Inc., Cupertino, CA (US)

(72) Inventors: Ryan C. Perkins, San Francisco, CA (US); Anthony M. Ashcroft, San Francisco, CA (US); Erik G. de Jong, San Francisco, CA (US); Tirshathah A. Hunter, Oakland, CA (US); Seul Bi Kim, Cupertino, CA (US); Erik L. Wang, Redwood City, CA (US); Christopher M. Werner, San Jose, CA (US)

(73) Assignee: APPLE INC., Cupertino, CA (US)

( * ) Notice: Subject to any disclaimer, the term of this patent is extended or adjusted under 35 U.S.C. 154(b) by 255 days.

(21) Appl. No.: 17/478,262

(22) Filed: Sep. 17, 2021

(65) Prior Publication Data

US 2022/0004725 A1    Jan. 6, 2022

Related U.S. Application Data

(63) Continuation of application No. PCT/US2020/028424, filed on Apr. 16, 2020.
(Continued)

(51) Int. Cl.
*E05B 73/00* (2006.01)
*A45F 5/00* (2006.01)
(Continued)

(52) U.S. Cl.
CPC .............. *A45F 5/00* (2013.01); *A61B 5/1116* (2013.01); *E05B 73/0005* (2013.01);
(Continued)

(58) Field of Classification Search
CPC ..................... E05B 73/0005; G06K 7/10396
See application file for complete search history.

(56) References Cited

U.S. PATENT DOCUMENTS

| 6,278,873 B1 | 8/2001 | Itakura et al. |
| 9,060,588 B2 | 6/2015 | Bransfield et al. |
| (Continued) | | |

FOREIGN PATENT DOCUMENTS

KR    20180025126    3/2018

OTHER PUBLICATIONS

International Search Report and Written Opinion, PCT/US2020/028424, 27 pages, dated Sep. 24, 2020.

*Primary Examiner* — Brian D Nash
(74) *Attorney, Agent, or Firm* — Brownstein Hyatt Farber Schreck, LLP

(57) ABSTRACT

A holder for a wirelessly locatable tag may be used with a wirelessly locatable tag comprising a housing member defining a region of an exterior surface of the wirelessly locatable tag configured to act as a speaker diaphragm. The holder may include a receptacle portion configured to at least partially surround the wirelessly locatable tag, the receptacle portion defining a first opening configured to allow the wirelessly locatable tag to be positioned in the receptacle portion, a second opening configured to at least partially surround an outer periphery of a battery door of the wirelessly locatable tag, and a third opening aligned with the region of the exterior surface configured to act as the speaker diaphragm. The holder may further include a fastener coupled to the receptacle portion and configured to releasably secure the first opening in a closed configuration to retain the wirelessly locatable tag in the receptacle portion.

20 Claims, 183 Drawing Sheets

Related U.S. Application Data

(60) Provisional application No. 63/101,182, filed on Sep. 26, 2019, provisional application No. 63/101,229, filed on Sep. 26, 2019, provisional application No. 62/922,249, filed on Sep. 26, 2019, provisional application No. 62/922,250, filed on Sep. 26, 2019, provisional application No. 63/101,180, filed on Sep. 26, 2019, provisional application No. 62/922,248, filed on Sep. 26, 2019, provisional application No. 63/101,242, filed on Sep. 26, 2019, provisional application No. 63/101,179, filed on Sep. 26, 2019, provisional application No. 63/101,212, filed on Sep. 26, 2019, provisional application No. 62/894,640, filed on Aug. 30, 2019, provisional application No. 62/855,768, filed on May 31, 2019, provisional application No. 62/835,469, filed on Apr. 17, 2019.

(51) Int. Cl.

| | | |
|---|---|---|
| *A61B 5/11* | (2006.01) | |
| *G01S 5/00* | (2006.01) | |
| *G01S 5/02* | (2010.01) | |
| *G04G 21/04* | (2013.01) | |
| *G04G 21/08* | (2010.01) | |
| *G06F 3/01* | (2006.01) | |
| *G06F 3/02* | (2006.01) | |
| *G06F 3/044* | (2006.01) | |
| *G06F 3/0485* | (2022.01) | |
| *G06F 3/04883* | (2022.01) | |
| *G06K 7/00* | (2006.01) | |
| *G06K 7/10* | (2006.01) | |
| *G06K 19/07* | (2006.01) | |
| *G06K 19/077* | (2006.01) | |
| *G06T 13/40* | (2011.01) | |
| *H01M 50/109* | (2021.01) | |
| *H01M 50/184* | (2021.01) | |
| *H01Q 1/22* | (2006.01) | |
| *H01Q 1/27* | (2006.01) | |
| *H01Q 5/25* | (2015.01) | |
| *H01Q 5/378* | (2015.01) | |
| *H01Q 7/00* | (2006.01) | |
| *H01Q 9/42* | (2006.01) | |
| *H04B 1/3888* | (2015.01) | |
| *H04B 5/79* | (2024.01) | |
| *H04L 9/08* | (2006.01) | |
| *H04L 9/30* | (2006.01) | |
| *H04M 1/02* | (2006.01) | |
| *H04M 1/21* | (2006.01) | |
| *H04R 1/02* | (2006.01) | |
| *H04R 3/00* | (2006.01) | |
| *H04R 7/02* | (2006.01) | |
| *H04W 4/029* | (2018.01) | |
| *H04W 12/02* | (2009.01) | |
| *H04W 12/03* | (2021.01) | |
| *A63B 24/00* | (2006.01) | |
| *H01Q 21/06* | (2006.01) | |
| *H04B 1/717* | (2011.01) | |
| *H04W 88/06* | (2009.01) | |

(52) U.S. Cl.
CPC .......... *G01S 5/0036* (2013.01); *G01S 5/0226* (2013.01); *G04G 21/04* (2013.01); *G04G 21/08* (2013.01); *G06F 3/017* (2013.01); *G06F 3/02* (2013.01); *G06F 3/044* (2013.01); *G06F 3/0485* (2013.01); *G06F 3/04883* (2013.01); *G06K 7/0008* (2013.01); *G06K 7/10396* (2013.01); *G06K 19/0701* (2013.01); *G06K 19/0702* (2013.01); *G06K 19/0708* (2013.01); *G06K 19/0723* (2013.01); *G06K 19/07711* (2013.01); *G06K 19/07758* (2013.01); *G06K 19/07766* (2013.01); *G06K 19/07773* (2013.01); *G06K 19/07779* (2013.01); *G06T 13/40* (2013.01); *H01M 50/109* (2021.01); *H01M 50/184* (2021.01); *H01Q 1/2208* (2013.01); *H01Q 1/2225* (2013.01); *H01Q 1/2291* (2013.01); *H01Q 1/273* (2013.01); *H01Q 5/25* (2015.01); *H01Q 5/378* (2015.01); *H01Q 7/00* (2013.01); *H01Q 9/42* (2013.01); *H04B 1/3888* (2013.01); *H04B 5/79* (2024.01); *H04L 9/0825* (2013.01); *H04L 9/30* (2013.01); *H04M 1/02* (2013.01); *H04M 1/21* (2013.01); *H04R 1/028* (2013.01); *H04R 3/00* (2013.01); *H04R 7/02* (2013.01); *H04W 4/029* (2018.02); *H04W 12/02* (2013.01); *H04W 12/03* (2021.01); *A45F 2005/006* (2013.01); *A45F 2200/0508* (2013.01); *A63B 24/0062* (2013.01); *G01S 5/0231* (2013.01); *G06F 3/016* (2013.01); *H01Q 21/06* (2013.01); *H04B 1/717* (2013.01); *H04R 2400/03* (2013.01); *H04R 2420/07* (2013.01); *H04W 88/06* (2013.01)

(56) References Cited

U.S. PATENT DOCUMENTS

| | | | |
|---|---|---|---|
| 10,165,694 | B1 * | 12/2018 | Werner .................. H04R 1/028 |
| 10,488,936 | B2 * | 11/2019 | Baranski ................. A61B 5/11 |
| 2006/0255947 | A1 | 11/2006 | Redler et al. |
| 2007/0251062 | A1 * | 11/2007 | Saitoh ..................... F21V 21/34 |
| | | | 24/303 |
| 2008/0018475 | A1 | 1/2008 | Breed et al. |
| 2010/0308998 | A1 | 12/2010 | Hesch, Jr. et al. |
| 2012/0094594 | A1 | 4/2012 | Rofougaran et al. |
| 2014/0185856 | A1 | 7/2014 | Koss, Jr. et al. |
| 2015/0122893 | A1 | 5/2015 | Warther et al. |
| 2015/0311960 | A1 * | 10/2015 | Samardzija ............ H01Q 1/273 |
| | | | 455/90.3 |
| 2016/0007697 | A1 * | 1/2016 | de Jong ................ A44C 5/2071 |
| | | | 63/3.1 |
| 2016/0037877 | A1 * | 2/2016 | Perkins .............. A44B 11/2596 |
| | | | 224/164 |
| 2016/0055729 | A1 | 2/2016 | Maddox et al. |
| 2016/0098016 | A1 * | 4/2016 | Ely ........................ G04G 21/00 |
| | | | 368/308 |
| 2016/0106202 | A1 * | 4/2016 | Ford ..................... H04N 19/103 |
| | | | 224/267 |
| 2016/0150355 | A1 * | 5/2016 | Yoo ..................... H04L 65/1083 |
| | | | 455/41.2 |
| 2016/0210482 | A1 * | 7/2016 | Shell, Jr. .......... G06K 19/07758 |
| 2016/0256082 | A1 * | 9/2016 | Ely ....................... A61B 5/7282 |
| 2017/0086535 | A1 * | 3/2017 | De Iuliis ................ A44C 5/246 |
| 2017/0303048 | A1 | 10/2017 | Hooton et al. |
| 2018/0024683 | A1 * | 1/2018 | Ely ........................ G04G 21/00 |
| | | | 345/174 |
| 2018/0026341 | A1 | 1/2018 | Mow et al. |
| 2019/0072912 | A1 * | 3/2019 | Pandya .............. A61B 5/02405 |
| 2019/0074729 | A1 * | 3/2019 | Wittenberg ............ H02J 50/90 |
| 2019/0081387 | A1 * | 3/2019 | Pandya ................... H04L 69/18 |
| 2019/0083715 | A1 | 3/2019 | Redmond et al. |
| 2019/0090806 | A1 * | 3/2019 | Clavelle ................ A61B 5/681 |
| 2021/0026450 | A1 * | 1/2021 | Fu .......................... G04G 17/04 |

\* cited by examiner

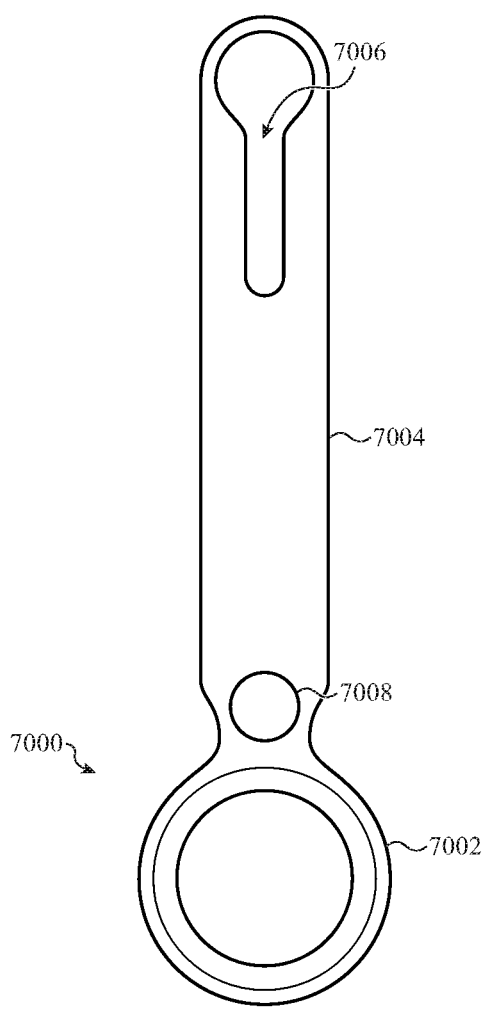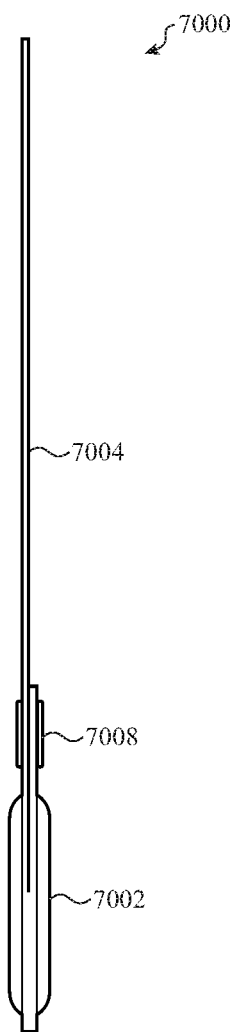
FIG. 70A                    FIG. 70B

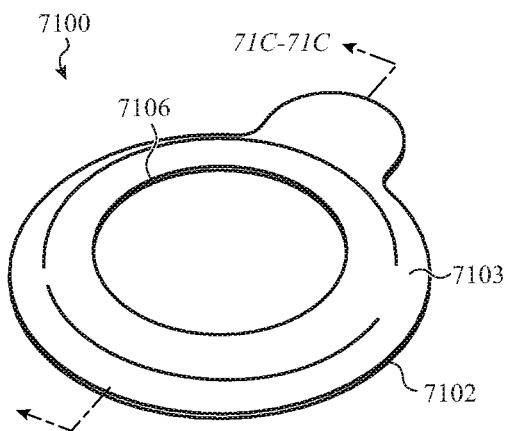
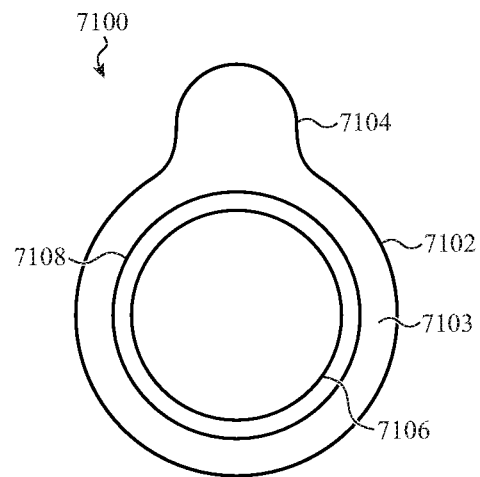
*FIG. 71A*  *FIG. 71B*
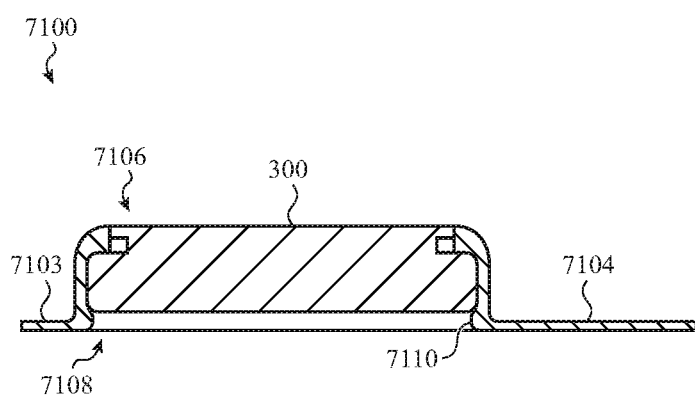
*FIG. 71C*

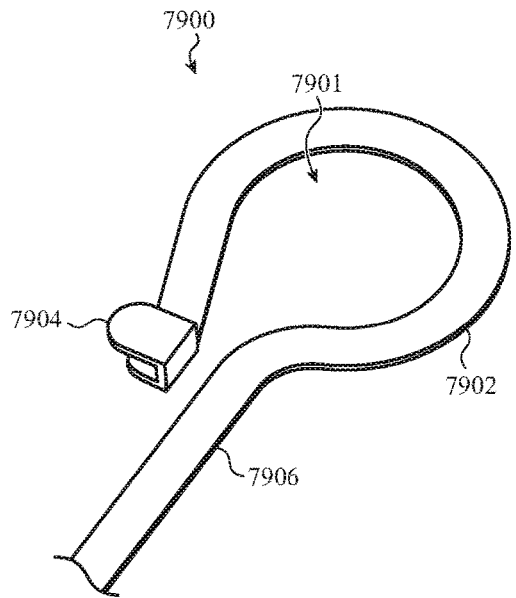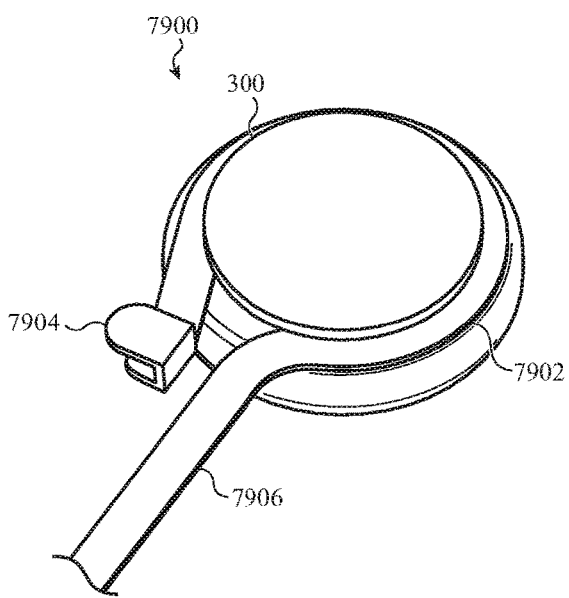
FIG. 79A    FIG. 79B
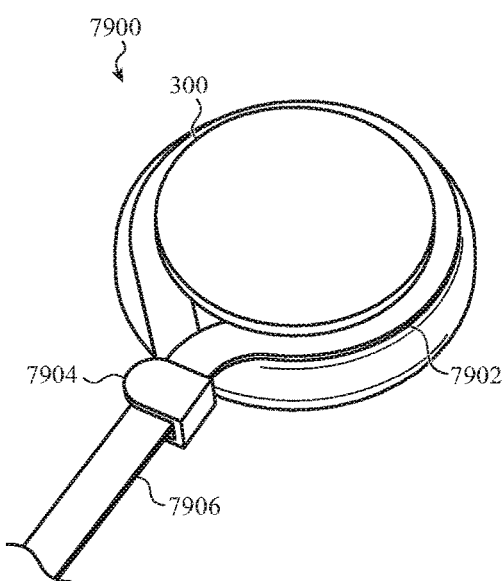
FIG. 79C

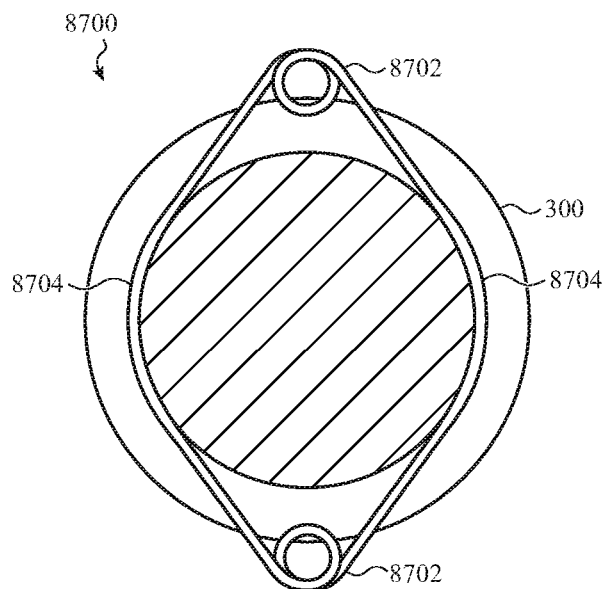
FIG. 87A
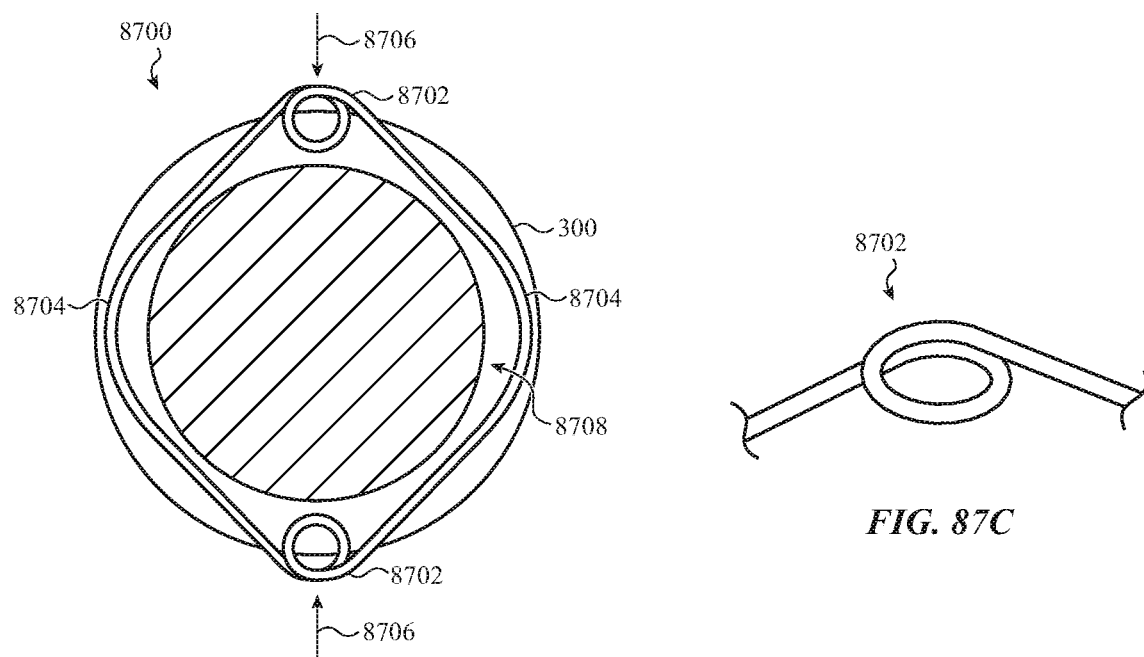
FIG. 87B
FIG. 87C

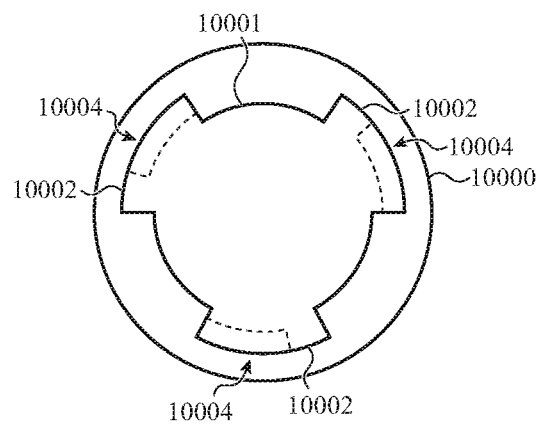
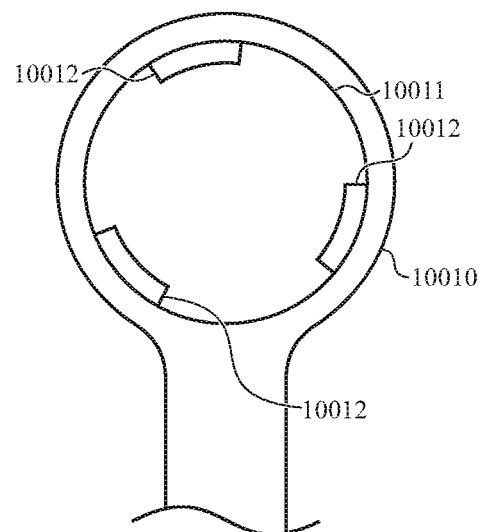
FIG. 100A
FIG. 100B
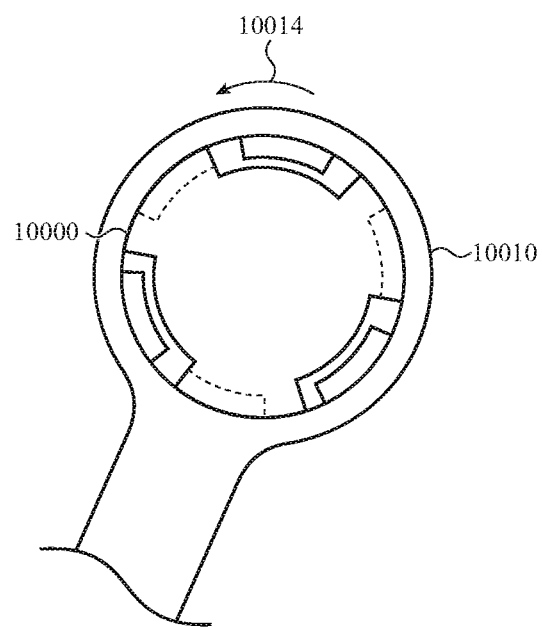
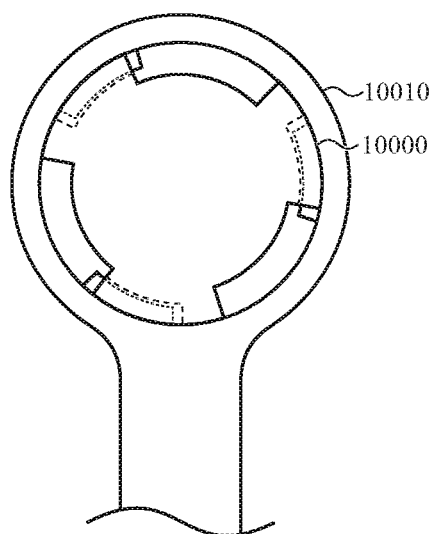
FIG. 100C
FIG. 100D

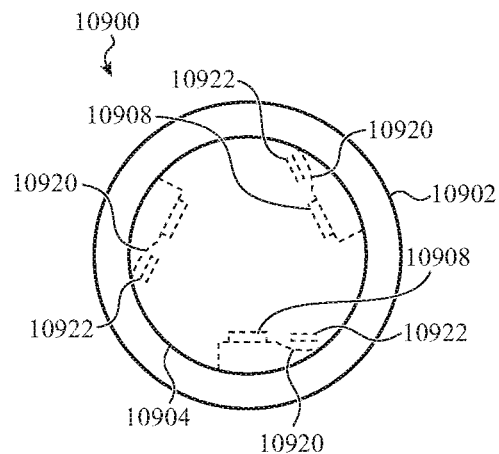
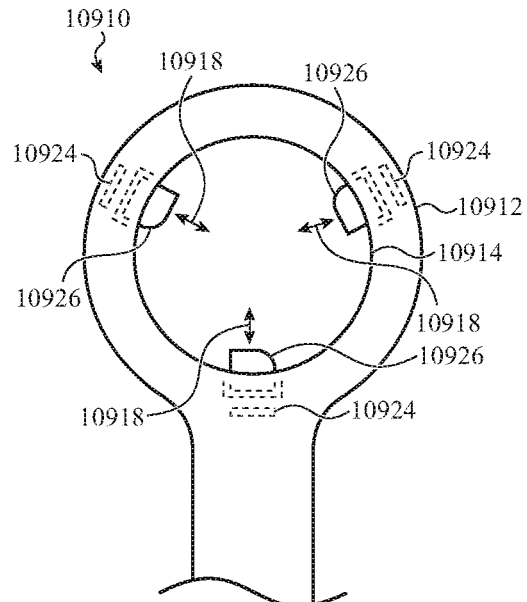
FIG. 109A          FIG. 109B
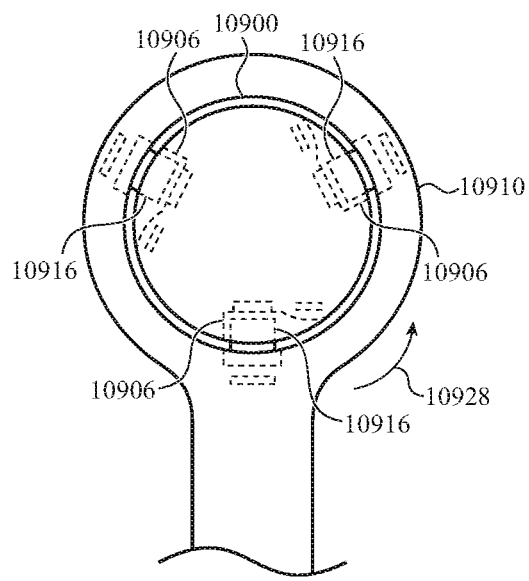
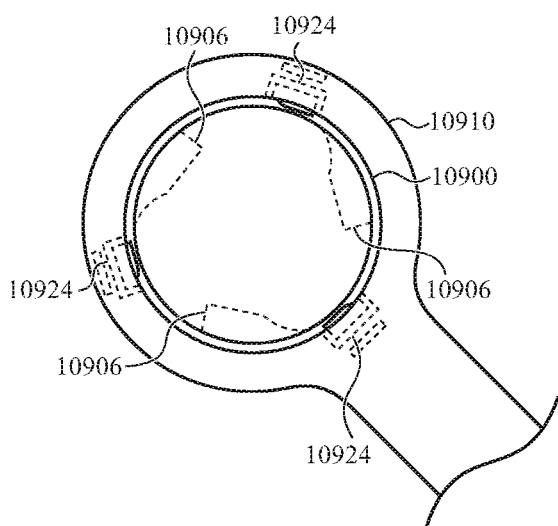
FIG. 109C          FIG. 109D

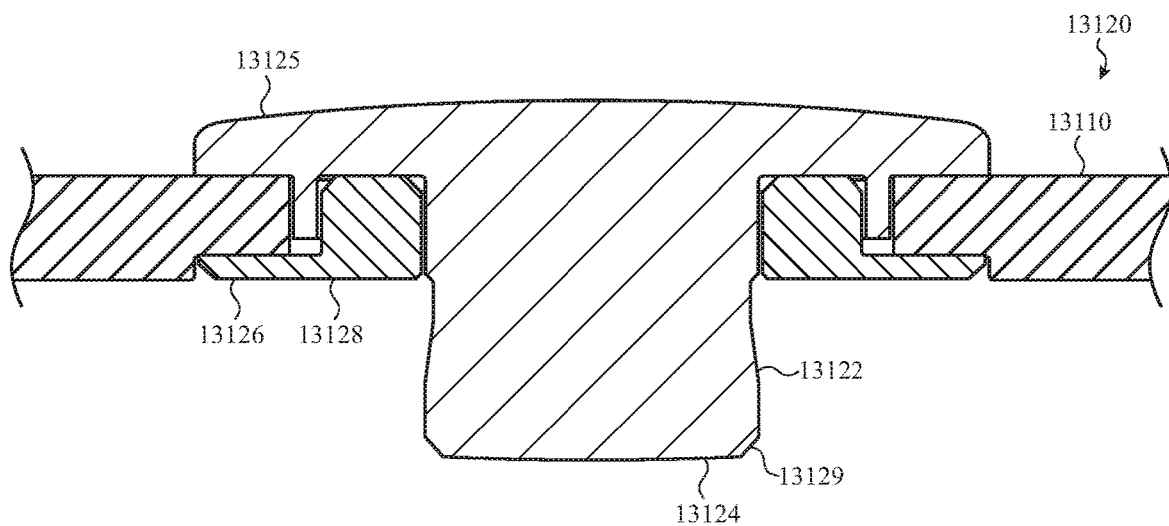
FIG. 131B
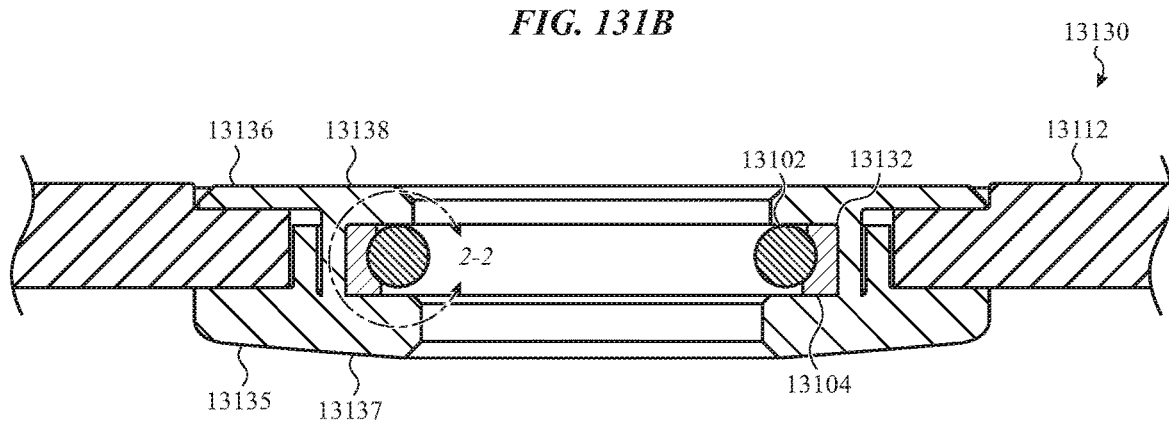
FIG. 131C
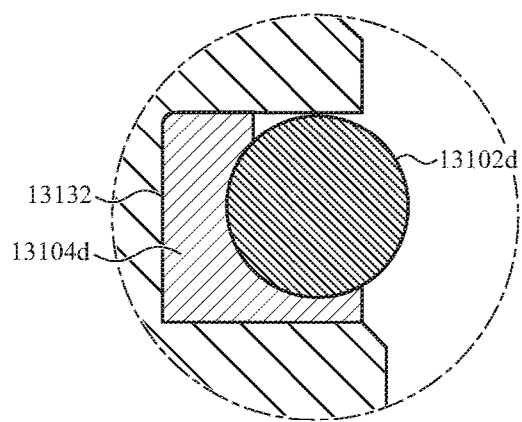 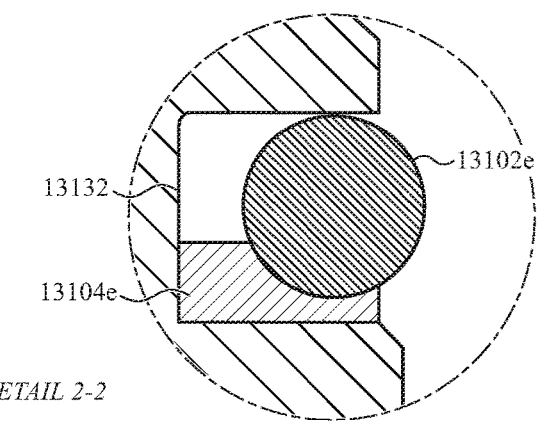
DETAIL 2-2
FIG. 131D FIG. 131E

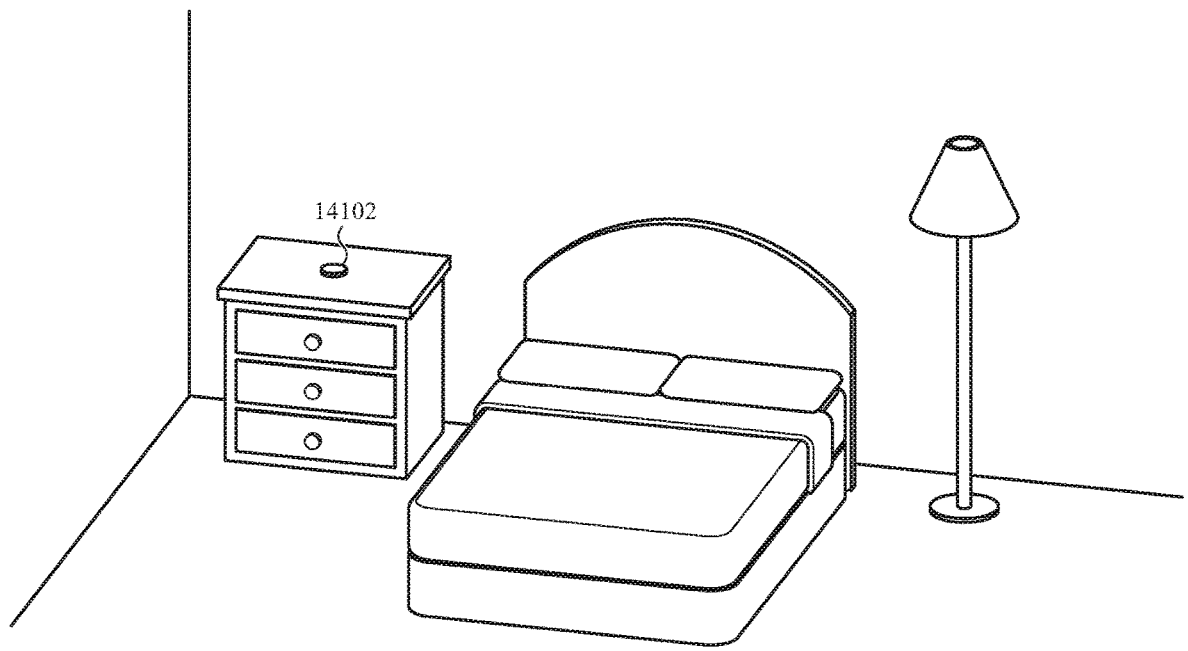
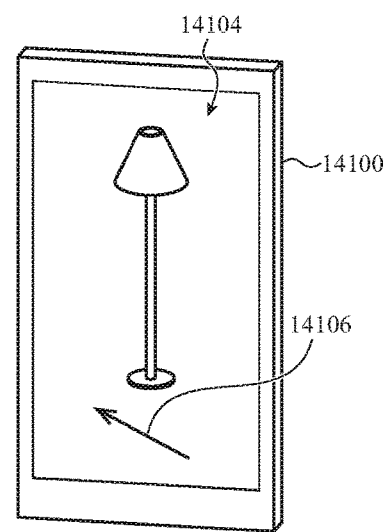
*FIG. 141A*

HOLDING ACCESSORY FOR A WIRELESSLY LOCATABLE TAG

CROSS-REFERENCE TO RELATED APPLICATION(S)

This application is a continuation patent application of PCT Patent Application No. PCT/US2020/028424, filed Apr. 16, 2020 and titled "Wirelessly Locatable Tag," which claims priority to U.S. Provisional Patent Application No. 62/835,469, filed Apr. 17, 2019 and titled "Wirelessly Locatable Tag," U.S. Provisional Patent Application No. 62/855,768, filed May 31, 2019 and titled "Wirelessly Locatable Tag," U.S. Provisional Patent Application No. 62/894,640, filed Aug. 30, 2019 and titled "Wirelessly Locatable Tag," U.S. Provisional Patent Application No. 63/101,179, filed Sep. 26, 2019 and titled "Enclosure for a Wirelessly Locatable Tag," U.S. Provisional Patent Application No. 62/922,248, filed Sep. 26, 2019 and titled "Holding Accessory for a Wirelessly Locatable Tag," U.S. Provisional Patent Application No. 63/101,180, filed Sep. 26, 2019 and titled "Audio Output System for a Wirelessly Locatable Tag," U.S. Provisional Patent Application No. 63/101,212, filed Sep. 26, 2019 and titled "Antenna Assembly for a Wirelessly Locatable Tag," U.S. Provisional Patent Application No. 62/922,250, filed Sep. 26, 2019 and titled "Battery Connection System for a Wirelessly Locatable Tag," U.S. Provisional Patent Application No. 63/101,182, filed Sep. 26, 2019 and titled "Mounting Base for a Wirelessly Locatable Tag," U.S. Provisional Patent Application No. 62/922,249, filed Sep. 26, 2019 and titled "Wirelessly Coupled Accessory System for an Electronic Device," U.S. Provisional Patent Application No. 63/101,242, filed Sep. 26, 2019 and titled "Fastener with a Constrained Retention Ring," and U.S. Provisional Patent Application No. 63/101,229, filed Sep. 26, 2019 and titled "Biomechanical Sensing System using Wirelessly Locatable Tags," the disclosures of which are hereby incorporated herein by reference in their entireties.

FIELD

The described embodiments relate generally to a holding accessory for a wirelessly locatable tag.

BACKGROUND

Electronic devices like mobile phones and portable computers are used extensively around the world. Traditionally, a geographic location of an electronic device may be determined using a global positioning system (GPS) or other locating system or technique. However, it may be difficult to locate personal property that is not an electronic device or to locate electronic devices that lack a GPS. The systems and techniques described herein are generally directed to a wirelessly locatable tag that may be used to determine the location of electronic devices or other personal property or objects.

SUMMARY

A holder for a wirelessly locatable tag may be used with a wirelessly locatable tag comprising a housing member defining a region of an exterior surface of the wirelessly locatable tag configured to act as a speaker diaphragm. The holder may include a receptacle portion configured to at least partially surround the wirelessly locatable tag, the receptacle portion defining a first opening configured to allow the wirelessly locatable tag to be positioned in the receptacle portion, a second opening configured to at least partially surround an outer periphery of a battery door of the wirelessly locatable tag, and a third opening aligned with the region of the exterior surface configured to act as the speaker diaphragm. The holder may further include a fastener coupled to the receptacle portion and configured to releasably secure the first opening in a closed configuration to retain the wirelessly locatable tag in the receptacle portion and a fastening strap configured to releasably attach the holder to an object. The object may be a split ring defining an opening, and the fastening strap may be looped through the opening of the split ring. The fastening strap may define a strap opening at a terminal end of the fastening strap, and the strap opening may be configured to allow the receptacle portion to pass through the strap opening to form a loop in the fastening strap.

The receptacle portion may define a cavity having a size and a shape that corresponds to a size and a shape of the wirelessly locatable tag. The cavity may be defined by an inner surface of the receptacle portion, and the inner surface contacts the wirelessly locatable tag when the wirelessly locatable tag is in the cavity. The second and third openings may be circular. The second and third openings may have a same diameter.

The fastener may be a snap, and the snap may include a male assembly that includes a protrusion component defining a circumferential groove that extends around the protrusion component, a compression ring positioned within the circumferential groove, a compliant member positioned in the circumferential groove and configured to apply a biasing force on the compression ring, and a female assembly defining an opening configured to receive the protrusion component, the compression ring configured to engage a surface of the female assembly to retain an engagement between the male and female assemblies.

A holder for a wirelessly locatable tag may be used with a wirelessly locatable tag comprising a housing member defining a region of an exterior surface of the wirelessly locatable tag configured to act as a speaker diaphragm. The holder may include a first layer defining a first portion of a receptacle portion configured to at least partially surround the wirelessly locatable tag, and a fastening strap. The holder may also include a second layer adjacent the first layer along an interface region and defining a second portion of the receptacle portion, the second layer attached to the first layer along a portion of the interface region, thereby defining an opening between the first layer and the second layer. The holder may further include a fastener comprising a first fastener assembly coupled to the first layer, and a second fastener assembly coupled to the second layer and configured to releasably secure the opening in a closed configuration to retain the wirelessly locatable tag in the receptacle portion.

The opening may be configured to allow the wirelessly locatable tag to be positioned in the receptacle portion. The opening may be a first opening, the first layer may define a second opening, the second layer may define a third opening, and at least one of the second opening or the third opening may be configured to expose the region of the exterior surface configured to act as the speaker diaphragm. The fastening strap may be attached to a clip configured to releasably attach the holder to an object. A terminal end of the fastening strap may be secured to a base of the fastening strap to define a loop. The terminal end of the fastening strap may be secured to the base of the fastening strap by the first fastener assembly. The fastening strap may define a strap opening at a terminal end of the fastening strap, and the strap opening may be configured to allow the receptacle portion to pass through the strap opening to form a loop in the fastening strap.

A holder for a wirelessly locatable tag may be used with a wirelessly locatable tag that includes a housing member defining a region of an exterior surface of the wirelessly locatable tag configured to act as a speaker diaphragm. The holder may include a receptacle portion configured to at least partially surround the wirelessly locatable tag, the receptacle portion defining a first opening configured to receive the wirelessly locatable tag such that it can be positioned in the receptacle portion, a second opening aligned with the region of the exterior surface configured to act as the speaker diaphragm, a tab extending from the receptacle portion proximate the first opening, the tab defining a third opening, and a strap extending from the receptacle portion proximate the first opening and configured to extend through the third opening to retain the first opening in a closed configuration.

The strap may be configured to be removed from the third opening to allow the first opening to expand to receive the wirelessly locatable tag. The strap may define a loop at a terminal end of the strap, and the holder further comprises a removable split ring attached to the loop. A dimension of the removable split ring may be larger than a dimension of the third opening, thereby preventing the terminal end of the strap from passing through the third opening when the removable split ring is attached to the loop. The receptacle portion may further define a fourth opening configured to at least partially surround an outer periphery of a battery door of the wirelessly locatable tag.

BRIEF DESCRIPTION OF THE DRAWINGS

The disclosure will be readily understood by the following detailed description in conjunction with the accompanying drawings, wherein like reference numerals designate like structural elements, and in which:

FIGS. 70A-70D depict another example tag retainer for holding a wirelessly locatable tag;

FIGS. 71A-71C depict another example tag retainer for holding a wirelessly locatable tag;

FIGS. 79A-79C depict another example tag retainer for holding a wirelessly locatable tag;

FIGS. 87A-87C depict another example spring member for attaching to a wirelessly locatable tag;

FIGS. 100A-100D depict another example tag retainer for holding a wirelessly locatable tag;

FIGS. 109A-109D depict an example wirelessly locatable tag and an associated tag retainer;

FIGS. 111A-111B depict the tag of FIGS. 110A-110B being attached to a tag retainer;

FIG. 112A-112B depict an example wirelessly locatable tag;

FIGS. 113A-113B depict the tag of FIGS. 112A-112B being attached to a tag retainer;

FIG. 114A depicts an example tag retainer for holding a wirelessly locatable tag;

FIG. 114B depicts the retainer of FIG. 114A being attached to a tag;

FIGS. 115A-115C depict an example wirelessly locatable tag and an associated tag retainer;

FIG. 115D depicts another example wirelessly locatable tag and an associated tag retainer;

FIGS. 116A-116B depict another example wirelessly locatable tag and an associated tag retainer;

FIGS. 117A-117C depict another example wirelessly locatable tag and an associated tag retainer;

FIGS. 118A-118C depict another example tag retainer for holding a wirelessly locatable tag;

FIGS. 119A-119B depict another example tag retainer for holding a wirelessly locatable tag;

FIGS. 120A-120B depict another example tag retainer for holding a wirelessly locatable tag;

Figure 121A:
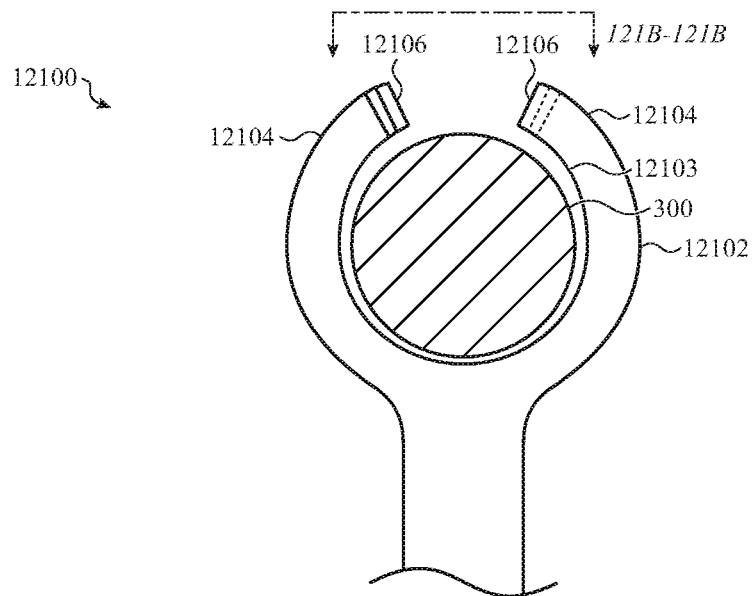
Figure 121B:
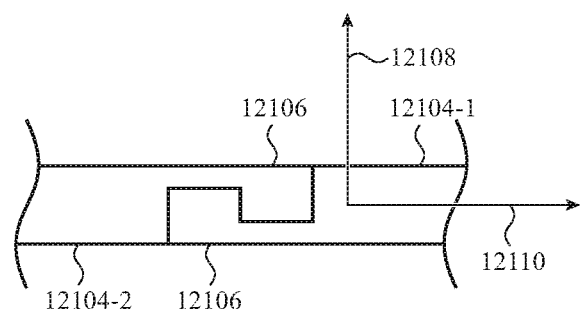
Figure 122:
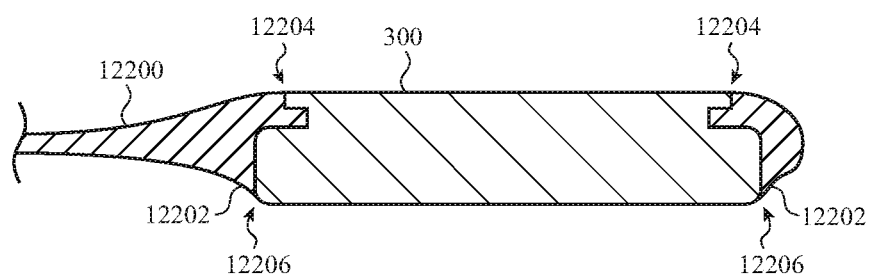
Figure 129A:
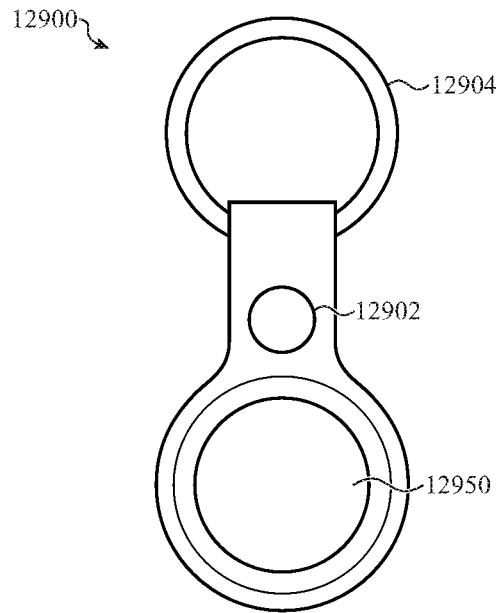
Figure 129B:
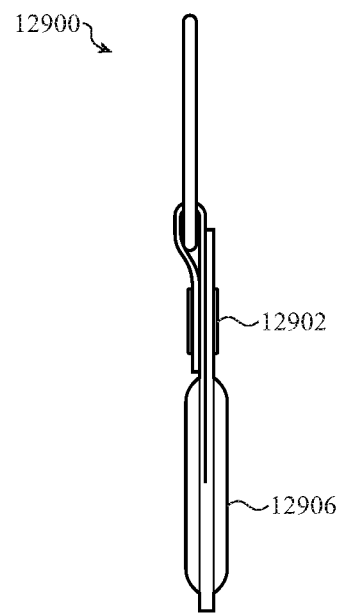
Figure 129C:
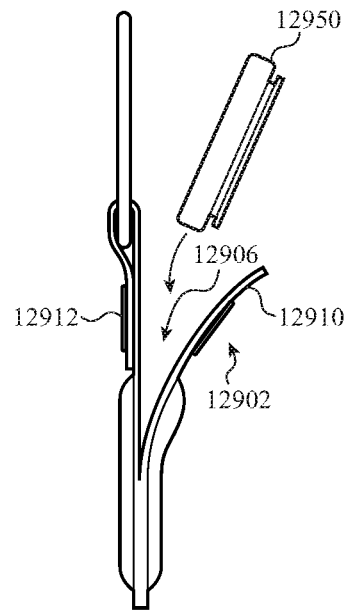
Figure 132A:
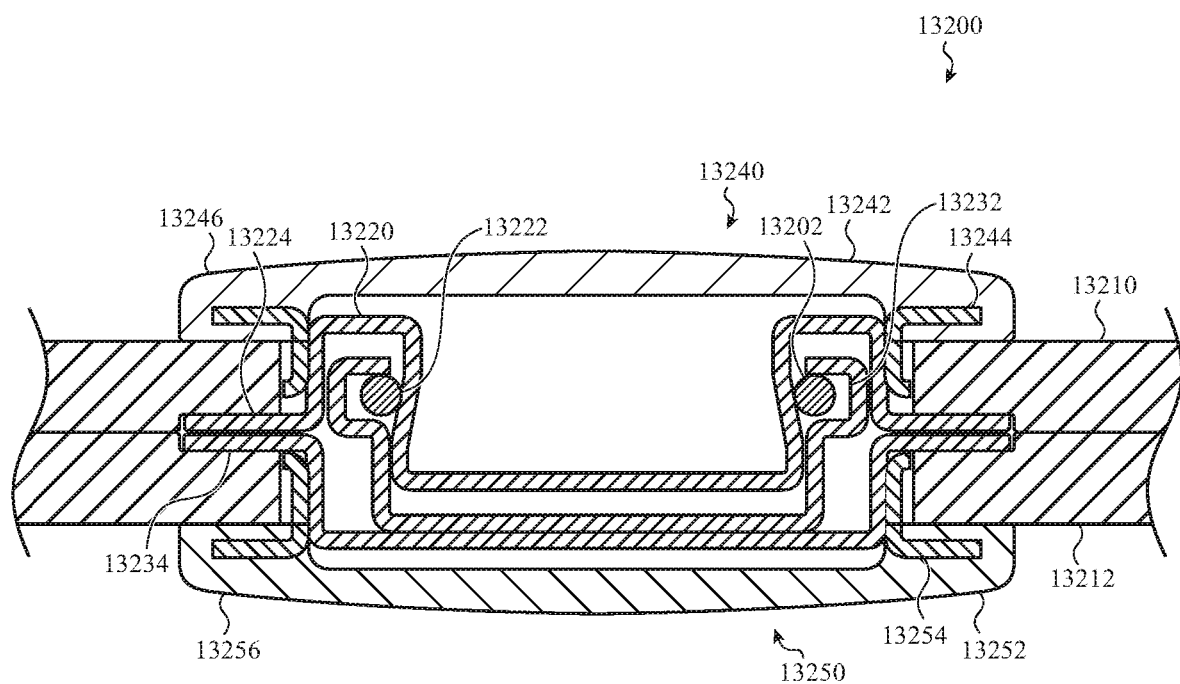
Figure 132B:
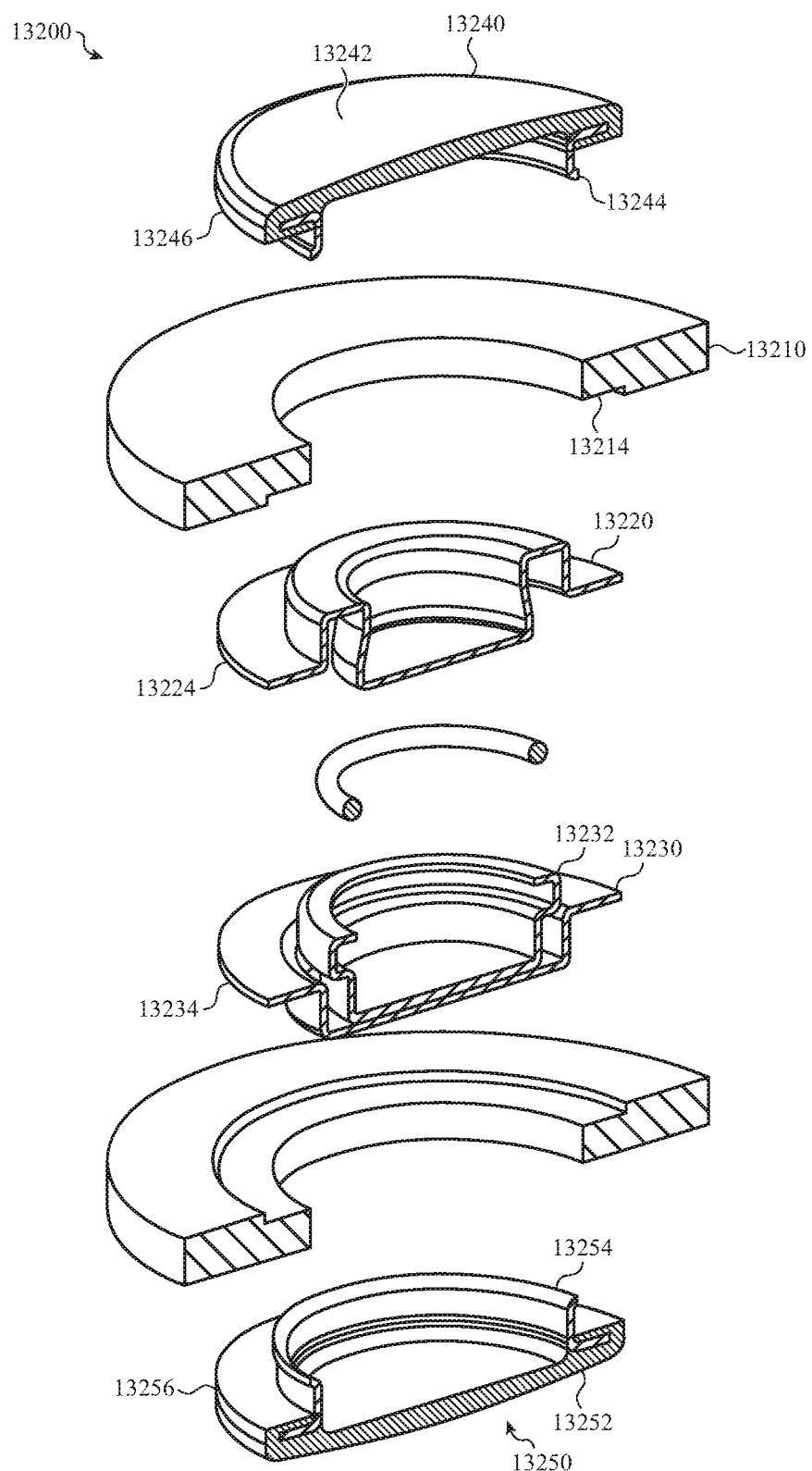
Figure 132C:
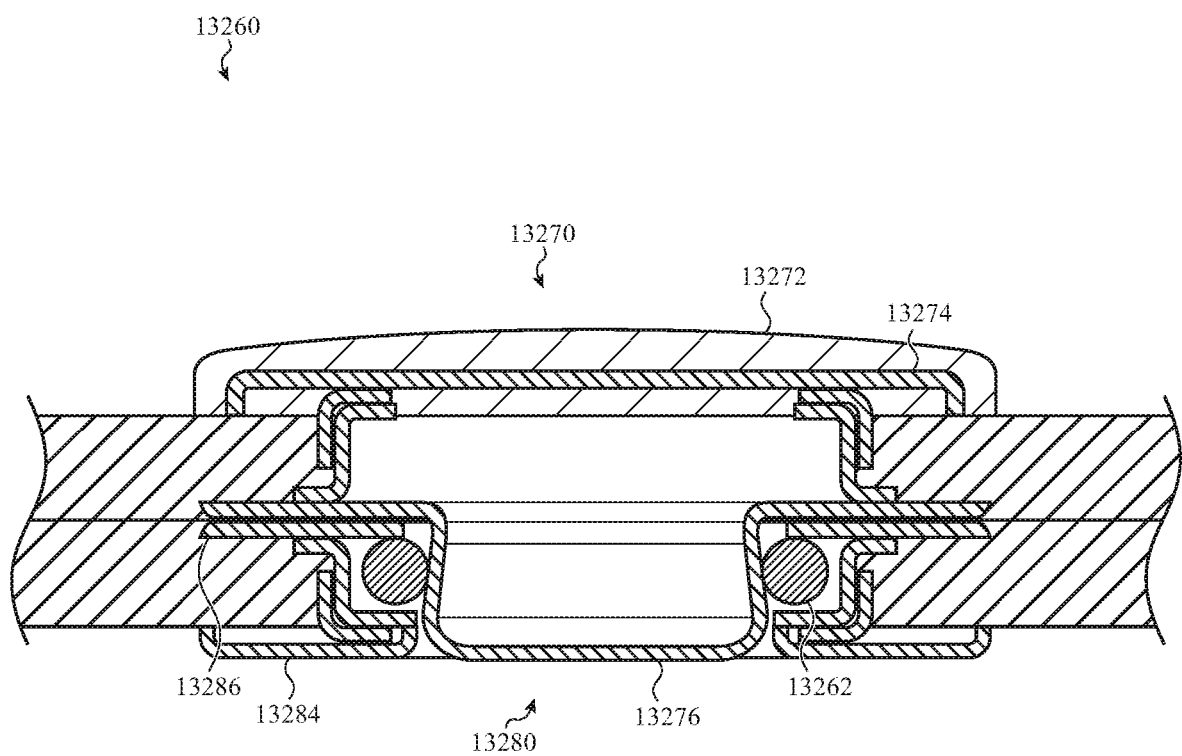
Figure 133A:
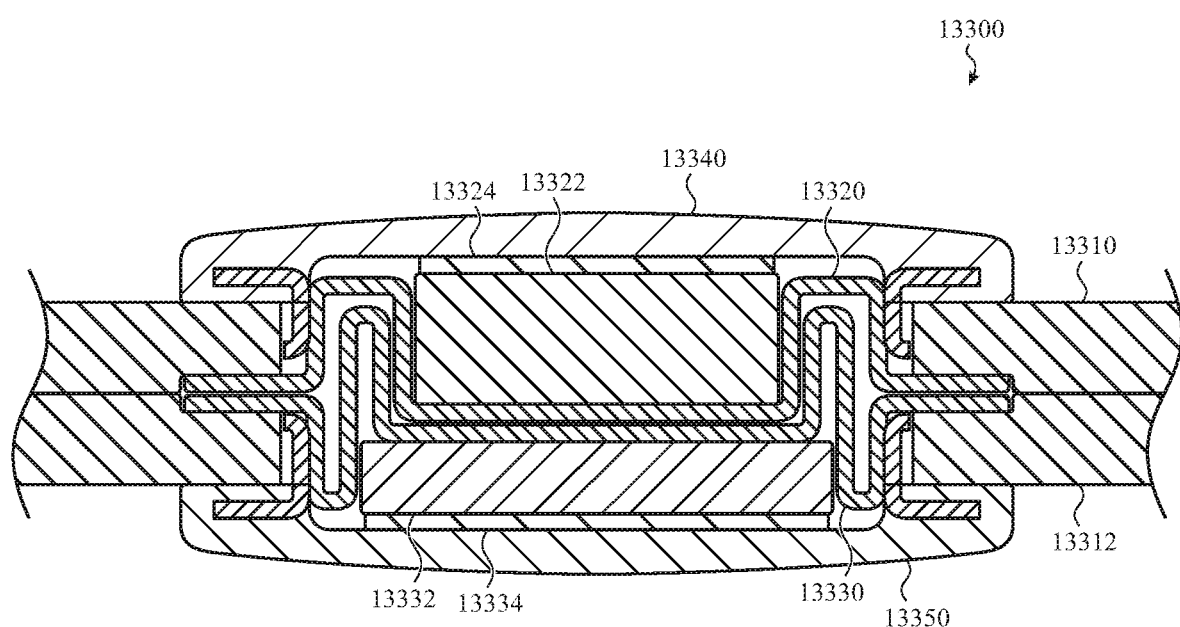
Figure 133B:
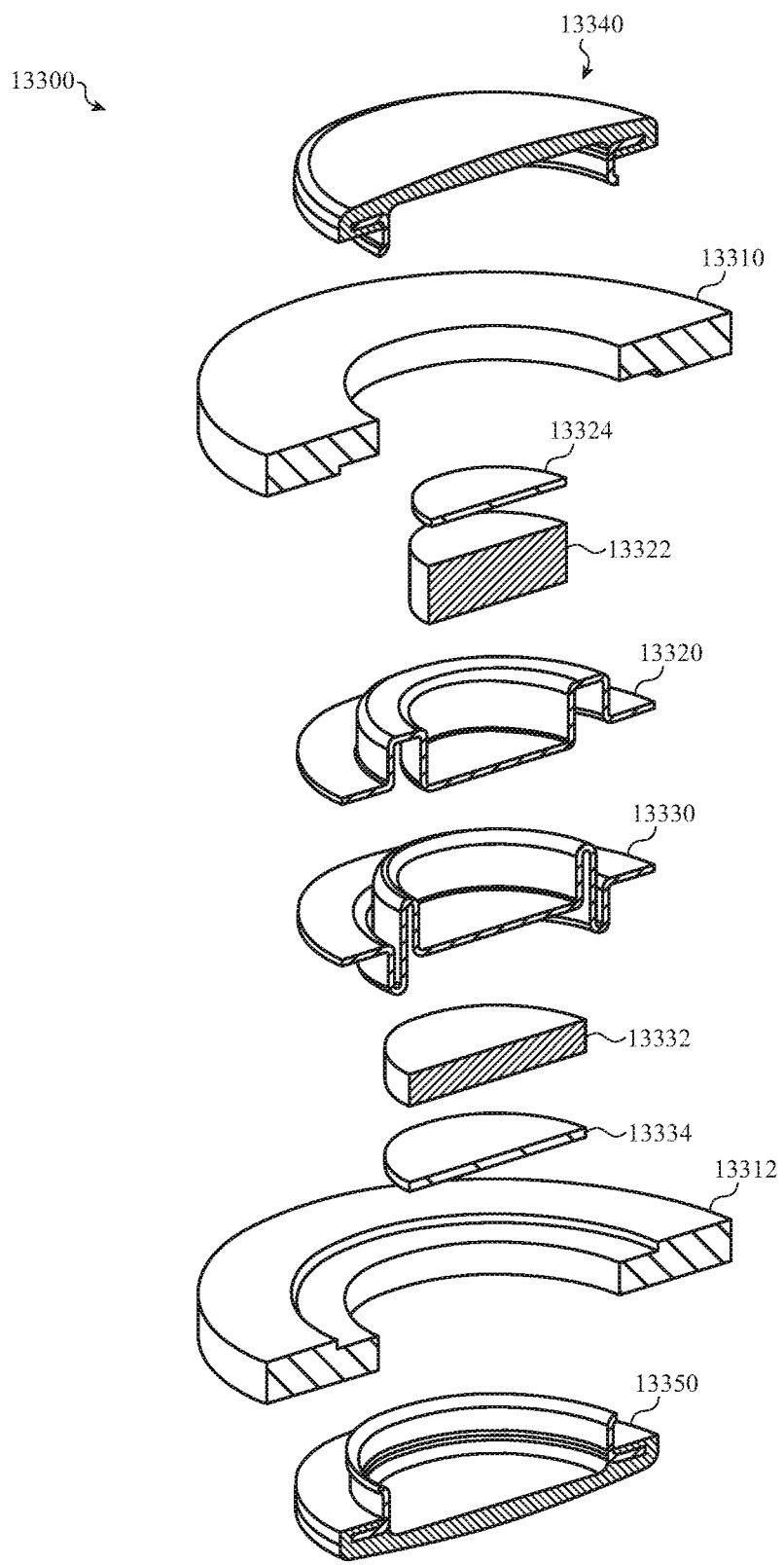
Figure 134A:
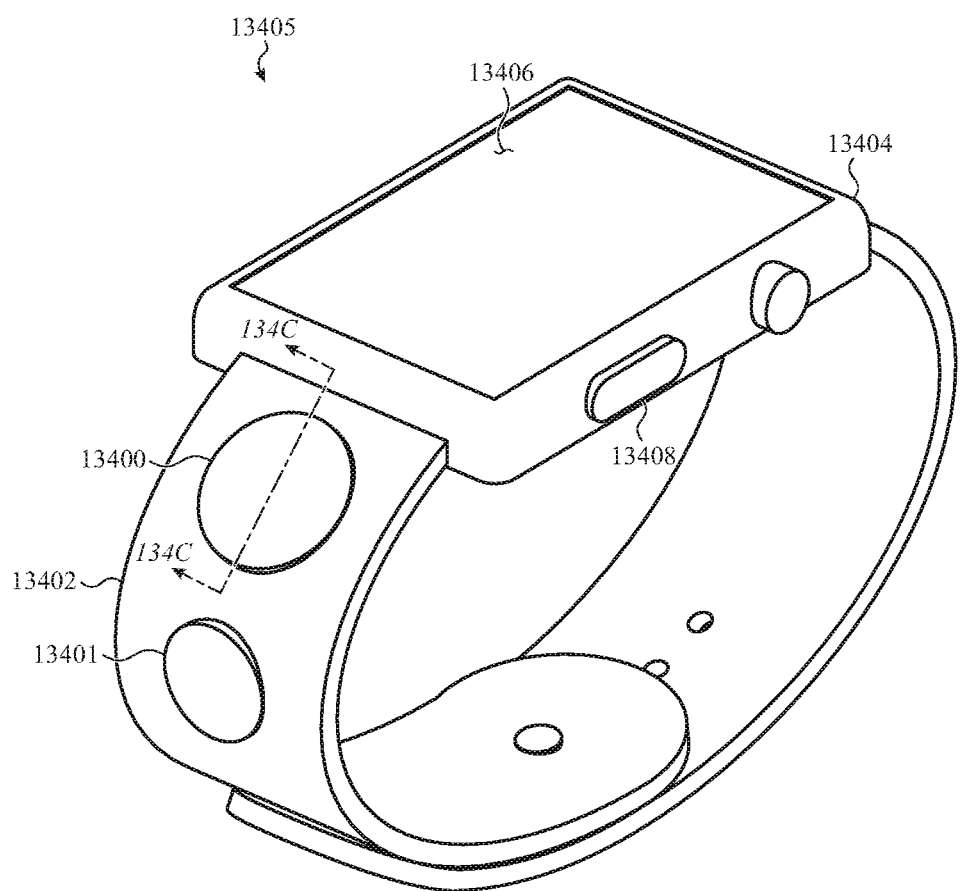
Figure 134B:
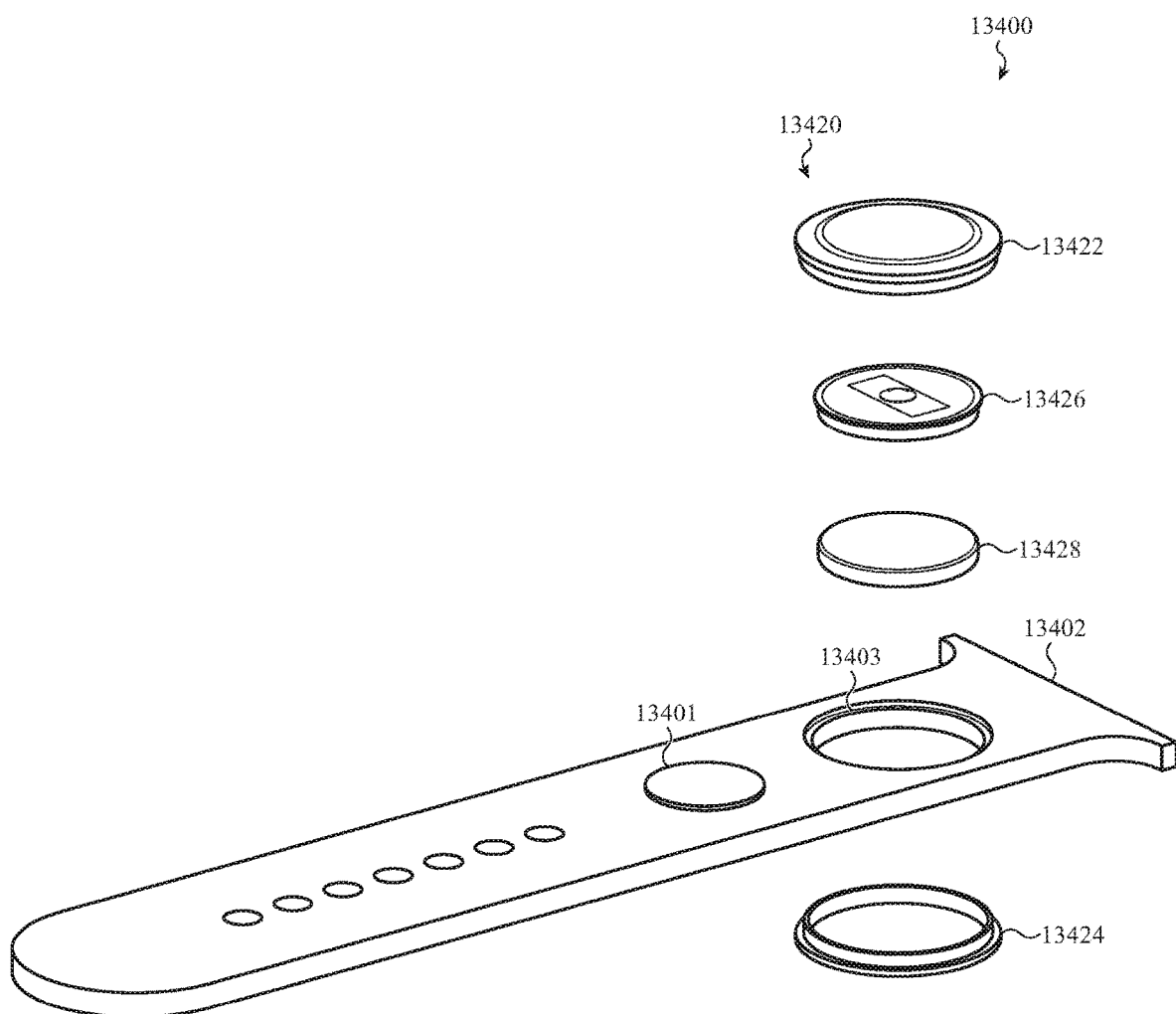
Figure 134C:
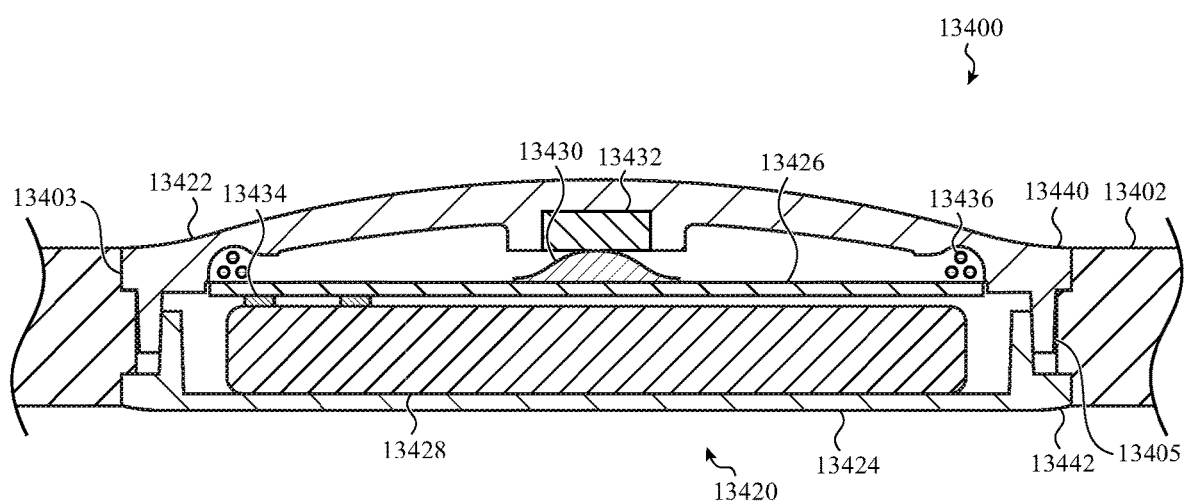
Figure 135A:
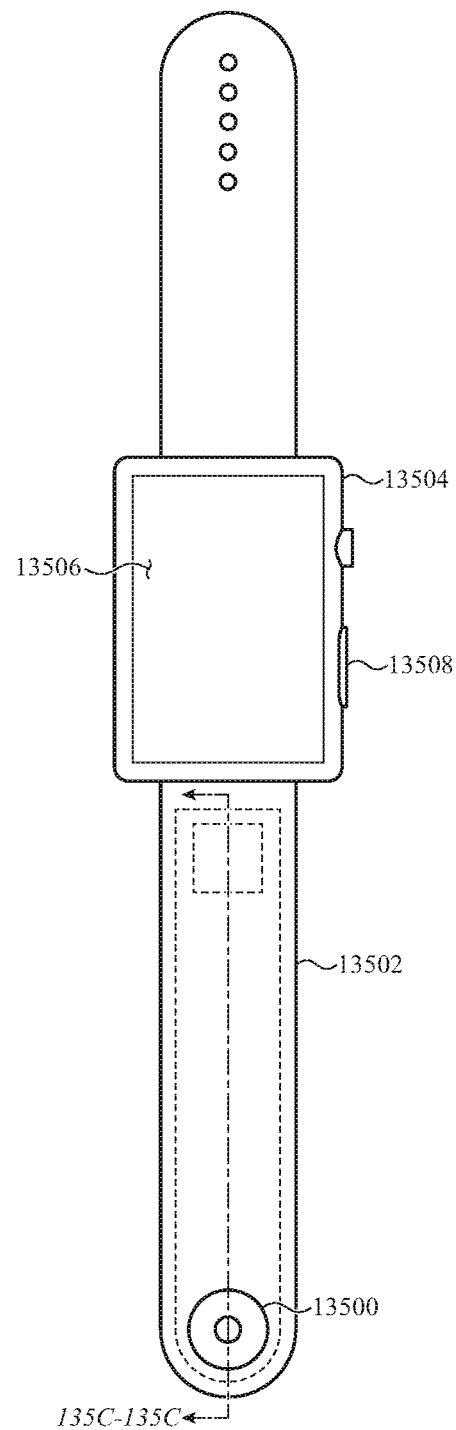
Figure 135B:
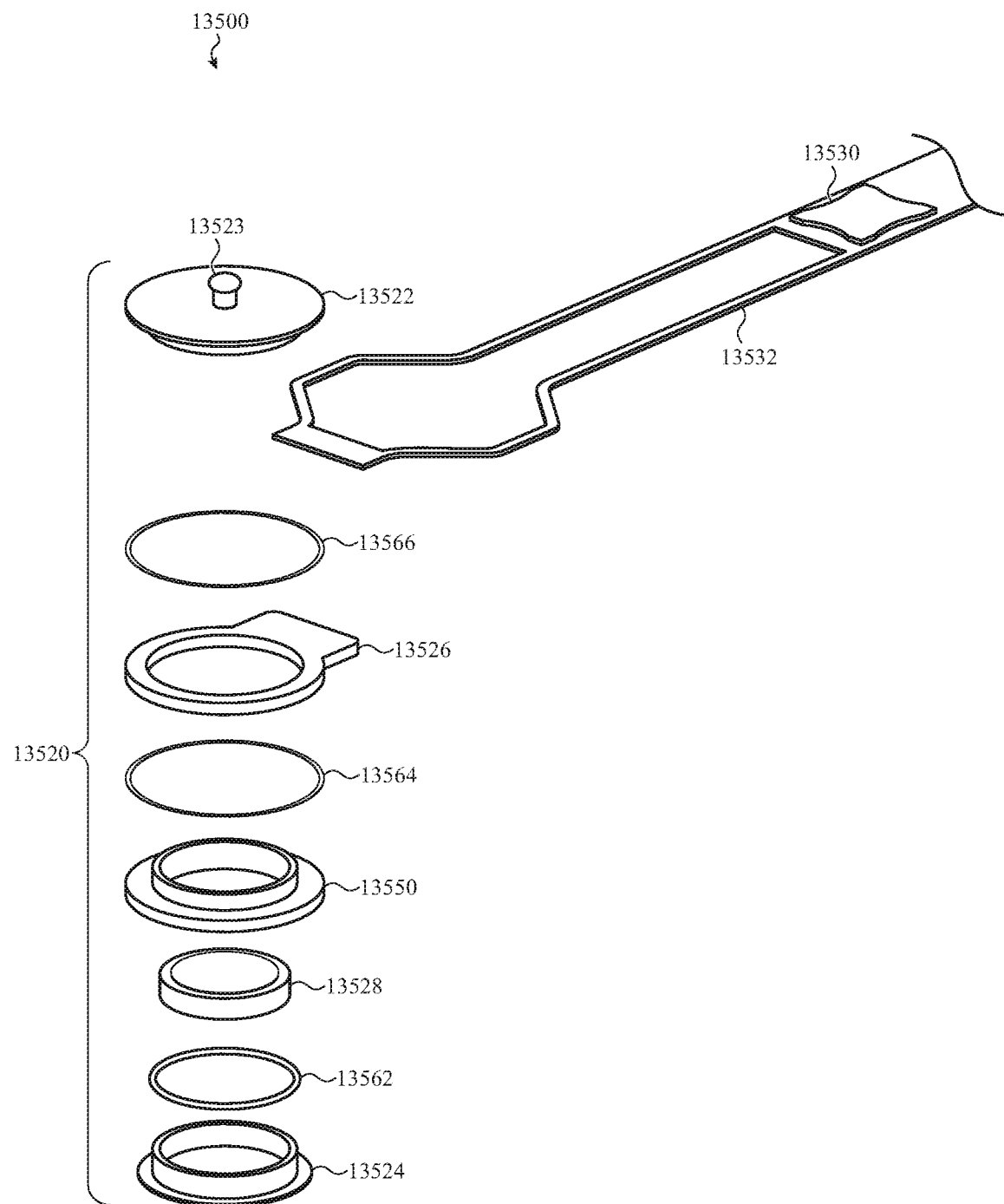
Figure 135C:
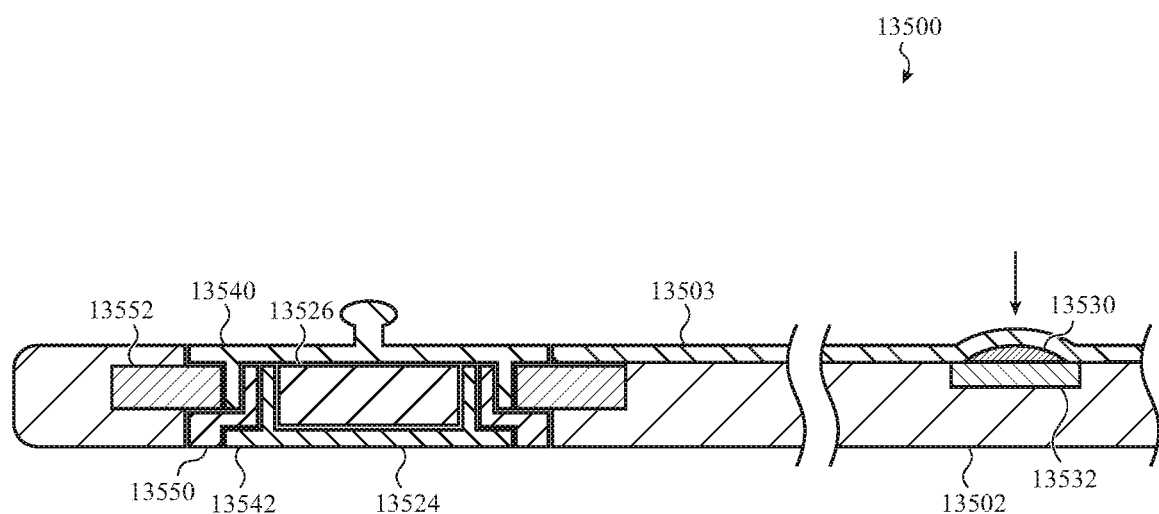
Figure 136A:
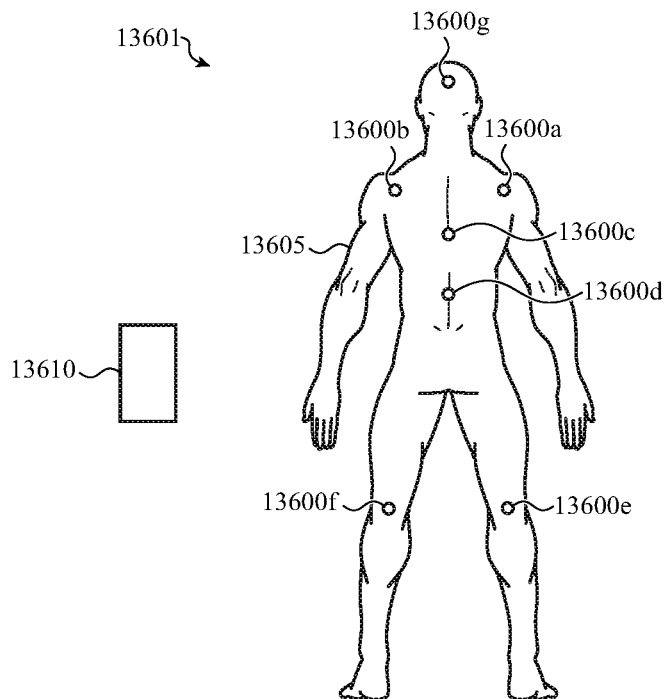
Figure 136B:
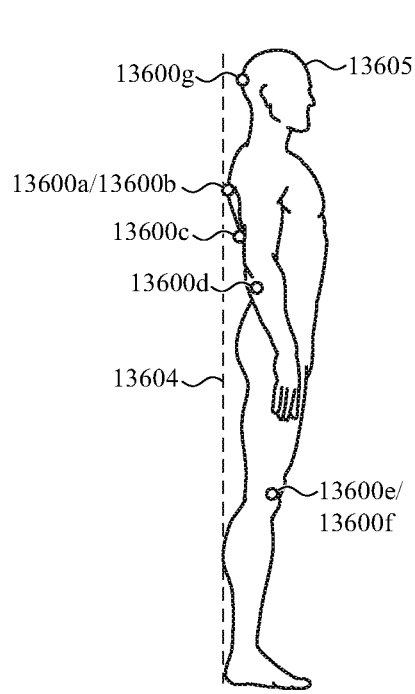
Figure 136C:
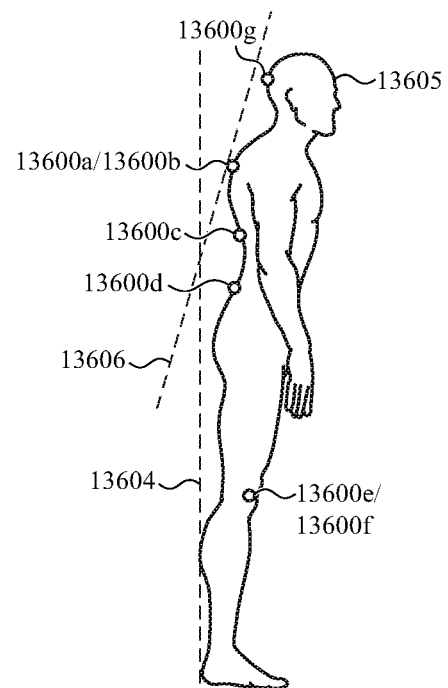
Figure 137A:
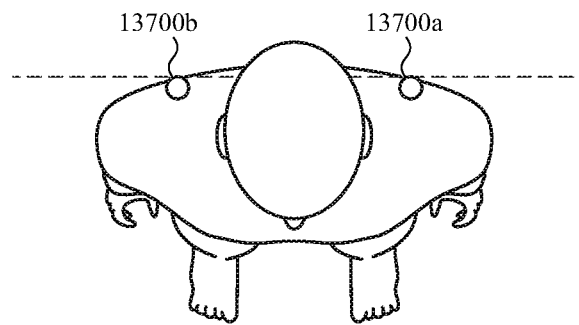
Figure 137B:
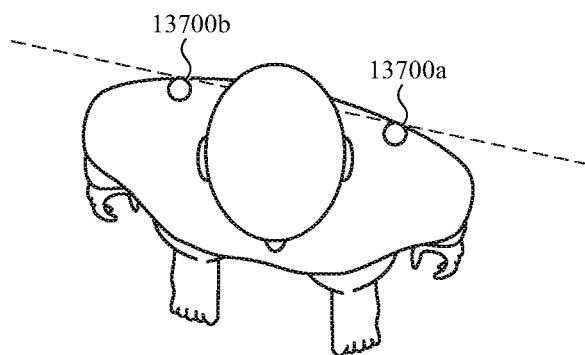
Figure 138A:
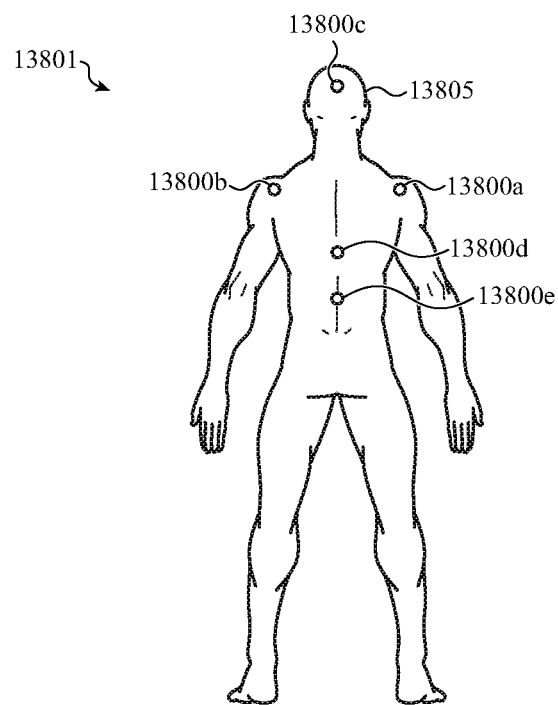
Figure 138B:
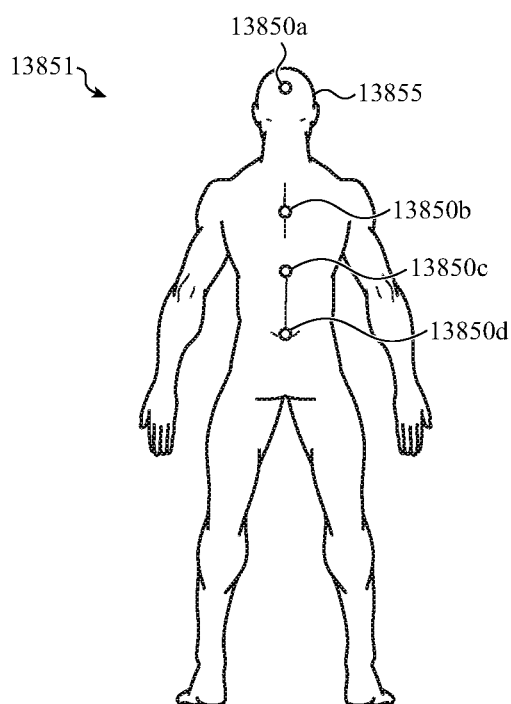
Figure 139:
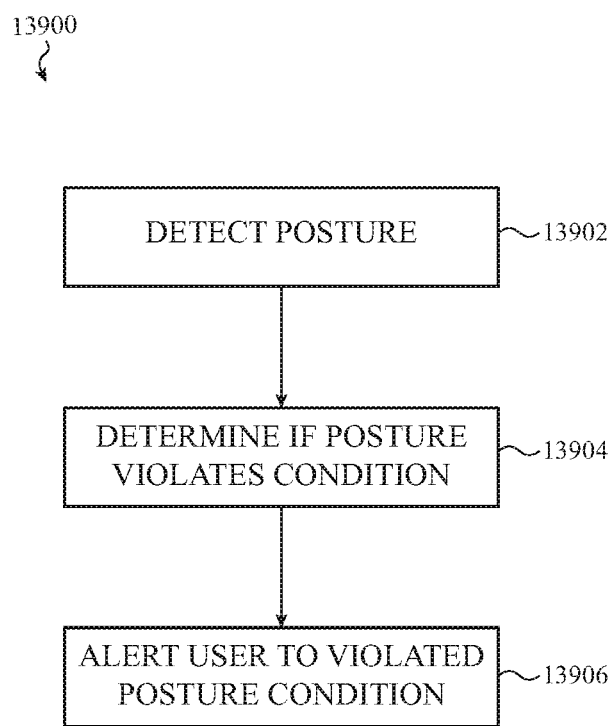
Figure 140:
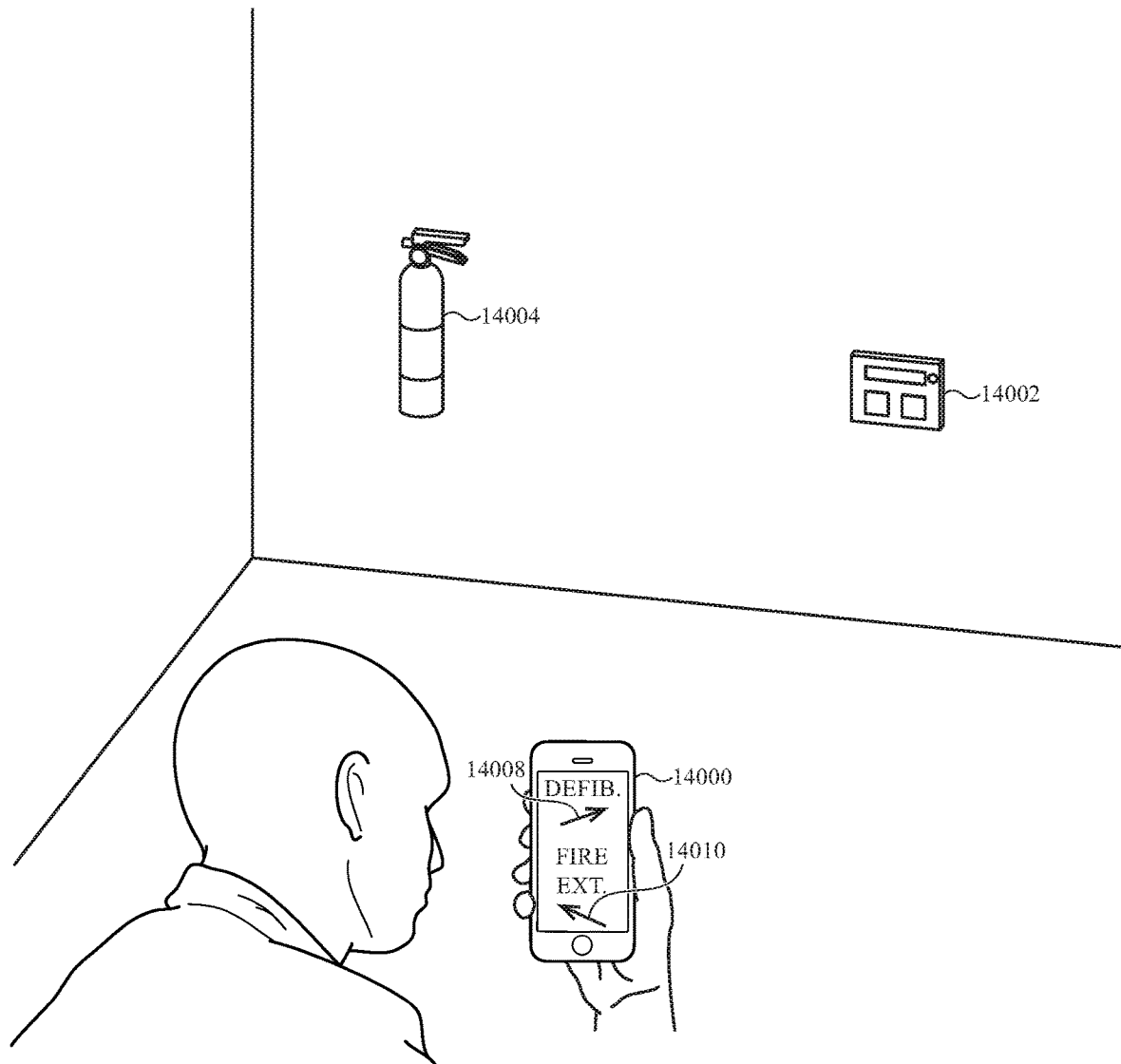
Figure 141B:
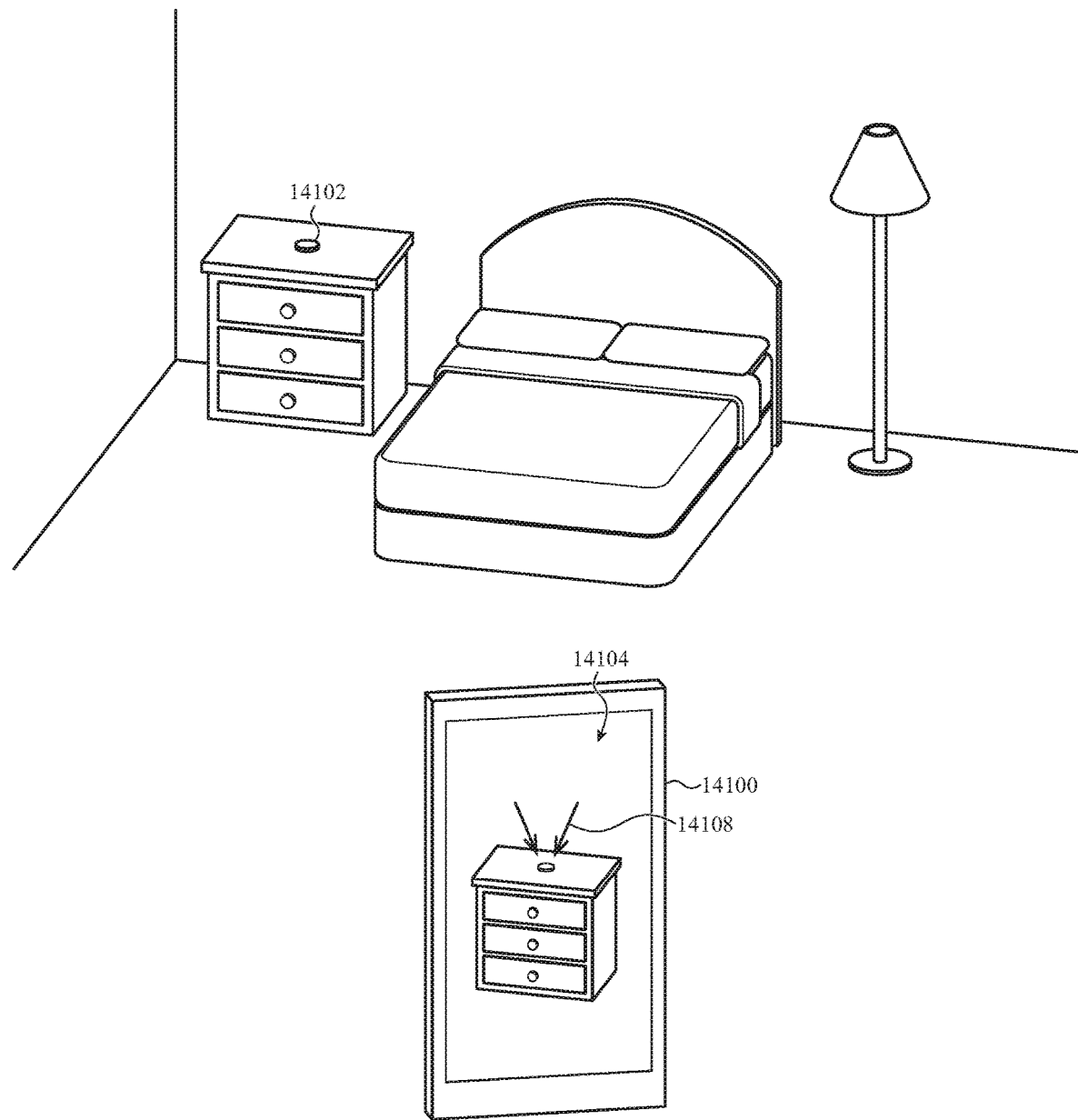
Figure 142:
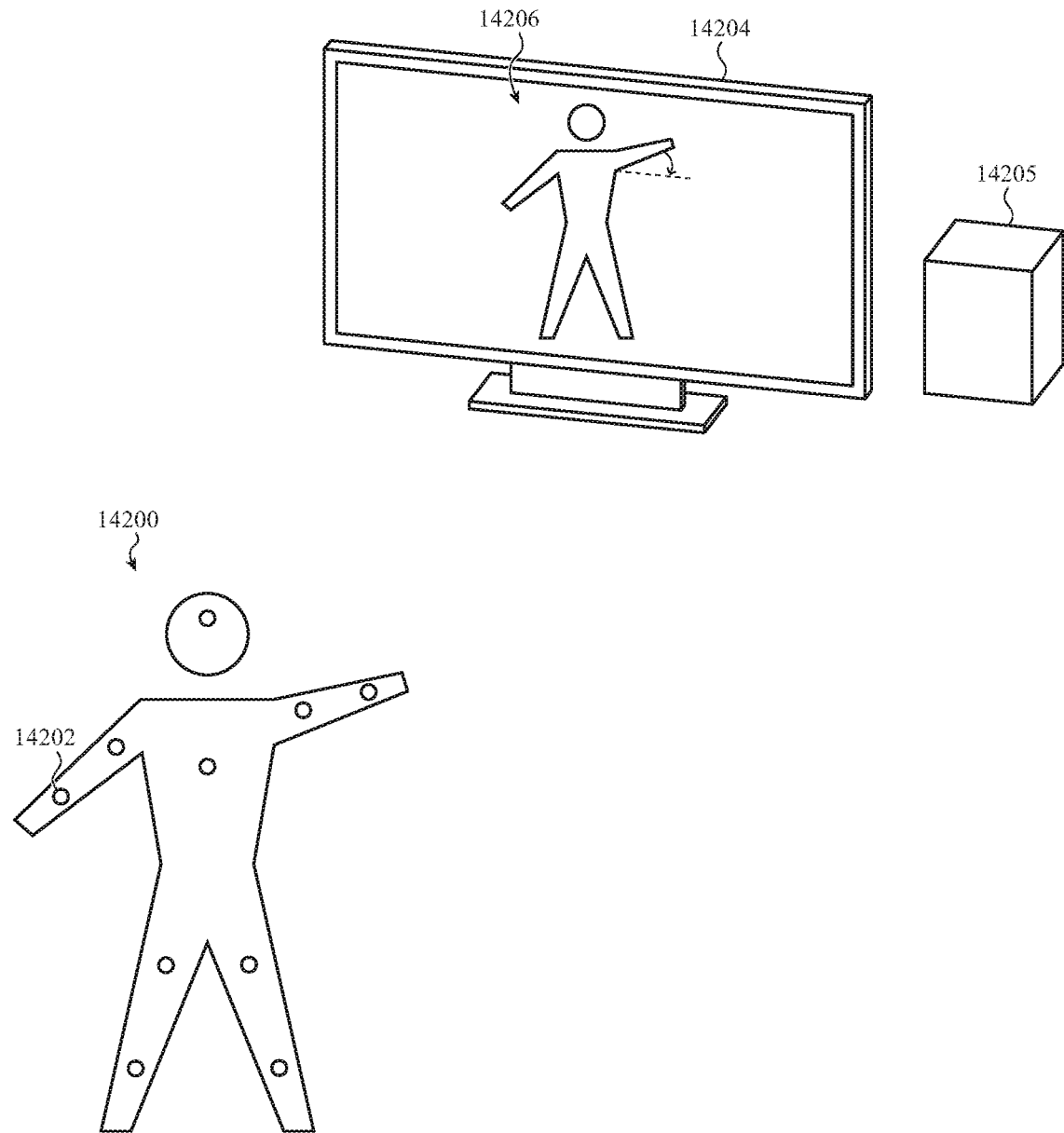
Figure 143:
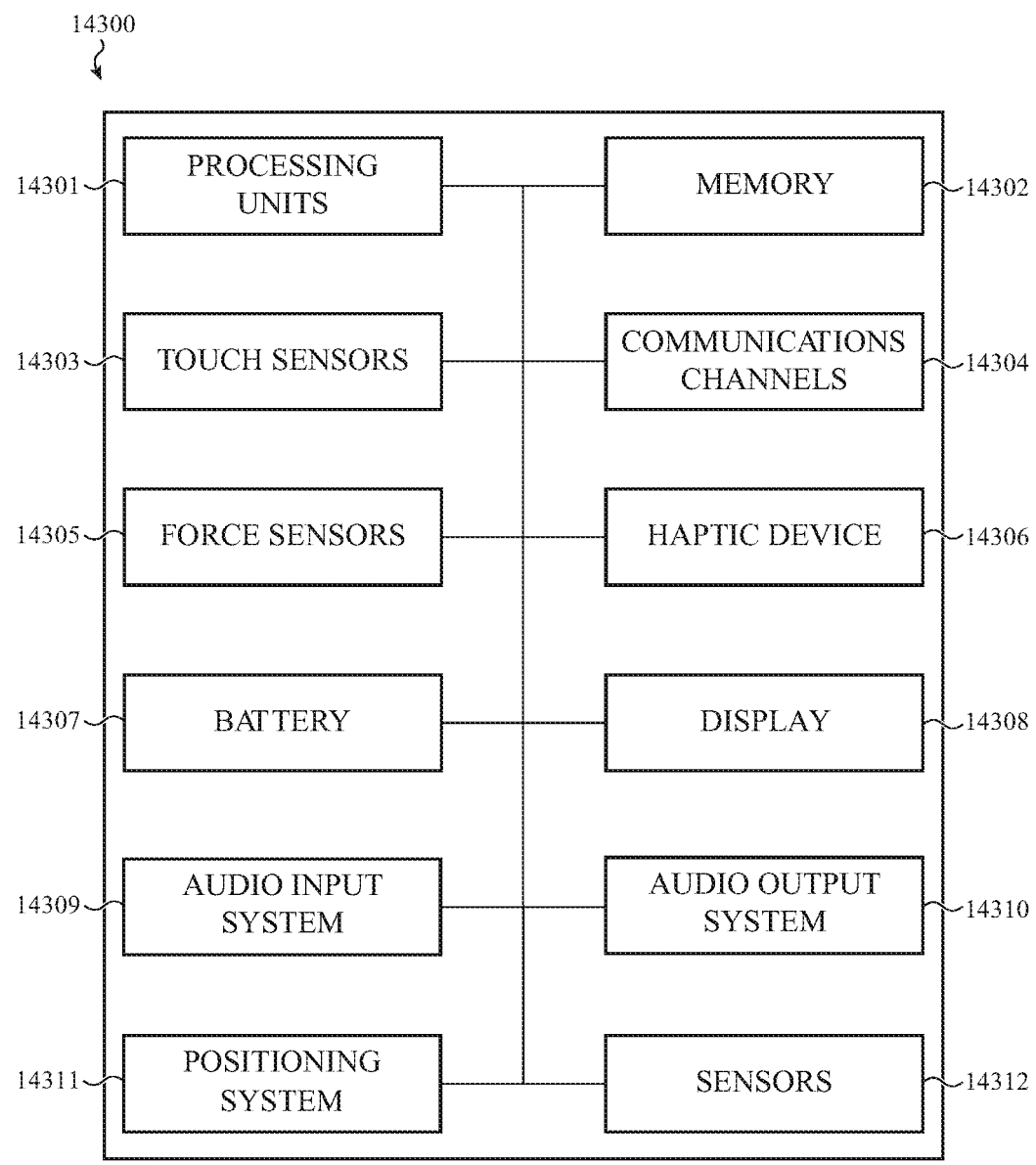

FIGS. 121A-121B depict another example tag retainer for holding a wirelessly locatable tag;

FIG. 122 depicts another example tag retainer for holding a wirelessly locatable tag;

FIGS. 123A-125B depict example clips for tag holding accessories;

FIGS. 126A-128 depict example rings for tag holding accessories;

FIGS. 129A-129C depict an accessory for a wirelessly locatable tag;

FIGS. 130A-130H depict example fasteners for an accessory of a wirelessly locatable tag;

FIGS. 131A-131H depict other example fasteners for an accessory of a wirelessly locatable tag;

FIGS. 132A-132C depict other example fasteners for an accessory of a wirelessly locatable tag;

FIGS. 133A-133B depict another example fastener for an accessory of a wirelessly locatable tag;

FIGS. 134A-134C depict an example wireless tag or wireless module that is integrated with an accessory of a device;

FIGS. 135A-135C depict another example wireless tag or wireless module that is integrated with an accessory of a device;

FIGS. 136A-136C depict an example posture-monitoring system having an array of wireless tags;

FIGS. 137A-137B depict wireless tags positioned along a user's shoulder for monitoring a posture of a user;

FIGS. 138A-138B depict alternative posture-monitoring systems having an array of wireless tags;

FIG. 139 depicts an example process for monitoring a user's posture using an array of wireless tags;

FIG. 140 depicts an electronic device locating wirelessly locatable tags in an example environment;

FIGS. 141A-141B depict an electronic device locating wirelessly locatable tags in another example environment;

FIG. 142 depicts wirelessly locatable tags attached to a user's body for monitoring movement or position of the user's body;

FIG. 143 depicts a schematic diagram of an example electronic device; and

Figure 144:
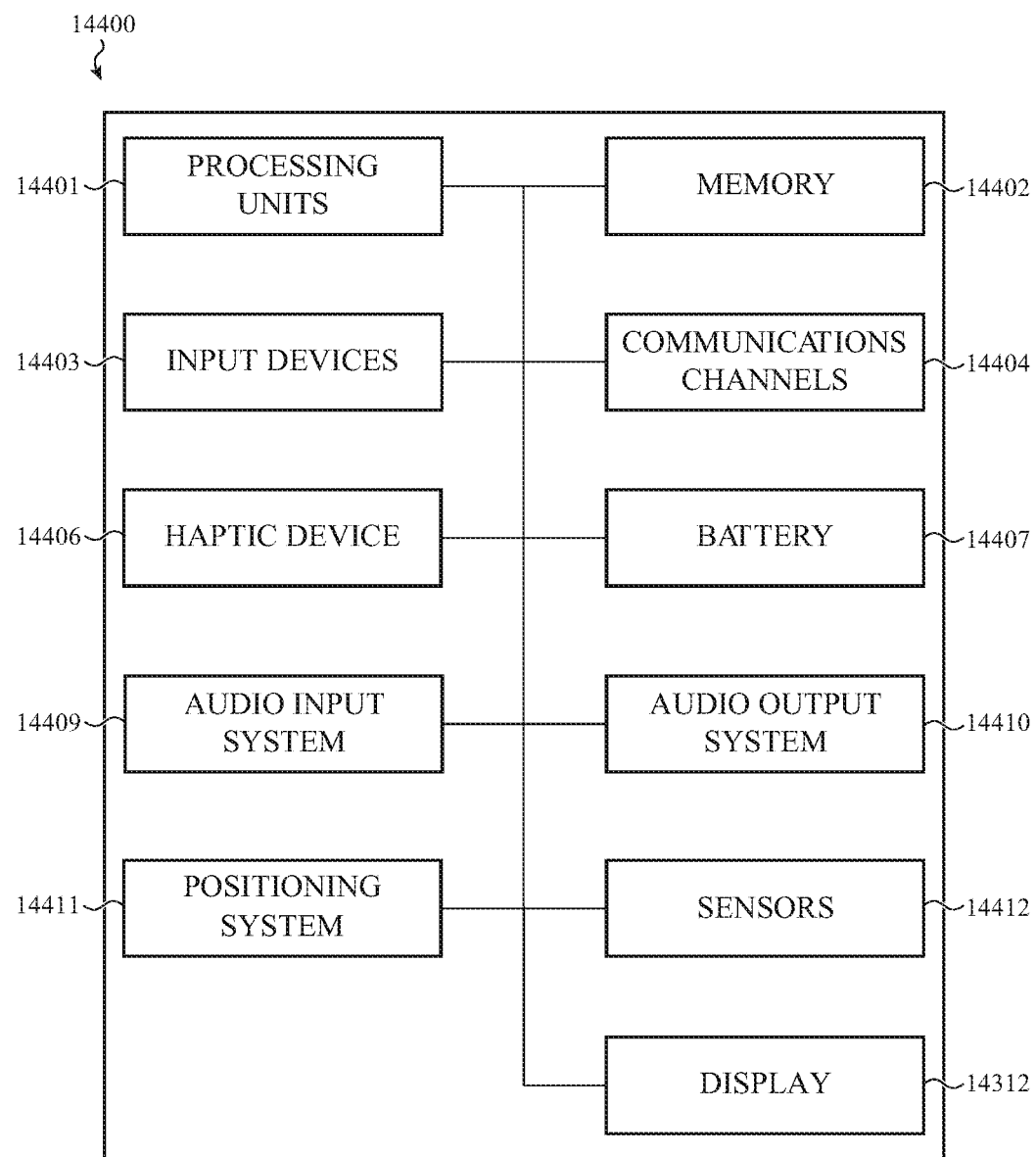

FIG. 144 depicts a schematic diagram of an example wirelessly locatable tag.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The embodiments herein are generally directed to a device, such as a small, battery-powered tag, puck, or other object of convenient size and shape, that can be physically and/or geographically located using wireless communications systems and techniques. For example, a tag may include an antenna that emits a wireless signal or beacon that is detectable by another electronic device such as a smartphone. Using the detected wireless signal (and using localization techniques such as time of flight, received signal strength indication, triangulation, etc.), the smartphone may be able to determine the position of the tag relative to the smartphone, and, using an absolute location of the smartphone from a GPS, the absolute location of the tag as well. The embodiments herein also relate to the overall network environment that includes (or is defined by) the tags, smartphones, computers, and other devices, and that facilitates the locating of tags as well as numerous other features and functions.

Knowing the location of a tag enables a wide range of location-based use cases. For example, the tag may be used to track the location of a portable object such as a set of physical keys, a purse, backpack, article of clothing, or other suitable object or item of personal property. Thus, if the portable object becomes lost or misplaced, a user may be able to find the object using his or her smartphone, tablet, or other suitable device. A tag may also be used to trigger some action on a computing device (e.g., a smartphone) when the device is within a certain proximity and/or orientation relative to the tag. For example, a tag may be positioned in a lobby of a building so that when individuals enter the lobby, their smartphone may detect that it is within a threshold distance of that tag, which in turn causes a map of the building to automatically be displayed on the smartphone. Notably, the devices and techniques described herein allow distance, position, location, and/or orientation determinations with a high degree of accuracy. For example, a smartphone may be capable of determining the location of a tag to an accuracy within three feet, and even to within one foot or less.

As described herein, a tag used for tracking physical objects may be a small, conveniently shaped device that can be attached to objects, such as keys, purses, or wallets, to help an owner find lost, misplaced, or stolen objects. The tag may feature a robust structural design that ensures reliable use through a variety of conditions and environments. For example, the tag may be waterproof or at least splash-proof, and may be capable of withstanding impacts, drop events, or other general trauma resulting from normal use of the tag. In part, the ruggedness of the tag may be facilitated by the absence of some types of components, such as glass covers, displays, openings in the housing, external moving parts, and the like.

The tag may include a battery, sensors, a wireless communication system, and one or more output devices that can produce audible and/or haptic outputs. Localization functions may be provided by the wireless communication system, and in particular, by the tag sending wireless signals to other devices (e.g., smartphones, tablet computers, etc.) that analyze the wireless signals to determine the distance, position, location, and/or orientation of the tag with a high degree of accuracy. As used herein, localization refers to determining one or more spatial parameters of a tag or other wirelessly locatable device. Spatial parameters include parameters of an object that define an aspect of its distance, position, location, and/or orientation in absolute space or relative to another object. For example, spatial parameters may include parameters such as a distance between objects, a location in a particular geography (e.g., latitude and longitude coordinates), a unit vector pointing from one object to another object, an orientation (also referred to as an angular position or attitude) of an object in three-dimensional space, or the like.

The output devices of a tag may also help a user find a lost tag by emitting sounds and/or haptic outputs. The tag may also include input devices that allow users to control or change the tag's operations. Further, the tag may have a shape and form factor that allows the tag to be easily attached to a user's property (or to a tag retainer or accessory).

As described herein, the tag may operate in any of multiple modes. In a normal operational mode, for example, the tag may conserve power and establish momentary or intermittent communications with one or more other devices (e.g., by sending a wireless beacon signal). The communications may function to confirm the location and may exchange some information about the state or location of the tag. In this way, the tag can essentially periodically update other devices (e.g., a user's smartphone) with its location and/or status. In some cases, the intermittent communications from the tag may be one-way communications, such as sending a wireless signal for other devices to receive, but not receiving any information from the other devices.

The tag may also operate in a lost mode. The lost mode may be triggered in response to an unexpected loss of communication between the tag and one or more other devices (e.g., the user's smartphone), which may indicate that the tag is no longer in the personal possession or immediate vicinity of the user. The lost mode may also be triggered by a user reporting the tag as lost to a host system or service. As described herein, when the tag is in a lost mode, the tag may be adapted to use third-party devices (e.g., devices of individuals other than the tag's owner) in order to relay information back to the user. When third-party devices are used to relay information between the tag and a user, the communications may use secured and/or encrypted communications to help ensure the privacy and security of the user.

In some cases, third-party devices that are transiently located proximate to the tag may operate as a mesh network or ad-hoc network to relay information back to the user. The information sent to or otherwise made available to the user may include encrypted data that includes an estimated location of the tag and/or one or more of the third-party devices. The secured communications may be decrypted by the user in a way that maintains the anonymity of the various third-party devices, while also allowing the user to locate the tag using the location data generated by the third-party devices.

While the foregoing examples primarily describe a tag communicating with a smartphone to allow the smartphone to determine the location of the tag, this is merely one example use case. More broadly, a tag's position, location, orientation, or other spatial parameter may be determinable by any device that is configured to communicate with the tag. Example devices include smartphones, tablets, laptop computers, wireless routers, desktop computing devices, home automation systems, or the like. In some cases, an environment, such as a user's home, may include multiple of these devices, and each device may communicate with the tag and determine the tag's location and/or maintain a record of the tag's location (or other spatial parameter such as orientation). Moreover, as described herein, these devices may update a server or other database with the tag's location. This may improve the ability to locate a lost tag, as a user may be able to determine the location of the tag by querying the server or database, even if the user is out of range of the tag. For example, if a user left her keys at home, a desktop computer at the user's home may have been periodically communicating with (or otherwise receiving signals from) a tag attached to the keys and updating a server with the location of the tag. The user can then simply request the current location of the tag from the server, even if she is miles away and unable to directly communicate with the tag with her smartphone. Further example use cases and device details are described herein. Outside of the user's home environment, other devices not associated with the user (e.g., other people's smartphones) may communicate with the tag (or otherwise receive signals from the tag) to securely and anonymously update the server with the location of the tag. For example, outside of the user's home environment there may be hundreds of thousands or even millions of devices that can securely and anonymously report the locations of tags. Any of these numerous devices that are close enough to a tag to receive signals or communicate with the tag (e.g., via Bluetooth) may securely and anonymously update the server with the tag's location. In this way, the multitude of devices that can communicate with or receive signals from a tag form a robust, multi-redundant device-location relay network that can continuously (and privately) monitor and update the locations of many individual tags.

Figure 1:
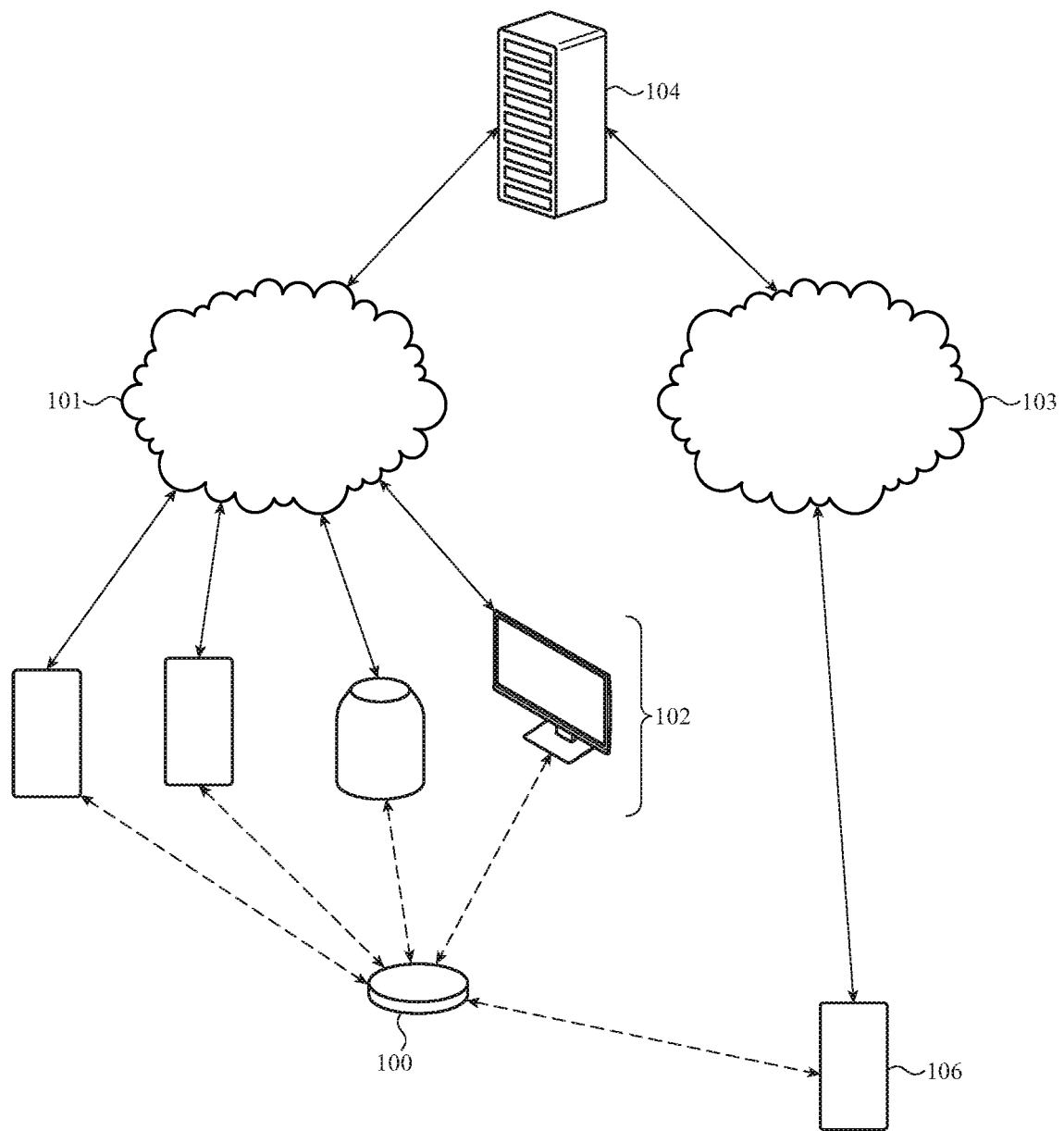
FIG. 1 depicts an example system for locating a wirelessly locatable tag.

FIG. 1 depicts an example system that may be used to physically and/or geographically locate a tag 100. The system may be facilitated in part by a cloud-based service or other host service with which multiple devices communicate to report and receive location information about other devices in the system. The operational links between devices (e.g., wirelessly locatable tags, phones, laptops, tablets, wireless headphones, etc.) and the cloud-based service may allow the system to provide robust localization of devices within the system. For example, devices in the system may be registered with the cloud-based service to allow the devices to communicate with the cloud-based service to both report and receive location data of tags and other devices in the system. Due to the communication and cooperation between and among the various devices in FIG. 1 to determine the location of tags and devices, the system shown in FIG. 1 may define and/or be referred to herein as a device-location relay network.

Because the device-location relay network facilitates determining the locations of a user's devices, maintaining security and privacy of the user's location and other information is of the utmost importance. Accordingly, encryption and anonymization schemes may be used to secure data and prevent access to location data by devices or individuals that are not authorized to do so. In this way, location information may be securely handled by the device-location relay network without exposing location data or other potentially sensitive or private data associated with the various devices in the network. For example, devices, such as smartphones, may execute software that facilitates the sending and receiving of encrypted location reports to and from the cloud-based service, and allows users to see the locations of other devices in the network (if they are authorized to do so). The cloud-based service may also facilitate the passing of encryption keys (e.g., public keys) between various devices to allow users of those devices to securely share their (or their devices') location without the risk of unauthorized users (including the cloud-service itself) having access to location information of a user's device.

Returning to FIG. 1, the tag 100 may be configured to wirelessly communicate with devices 102 (e.g., mobile phones, laptop computers, desktop computers, wireless access points, digital assistants) when the tag is physically proximate to those devices (e.g., within a range of a wireless communication protocol such as ultra-wideband or Bluetooth). The devices 102 may determine the location (and/or other spatial parameter) of the tag 100 and display and/or report the location (and/or other spatial parameter) of the tag to a remote service.

One or more of the devices 102 may be associated with the owner of the tag. For example, one or more of the devices 102 may be the tag owner's phone, digital assistant, laptop or desktop computer, tablet computer, or the like. In such cases, the devices 102 associated with the same user or owner as the tag 100 may directly display the location of the tag 100 to a user. In other cases, such as where the tag 100 (or an object to which the tag is attached) is lost or misplaced outside of the user's home, the devices 102 may be or include other devices that are not owned or controlled by the user. For example, such devices may include any device that receives signals from the tag or establishes some form of wireless communication with the tag, and can also communicate with a server 104 (or any device associated with a network-accessible service) to report an encrypted, anonymized report that includes the location of the tag. Such devices may include phones, tablet computers, watches, or laptop computers of individuals who have no relationship to the tag's owner. As used herein, an "owner" of a tag refers to an individual or entity that controls, manages, supervises, operates, leases, owns, or otherwise exercises authority over a tag, and is not necessarily limited to an individual with legal ownership of the tag.

The tag itself may not be able to communicate directly to the server 104 to report its location, and indeed, it may not even be aware of its location, as it may lack a GPS or other system for independently determining its own absolute location. Devices that communicate with the tag 100, however, may be able to communicate to the server 104 to report the location of the tag 100. For example, devices such as phones, computers, and tablets may communicate with or otherwise detect the presence of a tag, and those devices may report, on an anonymous basis, the tag's location (and optionally an identifier of the tag and any other information, such as the time) to the server 104 (e.g., via a network 101). In addition to devices 102 reporting the locations of tags, the devices 102 themselves may act as tags and report their own locations to the server 104, and may report the locations of other devices 102 to the server 104 as well.

While FIG. 1 shows a few devices 102 and a single tag 100, this figure may represent only a small segment of a significantly larger network of tags and devices. Indeed, due to the ubiquity of mobile phones, tablet computers, and the like, the overall device-location relay network may be a dense, ad hoc or mesh-style network that can be used to track the location of many tags and devices. For example, in an urban environment, there may be hundreds of thousands or even millions of devices that can securely and anonymously report the positions and/or locations of tags. In this way, the devices and tags form a robust, multi-redundant device-location relay network that can continuously (and privately) monitor and update the locations of very many devices.

In some cases, the devices use their own locations as estimated locations of the tag. For example, if the device is able to connect to the tag via Bluetooth, it may be assumed that the tag is within about 30 feet of the device (or another distance, depending on the parameters of the Bluetooth communication). Thus, for example, the device may report the tag's location as an area centered about the user's device and having a radius that corresponds to the estimated range of the wireless communication protocol used to communicate to the tag. In other cases, the device may determine or estimate the location of the tag with greater accuracy. For example, the device may use time of flight (TOF), angle of arrival (AOA), time difference of arrival (TDOA) received signal strength indication (RSSI), triangulation, synthetic aperture, and/or any other suitable technique, to determine a location of the tag relative to the user's device. These localization techniques may use ultra-wideband signals from the tag, which may allow the device to locate the tag with a high degree of accuracy (e.g., to within one foot of the tag's actual location). Techniques for determining the spatial parameters of a tag, such as a distance between a tag and another device, a position of the tag relative to another device, a location of the tag, and an orientation of the tag, are described in greater detail with respect to FIGS. 2D-2E.

Figure 2A:
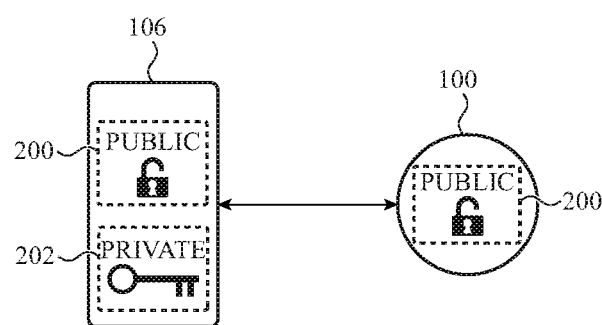
FIGS. 2A-2C depict an example public-private key encryption scheme for locating a wirelessly locatable tag.
Figure 2B:
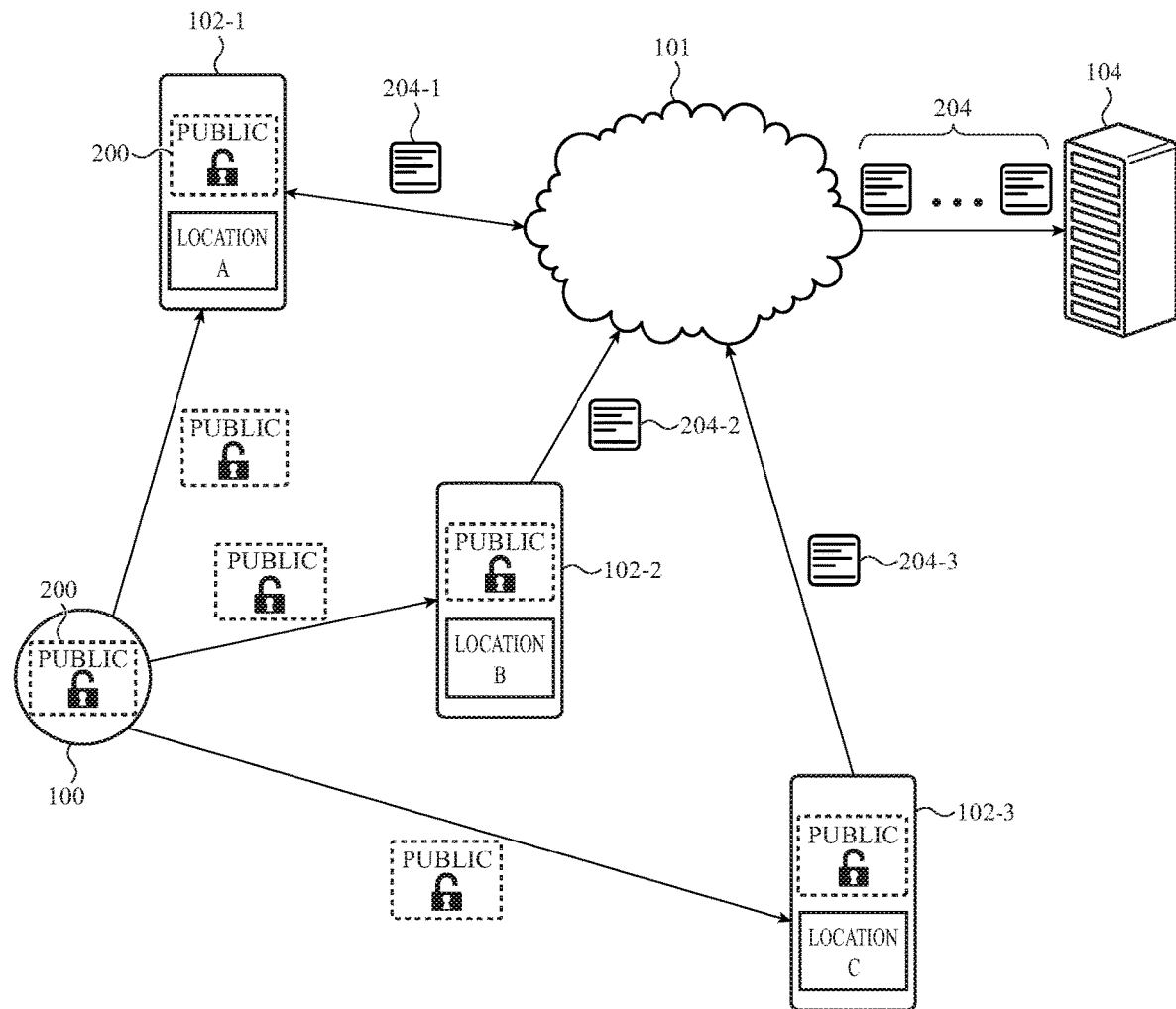

The location reports sent from the devices that detect the presence of a tag may be encrypted using a public-private key encryption scheme (shown, for example, in FIGS. 2A-2C) to ensure that only the owner of a tag can ultimately see the location of the tag. For example, if a tag is lost, devices that happen to be nearby the tag—even if the devices are not associated with the owner of the tag—may detect the tag and receive a public key from the tag (FIG. 2B). A device that detects the tag may query the server 104 to determine if that particular tag has been reported lost. If so (or if the tag and/or device are configured to send encrypted location reports even if the device is not reported as lost), the device may determine a location of the tag, encrypt the location of the tag (and optionally other information) using the public key, and submit the encrypted location report to the server 104 (FIG. 2B). The device may also send information to the tag, such as a message indicating that the tag has been reported as lost. This may cause the tag to change one or more aspects of its operation or to trigger one of multiple operational modes. For example, upon detecting that the tag has been reported lost, the tag may change the frequency that it sends out a beacon (described below), change a message associated with its near-field wireless communications antenna, enter a power-saving mode, or alter some other function or operation of the tag.

Figure 2C:
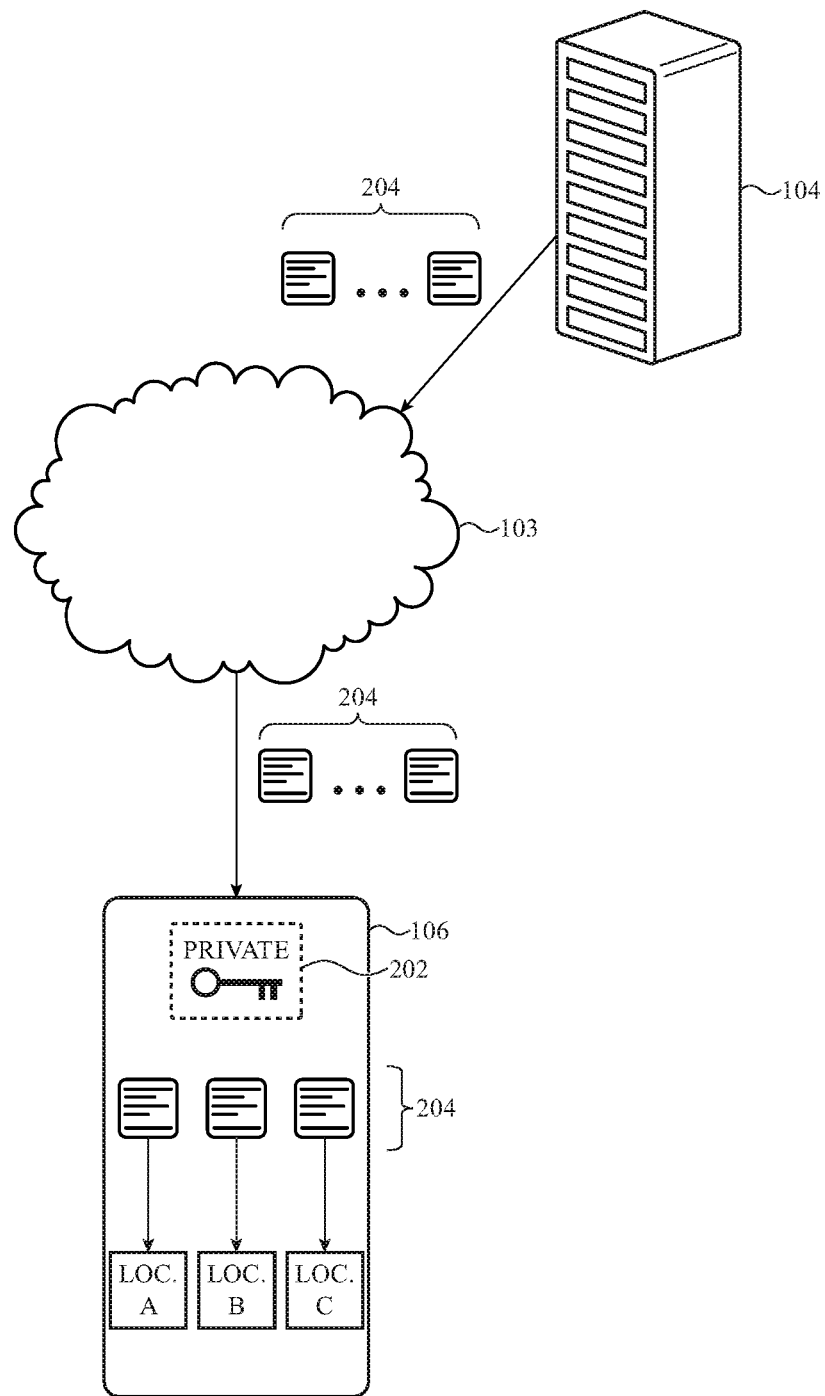

An owner of the lost tag may query the server 104, using the public key, for any location reports encrypted using that public key (e.g., via a network 103, which may be the same network as the network 101 or a different network). If there are location reports associated with the public key, the owner may receive the encrypted location reports and use a private key to decrypt the location reports to determine the location (or estimated location) of the tag (FIG. 2C). The owner may then travel to the location and attempt to locate the tag and any object to which the tag is attached or associated (e.g., a backpack, laptop computer, coat, purse, etc.).

The tag may communicate with nearby devices by sending a periodic wireless beacon signal. The wireless beacon signal, which may be transmitted using a Bluetooth communication protocol, ultra-wideband communication protocol, or any other suitable protocol, may be detectable by any device that is monitoring that protocol (e.g., receiving communications via that protocol). The wireless beacon signal, also referred to herein simply as a "beacon signal" or "beacon," may be transmitted at any suitable frequency, and the particular frequency may depend at least in part on a mode of the tag. For example, when the tag is in an initialization mode or pairing mode, the beacon may be transmitted at a first frequency; when the tag is in a lost mode (e.g., it has been reported to the device-location relay network as being lost, and that status has been provided to the tag), the beacon may be transmitted at a second frequency; and when the tag is in a normal or non-lost mode, the beacon may be transmitted at a third frequency. In some cases, the first frequency is greater than the second frequency, and the second frequency is greater than the third frequency. In other cases, the first and second frequencies are substantially equal, but are greater than the third frequency. As one specific example, the first frequency may be one beacon signal per second (or more frequent), the second frequency may be between one beacon signal per minute and one beacon signal per second, and the third frequency may be one beacon signal per minute (or less frequent). As used herein, a beacon signal may correspond to an advertising packet of a suitable communications protocol, or any other suitable wireless data transmission packet or signal.

The beacon may include the public key of the tag and optionally other information such as a tag identifier, a last reported location, a time since a last direct connection to another device, or the like. In some cases, the beacon and the optional additional information are sent to other devices using separate communications channels, protocols, or the like. For example, a tag may send a beacon signal using an ultra-wideband radio and send other information, such as the public key, via Bluetooth. Of course, other assignments of information types to different communications channels or protocols are also possible.

The wireless beacon signal may be configured to cause a device to send a location report to the remote server. For example, a tag may transmit a wireless beacon signal to an external device, such as a mobile phone, tablet or laptop computer, or the like. The tag may also transmit a public encryption key to the device. The public encryption key may be included in the beacon signal, or provided to the device from the tag via a different message or communication protocol. In response to receiving the beacon signal, the device may determine a location of the wireless module based at least in part the wireless beacon signal (using localization techniques such as those described herein). The device may prepare an encrypted location report using the public encryption key, where the encrypted location report includes the location of the wireless module, and wirelessly transmit the encrypted location report to a remote server (e.g., the server 104). In this way, the tag can cause location reports to be generated on an ongoing basis, such that an accurate, up-to-date location of the tag is available to the tag's owner.

The public-private key encryption scheme may include other techniques to help anonymize the tag and prevent efforts to track individuals or objects. For example, the key pairs may iterate according to an algorithm, such that a tag does not always have the same public key (thus reducing the ability to track a tag by its public key). Alternatively or additionally, the tag may store multiple public keys that can all be decrypted by the same private key, and it can periodically change to a new one of the multiple public keys.

As described above, the tag may also include various systems that allow it to be more easily located once the owner is nearby (e.g., within a wireless communication range that allows the tag and another device to communicate, such as 300 feet, 100 feet, 30 feet). For example, the tag may include a speaker or other audible-output system. The owner of the tag may wirelessly command the tag (e.g., via Bluetooth and/or ultra-wideband protocols) to produce an audible output, which the owner can then use to find the tag. As another example, the tag may include an ultra-wideband (UWB) radio, and an owner's device may also include one or more UWB radios. The owner's device may be able to use a UWB localization signal emitted by the tag to estimate a position and/or location of the tag and/or guide the owner to the tag. For example, a user interface on the owner's device may display an arrow or other indicator that points the user towards the location of the tag. The arrow or other indicator may be a live view that continuously updates based on the position of the tag relative to the device, as well as the orientation of the device relative to the tag. FIGS. 140-141B, below, illustrate example user interfaces that visually direct a user to a tag.

Even if the tag is not lost, the device-location relay network may be used to provide other location services. For example, location reports for a tag may be provided by devices in proximity to the tag even when the tag is not lost. In a user's home, for example, the user's computer, phone, digital assistant, or any other suitable device(s) may periodically provide, to the server 104, location reports of the user's tag(s). Such reports may be used to allow a user to track the locations of his or her objects over time, identify patterns or habits, and the like. Similar location information and/or location reports may also be provided for other devices associated with the user (e.g., the user's laptop computer, phone, etc.). In this way, locations of many of a user's devices may be accessible to the user.

Localization of user's devices, such as phones, laptops, etc., may be achieved in various ways. For example, a tag may simply be attached to such devices, thus leveraging the tag's localization functionality to track the location of the device to which it is attached. Alternatively or additionally, devices may include built-in hardware that provides the same or similar functionality as the tags described herein. Thus, even without an attached external tag, a lost laptop, for example, may use the same or similar systems and leverage the device-location relay network to allow the laptop to be located in the same manner as the tags described herein. Example devices that may include the components and/or provide the functionality of the tags described herein (but without the same physical structure as the tags) include, without limitation, laptop computers, desktop computers, phones (e.g., mobile phones, conventional cordless phones), tablet computers, watches, headphones, wearable electronic devices, computer storage devices (e.g., USB drives, portable hard drives, memory cards, etc.), cameras, remote controls, toys, wireless car keys/key fobs, watches, flashlights, first aid equipment (e.g., automatic electronic defibrillators), cars, motorcycles, smart home devices, head-mounted displays, and computer peripherals (e.g., mice, trackpads, keyboards).

Tags may also be configured to interact with devices, such as mobile phones, to cause those devices to take certain actions. For example, a tag may send an instruction, request, or other suitable communication to a device, and in response to receiving the instruction, request, or communication, the device may take an action such as displaying a message on an associated display, sending an encrypted location report, or the like.

Tags may trigger remote devices to take various types of actions, and various types of conditions or events may cause the actions to be triggered. In some cases, a determination that a tag is within a threshold distance of a device causes the device to take a certain action. For example, a tag and/or device (e.g., a mobile phone) may cooperate to determine a distance between the tag and device, as described herein. If the distance satisfies a threshold (e.g., if the device is within a threshold distance of the tag), the tag may cause the device to take an action. The particular action that is to be taken by the device may be specified by the tag. For example, in response to the determination that the distance threshold is satisfied, the tag may instruct the device to display a graphical object on the device's screen. As another example, in response to the determination that the distance threshold is satisfied, the tag may instruct the device to send or relay a message to another device or system. Specifically, the tag may instruct the device to send a location report to a server (e.g., the server 104), or to cause a message to be sent to the owner of the tag (e.g., a message indicating that the tag has been found and/or providing a location of the tag). The tag may cause devices to take other kinds of actions as well, as described herein.

Instructions sent by a tag to a device may be acted upon by the device, or they may be ignored by the device. For example, a device's owner may opt-in or opt-out of some or all instructions that originate from tags. Other settings, user preferences, or other criteria may also be used to determine whether a device will respond to or take any actions based on instructions received from a tag. In this way, users can select the degree to which their devices respond to instructions from various tags. In some cases, a user may opt out of all tag-related communications.

In cases where the tag triggers a graphical object to be displayed on a device's screen, the tag may send the content of the graphical object to the device via one of the tag's available wireless communications systems. More particularly, the tag may store a message in its onboard memory, and when a condition or event is satisfied (e.g., the tag and device are within a threshold distance), the tag may send the message to the device. Upon receiving the message from the tag, the device may display the message on a screen of the device. As a specific example, for a tag that is associated with an object such as a suitcase, the tag may store a message with the request "You are near my suitcase—please return it to the airport lost-and-found for a reward." The tag may also instruct the device to prompt the device's user to take a photograph of the lost item (or the location where the tag is estimated to be), and request permission from the device's user to send the photograph to the tag's owner (e.g., via the device-location relay network). The tag may also send instructions to the device to cause the device show the location of the item or to display an option to initiate an augmented reality application to assist the user of the device in locating the lost item. As another example, for a tag that is associated with a more static type of object such as a painting in a museum, the tag may store (and send to the device when appropriate) the message "You are near the Mona Lisa—click here for directions to the world's most famous painting." The particular content of the message may be customized by an owner or operator of the tag.

In other cases, the content of messages may be stored on the device, and the tag may send an identifier of the message to be displayed on the device. For example, the device may store a "lost item" message saying "You are near a lost item—please report to the nearest lost and found," and the tag may send an instruction indicating that the device should display the "lost item" message. Devices may store multiple messages, and the instructions from the tag may include a unique identifier of the message to be displayed.

Tags may be configured to trigger actions on remote devices based on various different conditions or events. In the examples above, the tags cause devices to take actions (e.g., display graphical information, send location reports) based on a device being within a certain proximity of the tag. Other example conditions or events include, for example, a device being beyond a certain distance from a tag, a tag being moved from a stationary position, a battery level of the tag, or the like.

Further, the particular actions or events that a tag triggers on other devices, as well as the conditions that cause those actions to be triggered, may depend on a mode of operation or a status of the tag. For example, a tag that is in a "not lost" state or condition may not cause nearby devices to display any information (though they may cause nearby devices to send encrypted location reports). Thus, in response to a determination that the tag is in a first mode (e.g., a "not lost) mode, the tag may not cause an external device to display a message (and may cause it to send encrypted location reports). If that tag is transitioned to a "lost" state or mode, however, the tag may attempt to trigger nearby devices to display a particular message (sent by the tag) to assist in the tag being returned. Thus, in response to a determination that the tag is in a second mode (e.g., a "lost" mode), the tag may cause the external device to display a message and/or perform other possible actions, as described above. Alternatively or additionally, when the tag is in the lost mode it may more frequently instruct remote devices to send location reports.

The tag may also be configured to trigger actions on only a subset of devices in its wireless range. For example, a tag may only trigger actions for devices within a certain distance threshold, which may be smaller than the wireless range of the tag. In this way, the tag may instruct actions only on the select few devices that happen to get close enough to the tag to be helpful. As another example, the tag may be limited to a certain number of actions for a given time window. More specifically, a tag may be limited to causing a "lost" message to appear on one device per minute. As yet another example, the tag may be configured to only trigger events on certain types of devices or devices having certain authority. More specifically, a tag may be configured to trigger "lost" messages to appear only on devices that are verifiably controlled by a trusted source (e.g., police, airport employees, friends or relatives of the tag owner, or the like). In some modes of operation, a tag may be configured to trigger certain actions on all device with which it can communicate (e.g., a broadcast).

The owner or operator of a tag may select exactly what actions a tag should trigger on nearby devices, as well as the particular conditions that will cause the tag to trigger such actions. The owner or operator may also tie certain actions and conditions to particular modes of the tag (e.g., a "lost"

mode, a "not lost" mode, a "lost but do not broadcast location or status" mode, a "low battery" mode). The tag may therefore be highly customizable by the tag's owner, allowing the tag to perform a variety of possible functions and interact with other devices in various user-selectable ways.

Due to the sensitive nature of location information of a user's possessions, the instant system may use sophisticated encryption and privacy schemes to ensure that unauthorized individuals cannot track the location of another person's property. FIGS. 2A-2C depict an example public-private key encryption system that may be used to ensure the privacy of a user's location data in the context of a device-location relay network. As shown in FIG. 2A, the tag 100 and a user's smartphone 106 may execute an initialization process in which a public-private key pair is generated or otherwise accessed or obtained. A public key 200 (represented as a lock) may be shared with the tag 100, and the user's smartphone 106 may store a private key 202.

Turning to FIG. 2B, and as described above, when the tag 100 is deployed to track the location of an object (e.g., a user's keys), the tag 100 may communicate with other devices 102 to allow the other devices 102 to send encrypted location reports to the server 104. More particularly, when the tag 100 and another device 102 are in sufficiently close proximity for wireless communications (e.g., via Bluetooth and/or UWB), the tag 100 may communicate the public key 200 to the nearby device 102. As shown in FIG. 2B, three devices 102-1, 102-2, and 102-3 may be close enough to the tag to communicate with the tag 100 (e.g., because a person carrying them walked or travelled nearby the tag 100). When the device 102-1 communicates with the tag 100, the tag 100 may provide the device 102-1 with the public key 200. The device 102-1 may determine or estimate the location of the tag 100 using the device's own location (e.g., from a GPS onboard the device 102-1) and optionally one or more localization techniques that determine a position of the tag 100 relative to the device 102-1 (e.g., a distance, azimuth, and elevation from the device 102-1 to the tag 100). The device 102-1 then uses the public key 200 to encrypt the location of the tag 100, optionally along with other information (e.g., a tag identifier, a time, etc.), into an encrypted location report 204-1. The encrypted location report 204-1 is then provided to the server 104 via the network 101. The devices 102-2 and 102-3 (as well as additional devices now shown in FIG. 2B) may likewise encrypt location reports 204-2, 204-3, using the public key 200 received from the tag 100, and send them to the server 104. (If the tag 100 is in a location where wireless communication services are unavailable, the device 102 may store the encrypted location reports and upload them to the server 104 once service becomes available.)

Because the location reports 204 are encrypted using the public key 200 of a public-private key pair, only an individual or device who possesses the private key 202 can decrypt the location reports 204, thus helping to maintain the security and privacy of the location of the user's property. Further, the devices 102 may be configured to perform the reporting functions without alerting a user of the devices 102 that it is occurring. Thus, the device 102 of a person walking past a lost object may send a location report for the lost object without its owner ever knowing that a lost object is nearby. Also, while the devices 102 may be described herein as not associated with the owner of the tag 100, the same encryption and location reporting techniques may be used even where some or all of the devices 102 are owned or controlled by the owner of the tag 100. For example, FIG. 2B may represent a user's home environment, and the devices 102 may be devices within the user's home. For example, the device 102-1 may be the user's desktop computer, the device 102-2 may be a home automation system, and the device 102-3 may be a laptop computer. These devices may transmit encrypted location reports 204 to the server 104 so that the user can access the reports to find a lost object in his or her home (or to perform other location-based functions).

FIG. 2C illustrates how an authorized device (e.g., the device 106) may access the location of the tag 100 from the encrypted location reports 204. In particular, the device 106 may, at the command of a user or automatically based on a triggering event or periodic update, query the server 104 for location reports for the tag 100. This query may include sending the public key 200 from the device 106 to the server 104. Notably, the public key 200 may not be capable of decrypting the location reports, but can be used to identify which location reports were encrypted using the public key 200.

In response to a query from the device 106, and optionally after authenticating that the device 106 is authorized to receive the location reports, the server 104 provides the encrypted location reports 204 to the device 106. The device may then use the private key 202 to decrypt the location reports 204 and read the reported locations of the tag 100 (e.g., location A, location B, location C). The device 106 may show the reported locations on a map, and may provide directions to the reported locations from the user's current location. Further, if and when the device 106 is within range of a wireless communication protocol such as UWB, the device 106 may display a direction indicating interface that leads the user directly to the tag 100 (e.g., with a direction indicating arrow overlaid on an image of the real-world environment). An example direction-indicating interface is described herein.

Other techniques may also be used to facilitate a user accessing location reports from the server 104. For example, in some cases, the device 106 may request and/or receive encrypted information from the server 104, which may include the encrypted location reports 204, as well as other encrypted location reports (e.g., of other tags), or other encrypted information. Notably, the user will not be able to decrypt location reports or information that was not originally encrypted using the user's public key, so any encrypted location reports that are not decryptable by the user's private key remain encrypted and may be discarded by the device 106. In cases where the device 106 receives more data than just its location reports 204, the device 106 and/or the server 104 may select the particular information that is sent to the device 106 in various ways. For example, the server 104 may send all of the encrypted location reports that are stored thereon, and any that are not encrypted using the public key 200 may be discarded by the device 106. In other cases, the server 104 selects a subset of its encrypted location reports to send to the device 106. For example, the subset may correspond to location reports that were created in a certain time window (e.g., the server 104 may send all encrypted location reports that were sent within 1 hour of when the tag 100 was last in direct peer-to-peer communications with the device 106), or the subset may correspond to location reports that were created in certain geographic regions associated with location reports (e.g., the server 104 may send all encrypted location reports that were created in a state or city where the tag 100 was last in direct peer-to-peer communications with the device 106). Other criteria or combinations of criteria are also contemplated.

As described herein, localization of a wirelessly locatable tag may include the tag sending a signal to another device (e.g., a smartphone), allowing the other device to determine spatial parameters of the tag. Spatial parameters may include distances, orientations, positions, and/or locations.

As used herein, "distance" may refer to a measurement of how far apart two points (e.g., electronic devices, other objects, reference points, etc.) are from one another, and may refer to the length of the shortest possible path through space between the two points.

As used herein, the term "orientation" may refer to an attitude or angular position of an electronic device (e.g., a tag) relative to another electronic device (e.g., another tag or a smartphone), other point of interest, or reference frame. Orientation may be designated in terms of a rotation about one or more axes required to rotate from a current placement to a reference placement. Example measures of orientation may include Euler angles, Tait-Bryan angles (e.g., yaw, pitch, and roll), orientation vectors, orientation matrices, and the like.

As used herein, "position" or "relative position" of an electronic device may refer to the positional relationship of the electronic device in relation to another device, object, or reference point, and may be expressed as the distance between two objects, in combination with a direction vector indicating a direction from one object to another object.

As used herein, "location" may refer to a geographical point where an electronic device, other object, or point of interest is positioned, such as a point on the Earth's surface or elsewhere, and may be designated in terms of a geographic coordinate system (e.g., latitude and longitude) or in terms of a position relative to another geographical point or point of interest.

Broadly, wireless signals (e.g., radio frequency signals) sent between two or more electronic devices, may be analyzed to determine spatial parameters. As used herein, "spatial parameters" may refer to information about the placement of an electronic device in the space it occupies. Spatial parameters for an electronic device may include, but are not limited to, any combination of a distance between the electronic device and a point of interest (e.g., another device, an object, a reference point, etc.), an orientation of the electronic device, and a location of the electronic device. As used herein, "localization" may refer to determining one or more spatial parameters of an electronic device.

The wireless signals used to determine spatial parameters of electronic devices may include ultra-wideband (UWB) signals. As used herein "UWB signals" may refer to signals transmitted over a large portion of the radio spectrum (e.g., having a bandwidth greater than 500 MHz or greater than 20% of a center carrier frequency). Using UWB signals to perform localization may be referred to herein as "UWB localization."

Electronic devices, such as the wirelessly locatable tags described herein (or other devices that incorporate the functionality of the tags described herein), may be configured as transmitting devices configured to transmit UWB signals, receiving devices configured to detect UWB signals, or both. Each device may include one or more antennas for transmitting and/or detecting UWB signals. A UWB signal transmitted by a transmitting device propagates in all directions or in one or more directions from a transmitting device, and the transmitted signal may be detected by one or more receiving devices. UWB signals used to determine spatial parameters of electronic devices may be sent as pulses. As used herein, a "pulse," may refer to a rapid, transient change in the amplitude of a signal from a baseline value to a higher or lower value, followed by a rapid return to the baseline value.

Figure 2D:
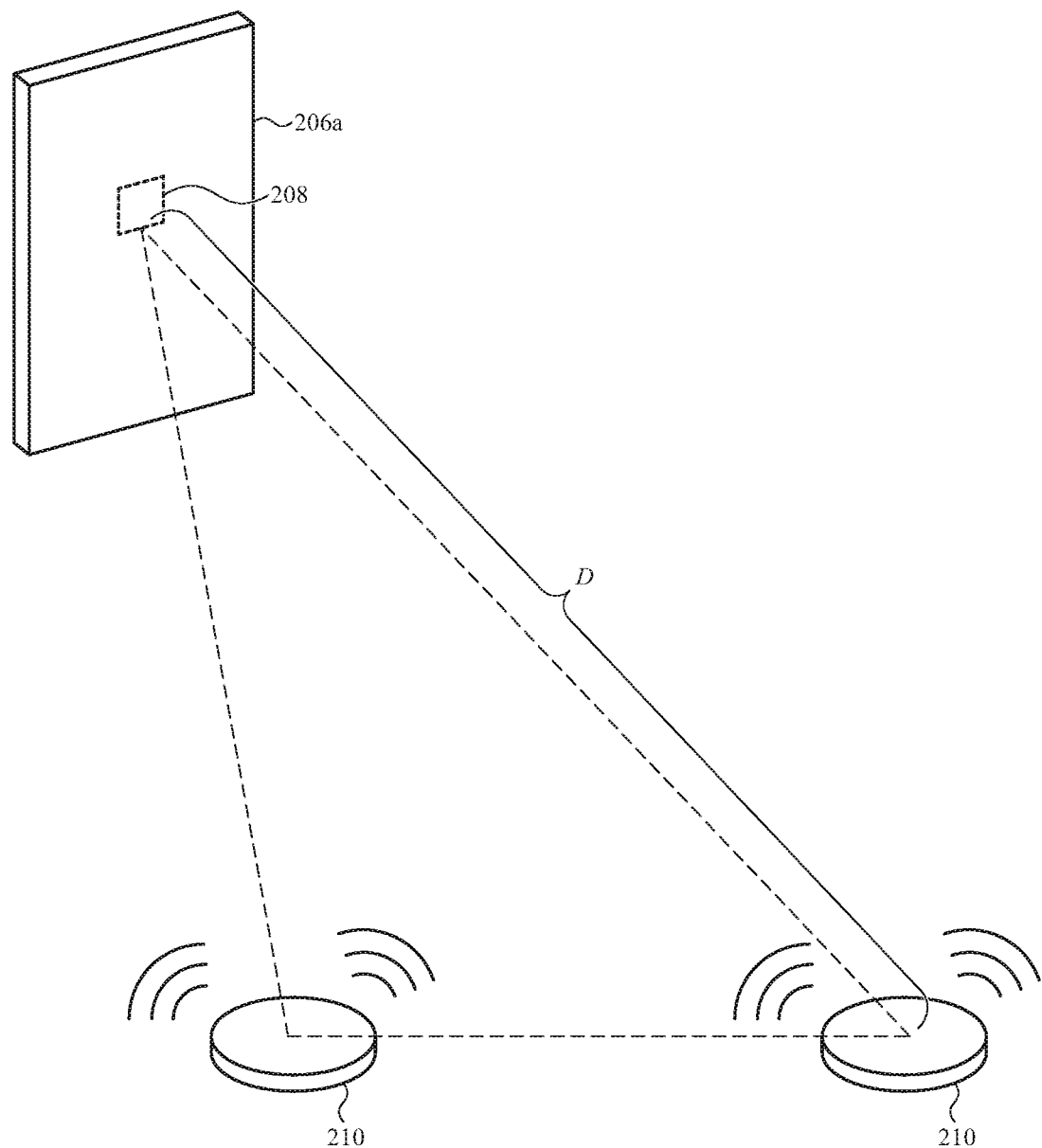
FIGS. 2D-2F depict example localization processes for a wirelessly locatable tag.

Turning to FIG. 2D, as noted above, UWB signals (which may also be referred to herein as beacon signals) may be used to determine a distance D between two electronic devices. In particular, UWB signals may be used to determine a distance between a receiving device (e.g., a smartphone) and a transmitting device 210 (e.g., a tag 100 as described herein). As noted above, a distance between a receiving device and a transmitting device may refer to a measurement of how far apart the receiving device and the transmitting device are from one another, and may refer to the length of the shortest possible path through space between the receiving device and the transmitting device.

The receiving device 206a (or a device operably coupled to a receiving device) may analyze a UWB signal pulse detected by an antenna 208 of the receiving device 206a to determine the distance D between the receiving device 206a and a transmitting device 210 that transmitted the UWB signal pulse. In particular, the receiving device 206a may determine a time of flight (TOF) of the UWB signal pulse and multiply the TOF by the propagation speed of the signal pulse (e.g., the speed of light) to determine or estimate the distance D between the transmitting device 210 and the receiving device 206a. As used herein, a UWB signal pulse may be a beacon signal or a portion of a beacon signal.

The TOF may be determined by calculating the difference between the transmission time (i.e., the time the signal was transmitted) and the time the signal was detected (also called the time of arrival (TOA)). The transmission time may be included in the detected UWB signal pulse, sent as part of a separate transmission, or known as a result of a previously performed synchronization process between the transmitting device 210 and the receiving device 206a.

Using UWB signals for determining distance may provide numerous advantages, including increased precision in determining TOA and/or TOF. As one example, UWB signals may have shorter wavelengths than other signals, which may reduce the time range in which the signals can be detected. This reduces errors in determining TOA and TOF, which results in more accurate distance estimation.

A single signal may be detected by multiple receiving devices and/or multiple antennas of a single receiving device (e.g., a smartphone), and the signal may be used as described above to determine distances between the transmitting device 210 and each receiving device or antennas. Additionally, multiple signals from different transmitting devices (e.g., tags) may be detected by a single receiving device, and the signals may be used as described above to determine distances between the receiving device and each transmitting device.

Figure 2E:
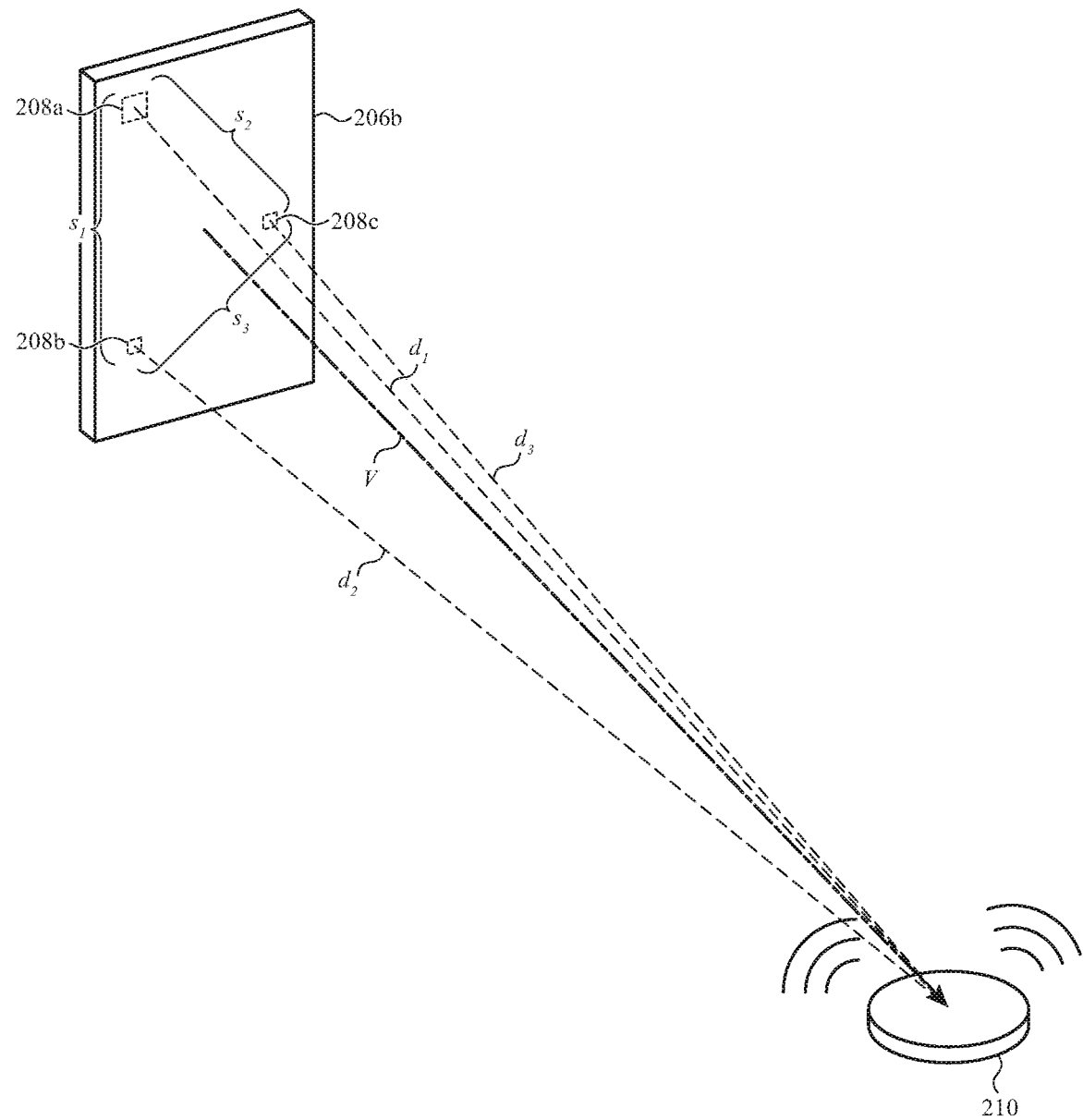

As noted above, UWB signals may be used to determine an orientation of an electronic device relative to a point of interest (e.g., an electronic device, an object, a reference point, etc.). Turning to FIG. 2E, UWB signals may be used to determine an orientation of a receiving device 206b (e.g., a smartphone) relative to a transmitting device 210 (e.g., tags 100). As used herein, the term "orientation" may refer to an attitude or angular position of an electronic device relative to another electronic device, other point of interest, or reference frame. Orientation may be designated in terms of a rotation about one or more axes required to rotate from a current placement to a reference placement. Example measures of orientation may include Euler angles, Tait-Bryan angles (e.g., yaw, pitch, and roll), orientation vectors, orientation matrices, and the like. The orientation of an electronic device relative to a point of interest may also be thought of as a direction to the point of interest with respect to the electronic device.

The receiving device 206b (or a device operably coupled to a receiving device) may analyze a UWB signal pulse detected by multiple antennas of the receiving device 206b to determine an orientation of the receiving device 206b relative to a transmitting device 210 (e.g., a tag 100) that transmitted the UWB signal pulse. As noted above, receiving devices may include multiple antennas. As one example, as shown in FIG. 2E, the receiving device 206b may include three or more antennas e.g., antennas 208a, 208b, 208c positioned on or within the receiving device 206b. The receiving device 206b may determine distances d1, d2, d3 between each antenna and a transmitting device 210 as set forth above. Differences between the distances d1, d2, d3 may indicate the orientation of the receiving device 206b relative to a transmitting device. Using the determined distances d1, d2, d3 and known separation distances s1, s2, s3 between the antennas, a vector V extending from the receiving device 206b to the transmitting device 210 may be determined. The vector V may be expressed in terms of a distance between the receiving device 206 and the transmitting device 210 and a direction of the vector V relative to a reference vector of the receiving device 206b (e.g., a vector normal to a plane shared by the three antennas or any other vector that is fixed with respect to the three antennas). The direction of the vector V may describe the orientation of the receiving device 206a relative to the transmitting device 210.

In some cases, the orientation of the receiving device 206b relative to the transmitting device 210 (or vice versa) may be determined independently of determining the distances d1, d2, d3. The receiving device 206b may determine a direction from the receiving device 206b to the transmitting device 210 (or from the transmitting device 210 to the receiving device 206b) by determining a time difference of arrival (TDOA) of the same UWB signal pulse to the three separate antennas 208a, 208b, 208c of the receiving device 206b. The TDOA for a UWB signal pulse may be determined as the pairwise time difference between the time of arrival of the signal at a first antenna (e.g., antenna 208a) and the time of arrival of the signal at a second antenna (e.g., antenna 208b). One or more pairwise time differences may be determined, and may be used to determine a direction from the receiving device 206b to the transmitting device 210, which, as noted above, may describe the orientation of the receiving device 206b relative to the transmitting device 210. Other methods for determining direction and orientation may also be used, including triangulation, phase difference of arrival (PDOA), and hybrid TDOA/PDOA methods.

The distance between the receiving device 206b and the transmitting device 210 and the relative orientation of the receiving device 206b may define a position of the receiving 206b device relative to the transmitting device 210. As used herein, "position" or "relative position" of an electronic device may refer to the positional relationship of the electronic device in relation to another device, object, or reference point, and may be expressed as the distance between two objects, in combination with a direction vector indicating a direction from one object to another object (e.g., a distance between a receiving device 206b and a transmitting device 210 and a direction vector indicating the direction from the receiving device 206b to the transmitting device 210). For example, the vector V of FIG. 2E may represent a relative position of the transmitting device 210 and the receiving device 206b.

In various embodiments, information about electronic device(s) (e.g., the spatial parameters discussed above) determined using UWB localization may be combined with other information from a variety of sources to determine spatial parameters. An electronic device may include and/or be operably coupled to one or more sensors or devices for determining spatial parameters or data that may be used to determine spatial parameters. Examples of sensors and devices include magnetometers, gyroscopes, accelerometers, optical sensors, cameras, global positioning system (GPS) receivers, and the like.

As one example, an electronic device (e.g., a smartphone) may include or be operably coupled to a GPS receiver configured to determine a location of the electronic device. As noted above, as used herein, "location" may refer to a geographical point where an electronic device is positioned, such as a point on the Earth's surface or elsewhere, and may be designated in terms of a geographic coordinate system (e.g., latitude and longitude) or in terms of a position relative to another geographical point or point of interest. The position of a transmitting device (e.g., tag) relative to a receiving device may be determined using UWB localization as discussed above. A location of the transmitting device may be determined using a location of the receiving device determined using GPS and the position of the transmitting device relative to the receiving device determined using UWB localization.

As another example, an electronic device may include or be operably coupled to a magnetometer or an accelerometer that may be used to determine an orientation of the electronic device relative to the earth. For example, a magnetometer may be used to determine an orientation of the electronic device relative to magnetic north or another known source of magnetic flux. Similarly, an accelerometer may be used to determine an orientation of the electronic device relative to the direction of gravitational acceleration (e.g., inward with respect to the earth's surface). A direction from the receiving device to the transmitting device relative to the receiving device may be determined using UWB localization as discussed above. The direction from the receiving device to the transmitting device relative to the earth or another known point of interest may be determined by combining the orientation of the electronic device relative to earth determined using a magnetometer or accelerometer with the direction from the receiving device to the transmitting device relative to the receiving device determined using UWB localization.

In some cases, the same antenna(s) are used for transmitting and detecting UWB signals. In some cases, the antenna(s) used for transmitting UWB signals are different from the antenna(s) used for detecting UWB signals. The antenna(s) may be operably coupled to one or more transmitters, receivers, processing units, or the like that may be used to generate transmitted signals and/or process detected signals.

Figure 2F:
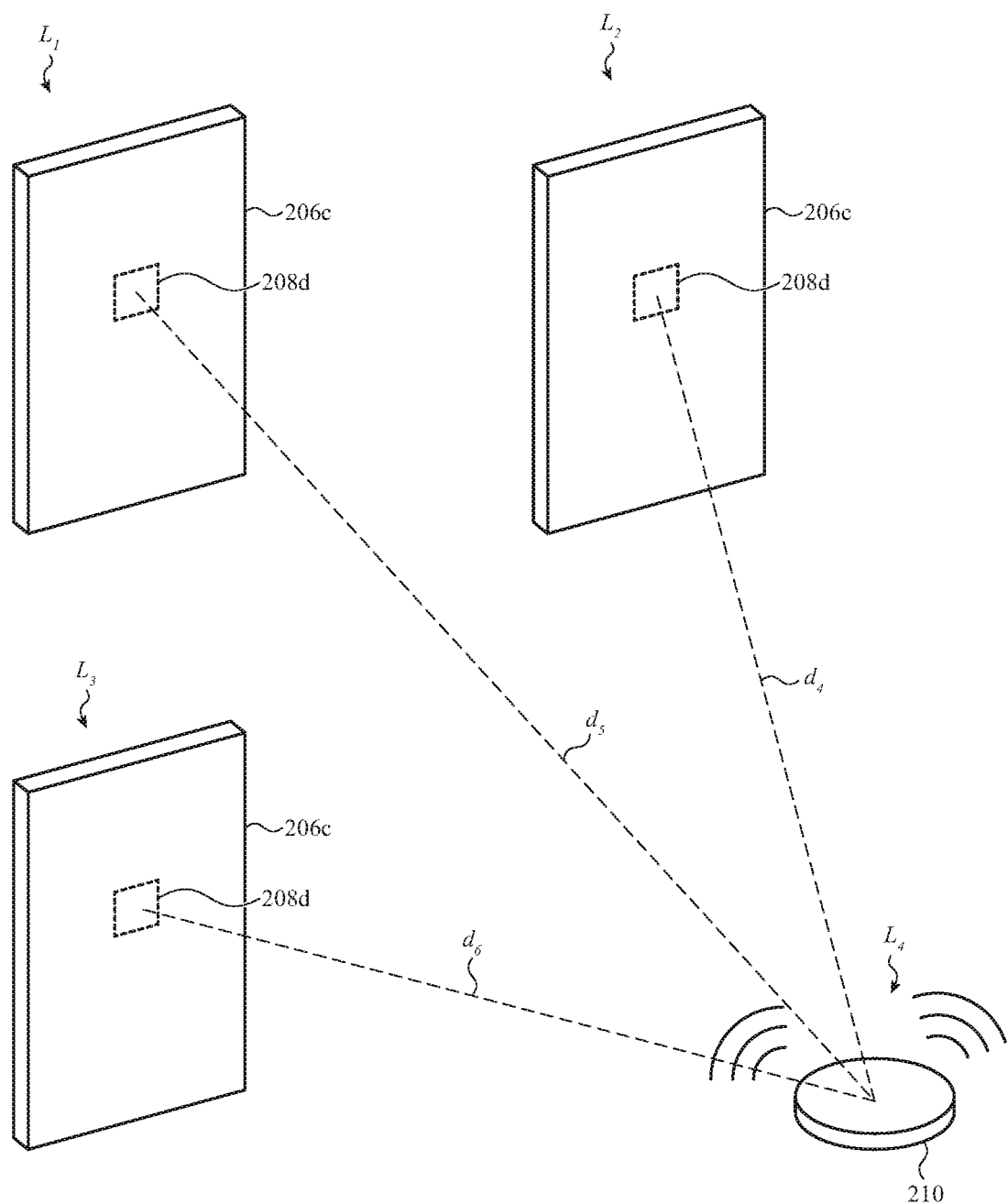

A location of the transmitting device 210 may also be determined by a receiving device 206c by determining the distance between the receiving device 206c and the transmitting device 210 when the receiving device 206c is at multiple different locations. This process triangulates the location of the transmitting device 210 without using multiple onboard antennas and TDOA analysis of a pulse from the transmitting device 210. FIG. 2F illustrates how the location of the transmitting device 210 is determined using this technique (which may be referred to as synthetic aperture).

As described above, the transmitting device 210 may emit a pulse (e.g., a UWB signal pulse) that is detectable by an antenna 208d, and the receiving device 206c may analyze the pulse (e.g., using TOF) to determine the distance from the receiving device 206c to the transmitting device 210. As shown in FIG. 2F, in order to determine the location of the transmitting device, the receiving device 206c may determine multiple distances (e.g., distances d4, d5, and d6) to the transmitting device 210 when the receiving device 206c is at multiple locations (e.g., L1, L2, and L3). Because the location of the receiving device 206c at locations L1, L2, and L3 is known (as determined by an onboard GPS, accelerometer(s), and/or other positioning systems) and the distances between the receiving device 206c and the transmitting device 210 are also known, the receiving device 206c can determine, using triangulation, the location L4 of the transmitting device 210. Further, using an onboard magnetometer, accelerometer, and/or other systems, the receiving device 206c can determine its orientation relative to the determined location of the transmitting device 210. The orientation of the receiving device 206c relative to the transmitting device 210 together with the location of the transmitting device 210 provides a full complement of spatial parameters of the transmitting device 210 to facilitate the functionalities described herein.

With reference to the process described in FIG. 2F, the transmitting device's location may be determined once the receiving device 206c determines at least three distance measurements between the receiving device 206c and the transmitting device 210. In some cases, once the location of the transmitting device 210 is established using at least three distance measurements, the receiving device 206c may perform more distance measurements at additional locations of the receiving device 206c. These subsequent measurements may be used to refine and/or update the determined location of the transmitting device 210, or otherwise to improve the accuracy of the location determination.

As noted above, a wirelessly locatable tag may take the form of a small device that can be easily attached to objects such as keys, backpacks, purses, and the like. Broadly, the tag may have a small size (e.g., having a diameter less than about 3 inches, less than about 2 inches, less than about 1 inch) that is rugged, water resistant (e.g., IP66, IP67, or IP68, according to international ingress protection standards), and portable. The tag may also have acoustic and haptic output systems, and optionally an input system (e.g., a button-like input). The tag may also include a battery that can be easily and conveniently replaced, and may be sealed against water, dust, and other contaminants.

Figure 3A:
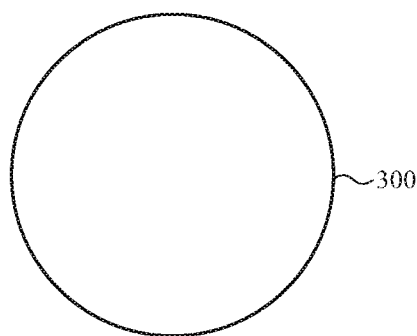
FIG. 3A depicts a top view of an example wirelessly locatable tag.
Figure 3B:
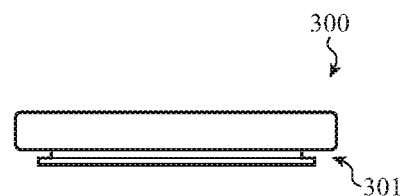
FIG. 3B depicts a side view of the example wirelessly locatable tag of FIG. 3A.
Figure 3C:
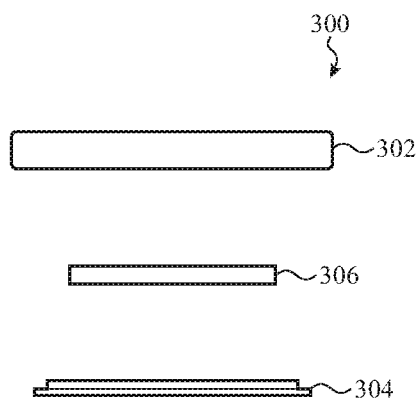
FIG. 3C depicts an exploded view of the example wirelessly locatable tag of FIG. 3A.

FIGS. 3A-3C depict an example wirelessly locatable tag 300 in accordance with the ideas described herein. The tag 300 may be an embodiment of the tag 100, and may include any or all of the components and may provide any or all of the functionality of the tag 100 (or any other wirelessly locatable tag or device described herein). For brevity such details may not be repeated here.

FIG. 3A depicts a top view of the tag 300, FIG. 3B depicts a side view of the tag 300 of FIG. 3A, and FIG. 3C depicts a side exploded view of the tag 300. As shown in FIG. 3C, the tag 300 may include main body portion 302, a removable bottom housing member 304, and a removable and/or replaceable battery 306. The bottom housing member 304, which may also be referred to as a battery door or battery cover, may be removed by pressing on the bottom housing member 304 and twisting it relative to the main body portion 302, thereby disengaging one or more latches, clips, arms, or other mechanisms that hold the bottom housing member 304 to the main body portion 302. Various configurations of housing members and engagement mechanisms may be used to allow access to a battery cavity of the tag 300 so that a battery can be removed and replaced, while also ensuring that the battery cavity remains safely secured and sealed against ingress of debris, water, or other contaminants. Additional example configurations for securing housing members are described herein. Together, the top and bottom housing members may define (or at least partially define) a housing of a tag (which may also be referred to as an enclosure).

The tag 300 may also define a housing gap 301 that facilitates attaching and retaining the tag 300 directly to other objects, such as backpacks, wallets, and purses, and/or to dedicated accessories that are adapted to receive the tag 300. The housing gap 301 may be a gap or channel defined between the main body portion 302 and the bottom housing member (battery door) 304. The housing gap 301 may extend around a complete circumference of the tag 300, or it may extend only partially around the tag 300. Where a tag has a shape other than a circular shape, such as a square shape, those tags may have a housing gap similar in appearance and/or function to the housing gap 301 to facilitate attachment to accessories. Housing gaps may also be formed between housing members other than the main body portion and bottom housing member, as described herein. In some cases, a housing gap may be defined by a single housing member (e.g., a groove or recess formed into a main body portion). Accessories for attaching to a tag, and for attaching the tag to other objects, may include, for example, straps, key fobs, lanyards, belts, luggage tags, and the like. Some example accessories are described herein with respect to FIGS. 69A-128.

Figure 4:
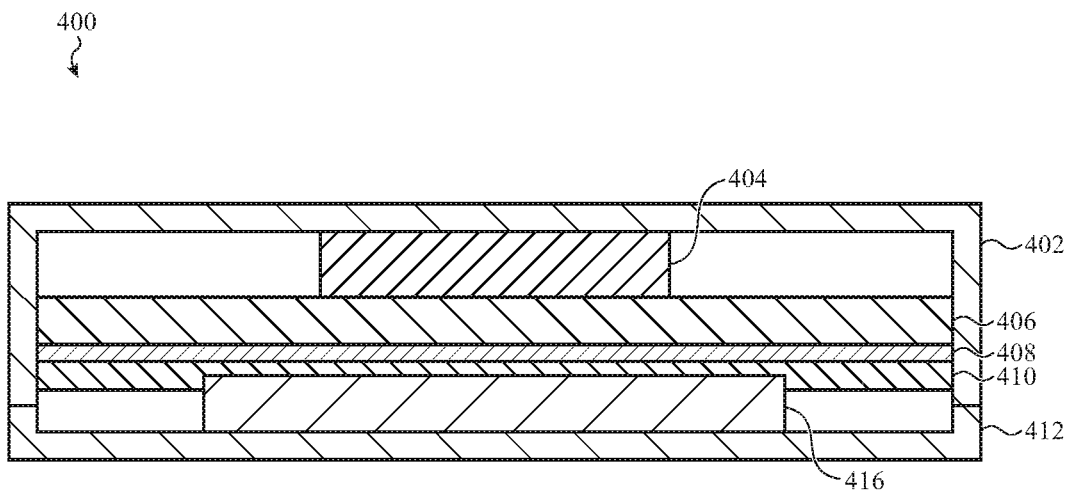
FIG. 4 depicts a cross-sectional view of an example wirelessly locatable tag.

FIG. 4 depicts a cross-sectional view of an example wirelessly locatable tag 400. The tag 400 may be an embodiment of the tag 100 or the tag 300, and may include any or all of the components and may provide any or all of the functionality of the tag 100 (or any other wirelessly locatable tag or device described herein). An example of the various hardware elements that may be included in the tag 400 is described below with respect to FIG. 144. For brevity such details may not be repeated here.

The tag 400 includes a top housing member 402, an audio system 404, an antenna assembly 406, a circuit board 408, a frame member 410, a battery 416, and a bottom housing member 412 (which may also be referred to as a battery door). The top housing member 402, audio system 404, antenna assembly 406, circuit board 408, and frame member 410 may all be part of or define a main body portion, such as the main body portion 302 (FIGS. 3A-3C).

The top housing member 402 may define a top exterior surface of the tag 400 and an interior surface opposite the top exterior surface. The top housing member 402 may also define some or all of a side exterior surface of the tag 400, where the side exterior surface extends around a periphery of the top exterior surface (as shown in greater detail with respect to FIGS. 3A-3B). The bottom housing member 412, which may also operate as and be referred to as a battery door, may define a bottom exterior surface of the tag 400. As shown, the bottom housing member 412 also defines part of the exterior side surface. The top and bottom housing members 402, 412 may engage one another to define substantially the entire exterior surface of the tag 400, and may define a substantially waterproof seal between the top and bottom housing members 402, 412. The top and bottom housing members 402, 412 may also define an interior volume of the tag 400.

The audio system 404 may be configured to produce audio outputs that can be used to help a user locate the tag 400. For example, when a user is attempting to locate a lost tag 400 (and thus locate any object attached to or associated with the lost tag), the user may use a smartphone to wirelessly command the tag 400 to produce an audible sound such as a beeping or other audible tone (e.g., constant tone, song, etc.). The user can then attempt to find the tag 400 by listening for the audible sound. The audio system 404 may be any suitable component or system for producing sound, such as a voice coil speaker, a piezoelectric speaker, or the like. Example audio systems are described herein.

In some cases, the audio system 404 produces audio outputs by moving a portion of the top housing member 402 like a diaphragm or cone of a speaker. For example, the audio system 404 or a portion thereof may be attached to the inside surface of the top housing member 402 to directly apply forces on the top housing member 402 that cause the top housing member 402 to flex, deform, or otherwise move to produce audio output. To facilitate movement of the top housing member 402, the top housing member 402 may have a movable area or portion that is not fixed to other components of the tag 400 or is not otherwise immobilized. The movable area may be configured to allow or facilitate audio output in the range of about 100 Hz to about 10000 Hz. The audio system 404 may also be configured to produce haptic or tactile outputs by moving the movable area of the top housing member 402. More particularly, because the audio system 404 can move the top housing member 402 to produce audio, the audio system 404 may be operated to produce a haptic or tactile output that a user can feel with his or her hand or other body part. In some cases, haptic or tactile responses may be different from audible outputs, though haptic outputs may also be audible, and audible outputs may be accompanied by tactilely detectable vibrations.

The antenna assembly 406 of the tag 400 may have one or more antennas attached to or otherwise integrated with an antenna frame of the antenna assembly 406. For example, the antenna assembly 406 may include separate (and/or shared) antennas for near-field wireless communications protocols (e.g., ISO/IEC 14443, ISO/IEC 18092, ISO/IEC 21481), UWB protocols, Bluetooth (e.g., IEEE 802.15), WiFi (e.g., IEEE 802.11), cellular protocols, or the like. In some cases, some or all of the antennas are integral to the antenna frame of the antenna assembly 406 (e.g., a single, monolithic antenna frame component). For example, antennas may be insert molded with the material of the antenna frame of the antenna assembly 406 such that the antennas are at least partially embedded in the material of the antenna frame. In other cases, antenna material (e.g., metal) may be formed and/or applied using laser direct structuring, whereby a laser beam is directed onto the material of the antenna frame to form a region that is then metallized using a plating (e.g., electroplating) or other deposition operation. Other techniques for attaching or forming antennas onto the antenna assembly 406 may also be used. The antenna frame of the antenna assembly 406 may be formed of or include a glass-fiber reinforced polymer or any other suitable material.

The circuit board 408 may include a substrate and may include processors, memory, and other circuit elements that generally perform the electrical and/or computational functions of the tag 400. The circuit board 408 may also include conductors and/or electrical interconnects that electrically couple the various electrical components of the tag 400. The circuit board 408 may also include or be coupled to a battery connector that contacts a battery or other power source for the tag 400. The circuit board 408 may be attached to the antenna assembly 406 and/or the frame member 410 of the tag 400.

The frame member 410 may act as a support structure to which other components of the tag 400 are attached. For example, the top housing member 402, the antenna assembly 406, the audio system 404, the circuit board 408, and the bottom housing member 412 may all be secured to the frame member 410. Accordingly, loads imparted to the device via these components may be fully or partially transferred to the frame member 410. The frame member 410 may also define a battery recess that is configured to receive, support, and align the battery 416 inside the housing of the tag 400. The frame member 410 may be formed of or include a tough, rigid material such as a polymer, fiber-reinforced polymer, metal, ceramic, or the like.

The particular configurations, positions, shapes, and integration details of the components in FIG. 4 represent one example embodiment of a tag. It will be understood that other embodiments of tags may have configurations, positions, shapes, and integration details that differ from what is shown in FIG. 4 while still providing the same or similar functions as the tag 400.

Figure 5A:
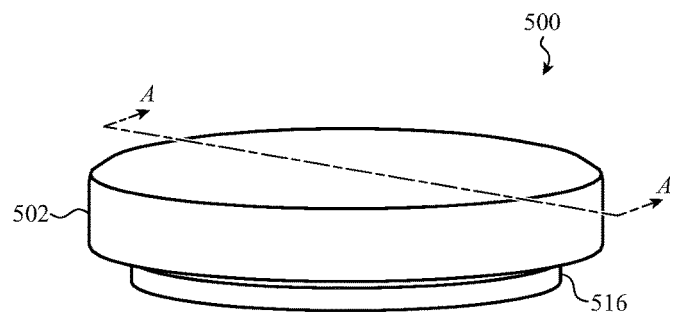
FIG. 5A depicts an example wirelessly locatable tag.
Figure 5B:
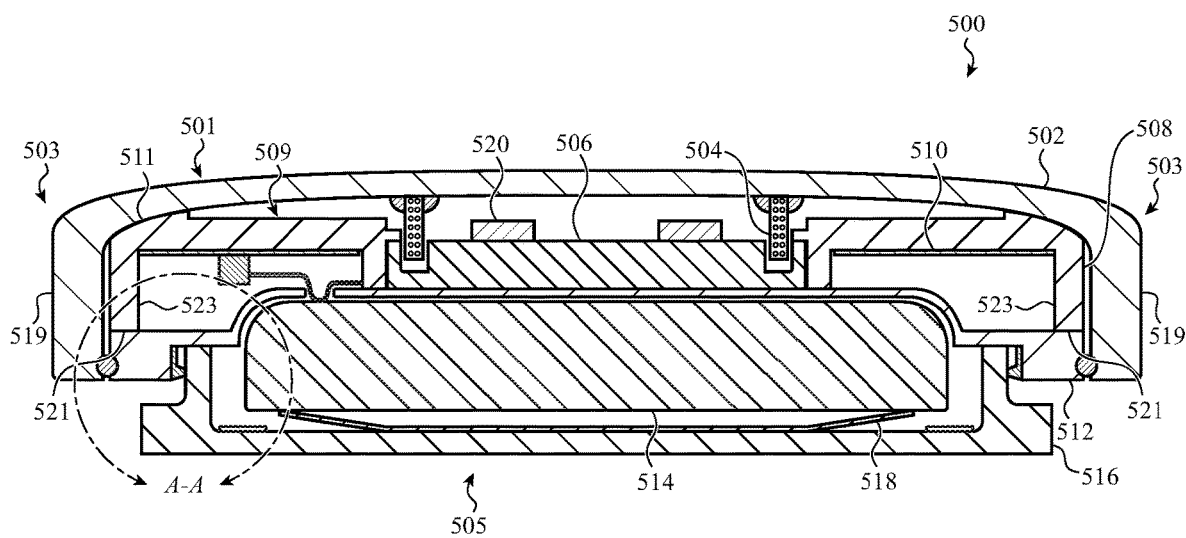
FIG. 5B depicts a cross-sectional view of the wirelessly locatable tag of FIG. 5A.

FIG. 5A depicts an example wirelessly locatable tag 500, and FIG. 5B depicts a cross-sectional view of the tag 500 as viewed along line A-A in FIG. 5A. The tag 500 may be an embodiment of the tag 100, and may include any or all of the components and may provide any or all of the functionality of the tag 100 (or any other wirelessly locatable tag or device described herein). An example of the various hardware elements that may be included in the tag 500 is described below with respect to FIG. 144. For brevity such details may not be repeated here.

As shown in FIG. 5B, the tag 500 includes a top housing member 502 (also referred to herein as an upper housing member) and a bottom housing member 516 (also referred to herein as a lower housing member), which together may form at least part of an enclosure of the tag. The top and bottom housing members 502, 516 may enclose or house components of the tag 500, as described herein.

The top housing member 502 may define a top exterior surface 501 of the tag 500. The top exterior surface 501 of the tag 500 may be an unbroken, seamless surface. For example, the entire top exterior surface 501 of the tag 500 may be defined by a single, unitary piece of material (uninterrupted by displays, buttons, openings, additional housing components, or the like). Accordingly, the top housing member 502 may define an entirety of the top exterior surface of the tag 500, and may be defined by a unitary structure (e.g., a unitary or single-piece polymer structure). The top housing member 502 may also define a peripheral side wall 519 defining a peripheral side surface of the tag 500.

Further, as described herein, a portion of the top housing member 502 that defines the top exterior surface 501 may act as a diaphragm of an audio system that produces audible and/or haptic outputs. For example, an audio system may move a portion of the top housing member 502 so that the moved portion of the top housing member 502 produces the pressure waves that correspond to the audible output. As noted above, the motion of the top housing member 502 may also be used to produce haptic outputs.

In some cases, substantially the entire exterior of the tag 500 may be defined by two components, the top housing member 502 and the bottom housing member 516. In such cases, the tag 500 may lack features such as displays (and associated housing components such as transparent covers), speaker/microphone openings, buttons, lenses, light sources, and the like. While some tag embodiments may include such components, embodiments that lack them may have better environmental sealing and energy efficiency, may be cheaper to manufacture, and may be simpler to use as compared to devices that include such features or components.

The top exterior surface 501 may also define some or all of a side exterior surface 503 that extends around a periphery of the top exterior surface 501. The side exterior surface 503 may have any suitable shape or profile, such as a continuously curved profile (in cross-section), or a curved portion. FIGS. 5A-5B illustrate an embodiment in which at least a portion of the top exterior surface 501 is curved (e.g., the portion that is proximate an edge where the top exterior surface 501 meets the side exterior surface 503). FIGS. 5A-5B illustrate an embodiment in which the side exterior surface 503 has a cross-sectional shape with a flat side. The bottom housing member 516 may define a bottom exterior surface 505 of the tag 500. The bottom housing member 516 may be removable from the remainder of the tag 500 to facilitate removal and replacement of a battery 514. The bottom housing member 516 may also be referred to as a battery door. The battery 514 may be any suitable type of battery, such as a button cell battery.

The tag 500 may also include an antenna assembly 508. The antenna assembly 508 may have one or more antennas attached to or otherwise integrated therewith. For example, the antenna assembly 508 may include separate (and/or shared) antennas for near-field wireless communications protocols, UWB protocols, Bluetooth, WiFi, cellular protocols, or the like. In some cases, some or all of the antennas are integral to the antenna frame of the antenna assembly. Additional details of antenna assemblies and associated antennas are described herein.

The antenna assembly 508 may act as a structural support for at least a portion of the top housing member 502. For example, a support portion 511 of the antenna assembly 508 (which may be considered a portion or surface of a peripheral support flange 523) may contact a portion of an interior surface of the top housing member 502. In some cases, the support portion 511 of the antenna assembly 508 may be attached to the bottom or inner surface of the top housing member 502 using adhesive, fasteners, mechanical features, or any other suitable mechanism. In other cases, the support portion 511 contacts but is not bonded to the top housing member 502. The support portion 511 may extend completely around the antenna assembly 508, defining a continuous, ring-shaped support portion 511 that defines an upper-most (e.g., top) surface of the antenna assembly 508. In other implementations the support portion 511 may include multiple non-continuous segments that extend from the antenna assembly 508 to contact the top housing member 502.

At least a portion of the top housing member 502 may be set apart from the antenna assembly 508 by a gap, such as the gap 509. The gap 509 may be defined in part by the support portion 511. More specifically, the gap 509 may be defined at least in part by a portion of the antenna assembly 508 that is recessed relative to the top surface of the support portion 511.

The gap 509 may allow the portion of the top housing member 502 to be moved to produce haptic and audio outputs without the antenna assembly 508 interfering with the audible or haptic output. In some cases, the size of the gap is greater than a maximum target deflection of the top housing member 502 during audible and/or haptic outputs. Thus, for example, if the tag 500 is configured to produce audio and/or haptic outputs having a certain characteristic (e.g., a maximum or target amplitude, volume, frequency, or other property), the size of the gap 509 may be selected to be greater than the deflection of the top housing member 502 that results from those audible and/or haptic outputs. In some cases, the maximum size of the gap 509 (e.g., the distance between the topmost surface of the antenna assembly 508 and the bottom surface of the top housing member 502) may be less than or equal to about 500 microns, 400 microns, 300 microns, 200 microns, 100 microns, 50 microns.

The antenna assembly 508 may also act as a structural support for the tag 500 and the components within the tag 500. More particularly, the antenna assembly 508 may be formed of materials, have a particular shape, and interact with other structural components to define a main load-bearing structure of the tag 500. For example, the tag 500 may include components that may be sensitive to loads, deflection, movement, shock, or the like. Such components may include a circuit board 510, solder joints between the circuit board 510 and other components (e.g., antennas, battery contacts, speakers and/or audio systems, sensors, haptic actuators, or the like). Such components may be relatively delicate, and may not be structurally capable of withstanding direct applications of forces from normal use of the tag 500 (including, for example, drops, impacts, or the like that may occur during normal use). In order to protect these components, they may be coupled to and/or protected by the antenna assembly 508, alone or in conjunction with other components of the device.

For example, as shown in FIG. 5B, the circuit board 510 may be mounted to or otherwise in contact with the antenna assembly 508, and may be mounted such that it does not contact either the top or bottom housing members 502, 516, thereby isolating the circuit board 510 from direct force application via the top or bottom housing members 502, 516 (e.g., from the tag 500 being dropped, squeezed, impacted, or the like). The circuit board 510 may be mounted to the antenna assembly 508 using an adhesive (e.g., temperature sensitive adhesive, heat sensitive adhesive), fasteners, clips, heat stakes, rivets, or any other suitable mechanism or technique.

The antenna assembly 508 (e.g., a peripheral support flange 523 of the antenna assembly 508) contacts a frame member 512 at an interface 521 and defines a recessed region or cavity on one side of the antenna assembly 508 in which the circuit board 510 may be positioned. The peripheral support flange 523 may at least partially surround an outer periphery of the circuit board 510, as shown in FIG. 5B. The recessed region or cavity of the antenna assembly 508 (which may be surround or defined at least in part by the peripheral support flange 523) may be referred to herein as a circuit board cavity.

The peripheral support flange 523, through the interface 521, defines a load path from the antenna assembly 508 to the frame member 512. In this way, forces applied to the tag 500 may be directed through the antenna assembly 508 and the frame member 512 and not applied to the circuit board 510. More broadly, the antenna assembly 508 (and in particular the top wall of the antenna assembly 508 and the peripheral support flange 523) may form a protective support and/or partial shell around the circuit board 510. As one specific example, if a force is applied to the top exterior surface 501 of the tag 500 (e.g., while the bottom exterior surface 505 is on a table or other surface), the force may be directed through the top housing member 502, through the antenna assembly 508 (e.g., the peripheral support flange 523), through the frame member 512, and into the bottom housing member 516. In this way, the force may be directed around the circuit board 510 to reduce or eliminate any deflection or deformation of the circuit board 510 or its components or connections. Further, the peripheral support flange 523 may be attached to the frame member 512 at the interface 521 (as well as at other interfaces), thereby defining an at least partially enclosed volume in which the circuit board 510 (among other possible components) is positioned. Such interfaces may be sealed with sealing members, adhesives, glue, O-rings, or other components, thereby sealing the at least partially enclosed volume along those interfaces.

FIG. 5B also depicts an audio system that includes a coil 504 coupled to a top housing member 502. The coil 504 may be proximate a magnet assembly 506. When a signal is applied to the coil 504 (which is in a magnetic field produced by the magnet assembly 506), Lorentz forces may be produced which, in turn, cause the top housing member 502 to move, oscillate, vibrate, or otherwise produce an audible and optionally tactile output. In some cases, the top housing member 502 locally deflects or deforms to produce the audible and/or tactile output. Appropriate clearances may be provided between the top housing member 502 and an antenna assembly 508 to allow the top housing member 502 to move a distance and in a manner that is sufficient to produce the target audio and/or tactile output, as described above. Other types of audio systems may be used instead of or in addition to the audio system shown in FIGS. 5A-5B, such as piezoelectric elements, a ported speaker module, or the like.

The tag 500 may also include a hard-stop 520, or travel limiting member, that limits deflection of the top housing member 502. The hard-stop 520 may reduce the perception of flexibility of the top housing member 502 by limiting the distance that the top housing member 502 can move when pressed by a user. In particular, while movement of the top housing member 502 may be necessary for producing audible and haptic outputs, and optionally to detect inputs, the flexibility of the top housing member 502 that is necessary to facilitate such outputs and inputs may decrease the physical sensation of quality and structural integrity of the tag 500 as a whole. By limiting the distance that the top housing member 502 can move towards the antenna assembly 508 below a threshold, users may not tactilely perceive the flexibility of the top housing member 502 to the extent that they would if the top housing member 502 were not so limited. Accordingly, the maximum distance of the gap between the topmost surface of the hard-stop 520 and the bottom surface of the top housing member 502 may be less than or equal to about 500 microns, 400 microns, 300 microns, 200 microns, 100 microns, or 50 microns. This distance may be sufficient to allow the audio system (which includes and/or is defined by the coil 504 and the magnet assembly 506) to produce audible and/or haptic outputs, as well as to allow the detection of inputs, while also providing a tactile sensation that the top housing member 502 is rigid or substantially non-movable.

In some cases, the audio system may act as an input system (e.g., a button) in addition to acting as an audible and haptic output system. For example, deflections of the top housing member 502 (above the coil 504 and magnet assembly 506) may result in movement of the coil 504 in the magnetic field of the magnet assembly 506, thereby causing a detectable current to flow in the coil. This may be used to trigger the tag 500 to take some action (e.g., enter an initialization mode, cease an audio output, enter a "found" mode, etc.). In some cases, a separate sensor or switch (e.g., a force sensor, a dome switch) may be used to detect inputs to the device. For example, a sensor or switch may detect deflection or deformation of the top housing member 502 as a result of a user pressing on or squeezing the tag. The gap between the hard-stop 520 and the bottom surface of the top housing member 502 may be sufficient to facilitate the detection of an input force applied to the top housing member 502. Where a dome switch or other type of mechanical or electromechanical switch component is used (instead of or in addition to using an audio system as an input system), it may be positioned between the top housing member 502 and an underlying frame member, or in any suitable gap (between any two components) that can be reduced in size by a user to provide an input.

Wirelessly locatable tags may also use other types of input devices or systems to detect user inputs. For example, tags may include accelerometers or other motion-sensing systems. In such cases, users can move or manipulate the tags in certain ways to provide inputs to the tags, such as shaking the tag, tapping the tag, sliding the tag, or the like. The tag may be configured to respond to individual instances of such motions (e.g., a single tap or a single shake), or to particular patterns of motions (e.g., multiple taps within a predetermined time window, a tap followed by a shake followed by another tap).

As another example, the tag may include movable components or members (other than or in addition to a deformable top housing member, as described above) that can be manipulated (e.g., pushed, squeezed, pressed) by a user to provide an input. For example, the tag may include a mechanical button that can be pressed to provide an input. As another example, a battery door may be movable such that a user can push the battery door like a button. The battery door may be biased in an undepressed position by a spring member, and a sensor may determine when the battery door is depressed. The biasing and sensing functions may be provided by any suitable mechanisms. For example, dome switches (e.g., tactile dome switches) may be used to provide both biasing and sensing functions to the battery door. In other cases, a spring may act as a biasing member, and sensing functions may be provided by optical sensors, capacitive sensors, Hall effect sensors, or the like. The biasing force that maintains the battery door in an undepressed position may be provided by a compliant member that also biases a battery into a battery cavity of a tag, such as the compliant member 518 (described herein).

Tags may also include force sensors that detect an input upon detecting a force, applied to an exterior surface of the tag, that satisfies a threshold force. For example, a force sensor may be positioned between two components (e.g., a top housing member and a frame member, a bottom housing member and a battery, etc.), and a squeezing or pressing force applied to the tag may deform the tag and thus the force sensor. When the tag detects a threshold level of force, it may register the force as an input to the tag.

Upon detecting an input to the tag, via the input described herein or any other suitable input mechanism, the tag may perform some action. For example, upon detecting an input, the tag may enter an initialization mode or begin an initialization process. As another example, upon detecting an input, the tag may change from a "lost" operating mode to a "found" operating mode (which may include changing a beacon frequency, as described herein, causing a message to be sent to a host service updating a status of the tag to "found", or the like). As yet another example, upon detecting the input, the tag may produce an output that provides some information about the device (e.g., an audible tone or visual output indicating information such as a battery charge state). As yet another example, upon detecting the input, the tag may produce an audio output (or if the tag has a display, a graphical output) providing instructions on how the tag is to be handled if found (e.g., "please call owner at this number" or "please contact police"). Other types of actions in response to detecting an input are also contemplated.

As noted above, the tag 500 includes a circuit board 510. The circuit board 510 may include a substrate (e.g., a printed circuit board substrate) with electrical components coupled thereto. Example electrical components include, for example, processors, memory, sensors (e.g., temperature sensors, accelerometers, magnetometers, gyroscopes, optical sensors, microphones, pressure sensors, barometric sensors, or the like), conductive elements (e.g., conductive traces), and the like. A battery connector may be conductively coupled to the circuit board 510 and configured to conductively couple to a battery of the tag 500 to provide electrical power to the electronic components of the tag 500.

The bottom housing member 516 may be removable from the top housing member 502 to facilitate removal and replacement of the battery 514. The bottom housing member 516 may be removably coupled to the tag via a latching or other engagement system that prevents or inhibits unintentional removal of the bottom housing member 516. For example, in order to ensure that the battery 514 does not unintentionally fall out of the tag 500 and is not easily accessible to children, the bottom housing member 516 may require a press-and-twist motion, as described with respect to FIGS. 3A-3C. Various example mechanisms for securing the bottom housing member 516 (also referred to as a battery door) to the tag 500 are described herein with reference to FIGS. 12A-12C and 14A-25C. The bottom housing member 516 may be removably coupled to the tag 500 by engaging with latching features of the top housing member 502, a frame member 512, or any other suitable component(s) of the tag 500.

The tag 500 may also include a compliant member 518 between the bottom housing member 516 and the battery 514 to bias the battery 514 into the battery cavity of the tag 500 and against the battery connector that electrically couples the battery 514 to the electrical components of the tag 500. The compliant member 518 may be or may include a spring (e.g., a leaf spring, a coil spring), a polymer (e.g., a foam or elastomer pad), or any other suitable compliant member that biases the battery towards the tag 500. The compliant member 518 may also help latch or otherwise bias the bottom housing member 516 in a locked or engaged state (e.g., by forcing the latch member against or otherwise into engagement with an engagement feature). For example, as described herein, the bottom housing member 516 and the frame member 512 may include complementary engagement features, and the compliant member 518 may bias the engagement features against and/or into engagement with each other in a manner that prevents or limits removal of the bottom housing member 516 (at least without manipulating the bottom housing member 516 in a specific manner.

Figure 6:
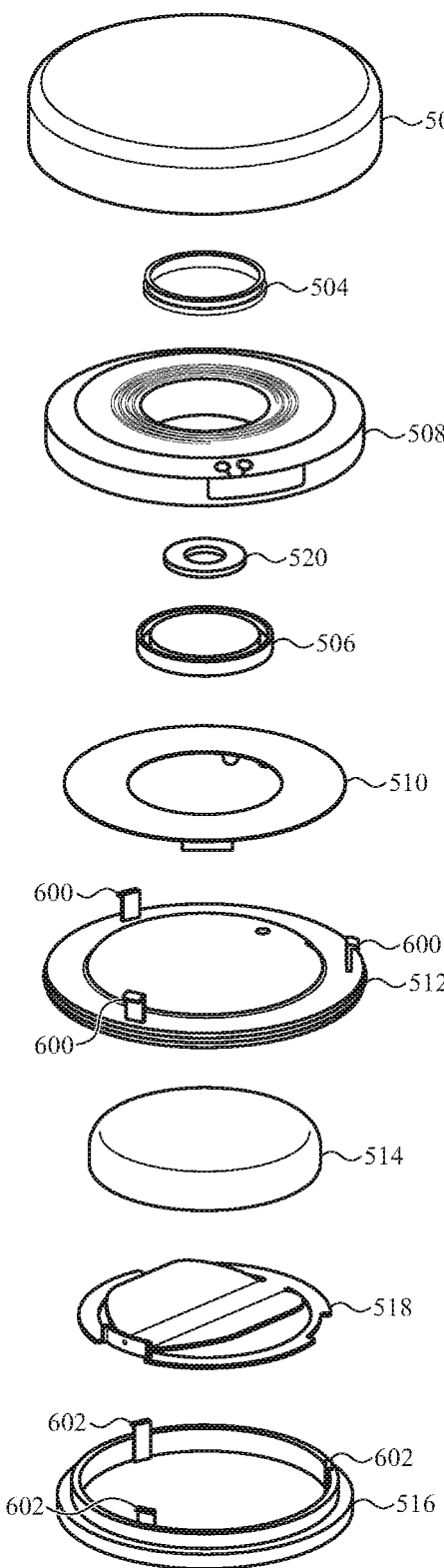
FIG. 6 depicts an exploded view of the wirelessly locatable tag of FIG. 5A.

FIG. 6 depicts an exploded view of the tag 500, showing another view of the components of the tag 500 and their arrangement. As shown in FIG. 6, the frame member 512 may include latch members 600 that engage the antenna assembly 508 to retain the frame member 512 to the antenna assembly 508. In some cases, the latch members 600 are positioned on the antenna assembly 508 and engage the frame member 512. The bottom housing member 516 may also include latch members 602 that engage the frame member 512 to removably couple the bottom housing member 516 to the frame member 512. The configurations and locations of the latch members 600 and 602 in FIG. 6 are merely examples, and other configurations and locations are also contemplated.

Figure 7:
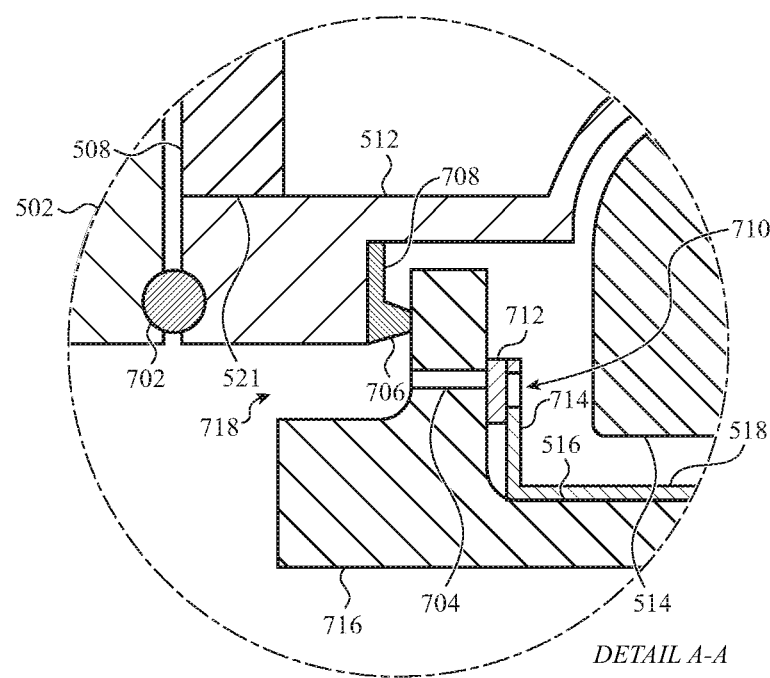
FIG. 7 depicts a partial cross-sectional view of the wirelessly locatable tag of FIG. 5A.

FIG. 7 depicts a detail view of a portion of the wirelessly locatable tag 500, corresponding to detail A-A in FIG. 5B. FIG. 7 shows interfaces between the top housing member 502, the bottom housing member 516, and the frame member 512. A first sealing member 702 may seal a joint or interface between the top housing member 502 and the frame member 512. A second sealing member 708 may seal a joint or interface between the bottom housing member 516 and the frame member 512. The first and second sealing members 702, 708 may be defined by different segments of a single piece of material that is co-molded or insert molded onto the frame member 512. In such cases, the first and second sealing members 702, 708 may be connected by a bridge segment that extends from the first sealing member 702 to the second sealing member 708. The bridge segment may be positioned in a channel along an interior side of the frame member 512 such that the bridge segment is not exposed along the exterior of the tag 500. In other example implementations, the first and second sealing members 702, 708 may be separate from one another (e.g., not joined by a bridge segment).

The first and second sealing members 702, 708 may form a substantially waterproof seal between the components with which they interface. The first and second sealing members 702, 708 may be formed from or include any suitable material, such as a compliant polymer material (e.g., an elastomer or foam). As noted, the first and second sealing members 702, 708 may be molded against the frame member 512 such that both the first and second sealing members 702, 708 bond to or are otherwise affixed to the frame member 512. In other cases, the first and second sealing members 702, 708 are molded or formed separately from the frame member 512 and then attached to the frame member 512 using an adhesive, ultrasonic welding, or any other suitable technique.

The top housing member 502 and the frame member 512 may be configured to remain attached to one another during normal operations (e.g., they may not be removably coupled, and detaching them from one another may damage the top housing member 502, the frame member 512, or both). Accordingly, the first sealing member 702 need not be configured to allow motion between the top housing member 502 and the frame member 512. By contrast, the bottom housing member 516 may be configured to be detached from the frame member 512 to provide access to the battery cavity (e.g., for replacing the battery). Accordingly, the second sealing member 708 may include a projecting portion 706 that is configured to contact and slide along a surface of the bottom housing member 516 when the bottom housing member 516 is attached to and detached from the frame member 512. The projecting portion 706 may have a triangular cross section that tapers or narrows along the length of the projecting portion 706 towards the free end. This shape may reduce the amount of force required to compress the second sealing member 708 (as compared to other shapes, such as circular cross-sectional shapes), thereby forming a waterproof seal while producing less force on the bottom housing member 516 during attachment and detachment than a differently shaped sealing member (e.g., one with a circular cross-section).

The tag 500 may also include a barometric vent to allow air to pass into and out of the tag 500 to allow pressure equalization between the ambient environment and the internal volume within the tag 500 (and to allow an optional barometric sensor or pressure sensor within the tag 500 to be exposed to the ambient pressure conditions exterior to the tag 500). The barometric vent may include or be defined by a passage 704 (or opening) that fluidly couples the external or ambient environment around the tag 500 to the internal volume of the tag 500, as well as a waterproof, air-permeable membrane 712 to prevent water ingress through the barometric vent while still allowing air to pass through to allow pressure equalization. The air-permeable membrane 712 may be positioned between a surface of the bottom housing member 516 and a flange portion 714 of the compliant member 518. The flange portion 714 may help to hold the membrane 712 in position and prevent it from moving or detaching when air or water pressure is applied to the membrane 712. The flange portion 714 may define an opening 710 that aligns with the passage 704 or is otherwise configured to allow air to pass through to facilitate pressure equalization. As shown, the flange portion 714 is an integral part of the compliant member 518 (which may be a unitary metal member), though in other implementations the flange portion 714 may be replaced with another bracket, backing, plate, or other component. The barometric vent may also include other components such as screens, additional membranes, fasteners, adhesives, and the like.

The barometric vent fluidly couples the ambient environment of the tag 500 with the battery cavity of the tag 500. The battery cavity may be fluidly coupled to the rest of the internal volume of the tag 500 such that the barometric vent is sufficient to allow pressure equalization between the ambient environment and the entire (or substantially entire) internal volume of the tag 500. In some cases, the frame member 512 defines openings for contacts of a battery connector to extend into the battery cavity from another area of the internal volume, and these openings may also allow air flow between the battery cavity and other internal areas of the tag 500. In this way, only one barometric vent is necessary to allow pressure equalization to the entire tag 500.

As described elsewhere herein, the bottom housing member 516 may define a flange or lip 716 that extends circumferentially around the bottom housing member 516 and defines one side of a housing gap 718. (The frame member 512 may define an opposite side of the housing gap 718). The flange or lip 716, and the housing gap 718 more generally, may be used to attach the tag 500 to an accessory, as described herein with respect to FIGS. 69A-128, for example.

Figure 8A:
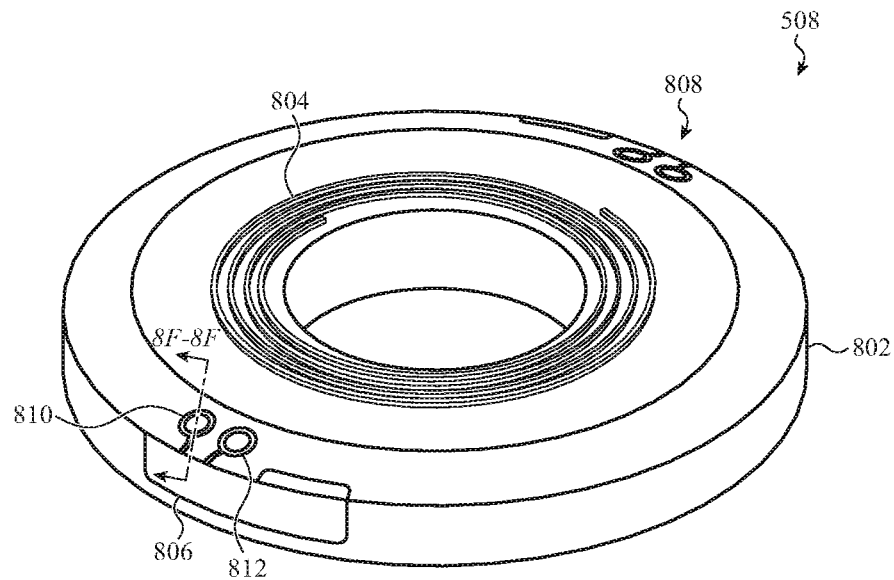
FIG. 8A depicts an example antenna assembly of the wirelessly locatable tag of FIG. 5A.

FIG. 8A depicts the antenna assembly 508 of the tag 500. The antenna assembly 508 may include one or more antennas 804, 806, 808 embedded in or otherwise attached to an antenna frame 802. The antenna frame 802 may be a polymer (e.g., a liquid crystal polymer, fiber-reinforced polymer) or any other suitable material, and the antennas 804, 806, 808 may be metal (or another suitable conductive material). In some cases, the antenna assembly 508 may be formed using insert molding techniques. For example, the antennas may be formed and then inserted into a mold, after which the polymer for the antenna frame 802 may be injected into the mold to at least partially encapsulate and interlock with (or otherwise retain) the antennas to the antenna frame 802. As another example, the antennas may be conductive tapes or films that are adhered or otherwise attached to the antenna frame 802. As another example, the antennas may be formed using laser direct structuring (LDS). In one example LDS process, the polymer material of the antenna frame 802 may be doped with a metallic material (or other suitable dopant), and a laser may be applied to the component to form regions where the metallic material or dopant is exposed or otherwise activated. These regions may then be metallized using a plating process in which the plating metal adheres to and/or grows on the laser-treated regions. In this way, the shapes of the antennas can be defined by the laser process, and the resulting antennas may be easily plated on the antenna frame 802 in the target shape and configuration. In other cases, the antennas may be formed and/or integrated with the antenna frame 802 in other ways. For example, antennas may be plated on the antenna frame 802, attached to the antenna frame 802 using an adhesive, fastener, or any other suitable attachment technique. Further, the laser process may remove some of the material of the antenna frame 802, thus forming recesses (which may be microscopic in size) in which the antenna material is deposited or grown. Depositing or growing the material of the antennas in the recesses may result in the antennas being at least partially embedded in the material of the antenna frame 802.

The antenna assembly 508 may include any number of antennas. As shown, the antenna assembly 508 includes a near-field wireless communications antenna 804, a UWB antenna 806, and a Bluetooth antenna 808. Each antenna may be tuned to communicate at certain frequencies and/or otherwise comply with applicable communications protocols and/or standards. More generally, an antenna assembly may include multiple antennas, with each antenna configured to communicate via a different wireless communications protocol. For example, a first antenna may communicate (including by transmitting a wireless signal) via a first wireless protocol, a second antenna may communicate (including by transmitting a wireless signal) via a second wireless protocol, and a third antenna may communicate (including by transmitting a wireless signal) via a third wireless protocol. More or fewer antennas may also be embedded in or otherwise attached to an antenna frame.

The near-field wireless communications antenna 804 may be configured for any suitable type or protocol of near-field wireless communications, including but not limited to near-field communications (NFC) protocols, radio frequency identification (RFID) protocols, or any other suitable type or protocol. The near-field wireless communications antenna 804 may be a loop antenna, and may include a flat coil of conductive material. The coil may include four turns of coil, or any other suitable number of turns.

In some cases, the near-field wireless communications antenna 804 is configured to cause nearby devices to display information. For example, a person may bring a phone, watch, tablet computer, or other device nearby the tag 500 (either intentionally or unintentionally), thereby establishing a communication link between the tag 500 and the person's device. The communication link may cause the person's device to display various types of information or take other actions. For example, the person's device may receive information, via the near-field wireless communications antenna 804, stating whether or not the tag 500 has been reported lost, information about how to handle the tag 500 (or object to which the tag is attached), information about how to contact the owner of the tag 500, or the like. The near-field wireless communications antenna 804 may also be used to initiate an initialization process between the tag 500 and another device. Other information may be communicated, or actions triggered, via the near-field wireless communications antenna 804.

The UWB antenna 806 may be configured to communicate using an ultra-wideband protocol, and may be part of a UWB radio system of the tag 500. The UWB antenna 806 may be configured to communicate in a frequency range from about 6.25 GHz to about 8.25 GHz. The UWB antenna 806 may be configured as an inverted-F antenna. The tag 500 may include a feed line 812 and a ground line 810 electrically coupled to the UWB antenna 806 to allow radio circuitry associated with the UWB antenna 806 to send and receive electromagnetic signals via the UWB antenna 806. The ground line 810 may be conductively coupled to an electrical ground plane of the tag.

The dimensions of the UWB antenna 806 and the locations of the feed and ground lines 812, 810 may determine the tuning of the antenna, such as the frequency range over which the antenna may communicate, as well as the bandwidth of the antenna. The feed and ground lines 812, 810 may be attached to vias that extend through the antenna frame 802 of the antenna assembly 508 and are conductively coupled to the circuit board 510 to conductively couple the UWB antenna 806 to radio circuitry on the circuit board 510.

In some cases, a greater the height of the UWB antenna 806 corresponds to a greater bandwidth. Accordingly, the UWB antena 806 may have a height that is 90% or greater of the height of a peripheral side surface of the antenna assembly 508. The height may be 95% or greater, 98% or greater, or 100% of the height of the peripheral side surface of the antenna assembly 508. Other heights are also contemplated.

The Bluetooth antenna 808 may be configured to facilitate communications using a Bluetooth protocol, such as Bluetooth Low Energy or any other suitable Bluetooth protocol or standard. The Bluetooth antenna 808 may be configured as an inverted-F antenna, and may include feed and ground lines similar to those described with respect to the UWB antenna 806. (The feed and ground lines of the Bluetooth antenna 808 may be connected to the circuit board 510 using vias similar to those described with respect to the UWB antenna 806. The Bluetooth antenna 808 and the UWB antenna 806 may be used for different functions. For example, the Bluetooth antenna 808 may be used primarily for communicating information between a tag and another device (e.g., a smartphone), while the UWB antenna 806 may be used primarily for sending localization signals to another device. Localization signals may be used to determine spatial parameters of a tag. Of course, the antennas 806, 808 may be used for different functions or combinations of functions. For example, the UWB antenna 806 may be used to communicate data or other information or signals to other devices instead of or in addition to the Bluetooth antenna 808.

The UWB antenna 806 and the Bluetooth antenna 808 may be positioned on an outer peripheral side surface of the antenna assembly 508. This positioning of the antennas helps maximize the distance between the radiating structures of the antennas and other conductive components within the tag 500. For example, capacitive coupling between the antennas and conductive components on the circuit board 510, the battery 514, or other metal or conductive objects may negatively impact the operation of the antennas. Accordingly, positioning the antennas on the outer peripheral side surface of the antenna assembly 508 (which may be circular) maximizes the distance between the antennas and other conductive components, thereby providing superior antenna performance. Positioning the antennas on the outer peripheral side surface may also position the antennas past the outer perimeter of the battery 514, thereby mitigating shielding and/or blocking effects of the battery 514.

Further, the UWB antenna 806 and the Bluetooth antenna 808 may be positioned on opposite sides of the antenna frame 802 (e.g., antipodally positioned about the substantially circular or cylindrical outer peripheral side). This configuration provides the maximum possible distance between the antennas with them both being on the same carrier. This arrangement may help mitigate interference or other deleterious effects that may occur if the antennas are close together.

Further, the UWB antenna 806 and the Bluetooth antenna 808 may have different lengths. For example, each antenna may be configured to communicate via a different frequency or set of frequencies, and the length of the antennas may at least partially define the frequencies with which the antennas communicate. Accordingly, the UWB antenna 806 may have a different length (e.g., longer or shorter than) the Bluetooth antenna 808.

The UWB antenna 806 and the Bluetooth antenna 808 may be positioned on opposite sides of the antenna frame 802 (e.g., antipodally positioned about the substantially circular or cylindrical outer peripheral side). This configuration provides the maximum possible distance between the antennas with them both being on the same carrier. This arrangement may help mitigate interference or other deleterious effects that may occur if the antennas are close together.

The antennas 804, 806, 808 may each be conductively coupled to circuitry on the circuit board 510 to facilitate communications via the antennas 804, 806, 808. As used herein, an antenna and the communication circuitry associated with that antenna may be referred to as a radio.

Figure 8B:
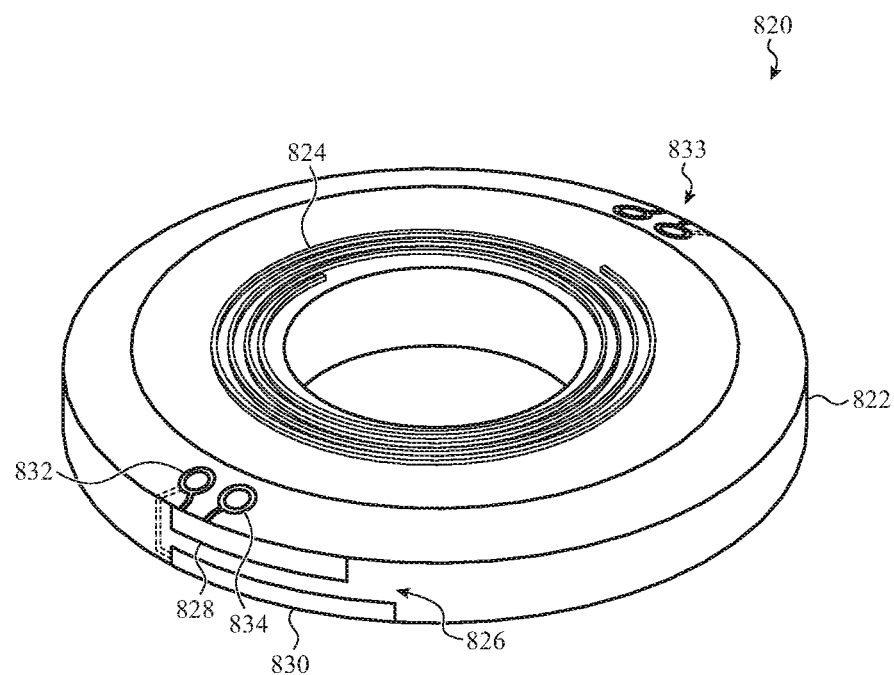
FIG. 8B depicts another example antenna assembly for a wirelessly locatable tag.

FIG. 8B depicts another example antenna assembly 820 that may be used as an alternative to the antenna assembly 508 described above. The antenna assembly 820 may be the same as or similar to the antenna assembly 508 except that the UWB antenna and the Bluetooth antennas may have a different configuration. Accordingly, the antenna assembly 820 may include an antenna frame 822 and a near-field wireless communication antenna 824, which may be the same as or similar to the corresponding components of the antenna assembly 508.

Whereas the UWB antenna 806 included a single radiating element, the UWB antenna 826 may include a first antenna element 828 and a second antenna element 830 that is set apart from the first antenna element 828. A feed line 834 and a ground line 832 may be conductively coupled to the first antenna element 828, and the ground line 832 may be conductively coupled to the second antenna element 830 (via a conductor that is at least partially embedded in the antenna frame 822, as shown, or via another conductor). The second antenna element 830 may not be directly conductively coupled to the feed line 834. The second antenna element 830 may act as a parasitic element that can amplify or enhance the effectiveness of the first antenna element 828, and may provide greater bandwidth than a single-antenna-element configuration.

The Bluetooth antenna 833 may include the two-element configuration of the UWB antenna 826, or it may have the same single-radiator configuration of the Bluetooth antenna 808. In all other ways, including the composition of the antennas and antenna frame, and the techniques for forming the antennas and integrating them with the antenna frame, the antenna assembly 820 may be the same as or similar to the antenna assembly 508 described above with respect to FIG. 8A.

Figure 8C:
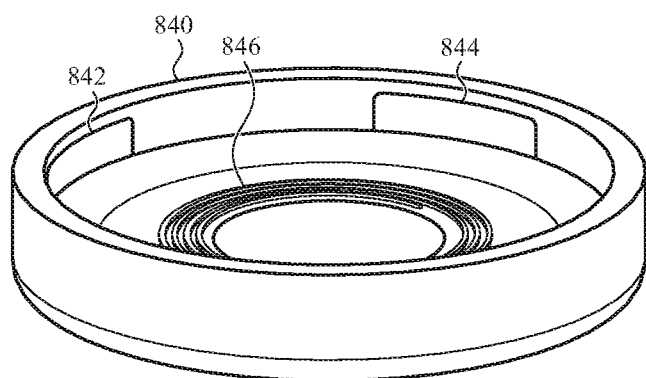
FIG. 8C depicts a partial cross-sectional view of the antenna assembly of FIG. 8A.

While FIGS. 8A-8B illustrate two example antenna assemblies, antennas may be integrated with tags in other ways instead of or in addition to those described with respect to FIGS. 8A-8B. FIG. 8C, for example, illustrates an example top housing member 840 (which may be an embodiment of the top housing member 502) in which antennas 842, 844, and 846 are attached to the interior walls of the top housing member 840. The antennas 842 844 may be UWB and Bluetooth antennas, respectively, and may be positioned on the interior surface of the outer peripheral wall of the top housing member 840. The antenna 846 may be a near-field wireless communication antenna, and may be positioned on the interior surface of the top wall of the top housing member 840. The antennas may be formed using the same techniques and materials described with respect to the other antenna assemblies described herein (e.g., laser direct sintering, insert molding, adhering conductors to the housing member, etc.). The antennas 842, 844, and 846 may be conductively coupled to circuitry on the circuit board 510 using wires, solder joints, vias, or the like.

Figure 8D:
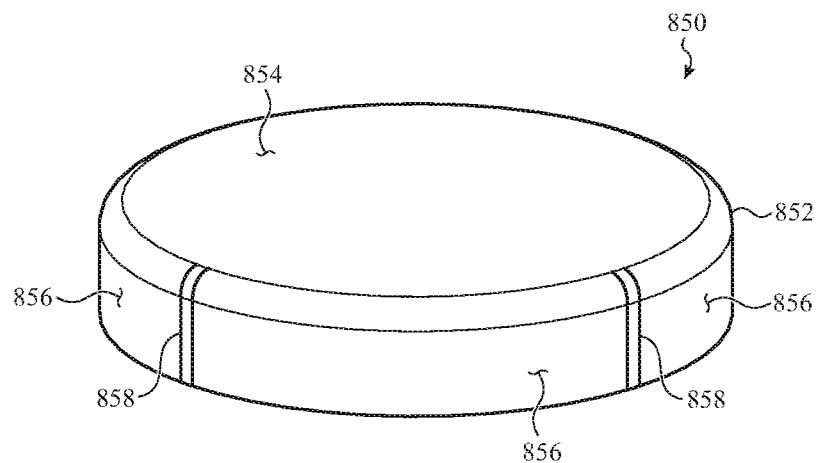
FIG. 8D depicts an example housing member with antennas for a wirelessly locatable tag.
Figure 8E:
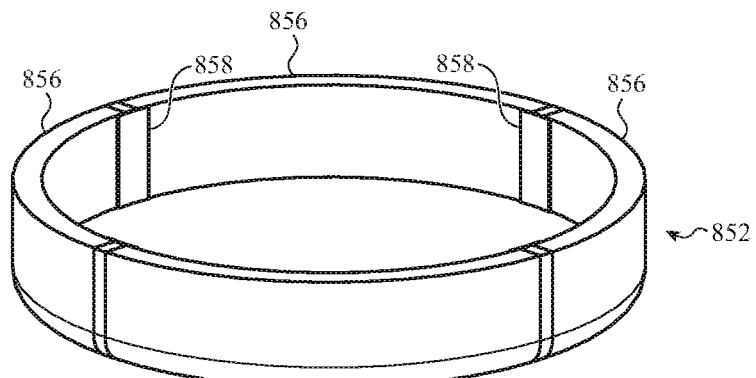
FIG. 8E depicts an example wirelessly locatable tag.

FIGS. 8D-8E illustrate another example antenna configuration for a tag 850. In particular, as shown in FIG. 8D, the tag 850 includes a top housing member 852 that includes a central member 854, which may be formed of a nonconductive material such as a polymer, and conductive elements 856 defining portions of the outer peripheral wall of the tag 850. The outer peripheral wall of the tag 850 may also be defined at least in part by nonconductive elements 858 that are positioned between the conductive elements 856. The conductive elements 856 may be set apart from one another by gaps, and the nonconductive elements 858 may be positioned within the gaps. The nonconductive elements 858 may also mechanically secure the conductive elements 856 together by engaging (e.g., interlocking) with the conductive elements 856.

FIG. 8E illustrates the inside of the top housing member 852, showing how both the conductive elements 856 and the nonconductive elements 858 may define part of the internal surfaces of the top housing member 852. As shown, the width of the nonconductive elements 858 may be greater on the inside of the top housing member 852 than on the outside. The increased internal size may result from the nonconductive elements 858 engaging with retention features, undercuts, openings, grooves, threads, or other features of the conductive elements 856. The conductive elements 856 may be used as antenna elements for the tag 850. The electrical isolation provided by the nonconductive elements 858 between the conductive elements 856 may facilitate tuning of the size and radiating characteristics of the conductive elements 856. The conductive elements 856 may be conductively coupled to circuitry on the circuit board 510 using wires, solder joints, vias, or the like, to allow the conductive elements 856 to operate as antennas.

As described above, antennas of an antenna assembly may be conductively (and mechanically) coupled to a circuit board or other electronic component using vias. For example, the ground line 810 and feed line 812 shown in FIG. 8A may be formed in part by vias that extend through the antenna frame and are conductively coupled to a circuit board. The vias in the antenna frames may allow the antenna frame to be surface mounted to the circuit board. More particularly, the vias of the antenna frame may be soldered directly to the circuit board, thus providing both a conductive coupling between circuit elements on the circuit board (e.g., radio circuitry) and components on the antenna frame (e.g., antennas), and also providing a mechanical attachment between the antenna frame and circuit board.

Figure 8F:
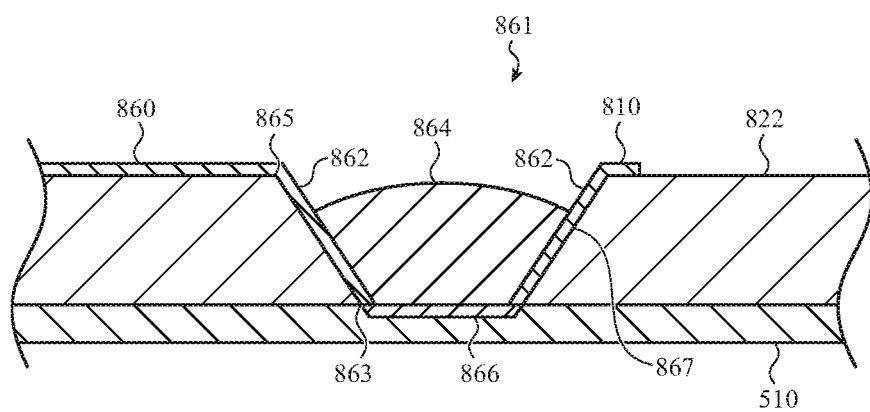
FIG. 8F depicts an example housing member of the wirelessly locatable tag of FIG. 8E.

FIG. 8F illustrates a partial cross-sectional view of the antenna assembly 508 of FIG. 8A, viewed along line 8F-8F in FIG. 8A. FIG. 8F illustrates an example configuration of a via for conductively and mechanically coupling the circuit board 510 to the antenna assembly 508.

The antenna frame 822 defines an opening 861 that extends from a top surface of the antenna frame 822 to a bottom surface of the antenna frame 822. The opening 861 may be tapered from a larger opening size (e.g., diameter) at the top surface 865 to a smaller opening size (e.g., diameter) at the bottom surface 863 of the antenna frame 822. In some cases, the opening 861 may be a frustoconical opening (e.g., an opening defined by a frustoconical wall), with the smaller end of the frustoconical opening along the bottom surface 863 of the antenna frame 822.

A surface 867 of the frustoconical opening (e.g., the surface of a frustoconical wall) is coated with a conductive material 862. The conductive material 862 may be or may include a metal or other conductive material, and may be formed using an LDS process, as described above. In some cases, the conductive materials of the vias, the antennas, and the conductive traces that join the antennas to the conductive materials of the vias (e.g., conductive trace 860) are all formed using the same LDS operations. For example, the surfaces of the antenna frame 822 that are to be metallized (e.g., the antenna 806, the trace 860, the surface 867 of the opening 861) may be treated with a laser to expose a dopant in the antenna frame 822 and/or to form a distinct surface texture on the antenna frame 822 at the locations where metallization is to occur. The antenna frame 822 is then plated (e.g., electroplated) or otherwise processed so that the laser-treated areas of the antenna frame 822 are coated with a conductive material (e.g., a metal layer). In this way, a continuous metal layer may define the antenna 806, trace 860, and the conductive coating or material on the surface of the opening 861.

To conductively couple the antenna to the circuit board, the via may be soldered to a conductive trace 866 of the circuit board 510. This may be achieved by soldering a solder ball 864 in the frustoconical opening 861 of the via, which defines a reliable conductive path from the conductive material 862 to the conductive trace 866.

Additionally, the tapered configuration of the opening 861, as well as the mechanical bond between the solder ball 864 and the conductive trace 866 and the solder ball 864 and the conductive material 862, results in the solder ball 864 mechanically interlocking the circuit board 510 with the antenna frame 822. For example, the process of soldering the solder ball 864 to the conductive trace 866 and to the conductive material 862 forms a bond (e.g., a metal fusion bond) between those materials, and the resulting tapered shape of the solder ball 864 essentially defines an undercut that captures or traps the narrower end of the opening 861 between the solder ball 864 and the surface of the circuit board 510. This interlocking structure, along with the metal-to-metal bonds, forms a structural attachment between the antenna frame 822 and circuit board. Further, the tapered configuration of the opening 861 results in an advantageous stress profile on the conductive material 862. For example, if a tag experiences a force that stresses the antenna frame-circuit board interface, the forces that are imparted to the conductive material 862 may be primarily compression and/or shear forces, rather than tensile forces (where tensile forces correspond to forces that lift the conductive material away from the antenna frame 822). Thus, a force that tends to pull the circuit board 510 away from the antenna frame 822 (e.g., downwards) results in the conductive material 862 being compressed between the solder ball 864 and the underlying surface of the antenna frame 822 (which tends to force the conductive material 862 against the underlying surface of the antenna frame 822, rather than pulling it away from the antenna frame 822).

Figure 9:
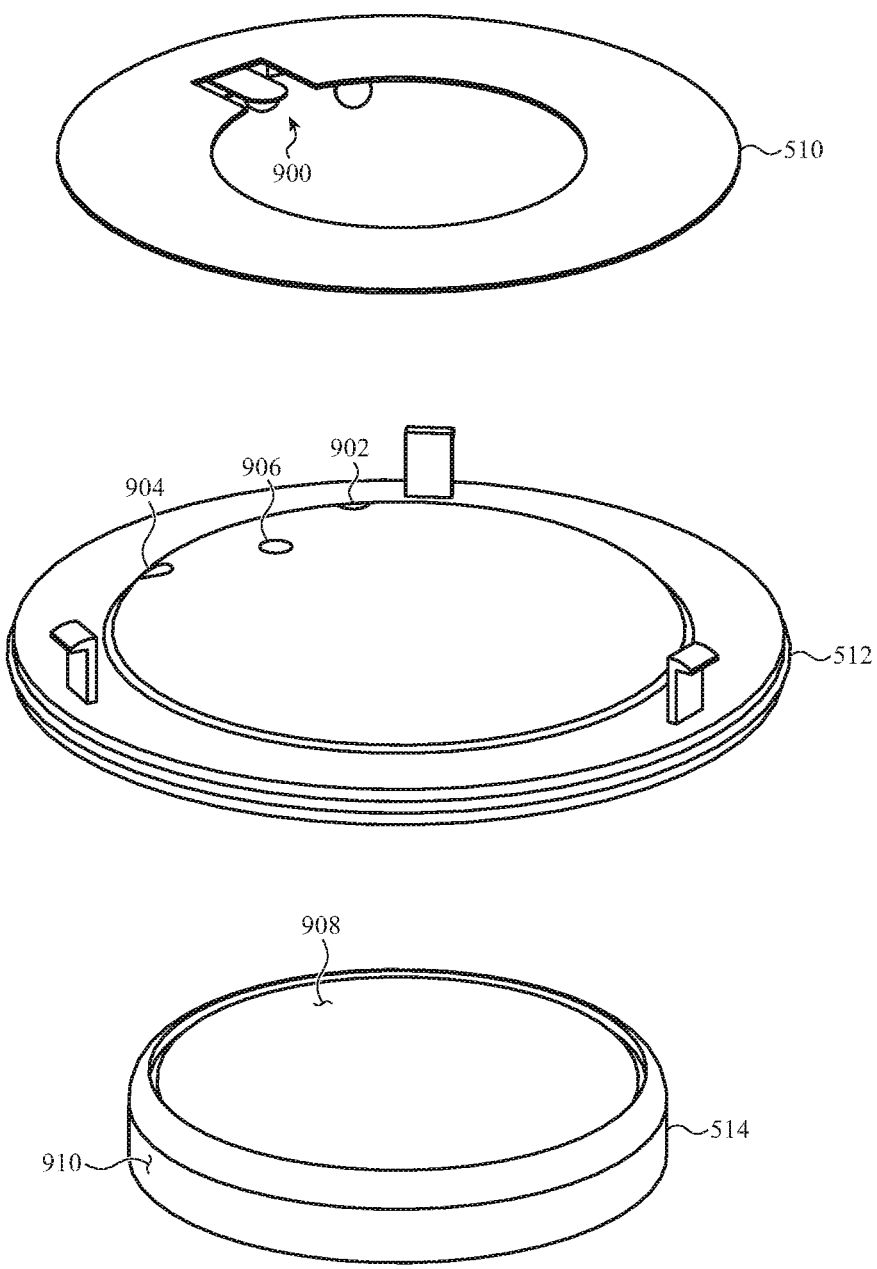
FIG. 9 depicts a partial exploded view of the wirelessly locatable tag of FIG. 5A.

FIG. 9 depicts a partial exploded view of a portion of an example wirelessly locatable tag 500, showing how a battery connector 900 may conductively couple the battery 514 to the circuitry of the device (e.g., via the circuit board 510). The battery connector 900 may include multiple deflectable arms (three, as shown), portions of which extend through openings 902, 904, and 906 in the frame member 512 to contact the positive and negative terminals of the battery 514. The deflectable arms may define battery contacts of the tag (e.g., conductive members that conductively couple to positive and/or negative terminals of a battery). The battery connector 900 may be mounted on and conductively coupled to the circuit board 510 to provide power from the battery 514 to the electronics of the tag 500.

In some cases, at least a portion of each of two of the three deflectable arms may extend through the openings 902, 904 to contact one of the terminals of the battery (e.g., the positive terminal 910, which may be or may be defined at least in part by a curved or cylindrical surface of the battery), and the third deflectable arm extends through the opening 906 to contact the other terminal of the battery (e.g., the negative terminal 908, which may be or may be defined at least in part by a planar surface of the battery). By contacting one of the battery terminals with two deflectable arms, the tag 500 is able to detect whether the battery is present in the battery cavity by detecting whether there is continuity between those two deflectable arms. When the battery is not present, the device may be shut down, and any residual voltage stored in capacitors or other circuit elements may be discharged so that the tag 500 ceases to function as soon as the battery is no longer detected in the tag 500. The openings 902, 904, and 906 may also fluidly couple the battery cavity to the other portions of the internal volume of the tag 500, such as the portions that are above the frame member 512 (based on the orientation shown in FIG. 9).

Figure 10A:
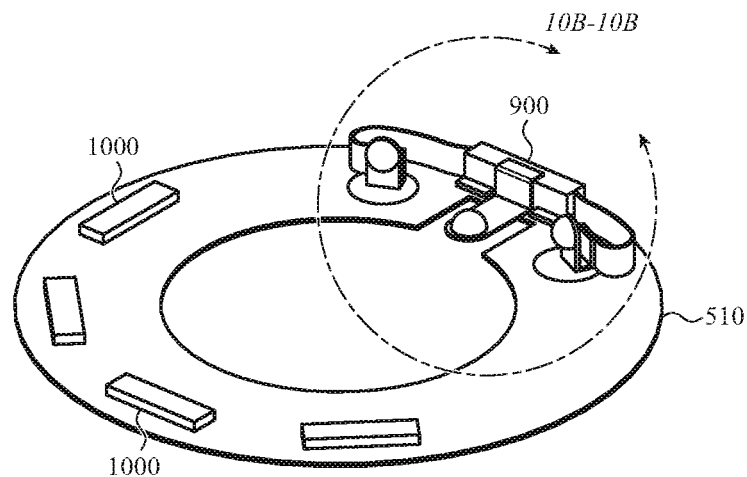
FIG. 10A depicts a circuit board of the wirelessly locatable tag of FIG. 5A.

FIG. 10A illustrates the opposite side of the circuit board 510 (compared to FIG. 9), showing the battery connector 900 attached to the circuit board 510. Also shown are electrical components 1000, which represent processors, memory, sensors, and/or other electrical components and/or circuit elements that may be coupled to the circuit board 510.

Figure 10B:
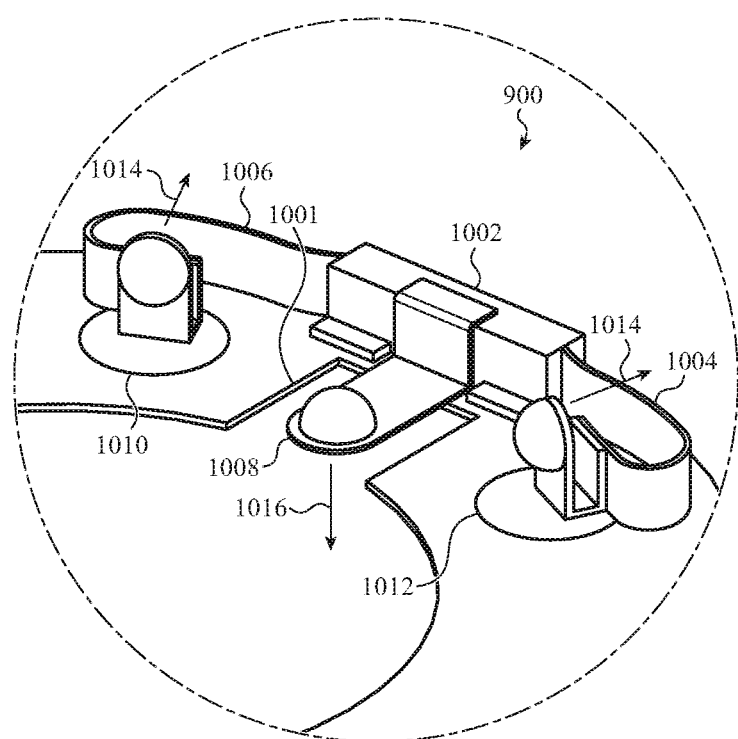
FIGS. 10B-10C depict a battery connector of the wirelessly locatable tag of FIG. 5A.

FIG. 10B is a detail view of the area 10B-10B in FIG. 10A, showing additional details of the battery connector 900 and its components. The battery connector 900 includes a body 1002, first and second deflectable arms 1004, 1006 extending from the body 1002 and configured to contact the positive terminal of the battery 514, and a third deflectable arm 1008 configured to contact the negative terminal of the battery 514. The deflectable arms may be electrically coupled to the circuit board 510 via conductors that are embedded in the body 1002 and soldered or otherwise conductively coupled to the circuit board 510.

The deflectable arms may be biased in a direction that forces them into contact with the battery 514 when the battery 514 is within the battery cavity of the tag 500. This biasing may help ensure that the deflectable arms are forced into contact with the battery 514 to maintain a positive conductive contact with the battery 514. The direction that the deflectable arms move and/or are biased is based at least partly on the orientation of the deflectable arms relative to the battery. For example, as is evident from the location of opening 906 (FIG. 9), the third deflectable arm 1008 contacts the battery 514 from above the battery 514 (relative to the orientation shown in FIG. 9). Accordingly, the third deflectable arm 1008 is configured to deflect along a direction indicated by arrow 1016 in FIG. 10B (e.g., towards and away from the circuit board 510). A cut-out 1001 in the circuit board 510 provides clearance so that the third deflectable arm 1008 can deflect without interference by the circuit board 510. By contrast, the first and second deflectable arms 1004, 1006 contact the battery 514 along the side of the battery 514, or at least along a surface that is not parallel to the circuit board 510. Accordingly, the first and second deflectable arms 1004, 1006 are configured to deflect along directions indicated by the arrows 1014.

As the battery 514 is being inserted into the battery cavity of the tag 500, however, the battery 514 may apply a force to the first and second deflectable arms 1004, 1006 tending to push the first and second deflectable arms 1004, 1006 towards the circuit board 510. The circuit board 510 may include friction pads 1010 and 1012 that are positioned below portions of the first and second deflectable arms 1004, 1006, respectively. The friction pads 1010, 1012 may be formed of metal (e.g., copper, gold), or any other suitable material that allows the first and second deflectable arms 1004, 1006 to slide along the circuit board 510 while providing a relatively low coefficient of friction between the circuit board 510 and the first and second deflectable arms 1004, 1006. The friction pads 1010, 1012 may also protect the circuit board's substrate and the first and second deflectable arms 1004, 1006 from wear due to sliding of the first and second deflectable arms 1004, 1006 along the surface. During installation of the battery 514, the battery may contact the first and second deflectable arms 1004, 1006 in a manner that pushes them towards the circuit board 510. By providing the friction pads 1010, 1012 on the circuit board 510 and configuring the first and second deflectable arms 1004, 1006 so that they are proximate the friction pads 1010, 1012 (and also configuring the ends of the first and second deflectable arms 1004, 1006 to have a rounded shape), the deflection of the first and second deflectable arms 1004, 1006 in the direction towards the circuit board 510 is limited by the contact between the arms and the friction pads. Limiting deflection in this direction allows the first and second deflectable arms 1004, 1006 to begin deflecting along the directions 1014, 1016, thereby allowing the first and second deflectable arms 1004, 1006 to move out of the way of the battery 514 and provide the biasing force in the appropriate direction to maintain the first and second deflectable arms 1004, 1006 in contact with the battery 514.

Figure 10C:
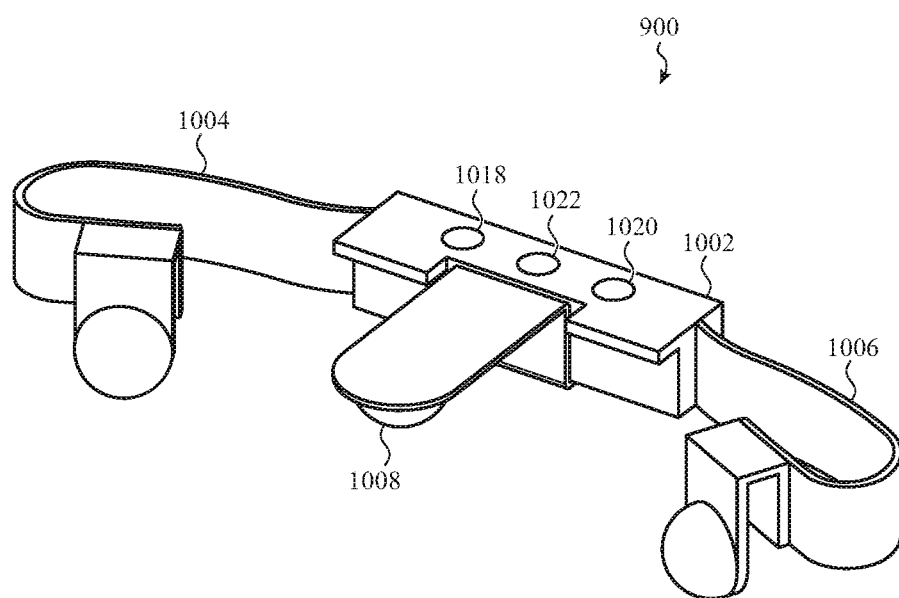

FIG. 10C shows a bottom side view of the battery connector 900. The battery connector 900 includes solder pads that are soldered to the circuit board 510 to conductively couple the deflectable arms 1004, 1006, 1008 to conductive traces on the circuit board. More specifically, the battery connector 900 includes a first solder pad 1018 that is conductively coupled to the first deflectable arm 1004, a second solder pad 1020 that is conductively coupled to the second deflectable arm 1006, and a third solder pad 1022 that is conductively coupled to the third deflectable arm 1008. In some cases, the solder pads and their respective deflectable arms are unitary metal structures (e.g., the solder pad and the deflectable arm are a single piece of metal, such as stamped metal). In other cases, the solder pads and their respective deflectable arms are separate components that are attached via welding, soldering, or another operation.

The battery connector 900 may be formed by insert molding. For example, the deflectable arms 1004, 1006, 1008 and the solder pads 1018, 1020, 1022 (or the unitary metal structures that define the deflectable arms and the solder pads) may be inserted into a mold, and an insulating, polymer material may be introduced into the mold, thereby at least partially encapsulating the deflectable arms 1004, 1006, 1008 and the solder pads 1018, 1020, 1022. Other techniques for forming the battery connector 900 are also contemplated.

Figure 10D:
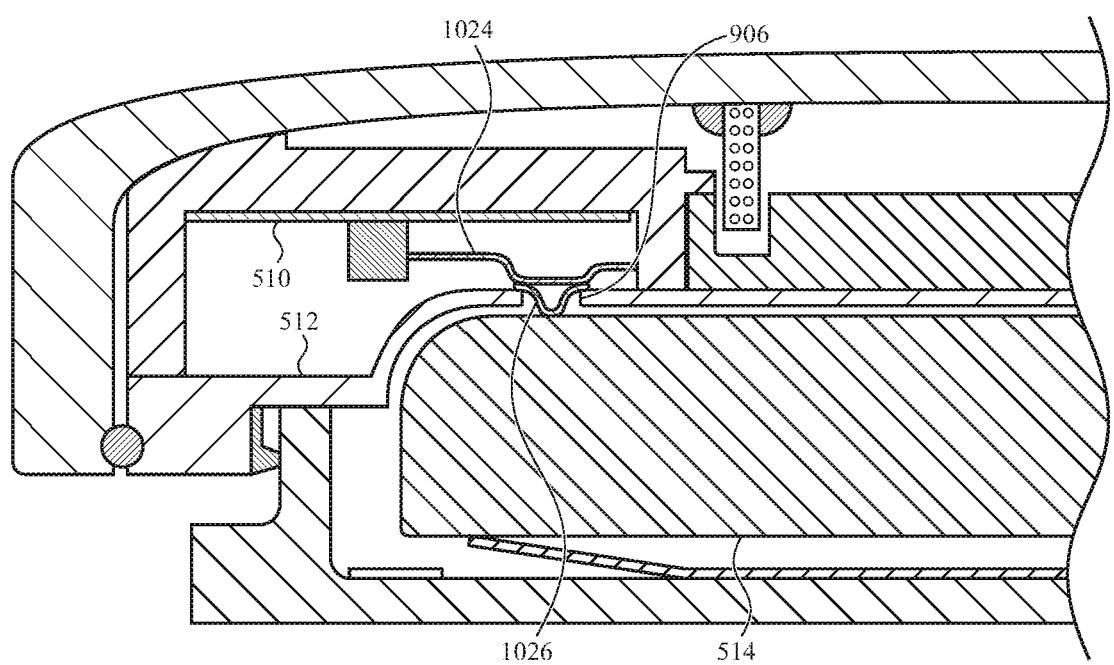
FIG. 10D depicts another example battery connector of the wirelessly locatable tag of FIG. 5A.

FIG. 10D illustrates a partial cross-sectional view of another example configuration for a battery connector. In particular, whereas the deflectable arms of the battery connector 900 extend into the battery cavity through openings in the main frame member 512 (so that the deflectable arms can conductively couple to the battery 514 by directly contacting the battery 514), in another configuration conductive plugs may be positioned in the openings in the main frame member, and the deflectable arms may conductively contact the conductive plugs to ultimately conductively couple the deflectable arms to the battery. FIG. 10D illustrates such a configuration. In particular, the tag includes a conductive plug 1026 positioned in the opening 906 in the main frame member 512 and extending into the battery cavity defined by the main frame member 512. The conductive plug 1026 may be formed of metal, and may be configured to physically contact and conductively couple to the battery 514. The conductive plug 1026 may be biased into the battery cavity by a deflectable arm 1024 (which may be similar to the third deflectable arm 1008 except that it does not extend into the battery cavity). The biasing force applied by the deflectable arm 1024 may be opposed by the force applied on the conductive plug 1026 by the battery 514, thereby causing the conductive plug 1026 to move upwards (relative to the orientation in FIG. 10D). The biasing force applied by the deflectable arm 1024 also maintains an intimate physical connection between the battery 514 and the conductive plug 1026. Further, the biasing force applied by the deflectable arm 1024 retains the conductive plug 1026 in place by capturing the conductive plug 1026 between the deflectable arm 1024 and the main frame member 512.

The conductive plug 1026 may be configured to self-align in the opening 906. For example, the conductive plug 1026 may have a rounded protrusion, and the opening 906 may be a circular hole, such that the rounded protrusion self-aligns in a substantially concentric position (with respect to the circular hole). This self-aligning property of the conductive plug 1026 may also help accommodate for misalignments between the deflectable arms 1004, 1006, 1008 and the openings 902, 904, 906 in the main frame member 512. For example, misalignments between the deflectable arms and the openings can be tolerated because the deflectable arms merely need to contact the conductive plugs to provide a biasing force and conductive connection. More particularly, because the conductive plugs are not fixed to the deflectable arms, as long as a deflectable arm conductively couples to and provides sufficient biasing and/or retention force on the conductive plug, the contact point between the deflectable arm and the conductive plug can vary. Accordingly, because the conductive plugs can self-align in the openings and misalignments between the deflectable arms and the conductive plugs are accommodated by the non-fixed arm/plug interface, assembly tolerances relating to the positioning of the battery connector and the position of the circuit board and main frame member may be relaxed.

While FIG. 10D illustrates one deflectable arm and conductive plug, the same or a similar configuration may be used for any and all battery contacts. For example, conductive plugs may be positioned in the openings 902, 904, and deflectable arms similar to the first and second deflectable arms 1004, 1006 may contact and bias those conductive plugs into the battery cavity. Indeed, any of the battery contacts shown or described herein may be portions of deflectable arms that extend into the battery cavity, or they may be conductive plugs that extend into the battery cavity, with deflectable arms biasing and retaining the conductive plugs as described above.

While FIGS. 9-10C depict one example battery connector and arrangement of deflectable arms (including where the deflectable arms contact the battery 514), this is merely one example configuration, and other configurations may also be used with the tag 500, or any other tag shown and described herein. FIGS. 11A-11D illustrate alternative arrangements of deflectable arms or other types of battery contacts that may be used to provide an electrical connection to the battery 514. Each of these alternative arrangements may use a battery connector that is similar to the battery connector 900. In some cases, each battery contact shown in FIGS. 11A-11D corresponds to an end of a deflectable arm similar to those of the battery connector 900. In some cases, instead of having all of the deflectable arms coupled to the same body (as is the case with the battery connector 900), one or more of the deflectable arms that define the battery contacts in FIGS. 11A-11D are coupled to separate bodies. While FIGS. 11A-11D discuss the position of battery contacts, it will be understood that the battery contacts may be the ends of deflectable arms similar to those described with respect to the battery connector 900. Further, battery contact configurations other than those shown in FIGS. 9-11D may also be used to conductively couple a battery to the circuitry of a tag.

Figure 11A:
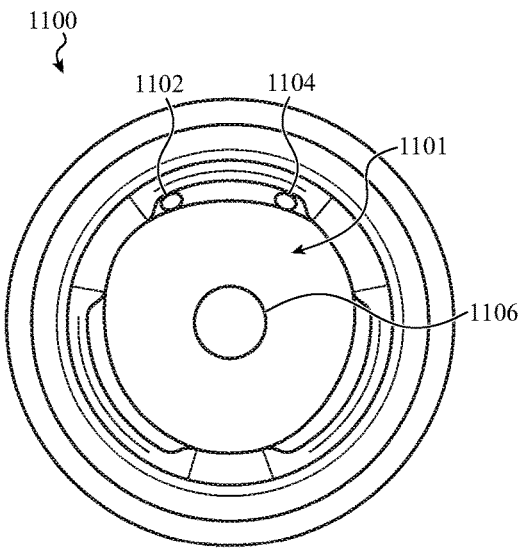
FIGS. 11A-11D depict other example battery connector arrangements for a wirelessly locatable tag.

FIG. 11A shows an example tag 1100 in which first and second battery contacts 1102, 1104 are positioned along a side wall of a battery cavity 1101, and a third battery contact 1106 is positioned at a center of the battery cavity 1101. The first and second battery contacts 1102, 1104 are configured to contact the positive terminal of the battery, and the third battery contact 1106 is configured to contact the negative terminal of the battery.

Figure 11B:
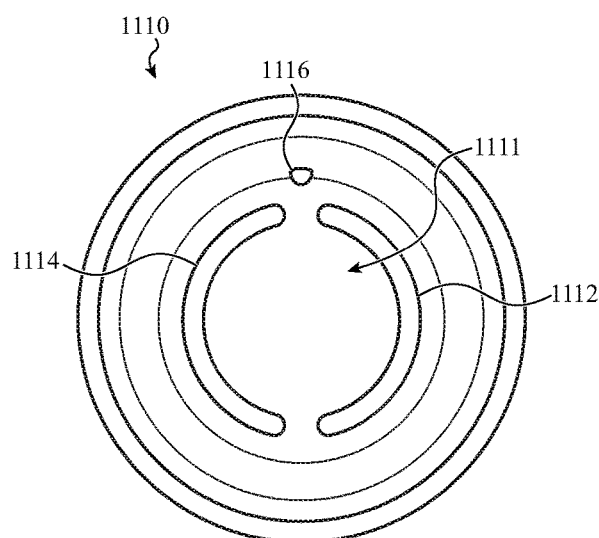

FIG. 11B shows an example tag 1110 in which two battery contacts are configured to contact the negative terminal of the battery, and one is configured to contact the positive terminal of the battery (in contrast to the battery connector 900 and the configuration in FIG. 11A, in which two battery contacts contact the positive terminal and one battery contact contacts the negative terminal). In particular, first and second battery contacts 1112, 1114 are positioned on a bottom surface of a battery cavity 1111 (relative to the orientation shown in FIG. 11B), and a third battery contact 1116 is positioned along a side wall of the battery cavity 1111. The first and second battery contacts 1112, 1114 have elongated arcuate shapes, which may be symmetrical about a center of the circular battery cavity 1111. The first and second battery contacts 1112, 1114 are configured to contact the negative terminal of the battery, and the third battery contact 1116 is configured to contact the positive terminal of the battery. Also, the tag 1110 may be configured to detect the presence of the battery by detecting continuity between the first and second battery contacts 1112, 1114. For example, if there is continuity between the first and second battery contacts 1112, 1114, that may indicate that a battery is present in the battery cavity 1111 (regardless of whether the charge state of the battery).

Figure 11C:
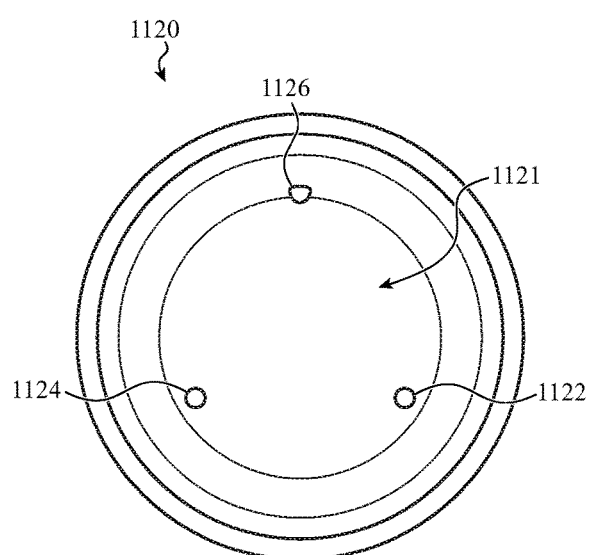

FIG. 11C shows another example tag 1120 in which two battery contacts are configured to contact the negative terminal of the battery, and one is configured to contact the positive terminal of the battery. In particular, first and second battery contacts 1122, 1124 are positioned on a bottom surface of a battery cavity 1121 (relative to the orientation shown in FIG. 11C), and a third battery contact 1126 is positioned along a side wall of the battery cavity 1121. The first and second battery contacts 1122, 1124 have rounded (e.g., circular) shapes, in contrast to the arcuate shapes of the contacts in FIG. 11B. The first and second battery contacts 1122, 1124 are configured to contact the negative terminal of the battery, and the third battery contact 1126 is configured to contact the positive terminal of the battery. Also, the tag 1120 may be configured to detect the presence of the battery by detecting continuity between the first and second battery contacts 1122, 1124.

Figure 11D:
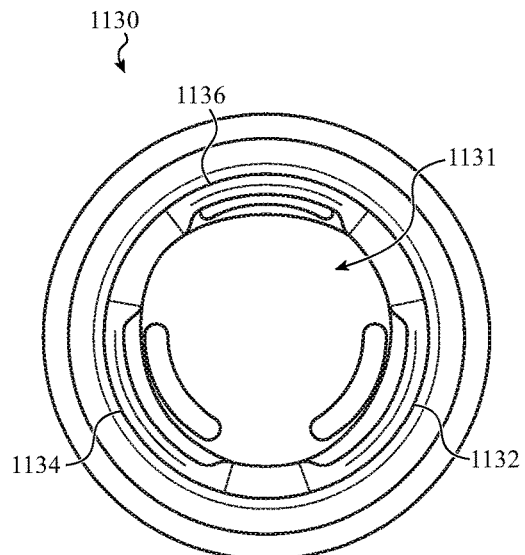

FIG. 11D shows another example tag 1130 in which two battery contacts are configured to contact the negative terminal of the battery, and one is configured to contact the positive terminal of the battery. In particular, first and second battery contacts 1132, 1134 are positioned on a bottom surface of a battery cavity 1131 (relative to the orientation shown in FIG. 11D), and a third battery contact 1136 is positioned along a side wall of the battery cavity 1131. The first and second battery contacts 1132, 1134 have elongated arcuate shapes, which may be symmetrical about a center of the circular battery cavity 1131. In this example, the third battery contact 1136 also has an elongated arcuate shape that conforms to the circular shape of the side wall of the battery cavity 1131.

In some cases, the battery door of a tag may also act as one of the battery contacts. For example, the battery door (e.g., the bottom housing member 516) may be formed of or include metal or another conductive material, and at least one terminal of the battery may be conductively coupled to the battery door. The battery door may, in turn, be conductively coupled to the circuit board. In this manner, at least one terminal of the battery (e.g., the positive terminal) may be conductively coupled to the circuit board via a conductive path that includes the battery door.

Figure 12A:
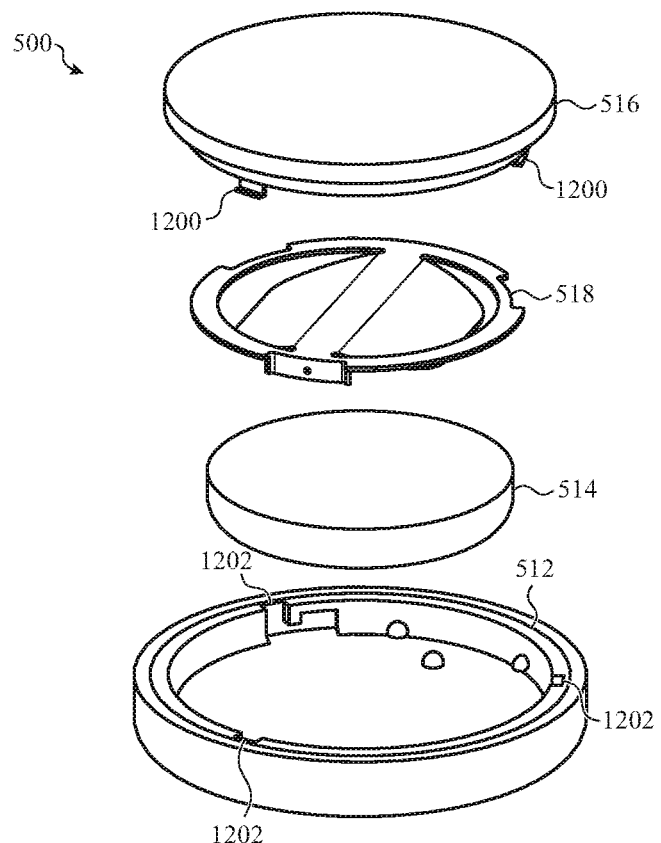
FIG. 12A depicts a partial exploded view of the wirelessly locatable tag of FIG. 5A.

FIG. 12A is a partial exploded view of the tag 500, illustrating features of the bottom housing member 516 (or battery door 516) and how the battery door 516 engages the rest of the tag 500 and how the battery 514 is retained in the tag 500 and biased towards the battery contacts of the tag 500.

The bottom housing member 516 may include latching members 1200 and the frame member 512 may define latching channels 1202 that are configured to engage the latching members 1200 to secure the bottom housing member 516 to the tag 500. The latching members 1200 and channels 1202 may be configured so that in order to remove the bottom housing member 516, the user must manipulate the bottom housing member 516 in multiple different directions (e.g., by both pressing on and turning the bottom housing member 516). This may help prevent unintended opening of the battery cavity, and may help prevent children from removing the button cell battery (which may pose choking or other hazards if removed from the tag 500).

Figure 12B:
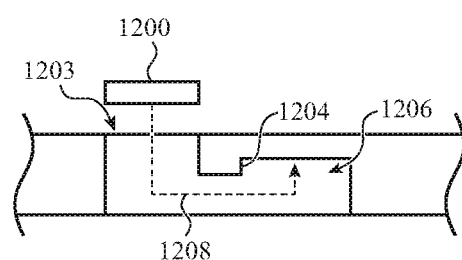
FIGS. 12B-12C depict operations of a latching member of the wirelessly locatable tag of FIG. 5A.

FIG. 12B illustrates a detail view of how a latching member 1200 engages a latching channel 1202 when the bottom housing member 516 is being attached to the tag 500. In particular, the bottom housing member 516 is aligned with the tag 500 (e.g., with the frame member 512 of the tag) such that the latching members 1200 are aligned with openings 1203 of the latching channels 1202. (For simplicity, the following description refers only to a single latching member and channel, but the tag 500 may include any suitable number of latching member/channel pairs, such as two, three, four, five, or more pairs.) The bottom housing member 516 is then pushed downwards, following the path 1208, until the latching member 1200 passes a retention protrusion 1204. The operation of pushing the latching member 1200 past the retention protrusion 1204 may include overcoming a spring force, provided by the compliant member 518, that tends to bias the bottom housing member 516 in an upwards direction, relative to the orientation shown in FIG. 12B.

After passing the retention protrusion 1204, and while maintaining a downward force on the bottom housing member 516 to overcome the biasing force, the user may twist or rotate the bottom housing member 516 to cause the latching member 1200 to continue along the path 1208 and move towards a recess 1206. Once the latching member 1200 is aligned with the recess 1206, such as because the latching member 1200 reaches the end of the latching channel 1202, the user may release the downward force on the bottom housing member 516, thereby causing the compliant member 518 to bias the bottom housing member 516 upwards and forcing the latching member 1200 into the recess 1206. Because the retention protrusion 1204 and the blind end of the latching channel 1202 block movement of the latching member 1200 in the horizontal direction (corresponding to a rotation or twisting of the bottom housing member 516), combined with the biasing force from the compliant member 518 tending to force the latching member 1200 into the recess 1206 (or with another surface of the latching channel 1202), the bottom housing member 516 may be securely retained to the tag 500 and may resist inadvertent or accidental opening.

Figure 12C:
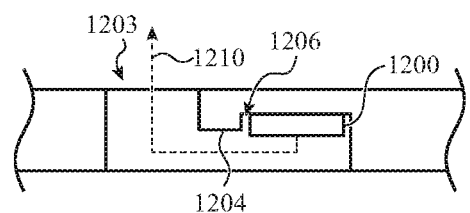

In order to detach the bottom housing member 516 from the tag, the operation described with respect to FIG. 12B may be reversed, as shown indicated by the path 1210 in FIG. 12C. Initially, a user applies a downward force to the bottom housing member 516 to move the latching member 1200 out of the recess 1206 and below the retention protrusion 1204. Once the latching member 1200 is clear of the retention protrusion 1204, and while maintaining the downward force on the bottom housing member 516, the bottom housing member 516 is rotated or twisted to move the latching member 1200 horizontally until it is aligned with the opening 1203 of the latching channel 1202, at which time the bottom housing member 516 may be forced upwards by the biasing force of the compliant member 518 and/or by the user pulling the bottom housing member 516 away from the tag 500.

The tag 500 may also include detents or other mechanisms to provide haptic or tactile sensations to a user during attachment and/or detachment of the bottom housing member 516. For example, the tag 500 may include a ball detent that engages a recess in the bottom housing member 516 when the bottom housing member 516 is rotated or twisted during attachment and/or detachment. As the ball detent engages the recess, the user may feel a clicking or other tactile sensation, indicating that the bottom housing member 516 is moving or has reached a particular position (e.g., a fully closed position). The detent (or other mechanism) may be attached to the bottom housing member 516 to engage a recess in the main frame member 512, or it may be attached to the main frame member 512 to engage a recess in the bottom housing member 516. Other configurations are also possible. Further, detents or other mechanisms may be provided for any moving or detachable components of tags described herein, and may be provided solely for the tactile indication that they provide during manipulation of the components, or for other additional functions (e.g., to removably retain a battery door, housing member, or other component in a particular position).

Figure 13A:
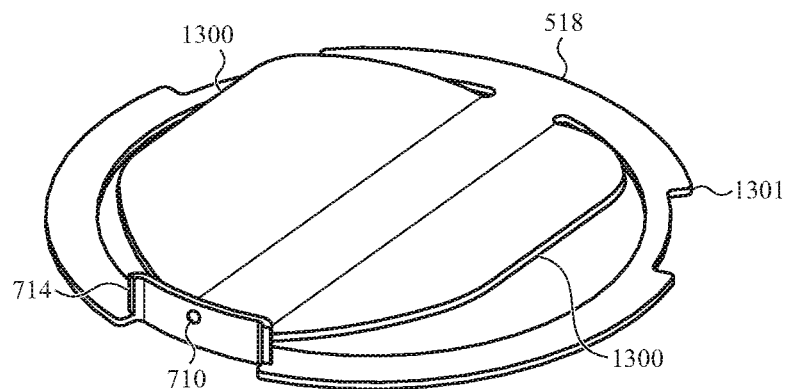
FIG. 13A depicts an example compliant member of the wirelessly locatable tag of FIG. 5A.

The compliant member 518 may provide a biasing force that both helps bias the bottom housing member 516 into an engaged or locked configuration (as described with respect to FIGS. 12A-12C), and bias the battery 514 towards the battery contacts of the battery connector 900. FIG. 13A illustrates the compliant member 518. The compliant member 518 defines a base 1301 that may be attached to an inner surface of the bottom housing member 516 (e.g., via adhesive, welding, soldering, fasteners, or any other suitable attachment technique). The compliant member 518 may also define spring arms 1300 that extend from the base 1301 and are configured to contact the battery 514. The base 1301 and spring arms 1300 may be defined by a single unitary piece of material. The material may be any suitable material, including but not limited to metal (e.g., stainless steel), a polymer, or the like.

As described above, the compliant member 518 also defines a flange portion 714, which may also be defined by the same single piece of material that defines the base 1301 and spring arms 1300. The flange portion 714 may be configured to help retain a membrane and/or other components near an opening that allows pressure equalization. The flange portion 714 may also define an opening 710 that aligns with the pressure equalization opening.

Figure 13B:
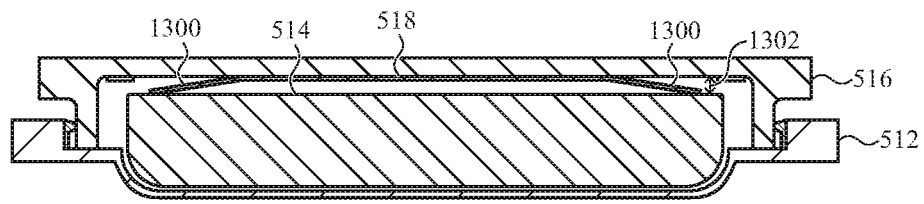
FIG. 13B depicts a partial cross-sectional view of a portion of the wirelessly locatable tag of FIG. 5A.

FIG. 13B is a partial cross-sectional view of the tag 500, illustrating the operation of the compliant member 518. As shown, the bottom housing member 516 is attached to the frame member 512, a state that results in the compliant member 518 being compressed or otherwise in a state that produces a biasing force. More particularly, the spring arms 1300 are pressed against the battery 514, causing the compliant member 518 to produce a force (indicated by arrow 1302) tending to push the battery 514 towards the frame member 512 and push the bottom housing member 516 away from the frame member 512. This ultimately forces the battery 514 into contact with the deflectable arms of the battery connector 900 and helps maintain the secure engagement of the latching members 1200 with the latching channels 1202 (FIGS. 12A-12C).

The presence of the compliant member 518 may also facilitate the use of battery connectors that do not deflect. For example, any of the battery contacts and/or deflectable arms described above for conductively coupling to a battery may be configured to not deflect when a battery is inserted into the battery cavity. In such cases, the compliance of the compliant member 518 both biases the battery 514 against the non-deflecting battery contacts to ensure conductive coupling, and also provides clearance to the battery to accommodate for any canting or misalignment of the battery due to the non-deflecting battery contacts.

Figure 13C:
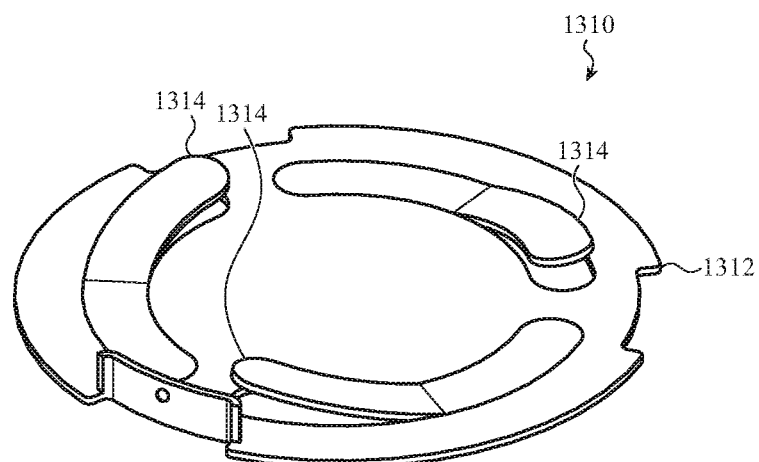
FIG. 13C depicts another example compliant member for a wirelessly locatable tag.

While FIG. 13A shows one example configuration of a compliant member for biasing the bottom housing member 516 and the battery 514, other types of compliant members may also be used. FIG. 13C illustrates one such alternative example compliant member 1310. The compliant member 1310, which may be formed from a single piece of metal, polymer, or the like, defines a base 1312 and three curved spring arms 1314, each extending along a circular path inside the perimeter of the base 1312 and extending from the base 1312. Other configurations of unitary metal compliant members are also contemplated. Further, other components, mechanisms, or systems may be used instead of or in addition to unitary metal compliant members, including but not limited to coil springs, elastomers, foams, leaf springs, or the like.

As noted above, button cell or other small form-factor batteries may be potentially hazardous to people or pets due to their small size and possibility of being ingested. To avoid the batteries from accidentally falling out of the tags, the tags may be configured so that their battery doors require more than a simple, single motion (e.g., twisting) to remove them. FIGS. 12A-12C, for example, illustrate one configuration that requires a user to both press and twist the battery door (e.g., the bottom housing member 516) in order to open it. Other mechanisms may also be used to securely retain a battery door to a tag in a manner that prevents or limits accidental opening and satisfies applicable laws or regulations for device safety. FIGS. 14A-25C illustrate several example configurations of such retention mechanisms.

Figure 14A:
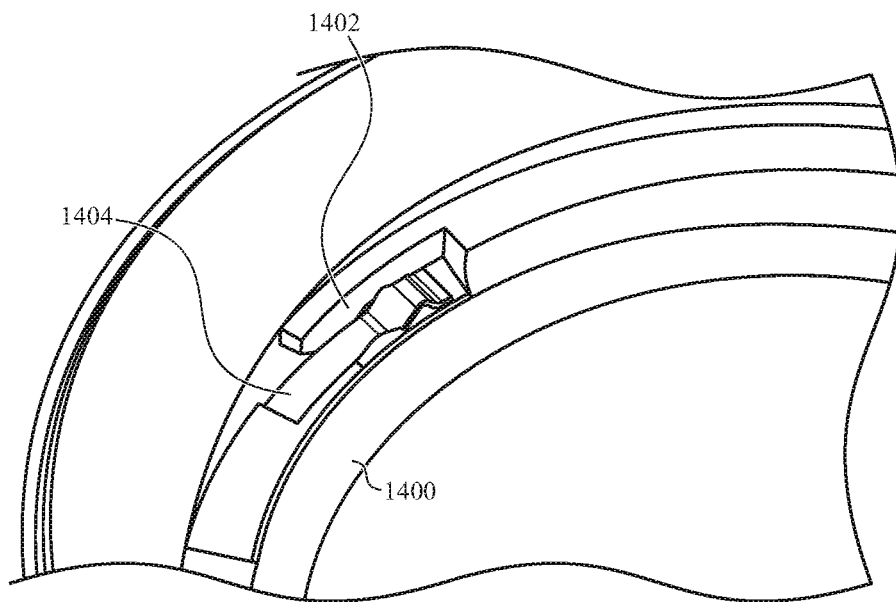
FIGS. 14A-16D depict an example mechanism for securing a battery door of a wirelessly locatable tag.

FIGS. 14A-16D illustrate various aspects of an example mechanism for securely retaining a battery door (e.g., a bottom housing member) to a tag. FIG. 14A illustrates a portion of a frame member 1400 that defines a channel 1402 and a spring member 1404 that extends into the channel 1402 and/or defines part of the channel. The frame member 1400 may be an embodiment of the frame member 512, and may include any or all of the components and may provide any or all of the functionality of the frame member 512 (and may be integrated with the tag 500 or any other tag described herein). For brevity such details may not be repeated here.

Figure 14B:
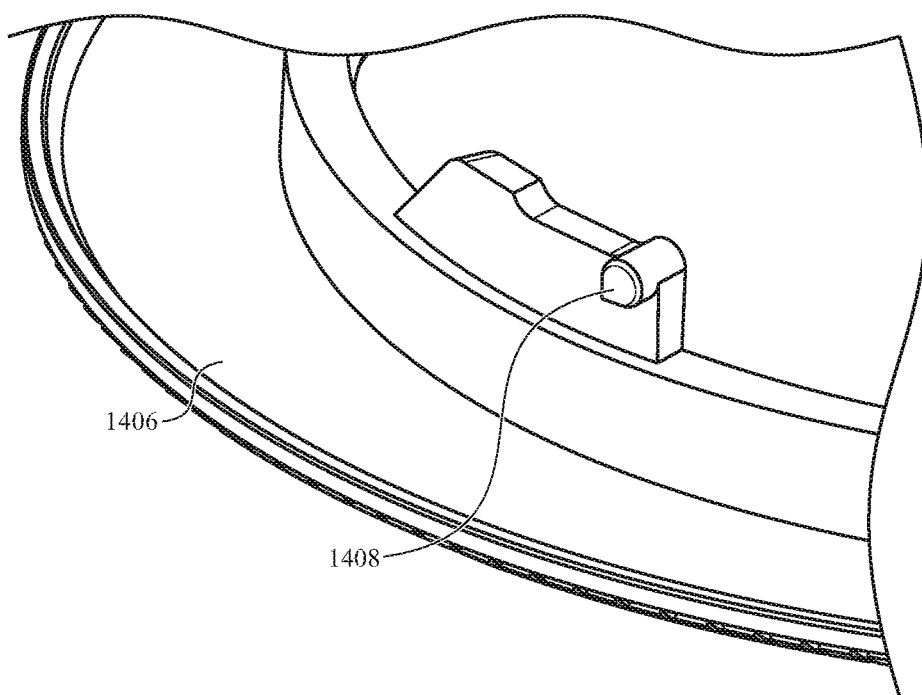

FIG. 14B illustrates a portion of a bottom housing member 1406 that is configured to mate with the frame member 1400 in FIG. 14A. The bottom housing member 1406 may be an embodiment of the bottom housing member 516, and may include any or all of the components and may provide any or all of the functionality of the bottom housing member 516. For brevity such details may not be repeated here. The bottom housing member 1406 includes a pin 1408 that is configured to engage with the frame member 1400 via the channel 1402 and/or the spring member 1404 to retain the bottom housing member 1406 to the frame member 1400.

Figure 15A:
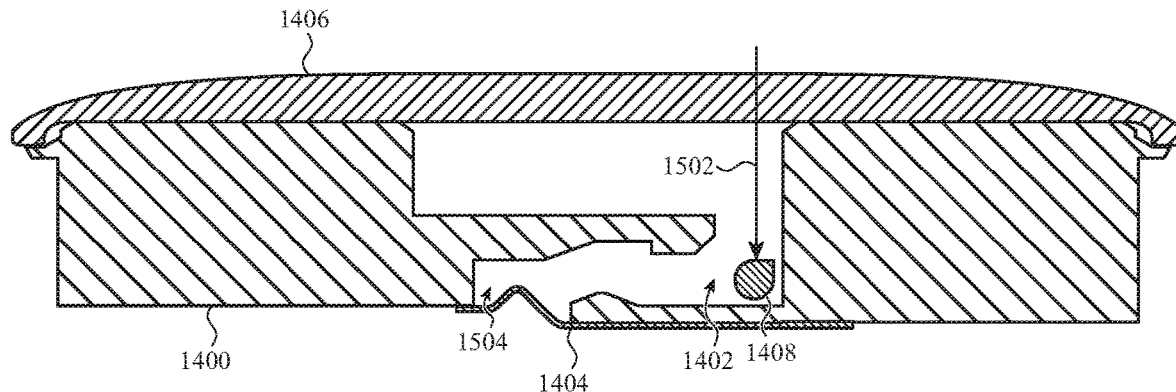
Figure 15B:
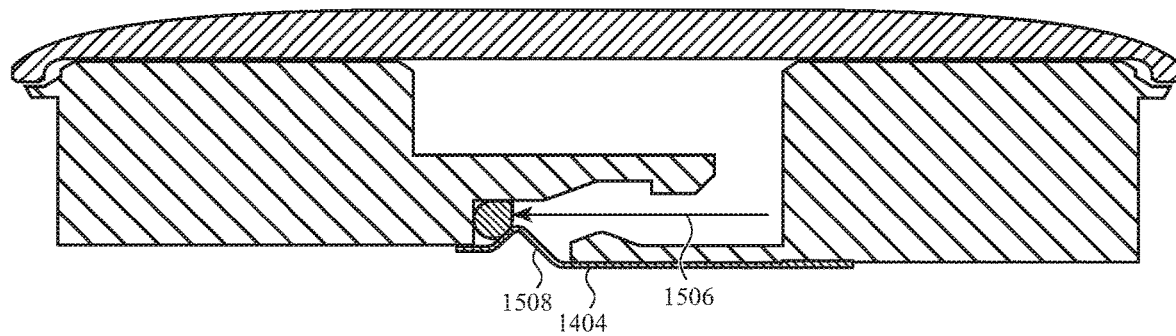

FIGS. 15A-15B illustrate a schematic view of the frame member 1400 and the bottom housing member 1406, showing how the pin 1408 engages the channel 1402 and the spring member 1404 when the bottom housing member 1406 is being attached to the frame member 1400. As shown in FIG. 15A, the bottom housing member 1406 is positioned relative to the frame member 1400 such that the pin 1408 enters the channel 1402, along the path 1502. More particularly, the bottom housing member 1406 may be moved vertically (relative to the orientation in FIG. 15A) to position the pin 1408 in the channel 1402. This manipulation may require overcoming a biasing force (acting in an upward direction) imparted to the bottom housing member 1406 by a spring or other mechanism (such as the compliant member 518, FIG. 5B).

After positioning the pin 1408 in the channel 1402 as shown in FIG. 15A, rotating or twisting the bottom housing member 1406 causes the pin 1408 to move through the channel 1402 along the path 1506 to a blind end 1504 (FIG. 15A) of the channel 1402. This manipulation results in the pin 1408 contacting a retention feature 1508 of the spring member 1404, resulting in the spring member 1404 deflecting downwards to accommodate the pin 1408. The retention feature 1508 may also contact the pin 1408 to retain the pin 1408 in the blind end 1504 of the channel 1402. The action of sliding the pin 1408 over the retention feature 1508 may also produce a tactile click-like feeling that is detectable by the user when twisting the bottom housing member 1406 into the closed configuration. This tactile sensation may indicate to the user that the bottom housing member 1406 has reached a fully closed and secured position, and that the user can cease turning the bottom housing member 1406.

Figure 16A:
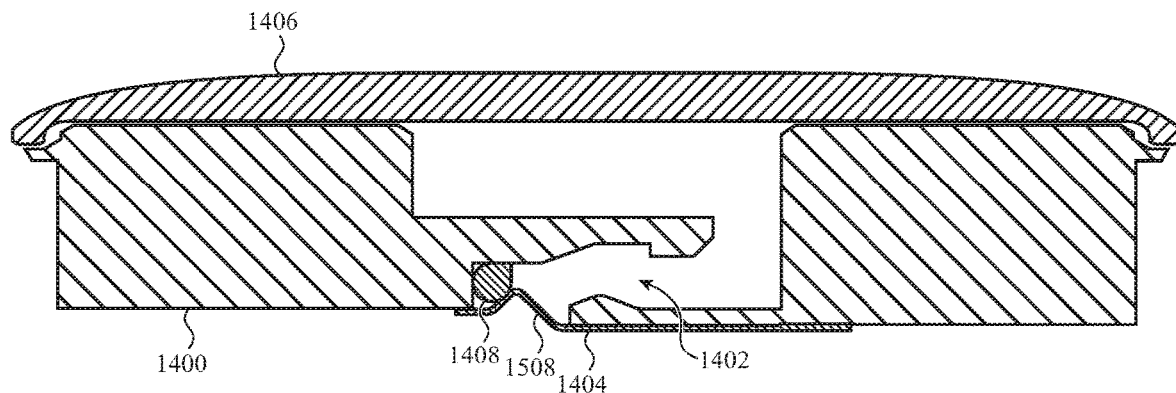
Figure 16B:
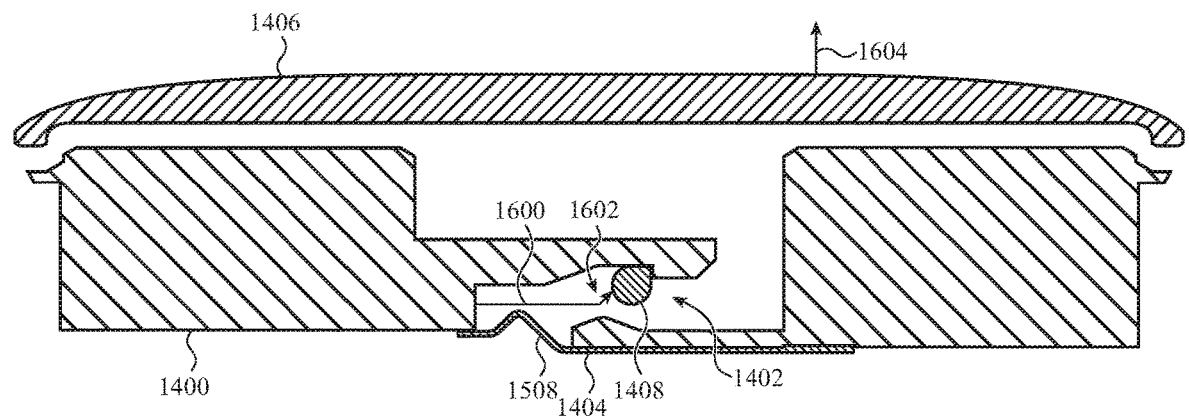

FIGS. 16A-16D illustrate a schematic view of the frame member 1400 and the bottom housing member 1406, showing how the pin 1408 disengages from the channel 1402 and the spring member 1404 when the bottom housing member 1406 is being detached from the frame member 1400. As shown in FIG. 16A, the bottom housing member 1406 is positioned relative to the frame member 1400 such that the pin 1408 is securely maintained in the blind end 1504 of the channel 1402. In order to detach the bottom housing member 1406, a user may twist or rotate the bottom housing member 1406, causing the pin 1408 to slide along the path 1600 in FIG. 16B. This motion causes the pin 1408 to contact the retention feature 1508, which in turn causes the spring member 1404 to deflect downwards. Because the spring member 1404 is biased upwards, the contact between the pin 1408 and the retention feature 1508 produces a resistance to rotation of the bottom housing member 1406 which, when overcome, pushes the spring member 1404 downwards. This interaction between the pin 1408 and the retention feature 1508 provides several benefits, including producing an increased resistance that the user must overcome in order to detach the bottom housing member 1406, and also potentially producing a tactile click or detent sensation that indicates to the user that the bottom housing member 1406 has been moved out of a securely locked condition.

Once the pin 1408 has been moved out of the blind end 1504 of the channel 1402 and as the bottom housing member 1406 continues to be rotated, the biasing force (indicated by arrow 1604) between the frame member 1400 and the bottom housing member 1406 forces the bottom housing member 1406 and thus the pin 1408 upwards and into a recess 1602. The biasing force may be produced by a compliant member between the battery and the bottom housing member 1406, as described above. The recess 1602 defines a lip that prevents or inhibits further rotation of the bottom housing member 1406. In order to continue detaching the bottom housing member 1406, the user must press on the bottom housing member 1406 to provide a downward force 1606 that overcomes the biasing force to push the bottom housing member 1406, and thus the pin 1408, downwards and out of the recess 1602 (as indicated by path 1608 in FIG. 16C).

Figure 16C:
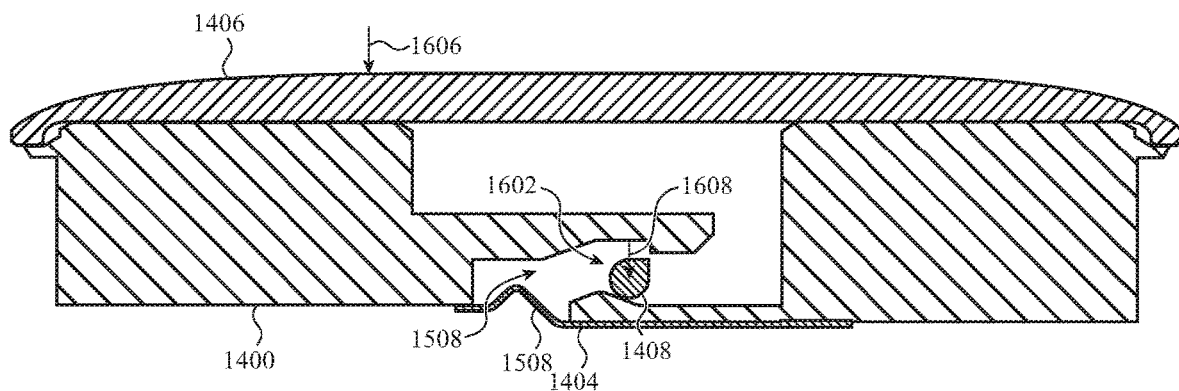
Figure 16D:
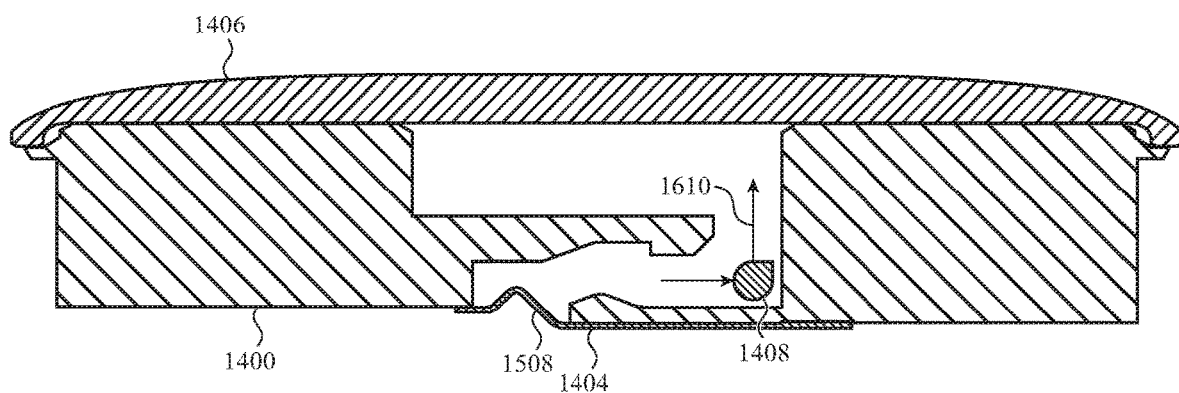

Once the pin 1408 is clear of the lip of the recess 1602, as shown in FIG. 16C, the user may continue to rotate the bottom housing member 1406 until the pin 1408 clears the top wall of the channel and is able to be removed from the channel, as indicated by path 1610 in FIG. 16D. More specifically, once the pin 1408 is positioned as shown in FIG. 16D, the bottom housing member 1406 can be simply lifted away from the frame member 1400 to access the battery.

Figure 17A:
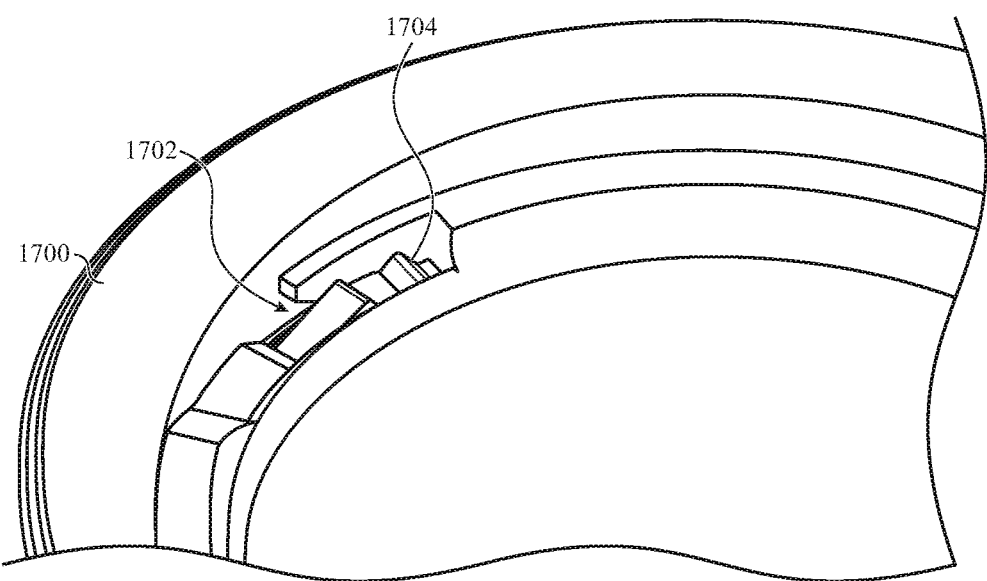
FIGS. 17A-19E depict another example mechanism for securing a battery door of a wirelessly locatable tag.

FIGS. 17A-19E illustrate various aspects of another example mechanism for securely retaining a battery door (e.g., a bottom housing member) to a tag. FIG. 17A illustrates a portion of a frame member 1700 that defines a channel 1702 and a spring member 1704 that extends into the channel 1702 and/or defines part of the channel. The frame member 1700 may be an embodiment of the frame member 512, and may include any or all of the components and may provide any or all of the functionality of the frame member 512 (and may be integrated with the tag 500 or any other tag described herein). For brevity such details may not be repeated here.

Figure 17B:
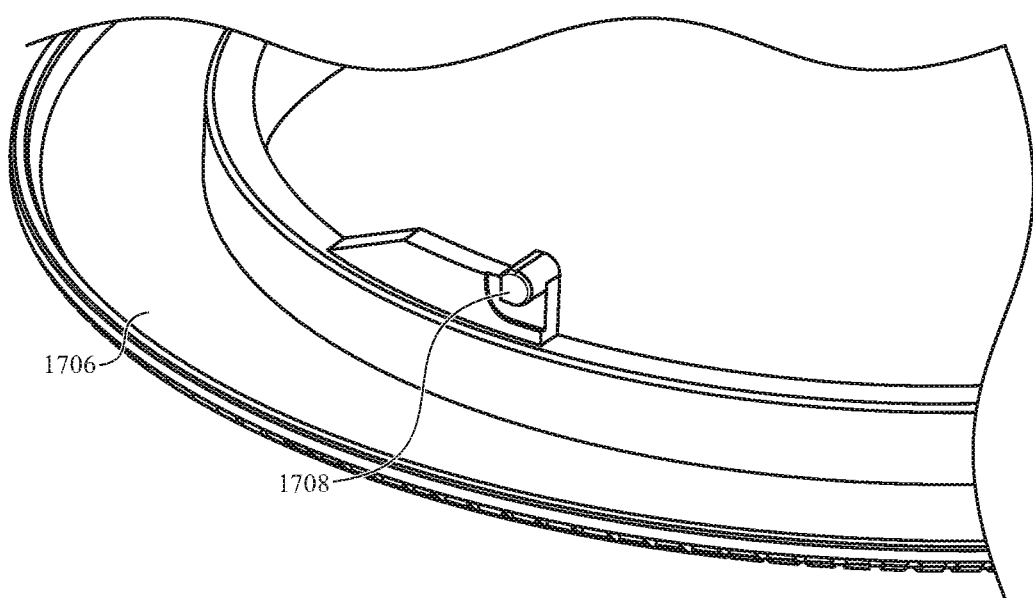

FIG. 17B illustrates a portion of a bottom housing member 1706 that is configured to mate with the frame member 1700 in FIG. 17A. The bottom housing member 1706 may be an embodiment of the bottom housing member 516, and may include any or all of the components and may provide any or all of the functionality of the bottom housing member 516. For brevity such details may not be repeated here. The bottom housing member 1706 includes a pin 1708 that is configured to engage with the frame member 1700 via the channel 1702 and/or the spring member 1704 to retain the bottom housing member 1706 to the frame member 1700.

Figure 17C:
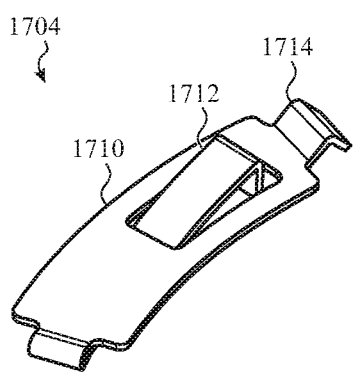

FIG. 17C shows the spring member 1704 removed from the frame member 1700. The spring member 1704 defines two at least partially independently actuatable retention features 1712, 1714. The first retention feature 1712 may be at least partially within an opening in a base 1710, and the second retention feature 1714 may be formed at an end of the base 1710. The spring member 1704 may be a unitary component formed of metal, polymer, or any other suitable material. Accordingly, the retention features and the base may be formed from the same piece of material.

Figure 18A:
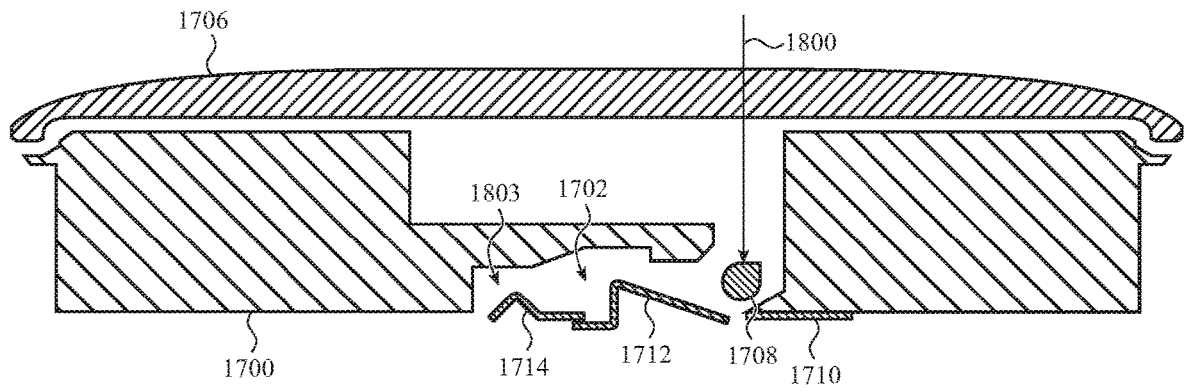
Figure 18B:
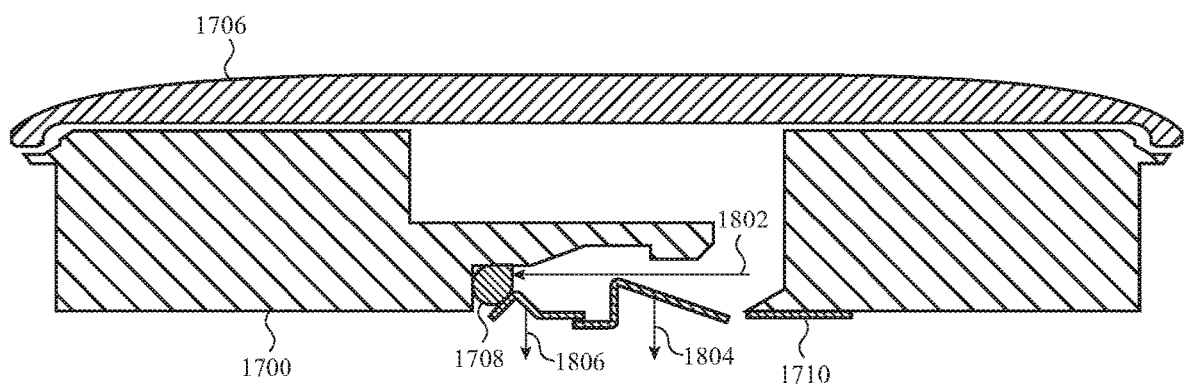

FIGS. 18A-18B illustrate a schematic view of the frame member 1700 and the bottom housing member 1706, showing how the pin 1708 engages the channel 1702 and the spring member 1704 when the bottom housing member 1706 is being attached to the frame member 1700. As shown in FIG. 18A, the bottom housing member 1706 is positioned relative to the frame member 1700 such that the pin 1708 enters the channel 1702, along the path 1800. More particularly, the bottom housing member 1706 may be moved vertically (relative to the orientation in FIG. 18A) to position the pin 1708 in the channel 1702. This manipulation may require overcoming a biasing force (acting in an upward direction) imparted to the bottom housing member 1706 by a spring or other mechanism (such as the compliant member 518, FIG. 5B).

After positioning the pin 1708 in the channel 1702 as shown in FIG. 18A, rotating or twisting the bottom housing member 1706 causes the pin 1708 to move through the channel 1702 along the path 1802 to a blind end 1803 (FIG. 18A) of the channel 1702. This manipulation results in the pin 1708 contacting both the first and second retention features 1712, 1714 of the spring member 1704, resulting in the both the first and second retention features 1712, 1714 deflecting downwards as the pin 1708 contacts them and passes them (as indicated by arrows 1804, 1806). The second retention feature 1714 may also contact the pin 1708 to retain the pin 1708 in the blind end 1803 of the channel 1702. The action of sliding the pin 1708 over the retention features 1712, 1714 may also produce a tactile click-like feeling that is detectable by the user when twisting the bottom housing member 1706 into the closed configuration.

Figure 19A:
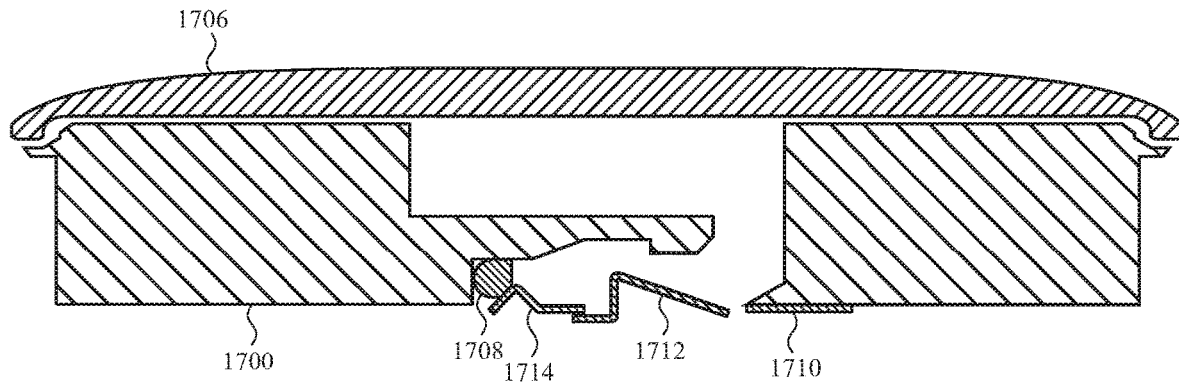

FIGS. 19A-19D illustrate a schematic view of the frame member 1700 and the bottom housing member 1706, showing how the pin 1708 disengages from the channel 1702 and the spring member 1704 when the bottom housing member 1706 is being detached from the frame member 1700. As shown in FIG. 19A, the bottom housing member 1706 is positioned relative to the frame member 1700 such that the pin 1708 is securely maintained in the blind end 1803 of the channel 1702. In order to detach the bottom housing member 1706, a user may twist or rotate the bottom housing member 1706, causing the pin 1708 to slide along the path 1900 in FIG. 19B. This motion causes the pin 1708 to contact the second retention feature 1714, which in turn causes the second retention feature 1714 to deflect downwards. Because the second retention feature 1714 is biased upwards, the contact between the pin 1708 and the second retention feature 1714 produces a resistance to rotation of the bottom housing member 1706 which, when overcome, pushes the second retention feature 1714 downwards. This interaction between the pin 1708 and the second retention feature 1714 provides several benefits, including producing an increased resistance that the user must overcome in order to detach the bottom housing member 1706, and also potentially producing a tactile click or detent sensation that indicates to the user that the bottom housing member 1706 has been moved out of a securely locked condition.

Figure 19B:
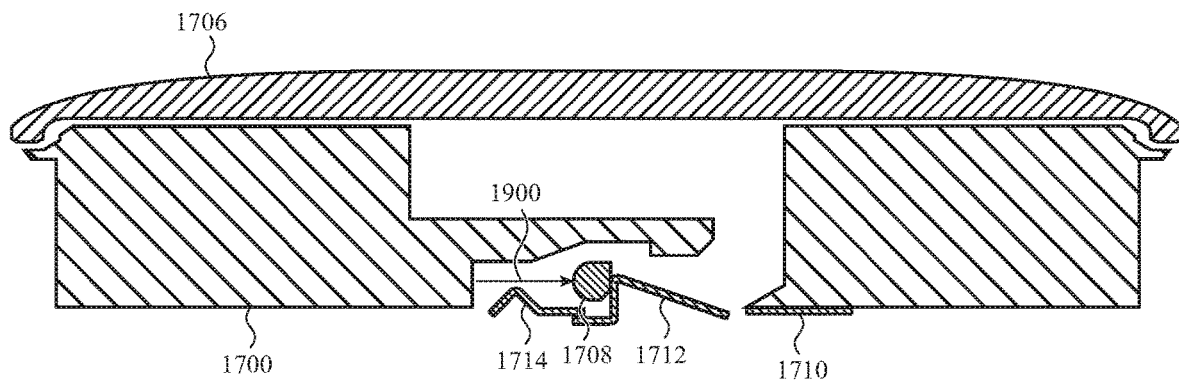
Figure 19C:
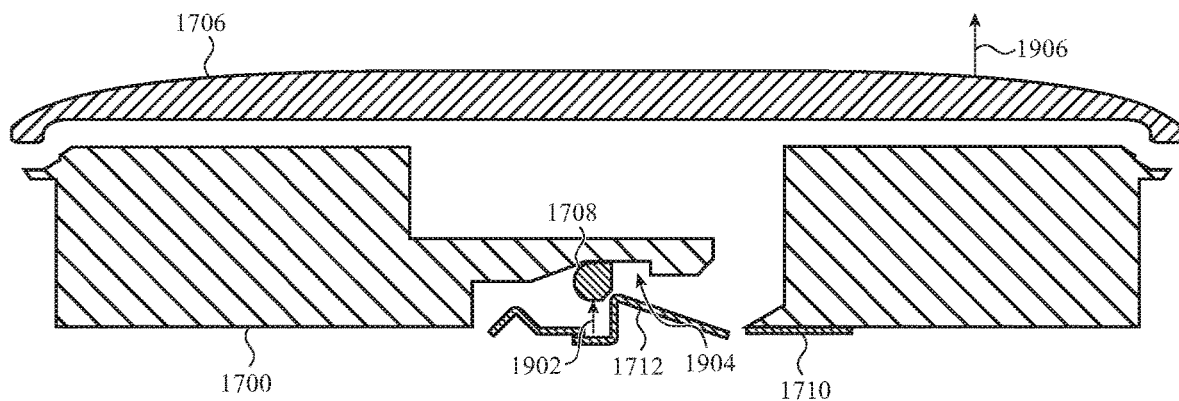
Figure 19D:
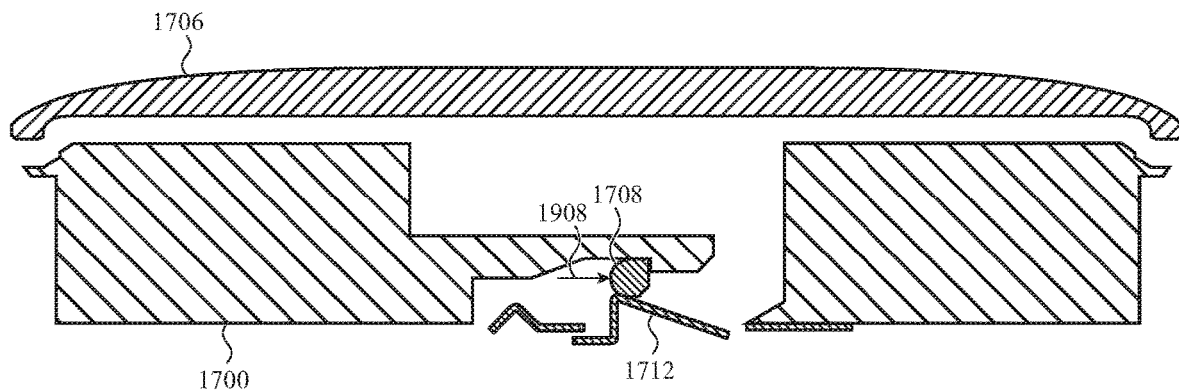
Figure 19E:
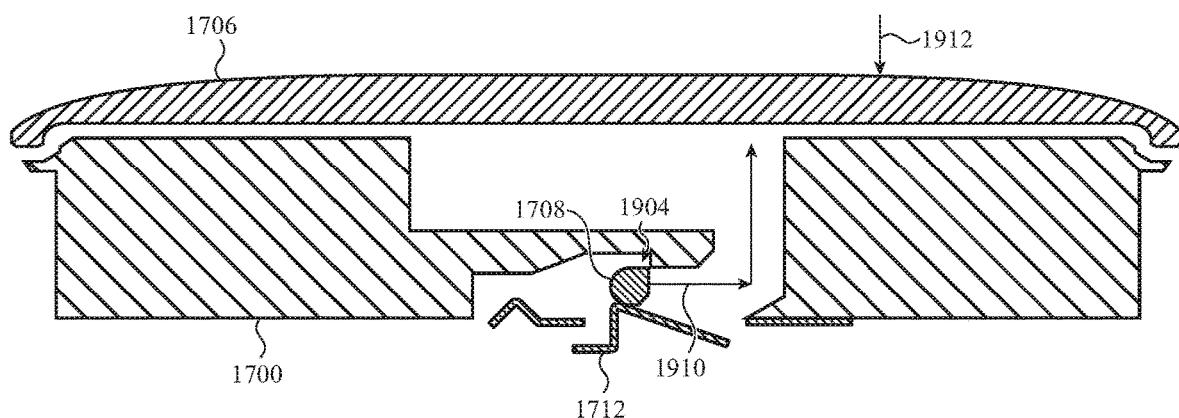

Once the pin 1708 has been moved past the second retention feature 1714, it may come into contact with a surface of the first retention feature 1712 that prevents further rotation of the bottom housing member 1706, as shown in FIG. 19B. Due to the biasing force (indicated by arrow 1906) between the frame member 1700 and the bottom housing member 1706, the bottom housing member 1706 and thus the pin 1708 may be forced upwards along the path 1902 and into a recess 1904. The biasing force may be produced by a compliant member between the battery and the bottom housing member 1706, as described above. When the pin 1708 is in the position shown in FIG. 19C, the first retention feature 1712 may still be overlapping the pin 1708, thereby inhibiting further rotational movement. The user may continue to rotate the bottom housing member 1706 to move the pin along the path 1908 (FIG. 19D). This rotation results in the pin 1708 (e.g., a chamfered or angled surface of the pin 1708) contacting the first retention feature 1712 and forcing the first retention feature 1712 downward. Like other manipulations resulting in an interaction between a pin and a spring member, this may produce a tactile output that indicates to a user that a particular manipulation has been successfully completed.

After the bottom housing member 1706, and thus the pin 1708, has been rotated to move the pin 1708 past the second retention feature 1712, further rotation of the pin 1708 may be inhibited by lip of the recess 1904. In order to continue detaching the bottom housing member 1706, the user must press on the bottom housing member 1706 to provide a downward force 1912 that overcomes the biasing force to push the bottom housing member 1706, and thus the pin 1708, downwards and out of the recess 1904 (as indicated by path 1910 in FIG. 19E). Once the pin 1708 is clear of the lip of the recess 1904, as shown in FIG. 19D, the user may continue to rotate the bottom housing member 1706 until the pin 1708 clears the top wall of the channel and is able to be removed from the channel, as indicated by path 1910.

Figure 20A:
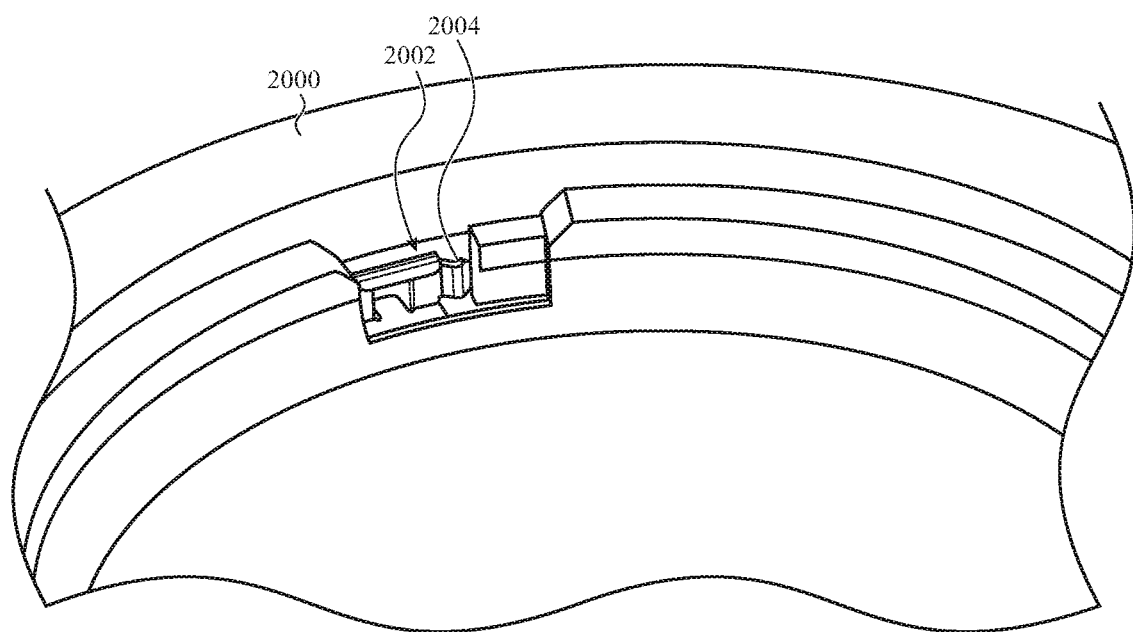
FIGS. 20A-22D depict another example mechanism for securing a battery door of a wirelessly locatable tag.

FIGS. 20A-22D illustrate various aspects of another example mechanism for securely retaining a battery door (e.g., a bottom housing member) to a tag. FIG. 20A illustrates a portion of a frame member 2000 that defines a latching region 2002 and a spring member 2004 that extends into the latching region 2002 and/or defines part of the latching region. The frame member 2000 may be an embodiment of the frame member 512, and may include any or all of the components and may provide any or all of the functionality of the frame member 512 (and may be integrated with the tag 500 or any other tag described herein). For brevity such details may not be repeated here.

Figure 20B:
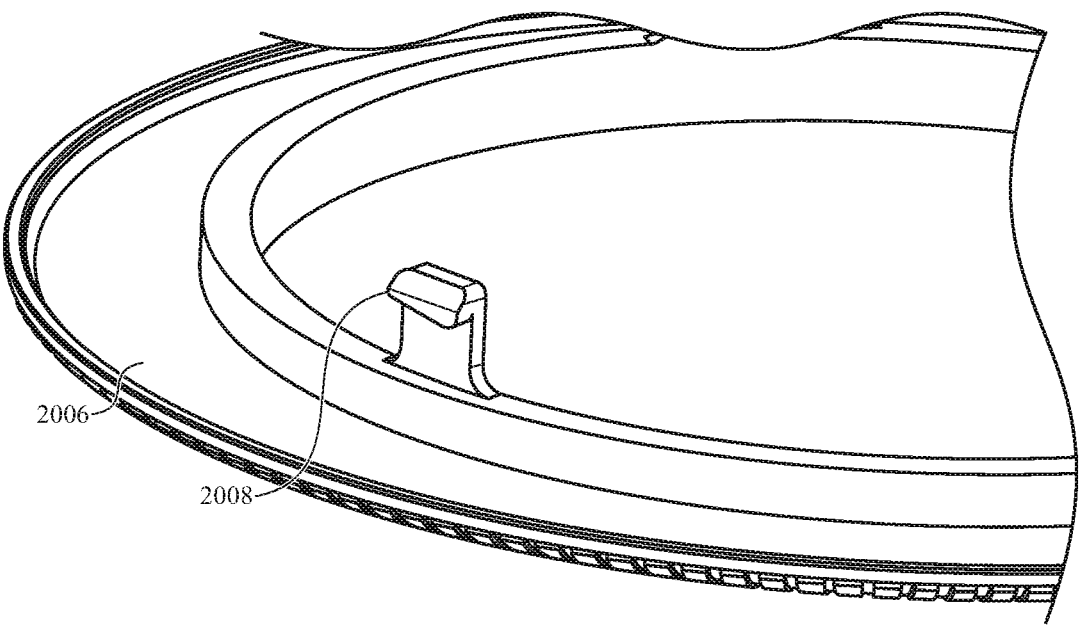

FIG. 20B illustrates a portion of a bottom housing member 2006 that is configured to mate with the frame member 2000 in FIG. 20A. The bottom housing member 2006 may be an embodiment of the bottom housing member 516, and may include any or all of the components and may provide any or all of the functionality of the bottom housing member 516. For brevity such details may not be repeated here. The bottom housing member 2006 includes a latch 2008 that is configured to engage with the frame member 2000 via the latching region 2002 and/or the spring member 2004 to retain the bottom housing member 2006 to the frame member 2000.

Figure 20C:
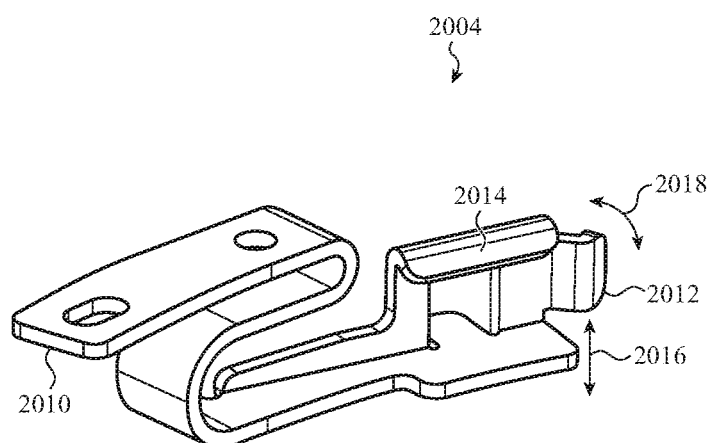

FIG. 20C shows the spring member 2004 removed from the frame member 2000. The spring member 2004 defines a first retention feature 2012 and a second retention feature 2014. The spring member 2004 may also define a base portion 2010 that is secured to the frame member 2000. The spring member 2004 may be configured to deflect or move in multiple directions during attachment and detachment of the bottom housing member 2006. For example, as described herein, an interaction between the latch 2008 and the second retention feature 2014 during attachment of the bottom housing member 2006 may cause the spring member 2004 to deflect along a direction indicated by arrow 2018, while an interaction between the latch 2008 and the second retention feature 2014 during detachment of the bottom housing member 2006 may cause the spring member 2004 to deflect along a direction indicated by arrow 2016. The spring member 2004 may be a unitary component formed of metal, polymer, or any other suitable material.

Figure 21A:
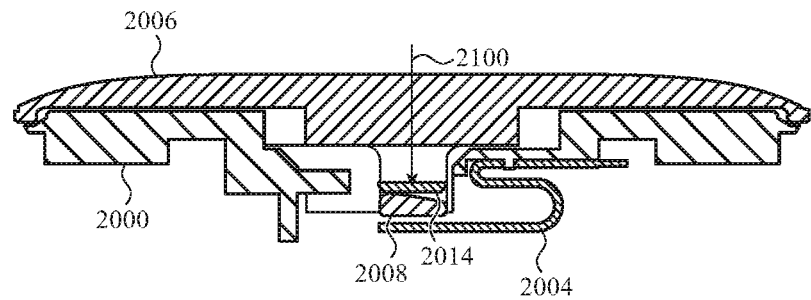
Figure 21B:
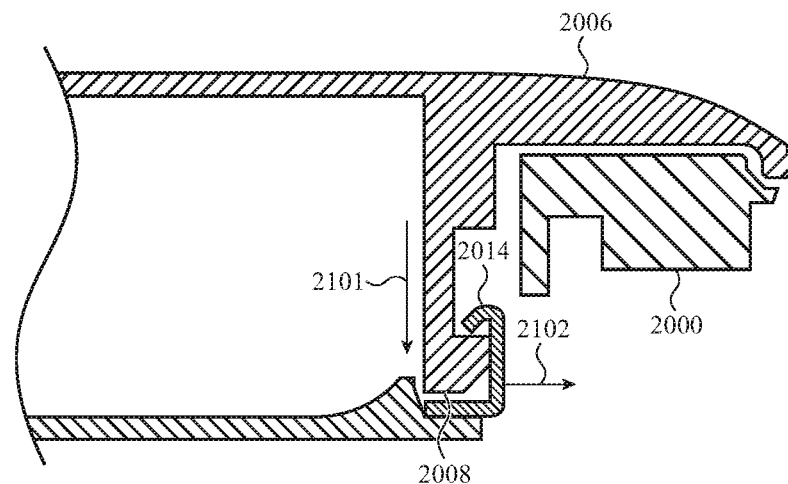
Figure 21C:
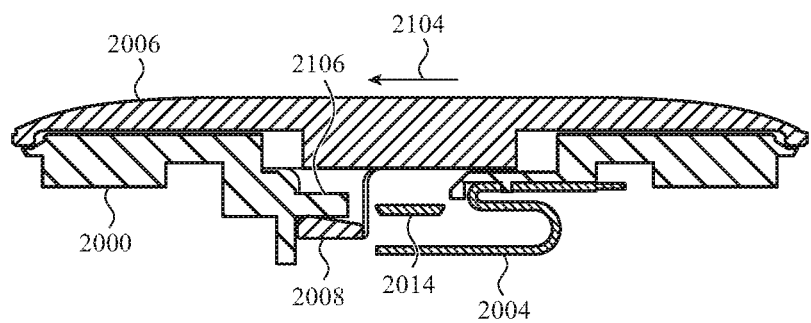

FIGS. 21A-21C illustrate a schematic view of the frame member 2000 and the bottom housing member 2006, showing how the latch 2008 engages the frame member 2000 and the spring member 2004 when the bottom housing member 2006 is being attached to the frame member 2000. As shown in FIG. 21A, the bottom housing member 2006 is positioned relative to the frame member 2000 such that the latch 2008 enters the latching region 2002, along the path 2100. More particularly, the bottom housing member 2006 may be moved vertically (relative to the orientation in FIG. 21A) to position the latch 2008 in the latching region 2002 and into an engagement with the spring member 2004. This manipulation may require overcoming a biasing force (acting in an upward direction) imparted to the bottom housing member 2006 by a spring or other mechanism (such as the compliant member 518, FIG. 5B).

FIG. 21B illustrates a partial cross-sectional view of the latch 2008 and the spring member 2004, showing how the latch 2008 and the spring member 2004 interact as the bottom housing member 2006 is attached to the frame member 2000. In particular, as the bottom housing member 2006 is moved vertically downwards (arrow 2101 in FIG. 21B), the latch 2008 (e.g., a chamfered or otherwise contoured surface of the latch 2008) pushes against the top of the second retention feature 2014 of the spring member 2004. This interaction forces the spring member 2004 to deflect away from the latch 2008 along a direction indicated by arrow 2102. Once the end of the latch 2008 passes the second retention feature 2014, the biasing force of the spring member 2004 forces the spring member 2004 back towards the latch 2008 such that the latch 2008 overlaps the second retention feature 2014 to retain the latch 2008 below the second retention feature 2014. Similar to other interactions with retention features, pushing the latch 2008 past the second retention feature 2014 requires an increased force from the user and may result in a click or other tactile sensation, thus indicating to the user that the bottom housing member 2006 has become engaged.

After engaging the latch 2008 and the second retention feature 2014 as shown in FIGS. 21A and 21B, further rotating or twisting of the bottom housing member 2006, indicated by arrow 2104) causes the latch 2008 to move out of engagement with the second retention feature 2014, slide over the first retention feature 2012 (resulting in another deflection of the spring member 2004 along the direction 2102 in FIG. 21B), and end up positioned at a blind end of the latching region 2002 and below a third retention feature 2106. The third retention feature 2106 may prevent or inhibit upwards movement of the latch 2008, while the first retention feature 2012 may remain in contact with the latch 2008 to retain the latch 2008 in the position shown in FIG. 21C. The action of sliding the latch 2008 over the first retention feature 2012, may also produce a tactile click-like feeling that is detectable by the user when twisting the bottom housing member 2006 into the closed configuration.

Figure 22A:
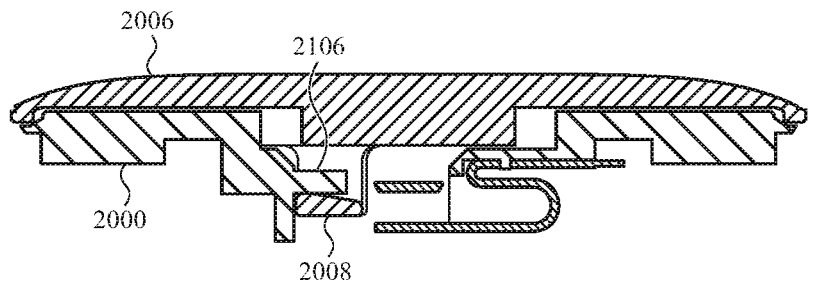
Figure 22B:
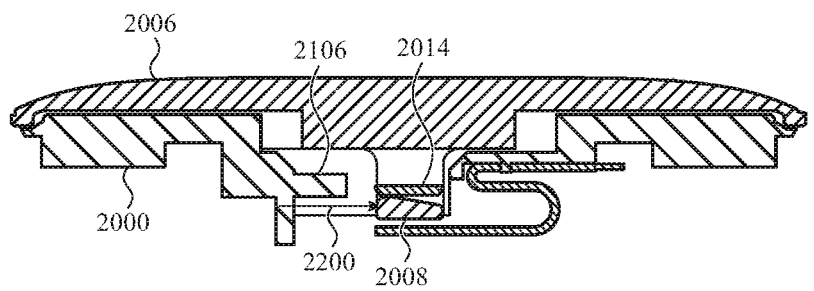
Figure 22C:
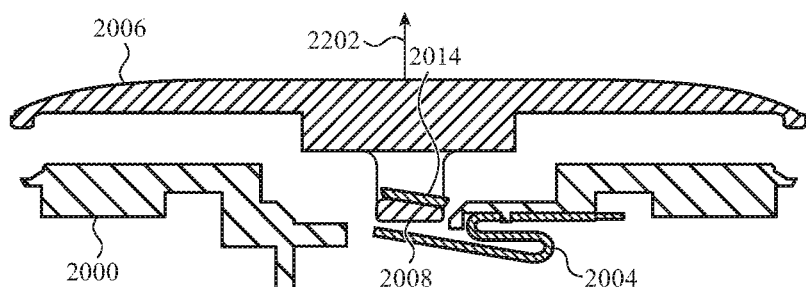
Figure 22D:
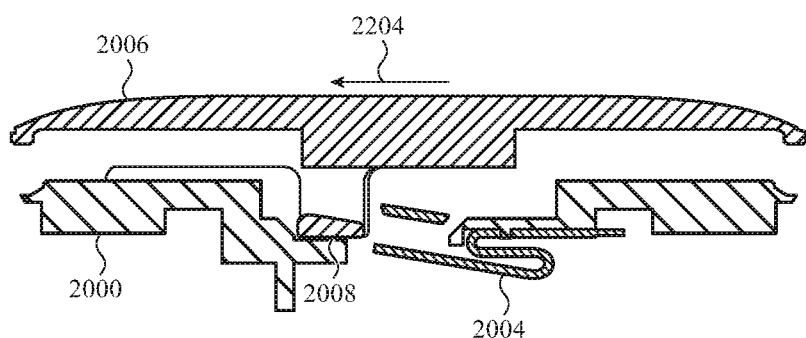

FIGS. 22A-22D illustrate a schematic view of the frame member 2000 and the bottom housing member 2006, showing how the latch 2008 disengages from the latching region 2002 and the spring member 2004 when the bottom housing member 2006 is being detached from the frame member 2000. As shown in FIG. 22A, the bottom housing member 2006 is positioned relative to the frame member 2000 such that the latch 2008 is securely maintained in the blind end of the latching region 2002 and below the third retention feature 2106. In order to detach the bottom housing member 2006, a user may twist or rotate the bottom housing member 2006, causing the latch 2008 to slide along the path 2200 in FIG. 22B. This motion causes the latch 2008 to contact the first retention feature 2012, which in turn causes the spring member 2004 to deflect outwards (e.g., along the direction 2102 in FIG. 21B). Because the first retention feature 2012 is biased towards the latch 2008, the contact between the latch 2008 and the first retention feature 2012 produces a resistance to rotation of the bottom housing member 2006 and potentially produces a tactile click or detent sensation that indicates to the user that the bottom housing member 2006 has been moved out of a securely locked condition.

Once the latch 2008 has been moved past the first retention feature 2012, it may return to the position shown in FIGS. 21A-21B, wherein the latch 2008 is below and overlaps the second retention feature 2014. To continue detaching the bottom housing member 2006, the user pulls the bottom housing member 2006 upwards, along the direction 2202, which causes the latch 2008 to pull the second retention feature 2014 upwards, thereby deflecting the spring member 2004 along the direction 2016 (FIG. 20C). Once the spring member 2004 is deflected, rotating the bottom housing member 2006 along direction 2204 (e.g., in the direction opposite that indicated in FIG. 22B) causes the latch 2008 to slide over the first retention feature 2012 once again, thereby disengaging the latch 2008 from the spring member 2004 and allowing the bottom housing member 2006 to be removed. The final engagement between the latch 2008 and the first retention feature 2012 may provide a final tactile indication that the bottom housing member 2006 has been detached.

The mechanism shown and described with respect to FIGS. 20A-22D may include hard-stops formed in the frame member 2000 and/or the spring member 2004 to help guide a user through the attachment and detachment operation. For example, at each position of the bottom housing member 2006, there may be only one direction in which the bottom housing member 2006 may be moved. Accordingly, the user can determine how to attach and detach the bottom housing member 2006 with a few simple motions. More particularly, the attachment operation may include a push and a twist, and the detachment operation may include a twist (in a first direction), followed by a pull, followed by another twist (in a second, opposite direction), followed by a final pull.

Figure 23A:
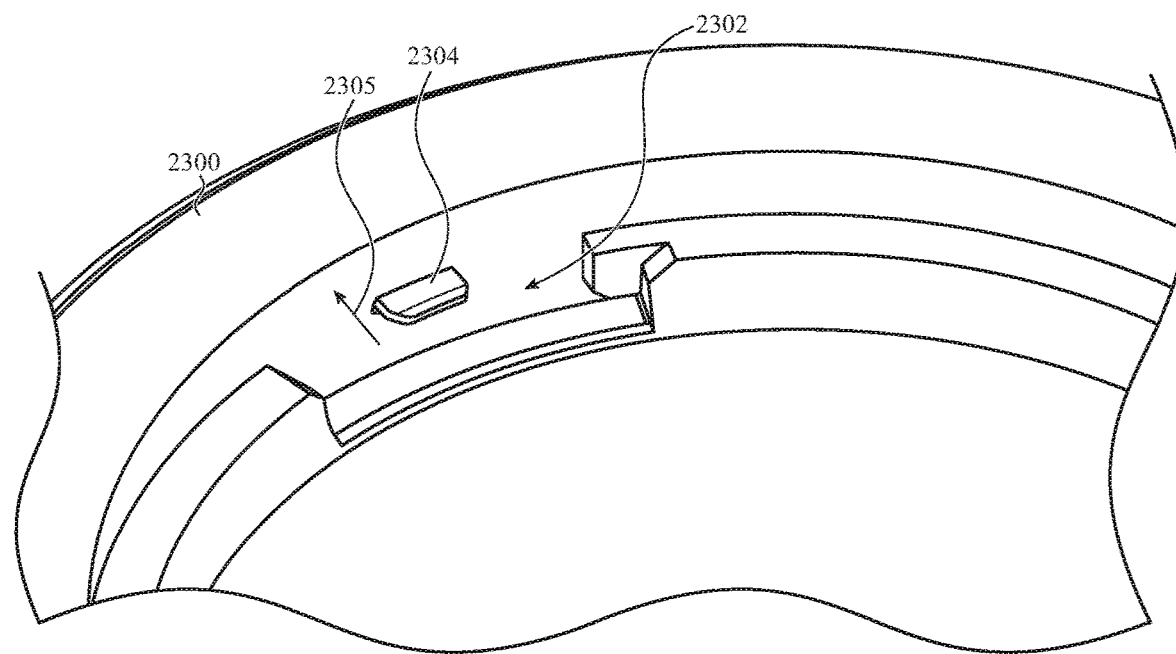
FIGS. 23A-23E depict another example mechanism for securing a battery door of a wirelessly locatable tag.

FIGS. 23A-23E illustrate various aspects of another example mechanism for securely retaining a battery door (e.g., a bottom housing member) to a tag. FIG. 23A illustrates a portion of a frame member 2300 that defines a latching region 2302 and a spring member 2304 that extends into the latching region 2302. The spring member 2304 may be biased to protrude into the latching region 2302, as depicted in FIG. 23A, and may be configured to retract away from the latching region 2302 along the direction 2305. The frame member 2300 may be an embodiment of the frame member 512, and may include any or all of the components and may provide any or all of the functionality of the frame member 512 (and may be integrated with the tag 500 or any other tag described herein). For brevity such details may not be repeated here.

Figure 23B:
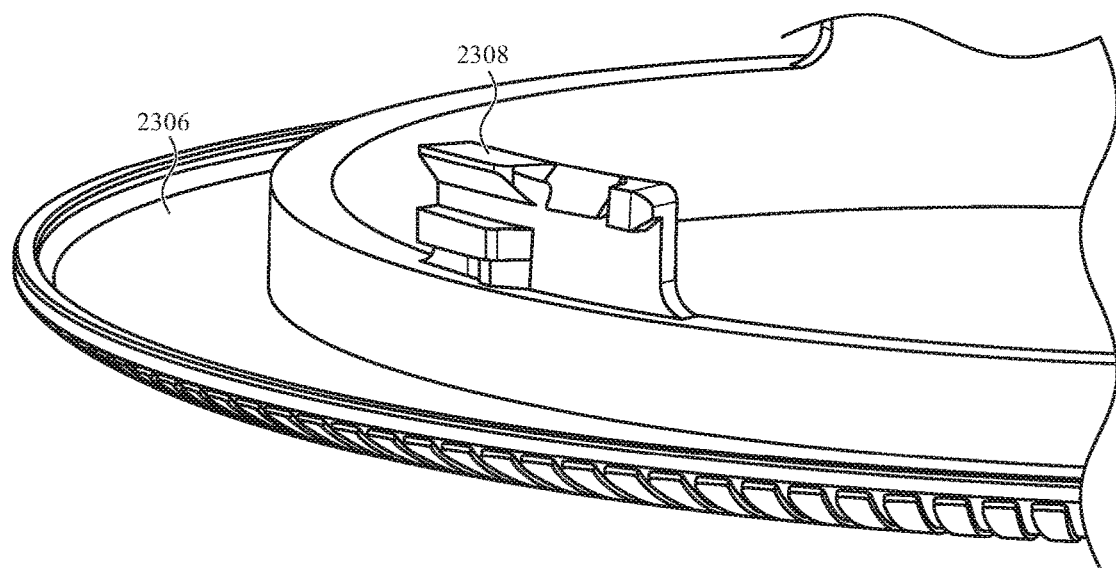

FIG. 23B illustrates a portion of a bottom housing member 2306 that is configured to mate with the frame member 2300 in FIG. 23A. The bottom housing member 2306 may be an embodiment of the bottom housing member 516, and may include any or all of the components and may provide any or all of the functionality of the bottom housing member 516. For brevity such details may not be repeated here. The bottom housing member 2306 includes a cam latch 2308 that is configured to engage with the frame member 2300 via the latching region 2302 and/or the spring member 2304 to retain the bottom housing member 2306 to the frame member 2300. The cam latch 2308 may define various surfaces and/or features that engage or otherwise interact with the spring member 2304 to facilitate attachment and detachment of the bottom housing member 2306.

Figure 23C:
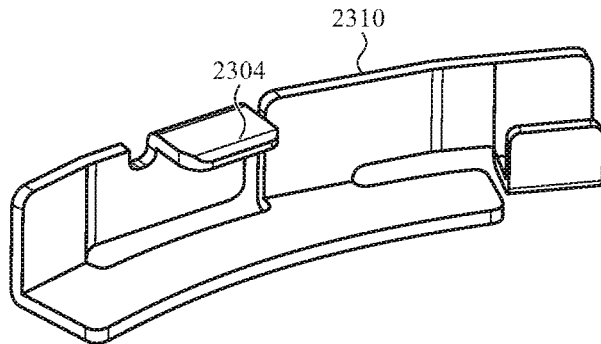

FIG. 23C shows the spring member 2304 removed from the frame member 2300. The spring member 2304 includes the portion that protrudes into the latching region 2302, as well as a base 2310 that is secured to the frame member 2300. The spring member 2304 may be a unitary component formed of metal, polymer, or any other suitable material.

Figure 23D:
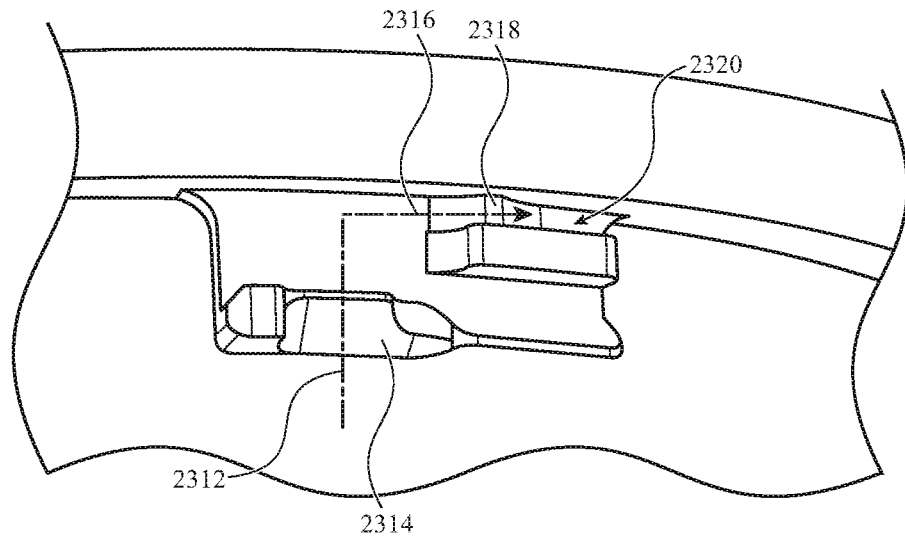

FIG. 23D illustrates the cam latch 2308, showing the path that the spring member 2304 (e.g., the portion of the spring member 2304 that protrudes into the latching region) would follow along the cam latch 2308 as the bottom housing member 2306 is attached to the frame member 2300. In particular, as the bottom housing member 2306 is initially engaged with the frame member 2300, the spring member 2304 moves along the path 2312 and slides over a first cam surface 2314. After clearing the first cam surface 2314, the bottom housing member 2306 is rotated such that the spring member 2304 moves along path 2316, sliding over the first retention feature 2318 and into a blind end 2320 of the cam latch 2308. At this stage, the first retention feature 2318 and the biasing force of the spring member 2304 retain the spring member 2304 in the blind end 2320, thereby retaining the bottom housing member 2306 in a closed configuration.

Figure 23E:
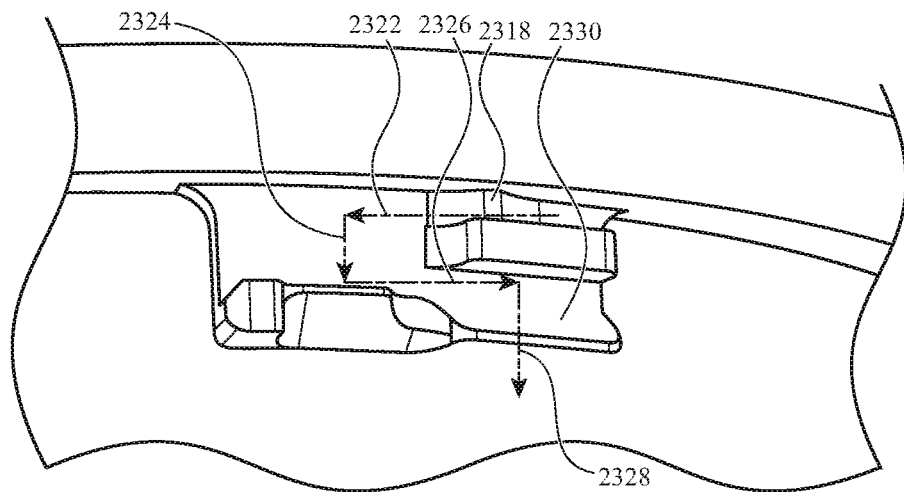

FIG. 23E illustrates the cam latch 2308, showing the path that the spring member 2304 would follow along the cam latch 2308 as the bottom housing member 2306 is detached from the frame member 2300. In particular, the bottom housing member 2306 is rotated so that the spring member 2304 slides over the first retention feature 2318 along path 2322. Once clear of the first retention feature 2318, the bottom housing member 2306 is pulled axially away from the frame member 2300, moving the spring member 2304 along the path 2324 and against a hard-stop defined by the underside of the first cam surface 2314. The bottom housing member 2306 is then rotated to move the spring member 2304 along the path 2326, and then finally pulled axially to slide the spring member along the path 2328 and over a second cam surface 2330, thereby detaching the bottom housing member 2306 from the frame member 2300.

The interactions and engagements between the features of the cam latch 2308 (e.g., the cam surfaces and retention feature) and the spring member 2304 may each require an overcoming force to be applied to the bottom housing member 2306, and may produce tactile sensations or feedback that are detectable by a user. These forces and feedbacks may help retain the bottom housing member 2306 in desired positions, and also provide useful physical information to the user.

Figure 24A:
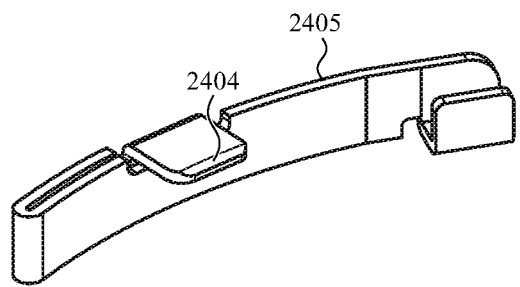
FIGS. 24A-24C depict another example mechanism for securing a battery door of a wirelessly locatable tag.
Figure 24B:
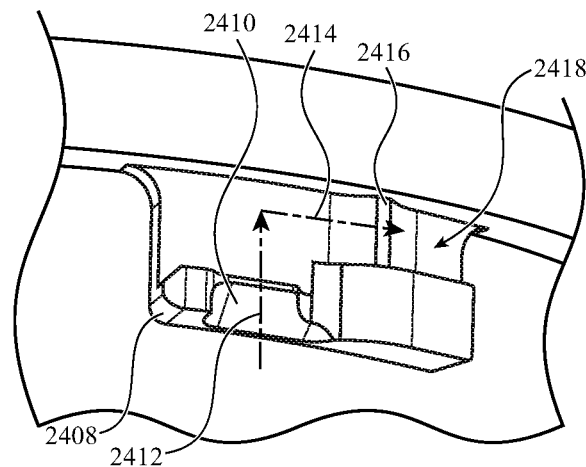
Figure 24C:
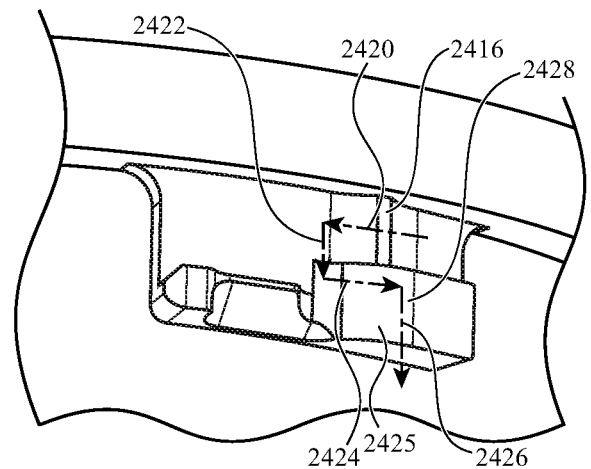

FIGS. 24A-24C illustrate another example spring member and cam latch that may be used with the frame member 2300 and the bottom housing member 2306 described above. FIG. 24A illustrates a spring member 2404 that includes a portion that protrudes into the latching region 2302 (FIG. 23A), as well as a base 2405 that is configured to be secured to the frame member 2300. The spring member 2404 may be a unitary component formed of metal, polymer, or any other suitable material.

FIG. 24B illustrates an example cam latch 2408, which may be used in place of the cam latch 2308 and which may be configured to interface with the spring member 2404 (or another spring member such as the spring member 2304). FIG. 24B shows the path that the spring member 2404 (e.g., the portion of the spring member 2404 that protrudes into the latching region) would follow along the cam latch 2408 as the bottom housing member 2306 is attached to the frame member 2300. In particular, as the bottom housing member 2306 is initially engaged with the frame member 2300, the spring member 2404 moves along the path 2412 and slides over a first cam surface 2410. After clearing the first cam surface 2410, the bottom housing member 2306 is rotated such that the spring member 2404 moves along path 2414, sliding over a first retention feature 2416 and into a blind end 2418 of the cam latch 2408. At this stage, the first retention feature 2416 and the biasing force of the spring member 2404 retain the spring member 2404 in the blind end 2418, thereby retaining the bottom housing member 2306 in a closed configuration.

FIG. 24C illustrates the cam latch 2408, showing the path that the spring member 2404 would follow along the cam latch 2408 as the bottom housing member 2306 is detached from the frame member 2300. In particular, the bottom housing member 2306 is rotated so that the spring member 2404 slides over the first retention feature 2416 along path 2420. Once clear of the first retention feature 2416, the bottom housing member 2306 is pulled axially away from the frame member 2300, moving the spring member 2404 along the path 2422. The bottom housing member 2306 is then rotated to move the spring member 2404 along the path 2424, and then finally pulled axially to slide the spring member along a second cam surface 2425, following the path 2426, thereby detaching the bottom housing member 2306 from the frame member 2300.

The interactions and engagements between the features of the cam latch 2408 (e.g., the cam surfaces and retention feature) and the spring member 2404 may each require an overcoming force to be applied to the bottom housing member 2306, and may produce tactile sensations or feedback that are detectable by a user. These forces and feedbacks may help retain the bottom housing member 2306 in desired positions, and also provide useful physical information to the user.

Figure 25A:
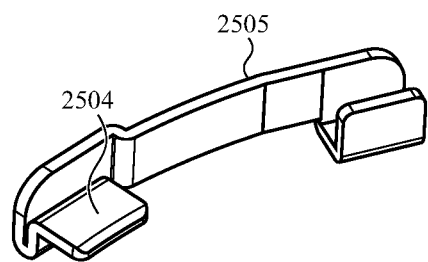
FIGS. 25A-25C depict another example mechanism for securing a battery door of a wirelessly locatable tag.
Figure 25B:
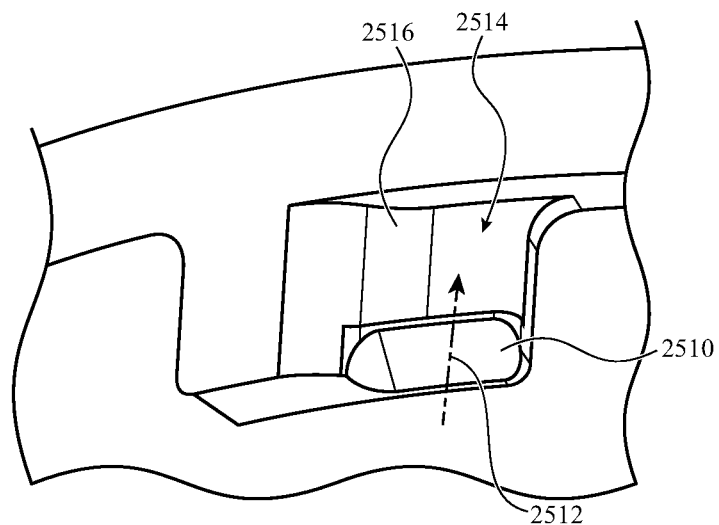
Figure 25C:
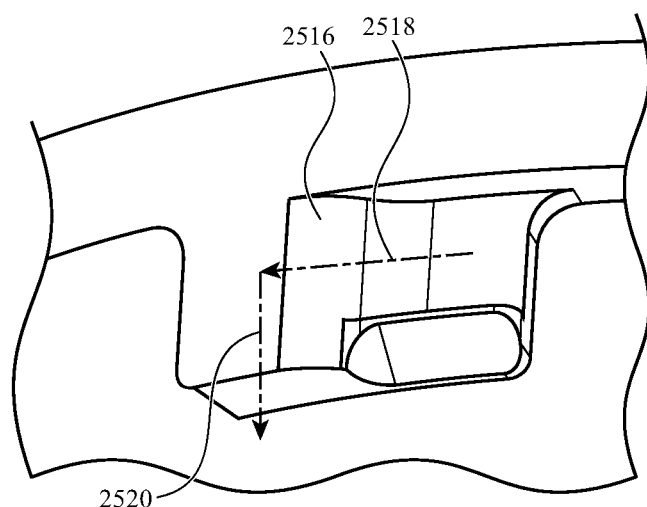

FIGS. 25A-25C illustrate another example spring member and cam latch that may be used with the frame member 2300 and the bottom housing member 2306 described above. FIG. 25A illustrates a spring member 2504 that includes a portion that protrudes into the latching region 2302 (FIG. 23A), as well as a base 2505 that is configured to be secured to the frame member 2300. The spring member 2504 may be a unitary component formed of metal, polymer, or any other suitable material.

FIG. 25B illustrates an example cam latch 2508, which may be used in place of the cam latch 2308 or the cam latch 2408 and which may be configured to interface with the spring member 2504 (or another spring member such as the spring member 2304). FIG. 25B shows the path that the spring member 2504 (e.g., the portion of the spring member 2504 that protrudes into the latching region) would follow along the cam latch 2508 as the bottom housing member 2306 is attached to the frame member 2300. In particular, as the bottom housing member 2306 is initially engaged with the frame member 2300, the spring member 2504 moves along the path 2512 and slides over a first cam surface 2510. After clearing the first cam surface 2510, the spring member 2504 is retained in a retaining area 2514 of the cam latch 2508. At this stage, the overhanging portion of the first cam surface 2510 and the biasing force of the spring member 2504 (as well as a second cam surface 2516) retain the spring member 2504 in the retaining area 2514, thereby retaining the bottom housing member 2306 in a closed configuration.

FIG. 25C illustrates the cam latch 2508, showing the path that the spring member 2504 would follow along the cam latch 2508 as the bottom housing member 2306 is detached from the frame member 2300. In particular, the bottom housing member 2306 is rotated so that the spring member 2504 slides along the second cam surface 2516 along path 2518. The bottom housing member 2306 is then pulled axially away from the frame member 2300, moving the spring member 2504 along the path 2520, thereby detaching the bottom housing member 2306 from the frame member 2300.

The interactions and engagements between the features of the cam latch 2508 (e.g., the cam surfaces and retention feature) and the spring member 2504 may each require an overcoming force to be applied to the bottom housing member 2306, and may produce tactile sensations or feedback that are detectable by a user. These forces and feedbacks may help retain the bottom housing member 2306 in desired positions, and also provide useful physical information to the user.

As noted above, wirelessly locatable tags may include audio systems that are configured to produce audio outputs. Audio outputs from a wirelessly locatable tag may be used to help a user locate the tag. For example, when a user is attempting to locate a lost tag, the user may use a smartphone to wirelessly command the tag to produce an audible sound such as a beeping or other audible tone (e.g., constant tone, song, etc.). More particularly, the smartphone may send an audio request signal to the tag, which may in turn cause the tag to produce an audible output with an audio system.

Figure 26A:
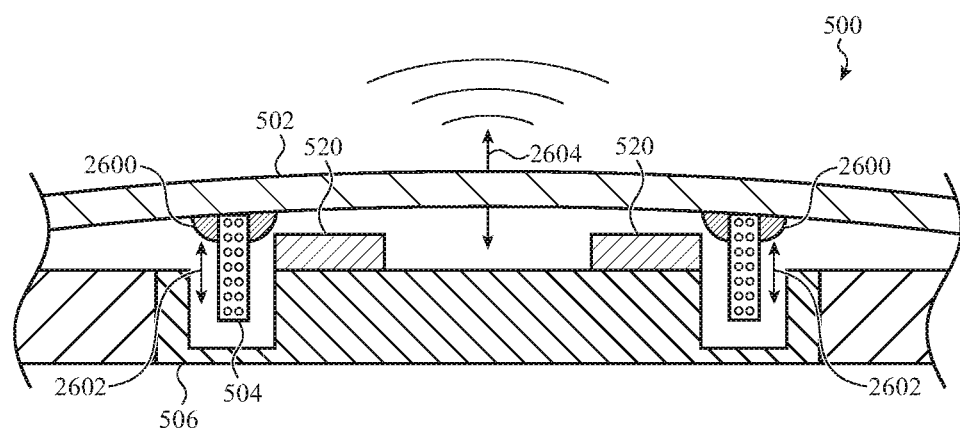
FIGS. 26A-26B depict aspects of an example audio system of the wirelessly locatable tag of FIG. 5A.
Figure 26B:
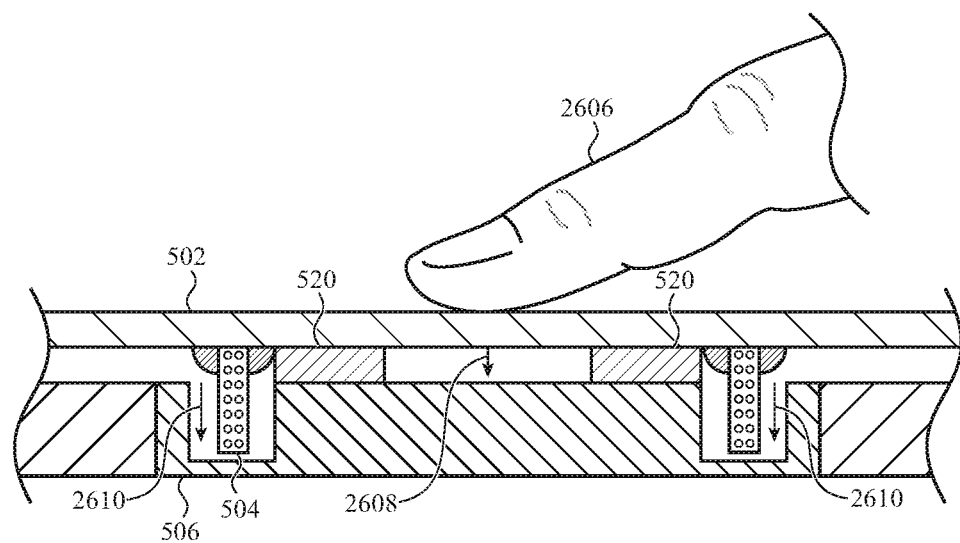

FIGS. 26A-26B depict partial cross-sectional views of the tag 500, showing an example configuration of an audio system, as well as illustrating various operational modes of the audio system. As shown in FIG. 26A, the audio system of the tag 500 may include a coil 504 coupled to a top housing member 502. The coil 504 may include multiple turns of a conductor (e.g., a metal wire) at least partially embedded in a matrix or potting material, such as an epoxy, resin, or other suitable material. The coil 504 may be attached to the inner surface of the top housing member 502 using any suitable method, such as with an adhesive 2600 (as shown), ultrasonic welding, or the like. In some cases, a bobbin or other base structure for the coil 504 may be formed as a unitary structure with the top housing member 502. For example, a single-piece molded or 3D-printed top housing member 502 may include an integrated bobbin around which a conductor is wound to produce the coil 504. As another example, conductors forming the coil may be plated onto a bobbin that is integrally formed with the top housing member 502 (e.g., using laser direct structuring or another suitable plating or metallization technique). Other techniques for forming a coil and/or integrating a coil with a top housing member 502 are also contemplated.

The coil 504 may be proximate a magnet assembly 506. The magnet assembly 506 may be any suitable material and may be formed of a single piece of magnetic material, or it may be formed of or include multiple components attached to one another, as shown with respect to FIG. 27A. The tag 500 may also include a hard-stop 520 that limits deflection of the top housing member 502. As described herein, the gap between the top of the hard-stop 520 and the inner surface of the top housing member 502 may be equal to or less than a threshold distance, such as about 500 microns, 400 microns, 300 microns, 200 microns, 100 microns, or 50 microns.

The tag 500 may use the coil 504 to move a portion of the top housing member 502 to cause the top housing member 502 to act as a diaphragm to produce audible outputs. For example, when an audio output is required, an appropriate signal is applied to the coil 504 (which is in a magnetic field produced by the magnet assembly 506), thereby producing Lorentz forces that act on the coil 504 (indicated by arrows 2602). The Lorentz forces on the coil 504 cause the top housing member 502 to move, oscillate, vibrate, or otherwise move (indicated by arrows 2604) to produce an audible and optionally tactile output. In some cases, the top housing member 502 locally deflects or deforms to produce the audible and/or tactile output. For example, the central portion of the top housing member 502 may deflect or deform to produce the audible and/or tactile outputs, while other portions of the top housing member 502 (e.g., a peripheral portion that is coupled to the antenna assembly 508) remains substantially stationary and/or otherwise does not contribute to the production of sound waves.

The audio system, as well as the portion of the top housing member 502 that deflects or deforms to produce audio and/or tactile outputs, may be configured to permit or facilitate the production of audio within a target frequency range. For example, the audio system may be configured to produce sound within a range of about 1 kHz to 4 kHz, 1 kHz to 3 kHz, or any other suitable range. This range may be beneficial due to the relative sensitivity of human hearing to different frequencies, as well as the ability to perceive the location of a sound. For example, human ears are more sensitive to sounds between about 1 kHz to 4 kHz. Also, based at least in part on the distance between a human's ears, humans can more easily perceive the location of a sound that is at or below 3 kHz (as the location may be perceived without requiring head movement). Accordingly, a range of about 1 kHz to 3 kHz is within a typical range of peak hearing sensitivity and enables simple auditory localization of the tag (e.g., without requiring head movement to perceive the sound's location). Audible outputs (or ultrasonic outputs, which may be produced by the audio system instead of or in addition to audible outputs) may also be detected by one or multiple microphones on another device (e.g., a smartphone, earbuds, etc.), and that device may use beamforming or other direction-finding techniques to determine or estimate the position of the tag based on the detected audible sounds. In some cases, multiple devices, each with one or more microphone, cooperate to estimate the position of a tag (e.g., by comparing their own position estimates or otherwise cooperating to produce one position estimate).

The materials and dimensions of the top housing member 502 may also be configured to facilitate the use of the top housing member 502 as an audio-producing diaphragm. For example, the materials and dimensions may be selected so that the top housing member 502 is sufficiently flexible to allow the top housing member 502 to be deflected and/or deformed by the force produced by the coil 504. In some cases, the top housing member 502 may be formed of or include a polymer material, such as a polymer, reinforced polymer, carbon fiber, or the like. The top housing member 502 may have a thickness of about 300 microns, 400 microns, 450 microns, 500 microns, 550 microns, or any other suitable thickness. In some cases, a portion of the top housing member 502 that deforms or bends to produce the audible and/or tactile output has a thickness between about 300 and 550 microns, while other portions of the top housing member 502 have different thicknesses (e.g., are thicker or thinner). Other thicknesses and dimension are also possible.

In embodiments where the audio system of the tag 500 uses the top housing member 502 as a diaphragm to produce audible and/or tactile outputs, the tag 500 may use the components of the audio system to detect inputs applied to the top housing member 502. FIG. 26B illustrates the tag 500 as a finger 2606 is applying an input force on the top housing member 502. This input may correspond to a press or squeeze of the tag 500, and may result in the top housing member 502 deforming such that the inner or bottom surface of the top housing member 502 moves downward, towards the magnet assembly 506, as indicated by arrow 2608. The movement of the top housing member 502 results in the coil 504 moving downward as well, as indicated by arrow 2610. Because the coil 504 is moving while it is in the magnetic field produced by the magnet assembly 506, a current may be produced in the coil 504 due to the electromagnetic interaction between a conductor moving in the presence of magnetic flux. This current may be detected by the tag 500 and may indicate that an input has been detected.

When the tag 500 detects a current indicative of a threshold amount of motion of the top housing member 502, the tag 500 may take one or more actions. For example, the tag 500 may initiate a pairing mode (optionally including changing the operation of one or more radios of the tag to facilitate communication with other devices), turn the tag 500 on or off, change a mode of operation of the tag 500, cause information to be sent via one or more of the tag's wireless communications systems (e.g., to a remote service, to a mobile phone, etc.), activate or deactivate an audio or tactile output, or the like.

The current produced in the coil 504 as a result of a deflection of the top housing member 502 may also be used to provide power to the tag 500 for tag operations and/or to charge the battery 514. The power may be harvested each time an input is provided, or it may be harvested when certain conditions are met (e.g., when a certain number or frequency of deflections is detected, when the battery is below a threshold charge level, etc.). In some cases, a tag without a battery (or with a fully discharged or dead battery) may be temporarily powered by the user deflecting the top housing member one or more times (e.g., using a number and frequency of deflections that is sufficient to at least momentarily power the tag). If certain conditions are satisfied, the tag may perform one or more actions in response to a repeated deflection. For example, if the battery is dead or missing and a sufficient power threshold is reached from repeated deflections of the top housing member, the tag may send a location report (as described with respect to FIGS. 2A-2C), along with an indication that the tag is out of power.

As noted above, tags may use other types of input systems or devices may be used to detect inputs to the tag, in addition to or instead of detecting current produced in a coil of an audio system. For example, a dome switch, tactile dome switch, or other electromechanical switching system may be positioned between the top housing member 502 and the magnet assembly 506 (or any other underlying component). When the top housing member 502 is deflected by a user, as shown in FIG. 26B, the dome switch or electromechanical switching component may be actuated and the corresponding input detected. In some cases, the magnet assembly 506 may define an opening, and the dome switch or other electromechanical switching system may be positioned in the opening. In such cases, the dome switch or other electromechanical switching system may be attached to the circuit board 510, the main frame member 512, or another underlying component.

Another type of switching mechanism that may be included in a tag includes conductive contacts attached to the top housing member 502 and an underlying component. For example, a first conductive contact, such as a metal sheet, foil, or other component, may be attached to the interior surface of the top housing member 502 (e.g., at a center of the top housing member 502, such as aligned with the central opening of the hard-stop 520), and one or more second conductive contacts may be positioned below the first conductive contact. When the top housing member 502 is deflected, as shown in FIG. 26B, the first conductive contact may contact the one or more second conductive contacts, and the tag may detect the resulting contact, for example, by detecting a change in conductivity between the conductive contacts. As a specific example, the tag may include two second conductive contacts, and the first conductive contact may be configured to conductively couple the two second conductive contacts when the top housing member 502 is depressed. The tag may detect the input by detecting continuity between the two second conductive contacts. Other arrangements of conductive contacts are also contemplated.

Other techniques for detecting deflection of the top housing member 502 are also contemplated, including but not limited to capacitive sensors, force sensors, ultrasonic sensors, and optical sensors. Further, other types of input systems may be provided in addition to or in place of input systems that detect deflection of the top housing member 502. For example, the tag may include buttons, switches, accelerometers (e.g., for detecting shake or tap inputs), or the like.

Figure 27A:
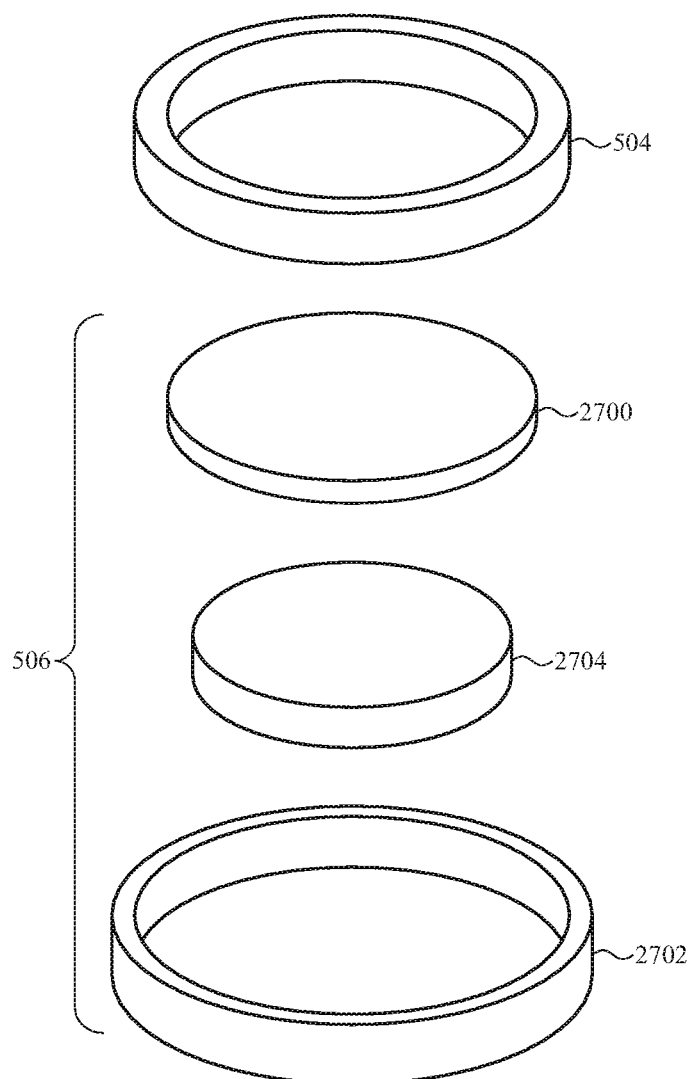
FIG. 27A depicts an exploded view of a magnet assembly of the wirelessly locatable tag of FIG. 5A.

FIG. 27A is an exploded view of a portion of the tag 500. In particular, FIG. 27A shows the coil 504 and an exploded view of the magnet assembly 506 according to one example implementation. The magnet assembly 506 includes a top plate 2700, an under yoke 2702 (e.g., a metal yoke), and a magnet 2704. The top plate 2700 and the under yoke 2702 may be formed of or include a metal material such as steel. The top plate 2700 and the under yoke 2702 may cooperate to direct magnetic flux produced by the magnet 2704 along a desired area, and to help reduce leakage flux outside of the tag 500. Minimizing or otherwise reducing the amount and/or strength of leakage flux (e.g., magnetic flux from the magnet 2704 that extends outside of the housing of the tag 500) may help prevent the magnetic flux from interfering with or damaging other objects or devices such as credit cards, magnetometers in other devices, or the like.

Figure 27B:
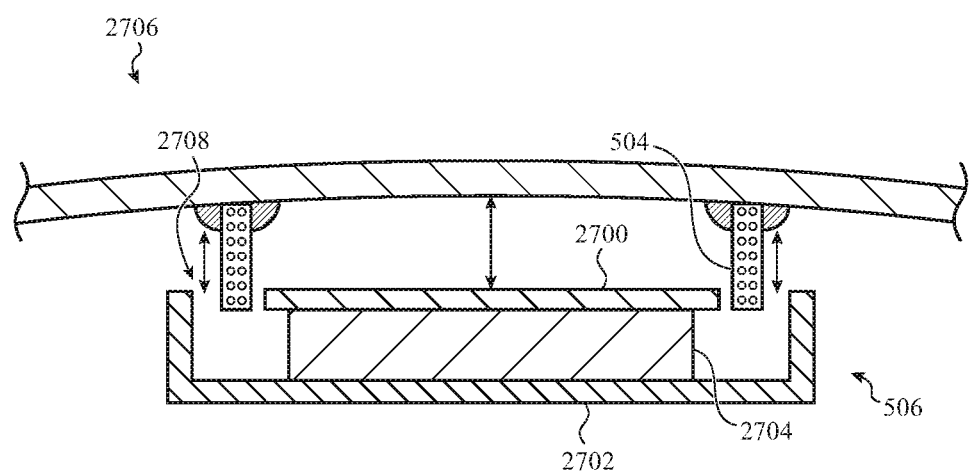
FIG. 27B depicts a partial cross-sectional view of the wirelessly locatable tag of FIG. 5A.

FIG. 27B illustrates a partial cross-sectional view of a portion of the tag 500, showing example magnetic flux lines in relation to the magnet assembly 506 and the top housing member 502. The magnet 2704 may produce magnetic flux, while the top plate 2700 and the under yoke 2702 guide or focus the magnetic flux. For example, the top plate 2700 and the under yoke 2702 may be configured to concentrate flux in the gap 2708 where the coil 504 is positioned. By concentrating flux in the gap 2708, the amount of flux 2706 leaking out beyond the exterior of the tag 500 may be maintained at an acceptable level (e.g., below a threshold level for demagnetizing credit cards).

The physical design of the tag 500 may also contribute to the management of leakage flux. For example, the top housing member 502 and the magnet assembly 506 may be configured so that the distance from the magnet assembly 506 (e.g., the top of the magnet assembly) to the exterior surface of the top housing member 502 (e.g., the portion of the exterior surface of the top housing member 502 that is nearest the magnet assembly 506) is equal to or greater than a threshold distance. For example, in some cases, the threshold distance is about 1.0 mm, 1.5 mm, 2.0 mm, or any other suitable distance.

Figure 28A:
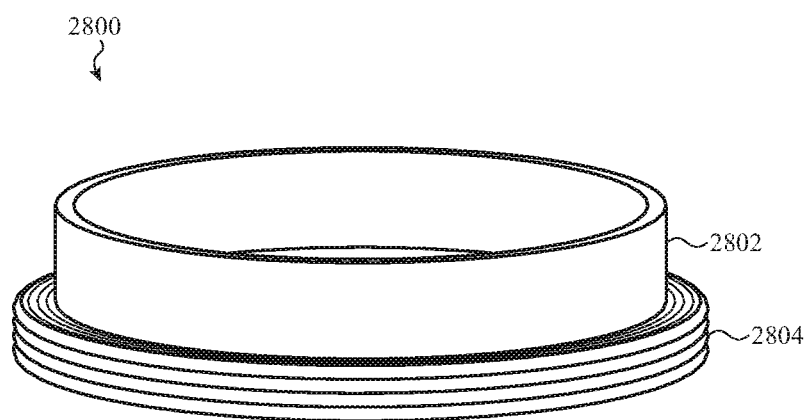
FIGS. 28A-28D depict example coil configurations for an audio system for a wirelessly locatable tag.

FIGS. 26A-27B illustrate an example coil 504 in which conductors (e.g., wires) are at least partially embedded in a potting material, and the potted conductor is attached to the top housing member 502. FIGS. 28A-28D illustrate other example coil configurations that may be used with a wirelessly locatable tag as described herein. FIG. 28A illustrates an example coil 2800 that includes a bobbin 2802 and a conductive coil 2804. The bobbin 2802 may be a ring-like structure about which the conductive coil 2804 is wound. The bobbin 2802 may be formed from or include a metal (e.g., an aluminum or other metal sheet or foil), polymer, or any other suitable material. The conductive coil 2804 may include a plurality of turns of a conductor such as a wire (e.g., copper wire).

Figure 28B:
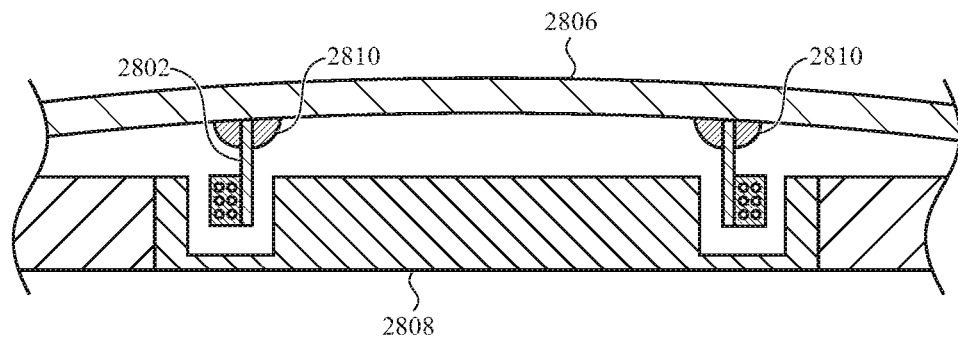

FIG. 28B is a partial cross-sectional view of a tag, showing how the coil 2800 may be integrated with the components of the tag. In particular, the bobbin 2802 of the coil is attached to the interior or bottom surface of the top housing member 2806 (which may be an embodiment of the top housing member 502). The bobbin 2802 may be attached to the top housing member 2806 using an adhesive 2810, such as an epoxy, or other suitable adhesive or attachment mechanism or technique. The coil 2800 is positioned on the top housing member 2806 such that the conductive coil 2804 is in a magnetic flux field produced by a magnet assembly 2808 (which may be an embodiment of the magnet assembly 506).

Figure 28C:
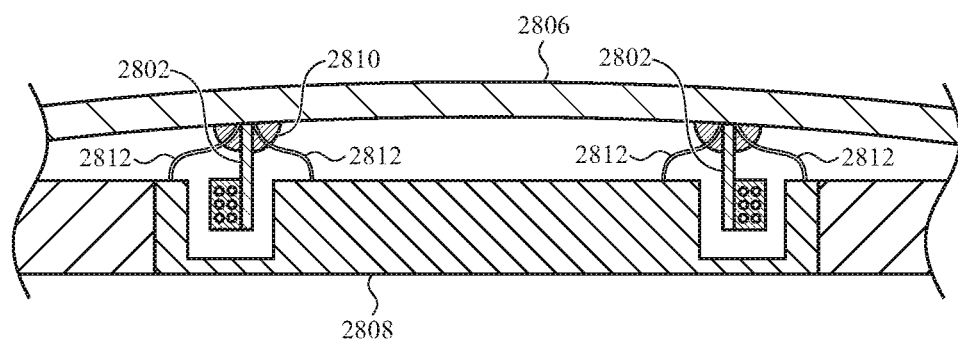

FIG. 28C is a partial cross-sectional view of a tag, showing another example of how the coil 2800 may be integrated with the components of the tag. In FIG. 28C, the bobbin 2802 is attached to the top housing member 2806 using the adhesive 2810, as shown in FIG. 28B, but also includes a shroud 2812 extending from the top housing member 2806 to the magnet assembly 2808 (or to another component inside the tag). The shroud 2812 may be formed of or include a flexible material, such as a polyester or other polymer film, and may be configured to deform when the tag produces audible and/or tactile outputs by moving the top housing member 2806 with the coil 2800. The shroud 2812 may be configured to protect the coil 2800 from debris or other contaminants that may affect the physical and/or electrical operation of the coil 2800.

Figure 28D:
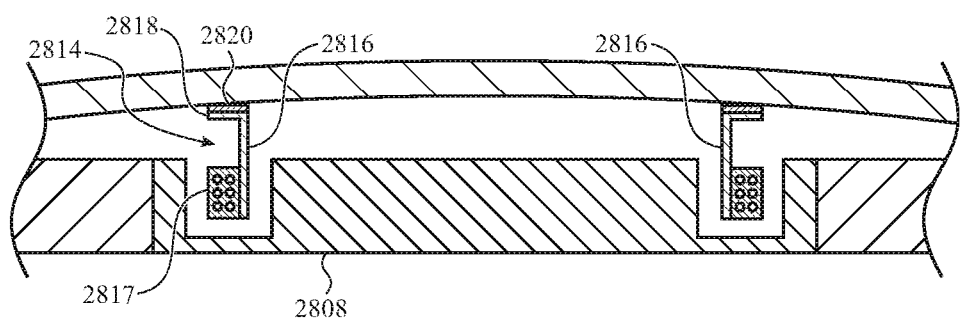

FIG. 28D is a partial cross-sectional view of a tag, showing how another coil 2814 may be integrated with the components of the tag. The coil 2814 in FIG. 28D includes a bobbin 2816 and conductive coil 2817, which are similar to the bobbin 2802 and conductive coil 2804, except that the bobbin 2816 includes a mounting flange portion 2818 that extends at an angle relative to the portion of the bobbin that is attached to the conductive coil 2817. The mounting flange portion 2818 may provide a larger contact area between the bobbin 2816 and the top housing member 2806 as compared to the bobbin 2802. The mounting flange portion 2818 may be secured to the top housing member 2806 via an adhesive 2820, which may be an epoxy, an adhesive film, a pressure, heat, or temperature sensitive adhesive, or any other suitable adhesive. In some cases a shroud, such as the shroud 2812, may be included in the implementation shown in FIG. 28D.

Figure 29A:
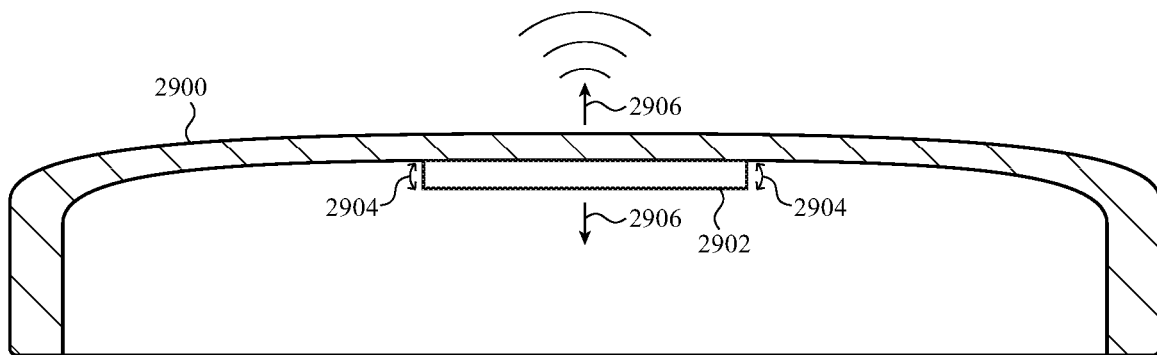
FIGS. 29A-30 depict other example audio systems for a wirelessly locatable tag.

As described above, audible and/or tactile outputs from a tag may be produced with an audio system that uses an electromagnetic coil and a magnet (a system that may be similar to a voice coil motor) to deflect or deform the top housing member of the tag. This is merely one example audio system that may be used to produce such outputs, however, and other audio systems may be used instead of or in place of the coil and magnet arrangements described herein. FIGS. 29A-30 illustrate other example audio systems that may be used to produce audible and/or tactile outputs.

Figure 29B:
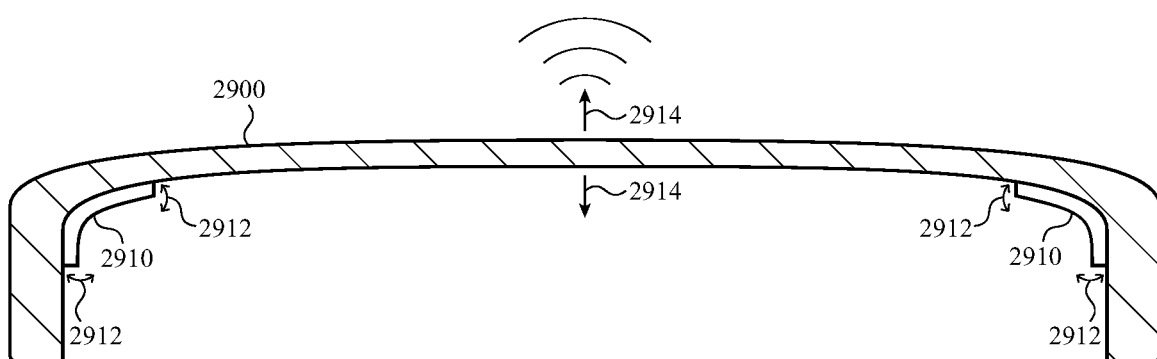
Figure 30:
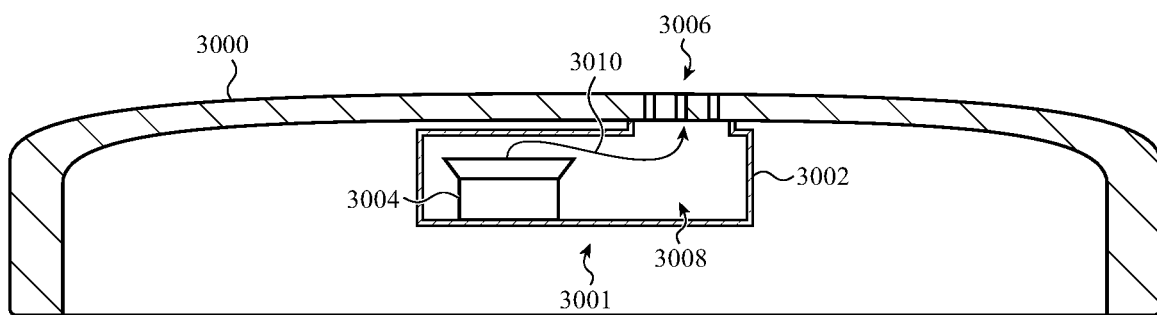

FIGS. 29A-29B illustrate examples in which piezoelectric elements are used to deflect and/or deform a top housing member of a tag to produce audible and/or tactile outputs, using a portion of the top housing member as a speaker diaphragm. FIG. 29A illustrates a portion of an example top housing member 2900, which may be an embodiment of the top housing member 502. A piezoelectric element 2902 is attached to the inner or bottom surface of the top housing member 2900 (e.g., using an adhesive or any other suitable fastening technique). The piezoelectric element 2902 may be a piezoelectric unimorph or bimorph. In order to cause the top housing member 2900 to deform or deflect, the tag may apply an electrical signal or current to the piezoelectric element 2902, thereby causing the piezoelectric element 2902 to bend (indicated by arrows 2904). Due to a secure attachment between the piezoelectric element 2902 and the top housing member 2900, the bending of the piezoelectric element 2902 may cause the top housing member 2900 to deflect or deform (indicated by arrows 2906) in a manner that produces audible and/or tactile outputs.

FIG. 29A illustrates an example in which a single piezoelectric element 2902 is attached to a center of the top housing member 2900, though this is merely one example implementation of an audio system that uses a piezoelectric element. FIG. 29B illustrates an example in which multiple separate piezoelectric elements 2910 are attached to the inner or bottom surface of the top housing member 2900. In particular, the piezoelectric elements 2910 are positioned in a corner where the top wall of the top housing member 2900 joins the side wall of the top housing member 2900. A tag using this arrangement may use two more piezoelectric elements 2910 spaced about the periphery of the top housing member 2900. In the case where two piezoelectric elements 2910 are used, they may be positioned opposite one another (e.g., with the two piezoelectric elements defining a line through a center of the shape defined by the top housing member 2900). The piezoelectric elements 2910 may be unimorph or bimorph piezoelectric elements.

In order to cause the top housing member 2900 to deform or deflect, the tag may apply an electrical signal or current to the piezoelectric elements 2910, thereby causing the piezoelectric elements 2910 to bend (indicated by arrows 2912). Due to a secure attachment between the piezoelectric elements 2910 and the top housing member 2900, the bending of the piezoelectric elements 2910 may cause the top housing member 2900 to deflect or deform (indicated by arrows 2914) in a manner that produces audible and/or tactile outputs.

The piezoelectric elements 2910 may be mounted remote from the portion of the top housing member that moves the greatest amount during an audible or tactile output, and may use the structure of the top housing member 2900 to amplify the amount of deflection of the piezoelectric elements 2910. For example, by positioning the piezoelectric elements 2910 in the corners of the top housing member 2900 as shown in FIG. 29B, small deflections of the piezoelectric elements 2910 may produce larger deflections at the center of the top housing member 2900.

The piezoelectric elements 2902, 2910 may be conductively connected to one or more electronic components and/or circuit elements. The electronic components and/or circuit elements may be positioned on a circuit board (e.g., the circuit board 510), and may be configured to provide electrical signals to the piezoelectric elements that cause them to deform in a manner that produces an audible and/or tactile output from the top housing member 2900.

FIG. 30 illustrates another example configuration of an audio system for a tag. In particular, FIG. 30 illustrates an example top housing member 3000 (which may be an embodiment of the top housing member 502) with an audio system 3001 positioned below the top housing member 3000. The audio system 3001 may be configured to direct sound through one or more openings 3006 that extend through the top housing member 3000.

The audio system 3001 may include an enclosure 3002 that defines an internal volume 3008. A speaker 3004 may be coupled to the enclosure 3002 or otherwise configured to direct sound into the internal volume 3008. The internal volume 3008 may have an opening that is aligned with or otherwise communicates with the openings 3006 in the top housing member 3000. Accordingly, sound from the speaker 3004 may be directed through the internal volume 3008 and out of the openings 3006 (as indicated by arrow 3010). The enclosure 3002 may be attached to the top housing member 3000 (e.g., via adhesive, fasteners, ultrasonic welding, etc.), or it may be attached to another component of a tag (e.g., an antenna assembly) and positioned such that it communicates audio through the openings in a top housing member. In tags that include an audio system with a speaker within an enclosure, the tag may employ screens, membranes, water ejection systems, or other systems or techniques to prevent the ingress of water, dust, or other contaminants into the audio system and/or the tag as a whole.

For tags in which the top housing member is deflected and/or deformed in order to produce audible and/or tactile outputs, the top housing member may be configured to be sufficiently flexible so that it can be deflected and/or deformed by a voice coil motor, piezoelectric element, or other actuator. In some cases, the top housing member may be a unitary structure formed of a single piece of material. In other cases, it may include multiple components or segments that together define the top housing member. FIGS. 31A-34C illustrate several different example top housing members that may be used with wirelessly locatable tags as described herein. The top housing members in FIGS. 31A-34C may be embodiments of the top housing member 502, or any other top housing member described herein.

Figure 31A:
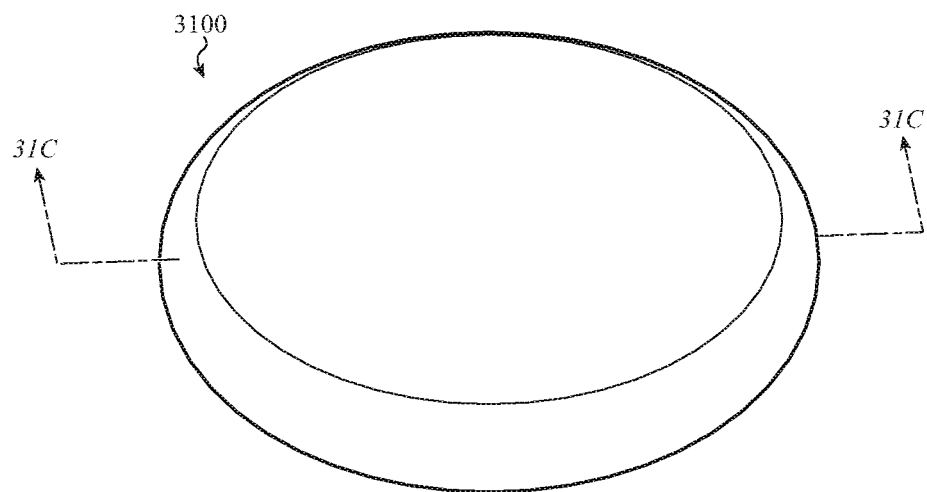
FIGS. 31A-31C depict an example top housing member for a wirelessly locatable tag.
Figure 31B:
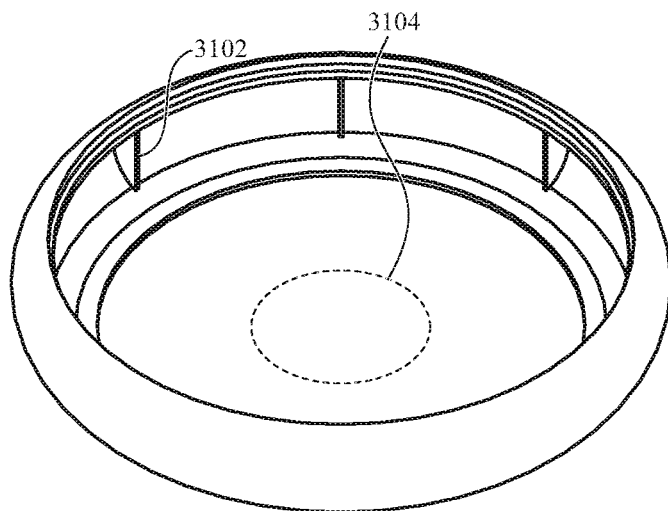
Figure 31C:
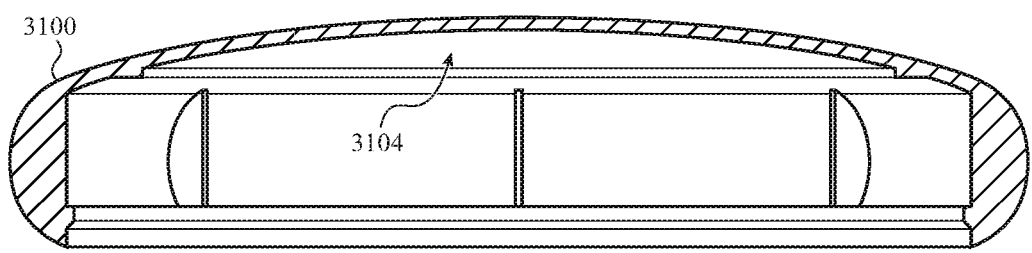

FIGS. 31A-31C illustrate an example top housing member 3100 that may be formed of a single piece of material. The top housing member 3100 may be formed from a polymer material such as acrylonitrile butadiene styrene (ABS), polyamide, polymethyl methacrylate (PMMA), or any other suitable polymer material (including fiber reinforced polymer materials). In other cases, the top housing member 3100 may be formed of metal.

FIG. 31A shows the outer surface of the top housing member 3100, which may define an exterior surface of the tag. As shown, the outer surface of the top housing member 3100 is substantially featureless (e.g., devoid of seams, gaps, grooves, discontinuities, displays, buttons, or other features). In other implementations, however, the outer surface may define or include such features.

FIG. 31B shows an underside view of the top housing member 3100. The top housing member 3100 may define reinforcing ribs 3102, which may be integrally formed with the rest of the top housing member 3100. For example, the top housing member 3100 may be molded as a single piece with the reinforcing ribs 3102. The top housing member 3100 may also define a coil attachment region 3104 where a coil (e.g., the coil 504) of an audio system may be attached to the top housing member 3100. The coil attachment region 3104 may be a substantially featureless surface, or it may include grooves, cavities, attachment elements, or other features.

FIG. 31C is a cross-sectional view of the top housing member 3100, viewed along line 31C-31C in FIG. 31A. As shown, the top housing member 3100 may not have a uniform thickness. For example, in some cases a central portion of the top housing member 3100 (e.g., at and/or around the coil attachment region 3104) may be thinner than a sidewall portion of the top housing member 3100. This may provide increased flexibility at the area of the top housing member 3100 that needs to deflect and/or deform to produce audible and/or tactile outputs.

Figure 32A:
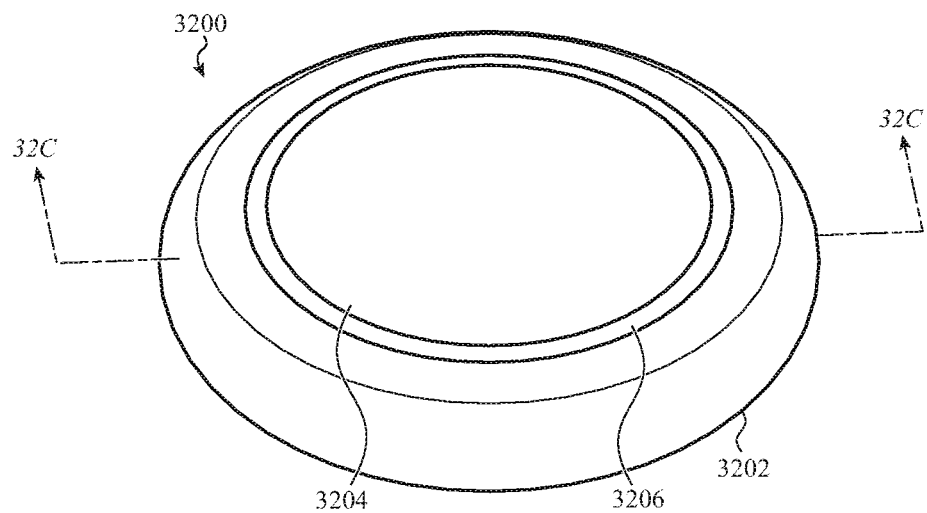
FIGS. 32A-32C depict another example top housing member for a wirelessly locatable tag.
Figure 32B:
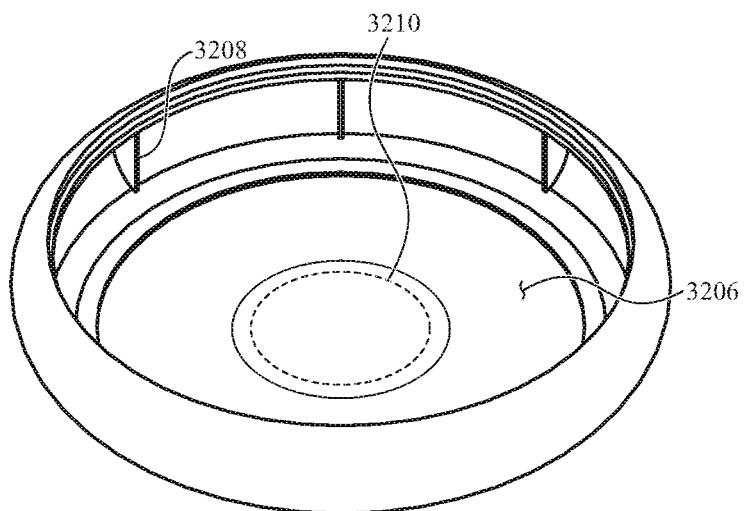
Figure 32C:
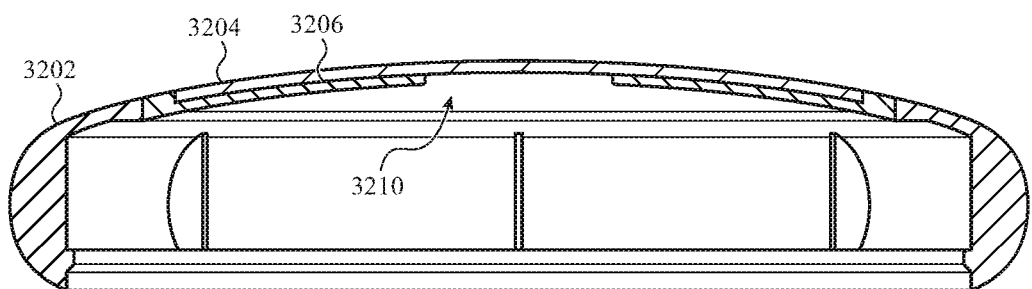

FIGS. 32A-32C illustrate an example top housing member 3200 that may include multiple components. FIG. 32A shows the outer surface of the top housing member 3200, which may define an exterior surface of the tag. The top housing member 3200 may include a peripheral member 3202, a central member 3204, and a compliant member 3206. The peripheral member 3202 may define a peripheral wall and a top wall, with the top wall defining an opening in which the central member 3204 may be at least partially positioned. The peripheral wall of the peripheral member 3202 may define a peripheral side wall (and thus the exterior peripheral side surface) of the tag.

The compliant member 3206 may be formed from a more flexible material than the peripheral member 3202 and the central member 3204. For example, the peripheral member 3202 (which may define a side wall of the top housing member 3200) and the central member 3204 (which may define a top outer surface of the top housing member 3200) may be formed from a first polymer material such as an ABS, PMMA, and the compliant member 3206 may be formed from a second polymer material that is more flexible than the first polymer material, such as silicone, thermoplastic polyurethane (TPU), or the like. The compliant member 3206 may be configured to allow the central member 3204 to move more freely relative to the peripheral member 3202 than would occur if the central and peripheral members were a unitary structure (such as the top housing member 3100).

FIG. 32B shows an underside view of the top housing member 3200. The top housing member 3200 may define reinforcing ribs 3208, which may be integrally formed with the peripheral member 3202. The central member 3204 may define a coil attachment region 3210, which may be similar to the coil attachment region 3104, described above.

FIG. 32C is a cross-sectional view of the top housing member 3200, viewed along line 32C-32C in FIG. 32A. As shown, the portion of the compliant member 3206 that is visible on the outer surface of the top housing member 3200 may only be a part of the compliant member 3206. More particularly, the compliant member 3206 may extend along a portion of the inner or bottom surface of the central member 3204, and may mechanically couple the central member 3204 to the peripheral member 3202. The compliant member 3206 may define an opening that exposes the coil attachment region 3210 so that the coil can be attached directly to the central member 3204, thereby directly transferring force to the central member 3204. In some cases, the part of the compliant member 3206 that is exposed adjacent the outer surfaces of the central and peripheral members are flush with the central and peripheral members, as illustrated in FIG. 32C. In other cases, the part of the compliant member 3206 that is exposed may be recessed or proud relative to the peripheral and central members. FIG. 33C, for example, illustrates an embodiment in which a compliant member is recessed relative to the central and peripheral members.

The top housing member 3200 may be formed by a co-injection molding or insert molding technique, where the central and peripheral members are formed first (and optionally inserted into a second mold after they are formed), and then the material of the compliant member 3206 is injected into the mold and against the central and peripheral members. This may cause the compliant member to be formed into the target shape, as well as to secure the material of the compliant member to the central and peripheral members (e.g., via chemical and/or adhesive bonding between the materials, and/or via mechanical interlocking between the components).

The decreased stiffness of the compliant member 3206 relative to the central and peripheral members may increase the amount of movement of the central member that is achieved for a given coil force, as compared to a single-piece top housing member. This, in turn, may improve the efficiency of the tag with respect to producing audible and/or tactile outputs. Further, the lower force requirement may allow the use of smaller coils, magnets, piezoelectric elements, or other force-producing elements of an audio system. Additionally, embodiments of top housing members that use separate central and peripheral members may employ a different mode of deformation or deflection than single-piece housing members. That is, the central member 3204 itself deforms less than the central region of a single-piece top housing member, and instead moves more vertically (e.g., like a plate moving along a vertical path). Stated another way, whereas a single-piece top housing member may be deformed in a bulge-like shape to produce audible and/or tactile outputs, the central member 3204 of the top housing member 3200 may remain substantially undeformed while it is moved vertically up and down (e.g., in a largely or entirely translational movement) to produce such outputs. In cases where the central member of the top housing member is separate from the peripheral member, the central member may be thicker and/or stiffer than a central member of a single-piece top housing member.

Figure 33A:
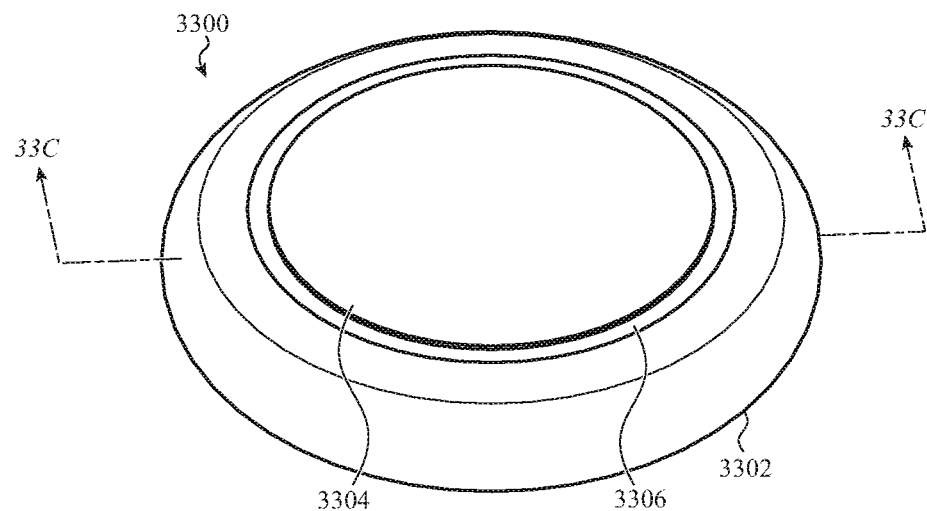
FIGS. 33A-33C depict another example top housing member for a wirelessly locatable tag.
Figure 33B:
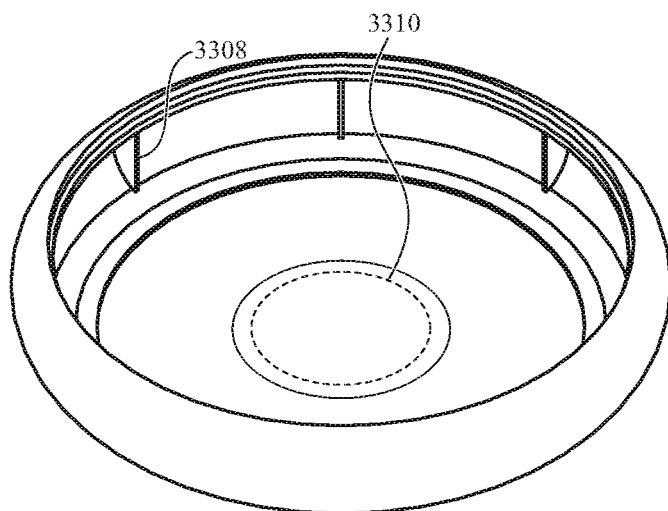
Figure 33C:
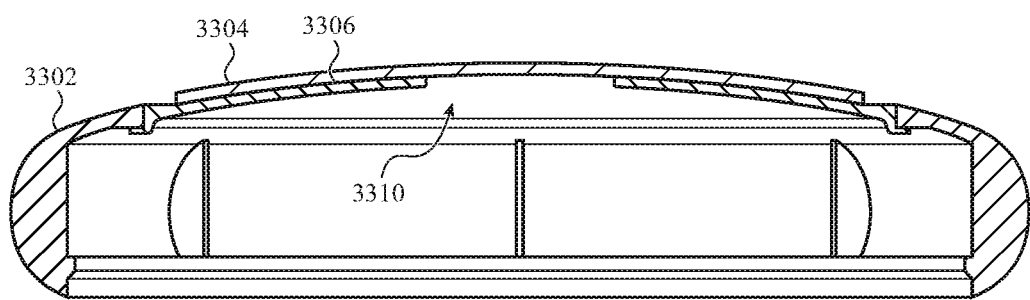

FIGS. 33A-33C illustrate another example top housing member 3300 that may include multiple components. FIG. 33A shows the outer surface of the top housing member 3300, which may define an exterior surface of the tag. The top housing member 3300 may define a peripheral member 3302, a central member 3304, and a compliant member 3306. The peripheral member 3302 may define a peripheral wall and a top wall, with the top wall defining an opening in which the central member 3304 may be at least partially positioned. The peripheral wall of the peripheral member 3302 may define a peripheral side wall (and thus the exterior peripheral side surface) of the tag.

The compliant member 3306 may be formed from a more flexible material than the peripheral member 3302 and the central member 3304. For example, the peripheral member 3302 (which may define a side wall of the top housing member 3300) and the central member 3304 (which may define a top outer surface of the top housing member 3300) may be formed from a first polymer material such as an ABS, PMMA, and the compliant member 3306 may be formed from a second polymer material that is more flexible than the first polymer material, such as silicone, thermoplastic polyurethane (TPU), or the like. The compliant member 3306 may be configured to allow the central member 3304 to move more freely relative to the peripheral member 3302 than would occur if the central and peripheral members were a unitary structure (such as the top housing member 3100).

FIG. 33B shows an underside view of the top housing member 3300. The top housing member 3300 may define reinforcing ribs 3308, which may be integrally formed with the peripheral member 3302. The central member 3304 may define a coil attachment region 3310, which may be similar to the coil attachment region 3104, described above.

FIG. 33C is a cross-sectional view of the top housing member 3300, viewed along line 33C-33C in FIG. 33A. As shown, the portion of the compliant member 3306 that is visible on the outer surface of the top housing member 3300 may only be a part of the compliant member 3306. More particularly, the compliant member 3306 may extend along a portion of the inner or bottom surface of the central member 3304, and may mechanically couple the central member 3304 to the peripheral member 3302. The compliant member 3306 may define an opening that exposes the coil attachment region 3310 so that the coil can be attached directly to the central member 3304, thereby directly transferring force to the central member 3304. The part of the compliant member 3306 that is exposed may be recessed relative to the peripheral and central members.

The top housing member 3300 may be formed by a co-injection molding or insert molding technique, as described above with respect to the top housing member 3200. Further, like the top housing member 3200, the top housing member 3300 may be configured to produce audible and/or tactile outputs using substantially linear movement (with no or only nominal deformation) of the central member 3304, rather than a bending or deformation mode (as is the case with the unitary top housing member 3100). In some cases, the central member 3304 may translate relative to the peripheral member 3302 to produce the audible output.

Figure 34A:
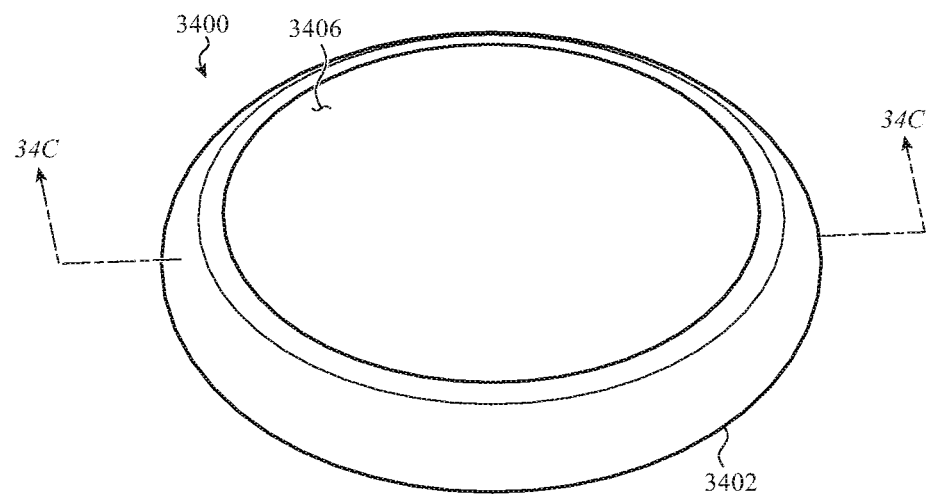
FIGS. 34A-34C depict another example top housing member for a wirelessly locatable tag.
Figure 34B:
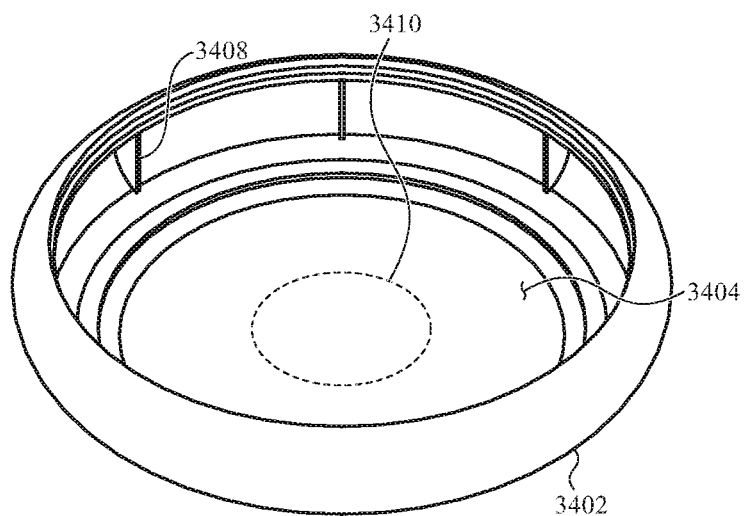
Figure 34C:
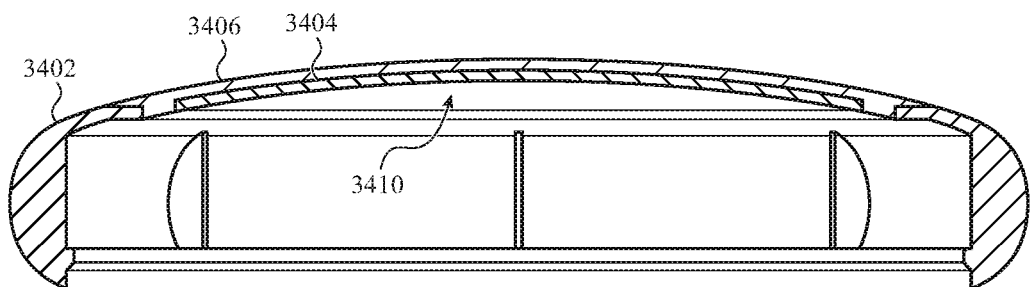

FIGS. 34A-34C illustrate another example top housing member 3400 that may include multiple components. FIG. 34A shows the outer surface of the top housing member 3400, which may define an exterior surface of the tag. The top housing member 3400 may define a peripheral member 3402, and a compliant member 3406. The compliant member 3406 defines a central region of the top housing member 3400, which is part of the exterior surface of the top housing member 3400 and thus part of the exterior surface of the device that uses the top housing member 3400. The compliant member 3406 may be formed of similar materials as the compliant members 3206, 3306 (e.g., silicone, thermoplastic polyurethane (TPU), or the like).

FIG. 34B shows an underside view of the top housing member 3400. The top housing member 3400 may define reinforcing ribs 3408, which may be integrally formed with the peripheral member 3402. The top housing member 3400 may also include a central member 3404 that is below the compliant member 3406. The central member 3404 may be formed from a more rigid material than the compliant member (and may be the same material as the peripheral member 3402). The central member 3404 may define a coil attachment region 3410, which may be similar to the coil attachment region 3104, described above. By providing the central member 3404 below the compliant member 3406, and leaving the central member 3404 exposed on the interior side of the top housing member 3400, the coil can attach directly to the relatively central member 3404 and use the stiffness of the central member 3404 to more efficiently translate the movement of the coil into vertical motion of the central member of the top housing member 3400 (as compared, for example, to a top housing member 3400 without the central member). The vertical motion may correspond to a translation of the central member 3404 relative to the peripheral member 3402.

FIG. 34C is a cross-sectional view of the top housing member 3400, viewed along line 34C-34C in FIG. 34A. As shown, the compliant member 3406 defines substantially all of the top exterior surface of the top housing member 3400, and the central member 3404 does not define any part of the exterior of the top housing member 3400.

The top housing member 3400 may be formed by a co-injection molding or insert molding technique, as described above with respect to the top housing member 3200. Further, like the top housing member 3200, the top housing member 3400 may be configured to produce audible and/or tactile outputs using substantially linear movement (with no or only nominal deformation) of the central member 3404 (and the overlying part of the compliant member 3406), rather than a bending or deformation mode (as is the case with the unitary top housing member 3100).

The wirelessly locatable tags described above are described with respect to one example form factor and configuration. For example, FIGS. 3A-34C illustrate example wirelessly locatable tags that have a generally round, puck-shaped design, with a battery door (e.g., bottom housing member) that can be detached from the rest of the tag to allow the battery to be swapped. However, the same or similar systems and functions described with respect to the generally puck-shaped configurations may be incorporated into tags having other form factors. FIGS. 35A-58C illustrate several example wirelessly locatable tags having various different form factors, battery cavity access systems, housing components, and the like.

Figure 35A:
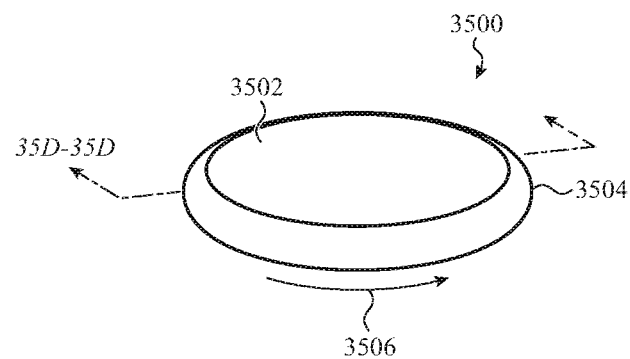
FIGS. 35A-35E depict an example configuration for a wirelessly locatable tag.

FIG. 35A illustrates an example tag 3500 that uses a battery access mechanism instead of a removable battery door to provide access to a battery cavity. The tag 3500 includes a body portion 3502 and a peripheral portion 3504. The body portion 3502 has a generally round, puck-shaped configuration, and the peripheral portion 3504 extends around the periphery of the body portion 3502. The body portion 3502 may define the top and bottom surfaces of the tag 3500, while the peripheral portion 3504 defines the peripheral side surface(s) of the tag 3500.

Figure 35B:
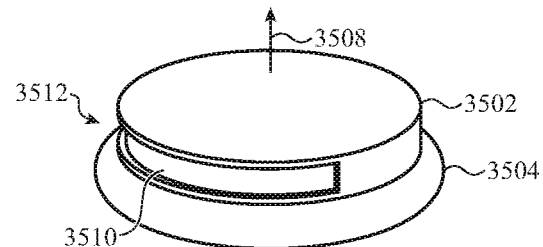
Figure 35C:
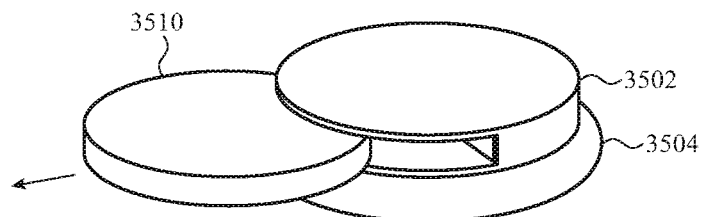

The peripheral portion 3504 may be manipulated relative to the body portion 3502 to cause a battery cavity to be exposed. For example, a user may rotate the peripheral portion 3504 about the body portion 3502 while holding the body portion 3502 stationary (as indicated by arrow 3506). As shown in FIG. 35B, this manipulation may cause the body portion 3502 to move axially out from the inner area of the peripheral portion 3504 (as indicated by arrow 3508), thereby exposing a battery cavity 3512 to allow a battery 3510 to be removed and/or replaced. FIG. 35C shows the battery 3510 being removed from the battery cavity 3512. The tag 3500 may be closed by rotating the peripheral portion 3504 about the body portion 3502 (while holding the body portion 3502 stationary) in the direction opposite that which is used to open the tag 3500. When the tag 3500 is closed, the peripheral portion 3504 may help retain the battery 3510 in the battery cavity 3512.

Figure 35D:
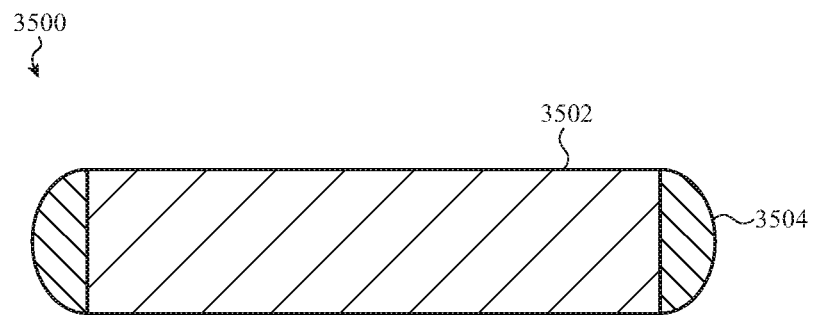
Figure 35E:
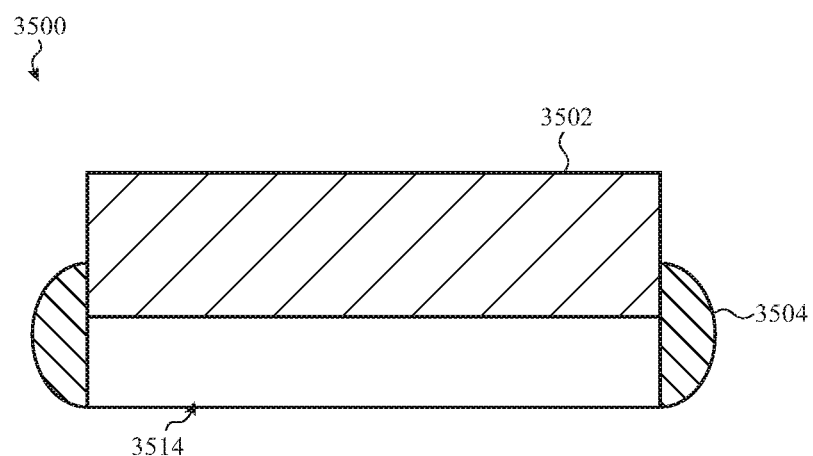

FIGS. 35D-35E are partial cross-sectional views of the tag 3500, viewed along line 35D-35D in FIG. 35A. These cross-sections are simplified for clarity, and do not show all components of the tag 3500. FIG. 35D shows the tag 3500 in a closed configuration, while FIG. 35E shows the tag 3500 in an open configuration (corresponding to the configuration shown in FIG. 35C). The top and bottom surfaces of the body portion 3502 may stay the same distance apart when the body portion 3502 is extended as shown in FIG. 35E. Thus, for example, when the peripheral portion 3504 is twisted to cause the body portion 3502 to extend axially and expose the battery cavity 3512, a recess 3514 is formed due to the movement of the body portion 3502.

Figure 36A:
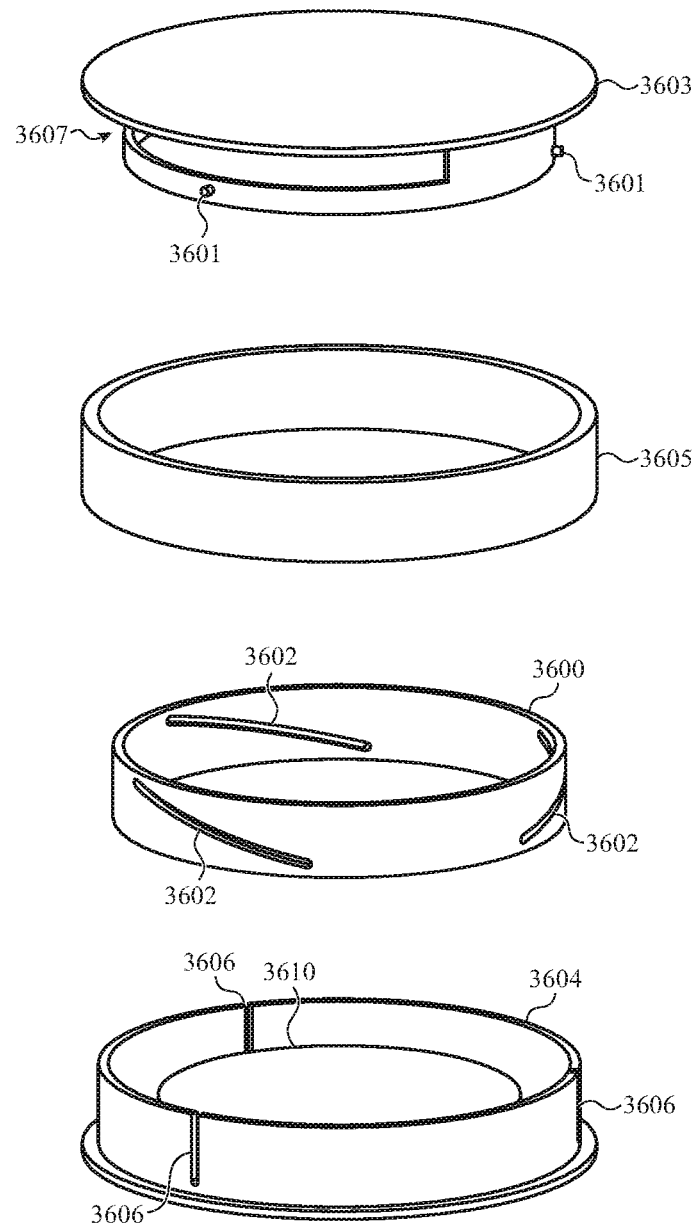
FIGS. 36A-36B depict another example configuration for a wirelessly locatable tag.

FIG. 36A is an exploded view of a portion of tag 3609, illustrating details of a mechanism that facilitates the opening and closing of the tag 3609 in a manner similar to that of the tag 3500 shown in FIGS. 35A-35E. The mechanism shown in FIGS. 36A-36B causes the body portion to expand or extend such that the bottom surface of the body portion remains in place relative to the peripheral portion, and only the top surface moves upwards to expose the battery cavity.

The tag 3609 includes an upper body portion 3603, which defines a battery cavity 3607, and a lower body portion 3604. Together, the upper and lower body portions 3603, 3604 may define some or all of a body portion of the tag 3609. The upper body portion 3603 may define a top exterior surface of the tag 3609 while the lower body portion 3604 defines a bottom exterior surface of the tag 3609. The lower body portion 3604 may include and/or support device components 3610. The device components 3610 may include circuit boards, circuit elements, processors, memory, sensors, radio circuitry (including antennas) for various wireless communications (e.g., UWB, WiFi, Bluetooth, etc.), or the like. Indeed, the device components 3610 may include any of the components that are used to provide the functions of a wireless tag as described herein.

The upper body portion 3603 includes guide pins 3601 extending from a peripheral side of the upper body portion 3603. The guide pins 3601 may engage first guide slots 3602 of a guide ring 3600. The first guide slots 3602 may extend through the guide ring 3600 (as shown), or they may be blind channels.

The guide ring 3600 may be attached to the peripheral portion 3605 such that the peripheral portion 3605 and the guide ring 3600 rotate together when a rotational force is applied to the peripheral portion 3605 (while the body portion is held stationary). The guide ring 3600 may be attached to the peripheral portion 3605 in any suitable way, such as with adhesives, clips, fasteners, springs, mechanical interlocks, or the like.

Figure 36B:
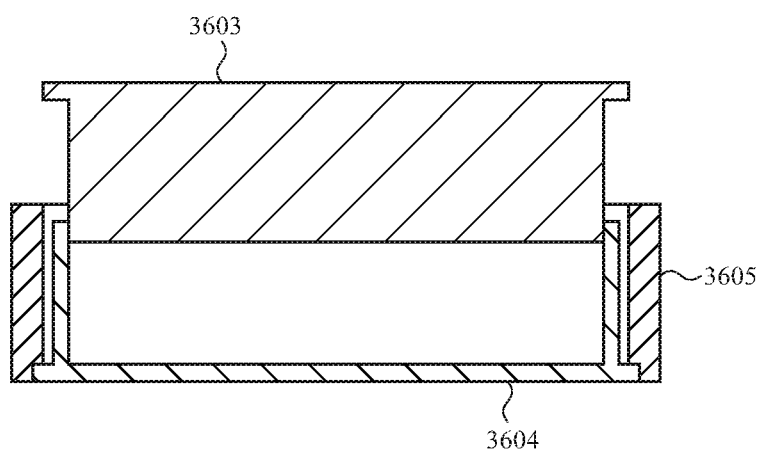

The lower body portion 3604 may define second guide slots 3606 that also engage the guide pins 3601 of the upper body portion 3603. Whereas the first guide slots 3602 are oriented at a slant relative to the axis of the tag 3609, the second guide slots 3606 are parallel to the axis. When assembled, the interaction between the guide pins 3601, the first guide slots 3602, and the second guide slots 3606 cause the upper body portion 3603 to move axially, relative to the peripheral portion 3605 and the lower body portion 3604, when the peripheral portion 3605 is rotated about the body portion. For example, the rotational movement of the guide ring 3600 (caused by rotational movement of the peripheral portion 3605) forces the guide pins 3601 to slide within the first guide slots 3602, while the second guide slots 3606 prevent the upper body portion 3603 from rotating. The combined effect of the interactions between the guide pins 3601 and the first and second guide slots 3602, 3606 causes the upper body portion 3603 to move axially upward (relative to the orientation in FIG. 36A), thereby exposing the battery cavity 3607. In some cases, the first and/or second guide slots 3602, 3606 may include bumps, catches, protrusions, or other features that provide a tactile indication that the tag is fully open or fully closed. Such features may also help retain the tag in a fully open or closed position. FIG. 36B shows a partial cross-sectional view of the tag 3609, illustrating how the lower body portion 3604 remains substantially flush with (or otherwise does not move relative to) the bottom edge of the peripheral portion 3605 when the upper body portion 3603 is extended axially upwards to expose the battery cavity 3607.

The tag 3609 may include conductors that conductively couple a battery contact (that connects to the battery terminals of the battery) to the device components 3610. The conductors may be flexible to accommodate the motion between the upper body portion 3603 and the rest of the tag 3609. In other cases, sliding electrical contacts, which may be similar to slip rings, may be used to conductively couple the battery connector to device components on a different structure of the tag 3609. A similar battery connector structure may be used for the tag 3500 as well.

Figure 37A:
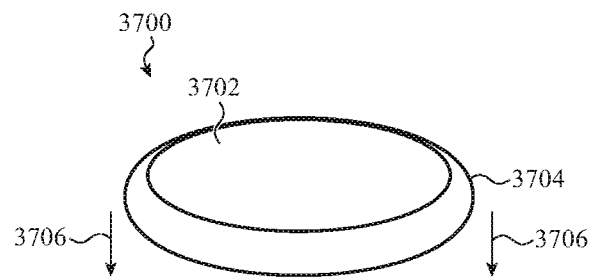
FIGS. 37A-37C depict another example configuration for a wirelessly locatable tag.
Figure 37B:
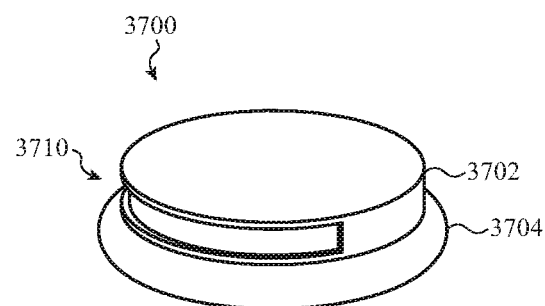
Figure 37C:
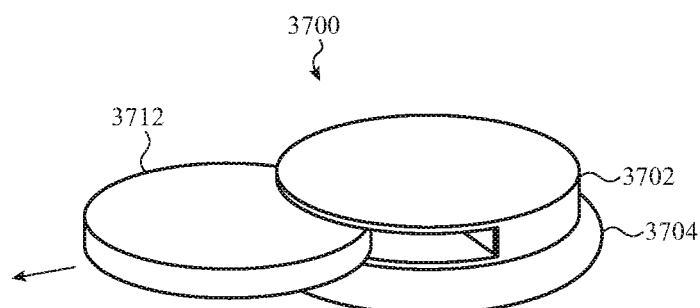

FIGS. 37A-37C illustrate another example tag 3700 that uses a battery access mechanism instead of a removable battery door to provide access to a battery cavity. The tag 3700 includes a body portion 3702 and a peripheral portion 3704. The body portion 3702 has a generally round, puck-shaped configuration, and the peripheral portion 3704 extends around the periphery of the body portion 3702. The body portion 3702 may define the top and bottom surfaces of the tag 3700, while the peripheral portion 3704 defines the peripheral side surface(s) of the tag 3700.

The peripheral portion 3704 may be manipulated relative to the body portion 3702 to cause a battery cavity to be exposed. For example, a user may push the body portion 3702 upward relative to the peripheral portion 3704, as illustrated by the arrows 3706. This may be achieved by a user pushing on the body portion 3702 from the bottom (e.g., with a thumb), while pulling down on the peripheral portion 3704.

As shown in FIG. 37B, this manipulation may cause the body portion 3702 to move axially upwards relative to the peripheral portion 3704, thereby revealing the battery cavity 3710. FIG. 37C shows the battery 3712 being removed from the battery cavity. Like the tag 3500, the peripheral portion 3704 may help retain the battery 3712 in the battery cavity 3710 when the tag 3700 is closed.

The tag 3700 may include guide mechanisms or features (e.g., guide pins and guide slots that engage the guide pins) to constrain the movement of the body portion 3702 relative to the peripheral portion 3704. For example, the guide mechanisms or features may guide the body portion 3702 so that it moves linearly relative to the peripheral portion 3704 and does not rotate relative to the peripheral portion 3704. The guide mechanisms or features may also limit the axial travel of the body portion 3702 relative to the peripheral portion 3704 and prevent them from separating from one another. Further, the guide mechanisms or features may include detents, latches, catches, or other features that tactilely indicate when the body portion 3702 is in a fully open or fully closed position, and also retain the body portion 3702 in a fully open or fully closed position.

Figure 38A:
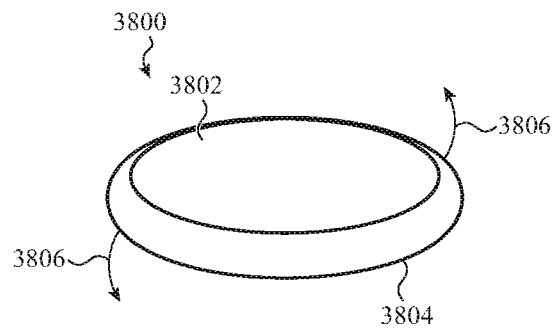
FIGS. 38A-38C depict another example configuration for a wirelessly locatable tag.
Figure 38B:
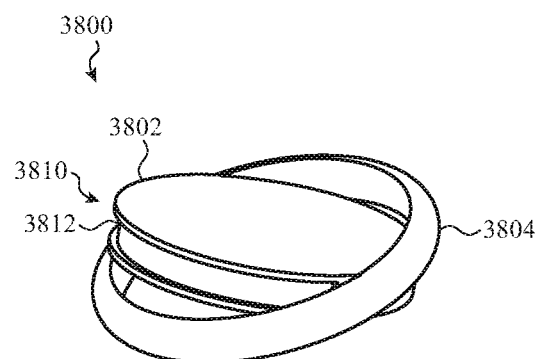
Figure 38C:
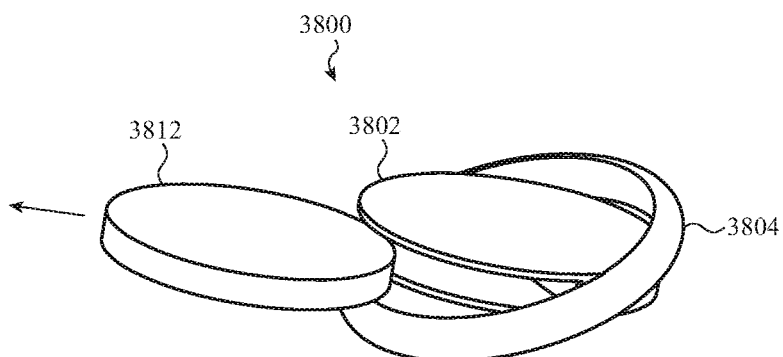

FIGS. 38A-38C illustrate another example tag 3800 that uses a battery access mechanism instead of a removable battery door to provide access to a battery cavity. The tag 3800 includes a body portion 3802 and a peripheral portion 3804. The body portion 3802 has a generally round, puck-shaped configuration, and the peripheral portion 3804 extends around the periphery of the body portion 3802. The body portion 3802 may define the top and bottom surfaces of the tag 3800, while the peripheral portion 3804 defines the peripheral side surface(s) of the tag 3800.

The peripheral portion 3804 may be manipulated relative to the body portion 3802 to cause a battery cavity to be exposed. For example, a user may pivot the peripheral portion 3804 relative to the body portion 3802, as illustrated by the arrows 3806. This may be achieved by a user grasping the peripheral portion 3804 and twisting the peripheral portion 3804 about a diametrical axis of the body portion 3802, while holding the body portion 3802 stationary (or any equivalent manipulations).

As shown in FIG. 38B, this manipulation may cause the peripheral portion 3804 to pivot relative to the body portion 3802, thereby revealing the battery cavity 3810. FIG. 38C shows the battery 3812 being removed from the battery cavity. Like the tag 3500, the peripheral portion 3804 may help retain the battery 3812 in the battery cavity 3810 when the tag 3800 is closed.

The tag 3800 may include a pivoting mechanism that pivotally couples the peripheral portion 3804 to the body portion 3802. The pivoting mechanism may include, for example, a complementary set of pins and receptacles (on the peripheral portion 3804 and body portion 3802) that engage to pivotally couple the components together. The tag 3800 may also include travel limiting features (such as lips, flanges, pins and slots, latches, catches, or other interacting structures) that limit the amount and/or direction that the peripheral portion 3804 can pivot about the body portion 3802. The tag 3800 may also include detents, latches, catches, or other features that tactilely indicate when the peripheral portion 3804 is in a fully open or fully closed position, relative to the body portion 3802, and also retain the peripheral portion 3804 in a fully open or fully closed position.

Figure 39A:
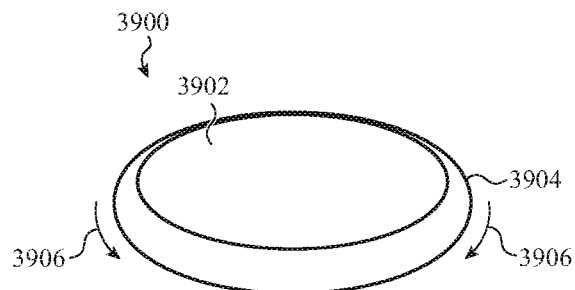
FIGS. 39A-39C depict another example configuration for a wirelessly locatable tag.
Figure 39B:
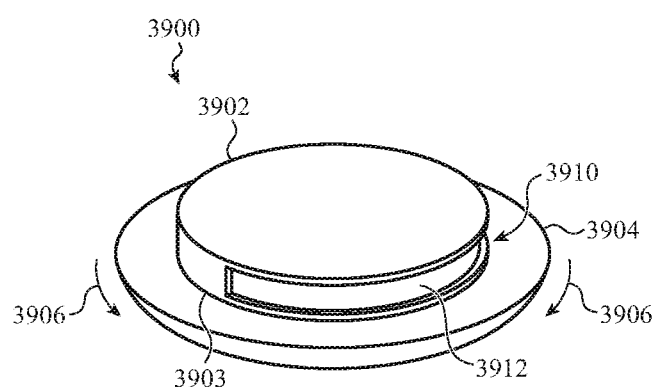
Figure 39C:
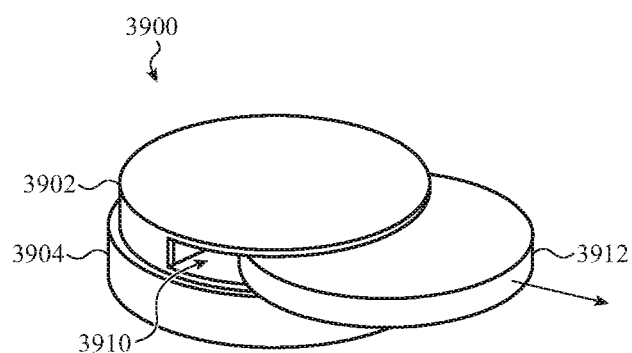

FIGS. 39A-39C illustrate another example tag 3900 that uses a battery access mechanism instead of a removable battery door to provide access to a battery cavity. The tag 3900 includes a body portion 3902 and a peripheral portion 3904. The body portion 3902 has a generally round, puck-shaped configuration, and the peripheral portion 3904 extends around the periphery of the body portion 3902. The body portion 3902 may define the top and bottom surfaces of the tag 3900, while the peripheral portion 3904 defines the peripheral side surface(s) of the tag 3900.

The peripheral portion 3904 may be formed from a compliant material that is attached to the body portion 3902 along a seam 3903, as shown in FIG. 39B. The peripheral portion 3904 may have a bistable configuration. In a first stable position (FIG. 39A) the peripheral portion 3904 covers the sides of the body portion 3902 and covers the battery cavity 3910 (FIG. 39B), thereby retaining the battery 3912 (FIG. 39B) in the battery cavity. In a second stable configuration, the peripheral portion 3904 is deflected or deformed downward and, while still attached to the body portion 3902 at the seam 3903 (and without requiring an applied force to maintain the peripheral portion 3904 in the second stable configuration), the battery cavity 3910 is exposed to allow the battery 3912 to be removed and/or replaced. In some cases, instead of being bistable, the peripheral portion 3904 may be biased towards the closed configuration (FIG. 39A), and the user must hold the peripheral portion 3904 in the open configuration while replacing the battery.

The peripheral portion 3904 may be moved to the second configuration by a user applying a rolling or peeling force on the peripheral portion 3904. FIGS. 39A-39B show an example rolling force, indicated by arrows 3906, that may be applied to the peripheral portion 3904 to expose the battery cavity 3910. In order to close the tag 3900, a user may apply a force to the peripheral portion 3904 in an opposite direction (if the peripheral portion 3904 is bistable), or simply cease holding the peripheral portion 3904 open (if the peripheral portion 3904 is biased to the closed configuration).

The peripheral portion 3904 may be formed from or include a polymer material, such as an elastomeric material. The material and the shape of the peripheral portion 3904 may cooperate to produce the bistable (or non-bistable) configurations described above. The peripheral portion 3904 may be attached to the body portion 3902 (at the seam 3903) in any suitable way. For example, the peripheral portion 3904 may be mechanically engaged with the body portion 3902. In some cases, the peripheral portion 3904 and the body portion 3902 may be insert molded or co-molded to form a mechanical interlock (and optionally chemical or adhesive bond) that attaches the peripheral portion 3904 to the body portion 3902.

Figure 40A:
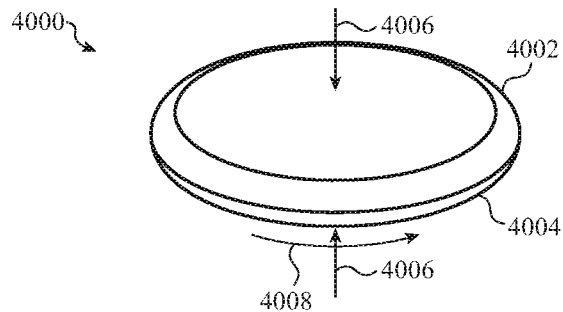
FIGS. 40A-40C depict another example configuration for a wirelessly locatable tag.
Figure 40B:
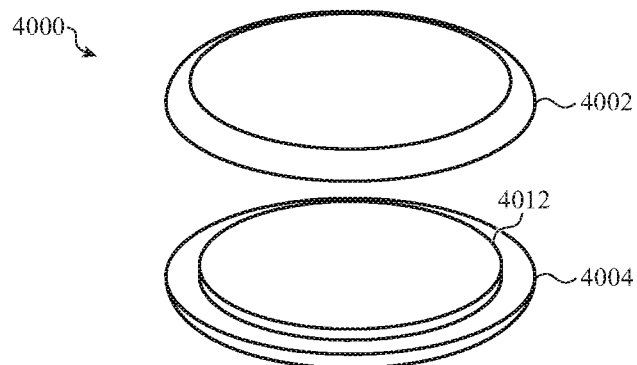
Figure 40C:
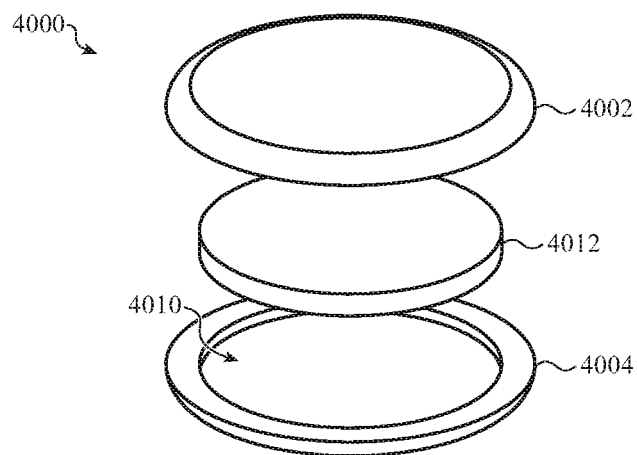

FIGS. 40A-40C illustrate another example tag 4000 that uses yet another housing configuration to provide access to a battery cavity. The tag 4000 includes a first body portion 4002 and a second body portion 4004. The first and second body portions 4002, 4004 may be substantially similar in shape and size. The first body portion 4002 may define a top surface and about half of a peripheral side surface of the tag 4000, while the second body portion 4004 may define a bottom surface and the other half of the peripheral side surface of the tag 4000.

The first and second body portions 4002, 4004 may be separated from one another to reveal a battery cavity 4010 (FIG. 40C) and allow the battery 4012 to be swapped. Both the first and the second body portions 4002, 4004 may define part of the battery cavity 4010.

The first and second body portions 4002, 4004 may be separated by a press-and-twist interaction, whereby the user must apply an axial force (represented by arrows 4006) prior to and/or while applying a twisting force (represented by arrow 4008). The user may then separate the first and second body portions 4002, 4004, as shown in FIG. 40B. The tag 4000 may include features such as latches, cam latches, springs, channels, protrusions, or the like to releasably engage the first and second body portions 4002, 4004 and allow them to be separated as shown in FIGS. 40A-40B. Some examples of such features and/or mechanisms are described above with respect to FIGS. 12A-12C and 14A-25C. Accordingly, for brevity, their details may not be repeated here.

Figure 41A:
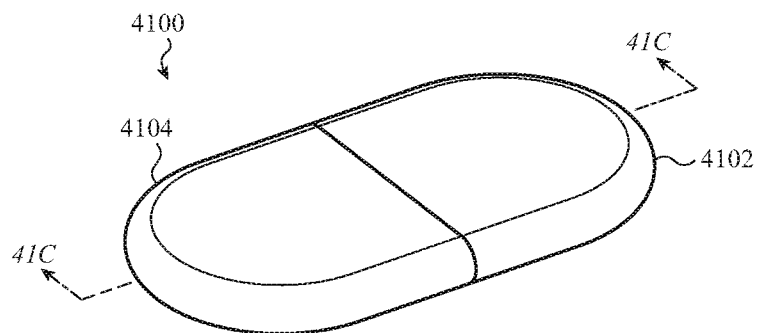
FIGS. 41A-41C depict another example configuration for a wirelessly locatable tag.
Figure 41B:
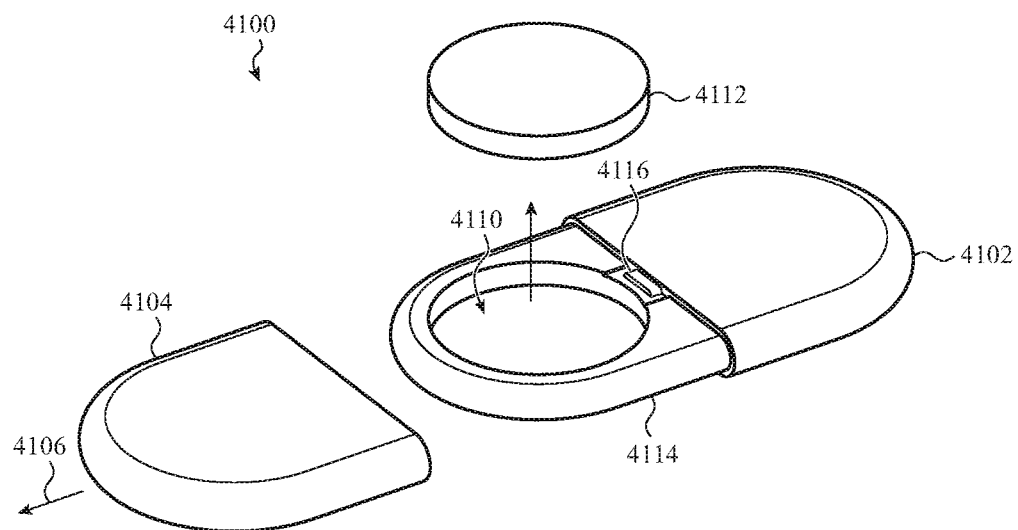
Figure 41C:
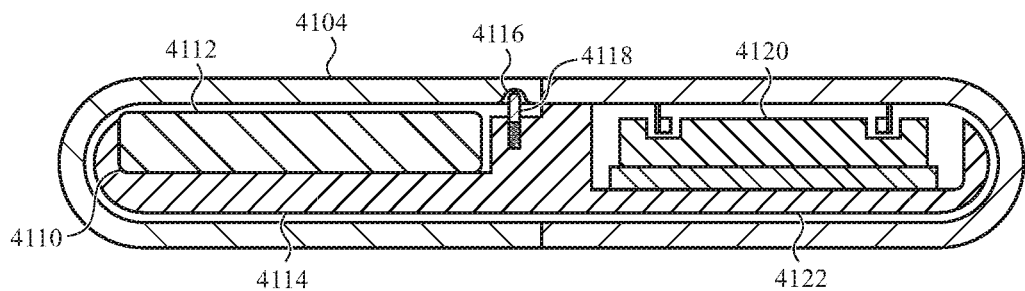

Wirelessly locatable tags may have form factors other than round, puck-shaped tags as shown in various figures of the instant application. Even where other form factors are used, similar features, functions, mechanisms, and systems may be included in the tags. FIGS. 41A-41C illustrate an example wirelessly locatable tag 4100 that has a generally lozenge-shaped appearance, as compared to the circular, puck-shaped tags described elsewhere herein.

The tag 4100 may include a first housing member 4102 and a second housing member 4104. The second housing member 4104 may be removable from the remainder of the tag 4100, and may be removed (e.g., by pulling the second housing member 4104 along the direction 4106) to expose a battery cavity and battery to facilitate battery replacement. FIG. 41B illustrates the tag 4100 with the second housing member 4104 detached from the tag 4100 and exposing the battery cavity 4110. The tag 4100 may include a frame member 4114. The frame member may at least partially define the battery cavity 4110, and may support other tag components such as a circuit board, antennas, an audio system, and the like.

The tag 4100 may also include a latch mechanism 4116 that releasably retains the second housing member 4104 to the frame member 4114. The latch mechanism 4116 may include an outwardly-biased latching feature that engages a recess, cavity, or other feature in the second housing member 4104 to retain the second housing member 4104 to the frame member 4114, while also permitting the second housing member 4104 to be removed by a user. The latch mechanism 4116 may include a locking mechanism or component such that a user cannot detach the second housing member 4104 simply by pulling on it. For example, the tag 4100 may include a button that must be pushed in order to allow the latch mechanism 4116 to release the second housing member 4104.

FIG. 41C is a partial cross-sectional view of the tag 4100, viewed along line 41C-41C in FIG. 41A. FIG. 41C shows the battery 4112 in the battery cavity 4110 defined by the frame member 4114. FIG. 41C further illustrates how the latch mechanism 4116 may engage a recess or other feature in the second housing member 4104. The latch mechanism 4116 and the second housing member 4104 may be configured so that the latch mechanism 4116 deflects downward in response to the second housing member 4104 being attached to the tag. For example, the top of the latch mechanism 4116 may be rounded, chamfered, or otherwise define an interface surface that, when contacted by the second housing member 4104, forces the latch mechanism 4116 to deflect in a way that permits the second housing member 4104 to be fully attached.

FIG. 41C also illustrates a circuit board 4122 and an audio system 4120 in an area that is at least partially covered by the first housing member 4102. The circuit board 4122 may include circuit elements, processors, memory, conductors, sensors, antennas, or any other components. Such components may also be positioned elsewhere in or on the tag 4100. For example, antennas may be integrated with the frame member 4114 in a manner similar to the antenna assembly 508, described above.

The audio system 4120 may operate similar to other audio systems described herein. For example, a coil may be attached to an interior surface of the first housing member 4102, and a magnet may provide a magnetic field to allow the coil to operate as a speaker. By passing a signal (e.g., current) through the coil, a portion of the first housing member 4102 can move in a manner similar to a speaker diaphragm. Further, the audio system 4120 may be used to produce tactile outputs that a user can feel when touching the first housing member 4102. Of course, other types of audio systems and/or tactile output generators may be used instead of or in addition to the audio system 4120.

Figure 42A:
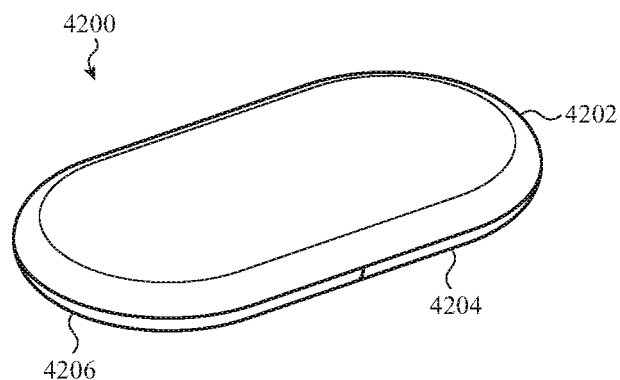
FIGS. 42A-42B depict another example configuration for a wirelessly locatable tag.
Figure 42B:
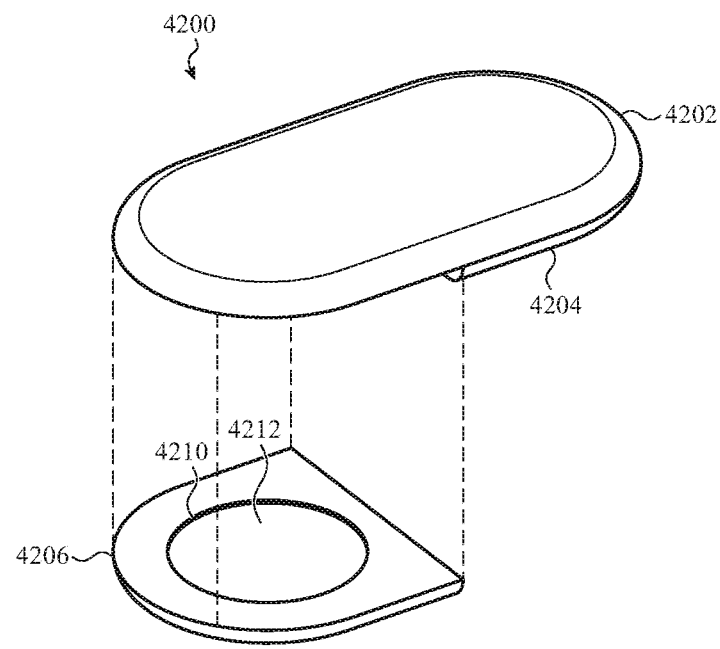

FIGS. 42A-42B illustrate another example wirelessly locatable tag 4200 that has a generally lozenge-shaped form factor. The tag 4200 includes a first housing member 4202 that defines all or substantially all of a top surface and part of the peripheral surface of the tag 4200. The tag 4200 also includes a second housing member 4204 that defines part of (e.g., approximately half of) a bottom surface of the tag 4200 and part of the peripheral surface of the tag 4200. The second housing member 4204 may not be intended to be removed by a user of the tag 4200. The tag 4200 may also include a third housing member 4206, which may also define part of (e.g., approximately half of) the bottom surface of the tag 4200 and part of the peripheral surface of the tag 4200.

The third housing member 4206 may be removable to provide access to a battery cavity. For example, FIG. 42A illustrates the third housing member 4206 removed from the rest of the tag 4200. The third housing member 4206 may define at least part of a battery cavity 4210 for a battery 4212. Features of the third housing member 4206 may engage corresponding features of the first and/or second housing members 4202, 4204, or any other component of the tag 4200 (e.g., a frame member), to retain the third housing member 4206 to the tag 4200 while also allowing it to be removed for battery replacement. Such features may include clips, latches, detents, or the like. The third housing member 4206 may be removed from the tag 4200 by prying with a fingernail, tool, or other implement inserted in a gap between the third housing member 4206 and another part of the tag 4200.

In other respects, such as the component set and the function and arrangement of such components (including circuit boards, audio systems, antennas, etc.), the tag 4200 may be substantially similar to the tag 4100. Further, the tag 4200 may include any of the components and/or provide any of the features of any tag described herein.

Figure 43A:
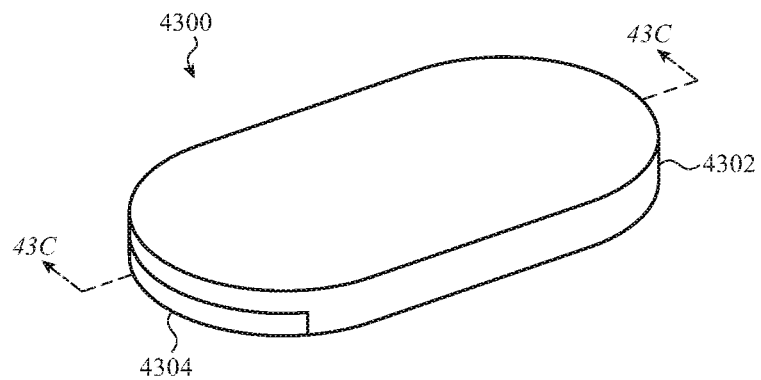
FIGS. 43A-43C depict another example configuration for a wirelessly locatable tag.
Figure 43B:
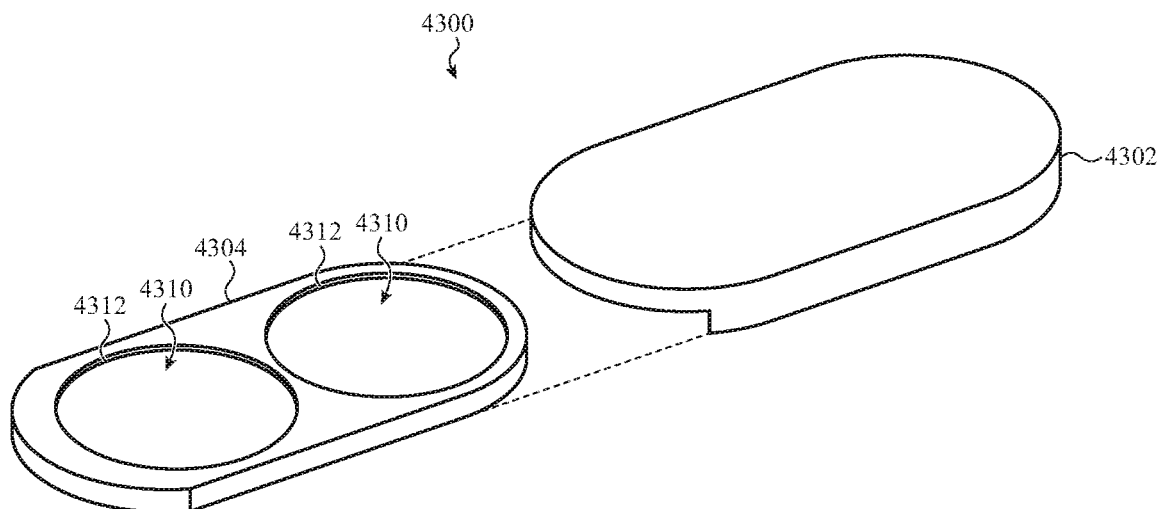
Figure 43C:
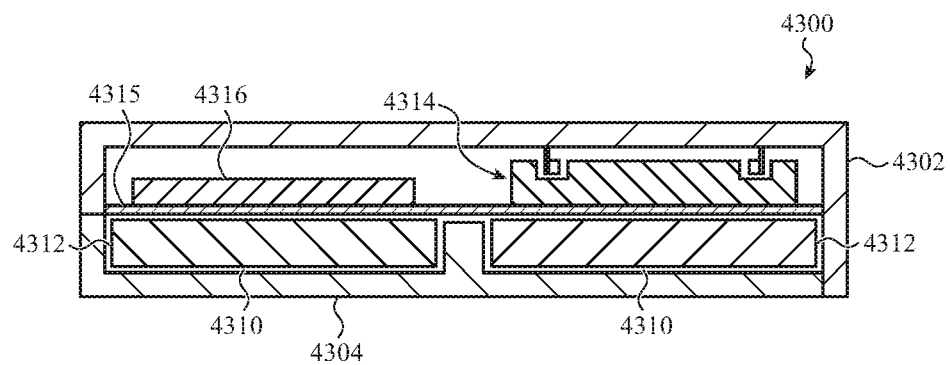

FIGS. 43A-43C illustrate another example wirelessly locatable tag 4300 that has a generally lozenge-shaped form factor. The tag 4300 includes a first housing member 4302 that defines all or substantially all of a top surface and part of the peripheral surface of the tag 4300. The tag 4300 also includes a second housing member 4304 that defines substantially all or part of a bottom surface of the tag 4300 and part of the peripheral surface of the tag 4300. The second housing member 4304 may be removable from the first housing member 4302 and may define one or more battery cavities.

The second housing member 4304 may act as a battery tray for the tag 4300. The second housing member 4304 may be slidably engaged with the tag 4300. For example, the second housing member 4304 may engage rails or slots of the first housing member 4302 (or defined by any other component of the tag 4300). The second housing member 4304 may be removed by pulling the second housing member 4304 outwardly (e.g., in a direction parallel to the long axis of the lozenge-shaped tag 4300). The tag 4300 may include retention features (e.g., clips, latches, locking mechanisms, etc.) that retain the second housing member 4304 in a closed configuration during use, and help prevent accidental removal of the second housing member 4304.

FIG. 43B illustrates the tag 4300 with the second housing member 4304 removed from the tag 4300. The second housing member 4304 defines two battery cavities 4310 for receiving two batteries 4312.

FIG. 43C is a partial cross-sectional view of the tag 4300, viewed along line 43C-43C in FIG. 43A. FIG. 43C shows the batteries 4312 in the battery cavities 4310 defined by the second housing member 4304. FIG. 43C also illustrates a circuit board 4316 and an audio system 4314, both of which may be mounted on a frame member 4315. The frame member, circuit board, and audio system may all have the same or similar components and may provide the same or similar functions to the other frame members, circuit boards, and audio systems described herein, and for brevity their details may not be repeated here. In other respects, such as the component set and the function and arrangement of such components (including circuit boards, audio systems, antennas, etc.), the tag 4300 may be substantially similar to other tags described herein.

Figure 44A:
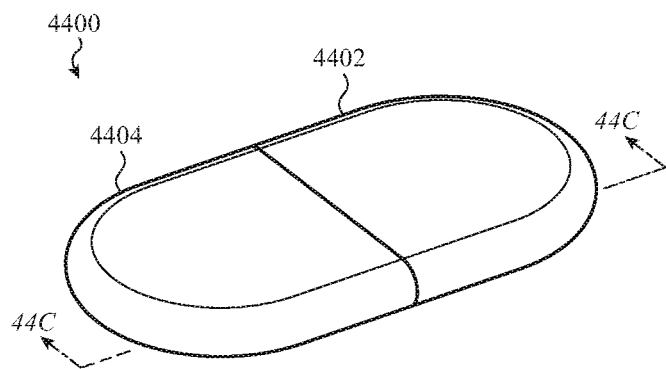
FIGS. 44A-44C depict another example configuration for a wirelessly locatable tag.
Figure 44B:
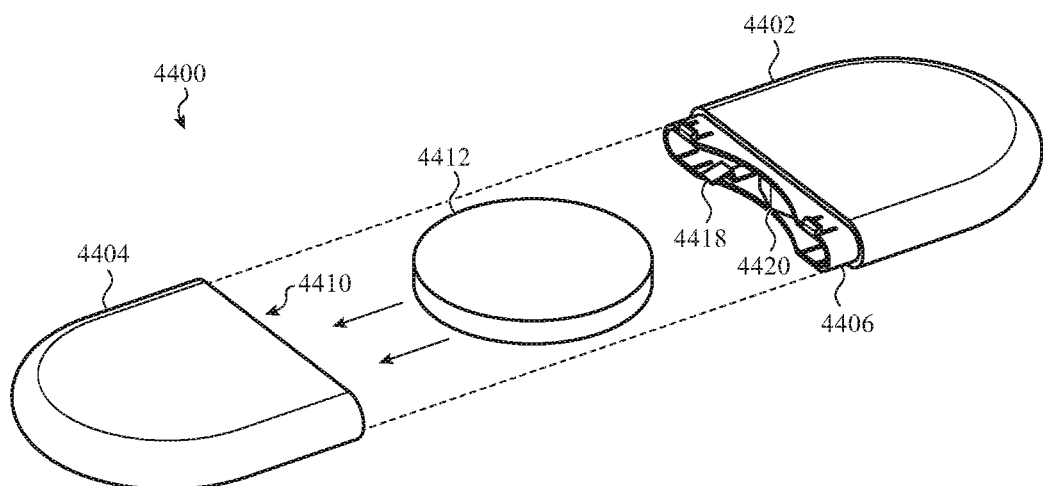
Figure 44C:
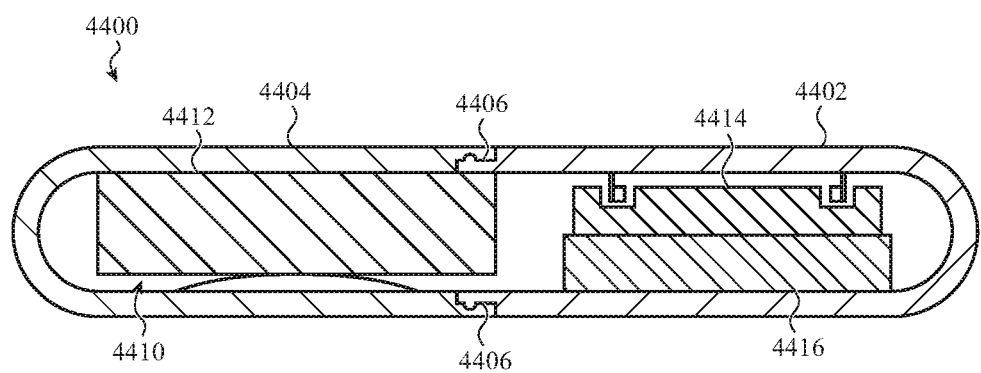

FIGS. 44A-44C illustrate another example wirelessly locatable tag 4400 that has a generally lozenge-shaped form factor. The tag 4400 includes a first housing member 4402 that defines part of a top surface, part of a bottom surface, and part of the peripheral surface of the tag 4400. The tag 4400 also includes a second housing member 4404 that defines the remaining parts of the top surface, bottom surface, and peripheral surface of the tag 4400. The second housing member 4404 may be removable from the first housing member 4402 and may define a battery cavity.

FIG. 44B shows the tag 4400 with the second housing member 4404 detached from the first housing member 4402. The second housing member 4404 may define a battery cavity 4410 for receiving the battery 4412. The first housing member 4402 may define a ledge 4406 that engages the second housing member 4404 to releasably retain the first and second housing members together. The ledge 4406 may include latches, catches, protrusions, channels, recesses, or other features that engage corresponding features on the second housing member 4404 to hold the first and second housing members together, while also allowing them to be separated by a user to access the battery cavity 4410 to remove and/or replace the battery. Such features may be integral with the ledge 4406 and the second housing member 4404, or they may be separate components attached to the ledge 4406 and/or the second housing member 4404.

FIG. 44C is a partial cross-sectional view of the tag 4400, viewed along line 44C-44C in FIG. 44A. FIG. 44C shows the battery 4412 in the battery cavity 4410 defined by the second housing member 4404. FIG. 44C shows how a protrusion defined by or otherwise attached to the ledge 4406 may engage a corresponding recess along an interior surface of the second housing member 4404. The protrusion and recess may retain the first and second housing members 4402, 4404 together, while allowing them to be detached if a user applies a sufficient force to overcome the retention force produced by the protrusion and recess (e.g., by pulling them apart).

FIG. 44C also illustrates a circuit board 4416 and an audio system 4414 within an internal cavity defined by the first housing member 4402. The tag 4400 may also include battery connectors 4418, 4420 (FIG. 44B) that contact the positive and negative terminals of the battery and provide power from the battery to the circuit board 4416 and/or other electrical components of the tag 4400. The circuit board and audio system may all have the same or similar components and may provide the same or similar functions to the other circuit boards and audio systems described herein, and for brevity, their details may not be repeated here. In other respects, such as the component set and the function and arrangement of such components (including circuit boards, audio systems, antennas, etc.), the tag 4400 may be substantially similar to other tags described herein.

Figure 45A:
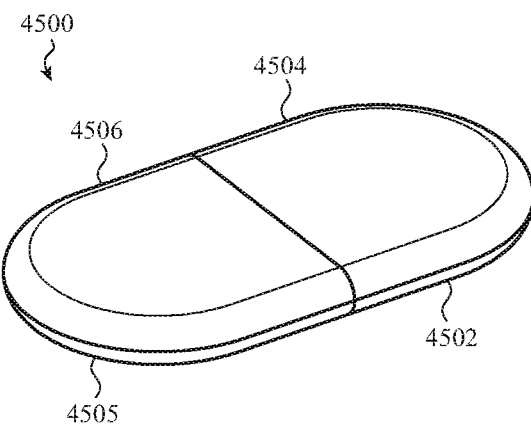
FIGS. 45A-45B depict another example configuration for a wirelessly locatable tag.
Figure 45B:
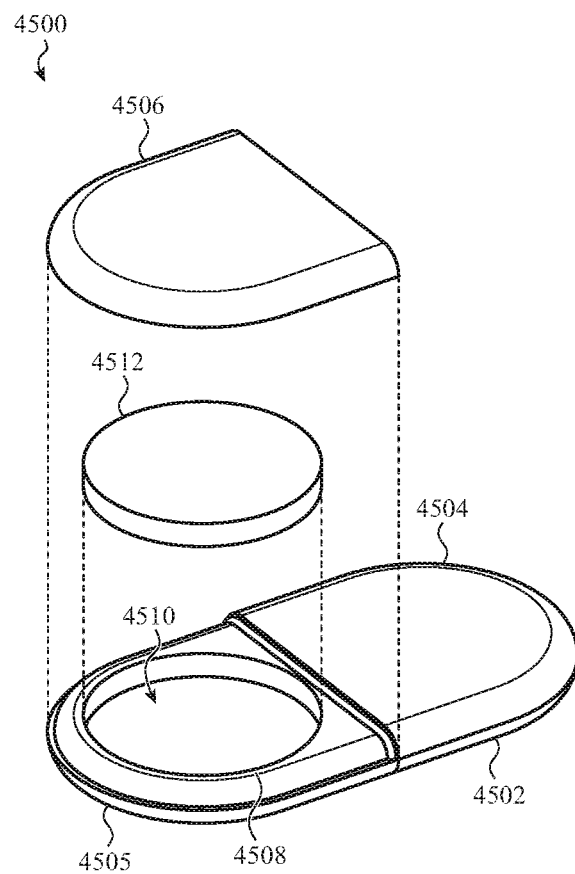

FIGS. 45A-45B illustrate another example wirelessly locatable tag 4500 that has a generally lozenge-shaped form factor. The tag 4500 includes a removable housing member 4506 that can be removed from the rest of the tag 4500 to provide access to a battery cavity 4510. The tag 4500 may include other housing members, such as a first housing member 4502, a second housing member 4504, and a third housing member 4505, which may be configured as non-user-removable housing members. In some cases, more or fewer housing members may be used. For example, a single housing member may be used instead of the separate first and second housing members.

FIG. 45B shows the tag 4500 with the second housing member 4504 detached from the tag 4500. The tag 4500 may include a frame member 4508, and the battery cavity 4512 may be defined in the frame member 4508. The first, second, and third housing members 4502, 4504, and 4505 may be attached to the frame member 4508, such as via clips, adhesives, ultrasonic welding, or the like. The removable housing member 4506 may be releasably retained to the frame member 4508 via clips, latches, detents, channels, recesses, or any other suitable retention feature that retains the removable housing member 4506 to the frame (or other component of the tag 4500) while allowing it to be detached if a user applies a sufficient force to overcome the retention force provided by the features.

In other respects, such as the component set and the function and arrangement of such components (including circuit boards, audio systems, antennas, etc.), the tag 4500 may be substantially similar to other tags described herein.

Figure 46A:
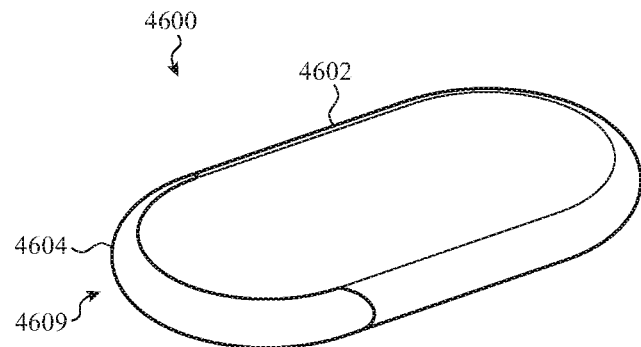
FIGS. 46A-46B depict another example configuration for a wirelessly locatable tag.
Figure 46B:
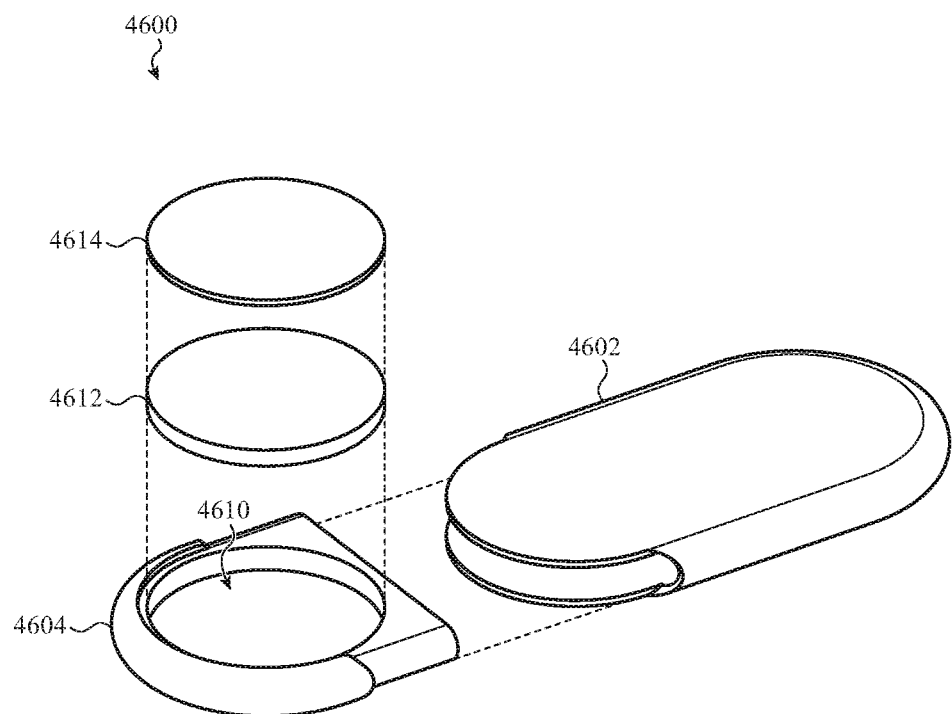

FIGS. 46A-46B illustrate another example wirelessly locatable tag 4600 that has a generally lozenge-shaped form factor. The tag 4600 includes a first housing member 4602 that defines all or substantially all of a top surface and a bottom surface, and part of the peripheral surface of the tag 4600. The tag 4600 also includes a second housing member 4604 that defines a remaining the remaining parts of the peripheral surface of the tag 4600. The second housing member 4604 may be removable from the first housing member 4602 and may define a battery cavity. In some cases, more or fewer housing members may be used. For example, multiple separate housing members may be used instead of the unitary first housing member 4602.

FIG. 46B shows the tag 4600 with the second housing member 4604 detached from the first housing member 4602. The second housing member 4604 may define a battery cavity 4610 for receiving the battery 4612. The tag 4600 may also include a battery cover 4614 that may be removably coupled to the second housing member 4604. The battery cover 4614 may be retained to the second housing member 4604 via clips, threads, or any other suitable features. The battery cover 4614 may help prevent accidental release of the battery 4612.

The second housing member 4604 may be releasably retained to the first housing member 4602 (or any other suitable component of the tag 4600) via clips, latches, detents, channels, recesses, or any other suitable retention feature that retains the second housing member 4604 to the tag 4600) while allowing it to be detached if a user applies a sufficient force to overcome the retention force provided by the features. In other respects, such as the component set and the function and arrangement of such components (including circuit boards, audio systems, antennas, etc.), the tag 4600 may be substantially similar to other tags described herein.

Figure 47A:
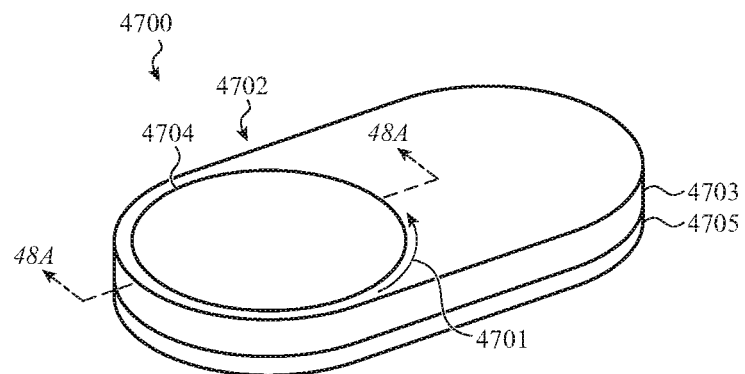
FIGS. 47A-47C depict another example configuration for a wirelessly locatable tag.
Figure 47B:
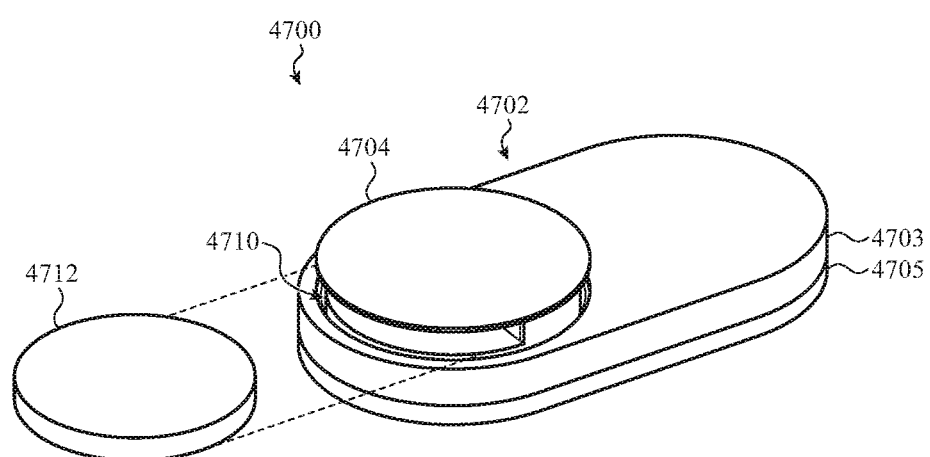
Figure 47C:
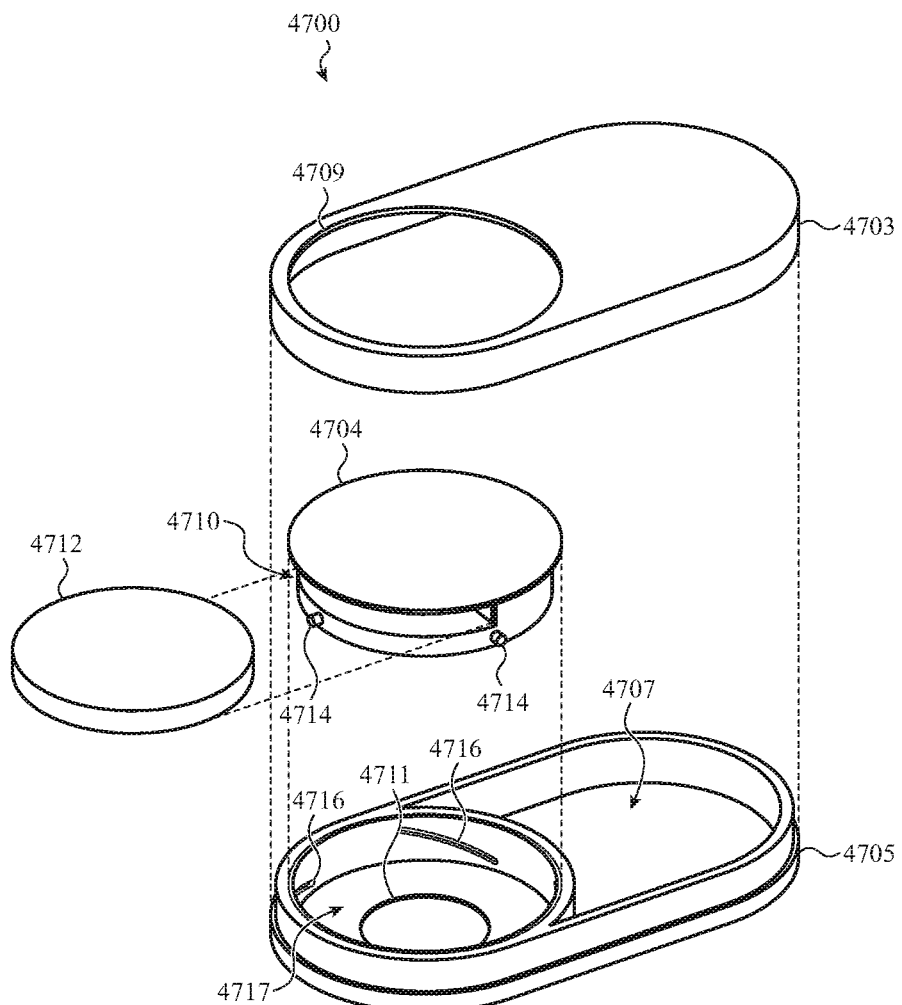

FIGS. 47A-47C illustrate another example wirelessly locatable tag 4700 that has a generally lozenge-shaped form factor. The tag 4700 includes a body portion 4702 and a battery holder 4704. The battery holder 4704 may be movable relative to the body portion 4702 to reveal a battery cavity. FIG. 47B illustrates the tag 4700 with the battery holder 4704 extended, revealing the battery cavity 4710 so that a battery 4712 may be replaced.

The body portion 4702 may include a first housing member 4705, which may define part of a bottom surface and some or all of the peripheral surface of the tag 4700, and a second housing member 4703, which may define part of a top surface of the tag 4700. The battery holder 4704 may also define part of the top surface and part of the bottom surface of the tag 4700. More particularly, the top and bottom surfaces of the battery holder 4704 may define part of the exterior top and bottom surfaces of the tag 4700 itself. In this way, the battery holder 4704 may be manipulated by a user via direct contact with the surfaces of the battery holder 4704.

The battery holder 4704 may be opened by manipulating the battery holder in a manner similar to that described with respect to the tag 3500 (FIGS. 35A-B). For example, while the user holds the body portion 4702, the user may apply a twisting or rotational motion to the battery holder 4704 (as indicated by arrow 4701). This manipulation causes the battery holder 4704 to raise up relative to the body portion 4702, thereby exposing the battery cavity 4710.

FIG. 47C illustrates a partial exploded view of the tag 4700. The first housing member 4705 defines a first cavity 4707 and a second cavity 4717. The first cavity 4707 may contain device components such as circuit boards, audio systems, antennas, antenna assemblies, processors, and the like. As noted for other tags, the function and arrangement of such components (including circuit boards, audio systems, antennas, etc.) may be substantially similar to other tags described herein. The second housing member 4703 is coupled to the first housing member 4705 to define the exterior surfaces of the body portion 4702 and to at least partially enclose the first cavity 4707. (Other configurations of housing members may be used instead of the first and second housing members, such as more or fewer housing members.) The battery holder 4704 is positioned in the second cavity 4717.

The first housing member 4705 may define a first opening 4711 and the second housing member 4703 may define a second opening 4709. The battery holder 4704 may be accessible through the first and second openings 4711, 4709. More particularly, the exterior surfaces of the battery holder 4704 may be within the first and second openings 4711, 4709 such that a user can pinch the surfaces of the battery holder 4704 to apply the necessary manipulation to extend or retract the battery holder 4704.

The battery holder 4704 and the body portion 4702 may include features that engage one another to cause the battery holder 4704 to extend upwards when twisted relative to the body portion 4702. For example, in the example implementation shown in FIG. 47C, the battery holder 4704 defines guide pins 4714, and the first housing member 4705 defines guide slots 4716 that engage the guide pins 4714. The guide slots 4716 are angled so that a twisting motion applied to the battery holder 4704 will extend or retract the battery holder 4704 as the guide pins 4714 slide along the guide slots 4716.

Figure 48A:
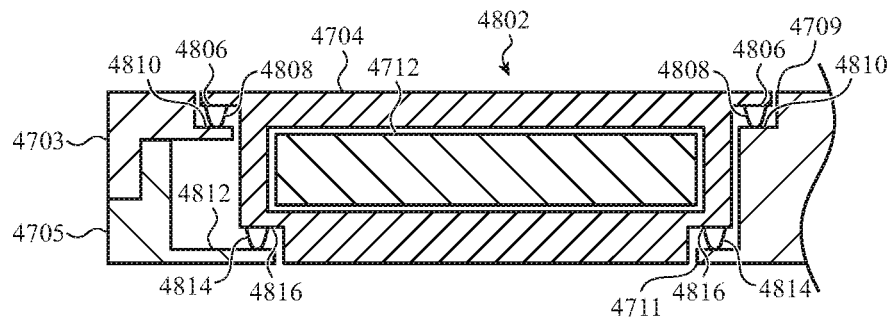
FIGS. 48A-48B depict a partial cross-sectional view of the tag of FIGS. 47A-47C.
Figure 48B:
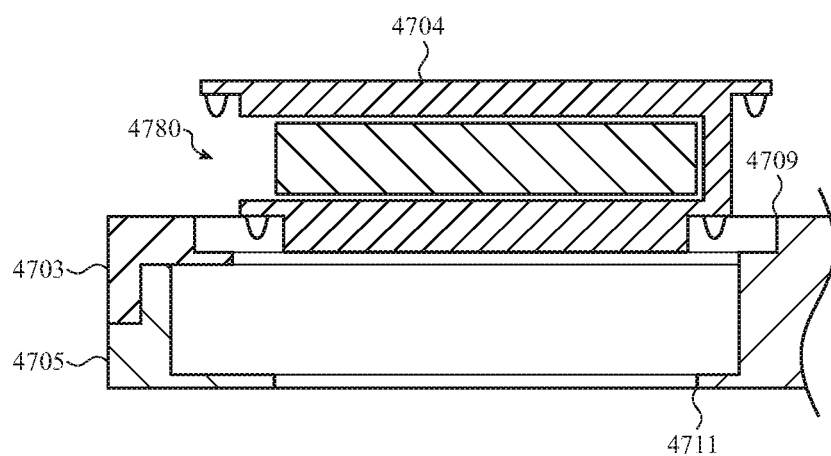

The tag 4700 may include seals to prevent ingress of liquid, dust, or other contaminants into the tag 4700 when the battery holder 4704 is in the retracted configuration. FIGS. 48A-48B are partial cross-sectional views of the tag 4700, viewed along line 48A-48A in FIG. 47A, showing the battery holder 4704 in a retracted state (FIG. 48A) and in an extended state (FIG. 48B). FIG. 48A shows example configurations for sealing the interface between the battery holder 4704 and the body portion 4702 of the tag 4700.

With reference to FIG. 48A, the interfaces between the battery holder 4704 and the first housing member 4705 (at the first opening 4711) and between the battery holder 4704 and the second housing member 4703 (at the second opening 4709) may be sealed using compliant seals. In the example shown, a first sealing member 4814 may be attached to a first interface surface 4816 of the battery holder 4704. In the retracted configuration, the first sealing member 4814 may contact a first sealing surface 4812 of the first housing member 4705. Similarly, a second sealing member 4808 may be attached to a second interface surface 4806 of the battery holder 4704. In the retracted configuration, the second sealing member 4808 may contact a second sealing surface 4810 of the second housing member 4703 (which may be a surface of a ledge defined along the wall of the second opening 4709). When the battery holder 4704 is in the retracted position, the first and second sealing members 4808, 4814 may be forced against their respective sealing surfaces, thereby inhibiting ingress of liquids, dust, or other contaminants.

The first and second sealing members 4808, 4814 may be formed of any suitable material, such as a compliant polymer material (e.g., an elastomer, silicone, or the like). They may be attached to their respective interface surfaces via adhesive or any other suitable attachment technique (e.g., co-molding, mechanical interlocking, etc.). While the first and second sealing members 4808, 4814 are shown attached to the battery holder 4704, they may instead be attached to the sealing surfaces of the housing members. Further, other configurations of interface surfaces, sealing surfaces, and sealing members are also contemplated.

In some cases, the guide slots 4716 may include bumps, catches, protrusions, or other features that provide a tactile indication that the battery holder 4704 is fully extended or fully retracted. Such features may also help retain the battery holder 4704 in the fully extended or retracted positions. In some cases, when the battery holder 4704 is in a fully retracted position (and retained in said position via the bumps, catches, protrusions, or other features), the sealing members may be compressed between their respective sealing and interface surfaces, thereby forming a positive seal against contaminants.

Figure 49A:
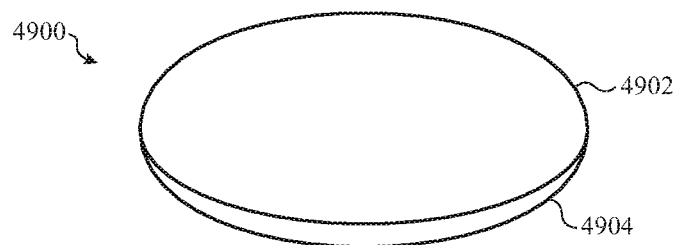
FIGS. 49A-49B depict another example configuration for a wirelessly locatable tag.
Figure 49B:
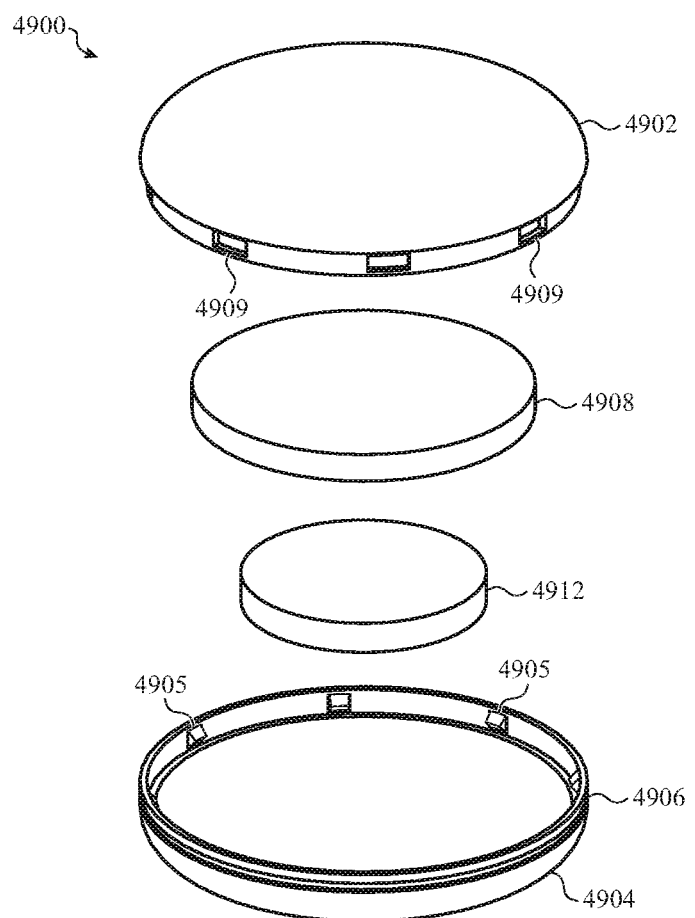

FIGS. 49A-49B illustrate another example wirelessly locatable tag 4900. The tag 4900 has a generally circular, puck-shaped form factor, similar to other tags described herein. The tag 4900 may include a first housing member 4902 and a second housing member 4904 that define substantially all of the exterior surfaces of the tag 4900. For example, the first housing member 4902 may define all of a top surface and a portion (e.g., approximately half) of a peripheral side surface of the tag 4900, while the second housing member 4904 may define all of a bottom surface and a portion (e.g., approximately half) of the peripheral side surface of the tag 4900. From the outside, the first and second housing members 4902, 4904 may appear substantially identical to one another, thereby defining a substantially symmetrical shape.

FIG. 49B is a partial exploded view of the tag 4900, showing the first and second housing members 4902, 4904 detached from one another. The tag 4900 may also include a sealing member 4906 configured to contact the first and second housing members 4902, 4904 to inhibit ingress of liquids or other contaminants.

The tag 4900 may include device components 4908. The device components 4908 may include frames (e.g., frame members, antenna assemblies) circuit boards, circuit elements, processors, memory, sensors, radio circuitry (including antennas) for various wireless communications (e.g., UWB, WiFi, Bluetooth, etc.), or the like. Indeed, the device components 4908 may include any of the components that are used to provide the functions of a wireless tag as described herein. The tag 4900 may also include a battery 4912 to provide power for the electronic components.

The first and second housing members 4902, 4904 may be attached together via interlocking features defined by the first and second housing members 4902, 4904. For example, as shown in FIG. 49B, the first housing member 4902 may define openings 4909 (or recesses or other suitable features) on a flange that mates with the second housing member 4904. Correspondingly, the second housing member 4904 defines clips 4905 that engage the openings 4909 to retain the first and second housing members 4902, 4904 together. The first and second housing members 4902, 4904 may be separable by a user by prying or otherwise pulling the first and second housing members 4902, 4904 apart (e.g., with a fingernail or other tool or implement).

The openings and clips may be unitary with the first and second housing members (e.g., formed as a single piece), or they may be separate components that are attached to the first and second housing members. For example, rings that define the openings and clips may be attached to the first and second housing members. Where separate components are attached together, the components may be formed of a different material than the housing members. For example, where the housing members are polymer, rings (or other components) defining the openings and clips may be formed from metal, a different polymer material, or the like. In some cases, the openings and clips may be distributed on the housing members differently. For example, each housing member may define some openings and some clips. Retention features other than clips and openings may be used instead of or in addition to openings and clips.

Figure 50A:
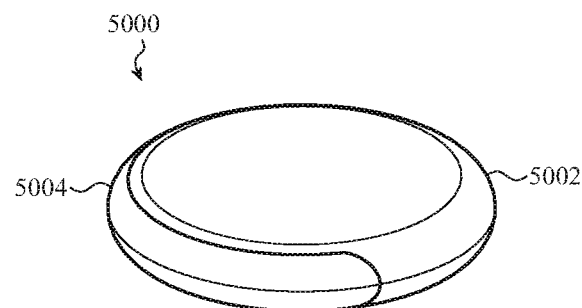
FIGS. 50A-50B depict another example configuration for a wirelessly locatable tag.
Figure 50B:
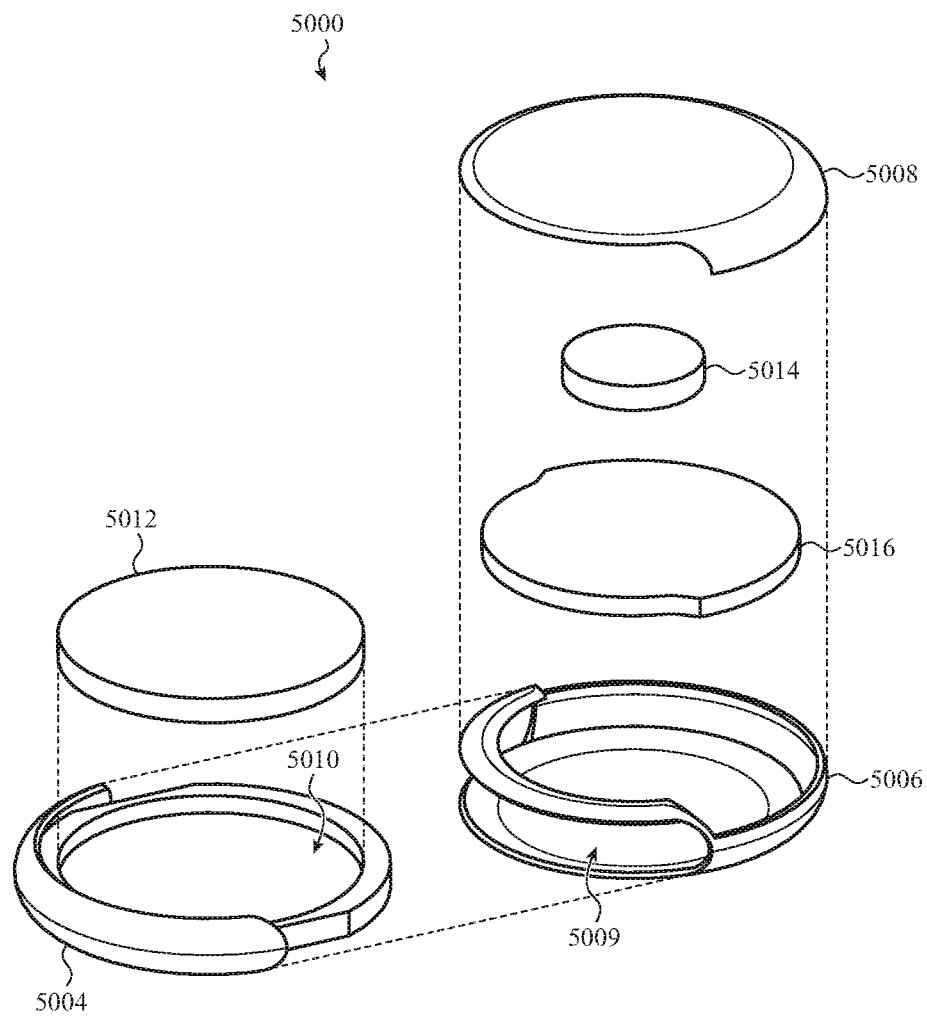

FIGS. 50A-50B illustrate another example wirelessly locatable tag 5000. The tag 5000 has a generally circular, puck-shaped form factor, similar to other tags described herein. The tag 5000 may include a body portion 5002 and a battery tray 5004 that define substantially all of the exterior surfaces of the tag 5000. For example, the body portion 5002 may define all of a top surface, all of a bottom surface, and a portion of a peripheral side surface of the tag 5000, while the battery tray 5004 may define a remaining portion of the peripheral side surface of the tag 5000. The battery tray 5004 may be openable relative to the body portion 5002 to expose a battery cavity and facilitate battery replacement. The battery tray 5004 and the body portion 5002 may include complementary slots, slides, channels, rails, or other features that engage one another to guide the battery tray 5004 along a linear path into the body portion 5002. The battery tray 5004 may be fully separable from the body portion 5002, or it may be captive to the body portion 5002 so that it remains attached to the body portion 5002 even when in an open or extended position. The battery tray 5004 may be opened by a user pulling outwardly on the battery tray 5004 while holding the body portion 5002.

FIG. 50B is a partial exploded view of the tag 5000, showing the battery tray 5004 removed from the body portion 5002. The battery tray 5004 may define a battery cavity 5010 for receiving a battery 5012 therein. The body portion 5002 may include a first housing member 5006 and a second housing member 5008, which together may define an opening 5009 that receives the battery tray 5004.

The tag 5000 may include device components 5016. The device components 5016 may include frames (e.g., frame members, antenna assemblies) circuit boards, circuit elements, processors, memory, sensors, radio circuitry (including antennas) for various wireless communications (e.g., UWB, WiFi, Bluetooth, etc.), or the like. Indeed, the device components 5016 may include any of the components that are used to provide the functions of a wireless tag as described herein. The tag 5000 may also include an audio system 5014, which may be any of the audio systems described herein (including, for example, an audio system that uses a portion of the second housing member 5008 as the diaphragm for producing audible output).

Figure 51A:
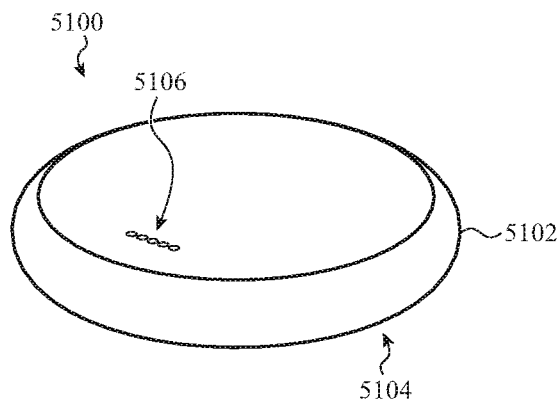
FIGS. 51A-51C depict another example configuration for a wirelessly locatable tag.
Figure 51B:
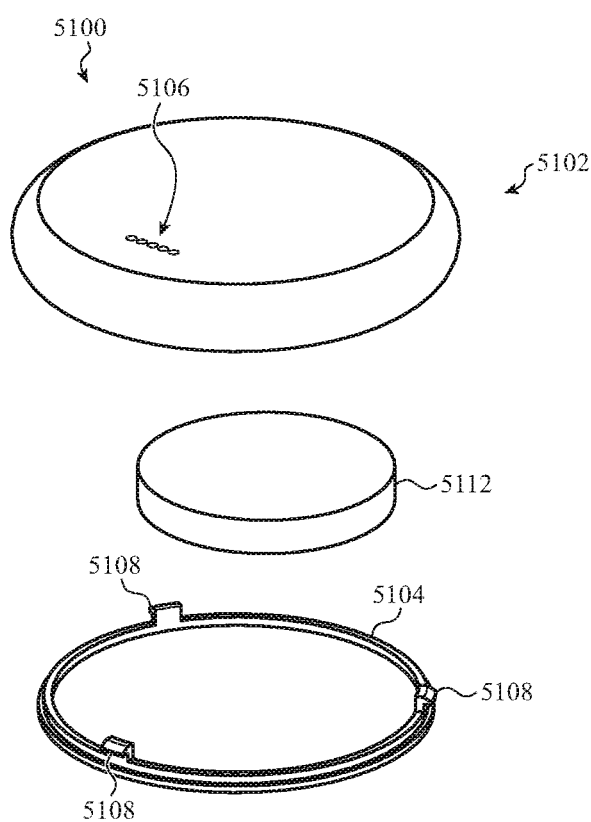
Figure 51C:
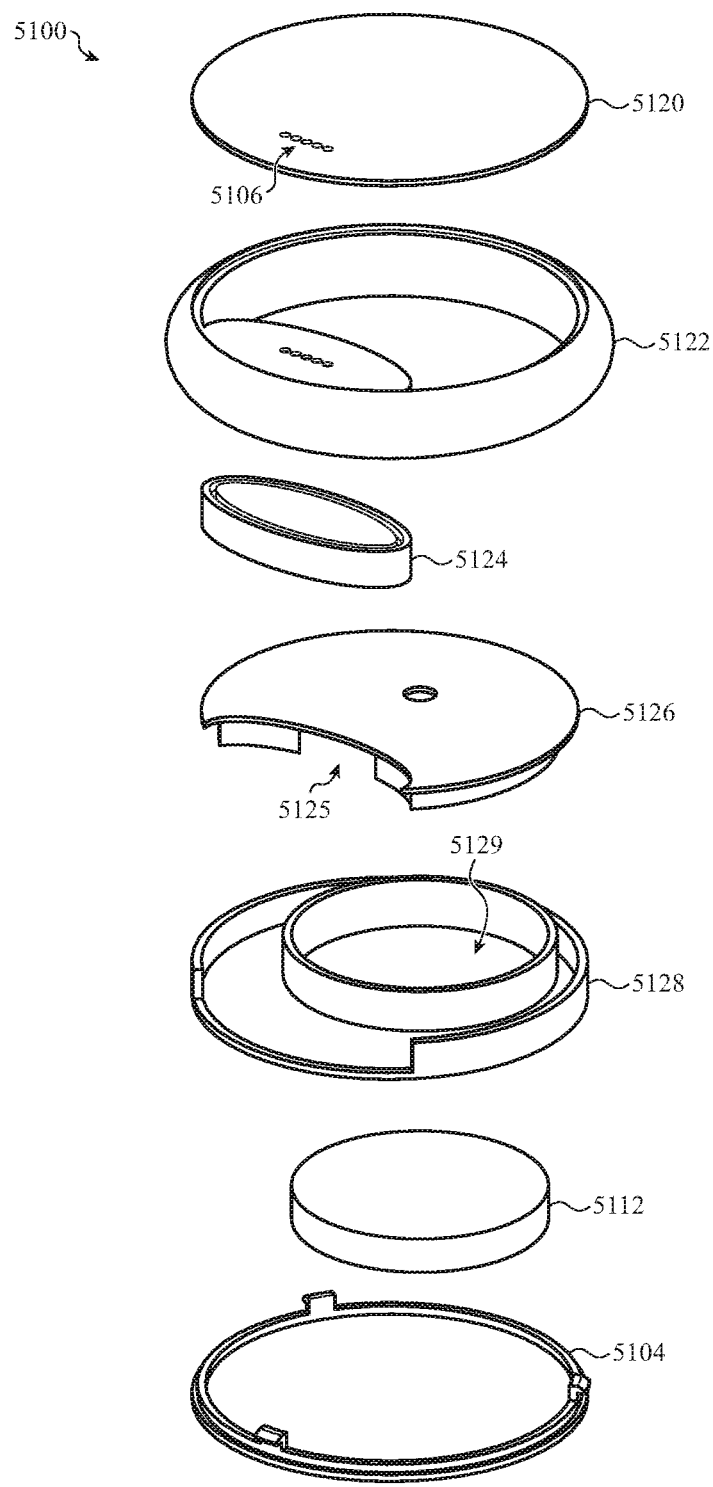

FIGS. 51A-51C illustrate another example wirelessly locatable tag 5100. The tag 5100 has a generally circular, puck-shaped form factor, similar to other tags described herein. Whereas other puck-shaped tags may stack the audio system, circuit board and battery along a central (e.g., axial) axis of the puck, the audio system of the tag 5100 is positioned next to (e.g., in a generally planar arrangement with) other device components.

The tag 5100 may include a top housing member 5102, which may define a top surface and a peripheral side surface of the tag 5100, and a bottom housing member (or battery door) 5104. The bottom housing member 5104 may be removably coupled to the top housing member 5102, or another component of the tag 5100, using any of the attachment techniques described herein, such as those described with respect to FIGS. 12A-12C and 14A-25C.

As described herein, the tag 5100 may include any suitable type of audio system. As shown, the tag 5100 includes an audio system, within the housing, that includes a speaker that produces audio outputs. Sound from the speaker exits the tag 5100 through speaker openings 5106 that extend through the top housing member 5102.

FIG. 51B shows the tag 5100 with the bottom housing member 5104 removed from the top housing member 5102, with the battery 5112 removed. The bottom housing member 5104 may include latch members 5108 that engage complementary features on the tag 5100. The bottom housing member 5104 may also include a compliant member that biases the battery 5112 into the tag 5100 and into engagement with battery connectors, as described above.

FIG. 51C is a partial exploded view of the tag 5100. The tag 5100 may include a cover 5120 and a peripheral member 5122 to which the cover 5120 is attached. The cover 5120 and the peripheral member 5122 may define some or all of the top housing member 5102. The cover 5120 may define the speaker openings 5106 of the top housing member 5102.

The tag 5100 also includes an audio system 5124, which may be positioned below the speaker openings 5106 and may include a speaker as described above. In some cases, the audio system 5124 includes a coil and magnet to move the top housing member as a diaphragm, similar to the other audio systems described herein.

The tag 5100 also includes a circuit board 5126. The circuit board 5126 may include device components such as circuit elements, processors, memory, sensors, radio circuitry (including antennas) for various wireless communications (e.g., UWB, WiFi, Bluetooth, etc.), or the like. The circuit board 5126 may have a shape that conforms to or otherwise allows the circuit board to be positioned next to the audio system 5124. For example, the circuit board 5126 may define a clearance area 5125, and the audio system 5124 may be nested or otherwise positioned in the clearance area 5125.

The tag 5100 may also include a frame member 5128. The frame member 5128 may define a battery cavity 5129 that receives the battery 5112. The frame member 5128 may also support other components of the tag 5100. For example, the circuit board 5126, antennas, and the audio system 5124 may be attached to the frame member 5128. Further, the top and bottom housing members 5102, 5104 may be attached to the frame member 5128. The frame member 5128 may perform some or all of the functions of the frame member 512 and/or antenna assembly 508 of the tag 500 (described above).

As shown in FIG. 51C, the audio system 5124, battery 5112, and circuit board 5126 are all positioned roughly in the same lateral plane. Stated another way, at least some portion of each component may lie in a single plane that is generally parallel to the top surface of the cover 5120. This configuration may produce a tag with a larger diameter, but a smaller axial height, than tags in which the audio system, battery, and circuit board are stacked along the axis (e.g., as shown in FIG. 5B).

Figure 52A:
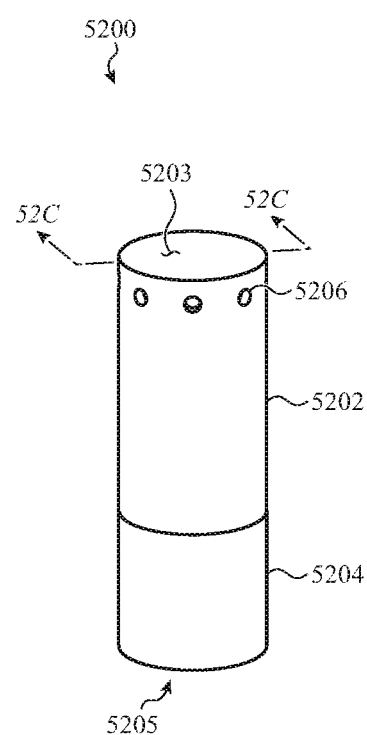
FIGS. 52A-52C depict another example configuration for a wirelessly locatable tag.
Figure 52B:
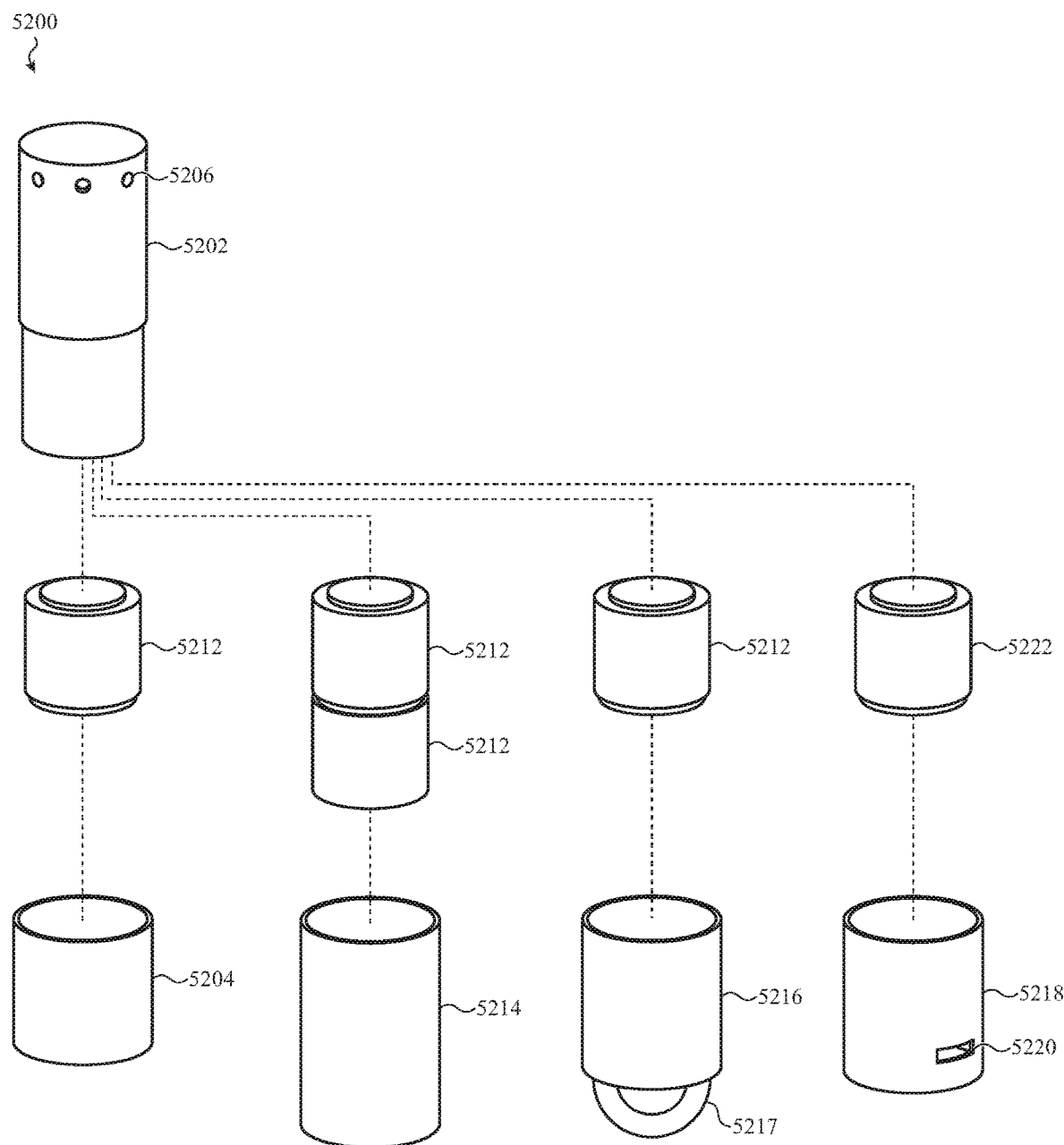
Figure 52C:
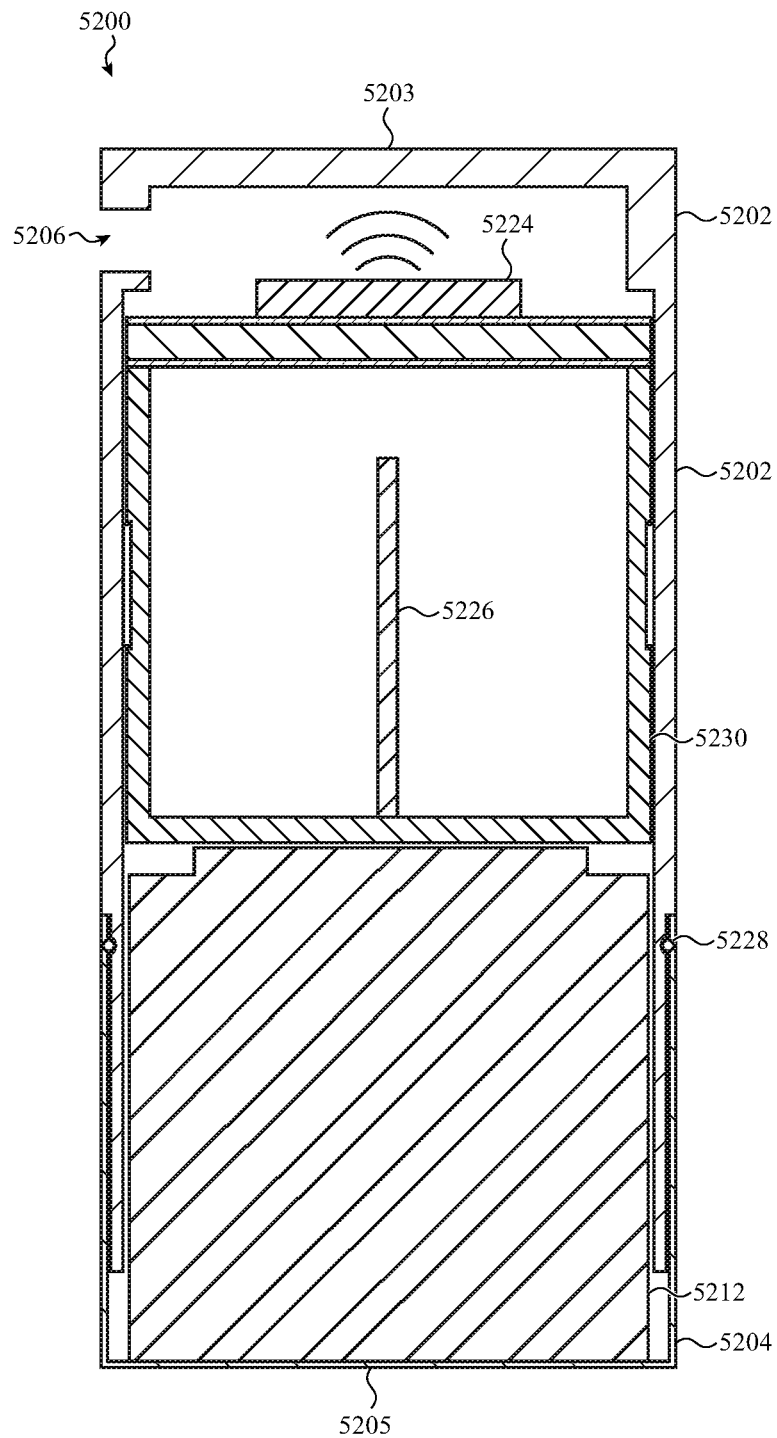

FIGS. 52A-52C depict an additional example embodiment of a wirelessly locatable tag 5200, showing another form factor for the tag. FIG. 52A illustrates a perspective view of the tag 5200, which has a generally cylindrical shape. The tag 5200 includes a body portion 5202 and a battery cover 5204 that may be removably coupled to the body portion 5202. The body portion 5202 may house device components, such as circuit boards, audio systems, antennas, antenna assemblies, processors, and the like. As noted for other tags, the function and arrangement of such components (including circuit boards, audio systems, antennas, etc.) may be substantially similar to other tags described herein. The tag 5200 may include an audio system that includes a speaker that produces audio outputs. Sound from the speaker exits the tag 5200 through speaker openings 5206 in the body portion 5202.

FIG. 52B depicts an exploded view of the tag 5200, illustrating various combinations of batteries and battery covers that may be used with the body portion 5202. These components may be interchangeable, allowing a user to select aspects of the tag's appearance and function.

As shown in FIG. 52B, a single battery 5212 may be used with the battery cover 5204, corresponding to the overall appearance of FIG. 52A. In another application, a larger battery cover 5214 may be used, along with two batteries 5212, thus providing increased battery life for the tag 5200. In another application, a battery cover 5216 may include an attachment feature 5217, shown in FIG. 52B as a loop. The attachment feature 5217 may be used to attach the tag 5200 to other objects, such as a key ring or split ring, lanyard, clip, strap, or the like. In another application, a battery cover 5218 may include a charging port 5220 and may be configured for use with a rechargeable battery 5222. The battery cover 5218 may optionally include charging and/or other battery control circuitry so that the user can choose to use either rechargeable or non-rechargeable batteries with the same body portion 5202.

FIG. 52C illustrates a partial cross-sectional view of the tag 5200, viewed along line 52C-52C in FIG. 52A. The tag 5200 may include a frame member 5230 in the body portion 5202. The frame member 5230 may serve as a mounting structure for other components of the tag 5200, such as a circuit board 5226, an audio system 5224 (which may include a speaker and which directs sound out of the speaker openings 5206), or the like. In some cases, one or more antennas are mounted to the frame member 5230 in a manner similar to the antenna assembly 508 described above. The circuit board 5226 may include a substrate and may include processors, memory, and other circuit elements that generally perform the electrical and/or computational functions of the tag 5200. The circuit board 5226 may also include conductors and/or electrical interconnects that electrically couple the various electrical components of the tag 5200. The circuit board 5226 may also include or be coupled to the battery 5212.

The battery cover 5204 may be releasably retained to the main body 5202 in any suitable way. For example, the battery cover 5204 may thread onto the main body 5202, or it may be retained using friction and/or an interference fit. The battery cover 5204 and/or the body 5202 may include locking or latching mechanisms to inhibit accidental removal of the battery cover 5204. More particularly, the battery cover 5204 may include latches, catches, or other features that must be released or disengaged (e.g., by squeezing, applying a tool, or the like) before the battery cover 5204 can be removed by pulling or twisting. The tag 5200 may include a sealing member 5228 configured to inhibit ingress of liquid, dust, or other contaminants into the tag 5200.

In some cases, the tag 5200 may have the same or substantially the same overall size and shape as a battery, such as an "AA" or "AAA" size battery (or any other size or form factor of battery). In such cases, the tag 5200 may be used in place of a conventional battery to allow convenient location tracking of many different battery-operated devices. Accordingly, a device like a remote control, flashlight, camera, or the like, may be made wirelessly locatable without having to attach an external component, modify the device, or otherwise change the functionality or usability of the device.

Where the tag 5200 is configured to replace a battery, the tag 5200 (or a different but similarly shaped tag) may define a positive terminal and a negative terminal on exterior locations that correspond to the locations of positive and negative terminals of an "AA" or other sized battery (e.g., at locations 5203, 5205 in FIG. 52A). The tag 5200 may be configured to pass current from the negative terminal 5205 to the positive terminal 5203 of the tag 5200 such that the tag 5200 does not disrupt the power circuit of the device and allows the device to operate normally (using the power provided from other batteries of the device), albeit with reduced battery capacity. In some cases the battery 5212 of the tag 5200 may provide power to the components of the tag 5200, while also providing power through the external terminals 5203, 5205 of the tag 5200, thereby allowing the tag 5200 to provide power to the device in which it is installed, while also providing wireless tracking functionality for the device.

Figure 53A:
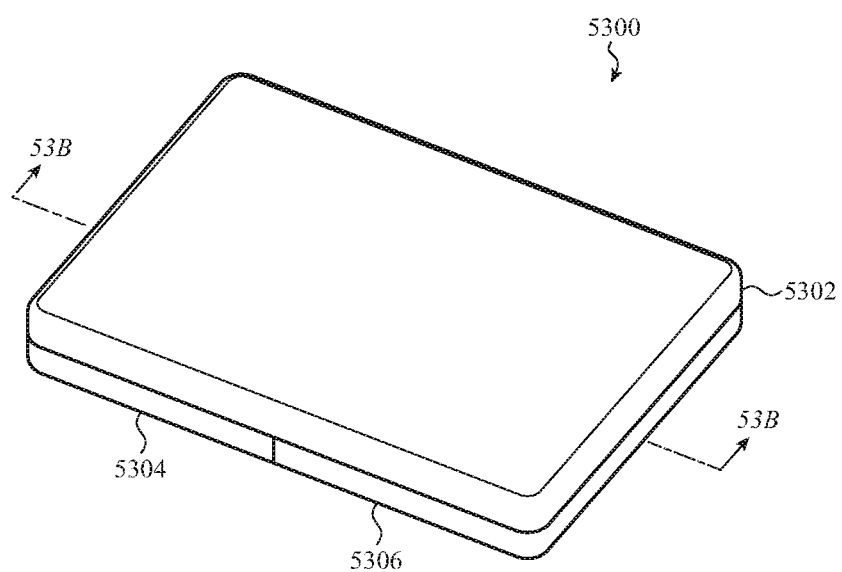
FIGS. 53A-53C depict another example configuration for a wirelessly locatable tag.
Figure 53B:
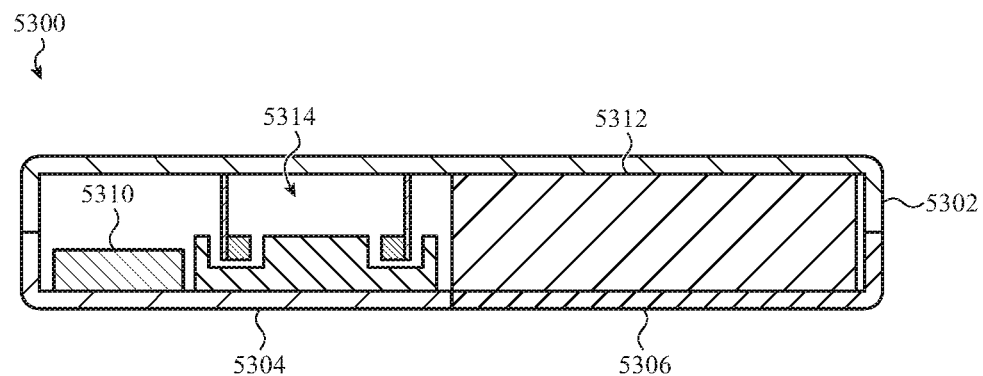
Figure 53C:
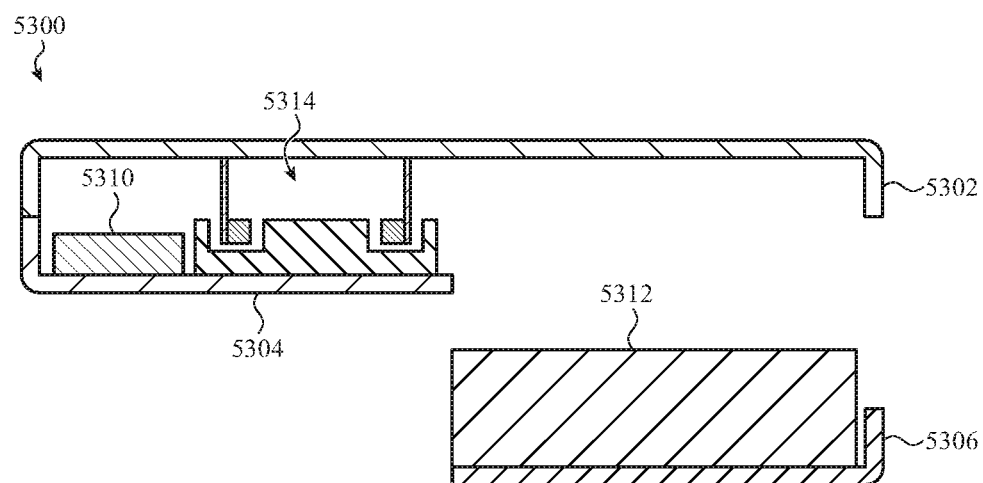

FIGS. 53A-53C illustrate another example wirelessly locatable tag 5300 having another form factor. In particular, the tag 5300 has a generally flat, rectangular-prism shaped exterior housing. The tag 5300 includes a first housing member 5302 that defines all or substantially all of a top surface and part of the peripheral surface of the tag 5300. The tag 5300 also includes a second housing member 5304 that defines part of (e.g., approximately half of) a bottom surface of the tag 5300 and part of the peripheral surface of the tag 5300. The second housing member 5304 may not be intended to be removed by a user of the tag 5300. The tag 5300 may also include a third housing member 5306, which may also define part of (e.g., approximately half of) the bottom surface of the tag 5300 and part of the peripheral surface of the tag 5300.

FIG. 53B shows a partial cross-sectional view of the tag 5300, viewed along line 53B-53B in FIG. 53A, showing an example arrangement of components within the tag 5300. The tag 5300 may include a battery 5312, an audio system 5314, and device components 5310. The device components 5310 may include circuit boards, circuit elements, processors, memory, sensors, radio circuitry (including antennas) for various wireless communications (e.g., UWB, WiFi, Bluetooth, etc.), or the like. Indeed, the device components 5310 may include any of the components that are used to provide the functions of a wireless tag as described herein. The audio system 5314 may operate similar to other audio systems described herein. For example, a coil may be attached to an interior surface of the first housing member 5302, and a magnet may provide a magnetic field to allow the coil to operate as a speaker. By passing a signal (e.g., current) through the coil, a portion of the first housing member 5302 can move in a manner similar to a speaker diaphragm. Further, the audio system may be used to produce tactile outputs that a user can feel when touching the first housing member 5302. Of course, other types of audio systems and/or tactile output generators may be used instead of or in addition to the audio system 5314.

The third housing member 5306 may be removable to provide access to a battery cavity. FIG. 53C illustrates a partial cross-sectional view of the tag 5300 with the third housing member 5306 removed from the rest of the tag 5300. The third housing member 5306 may define at least part of a battery cavity for a battery 5312. Features of the third housing member 5306 may engage corresponding features of the first and/or second housing members 5302, 5304, or any other component of the tag 5300 (e.g., a frame member), to retain the third housing member 5306 to the tag 5300 while also allowing it to be removed for battery replacement. Such features may include clips, latches, detents, or the like. The third housing member 5306 may be removed from the tag 5300 by prying with a fingernail, tool, or other implement inserted in a gap between the third housing member 5306 and another part of the tag 5300.

In other respects, such as the component set and the function and arrangement of such components (including circuit boards, audio systems, antennas, etc.), the tag 5300 may be substantially similar to other tags described herein, and the tag 5300 may include any of the components and/or provide any of the features of any tag described herein.

Figure 54A:
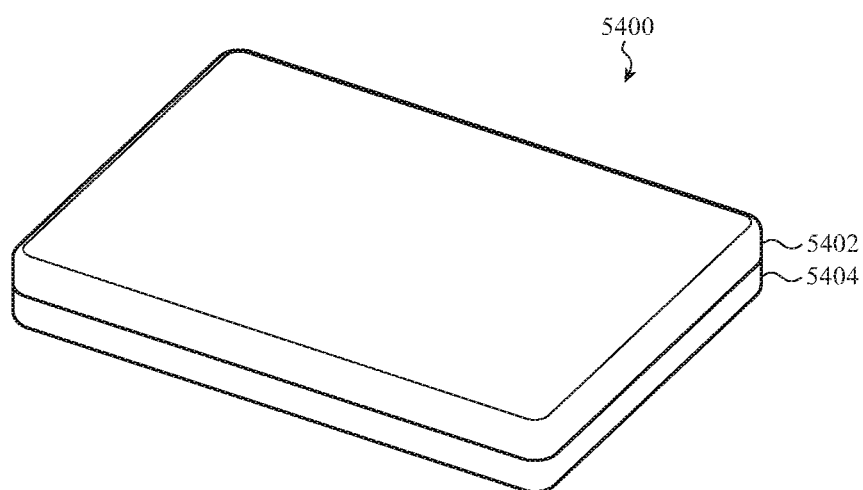
FIGS. 54A-54B depict another example configuration for a wirelessly locatable tag.
Figure 54B:
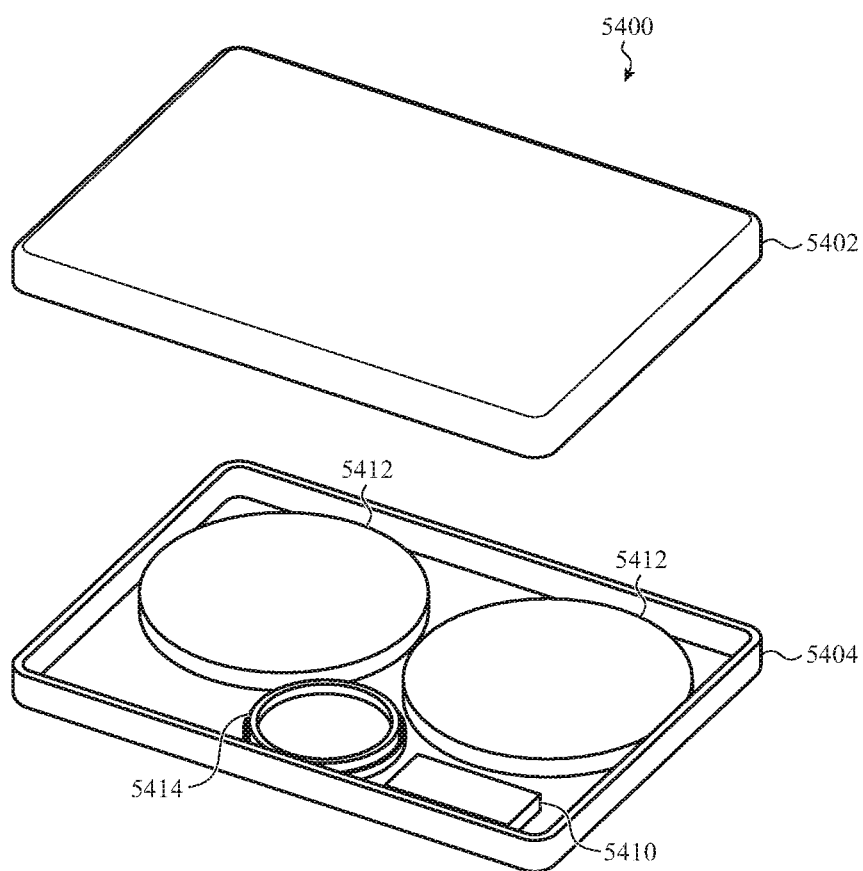

FIGS. 54A-54B illustrate another example wirelessly locatable tag 5400 having a generally flat, rectangular-prism shaped exterior housing. The tag 5400 includes a first housing member 5402 and a second housing member 5404, which may be removably coupled to the first housing member 5402.

The tag 5400 is similar to the tag 5300, but has a different arrangement of components within the housing. FIG. 54B illustrates the tag 5400 with the first housing member 5402 detached from the second housing member 5404. The tag 5400 includes two batteries 5412, an audio system 5414, and device components 5410. The device components 5410 and audio system 5414 may be the same as or similar to the corresponding components in the tag 5300, and for brevity their details may not be repeated here. Due to the extra battery, the tag 5400 may have increased battery life as compared to single-battery tags.

Figure 55A:
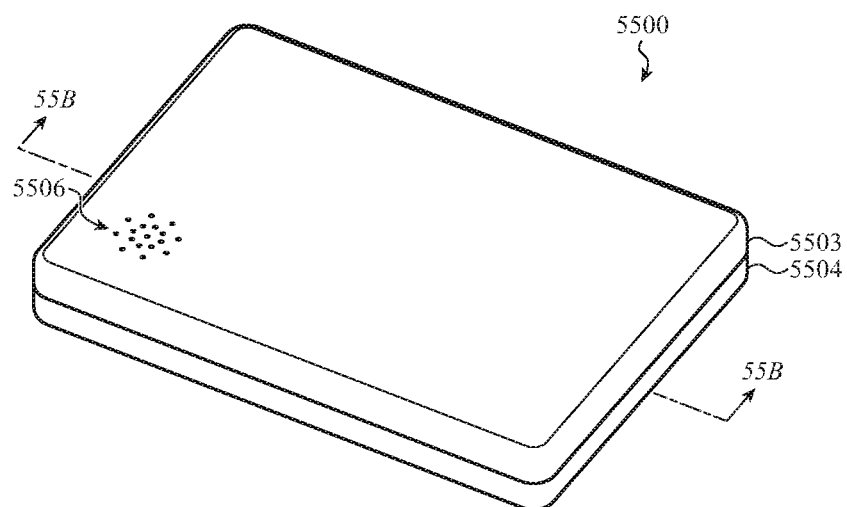
FIGS. 55A-55B depict another example configuration for a wirelessly locatable tag.
Figure 55B:
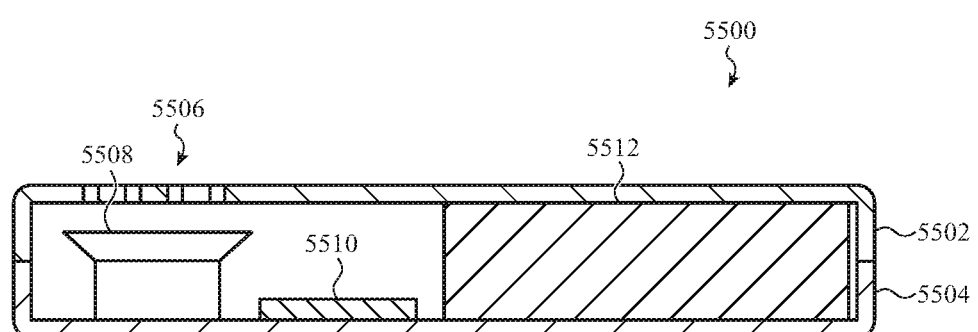

FIGS. 55A-55B illustrate another example wirelessly locatable tag 5500 having a generally flat, rectangular-prism shaped exterior housing. The tag 5500 includes a first housing member 5502 and a second housing member 5504, which may be removably coupled to the first housing member 5502. The tag 5500 may be configured to use a conventional speaker or other audio-producing component, and may therefore include speaker openings 5506 that extend through the first housing member 5502.

FIG. 55B is a partial cross-sectional view of the tag 5500, viewed along line 55B-55B in FIG. 55A. The tag 5500 includes a battery 5512 and device components 5510, which may be the same as or similar to the corresponding components in other tags described herein, and for brevity their details may not be repeated here. The tag 5500 also includes a speaker 5508 (or other suitable audio-producing component) that produces audio outputs, which in turn pass through the speaker openings 5506 to be perceived by a user.

Figure 56A:
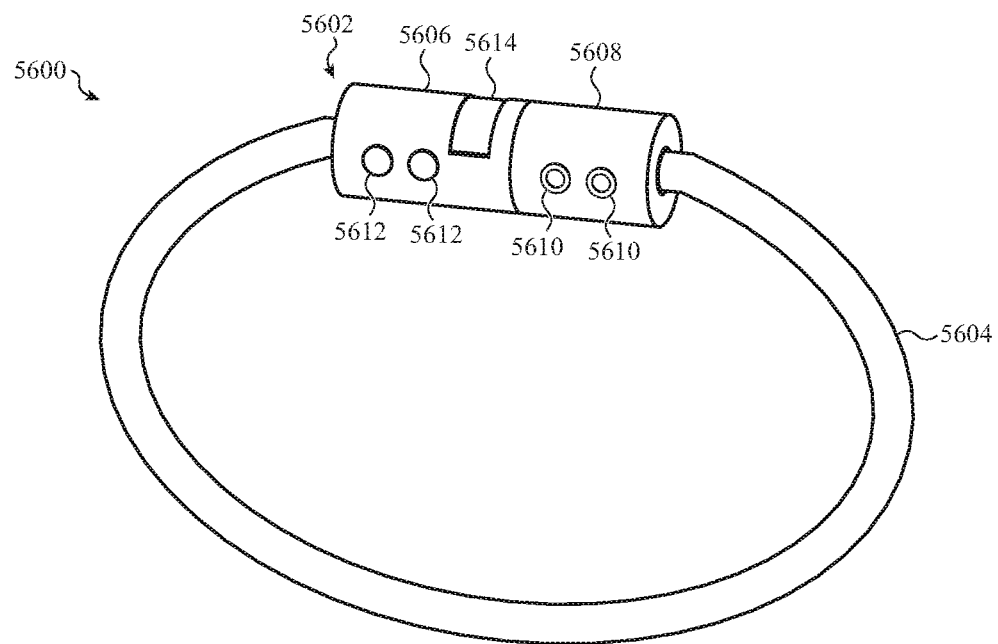
FIGS. 56A-56B depict another example configuration for a wirelessly locatable tag.
Figure 56B:
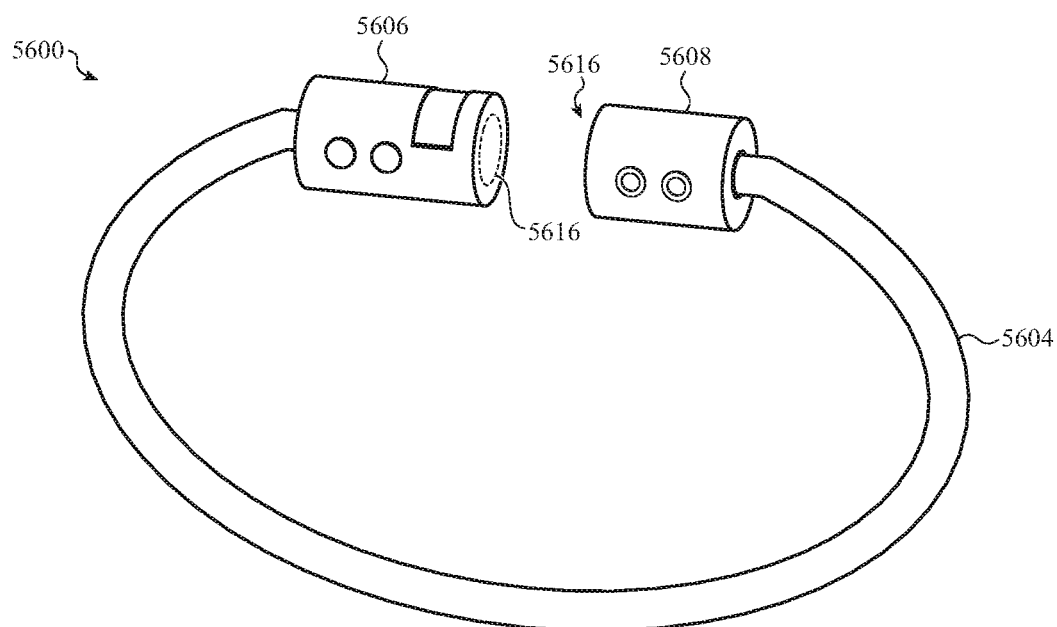

As described elsewhere herein, the functionality of a wirelessly locatable tag may be incorporated into other types of devices and/or integrated with other components, accessories, features, or the like. In one such example, as shown in FIGS. 56A-56B, a wirelessly locatable tag may be incorporated into a device that includes a built-in attachment cord or strap.

The tag 5600 may include a body portion 5602 and a cord portion 5604. The body portion 5602 may include some or all of the components that provide the functionality of a wirelessly locatable tag, such as circuit boards, circuit elements, processors, memory, sensors, radio circuitry (including antennas) for various wireless communications (e.g., UWB, WiFi, Bluetooth, etc.), or any other components that are used to provide the functions of a wireless tag as described herein. The cord portion 5604 may be a flexible rope, cable, or other member that can be attached to another object. In some cases, electronic components of the tag 5600 are housed in or incorporated in the cord portion 5604. For example, an antenna (e.g., a flexible conductor such as a wire or metallized thread) may be incorporated in the cord portion 5605. Flexible conductors incorporated into a cord portion may be used for other operations or features as well, such as carrying signals, detecting contact with other objects or people, or the like.

The body portion 5602 may define a first portion 5606 and a second portion 5608, which can be separate from one another to allow the loop to be opened and the tag 5600 to be attached to another object. FIG. 56B shows the tag 5600 in an open configuration, in which the first portion 5606 is separated from the second portion 5608. The first and/or second portions 5606, 5608 may include retention features 5616 that releasably retain the first and second portions together. The retention features 5616 may include, for example, clips, latches, magnets, or the like. The body portion 5602 may be separable by simply pulling the first and second portions 5606, 5608 apart, though in other cases a user must perform other manipulations, such as unlocking or unlatching a retention feature, twisting, prying, using a tool, or the like.

The tag 5600 may include sensors or other systems that detect whether the tag 5600 is in an open (FIG. 56B) or closed (FIG. 56A) configuration. Such sensors may include for example Hall effect sensors, accelerometers (which detect a characteristic motion caused by the tag being opened or closed), microphones (which detect a characteristic sound caused by the tag being opened or closed), optical sensors, or the like. The tag 5600 may perform different actions based on whether the tag 5600 is open or closed. For example, the tag 5600 may power down or transition to a low-power mode (e.g., deactivating one or more systems or processes) when the tag 5600 is open, and power up or transition to a normal operating mode when the tag 5600 is closed. As another example, upon detecting that the tag 5600 has been opened or closed, the tag 5600 may send, via a cloud-based service, a message indicating the change in the tag's status. An owner or other authorized individual may receive a message from the cloud-based service that provides information about the tag, such as its location, when it was opened, where it was when it was opened, the time when it was opened, or the like.

The tag 5600 may include input and/or output components accessible on the outside of the tag 5600. For example, the tag 5600 includes optional buttons 5612 with which a user may interact to control aspects of the tag 5600. For example, the buttons 5612 may control operations such as turning the tag 5600 on or off, causing the tag to enter a pairing mode, causing the tag to send a "lost" message, or the like. The buttons 5612 may include moving parts and mechanical actuating components (e.g., dome switches). In some cases, the buttons 5612 may be defined by touch-sensitive input regions (e.g., capacitive touch-sensing regions).

The tag 5600 may also include output components, such as a display 5614, which may include or use any suitable display technology such as LED, LCD, OLED, E ink, or the like. The display 5614 may display various types of information. For example, the display 5614 may display status information about the tag 5600, including battery charge level, an owner's name, the status of the tag (e.g., if it has been reported lost), or the like. In some cases, the display 5614 may display different information if the tag is reported lost. For example, upon receiving an indication that the tag has been reported to be lost, the display 5614 may begin displaying a message indicating that it has been reported lost and providing instructions on how the user wants the lost item to be handled (e.g., do not move from this location, return to owner, call owner, etc.).

The tag 5600 may also include indicator lights 5610. The indicator lights 5610 may be LEDs or any other suitable light sources. The indicator lights 5610 may indicate a status of the device, such as a power state, battery charge level, operating mode, lost/not lost status, or the like. In some cases, the indicator lights 5610 may be activated in response to the tag 5600 being reported lost. For example, the indicator lights may flash (or remain steadily illuminated) to alert nearby people to the presence of the tag and its status as being lost. The indicator lights 5610 may be used for other purposes as well.

Figure 57:
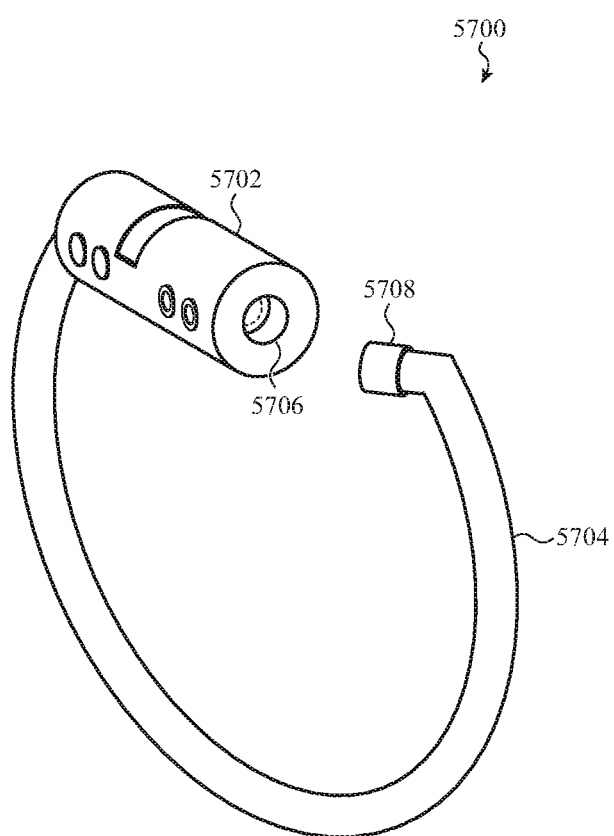
FIG. 57 depicts another example configuration for a wirelessly locatable tag.

FIG. 57 depicts another example tag 5700 having a similar configuration as the tag 5600 but having a different approach to opening and closing the loop of the cord. In particular, the tag 5700 includes a body portion 5702, which may be the same as or substantially similar to the body portion 5602, except that the body portion 5702 may not be separable. Instead, the cord portion 5704 is removably coupled to the body portion 5702 at least at one end of the cord portion 5704, thereby allowing the tag 5700 to be attached to other objects by forming a loop with the cord portion 5704. The cord portion 5704 may include a connector 5708 that mates with a connector 5706 of the body portion 5702. The connectors 5708, 5706 may include retention features such as clips, latches, magnets, or the like. The tag 5700 may detect whether the cord portion 5704 is attached to or detached from the body portion 5702, and cause the tag 5700 to operate in a certain way based on the determination, as described above. The tag 5700 may include sensors to determine when the cord portion is attached or detached. Such sensors may include for example Hall effect sensors, accelerometers (which detect a characteristic motion caused by the cord portion being attached or detached), microphones (which detect a characteristic sound caused by the cord portion being attached or detached), optical sensors, or the like.

Figure 58A:
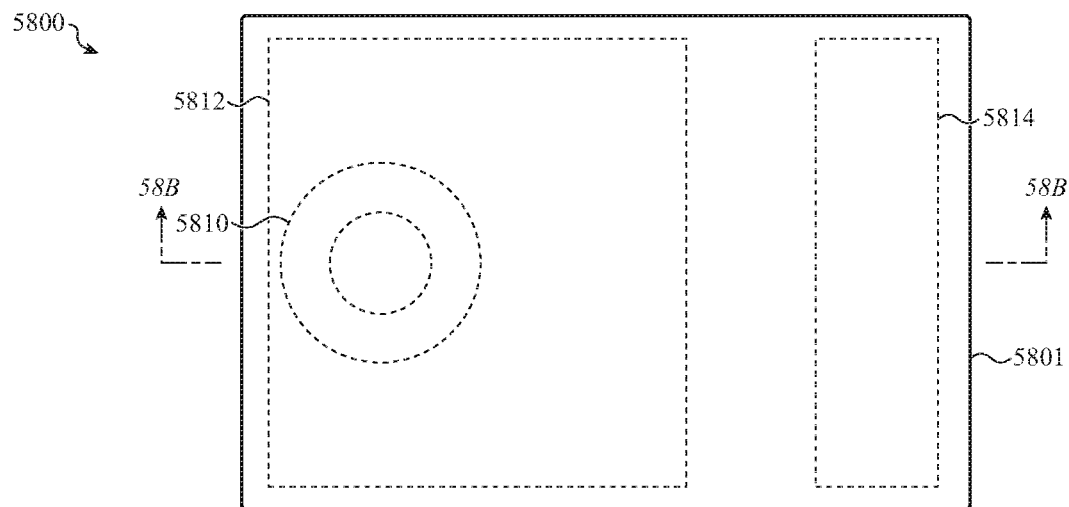
FIGS. 58A-58C depict another example configuration for a wirelessly locatable tag.
Figure 58B:
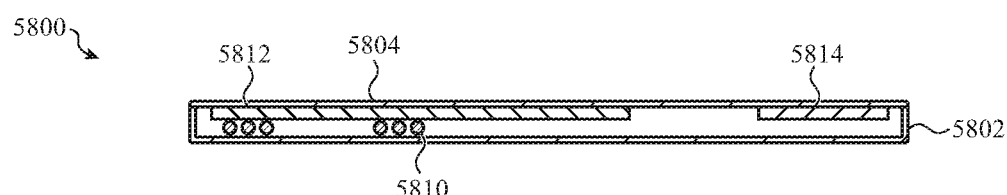
Figure 58C:
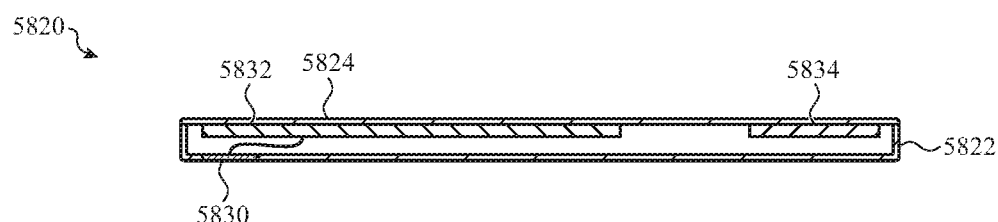

FIGS. 58A-58C illustrate another example wirelessly locatable tag 5800, showing yet another form factor for a tag that provides some or all of the tag functionality described herein. In particular, the tag 5800 has a generally rectangular shape with a small thickness dimension, allowing the tag 5800 to fit into small places like a credit card slot in a wallet, or a side pocket of a purse, or the like. In some cases, the tag 5800 has a thickness dimension (e.g., the height of the tag 5800 as viewed in FIG. 58B) that is less than about 5.0 mm, about 4.0 mm, about 3.0 mm, about 2.0 mm, or about 1.0 mm.

FIG. 58A shows a top view of the tag 5800. Some internal components of the tag 5800 are shown in phantom lines. For example, the tag 5800 may include a battery 5812, a wireless charging coil 5810, and device components 5814. The device components 5814 may include some or all of the components that provide the functionality of a wirelessly locatable tag, such as circuit boards, circuit elements, processors, memory, sensors, radio circuitry (including antennas) for various wireless communications (e.g., UWB, WiFi, Bluetooth, etc.), or any other components that are used to provide the functions of a wireless tag as described herein.

FIG. 58B shows a partial cross-sectional view of the tag 5800, viewed along line 58B-58B in FIG. 58A. FIG. 58B shows an example arrangement of the components of the tag 5800. The tag 5800 may include a housing 5801 (FIG. 58A) that defines the exterior surfaces of the tag 5800 and defines an internal volume of the tag. The housing 5801 may include a bottom housing member 5802, which may define the bottom surface and some or all of the peripheral side surface of the tag 5800, and a top housing member 5804, which may define the top surface of the tag 5800. Other configurations of housing members are also contemplated.

The battery 5812 may be stacked above the wireless charging coil 5810. The battery 5812 may be charged by placing the tag 5800 on a suitable wireless charger, which may have a transmitting coil configured to inductively couple to the charging coil 5810 and provide wireless power to the coil 5810 that is then used to charge the battery. The device components 5814 may include control circuits that control the power being provided to the battery 5812 from the charging coil 5810.

FIG. 58C illustrates another example wirelessly locatable tag 5820. The tag 5820 may be substantially identical to the tag 5800, except that instead of a wireless charging coil 5810, the tag 5820 includes charging contacts 5830 that provide power to the battery 5832 and/or other electronic components of the tag 5820. The charging contacts 5830 may include exposed electrically conductive members (e.g., copper pads) that are exposed along or otherwise define part of the bottom exterior surface of the tag 5820. The tag 5820 may be charged by placing the charging contacts 5830 in contact with corresponding contacts of a battery charger.

The tag 5820 may also include first and second housing members 5824, 5822, and device components 5834, each of which may be the same as or similar to the corresponding components of the tag 5800. Further, the tags 5800, 5820 may include audio systems to provide audible and/or tactile outputs. The audio systems may include piezoelectric elements or other materials or components that can be implemented in a low-profile housing such as that shown in FIGS. 58A-58C.

The housing members of the various tags described herein (e.g., the components of the tags that define the exterior surfaces of the tags and/or the body portions of the tags) may be formed from any suitable material. For example, the housing members may be formed from or include polymers, metals, composites (e.g., fiber-reinforced polymers), or the like. Similarly, any of the frames, frame members, antenna assemblies, of the tags described herein may be formed from materials such as polymers, composites (e.g., fiber-reinforced polymers), or the like. Tag components such as frames, housing members, circuit boards, or the like, may be coupled to one another in various ways, including but not limited to ultrasonic welds, adhesives, heat stakes, rivets, mechanically interlocked features, laser welds, melt bonds, or the like.

While the various example tags described herein may focus on a particular set of components and features, the tags may include or provide more, fewer, or different components and features. For example, tags as described herein may include displays that can provide graphical outputs including text, images, or the like. Such displays may be incorporated in the tags so that they can be seen by a user. The displays may include any suitable display technology, including LED, LCD, OLED, E ink, or the like. Displays may also incorporate touch and/or force sensing systems that detect touch- and or force-based inputs applied to the display. Inputs applied to a touch- and/or force-sensitive display may control operational aspects of a tag, such as by changing operating modes, changing settings, inputting data, and the like. Tags may also include other visual output systems, such as indicator lights, which also provide visual output to a user (e.g., indicating an operating mode of the tag, a power state, whether the tag has been reported as lost, etc.).

As noted above, various different types of audio systems are contemplated for use with the wirelessly locatable tags described herein. For example, one type of audio system may use a wall of a housing member that defines an exterior surface of the tag as a sound-producing element or diaphragm. Another type of audio system may include a speaker that produces sound which then passes through openings in the housing. Yet another type of audio system is a piezoelectric element that can either move a portion of a housing member (as a diaphragm) or move a separate diaphragm or member to produce sound. It will be understood that tags that are described as using one type of audio system may additionally or instead use another type of audio system.

In order to begin using the tags described herein, an initialization or pairing process may be performed, in which the tag communicates with another device, such as a smartphone, laptop, desktop, or tablet computer, or the like. The initialization process may be used to associate a particular tag with a particular user or user account in the device-location relay network. The initialization process may also be used to establish a trusted communication link between the tag and a particular device. This trusted communication link may allow the device to interact with the tag in ways that are not accessible to other (e.g., untrusted) devices. For example, a tag that has been paired with a user's smartphone may allow that smartphone to control the operation of the tag, change its mode of operation, or the like, while other devices (e.g., devices with which the tag has not been paired) may be unable to perform these actions.

In some cases, an initialization mode may be entered by providing an input to a tag. For example, a tag may include a button, switch, or other input mechanism that a user can manipulate (e.g., push) to cause the tag to enter an initialization mode. When the input is detected by the tag, the tag may enter the initialization mode in which the tag may perform certain actions. For example, as described above, the tag may begin sending a beacon signal or change (e.g., increase) the frequency at which it is sending a beacon signal. The beacon signal may be a wireless communication via a Bluetooth protocol, a UWB protocol, or the like, and may be detectable by another device such as a smartphone or computer. Once an initialization process is complete, the tag may enter a "normal" operating mode, which may include changing (e.g., decreasing) the frequency of its beacon signal.

In some cases, tags may not have input devices, or they may be configured so that its input devices do not function to activate an initialization mode. In such cases, other techniques may be used to cause the device to enter an initialization mode. For example, a tag may be configured to enter an initialization mode in response to the onset of power being provided to the tag from a battery or other power source. In such cases, upon power being provided to the tag, the tag may activate an initialization mode for a duration, such as one minute, five minutes, or any other suitable duration. After this duration expires, the user can reactivate the initialization mode, if required, by removing and reinserting the battery (or otherwise interrupting the power supply to the tag). Where tags are provided or sold with the batteries in place, such as in one of the battery cavities of the tags described above, the tag may include an insulating material between the battery and a contact of a battery connector. Upon removal of the insulating material (which a user may simply pull out of the tag using a provided pull-tab or handle), power is supplied to the tag and the initialization mode is activated.

Other techniques for causing tags to activate an initialization mode are also contemplated. For example, a tag may include a battery door that can be moved between two positions. In a first position, the battery door may be securely retained to the tag but configured so that power does not flow from the battery to the tag's circuitry, and in a second position, the battery door may also be securely retained to the tag but configured so that power does flow to the tag's circuitry. The user can simply move the battery door from the first position to the second position, which will cause power to be provided to the tag's circuitry and thus activate the initialization mode. The flow of power from the battery may be interrupted by an internal switching mechanism, by physically separating the battery from a battery contact, or any other suitable technique. In some cases, the tag may include a sensor to determine the position of the battery door. For example, the tag may include a Hall effect sensor, optical sensor, capacitive sensor, or the like. Upon sensing that the battery door has been moved to the second position, the tag may activate the initialization mode.

As yet another example, a tag may be provided with a battery tray or door partially or fully detached from the rest of the tag. Attaching or inserting the battery tray or door may cause the tag to begin receiving power and thus enter the initialization mode. As another example, a tag may include an accelerometer, and upon detecting an acceleration or motion characteristic of a particular type of input (e.g., a tap, a particular pattern of taps, a shake, or the like), the tag may activate the initialization mode. As yet another example, if the tag includes an audio system that can be used to detect deformations of the housing (such as the audio systems described with respect to FIG. 26B), the tag may activate the initialization mode in response to detecting a particular input via the audio system (e.g., a single press, a single press having a particular duration, a particular pattern of presses).

The tag may include sensors that determine when the tag has been removed from packaging, and activate an initialization mode upon detecting that it has been removed from the packaging. For example, the tag may include a light sensor that detects when it is removed from an opaque packaging. As another example, it may include an oxygen sensor that detects when it is removed from a sealed packaging. As yet another example, it may include a Hall effect sensor, capacitive sensor, magnetic sensor, or other suitable sensor that detects when a conductive or magnetic component of a packaging (e.g., a strip of metal attached to a box lid) is moved away from the tag. As yet another example, tag packaging may include a spring-loading mechanism that imparts a characteristic motion to the tag when the packaging is opened. An accelerometer in the tag may detect the characteristic motion and trigger the initialization mode upon detecting the motion. As yet another example, tag packaging may include or define a Faraday cage, and the tag may activate an initialization mode upon detecting wireless signals (which may occur once the tag is removed from the Faraday cage).

When initializing a tag, a smartphone (or other device such as a tablet computer) communicates with the tag, as described above. The tag may be configured to activate or trigger an initialization mode on the smartphone. For example, as described herein, wirelessly locatable tags may include NFC antennas. The smartphone may include an NFC reader that can detect when it is within a certain distance of the NFC antenna of the tag (e.g., three inches, or any other suitable distance), and in response to detecting that it is within that distance, trigger an initialization mode or initialization process. This may include launching an application on the smartphone or displaying graphical objects (e.g., a graphical user interface) that guides a user through the initialization process.

In some cases, the tag itself may detect when an NFC reader of another device communicates with the tag via NFC, and upon detecting a communication with the other device, the tag may activate its initialization mode. Thus, the initialization mode of the tag may be activated by the action of bringing the tag and other device into close proximity (e.g., within NFC communication range, such as about three inches or less). In such cases, prior to bringing a smartphone into NFC range of the tag, the user may activate an application or otherwise cause his or her smartphone to enter a mode in which the phone's NFC reader will communicate with the tag. In this manner, initialization of the tag may be simplified and streamlined, as the user can simply request the initialization mode on a phone, tap the phone on the tag, and the initialization process will begin.

Tags described herein use batteries to provide power to the electrical components. The batteries may be non-rechargeable batteries, which can be replaced when they are exhausted, or they may be rechargeable batteries, which can be recharged and reused multiple times. Battery replacement, either of rechargeable or non-rechargeable batteries, may be facilitated by the housing designs, described herein, that provide access to a battery cavity to allow the batteries to be removed by a user. In implementations where rechargeable batteries are used, tags may be provided with non-removable batteries, and the tags may include charging components that allow the batteries to be recharged while they remain housed in the tags.

Figure 59:
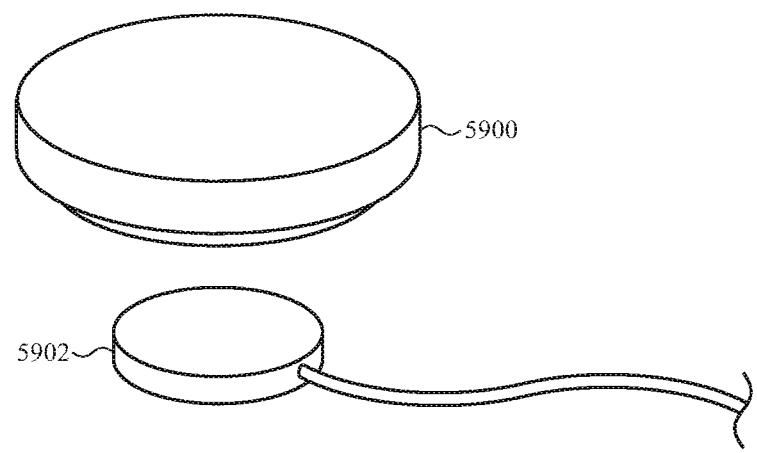
FIG. 59 depicts a rechargeable wirelessly locatable tag.
Figure 60:
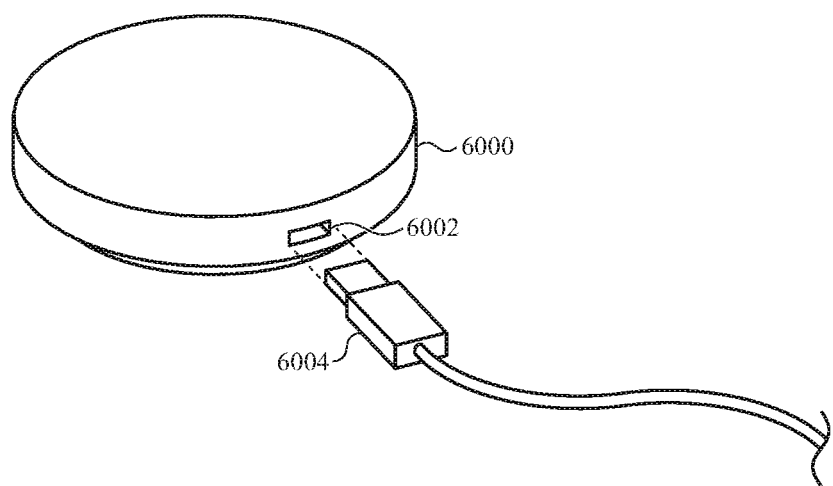
FIG. 60 depicts another rechargeable wirelessly locatable tag.

Various types of charging components may be incorporated into wirelessly locatable tags to facilitate the charging of rechargeable batteries. FIGS. 59-60 illustrate two example wirelessly locatable tags using different charging components. FIG. 59 shows a wirelessly locatable tag 5900 that is configured for wireless charging. More particularly, the tag 5900 may be configured to be placed on or proximate to a wireless charger 5902. The wireless charger 5902 may include an output coil that is configured to inductively couple to a charging coil in the tag 5900. Via electromagnetic interaction with the output coil, the charging coil in the tag provides (wireless) power to battery charging circuitry in the tag 5900, thereby charging the battery (and optionally providing power directly to circuitry of the tag 5900). In particular, the output coil may produce a magnetic field, which in turn induces a current in the charging coil of the tag, and the induced current may be used to recharge the tag's battery. The housings of the tag 5900 and the charger 5902 may be configured to limit or minimize shielding of or interference with the inductive coupling between the charging and the output coil. For example, the tag 5900 and the charger 5902 may be configured so that the portions of the housing that are between the output and charging coils are substantially nonconductive, such as a polymer material.

The charger 5902 and tag 5900 may also include an alignment system to help a user properly align the tag 5900 relative to the charger 5902 to facilitate wireless charging. Such alignment systems may include magnets, complementary protrusions/recesses (or other complementary physical features), visual alignment indicators, or the like. While the charger 5902 is shown as a circular puck-style charger, this is merely one example embodiment of an external charging device, and the concepts discussed herein may apply equally or by analogy to other external charging devices, including charging mats, docks, electronic devices with built-in wireless charging functionality (e.g., alarm clocks, another electronic device such as a mobile phone or tablet computer), differently shaped chargers, or the like.

FIG. 60 shows a wirelessly locatable tag 6000 with a charging port 6002 configured to receive power cable 6004. The power cable 6004 supplies electrical power to the tag 6000, which is used to charge the battery and optionally provide power to the tag 6000 while the battery is charging. In some cases, tags may include both a charging port and wireless charging systems, thereby allowing a user to use either wired or wireless charging.

In some cases, it may be desirable to operate a wirelessly locatable tag indefinitely, without having to replace or recharge a battery. This may be particularly useful in cases where tags are used in static installations to help users locate certain objects (e.g., fire extinguishers, defibrillators), to automatically trigger users' devices to take certain actions (e.g., triggering a user interface object to appear on a user's phone when a user approaches a location such as a painting, retail display, or the like), or any other instance where tags are stationary and/or it is desired to provide continuous power or otherwise obviate the need to replace batteries (e.g., in a vehicle). To accommodate these and other use cases, mounting bases may be provided that attach to tags in place of the batteries (and optionally in place of a battery door). The mounting bases may securely support the tags and also provide electrical power to the tags instead of a battery.

Figure 61A:
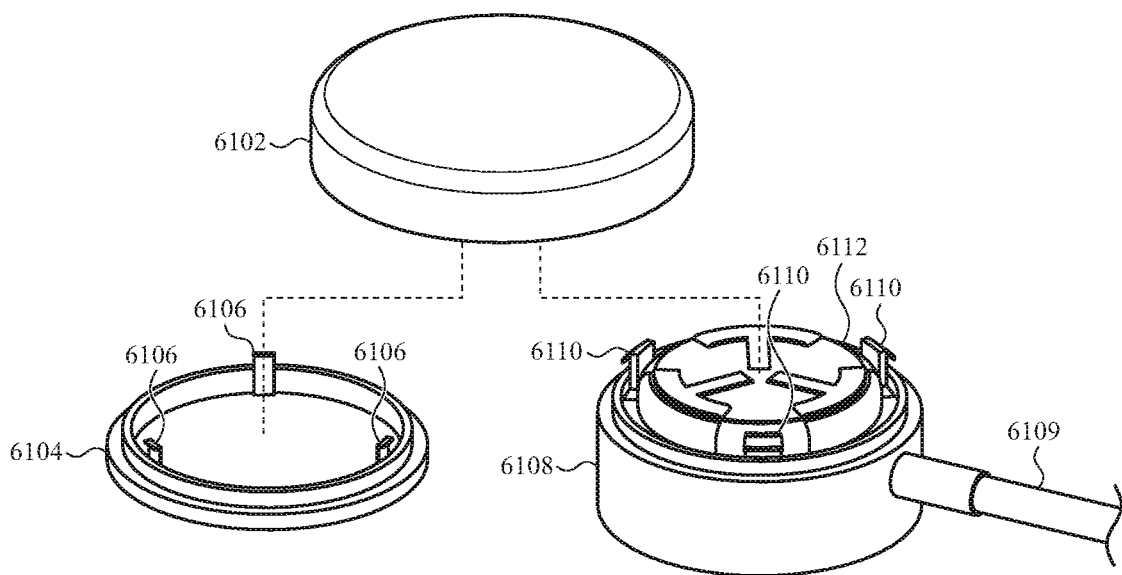
FIGS. 61A-65B depict an example mounting base system for wirelessly locatable tags.

FIGS. 61A-65B illustrate an example mounting base system that may be used to hold and provide power to wirelessly locatable tags. FIG. 61A illustrates an example tag 6102, which may be an embodiment of the tag 500, described above. The tag 6102 is shown with a bottom housing member (or battery door) 6104 and battery removed. The bottom housing member 6104 includes latch members 6106 that engage corresponding features of the tag 6102 (e.g., channels or recesses) to releasably retain the bottom housing member 6104 to the tag 6102.

Figure 61B:
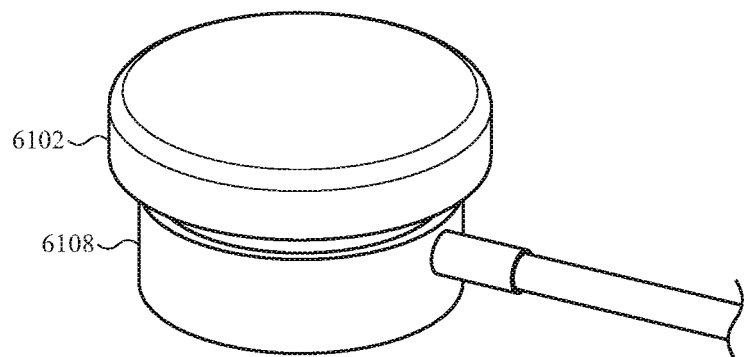

FIG. 61A also shows a mounting base 6108 to which the tag 6102 may be coupled in place of the bottom housing member 6104 and the battery. FIG. 61B shows the tag 6102 coupled to the mounting base 6108.

The mounting base 6108 includes latch members 6110, which may have a shape that is the same as or substantially similar to the latch members 6106 of the bottom housing member 6104. For example, the latch members 6110 may be configured to engage the same features of the tag 6102 that the latch members 6106 engage to retain the bottom housing member 6104 to the tag 6102. In this way, the tag 6102 may be attached to and detached from the mounting base 6108 in substantially the same manner as the bottom housing member 6104 and without requiring a different set of attachment features in the tag 6102 for each of the bottom housing member and the mounting base.

The mounting base 6108 may also include a contact block 6112 that is disposed in the battery cavity of the tag 6102 when the tag 6102 is attached to the mounting base 6108. The contact block 6112 may have a shape that is the same as or similar to at least a portion of the battery that is designed to fit in the tag 6102. In this way, the contact block 6112 may extend into the battery cavity of the tag 6102 and engage the battery connector of the tag 6102 in a manner that is the same as or similar to the type of battery that powers the tag 6102.

The mounting base 6108 may include or be attached to a cable 6109, which may provide power (e.g., an input current) to the tag 6102 through the mounting base 6108, and more particularly, through conductive members that are integrated with the contact block and engage with the battery connector of the tag 6102. The contact block 6112 may be formed of a polymer or other insulating or substantially non-conductive material. The non-conductive material allows the mounting base 6108 to support conductive members (described with respect to FIG. 62) that provide electrical current to the tag 6102, without shorting the conductive members together.

Figure 62:
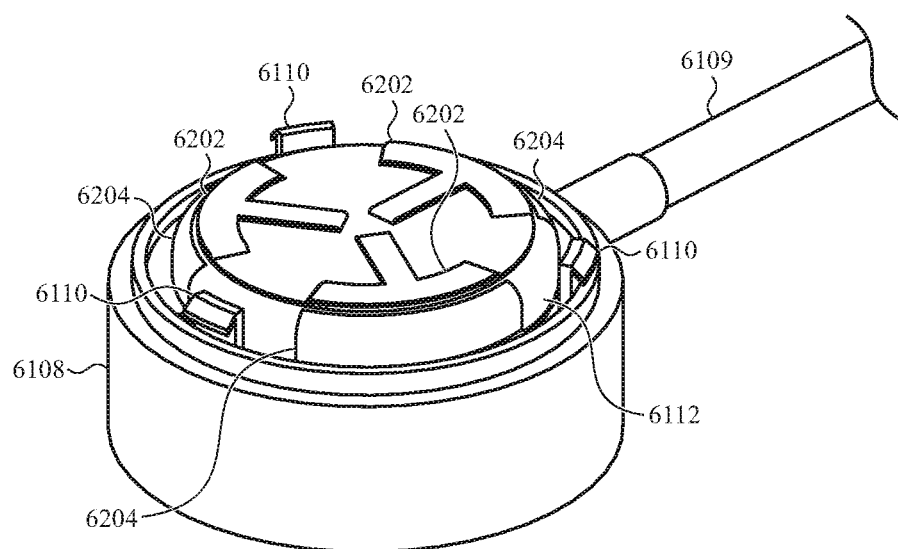

FIG. 62 shows additional details of the mounting base 6108. The mounting base 6108 includes the contact block 6112. The mounting base 6108 may also include first and second conductive members 6202, 6204. The first conductive members 6202 may be positioned in a location that generally corresponds to the negative terminal of a button cell battery. Accordingly, due to the position of the first conductive members 6202, when the tag 6102 is mounted on the mounting base 6108, the first conductive members 6202 may conductively couple to the deflectable arm of the battery connector that is configured to contact the negative terminal of the button cell battery (e.g., the third deflectable arm 1008, FIG. 10B). Similarly, the second conductive members 6204 may be positioned more towards the periphery of the contact block 6112, at a location that generally corresponds to the positive terminal of the button cell battery. The second conductive members 6204 may thus conductively couple to the deflectable arms of the battery connector that is configured to contact the positive terminal of the button cell battery (e.g., the first and second deflectable arms 1004, 1006, FIG. 10B).

The first and second conductive members 6202, 6204 may provide electrical power to the tag 6102 to power the tag in the absence of the battery. The power provided may mimic the power provided by a battery. For example, the mounting base 6108 may provide 1.5 volt direct current to the tag 6102 via the first and second conductive members 6202, 6204. In some cases, the power delivered through the cable 6109 is 1.5 volt direct current, in which case the current may be provided directly from the cable 6109 to the first and second conductive members 6202, 6204. More generally, the power delivered through the cable 6109 may be supplied from a DC power supply that provides the same or similar DC power that would otherwise be provided by the battery or batteries that power the tag.

In other cases, the cable 6109 delivers electrical power with different characteristics to the mounting base 6108 (e.g., 120 volt alternating current, 5 volts direct current, etc.). In such cases, the mounting base 6108 may include one or more power conversion systems to convert incoming power to a voltage or current suitable to operate the tag 6102 (e.g., an ac-to-dc converter). Such systems may include, for example, air core or magnetic core transformers, switched-mode power supplies (e.g., boost converters, buck converters, boost-buck converters, or other chopper circuits), analog voltage regulation circuits (e.g., voltage regulators, voltage reducers, clamp circuits, voltage divider circuits, voltage multiplier circuits, compensation networks, rectifier circuits, inverter circuits, and the like), or the like. The cable 6109 may be permanently attached to the mounting base 6108 (as shown), or it may be removable. For example, the mounting base 6108 may include a port for receiving the plug of a USB cable or other suitable power cable.

The power cable 6109 may be configured to plug into a power supply. For example, the power cable 6109 may be configured to plug into a residential AC power supply. In some cases, instead of or in addition to the power cable 6109, a plug (e.g., a two- or three-prong plug) may be integrated with the mounting base. In such cases, when the mounting base 6108 is plugged into an outlet, the mounting base may be mechanically supported in place by the physical plug/outlet connection.

The first and second conductive members 6202, 6204 are arranged so that at least one of the first conductive members 6202 and at least one of the second conductive members 6204 contacts the battery connector of the tag 6102 regardless of the radial position of the tag 6102 relative to the mounting base 6108 when they are attached. In the example shown, the tag 6102 can be attached to the mounting base 6108 in three different orientations, due to the three latch members and three corresponding engagement features of the tag 6102. The first and second conductive members 6202, 6204 are arranged in three pairs so that power is supplied to the battery connector regardless of which orientation the tag 6102 is in. Other configurations of first and second conductive members 6202, 6204 are also contemplated to ensure that power is provided regardless of tag orientation. Further, the orientation, position, shape, or other aspect of the first and second conductive members 6202, 6204 may be designed in conjunction with the particular battery connector configuration of the tag 6102. Thus, while the arrangement of the first and second conductive members 6202, 6204 are configured to mate with the battery connector 900 (FIG. 9), different arrangements may be used to mate with different battery connectors (e.g., those shown in FIGS. 11A-11D).

Figure 63:
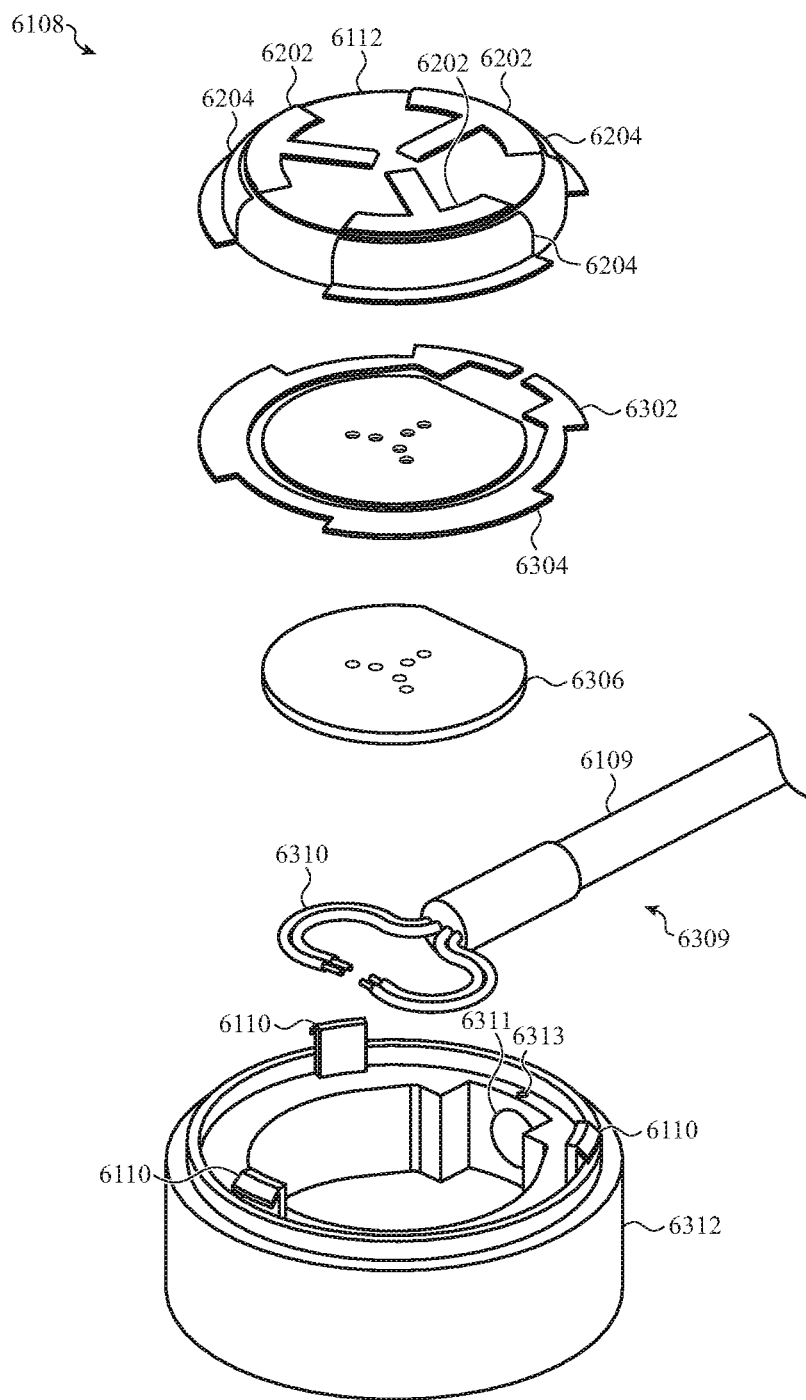

FIG. 63 is an exploded view of the mounting base 6108. The mounting base may include the contact block 6112 and its associated first and second conductive members 6202, 6204. The mounting base 6108 may include a housing 6312 to which the other components of the mounting base 6108 may be coupled. The housing 6312 may define the latch members 6110 (e.g., the latch members 6110 and the housing 6312 may be a single unitary piece of material), or they may be separate members that are attached to the housing 6312.

The housing 6312 may define an opening 6311 through which the end of the cable 6109 may extend. The cable 6109 may include a strain relief structure 6309 that helps prevent damage to the cable 6109 (and/or termination points of the wires inside the housing 6312) due to bending or twisting relative to the housing 6312. The cable 6109 may include conductors 6310 that carry electrical power to the mounting base 6108 and that are terminated on a circuit board 6306. Where the cable 6109 includes other conductors that are not used for carrying power to the mounting base 6108 (e.g., wires for data transfer), those conductors may be terminated to the circuit board but not used (e.g., they may be grounded), or they may be terminated to communications circuitry to allow communications between the mounting base 6108 and other devices. The cable 6109 may include other components such as chokes, filters, or the like. The cable 6109 may have a plug or connector at a free end, such as a USB connector, a wall plug, or the like. In some cases, instead of a flexible cable such as the cable 6109, a power connector (e.g., a plug for a wall outlet) may be incorporated directly with the housing of the housing 6312 of the mounting base 6108. For example, a plug for a wall outlet may extend from a surface of the housing 6312. With such a system, a user can plug mounting bases directly into wall outlets and attach tags directly to those bases, thereby providing convenient power and mounting locations for the tags.

In some cases, a tag may be programmed, controlled, or communicated with through the mounting base 6108 via the cable 6109. Further, mounting bases may include additional components or circuitry that supplements that of an attached tag. For example, the mounting base 6108 may include communications systems (wired or wireless) that the tag lacks, or communications systems with a longer wireless range than the tag itself. In such cases, the tag may communicate with other devices (e.g., phones, computers, other tags) through the communications circuitry of the mounting base.

The circuit board 6306 may include other electronic components, such as processors, memory, power control circuitry, communications circuitry, or any other components that facilitate operation of the mounting base 6108 and/or an attached tag.

The housing 6312 may also define a barometric vent 6313. The barometric vent 6313 may be an opening that fluidly couples an interior volume of the mounting base 6108 to the exterior environment. As shown, the barometric vent 6313 fluidly couples the interior volume of the mounting base to the opening 6311. The opening 6311 may be fluidly coupled with the exterior environment even when the cable 6109 extends through the opening 6311. The barometric vent 6313 facilitates the equalization of pressure between the interior volume of the mounting base 6108, as well as the interior volume of an attached tag, and the exterior environment. The barometric vent 6313 may include other components such as screens, waterproof and air-permeable membranes, and the like. Further, the barometric vent 6313 may be positioned elsewhere on the housing 6312, such as through a bottom wall or side wall of the housing 6312.

The contact block 6112 may be attached to the housing 6312 and the circuit board 6306 via adhesive layers 6302, 6304, respectively. The adhesive layers (as well as the circuit board 6306) may include openings, gaps, or discontinuities, or otherwise be configured so that air can pass between an attached tag and the interior volume of the housing 6312, thereby facilitating pressure equalization throughout the assembly.

Figure 64:
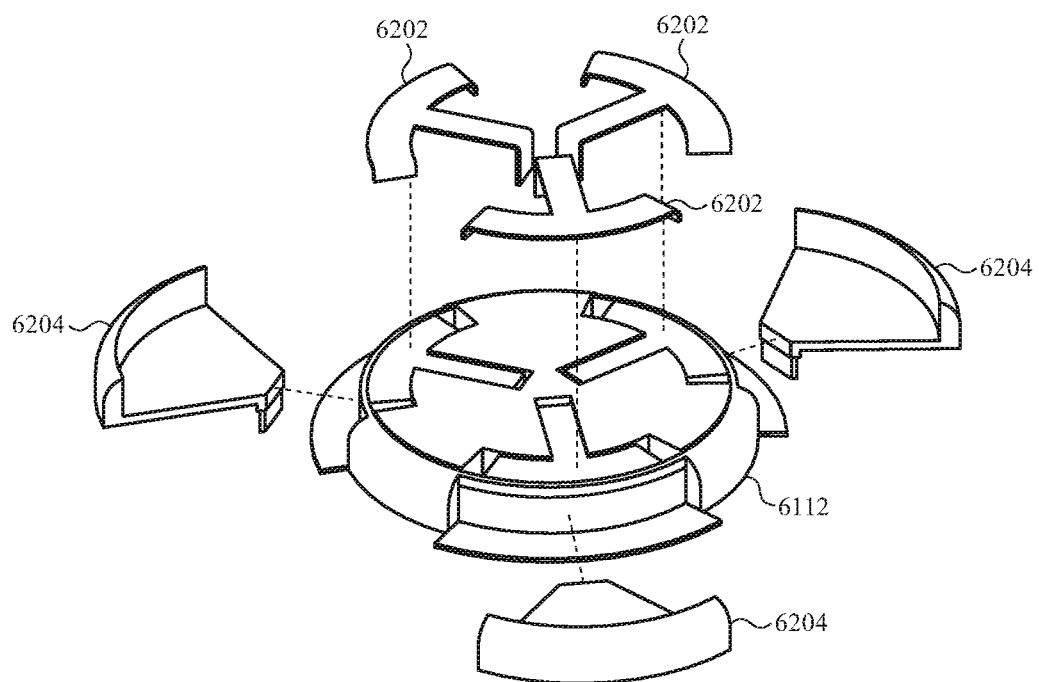

FIG. 64 shows an exploded view of a portion of the mounting base 6108, showing the contact block 6112 and the first and second conductive members 6202, 6204. The first and second conductive members 6202, 6204 may be positioned in openings, recesses, cavities, or other features in the contact block 6112, and may be conductively coupled to the circuit board 6306 (FIG. 63) so that electrical power can be supplied to an attached tag through the first and second conductive members 6202, 6204. The first and second conductive members 6202, 6204 may be secured to the contact block 6112 via adhesives, fasteners, or the like. In some cases, the first and second conductive members 6202, 6204 are insert molded with the contact block 6112, thereby securing the first and second conductive members 6202, 6204 to the contact block 6112 and forming an integrated assembly.

Figure 65A:
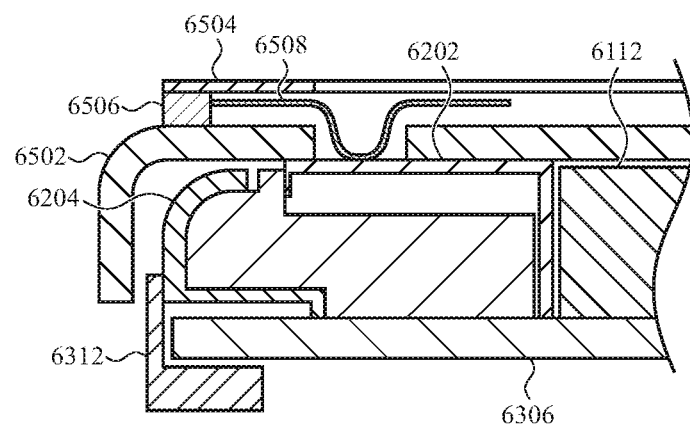
Figure 65B:
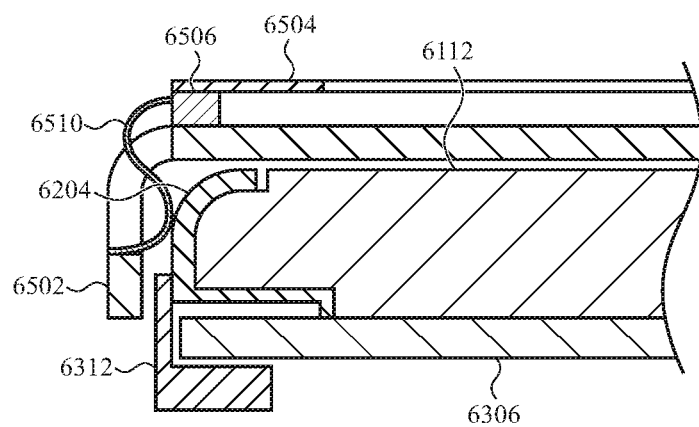

The first and/or second conductive members 6202, 6204 may be deflectable and/or deformable, and may be biased towards the battery connector of a tag to facilitate intimate contact between the first and/or second conductive members 6202, 6204 and the battery connector to ensure electrical conductivity between the deflectable arms and the conductive members. FIGS. 65A-65B illustrate partial cross-sectional views of the mounting base 6108 with the tag 6102 coupled to the mounting base 6108 such that the first and second conductive members 6202, 6204 contact the deflectable arms of a battery connector. For ease of illustration and understanding, some components of the mounting base 6108 and the tag 6102 are omitted or modified. Further, while the tag 6102 may be an embodiment of the tag 500, some of the components (e.g., the battery connector, the first and second conductive members 6202, 6204) may be modified for clarity and/or to aid in illustration and explanation. It will be understood that the features, functions, and/or principles shown and described with respect to the tag 6102 in FIGS. 65A-65B apply equally to the tag 500 and its specific components and configurations.

FIG. 65A illustrates a partial cross-sectional view through a portion of the mounting base 6108 and tag 6102 where a first conductive member 6202 contacts a first deflectable arm 6508 of a battery connector 6506 of the tag 6102. The battery connector 6506 may be an embodiment of the battery connector 900 (FIG. 9), and may be attached to a circuit board 6504, which may be an embodiment of the circuit board 510 (FIG. 5B). At least a portion of the first deflectable arm 6508 may extend through an opening in a frame member 6502 of the tag, which may be an embodiment of the frame member 512 (FIG. 5B), to allow the first deflectable arm 6508 to contact the first conductive member 6202.

The first deflectable arm 6508 may be biased downwards, while the first conductive member 6202 may be biased upwards. When the tag 6102 is coupled to the mounting base 6108, the first deflectable arm 6508 may be deflected upwards by the first conductive member 6202. In some cases, the first conductive member 6202 may be deflected downwards by the first deflectable arm 6508 (and/or it may be deflected downwards by a surface of the tag, such as a surface of the frame member 6502). The biasing forces of the first deflectable arm 6508 and the first conductive member 6202 thus force the first deflectable arm 6508 and first conductive member 6202 into contact with one another.

Additionally, the first conductive member 6202 may contact the bottom surface of the frame member 6502, thereby forcing the tag 6102 generally upwards relative to the mounting base 6108. This upward force on the tag 6102 may help retain the tag 6102 to the mounting base 6108. For example, as described above, a biasing force between the bottom housing member and the main body portion of a tag may provide a force that maintains the latch members of the bottom housing member in a secure engagement with the engagement features (e.g., recesses) of the tag. When the battery door is attached to the tag, this biasing force may be provided by a compliant member, such as the compliant member 518 (FIG. 5B). Accordingly, the first conductive member 6202 may provide a similar biasing force against the tag 6102 to maintain the engagement between the latch members 6110 and the tag 6102.

FIG. 65B illustrates a partial cross-sectional view through a portion of the mounting base 6108 and tag 6102 where a second conductive member 6204 contacts a second deflectable arm 6510 of a battery connector 6506 of the tag 6102. At least a portion of the second deflectable arm 6510 may extend through an opening in a frame member 6502 of the tag to allow the second deflectable arm 6510 to contact the second conductive member 6204.

The second deflectable arm 6510 may be biased towards the battery cavity (e.g., to the right in FIG. 65B). The second conductive member 6204 may be static (e.g., not deflectable and/or not biased in any particular direction), or it may be biased towards the second deflectable arm 6510 (e.g., to the left in FIG. 65B). The biasing force of the second deflectable arm 6510 may facilitate intimate contact between the second deflectable arm 6510 and the second conductive member 6204 to ensure electrical conductivity between the second deflectable arm 6510 and the second conductive member 6204.

The mounting base 6108 uses latch members 6110 to couple to the tag 6102. As noted, the latch members 6110 may be configured substantially the same as the latch members of the battery door used for the tag 6102. Thus, the operation of coupling the tag 6102 to the mounting base 6108 may be the same as or similar to the operation of coupling the battery door to the tag 6102. Where the tag 6102 is an embodiment of the tag 500, this may include pressing the tag 6102 and the mounting base 6108 together axially, and then twisting the tag 6102 relative to the mounting base 6108 to engage the latch members 6110 with a recess or undercut region that traps the latch members 6110 to retain the tag 6102 to the mounting base 6108. Other types of fastening mechanisms may be used instead of or in addition to the latch members 6110. For example, FIGS. 66-67 illustrate several other examples of mounting bases that use different techniques to couple to a tag.

Figure 66:
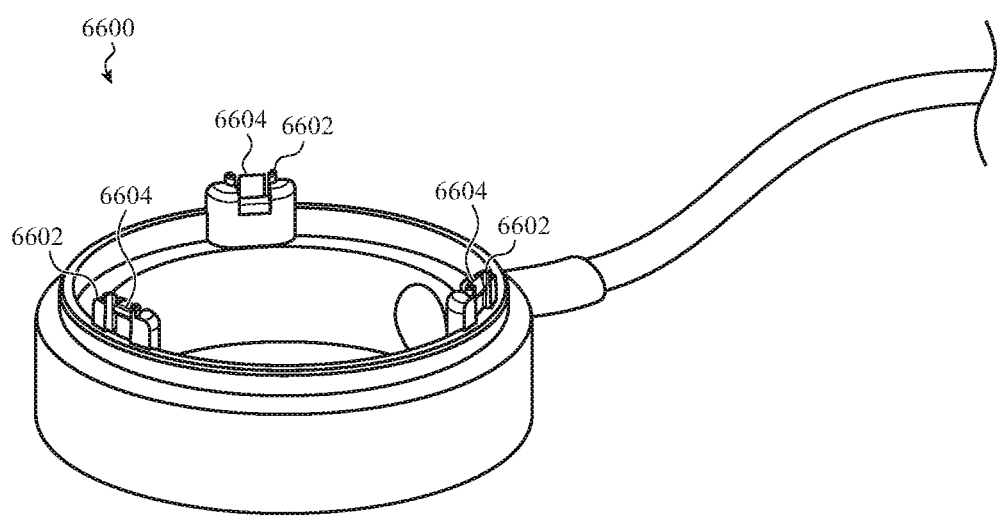
FIG. 66 depicts another example mounting base system for wirelessly locatable tags.

FIG. 66 illustrates an example mounting base 6600 that is configured to semi-permanently attach to a tag, such as the tag 6102. In particular, instead of latch members that are configured to operate substantially identically to the latch members of the tag's battery door, the mounting base 6600 is configured so that the tag cannot be detached without breaking or risking breaking the tag and/or the mounting base 6600. To accomplish this, the mounting base 6600 may include latch members 6604 and blocking features 6602 proximate the latch members 6604. The latch members 6604 may be configured to engage a channel, ledge, recess, or other feature of the tag such that the tag is axially retained to the mounting base 6600. The blocking features 6602 may also engage the tag to prevent or inhibit rotational movement of the tag. In this way, it may be difficult or impossible to rotate the tag relative to the mounting base 6600 in a way that will non-destructively disengage the latch members 6604 from the tag. Further, the latch members 6604 may not be accessible to a user to allow the user to disengage the latch members 6604 from the tag. Accordingly, the tag may be securely retained to the mounting base 6600. This may be useful in instances where the tags are to be used with the mounting base 6600 indefinitely, and/or are installed in static locations or displays. For example, the mounting base 6600 may be used to secure a tag to or near a fire extinguisher, emergency exit, exhibit (e.g., in a museum), retail display, or the like. The mounting base 6600 may provide power to the battery using a contact block as described with respect to other mounting bases described herein.

Figure 67:
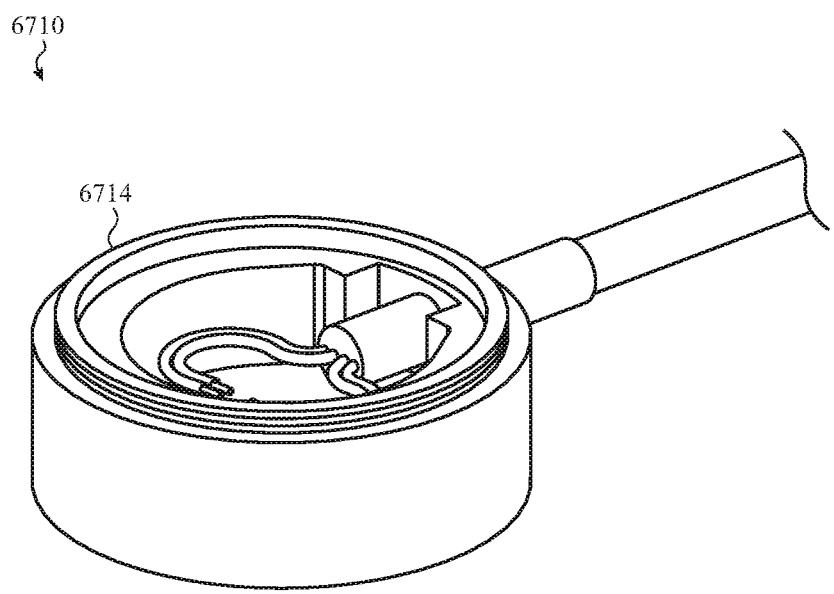
FIG. 67 depicts another example mounting base system for wirelessly locatable tags.

FIG. 67 illustrates an example mounting base 6710 that is configured to attach to a tag using a threaded attachment system. In particular, a tag, which is otherwise similar to the tag 6102, may include a threaded interface (e.g., a threaded recess) that may be used to attach a battery door with a corresponding threaded feature. Accordingly, the mounting base 6710 may include or define a threaded feature 6714 (e.g., a threaded cylinder) that is configured to engage the corresponding threaded feature of a wirelessly locatable tag. The mounting base 6710 may include latching features, such as pawls, that semi-permanently retain the tag to the mounting base. For example, one or more pawls of the mounting base 6710 may engage the tag when the tag is threaded onto the mounting base 6710, thereby inhibiting the tag from being un-threaded from the mounting base 6710 (without risking damage to the tag and/or the mounting base). Such features may be implemented for applications where the tag is not meant to be removed from the mounting base 6710 such as permanent installations in buildings, museums, retail displays, or the like. The mounting base 6710 may provide power to the battery using a contact block as described with respect to other mounting bases described herein.

While example mounting bases are described as engaging with the same features that are used to attach a battery door to the tag, this is not necessarily required. Rather, in some cases a battery door and a mounting base may attach to a tag using different mounting features or techniques. For example, a battery door may attach to a tag using an engagement between a latch member and a recess, while a mounting base may attach to the same tag using a threaded feature of the tag.

Figure 68:
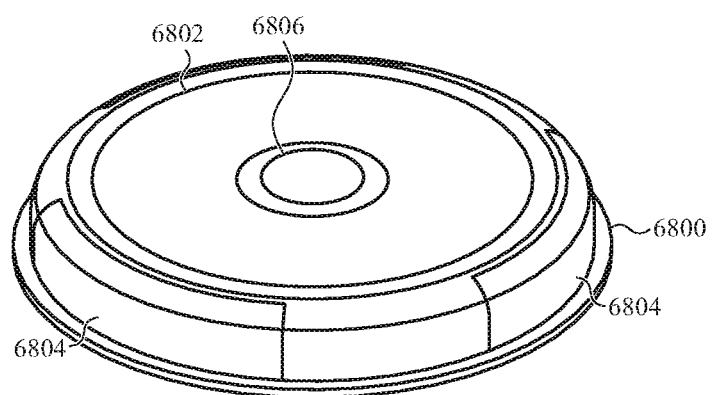
FIG. 68 depicts an example contact block for a mounting base system.

FIG. 68 illustrates an example contact block 6800 that is configured to engage the battery connector of a tag to provide power to the battery connector. The contact block 6800 may be used as an alternative to the contact block 6112, and may be incorporated into any suitable mounting base, such as the mounting bases described herein. The contact block 6800 includes a first conductive member 6802 positioned on a top surface of the contact block 6800 and configured to engage a deflectable arm of a battery connector (e.g., the deflectable arm 6508, FIG. 65A). The first conductive member 6802 may have a disk-like shape, and may define all or substantially all of the top surface of the contact block 6800. Because the first conductive member 6802 has a continuous surface around the top of the contact block 6800, the first conductive member 6802 will contact the battery connector regardless of the rotational position of the tag relative to the contact block 6800. The contact block 6800 may also include second conductive members 6804, which may be configured substantially the same as other second conductive members described herein (e.g., the second conductive members 6204). In some cases, instead of multiple discontinuous second conductive members 6804, a single second conductive member 6804 may extend annularly around the periphery of the contact block 6800, thereby ensuring that a portion of the second conductive member 6804 will contact the battery connector of the tag regardless of the rotational position of the tag relative to the contact block 6800.

The contact block 6800 may also include a biasing member 6806 that is configured to apply a biasing force on the tag. As described above, a biasing force from a contact block may force latch members of a contact block into engagement with corresponding features of a tag. The biasing member 6806 may be a spring, foam, elastomer, or any other suitable material or component that can apply the requisite biasing force to the tag.

The foregoing example mounting bases describe some example features and/or mechanisms for attaching to tags. Of course, other configurations are also contemplated. For example, the features or members that are described as being on a mounting base may be provided on a tag instead, and the tag's features may instead be on the corresponding mounting base. Further, where tags use other types of mechanisms to retain a battery door or other housing member, a mounting base may use the same type of mechanism to attach to that tag.

One advantage of the size and form factor of the tags described herein is that they can be securely attached to numerous types of accessories using numerous attachment techniques and components. For example, accessories may be provided that allow the tag to be attached to a key ring (also referred to herein as a split ring), a wallet, a briefcase, a purse, an article of clothing, luggage, a notebook or tablet computer, a pet's collar, or any other item that a user desires to track with a wirelessly locatable tag, as described herein.

Figure 69A:
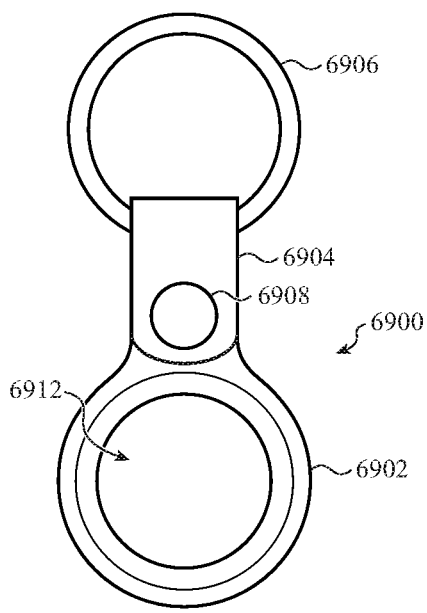
FIGS. 69A-69C depict an example tag retainer for holding a wirelessly locatable tag.
Figure 69B:
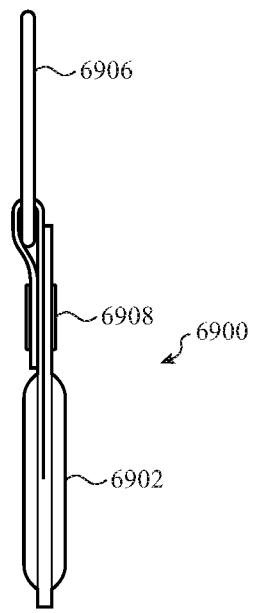
Figure 69C:
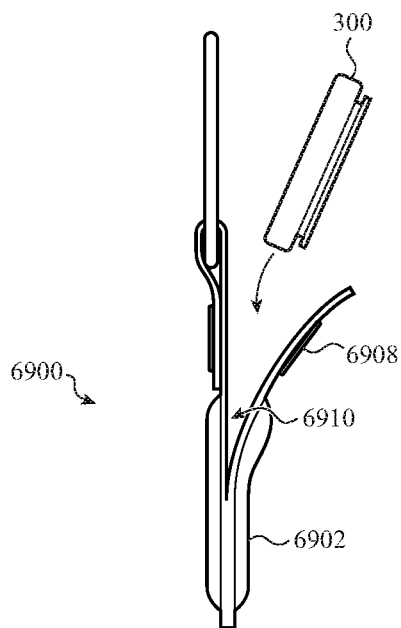
Figure 128:
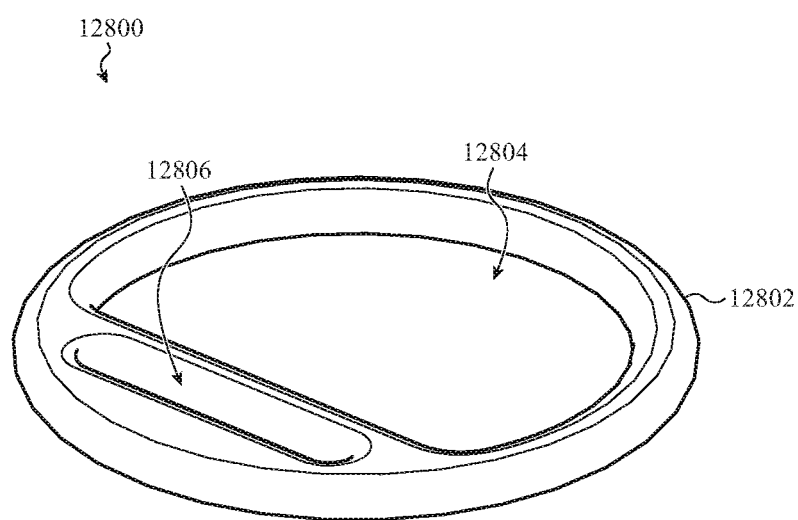

FIGS. 69A-128 illustrate various example accessories and attachment techniques that may be used with the tags described herein. FIGS. 69A-69C, for example, illustrate an example tag retainer 6900 for holding a tag, such as the tag 300 (FIG. 3) or any other tag embodiment described herein. The tag retainer 6900 may also be referred to as a holder, tag holder, tag accessory, or simply accessory. The tag retainer 6900 may include a tag receptacle portion 6902 and an attachment portion 6904 (which may be or may resemble a strap and may be referred to herein as a strap or a fastening strap). The tag receptacle portion 6902 is configured to receive and hold the tag 300 securely, and the attachment portion 6904 is configured to attach the tag retainer 6900 to another object. The tag receptacle portion 6902 may also be referred to as a pocket, recess, or tag retaining feature. As shown in FIGS. 69A-69B, the attachment portion 6904 is attached to a split ring 6906, though this is merely one example object to which it could be attached. For example, the attachment portion 6904 may be attached to a luggage or purse handle, a pet collar, or any other suitable object.

The tag retainer 6900 may define an opening 6910, defined along less than a complete circumference of the tag receptacle portion 6902, that allows the tag 300 to be placed in and removed from the tag retainer 6900. The tag retainer 6900 also includes a fastener 6908 that is configured to releasably secure the opening 6910 in a closed position. The fastener 6908 may also be configured to secure the attachment portion 6904 in a closed or looped position (as shown in FIGS. 69A-69C) to couple the attachment portion 6904 (fastening strap) to another object, such as the split ring 6906. The fastener 6908 may permanently secure the end of the attachment portion 6904 to the base of the attachment portion 6904 (thereby permanently forming the loop in the attachment portion 6904), or it may releasably secure the end of the attachment portion 6904 to the base of the attachment portion 6904 such that the loop can be selectively opened or closed (so the attachment portion 6904 can be easily attached to or detached from an object such as the split ring 6906, a suitcase or briefcase, or the like).

The fastener 6908 may be a snap, clip, button, or any other suitable fastener. In some cases, the fastener 6908 includes multiple snap elements to allow the opening 6910 in the tag receptacle portion 6902 to be fastened and unfastened independently of the loop formed in the attachment portion 6904. Stated another way, the loop in the attachment portion 6904 may be fastened and unfastened (e.g., to allow the tag retainer 6900 to be attached to or detached from other objects) while the opening 6910 remains fastened closed.

The tag receptacle portion 6902 may define a circular cavity in which the tag 300 is placed. The circular cavity may have a size and shape that generally corresponds to that of the tag 300, such that the surface of the tag receptacle portion 6902 that defines the cavity (e.g., the inner surface of the receptacle portion) touches and/or is in intimate contact with the exterior surfaces of the tag 300 when the tag 300 is in the cavity. This may help prevent movement of the tag 300 within the cavity and help secure the tag 300 in the cavity. Thus, for example, the size and shape of the cavity may be the same as or substantially the same as the size and shape of the tag 300.

The tag receptacle portion 6902 may have one or more openings 6912 that allow a user to see into the tag receptacle portion 6902 and easily determine if the tag 300 is or is not currently in the tag receptacle portion 6902. The openings 6912 may also allow speakers, microphones, environmental sensors, and/or other inputs and/or outputs of the tag 300 to access the outside environment. For example, at least one of the openings 6912 may be aligned with a portion of a tag housing that acts as a speaker diaphragm. In this manner, the surface of the housing that moves to produce audible and/or tactile outputs may be exposed and/or un-occluded so that audible and/or tactile outputs are not inhibited. The openings 6912 may be specifically configured in view of the tag 300 (or any tag for which the retainer 6900 is designed) to have sizes and/or shapes that are smaller than the tag 300, such that the tag 300 cannot fall out of the tag retainer 690 through the openings 6912. For example, the openings 6912 may be circular openings with a diameter that is less than the largest diameter of a circular tag. In some cases, the diameters (or the largest dimension) of the openings 6912 are less than about 3 inches, less than about 2 inches, or less than about 1 inch. Other embodiments may be completely enclosed or otherwise not provide visual access to the inside of the tag receptacle portion 6902.

The tag retainer 6900 may be formed from or include any suitable materials. For example, the tag retainer 6900 may be formed from leather, polymer (e.g., silicone, thermoplastic polyurethane (TPU)), fabric or cloth, or the like. If the tag retainer 6900 is formed of polymer, it may be formed as a single unitary polymer part (with the exception of the fastener 6908). The tag retainer 6900 may also be formed by joining multiple different layers, materials, and/or parts together. For example, the tag receptacle portion 6902 may include a first layer that defines a first portion of the tag receptacle portion 6902 (and optionally including the attachment portion 6904), and a second portion that defines a second portion of the tag receptacle portion 6902. The first layer may correspond to the material on the left side of the vertical seam shown in FIGS. 69A and 69B (e.g., the seam that defines and/or corresponds to the opening 6910), while the second layer may correspond to the material on the right side of the vertical seam. The first and second layers of the tag retainer 6900 may each include one layer of material, or they may each be formed of multiple sublayers of materials, with the sublayers being attached to one another (e.g., laminated) using adhesives, ultrasonic welding, laser welding, stitching, insert molding, or any other suitable technique.

The first and second layers may be sewn, stitched, adhered, or otherwise coupled together around part of the circumference of the tag receptacle portion 6902 to join the first and second layers while also defining the opening 6910 that allows the tag 300 to be inserted into and removed from the tag receptacle portion 6902. For example, the first layer may be adjacent the second layer along an interface region (e.g., the surfaces of the first and second layers that face and/or abut one another when the tag retainer 6900 is assembled and closed). The second layer may be attached to the first layer along a first segment of the interface region (e.g., around the bottom portion of the tag retainer, as illustrated in FIGS. 69B-69C by the absence of a seam or line between the left and right portions), and may be unattached to the first layer along a second segment of the interface region, thereby defining the opening 6910 between the first layer and the second layer.

FIGS. 69D-69G illustrate another example tag retainer 6920 that is similar to the tag retainer 6900, but secures the tag retainer in a closed configuration using a strap interlaced with a tab, instead of a fastener such as a snap. The tag retainer 6920 may otherwise be substantially similar to the tag retainer 6900. The details of the tag retainer 6900 apply equally or by analogy to the tag retainer 6920, and may not be repeated here to avoid redundancy.

Figure 69D:
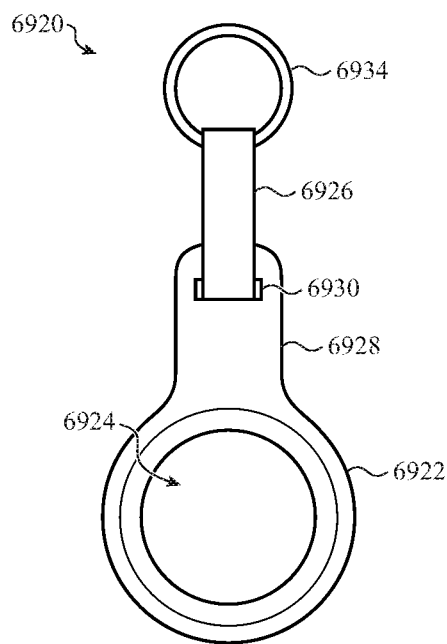
FIGS. 69D-69G depict another example tag retainer for holding a wirelessly locatable tag.
Figure 69E:
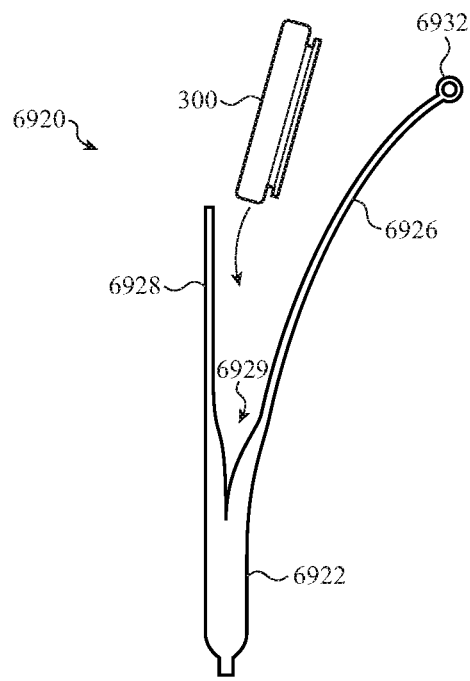
Figure 69F:
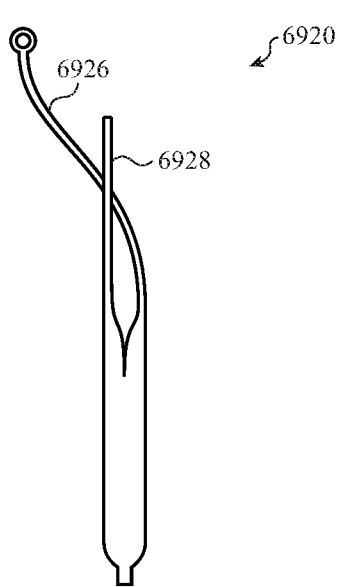
Figure 69G:
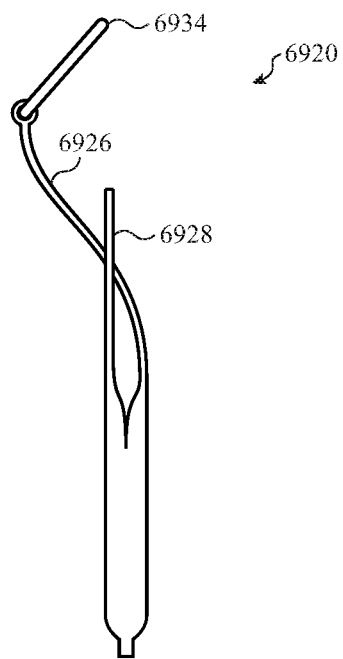

The tag retainer 6920 may include a tag receptacle portion 6922 and an attachment portion or strap 6926. The tag receptacle portion 6922 is configured to receive and hold the tag 300 securely, and the strap 6926 is configured to attach the tag retainer 6920 to another object. As shown in FIGS. 69D and 69G, the strap 6926 is attached to a split ring 6934 (which passes through a loop 6932 at a terminal end of the strap 6926), though this is merely one example object to which it could be attached. For example, the strap 6926 may be attached to a luggage or purse handle, a pet collar, or any other suitable object. The strap 6926 extends from the tag receptacle portion 6922 proximate the first opening 6929.

The tag retainer 6920 may define an opening 6929, defined along less than a complete circumference of the tag receptacle portion 6922, that allows the tag 300 to be placed in and removed from the tag retainer 6920. The tag retainer 6920 also includes a tab 6928 extending from the tag receptacle portion 6922 proximate the first opening 6929. The tab 6928 defines a strap opening 6930, that is configured to receive the strap 6926 therethrough (e.g., the strap 6926 is configured to extend through the opening 6930) to retain the first opening 6929 in a closed configuration. The strap 6926 is also configured to be removed from the strap opening 6930 to allow the first opening 6929 to expand to accept the tag 300.

The split ring 6934 may be removed from the strap 6926 to facilitate passing the strap 6926 through the opening 6930 and/or removing the strap 6926 from the opening 6930. When attached to the strap 6926, the size of the split ring 6934 may prevent the strap 6926 from being removed from the opening 6930, thereby maintaining the opening 6929 in a closed configuration. For example, a dimension of the split ring 6934 (e.g., a diameter) is larger than a dimension of the opening 6930 (e.g., a largest linear dimension of the opening), thereby preventing the terminal end of the strap 6926 from passing through the opening 6930 when the split ring 6934 is attached to the loop 6932 of the strap 6926. FIG. 69E shows the tag retainer 6920 with the opening 6929 in an open configuration to receive the tag 300. In this configuration, the strap 6926 is not extended through the opening 6930. FIG. 69F shows the tag retainer 6920 with the opening 6929 in a closed configuration, after the strap 6926 has been passed through the opening 6930. FIG. 69G shows the tag retainer 6920 after the split ring 6934 has been attached to the strap 6926 (through the loop 6932). In the configuration of FIG. 69G, the opening 6929 may be retained in a closed configuration by the interference of the split ring 6934 with the opening 6930. By retaining the opening 6929 closed, inadvertent opening of the tag receptacle portion 6922 and release of the tag 300 may be prevented or inhibited.

The tag receptacle portion 6922 may define a circular cavity in which the tag 300 is placed. The circular cavity may have a size and shape that generally corresponds to that of the tag 300, such that the surface of the tag receptacle portion 6922 that defines the cavity (e.g., the inner surface of the tag receptacle portion 6922) touches and/or is in intimate contact with the exterior surfaces of the tag 300 when the tag 300 is in the cavity. This may help prevent movement of the tag 300 within the cavity and help secure the tag 300 in the cavity. Thus, for example, the size and shape of the cavity may be the same as or substantially the same as the size and shape of the tag 300.

The tag receptacle portion 6922 may have one or more openings 6924 that allow a user to see into the tag receptacle portion 6922 and easily determine if the tag 300 is or is not currently in the tag receptacle portion 6922. The openings 6924 may also allow speakers, microphones, environmental sensors, and/or other inputs and/or outputs of the tag 300 to access the outside environment. For example, at least one of the openings 6924 may be aligned with a portion of a tag housing that acts as a speaker diaphragm. In this manner, the surface of the housing that moves to produce audible and/or tactile outputs may be exposed and/or un-occluded so that audible and/or tactile outputs are not inhibited. Other embodiments may be completely enclosed or otherwise not provide visual access to the inside of the tag receptacle portion 6922.

Figure 70C:
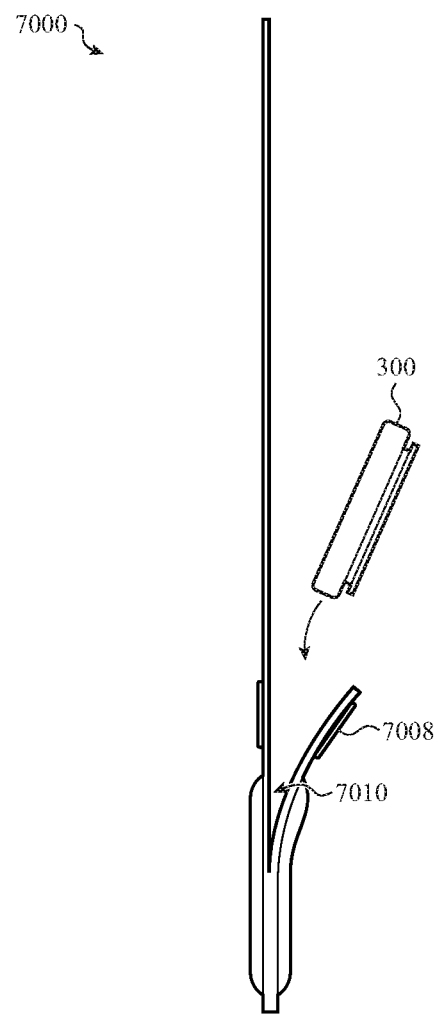
Figure 70D:
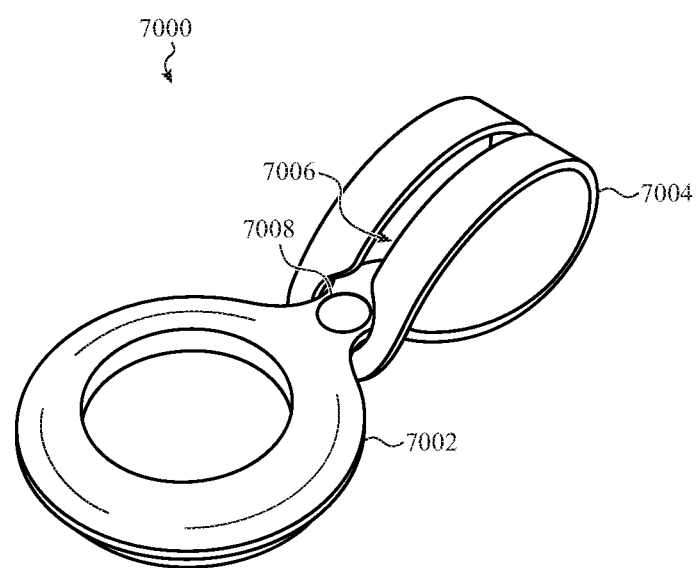

FIGS. 70A-70D illustrate an example tag retainer 7000, which is similar to the tag retainer 6900 but has a different attachment portion. In particular, while the attachment portion 6904 of the tag retainer 6900 is configured to be releasably secured in a loop by a mechanical fastener 6908, the tag retainer 7000 includes an attachment portion 7004 that defines an opening 7006 that allows the attachment portion 7004 to define a loop with itself. For example, FIG. 70D illustrates how the attachment portion 7004 can be formed into a loop using the opening 7006 by passing the tag receptacle portion 7002 through the opening 7006. The attachment portion 7004 may be used to fasten the tag retainer 7000 to any suitable object such as a key ring, purse, luggage handle, or the like.

The tag retainer 7000 may otherwise be similar in construction and use to the tag retainer 6900. For example, FIG. 70C shows how the tag retainer 7000 may be opened (at opening 7010) to allow the tag 300 to be placed in and/or removed from the tag receptacle portion 7002. Further, the tag retainer 7000 may define openings (e.g., circular openings) that allow speakers, microphones, environmental sensors, and/or other inputs and/or outputs of the tag 300 to access the outside environment. The tag retainer 7000 may include a fastener 7008 that is configured to releasably secure the opening 7010 in a closed position (as shown in FIGS. 70B and 70D). The fastener 7008 may be a snap, button, or any other suitable fastening mechanism. In some cases, the tag retainer 7000 may selectively retain its opening 7010 in the closed configuration using an arrangement as shown in FIGS. 69D-69G (e.g., a tab with an opening configured to receive the strap or attachment portion 7004). Other details of the tag retainer 7000 may be the same as or similar to those of the tag retainer 6900, and for brevity may not be repeated here.

FIGS. 71A-71C illustrate an example tag retainer 7100. FIG. 71A illustrates a top perspective view of the tag retainer 7100, and FIG. 71B illustrates a bottom view of the tag retainer 7100. The tag retainer 7100 may act as a protective shell for a tag, and may also facilitate the attachment of the tag to other components. The tag retainer 7100 may be formed from a flexible and/or compliant material so that the tag retainer 7100 can be stretched or otherwise deformed to allow the tag 300 to be inserted into and removed from the tag retainer 7100. For example, the tag retainer 7100 may be formed from or include silicone, TPU, or another suitable polymer or other material. The tag retainer 7100 may be formed from a unitary piece of a single material.

The tag retainer 7100 may include a tag receptacle portion 7102 and a gripping portion 7104 (which may be used to grip the tag retainer and/or attach the tag retainer to another object). The tag receptacle portion 7102 may define a first opening 7106 along a first side of the tag receptacle portion 7102 and a second opening 7108 along a second side of the tag receptacle portion 7102. The first opening 7106 may be sized and configured so that a battery door of the tag 300 extends into the first opening 7106 when the tag 300 is positioned in the tag retainer 7100, and may be smaller than the second opening 7108. As shown in FIG. 71C, which is a partial cross-sectional view of the tag retainer 7100, viewed along line 71C-71C in FIG. 71A, the thickness of the material that defines the perimeter of the tag receptacle portion 7102 may be substantially equal to the distance that the battery door extends above the surface of the main body portion of the tag 300. Accordingly, an exterior surface of the tag receptacle portion 7102 proximate the first opening 7106 may be substantially flush with the surface of the battery door.

The second opening 7108 may be sized and configured to allow the tag 300 to be placed in and removed from the tag retainer 7100. The second opening 7108 may be at least partially defined by or proximate to a tag retention feature 7110 that contacts the tag 300 and retains the tag 300 in the tag retainer 7100. The tag retention feature 7110 may be or resemble a lip, flange, protrusion, or other feature. The tag retention feature 7110 may extend around the entire circumference of the second opening 7108.

The tag 300 may be inserted into and removed from the tag retainer 7100 by deforming or stretching the second opening 7108 so that the tag 300 can be fit into the tag retainer 7100. The first and second openings 7106, 7108 may be configured to allow speakers, microphones, environmental sensors, and/or other inputs and/or outputs of the tag 300 to access the outside environment when the tag 300 is placed in the tag retainer 7100.

The tag retainer 7100 may also define a flange 7103 that extends at least partially (and optionally completely) around the outer periphery of the tag retainer 7100. The flange 7103 may allow the tag retainer 7100 to be attached to other objects. For example, the flange 7103 may be sewn, adhered, bonded, or otherwise attached to another object such as an article of clothing, a purse, a wallet, or the like. The gripping portion 7104 may be considered an extension of or enlarged portion of the flange 7103. The tag retainer 7100 may also define a vent similar to the vent 7204 (FIGS. 72A-72C) to allow sound waves, which may be produced by moving the housing member of the tag 300, to escape a volume defined between space between the tag 300 and a surface to which it is attached.

Figure 72A:
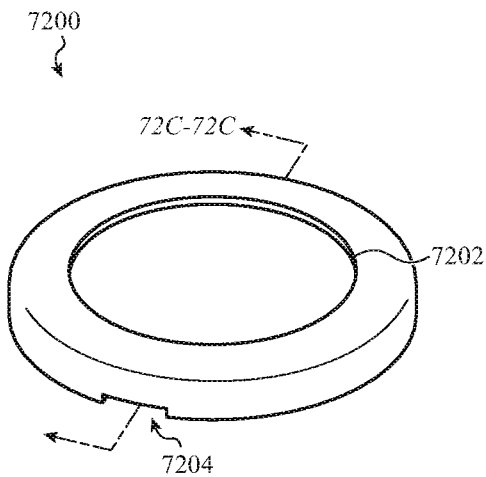
FIGS. 72A-72C depict another example tag retainer for holding a wirelessly locatable tag.
Figure 72B:
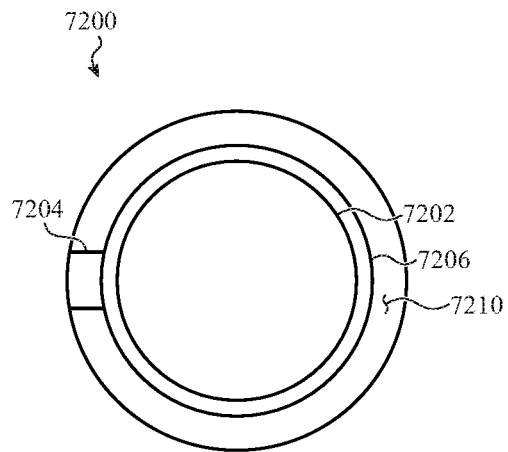
Figure 72C:
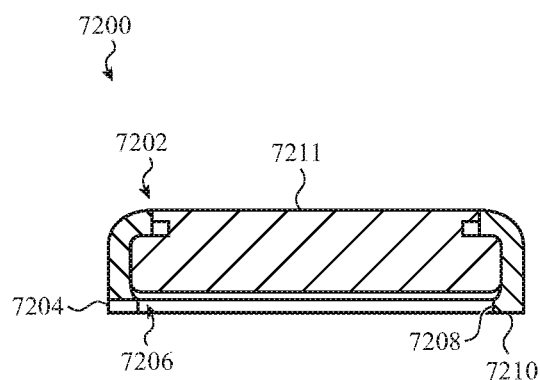

FIGS. 72A-72C illustrate an example tag retainer 7200. FIG. 72A illustrates a top perspective view of the tag retainer 7200, and FIG. 72B illustrates a bottom view of the tag retainer 7200. FIG. 72C is a partial cross-sectional view of the tag retainer 7200, viewed along line 72C-72C in FIG. 72A. The tag retainer 7200 may be similar in size and construction to the tag retainer 7100 (but without the grip portion). For example, the tag retainer 7200 may be formed from or include silicone, TPU, or another suitable polymer or other material. The tag retainer 7200 may be formed from a unitary piece of a single material.

The tag retainer 7200 defines a first opening 7202 that at least partially receives a battery door of the tag 300 (similar to the first opening 7106 of the tag retainer 7100) and a second opening 7206 that allows the tag 300 to be inserted into and removed from the tag retainer 7200. Similar to the tag retainer 7100, the second opening 7206 may be at least partially defined by or proximate to a tag retention feature 7208 (e.g., a lip, flange, protrusion) that contacts the tag 300 and retains the tag 300 in the tag retainer 7200.

The tag retainer 7200 may be adapted to be adhered to other components along a bottom surface 7210 of the tag retainer 7200. For example, an adhesive layer may be applied to the bottom surface 7210 to allow the tag retainer 7200 to be adhered to another object after the tag 300 is inserted into the tag retainer 7200. In some cases the adhesive may include a tear-away backing so that the tag retainer 7200 may be sold with the adhesive attached. A user can then simply place a tag 300 into the tag retainer 7200, remove the backing, and adhere the tag retainer 7200 to an object (e.g., a computer, luggage, a mobile phone, etc.).

The tag retainer 7200 may define a vent 7204 along the bottom surface 7210. The vent 7204 may fluidly couple the external environment around the tag retainer 7200 to the space defined between an outer surface 7211 of the tag 300 and the surface on which the tag retainer 7200 is mounted. This may allow sound produced by the tag 300 to be transmitted more effectively to the outside environment. More particularly, as described above, the tag 300 may include an audio system that produces audible output, optionally using the outer surface 7211 of the tag 300 as a speaker diaphragm. The vent 7204 may allow air pressure waves to exit the otherwise enclosed space between the tag 300 and the surface to which it is attached, so that the sounds can be more easily heard (e.g., the vent 7204 reduces the sound attenuation as compared to an un-vented tag retainer 7200). The size and shape of the tag retainer 7200 may be configured so that the volume defined between the outer surface 7211 of the tag 300 and a surface to which the tag retainer 7200 is attached operates as a Helmholtz resonator, or is otherwise tuned to provide satisfactory acoustic performance.

As noted above, the size and shape of the tags described herein may allow the tags to be secured to accessories in various different ways. For example, the tag retainers 6900 and 7000 contact the tag on multiple sides to partially (or fully) enclose the tag. The tag retainers 7100, 7200 have circumferential tag retention features (e.g., a circular lip around an opening) that retain a tag in the tag retainers.

Figure 73A:
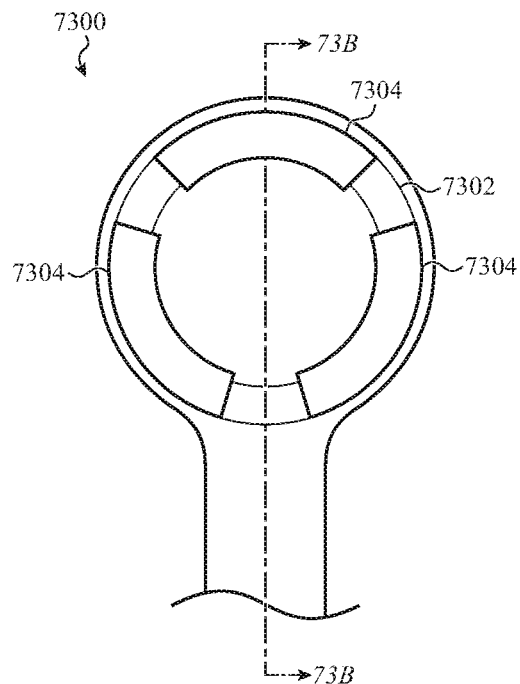
FIGS. 73A-73B depict another example tag retainer for holding a wirelessly locatable tag.

However, numerous other techniques for retaining a tag are also contemplated. As used herein, the structures and/or components used to retain a tag to an accessory or another object may be referred to as "tag retainers." Thus, the tag retention features 7110 and 7208 may be examples of tag retainers. FIGS. 73A-128 show numerous examples of tag retainers. For simplicity, FIGS. 73A-128 show examples of tag retainers in the context of one example accessory (an accessory with an elongated segment for forming a loop around a key ring, as one example), though it will be understood that any of the tag retainers shown in FIGS. 73A-128 may be used with other types of accessories as well. For example, a tag retainer that is used in a keychain accessory may instead be incorporated with a luggage-attachment accessory.

FIG. 73A depicts an example tag retainer 7300 that includes a body 7302 and one or more retention flanges 7304 secured to the body 7302, where the retention flanges 7304 have a greater stiffness than the body 7302. The retention flanges 7304 may be configured to extend at least partially into a gap or channel between a battery door and a main body portion of a tag to retain the tag to an accessory. The increased stiffness of the retention flanges 7304 relative to the body 7302 helps increase the strength and security of the attachment. As used herein, the gap between the battery door and the main body portion of a tag may be referred to as a "housing gap." Further, a housing gap of a tag need not be defined by a battery door and a main body portion, and instead may be defined between other components of a tag (e.g., two housing members, neither of which operate as a battery door).

When installing a tag into the tag retainer 7300, the body 7302 may be configured to stretch to allow an opening of the body 7302 to be enlarged to accommodate the tag, and then return to an un-stretched (or less stretched) configuration to bias the retention flanges 7304 into the housing gap. The retention flanges 7304 may be snapped into and out of position in the housing gap when inserting and removing the tag 300.

Figure 73B:
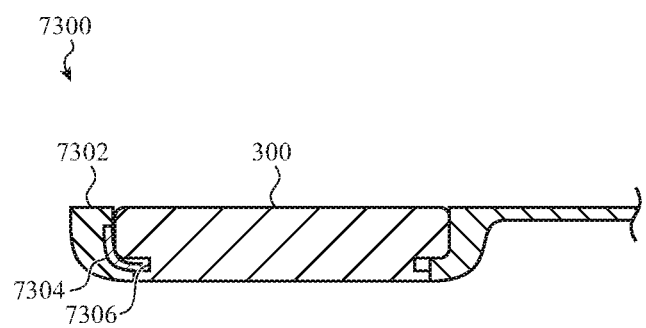

FIG. 73B is a partial cross-sectional view of the tag retainer 7300 of FIG. 73A, viewed along line 73B-73B in FIG. 73A, showing how the tag 300 may be installed and retained in the tag retainer 7300. As shown, the tag 300 defines a gap 7306 between part of a battery door and a main body portion of the tag 300 (e.g., a housing gap). The retention flanges 7304 are configured so that a portion of the retention flanges 7304 extend into the housing gap 7306 to retain the tag 300 in the tag retainer 7300.

The retention flanges 7304 may be attached to the body 7302 in any suitable way. For example, the retention flanges 7304 may be inserted into a mold, and then material for the body 7302 may be injected into the mold to at least partially encapsulate the retention flanges 7304 and retain the retention flanges 7304 to the body 7302. The retention flanges 7304 may also be adhered to the body 7302 or secured in any other suitable way.

Figure 74A:
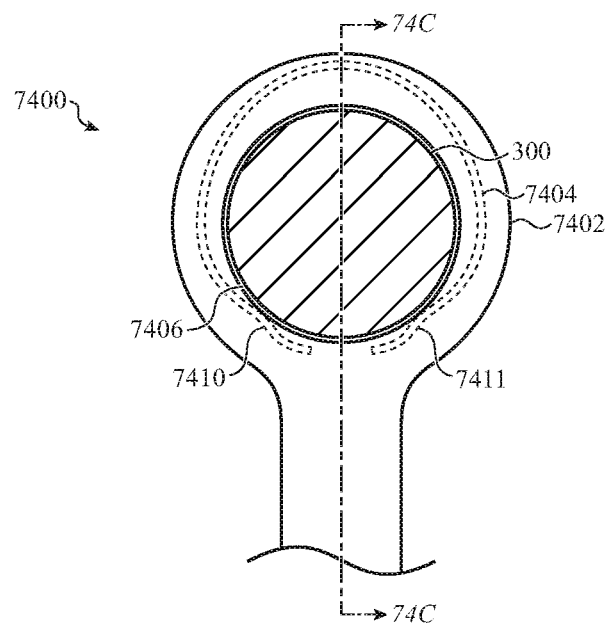
FIGS. 74A-74F depict another example tag retainer for holding a wirelessly locatable tag.
Figure 74B:
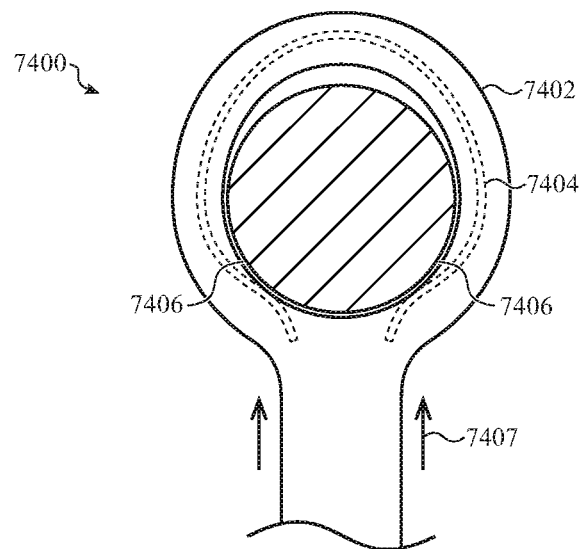
Figure 74C:
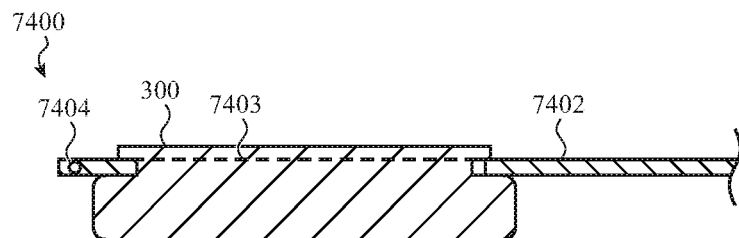

FIGS. 74A-74F illustrate an example tag retainer 7400 that includes a spring member 7404 embedded in a body 7402. The body 7402 may be formed from a compliant, flexible material or materials (such as silicone, TPU, or another suitable polymer), and the spring member 7404 may be formed from a material having a higher stiffness, such as a metal (e.g., spring steel) or less flexible polymer. The body 7402 and the spring member 7404 may cooperate to engage a housing gap of a tag. In particular, as shown in FIG. 74A, the body 7402 is biased into a housing gap of a tag by the spring member 7404. To more clearly illustrate how the tag retainer 7400 engages the tag 300, FIG. 74A illustrates a sectional view of the tag 300, showing the tag 300 without an upper portion of the battery door. (The section line 7403 of the tag 300 is shown in FIG. 74C.)

In order to attach or detach the tag 300 from the tag retainer 7400, the tag retainer 7400 is manipulated so that the spring member 7404 and the body 7402 can expand. For example, a force applied to the body 7402 (indicated by arrows 7407) may force engagement ends 7410 of the spring member 7404 against the tag 300, thereby allowing the engagement ends 7410 to spread apart, ultimately enlarging the opening in the body 7402 to allow the tag 300 to be more easily removed from or inserted into the opening.

FIGS. 74C-74F are partial cross-sectional views of the tag retainer 7400 and the tag 300 of FIG. 74A, viewed along line 74C-74C in FIG. 74A, illustrating an example process for disengaging the tag 300 from the tag retainer 7400. In FIG. 74C, the tag 300 is positioned in an opening of the tag retainer 7400 such that the a portion of the body 7402 of the tag retainer 7400 is positioned in a housing gap, thereby retaining the tag 300 to the tag retainer 7400. The spring member 7404 biases the body 7402 into the housing gap, as described above.

Figure 74D:
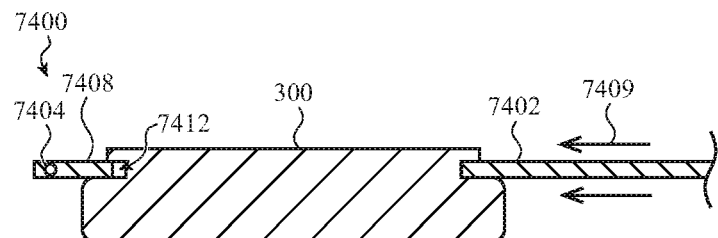
Figure 74E:
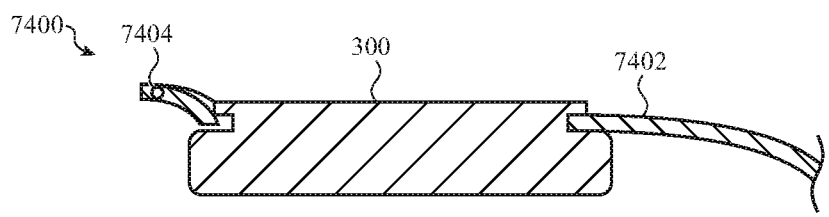
Figure 74F:
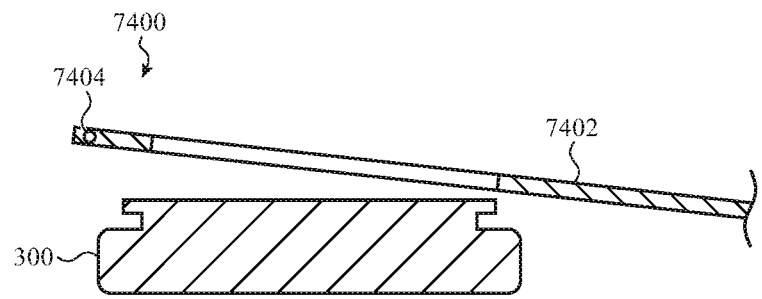

In FIG. 74D, a force is applied to the tag retainer 7400 (and/or the tag 300), as indicated by arrows 7409. (This operation corresponds to FIG. 74B.) The force may be applied by grasping the tag 300 and/or the tag retainer 7400 in hand and applying a force that tends to move the tag 300 towards the engagement ends 7410 of the spring member 7404. This operation expands the size of the opening and introduces a gap 7412 between a flap 7408 of the body 7402 and the tag 300. In FIG. 74E, the tag retainer 7400 is angled to disengage the flap 7408 of the body 7402 from the housing gap. When the flap 7408 is removed from the housing gap, the rest of the body 7402 may be easily disengaged from the housing gap to fully remove the tag 300 from the tag retainer 7400, as shown in FIG. 74F. The tag 300 may be coupled to the tag retainer 7400 by reversing these steps.

Notably, the force that is required to easily detach the tag 300 from the tag retainer 7400 is in an opposite direction than the types of accidental forces that may be imparted to the tag 300 during use. For example, if the tag retainer 7400 is coupled to a purse via a strap 7411, if the tag 300 were to snag on another object such as a piece of clothing, the force would tend to pull the tag 300 away from the strap, which is in the opposite direction to the force that is used to decouple the tag 300. Forces in this direction may actually serve to further tighten or secure the tag 300 to the tag retainer 7400. In this way, the tag retainer 7400 may allow the tag 300 to be attached and detached easily, while reducing the risk of accidental detachment due to snags and the like.

In some cases the tag retainer 7400 may have a stiffening element (or the body 7402 may be formed from a sufficiently stiff material) so that the force applied to the body 7402 may be effectively transferred to the engagement ends 7410 of the spring element. For example, a strap or handle portion of the body 7402 may be formed from or include a metal, plastic, or other material that is stiffer than the portion of the body 7402 that defines the opening and engages the tag 300. The engagement ends 7410 of the spring member 7404 may define curved regions that are nearer to the tag 300 than other portions of the spring member 7404. These curved regions may result in a primary body/tag interface at location 7406 (FIGS. 74A-74B) during the coupling and decoupling operations. By focusing the force at this location 7406, a sufficiently large portion of the force applied by a user may be transferred to the spring member 7404 to cause it (and thus the opening) to expand.

The spring member 7404 may be at least partially embedded in the body 7402. For example, the spring member 7404 and the body 7402 may be insert molded to produce the tag retainer 7400.

Figure 75A:
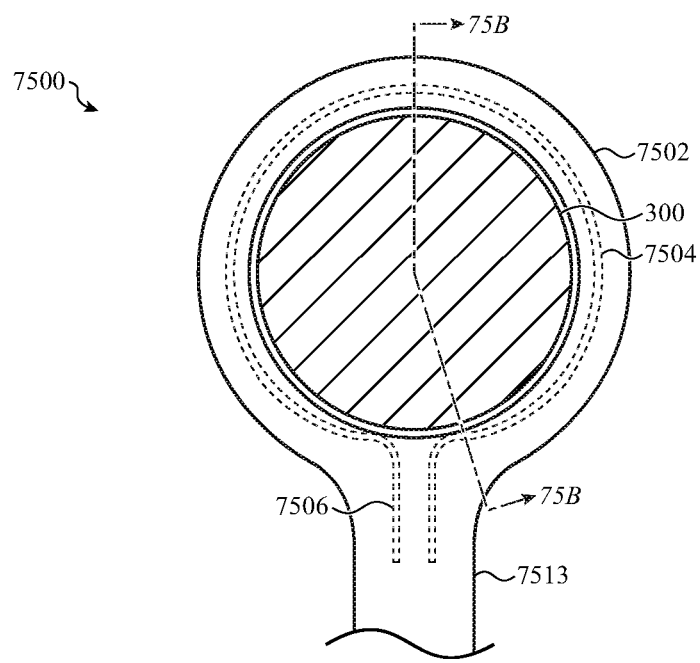
FIGS. 75A-75C depict another example tag retainer for holding a wirelessly locatable tag.
Figure 75B:
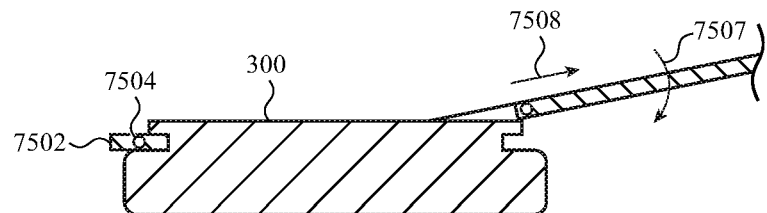
Figure 75C:
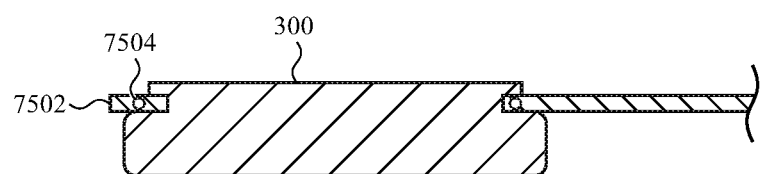

FIGS. 75A-75C illustrate a tag retainer 7500 similar to the tag retainer 7400 but with a different spring member configuration. The tag retainer 7500 may include a body 7502, which may be formed from or include a polymer material or other compliant material (including combinations of materials), and a spring member 7504, which may be formed from a material with a greater stiffness than the body (e.g., spring steel, a polymer, etc.). The spring member 7504 may define extension ends 7506 that extend away from the opening in the body 7502 and optionally into a handle portion 7513 of the body 7502. The extension ends 7506 may help increase the stiffness of the body 7502 so that a force applied to the tag retainer 7500 and/or the tag 300 to couple or decouple the tag 300 may be transferred efficiently to the tag/body interface.

FIGS. 75B-75C are partial cross-sectional views of the tag retainer 7500 and the tag 300 of FIG. 75A, viewed along line 75B-75B in FIG. 75A, illustrating a process of attaching the tag 300 to the tag retainer 7500. As shown in FIG. 75B, a first side of the body 7502 is engaged with the tag 300, and a force (indicated by arrow 7507) is applied to the body 7502 tending to pivot the body 7502 into engagement with the housing gap. The force may cause the spring member 7504, and thus the opening size, to expand to allow the body 7502 to stretch over the battery door of the tag 300 and engage the housing gap. FIG. 75C shows the tag retainer 7500 fully engaged with the housing gap.

The tag retainers 7400 and 7500 each include an example spring member, though alternative types of spring members may be used in their place. For example, a c-clip may be used, and the c-clip may include holes for engaging an opening tool. In such cases, a tag may be coupled by forcing the c-clip open using a tool, inserting the tag into the opening, and removing the tool to allow the c-clip to force the tag retainer to engage the tag.

Figure 76A:
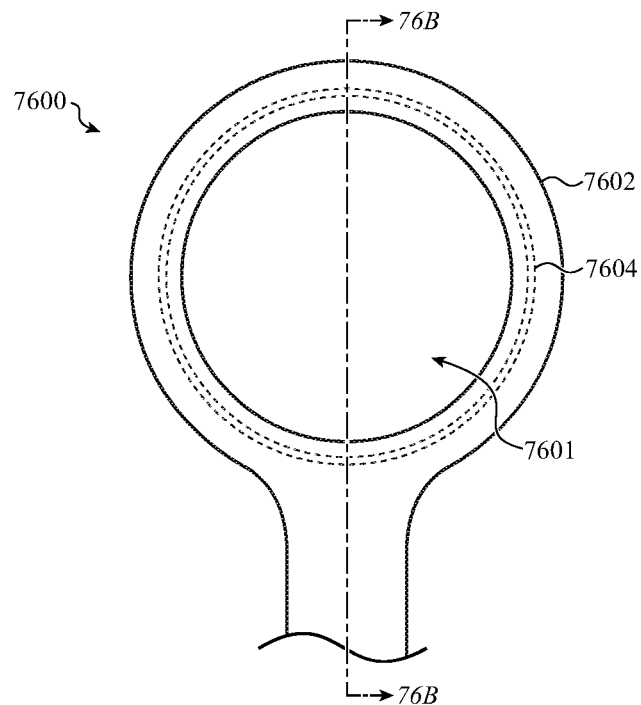
FIGS. 76A-76C depict another example tag retainer for holding a wirelessly locatable tag.
Figure 76B:
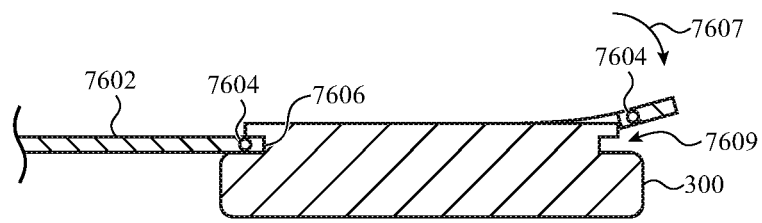
Figure 76C:
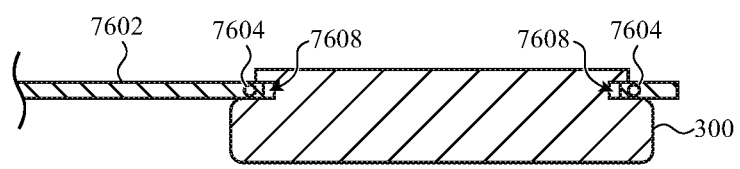

FIGS. 76A-76C illustrate a tag retainer 7600 with a closed-ring spring member 7604 embedded in a body 7602. In contrast to the spring members in the tag retainers 7400 and 7500, which each define two free ends, the closed-ring spring member 7604 defines a continuous, closed ring shape. The body 7602, and in particular the body material and the size and shape of the opening 7601 may be configured so that the tag can be inserted into and removed from the opening 7601 without the closed-ring spring member 7604 significantly flexing or expanding. Instead, the opening 7601 is slightly larger than the size of the part of the tag that the opening 7601 surrounds.

FIGS. 76B-76C are partial cross-sectional views of the tag retainer 7600 of FIG. 76A, viewed along line 76B-76B in FIG. 76A, illustrating a process of attaching the tag 300 to the tag retainer 7600. As shown in FIG. 76B, a first side of the body 7602 is engaged with the tag 300 (at location 7606) such that the body 7602 contacts the tag 300 at that location, or is otherwise sufficiently close to the tag to allow the other end of the body 7602 to pass over the tag 300 at location 7609 (as indicated by arrow 7607). The body 7602 may have sufficient compliance so that it can stretch slightly when the tag 300 is being inserted.

Once the tag 300 is in the opening of the tag retainer 7600, a portion of the body 7602 and the closed-ring spring member 7604 may be positioned in the housing gap under the overhang of the battery door, though there may remain a space 7608 between the body 7602 and the tag 300, resulting from the larger diameter of the opening 7601 to accommodate the greater stiffness (e.g., lower deformability) of the tag retainer 7600 due to the closed-ring spring member 7604.

Figure 77A:
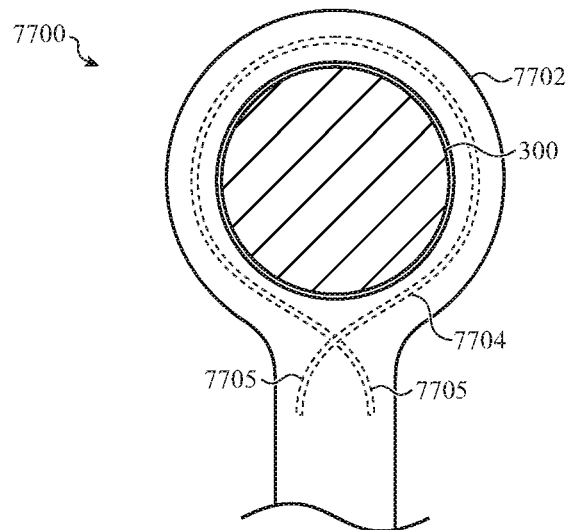
FIGS. 77A-77B depict another example tag retainer for holding a wirelessly locatable tag.
Figure 77B:
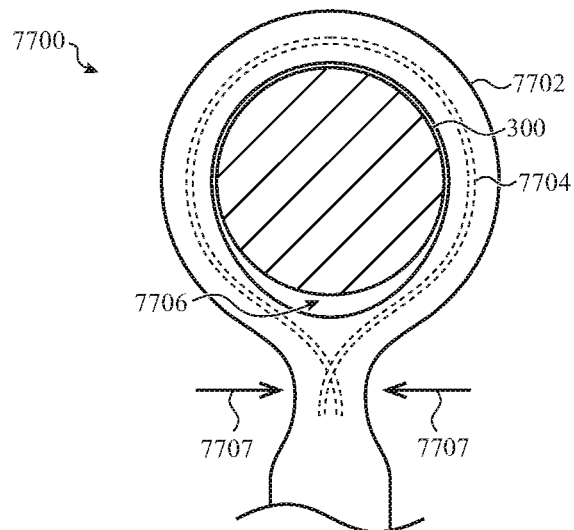

FIGS. 77A-77B illustrate a tag retainer 7700 with another type of spring member 7704 embedded in a body 7702. In particular, the free ends of the spring member 7704 are crossed over one another to define manipulation ends 7705. A force can be applied to the manipulation ends 7705 by a user, as indicated by arrows 7707 in FIG. 77B, to cause the opening of the tag retainer 7700 to expand. This expansion produces additional space 7706 between the body 7702 and the tag 300 to allow the tag 300 to be attached and/or detached from the tag retainer 7700. When the force is removed, the spring member 7704 returns to its smaller state, thereby biasing the opening to its un-expanded state to help maintain the tag retainer 7700 in the housing gap and thus keep the tag 300 secured to the tag retainer 7700.

Figure 78A:
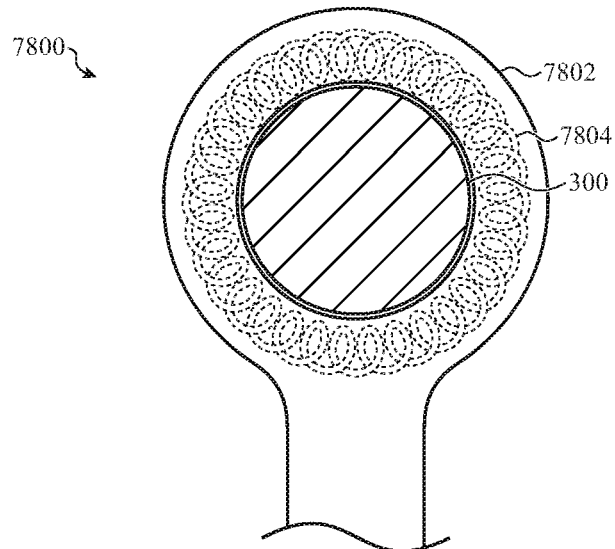
FIGS. 78A-78B depict another example tag retainer for holding a wirelessly locatable tag.
Figure 78B:
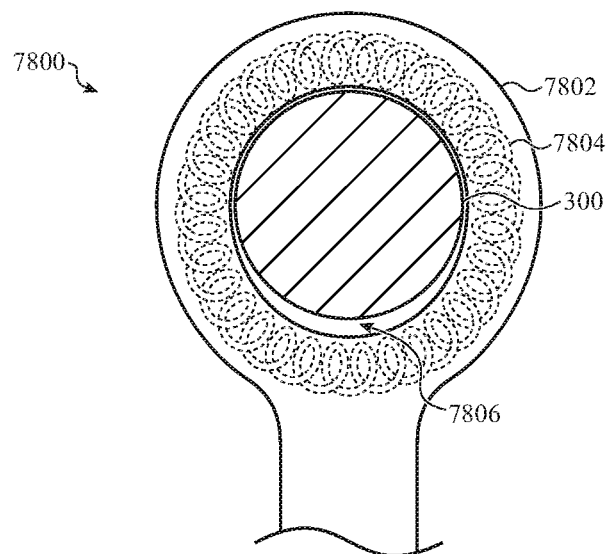

FIGS. 78A-78B illustrate a tag retainer 7800 with another type of spring member 7804 embedded in a body 7802. The spring member 7804 may be a circular coil spring that can be expanded when a radial force is applied to the spring member 7804. Thus, for example, a force can be applied to the tag 300 tending to pull the tag 300 radially outward with respect to the circular spring member 7804, thereby causing the opening of the tag retainer 7800 to expand (as shown in FIG. 78B). This expansion produces additional space 7806 between the body 7802 and the tag 300 to allow the tag 300 to be attached and/or detached from the tag retainer 7800. When the force is removed, the spring member 7804 returns to its smaller state, thereby biasing the opening to its un-expanded state to help maintain the tag retainer 7800 in the housing gap and thus keep the tag 300 secured to the tag retainer 7800. The spring member 7804 may be a conventional coil spring wrapped about the opening. In other cases, the spring member 7804 resembles a flattened coil spring (e.g., the height of the spring member is less than a diameter of the coil loops).

FIGS. 79A-79B illustrate another example tag retainer 7900. The tag retainer 7900 includes a body 7902 that is formed into a circular end that defines an opening 7901 for receiving a tag therein. The body 7902 may be formed from a stiff core with a soft-touch outer coating. For example, the body 7902 may include a metal internal core with a polymer outer coating, jacket, or layer. Or the body 7902 may be formed from two plastics having different stiffnesses (e.g., a stiffer internal core and a less stiff outer coating). Alternatively, the body 7902 may be formed of a single piece of plastic. The internal core (or the single piece of plastic) may provide a spring-like force to the body 7902 so that the body 7902 can be forced into a configuration where the opening 7901 defines a closed loop (e.g., to attach to a tag), and the spring force can bias the body 7902 into a latched or secured configuration. The internal core may extend through at least the part of the body 7902 that defines the opening 7901, and optionally through at least part of the clip feature 7904.

The body 7902 includes or defines a clip feature 7904 that can be engaged and disengaged with a retaining portion 7906 of the body 7902 to selectively open or close the circular end. For example, FIG. 79B shows the tag retainer 7900 with the clip feature 7904 disengaged from the retaining portion 7906 of the body 7902. This shape may correspond to the shape of the body 7902 when no forces are applied to the body 7902 (e.g., the body 7902 is in an unstressed or undeflected state). The opening 7901 in this state may be sufficiently large for the tag 300 to be easily inserted into the opening 7901. FIG. 79C shows the tag retainer 7900 with the clip feature 7904 engaged with the retaining portion 7906 of the body 7902, thereby forming a closed loop that retains the tag retainer 7900 to the tag 300. In this state, the opening 7901 may be smaller so that the body 7902 is retained in the housing gap of the tag 300. Further, the spring force produced by the body 7902 tends to force the clip feature 7904 away from the retaining portion 7906, thereby forcing the clip feature 7904 into secure engagement with the retaining portion 7906 (e.g., due to the hook-like shape of the clip feature 7904). Detaching the tag 300 from the tag retainer 7900 may be achieved by pulling on the clip feature 7904 so that it can be unhooked from the retaining portion 7906 and allowed to return to its undeflected state (shown in FIG. 79B) and the tag 300 can be removed.

Figure 80A:
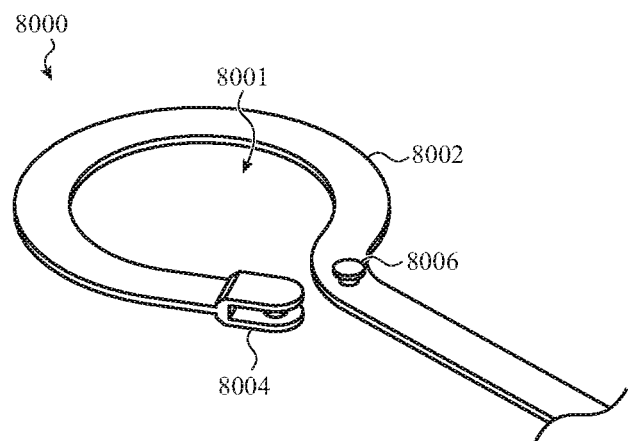
FIGS. 80A-80C depict another example tag retainer for holding a wirelessly locatable tag.
Figure 80B:
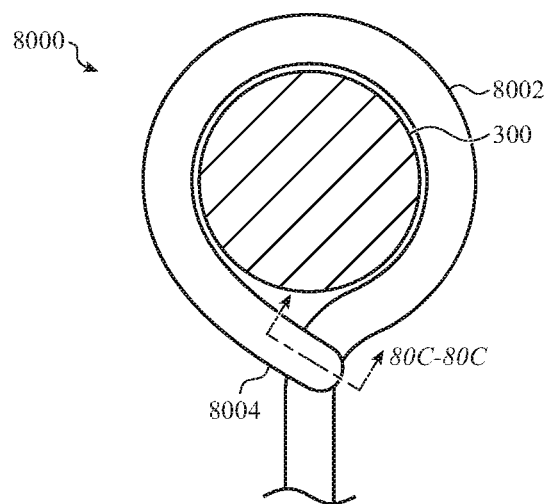
Figure 80C:
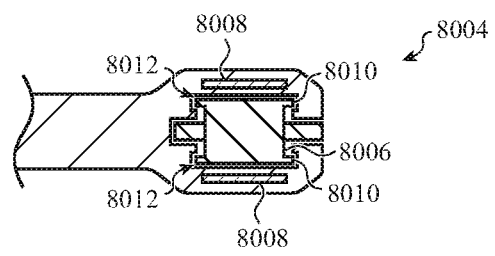

FIGS. 80A-80C illustrate another example tag retainer 8000. Similar to the tag retainer 7900, the tag retainer 8000 may rely on a body 8002 that is relatively stiff so that the body can engage a housing gap of a tag to secure the tag to the tag retainer 8000. In particular, the body 8002 may define an opening 8001 that is biased in an open loop shape, and can be retained in a closed-loop shape via a retention mechanism.

To act as a retention mechanism, the tag retainer 8000 includes a clip end 8004 and a post 8006. The clip end 8004 is configured to engage the post 8006 to retain the opening 8001 in a closed loop configuration. FIG. 80A shows the tag retainer 8000 in an un-clipped, open loop state, while FIG. 80B shows the tag retainer 8000 in a closed loop state and engaging a housing gap of the tag 300.

FIG. 80C is a partial cross-sectional view of the tag retainer 8000, viewed along line 80C-80C in FIG. 80B, showing the clip end 8004 engaged with the post 8006 to maintain the opening 8001 in a closed state and retain the tag 300. The clip end 8004 may include or define recesses 8012 with undercuts. The post 8006 may extend at least partially into the recesses 8012 such that a flange 8010 or lip element of the post 8006 engages the undercut of the recesses 8012 to retain the clip end 8004 to the post 8006. In some cases, the clip end 8004 and the post 8006 may use magnetic attraction to help retain the clip end 8004 to the post 8006. For example, the post 8006 may be formed from or include a magnet, and the clip end 8004 may include ferromagnetic elements 8008 (e.g., steel inserts) that are attracted to the magnetic post 8006. Other configurations and positions of magnets, ferromagnetic materials, etc., are also contemplated. The magnetic attraction between the clip end 8004 and the post 8006 may provide several functions. For example, it may help snap the clip end 8004 and the post 8006 into an engaged position, thereby simplifying the attachment process. Additionally, it may retain the clip end 8004 and the post 8006 together during use, and may help maintain the engagement between the flange of the post 8006 and the undercuts of the recesses 8012 (which may provide greater security against decoupling than the magnetic attraction alone).

Figure 81A:
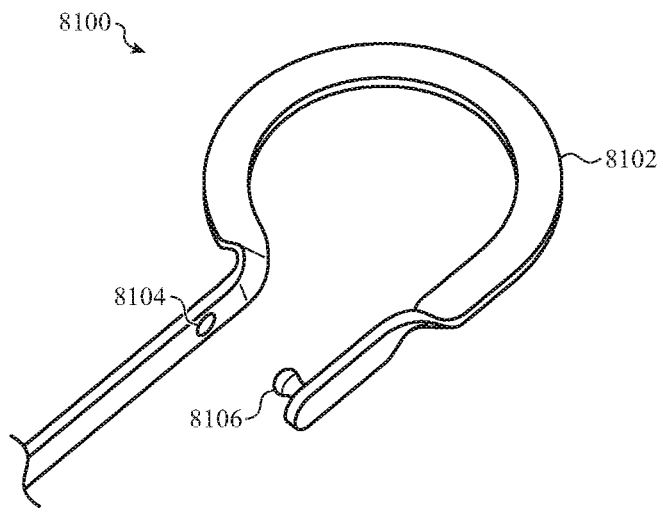
FIGS. 81A-81B depict another example tag retainer for holding a wirelessly locatable tag.
Figure 81B:
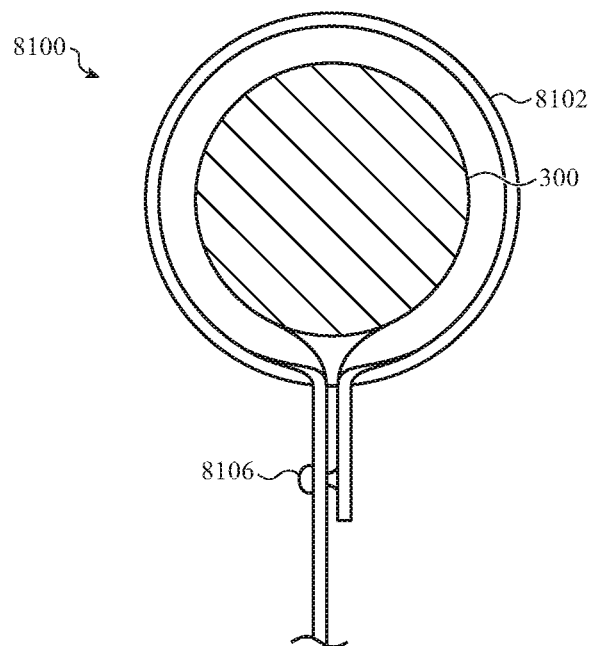

FIGS. 81A-81B illustrate an example tag retainer 8100 in which a body 8102 forms a loop around a tag, and is secured by a post and hole fastening system. In particular, the tag retainer 8100 includes a post 8106 and the body 8102 defines an opening 8104 configured to receive the post 8106. When the post 8106 is inserted into the opening 8104, the body 8102 defines a loop that surrounds the tag 300 (FIG. 81B) in the housing gap of the tag 300. The post 8106 may define a free end that is larger than the opening 8104 and a shaft that is smaller than the free end. The free end may deform the opening 8104 when the post is pushed into the opening 8104, and the opening 8104 may undeform after the post 8106 is inserted, thus causing the opening 8104 and the shaft of the post 8106 to engage, with the free end serving as a retention feature that retains the post 8106 in the opening 8104 (and thus retains the tag retainer 8100 in a loop that holds the tag 300).

Figure 82A:
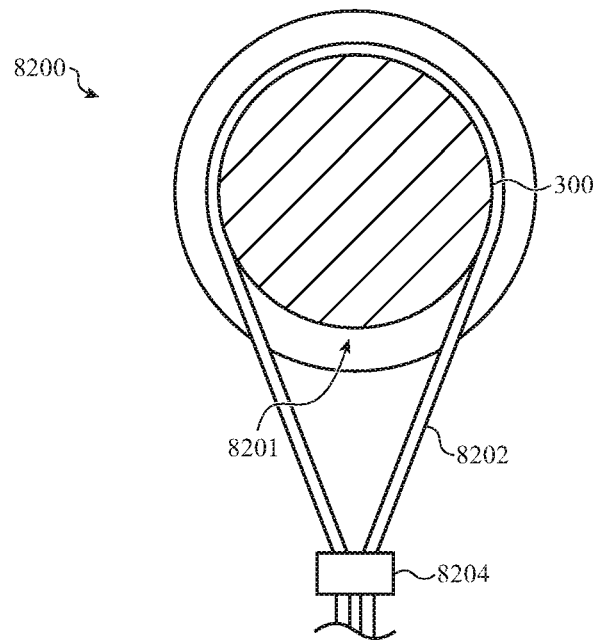
FIGS. 82A-82B depict another example tag retainer for holding a wirelessly locatable tag.
Figure 82B:
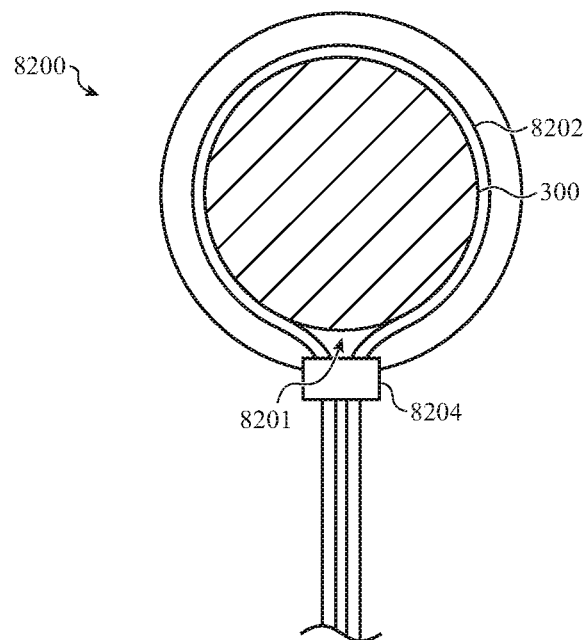

FIGS. 82A-82B illustrate an example tag retainer 8200 in which a loop is secured around a tag with a slider. FIG. 82A shows the tag retainer 8200, which may include a cord 8202 formed into a loop 8201 and wrapped around the tag 300. To secure the tag retainer 8200 to the tag 300, a user may slide the slider 8204 towards the tag 300, thereby tightening the loop 8201 around the tag 300 (and within the housing gap), as shown in FIG. 82B. The tightened loop 8201 in the housing gap provides sufficient engagement with the tag 300 to retain the tag 300 to the tag retainer 8200. The slider 8204 may be configured so that friction between holes in the slider 8204 and the cord 8202 (which may extend through the holes) is sufficient to prevent accidental movement of the slider 8204, thereby maintaining the loop 8201 in a tightened state. In other cases the slider 8204 may include a locking mechanism, such as a cam lock, clamp, cord lock, releasable ratcheting mechanism (e.g., similar to a zip tie), or the like, to help prevent the slider 8204 from moving unintentionally.

Figure 83A:
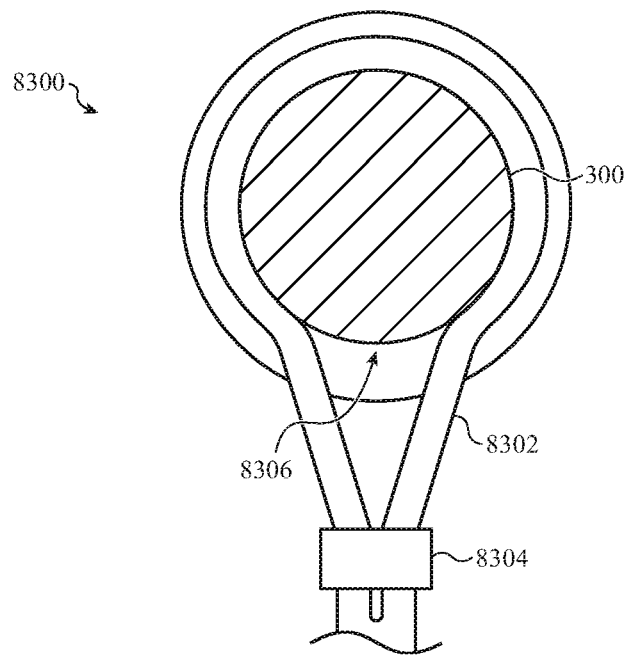
FIGS. 83A-83B depict another example tag retainer for holding a wirelessly locatable tag.
Figure 83B:
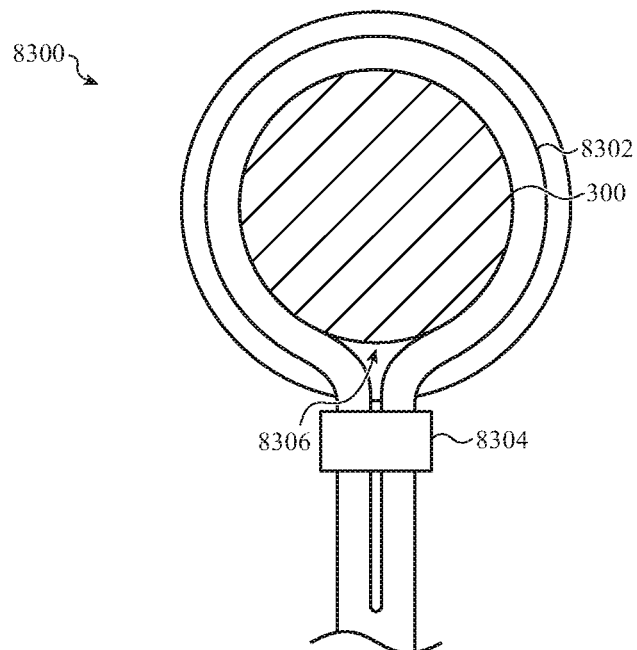

FIGS. 83A-83B illustrate an example tag retainer 8300 in which a loop is secured around a tag with a slider. The tag retainer 8300 is similar to the tag retainer 8200, except that instead of a single cord with two free ends defining the loop, the tag retainer 8300 includes a body 8302 that defines a closed loop opening 8306. A slider 8304 may operate similarly to the slider 8204. For example, the slider 8304 may be slid away from the opening 8306 to increase the size of the opening 8306 and allow the tag 300 to be positioned in the opening 8306 (FIG. 83A). The slider 8304 may then be slid towards the tag 300 to reduce the size of the opening 8306 and capture the tag 300 in the opening 8306 (e.g., by tightening the opening 8306 into the housing gap), as shown in FIG. 83B. The slider 8304 may use friction, ratchet mechanisms, clamps, cams, or other devices or techniques to prevent or limit unintended loosening.

Figure 84A:
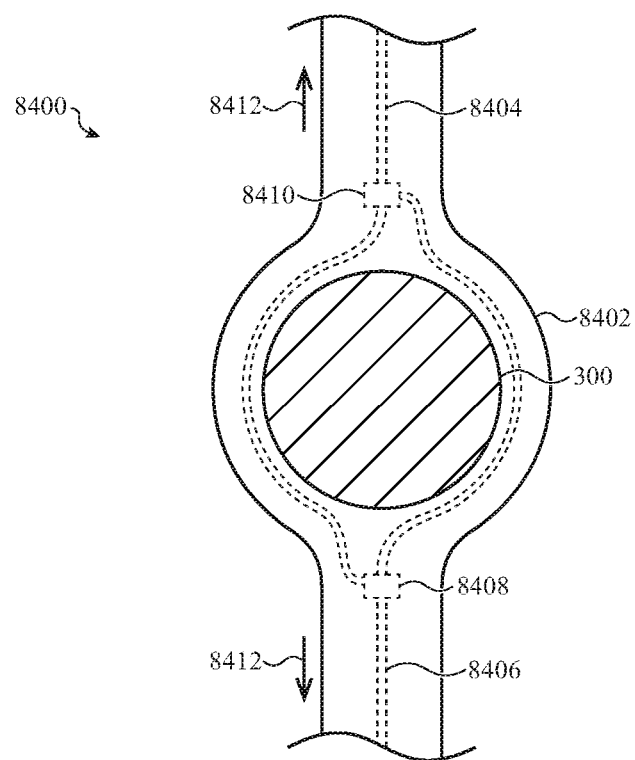
FIG. 84A depicts another example tag retainer for holding a wirelessly locatable tag.

FIG. 84A illustrates another example tag retainer 8400. The tag retainer 8400 includes a body 8402 with two interconnected ratchet cords 8404, 8406 at least partially embedded in the body 8402. The interconnected ratchet cords 8404, 8406 each include a ratchet mechanism 8408, 8410, respectively. Thus, the ratchet cord 8404 may include the ratchet mechanism 8408, and may extend through and engage with the ratchet mechanism 8410. Similarly, the ratchet cord 8406 may include the ratchet mechanism 8410, and may extend through and engage with the ratchet mechanism 8408. The ratchet mechanisms 8408, 8410 may be configured to allow a corresponding ratchet cord to move therethrough in one direction, but restrain motion in another direction (similar to the operation of a zip tie). This ratcheting operation may be exploited to allow the tag retainer 8400 to be tightened by pulling on opposite sides of the tag retainer 8400, as indicated by arrows 8412. This force may cause both ratchet cords 8404, 8406 to tighten around the tag 300, and the ratchet mechanisms 8408, 8410 lock the cords into the tightened state.

The ratchet cords 8404, 8406 may be semi-permanently retained in the tightened position by the ratchet mechanisms 8408, 8410, such that they cannot be decoupled without damaging the ratchet mechanisms 8408, 8410, the tag 300, and/or some other portion of the tag retainer 8400. In other cases, the ratchet mechanisms 8408, 8410 may be selectively releasable, such that a user can release the ratchet mechanisms 8408, 8410 with a button, latch, lever, or other mechanism and detach the tag 300 from the tag retainer 8400. The ratchet cords 8404, 8406 may be formed from a polymer, metal, or any other suitable material, and may be at least partially embedded in the material of the body 8402 (which may be a polymer such as TPU, silicone, etc.).

Figure 84B:
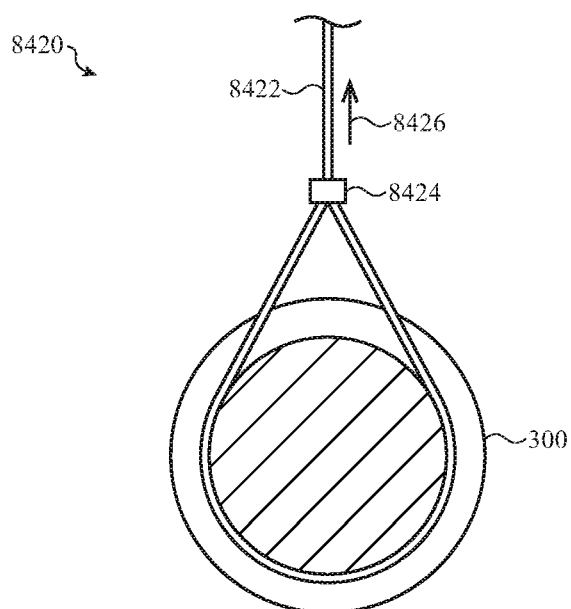
FIG. 84B depicts another example tag retainer for holding a wirelessly locatable tag.

FIG. 84B illustrates another example tag retainer 8420 that uses a ratchet mechanism to attach the tag retainer 8420 to the tag 300. Whereas the tag retainer 8400 included two ratchet cords, the tag retainer 8420 includes a single ratchet cord 8422 that is looped about a portion of the tag 300. For example, the ratchet cord 8422 may fit at least partially in and/or engage a housing gap of a tag, and a ratchet mechanism 8424 may releasably secure the ratchet cord 8422 in a closed, tightly looped configuration that retains the ratchet cord 8422 to the tag 300. The ratchet cord 8422 may be tightened by pulling the ratchet cord 8422 along the direction 8426 while holding the tag 300 stationary. Releasing the ratchet cord 8422 may be achieved by actuating a button, latch, lever, or other mechanism of the ratchet mechanism 8424, by using a tool, or by any other suitable manipulation of the ratchet cord 8422 or ratchet mechanism 8424. The ratchet cord 8422 may be formed from a polymer, metal, or any other suitable material, and may be at least partially embedded in another material (which may be a polymer such as TPU, silicone, etc.).

FIGS. 85A-91B illustrate various example spring members for attaching to wirelessly locatable tags. These spring members all attach to a tag in a similar manner, namely by engaging the housing gap with a biasing force that maintains the tag retainer in the housing gap (and thus engaged with the undercuts and/or flanges defined by the housing gap). The spring members in FIGS. 85A-91B may be used to attach directly to tags. When used to attach directly to tags, the spring members may be configured to attach to straps, cords, cables, ropes, clips, or other components so that the tag can be attached to something else (e.g., keys, a purse, luggage, a backpack, etc.). The spring members in FIGS. 85A-91B may also be used as the spring members inside the bodies of other tag retainers. For example, the spring member 7404 in the tag retainer 7400 (FIG. 74A) may be replaced with any of the spring members in FIGS. 85A-91B.

Figure 85A:
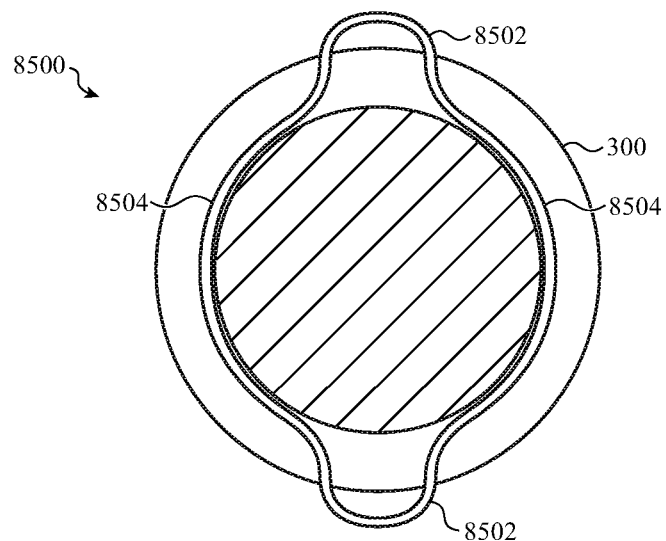
FIGS. 85A-85B depict an example spring member for attaching to a wirelessly locatable tag.

FIG. 85A shows an example spring member 8500 engaged with the tag 300 (e.g., secured in the housing gap). The spring member 8500 defines engagement regions 8504, which are biased into the housing gap to attach the spring member 8500 to the tag 300, and manipulation regions 8502. The spring member 8500 may be formed from a round (in cross-section) wire formed from metal (e.g., spring steel, stainless steel, etc.), a polymer material, or the like.

Figure 85B:
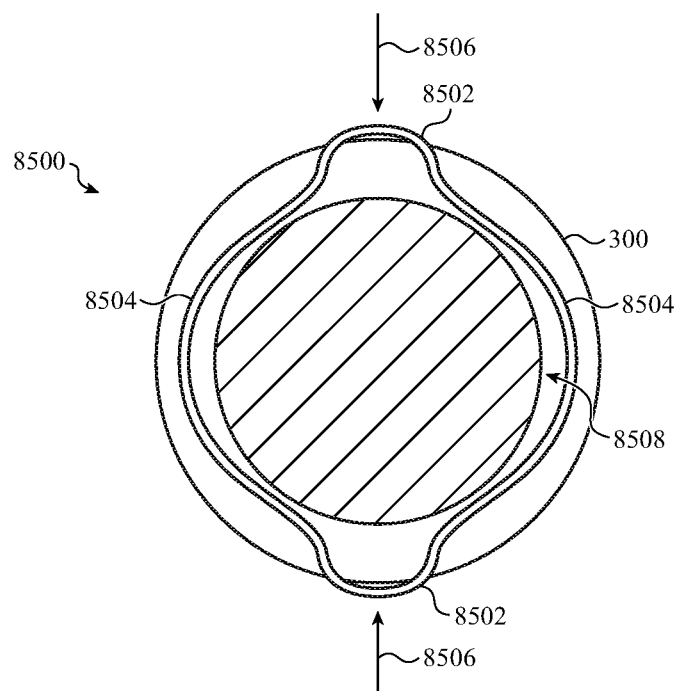

The manipulation regions 8502 (also referred to herein as manipulators) are portions of the spring member 8500 that when pressed, pulled, or otherwise manipulated, allows the spring member 8500 to be easily decoupled from the tag 300. For example, as shown in FIG. 85B, when opposing forces 8506 are applied to the manipulators 8502 (such as when a user pinches or squeezes the spring member 8500), the engagement regions 8504 spread out to define or increase a gap 8508 between the tag 300 and the engagement regions 8504. This increased gap may be sufficiently large that the flange or lip of the battery door of the tag 300 can pass through the opening defined by the spring member 8500 to allow the tag 300 to be attached to and/or detached from the spring member 8500.

Figure 86A:
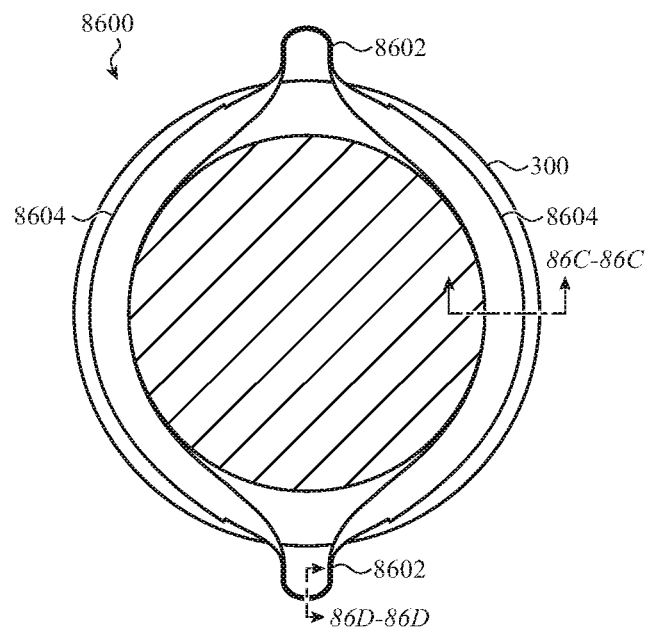
FIGS. 86A-86D depict another example spring member for attaching to a wirelessly locatable tag.
Figure 86B:
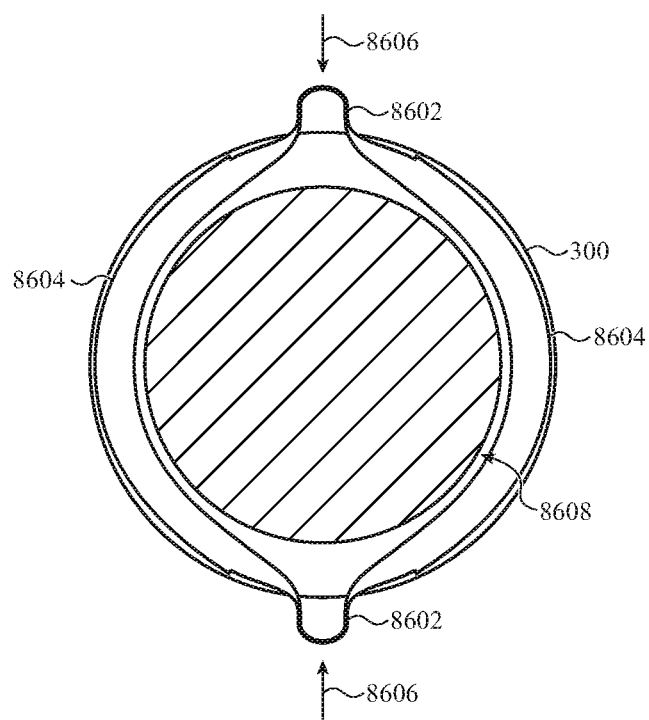

FIG. 86A shows another example spring member 8600 engaged with the tag 300 (e.g., secured in the housing gap). The spring member 8600 defines engagement regions 8604, which are biased into the housing gap to attach the spring member 8600 to the tag 300, and manipulation regions 8602. The spring member 8600 operates similar to the spring member 8500. For example, forces 8606 applied to the manipulation regions 8602 cause the spring member 8600 to deform and define a gap 8608 (FIG. 86B) that allows the tag 300 to be attached and/or detached.

Figure 86C:
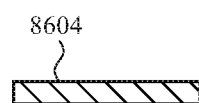
Figure 86D:
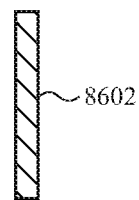

Whereas the spring member 8500 may be formed from a circular wire (in cross-section), the spring member 8600 may be formed from a wire or ribbon with an elongated (e.g., rectangular) cross-sectional shape. The non-circular cross-sectional shape may be exploited to provide advantageous physical and/or mechanical properties to the spring member 8600. For example, the spring member 8600 may be configured so the wider dimension is parallel with the radial dimension of the spring member 8600. This orientation may provide a greater stiffness or resistance to deformation in the engagement regions 8604 as compared to the manipulation regions 8602. The manipulation regions 8602, on the other hand, may have the cross-section rotated by about 90 degrees, thus allowing the forces 8606 to deform the manipulation regions 8602 while limiting deformation of the engagement regions 8604. FIGS. 86C and 86D are partial cross-sectional views of the spring member 8600, viewed along lines 86C-86C and 86D-86D, respectively, in FIG. 86A. FIGS. 86C and 86D illustrate the orientations of the cross-sectional shape of the spring member 8600 at the engagement regions 8604 and manipulation regions 8602, respectively. The spring member 8600 may be formed from an elongate (in cross-section) ribbon formed from metal (e.g., spring steel, stainless steel, etc.), a polymer material, or the like. The elongate ribbon may have a substantially rectangular cross-section.

FIGS. 87A-87C show another example spring member 8700 engaged with the tag 300 (e.g., secured in the housing gap). The spring member 8700 defines engagement regions 8704, at least portions of which are biased into the housing gap to attach the spring member 8700 to the tag 300, and manipulation regions 8702. The spring member 8700 operates similar to the spring member 8500. For example, forces 8706 applied to the manipulation regions 8702 cause the spring member 8700 to deform and define a gap 8708 (FIG. 87B) that allows the tag 300 to be attached and/or detached.

The manipulation regions 8702 may define coiled springs, as shown in FIG. 87C. The coiled springs may provide the biasing force to maintain the engagement regions 8704 in engagement with the housing gap, while also defining manipulators 8702 that effectively direct forces to expand the engagement regions 8704. The coiled springs may require relatively less actuation force than a spring member of similar cross-sectional shape but without the coiled springs.

Figure 88A:
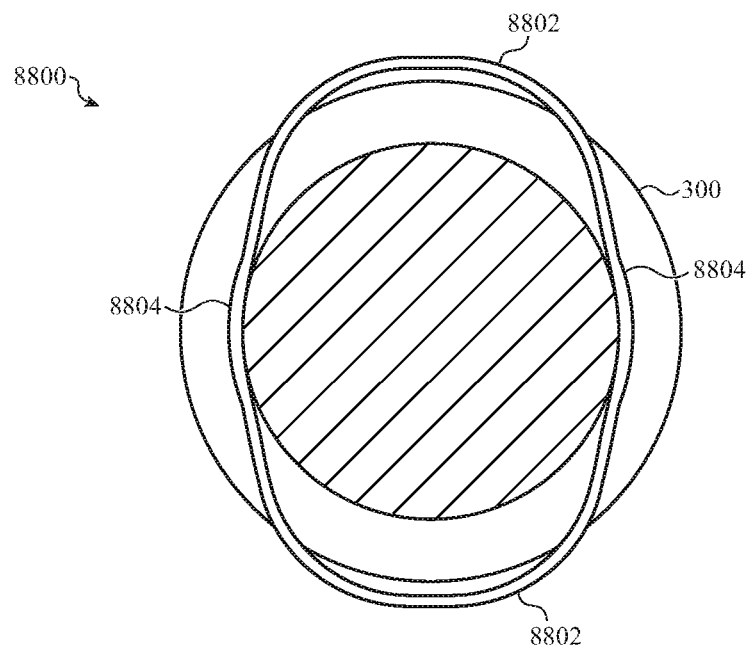
FIGS. 88A-88B depict another example spring member for attaching to a wirelessly locatable tag.
Figure 88B:
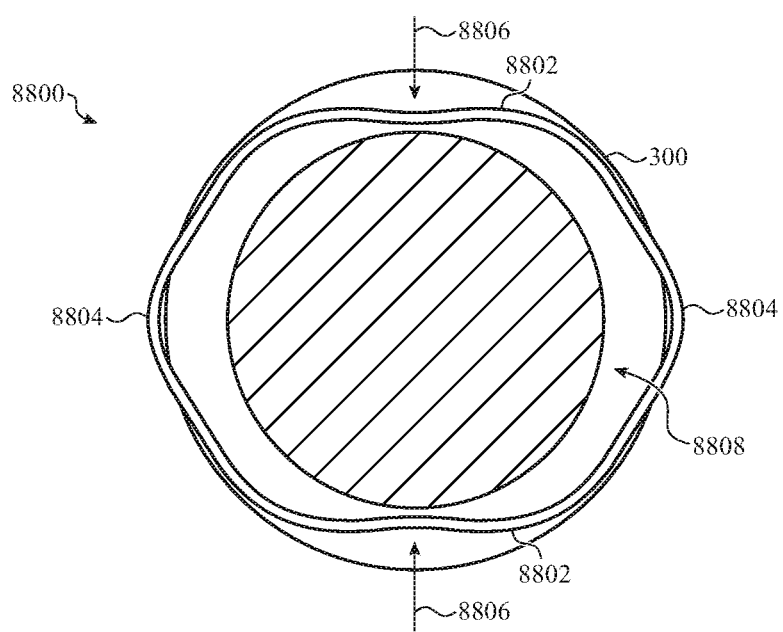

FIGS. 88A-88B show another example spring member 8800 engaged with the tag 300 (e.g., secured in the housing gap). The spring member 8800 defines engagement regions 8804, at least portions of which are biased into the housing gap to attach the spring member 8800 to the tag 300, and manipulation regions 8802. The spring member 8800 defines a hexagonal shape, with the engagement regions 8804 each defined by at least part of two respective sides (and the apex between those sides). The spring member 8800 operates similar to the spring member 8500. For example, forces 8806 applied to the manipulation regions 8802 cause the spring member 8800 to deform and define a gap 8808 (FIG. 88B) that allows the tag 300 to be attached and/or detached.

Figure 89A:
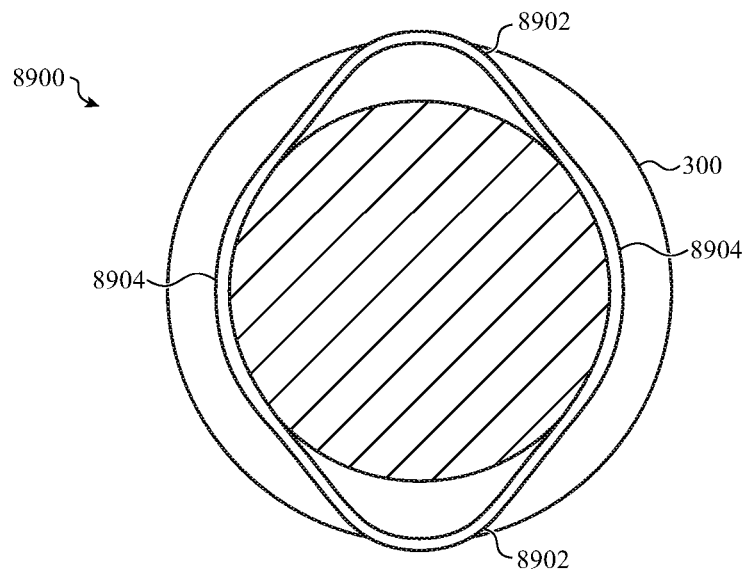
FIGS. 89A-89B depict another example spring member for attaching to a wirelessly locatable tag.
Figure 89B:
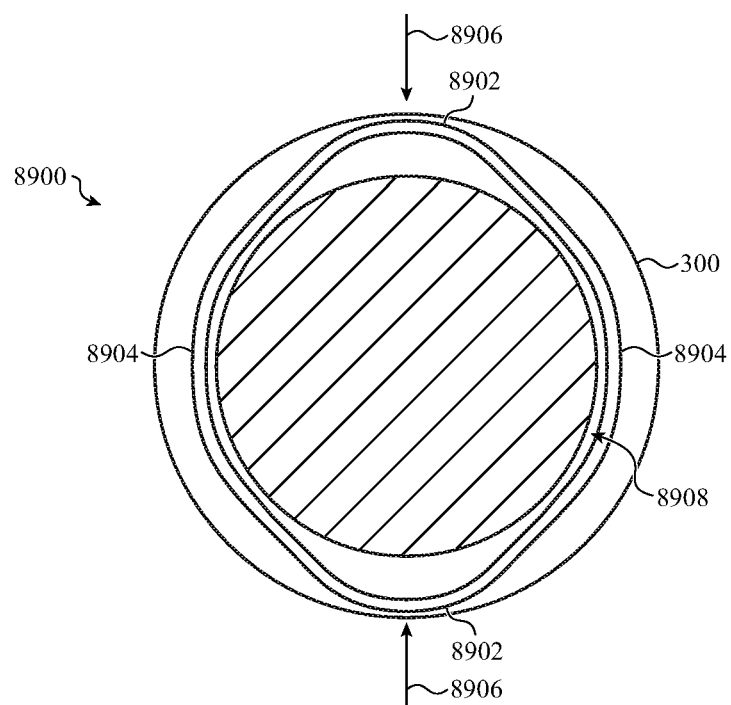

FIGS. 89A-89B show another example spring member 8900 engaged with the tag 300 (e.g., secured in the housing gap). The spring member 8900 defines engagement regions 8904, at least portions of which are biased into the housing gap to attach the spring member 8900 to the tag 300, and manipulation regions 8902. The spring member 8900 defines an oblong shape, with the engagement regions 8904 each defined by a respective curved region having a first radius, and the manipulation regions 8902 each defined by a respective curved region having a second radius that is smaller than the first radius. The spring member 8900 operates similar to the spring member 8500. For example, forces 8906 applied to the manipulation regions 8902 cause the spring member 8900 to deform and define a gap 8908 (FIG. 89B) that allows the tag 300 to be attached and/or detached.

Figure 90A:
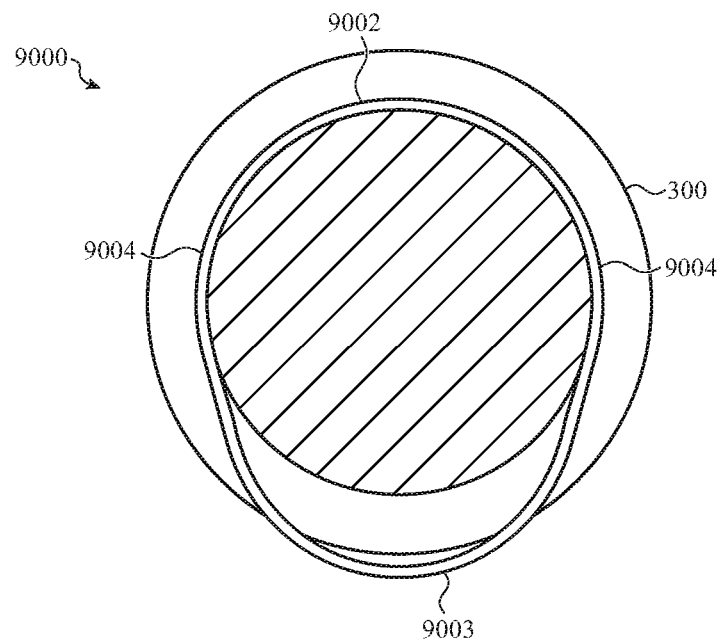
FIGS. 90A-90B depict another example spring member for attaching to a wirelessly locatable tag.
Figure 90B:
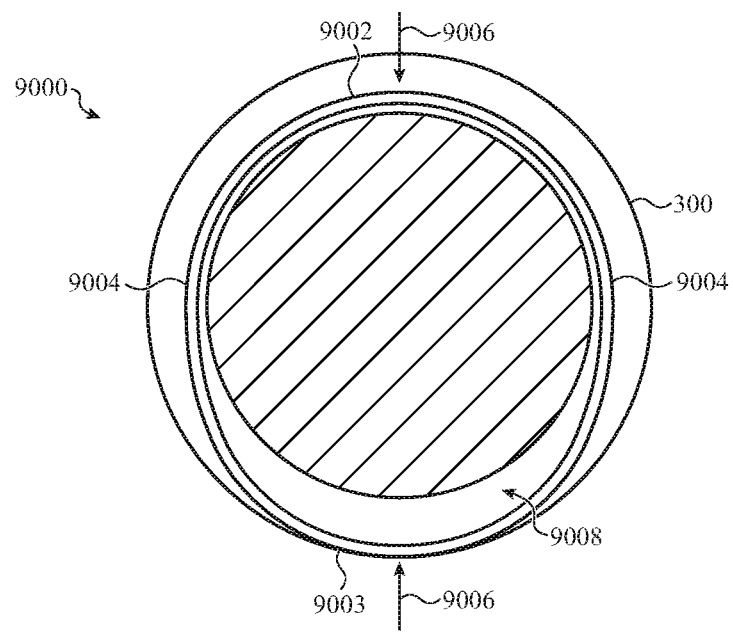

FIGS. 90A-90B show another example spring member 9000 engaged with the tag 300 (e.g., secured in the housing gap). The spring member 9000 defines engagement regions 9004, at least portions of which are biased into the housing gap to attach the spring member 9000 to the tag 300, and first and second manipulation regions 9002, 9003. The manipulation regions 9002, 9003 have different shapes and may be positioned differently with respect to the tag 300 when the spring member 9000 is attached to the tag 300. For example, when the spring member 9000 is attached to the tag, the first manipulation region 9002 extends beyond the housing gap (e.g., it is proud of the housing gap and defines a loop where straps, cords, cables, strings, or other components may be attached to couple the spring member 9000 to another object). The second manipulation region 9003, by contrast, may remain within the housing gap (e.g., the second manipulation region 9003 may not extend past the flanges, lips, overhangs, or the like, that define the housing gap). In some cases, the second manipulation region 9003 may act as another engagement region, and may contact the tag 300 within the housing gap, when the spring member 9000 is not being attached to and/or detached from the tag 300.

The spring member 9000 operates similar to the spring member 8500. For example, forces 9006 applied to the first and second manipulation regions 9002, 9003 cause the spring member 9000 to deform and define a gap 9008 (FIG. 90B) that allows the tag 300 to be attached and/or detached. Because the second manipulation region 9003 may be within the housing gap, the user may apply the opposing forces 9006 in various ways. As a first example, the user may press a fingernail, a coin, an edge of a credit card, a small tool, or some other implement against the second manipulation region 9003 (within the housing gap) while pushing the first manipulation region 9002 with a finger. This may allow the application of the opposing forces 9006 that expand the opening of the spring member 9000 and create the gap 9008. As another example, a user may first apply a force 9006 to the first manipulation region 9002, which may partially deform the spring member 9000 and force the second manipulation region 9003 out of the housing gap, at which time it will be accessible to a user to press against to more fully deform the spring member 9000 to produce the gap 9008 and allow the tag 300 to be attached and/or detached.

Figure 91A:
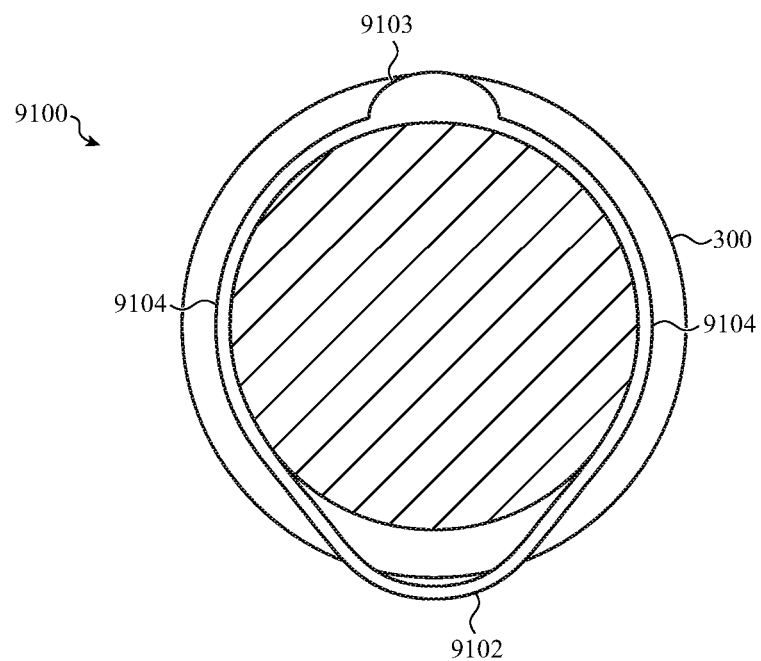
FIGS. 91A-91B depict another example spring member for attaching to a wirelessly locatable tag.
Figure 91B:
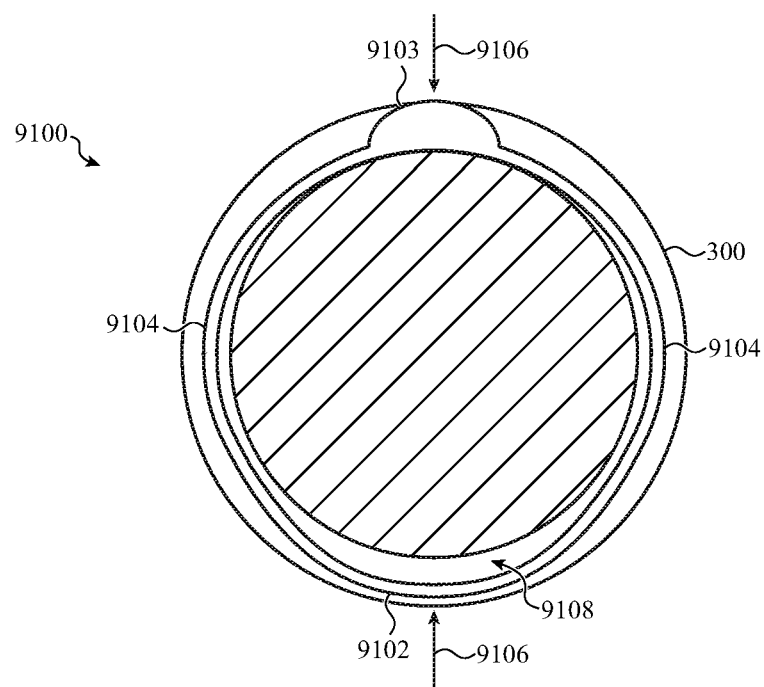

FIGS. 91A-91B show another example spring member 9100 engaged with the tag 300 (e.g., secured in the housing gap). The spring member 9100 defines engagement regions 9104, at least portions of which are biased into the housing gap to attach the spring member 9100 to the tag 300, and first and second manipulation regions 9102, 9103. The overall shape of the spring member 9100 may be similar to that of the spring member 9000, except that the second manipulation region 9103 may include a tab-like protrusion that extends beyond the housing gap such that a user can contact the second manipulation region 9103 without having to extend a tool or object into the housing gap (and without having to first deform the spring member 9100 by applying a force to the first manipulation region 9102). The tab-like protrusion of the second manipulation region 9103 may be integral with the remainder of the spring member 9100. For example, the spring member 9100 may be formed from a single (e.g., monolithic) metal structure. In other implementations, the tab-like protrusion may be a separate component that is attached to or otherwise integrated with the remainder of the spring member 9100.

In order to deform the spring member 9100 so that a tag 300 can be attached and/or detached, forces 9106 applied to the first and second manipulation regions 9102, 9103 cause the spring member 9100 to deform and define a gap 9108 (FIG. 91B) that allows the tag 300 to be attached and/or detached. The tab-like protrusion of the second manipulation region 9103 may be sufficiently stiff to transmit the force 9106 to the remainder of the spring member 9100 without breaking or otherwise bending in a manner that would prevent or negatively affect the transfer of force to the remainder of the spring member 9100.

The spring members shown and described with respect to FIGS. 85A-91B may be formed in any suitable manner. For example, they may be formed by shaping (e.g., bending) metal wires or rods into the configurations shown. In such cases, the free ends of the metal used to form a spring member may be affixed to one another (e.g., by welding, brazing, adhesives, mechanical fasteners, etc.), or they may remain un-affixed (e.g., a seam or gap may remain between the free ends). As other examples, the spring members may be cast or molded. Where the spring members are formed from polymer materials and/or composites, they may be molded (e.g., injection molded), formed via additive manufacturing processes (e.g., 3D printing), or via any other suitable technique. Other methods of forming the spring members and other materials and/or combinations of materials are also contemplated.

Figure 92A:
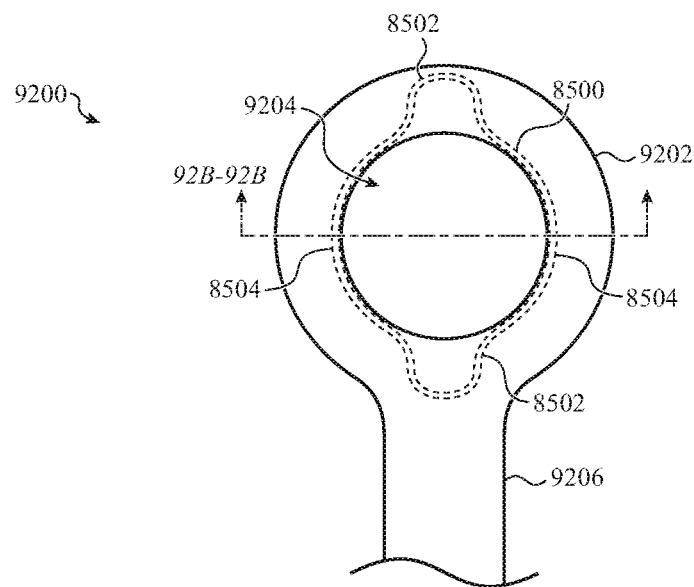
FIGS. 92A-92B depict another example tag retainer for holding a wirelessly locatable tag.

As noted above, the spring members shown and described with respect to FIGS. 85A-91B may be used as stand-alone components to help couple wirelessly locatable tags to other objects, or they may be integrated with other components of tag retainers. In the former cases, users may, for example, put clips, split rings (e.g., key rings), ropes, zip ties, or other components through or around the loops or other accessible areas of the spring members. In the latter cases, the spring members may be provided inside the bodies of other tag retainers, or may include carrying straps attached thereto. FIGS. 92A-93 depict two example tag retainers that may use spring members such as those shown and described with respect to FIGS. 85A-91B.

FIG. 92A illustrates a portion of a tag retainer 9200 (which may be similar to the tag retainer 7400 in FIG. 74A). The tag retainer 9200 includes the spring member 8500 (FIG. 85A) at least partially embedded in a body 9202. The body 9202 may be a polymer (e.g., TPU, silicone), a cloth or fabric, leather, or any other suitable material or combination of materials. The spring member 8500 may provide the biasing force that retains the portion of the body 9202 that defines the opening 9204 in a housing gap when the tag retainer 9200 is attached to a tag. The body 9202 may define or be coupled to a strap 9206, which, as described above, may be any suitable type of strap or member that can be used to attach the tag retainer 9200 to another object.

Figure 92B:
Figure 93:
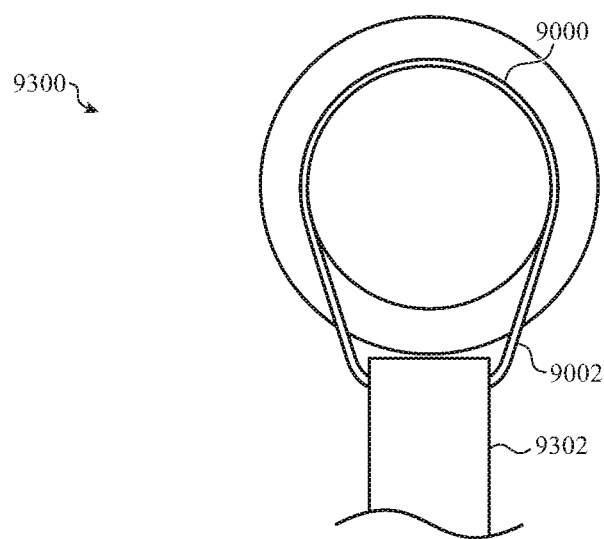
FIG. 93 depicts another example tag retainer for holding a wirelessly locatable tag.

FIG. 92B is a partial cross-sectional view of the tag retainer 9200 of FIG. 92A, viewed along line 92B-92B in FIG. 92A. FIG. 92B illustrates how the spring member 8500 may be embedded in the material of the body 9202. In this case, the body 9202 may be a polymer material that is molded around the spring member 8500 (which may be inserted into a mold prior to the polymer material being injected).

FIG. 93 illustrates a portion of a tag retainer 9300 that includes the spring member 9000 (FIG. 90A) and a strap member 9302 attached to the manipulation region 9002 of the spring member 9000. The strap member 9302 may be attached to the spring member 9000 in any suitable way. As one example, it may be attached via insert molding in which the strap member 9302 encapsulates a portion of the spring member 9000. Alternatively, it may be attached using stitches (e.g., sewn), snaps, buttons, staples, glue, hook-and-loop fasteners, or the like.

Figure 94A:
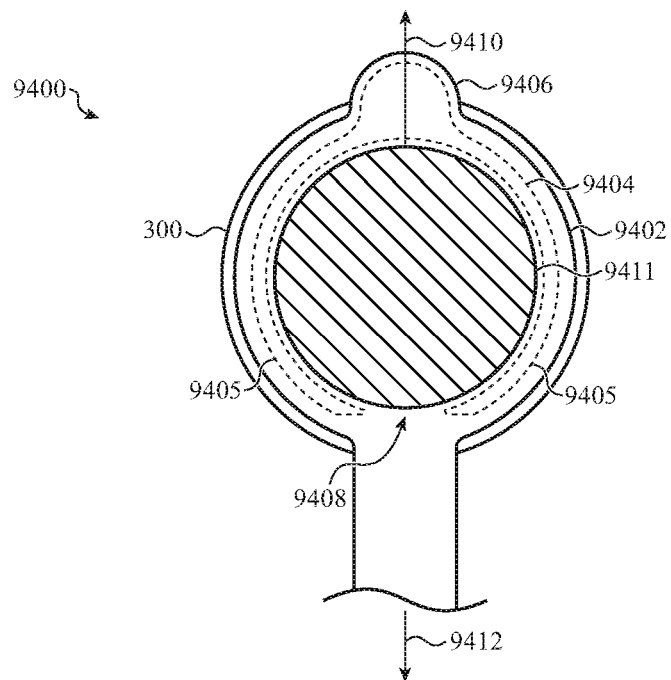
FIGS. 94A-94B depict another example tag retainer for holding a wirelessly locatable tag.
Figure 94B:
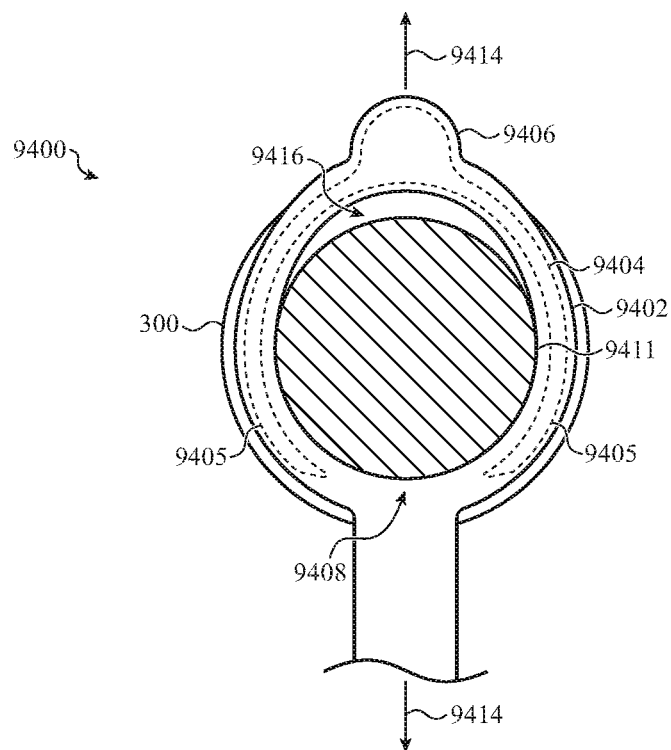

FIGS. 94A-94B illustrate another example tag retainer 9400 for attaching to a tag. The tag retainer 9400 may include a body 9402, which may be formed from or include a polymer material or other compliant material (including combinations of materials), and a spring member 9404, which may be formed from a material with a greater stiffness than the body (e.g., spring steel, a polymer, etc.). The spring member 9404 may be configured to bias the body 9402 into the housing gap of a tag, as described with respect to other spring members. The spring member 9404 and the body 9402 may cooperate to define a pull tab 9406 that is used to help expand the opening of the tag retainer 9400 to facilitate attachment and detachment of the tag 300, as described with respect to FIG. 94B. The spring member 9404 may define engagement ends 9405 that are separated by a gap 9408.

The body 9402 and the spring member 9404 may be configured to help prevent accidental detachment of the tag 300 from the tag retainer 9400. For example, when a force 9410 is applied to the tag 300 while the tag 300 is attached to the tag retainer 9400, the force may be transferred through the tag retainer to the object to which it is connected (as represented by arrow 9412). The force 9410 may correspond to the tag 300 snagging or catching on another object, such as may occur during normal everyday use of the tag retainer 9400. Because the force 9410 is being applied to the tag retainer 9400 through the tag 300 (at interface 9411), the opening in the body 9402 resists expansion and thus helps retain the tag 300 in place despite the force.

On the other hand, the tag 300 may be attached to and detached from the tag retainer 9400 by applying a force to the pull tab 9406. FIG. 94B illustrates the tag retainer 9400 when a force 9414 is applied to the pull tab 9406 (and an opposite side of the tag retainer 9400). Because the force is applied to the pull tab 9406, the tag 300 engages the engagement ends 9405 of the spring member 9404 resulting in the gap 9408 expanding and a gap 9416 being produced proximate the pull tab 9406. This gap 9416 facilitates removal of the tag 300 from the tag retainer 9400. Because applying a force to the pull tab 9406 requires a more deliberate and purposeful action by a user (as compared, for example, to a tag 300 becoming snagged on a passing object), the tag retainer 9400 helps keep the tag 300 attached during normal use, while providing an easy and straightforward way to attach and detach the tag 300 when desired.

Figure 95A:
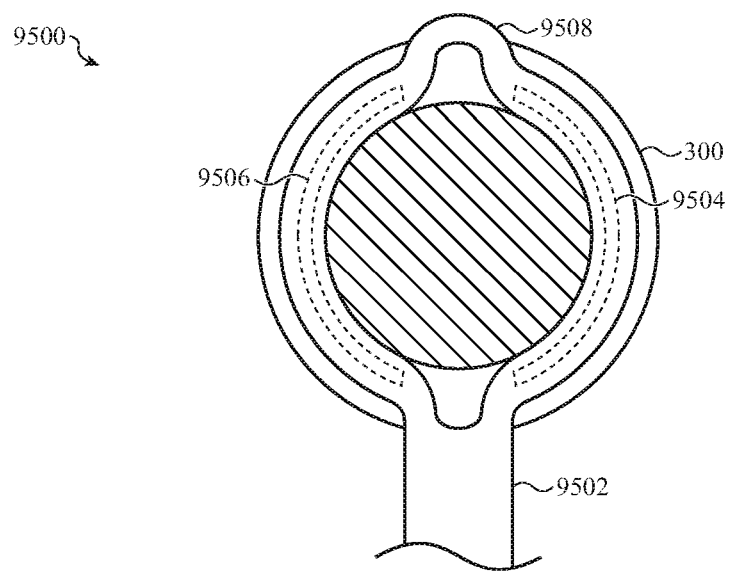
FIGS. 95A-95B depict another example tag retainer for holding a wirelessly locatable tag.
Figure 95B:
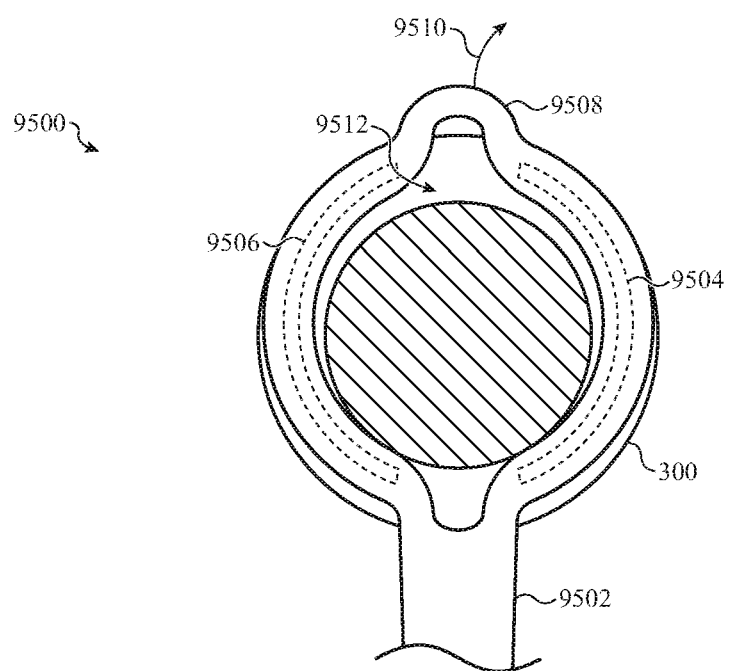

FIGS. 95A-95B illustrate another example tag retainer 9500 for attaching to a tag. The tag retainer 9500 may include a body 9502, which may be formed from or include a polymer material or other compliant material (including combinations of materials), and spring members 9504, 9506, which may be formed from a material with a greater stiffness than the body (e.g., spring steel, a polymer, etc.). The spring members 9504, 9506 may be configured to bias the body 9502 into the housing gap of a tag, as described with respect to other spring members. The spring members 9504, 9506 may have semi-circular shapes and may be positioned on opposite sides of the opening in the body 9502. The spring members 9504, 9506 may also increase the stiffness of portions of the tag retainer 9500 that extend into the housing gap, thereby decreasing the likelihood that the tag 300 will simply deform or fold the body 9502 out of the way and allow the tag 300 to unexpectedly detach from the tag retainer 9500.

The body 9502 may define a pull tab 9508. The pull tab 9508 may lack any spring members. As shown in FIG. 95B, a user may grasp the pull tab 9508 to apply a force 9510 to the pull tab 9508, thereby deforming the body 9502 (and optionally one or both of the spring members 9504, 9506) and introducing or increasing the size of a gap 9512 between the tag 300 and the body 9502, thereby facilitating attachment or detachment of the tag 300.

Figure 96A:
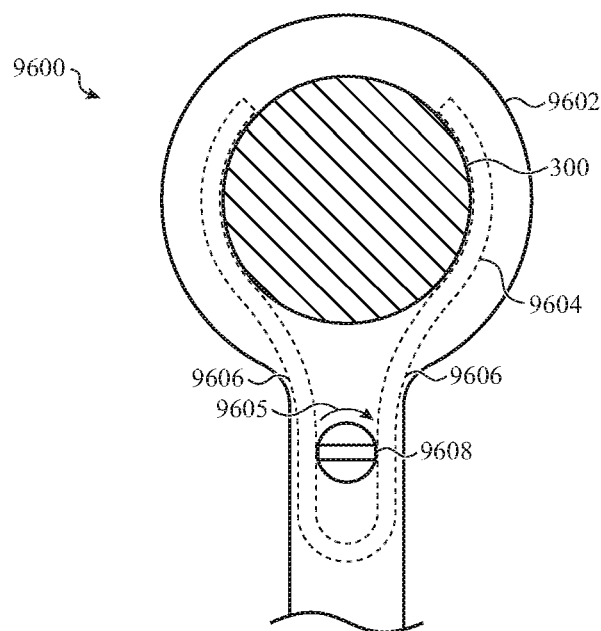
FIGS. 96A-96B depict another example tag retainer for holding a wirelessly locatable tag.
Figure 96B:
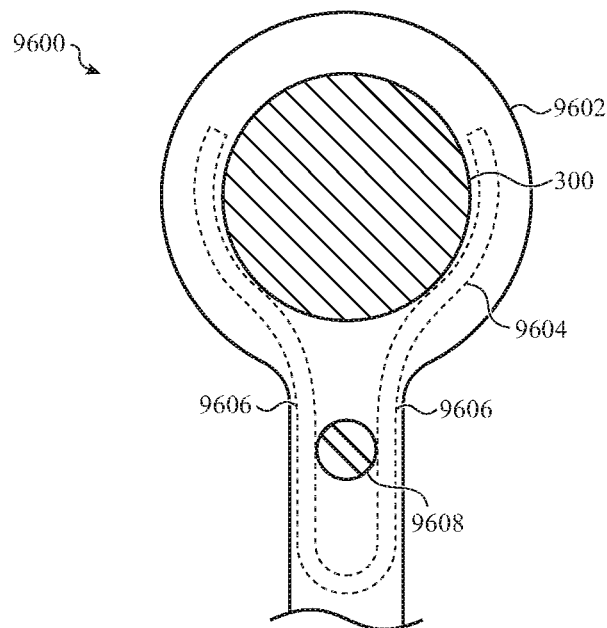

FIGS. 96A-96B illustrate another example tag retainer 9600 for attaching to a tag. The tag retainer 9600 may include a body 9602, which may be formed from or include a polymer material or other compliant material (including combinations of materials), and a spring member 9604 which may be formed from a material with a greater stiffness than the body (e.g., spring steel, a polymer, etc.). The spring member 9604 may be configured to bias the body 9602 into the housing gap of a tag, as described with respect to other spring members.

The spring member 9604 may define two spring arms 9606 that can be selectively secured together (or released) using a clip mechanism 9608. FIG. 96A shows the tag retainer 9600 with the clip mechanism 9608 in a closed configuration in which the spring arms 9606 are secured together. This may retain the tag retainer 9600 in a tightened or secure state in which the tag 300 is securely attached to the tag retainer 9600. FIG. 96B shows the tag retainer 9600 with the clip mechanism 9608 in an open configuration. When the clip mechanism 9608 is open, the spring member 9604 returns to a relaxed state in which the spring arms 9606 pull away from one another, thereby generally expanding the spring member 9604 and expanding the opening in which the tag 300 is received. This expansion facilitates the attachment and/or detachment of the tag retainer 9600 and the tag 300. The clip mechanism 9608 may be opened, for example, by rotating or twisting the clip mechanism 9608 (or a portion or component of the clip mechanism 9608), as illustrated by arrow 9605. Other types and/or configurations of clip mechanisms may be opened and/or closed using other types of manipulations.

Figure 97:
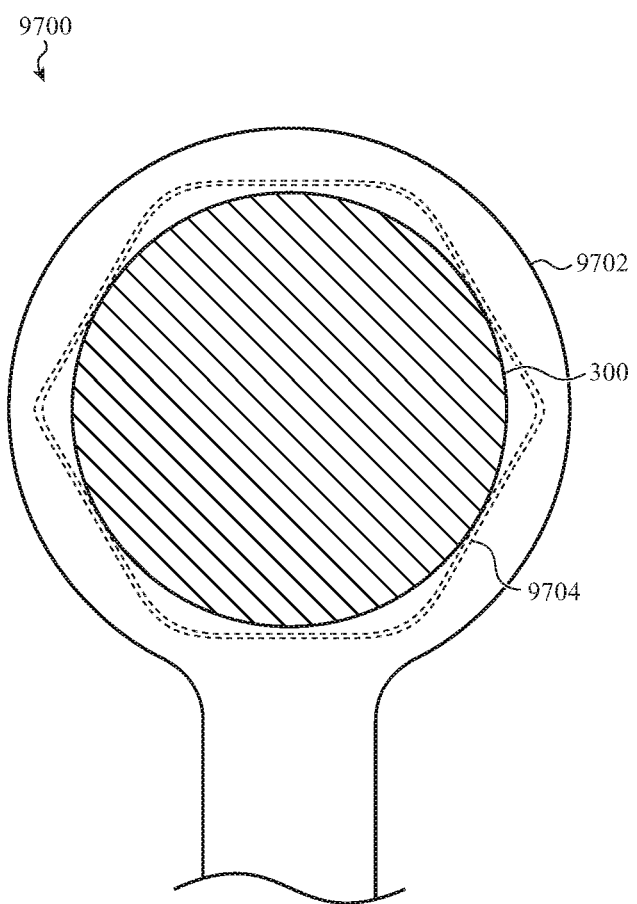
FIG. 97 depicts another example tag retainer for holding a wirelessly locatable tag.

FIG. 97 illustrates another example tag retainer 9700 for attaching to a tag. The tag retainer 9700 may include a body 9702, which may be formed from or include a polymer material or other compliant material (including combinations of materials), and a spring member 9704 which may be formed from a material with a greater stiffness than the body (e.g., spring steel, a polymer, etc.). The spring member 9704 may be configured to bias the body 9702 into the housing gap of a tag, as described with respect to other spring members. The spring member 9704 may have an octagonal shape with eight substantially linear sides, which each extend into the housing gap of the tag 300 to help retain the tag 300 to the tag retainer 9700. In some cases, the spring member 9704 may define uncoupled ends to allow the spring member 9704 to expand in order to facilitate attachment and detachment of the tag 300. In some cases, the ends of the spring member 9704 are connected (e.g., welded), and the spring member 9704 deforms (e.g., one or more of the straight sides deflects) during attachment and/or detachment of the tag 300.

Figure 98A:
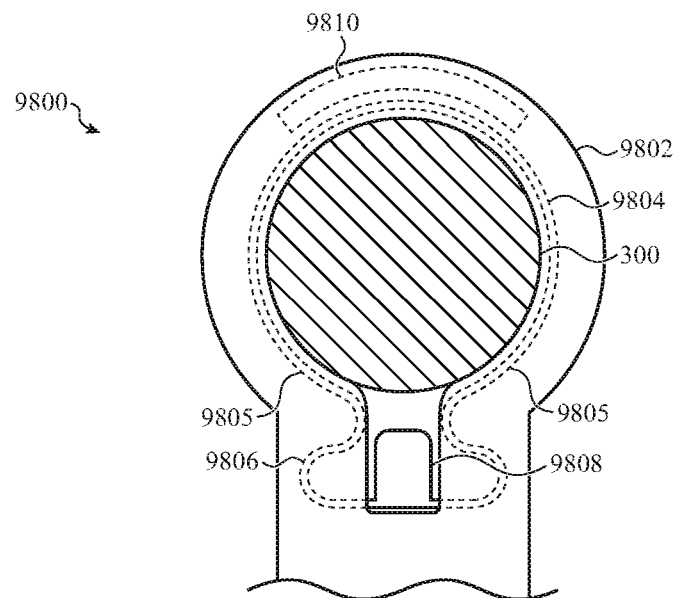
FIGS. 98A-98B depict another example tag retainer for holding a wirelessly locatable tag.
Figure 98B:
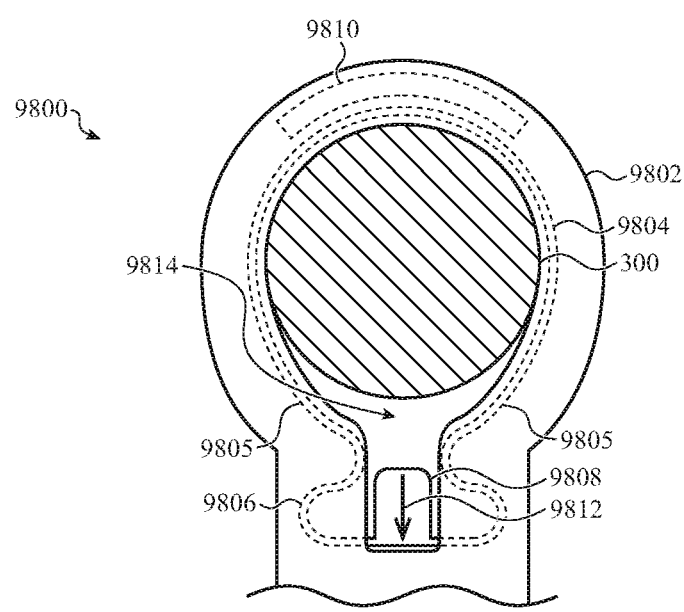

FIGS. 98A-98B illustrate another example tag retainer 9800 for attaching to a tag. The tag retainer 9800 may include a body 9802, which may be formed from or include a polymer material or other compliant material (including combinations of materials), and a spring member 9804 which may be formed from a material with a greater stiffness than the body 9802 (e.g., spring steel, a polymer, etc.). The spring member 9804 may be configured to bias the body 9802 into the housing gap of a tag, as described with respect to other spring members. The tag retainer 9800 may also include a stiffener 9810 along a portion of the opening for the tag, which may help maintain the shape of the tag retainer 9800 during manipulations of the spring member 9804 (for attaching/detaching the tag 300) and may provide additional stiffness to the portion of the body 9802 that extends into the housing gap.

The spring member 9804 may define engagement regions 9805 and an actuation region 9806. The engagement regions 9805 may be biased towards the tag 300 and engage the tag 300 in the housing gap. The actuation region 9806 may be defined by a curved portion of the spring member 9804, and may include or be coupled to a manipulation tab 9808 (which may be integral with the spring member 9804 or may be a separate component that is attached to the spring member 9804). The manipulation tab 9808 may be exposed or otherwise accessible to a user, and may be used to apply a force to the actuation region 9806 to expand the spring member 9804 to facilitate attachment and detachment of the tag 300. For example, the undeformed or unstressed configuration of the spring member 9804 may be shown in FIG. 98A. In this configuration, the spring member 9804 is biased into engagement with the tag 300 (e.g., in the housing gap) and retains the tag 300 to the tag retainer 9800. In order to conveniently attach or detach the tag 300, a user may grasp the manipulation tab 9808 and apply a force away from the tag 300 (while optionally grasping the tag 300). The force, represented by arrow 9812 in FIG. 98B, deforms the spring member 9804, including by pulling the engagement regions 9805 (and the nearby portions of the body 9802) away from the tag 300 and producing a gap 9814 that facilitates attachment and detachment of the tag 300.

Figure 99A:
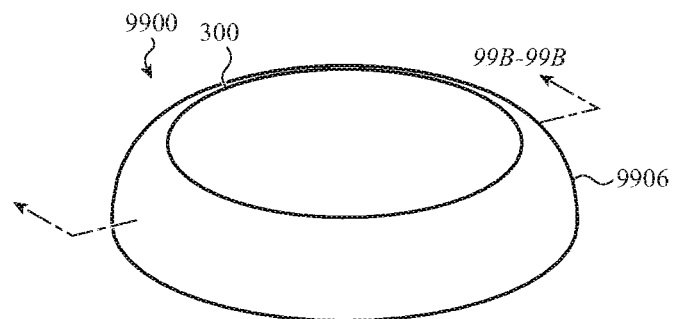
FIGS. 99A-99C depict an example cover for a wirelessly locatable tag.
Figure 99B:
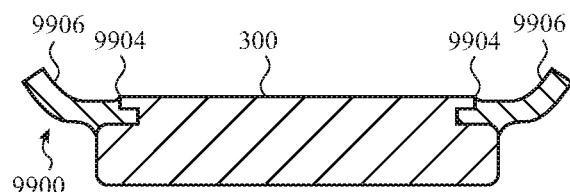
Figure 99C:
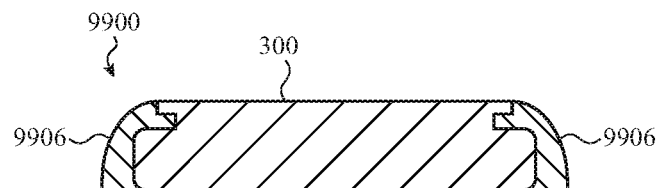

FIGS. 99A-99C illustrate an example tag cover 9900 for attaching to a tag. The tag cover 9900 may be configured to protect the tag from impacts, scratches, or other damage. The tag cover 9900 may also change the size and/or friction characteristics of the tag 300. For example, the tag cover 9900 may have a higher coefficient of friction than the tag itself, and may make the tag 300 easier to handle, less likely to slip out of the user's hand, or the like.

The tag cover 9900 may include an engagement flange 9904 that defines a first opening, and a sidewall 9906 that defines a second opening. The engagement flange 9904 may be configured to extend into a housing gap of the tag 300, as shown in FIGS. 99B and 99C (which are partial cross-sectional views of the tag and tag cover of FIG. 99A, viewed along line 99B-99B in FIG. 99A). The sidewall 9906 may have two stable configurations when the tag cover 9900 is attached to the tag 300 (e.g., it may be bistable). FIG. 99B shows the tag cover 9900 in a first configuration, where the sidewall 9906 is extended upward, away from the tag 300. This configuration may facilitate attachment and detachment of the tag cover 9900, as the sidewall may be moved out of the way of the engagement flange 9904 so that the engagement flange 9904 can be inserted into or removed from the housing gap of the tag 300. FIG. 99C shows the tag cover 9900 in a second configuration, where the sidewall 9906 is positioned against the tag 300. This configuration may correspond to the normal use configuration of the tag cover 9900, as the sidewall 9906 is at least partially covering, and optionally in direct contact with, the outer peripheral side of the tag 300.

FIGS. 100A-100D illustrate another example tag retainer 10010 (FIG. 100B) for attaching to a tag 10000 (FIG. 100A). The tag 10000 and tag retainer 10010 may include complementary mating features that allow the tag retainer 10010 to securely attach to the tag 10000. In particular, with reference to FIG. 100A, the tag 10000 may include a battery door 10001 (similar to the bottom housing member 304, or battery door, of the tag 300 in FIG. 3) that defines engagement features 10002. The engagement features 10002 may each define undercut slots 10004, which may be open on one end and blocked at the opposite end.

With reference to FIG. 100B, the tag retainer 10010 may include a body, which may be formed from or include a polymer material or other compliant material (including combinations of materials). The corresponding engagement features 10012 may be formed from a material with a greater stiffness than the body (e.g., spring steel, a polymer, etc.). The tag retainer 10010 defines an opening 10011 that is configured to receive at least part of the tag 10000 therein, and corresponding engagement features 10012 that are complementary to the engagement features 10002 of the tag 10000. The corresponding engagement features 10012 may be tabs, clips, flanges, protrusions, or other suitable features. In the illustrated example, the engagement features 10002 of the tag 10000 define slots, and the corresponding engagement features 10012 define tabs with a shape and size to be received in the slots, though this is merely one example set of complementary engagement features, and others are also contemplated.

FIG. 100C illustrates the tag retainer 10010 being attached to the tag 10000. The tag retainer 10010 is positioned so that the corresponding engagement features 10012 are positioned between the engagement features 10002 of the tag 10000, thereby aligning the corresponding engagement features 10012 with the slots defined by the engagement features 10002. The tag retainer 10010 is rotated, as illustrated by arrow 10014, to slide the corresponding engagement features 10012 into the engagement features 10002. Once the engagement features 10002, 10012 are engaged, the tag retainer 10010 is attached to the tag 10000, as shown in FIG. 100D.

The engagement features 10002, 10012 may include clips, latches, detents, undercuts, and/or other features that help maintain the features 10002, 10012 in secure engagement. Such features may, for example, require a greater force to initially disengage the engagement features 10002, 10012, followed by a lower force requirement to fully slide the engagement features 10002, 10012 completely apart.

Figure 101A:
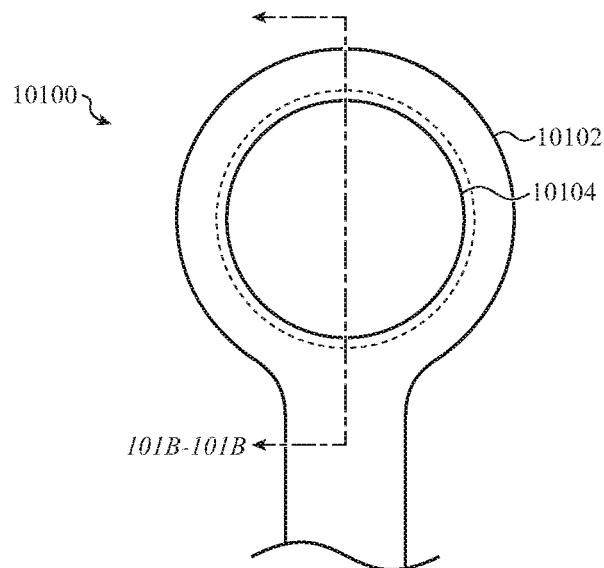
FIGS. 101A-101C depict another example tag retainer for holding a wirelessly locatable tag.
Figure 101B:
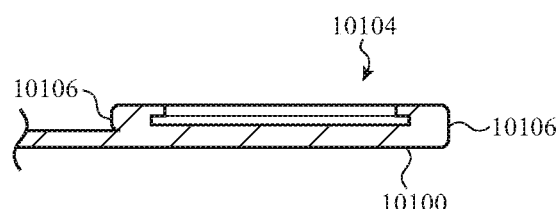
Figure 101C:
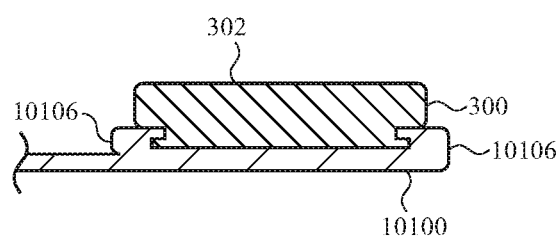

FIGS. 101A-101C illustrate another example tag retainer 10100 for attaching to a tag. The tag retainer 10100 may include a body 10102, which may define an opening 10104. The body 10102 may be formed from or include a polymer material or other compliant material (including combinations of materials), and may include other components or materials such as spring members, stiffeners, etc. The opening 10104 may be an opening to a partially enclosed pocket that receives a portion of a tag.

FIG. 101B is a partial cross-sectional view of the tag retainer 10100 of FIG. 101A, viewed along line 101B-101B in FIG. 101A. The opening 10104 may be defined by a wall (e.g., a circular wall) 10106 that is configured to engage a tag via a housing gap.

FIG. 101C is another partial cross-sectional view of the tag retainer 10100 of FIG. 101A, viewed along line 101B-101B in FIG. 101A, showing the tag retainer 10100 attached to the tag 300. As shown, the partially enclosed pocket has a size (e.g., a diameter, volume, etc.) that is substantially equal to the outer part of the battery door of the tag 300, and the battery door is substantially contained and/or enclosed in the pocket. The wall 10106 extends into the housing gap of the tag 300 to retain the tag 300 to the tag retainer 10100. The stiffness of the material of the wall 10106 (including any stiffeners within or attached to the body 10102) may bias the wall 10106 into the housing gap to provide a secure attachment.

By attaching to the battery door, the main body portion 302 of the tag 300 is exposed and uncovered. As the main body portion 302, and more particularly the top housing member of the tag, may define a diaphragm-like member to produce audio outputs, attaching the tag retainer 10100 to the tag 300 in a manner that exposes the top housing member may help avoid degrading or muting the audio output.

Figure 101D:
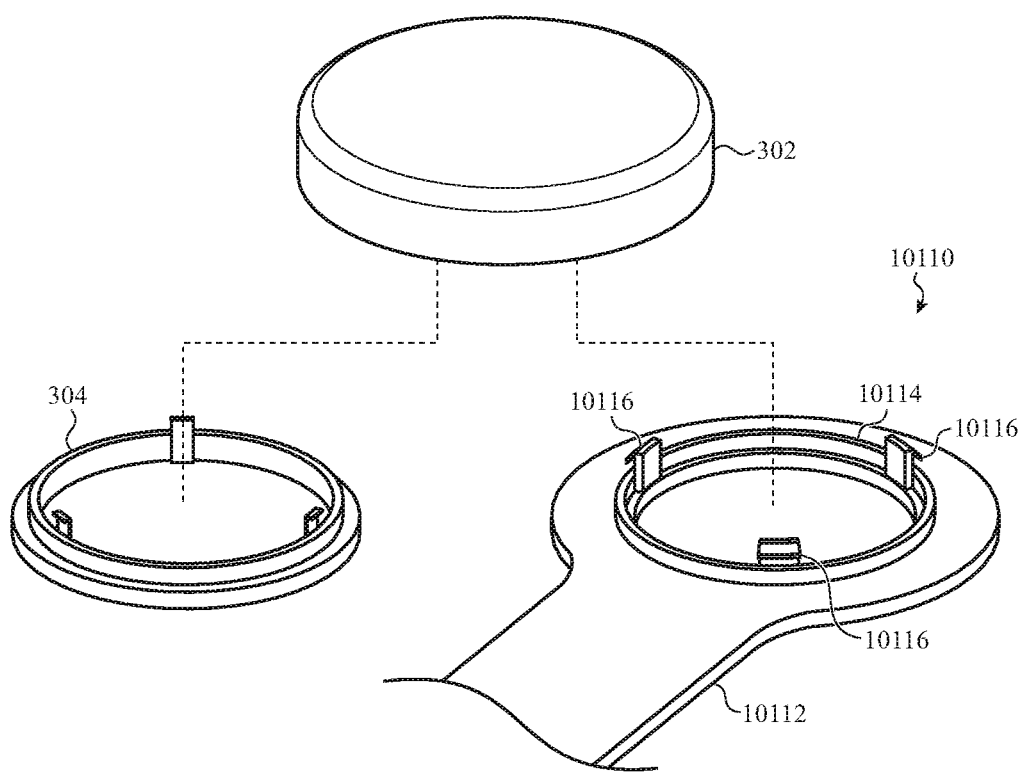
FIG. 101D depicts another example tag retainer for holding a wirelessly locatable tag.

While FIGS. 101A-101C illustrate a tag retainer that attaches to a battery door of a tag, FIG. 101D illustrates an example tag retainer that attaches to the tag 300 in place of the battery door 304. FIG. 101D illustrates the tag 300 with the bottom housing member or battery door 304 removed from the main body portion 302. A tag retainer 10110 may include or define a strap 10112 or attachment portion that is used to attach the tag retainer 10110 to another object.

The tag retainer 10110 may also include a flange 10114 and latching members 10116. The flange 10114 may resemble a similar structure of the battery door 304, and the latching members 10116 may have substantially the same size, shape, and overall configuration of the latching members of the battery door 304. The latching members 10116 may be configured to engage the tag 300 in the same or similar manner to the latching members of the battery door 304. In this manner, the main body portion 302 may be interchangeably attached to the battery door 304 or the tag retainer 10110 using the same engagement features of the main body portion 302.

Figure 102A:
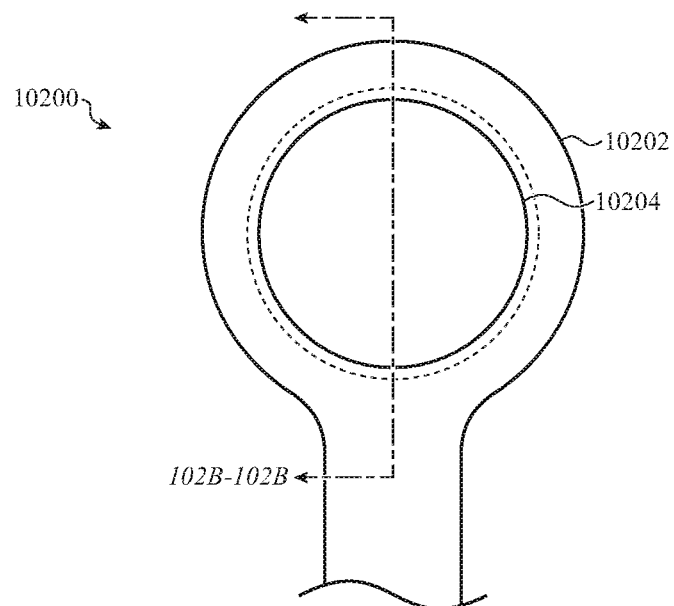
FIGS. 102A-102C depict another example tag retainer for holding a wirelessly locatable tag.
Figure 102B:
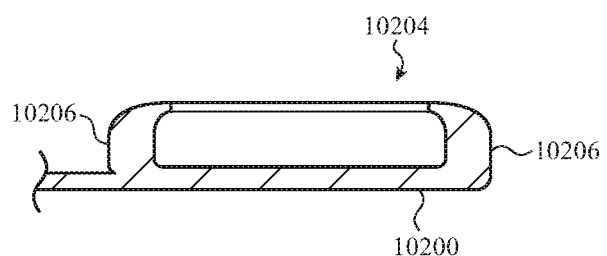
Figure 102C:
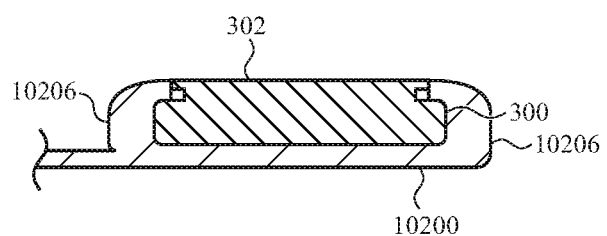

FIGS. 102A-102C illustrate another example tag retainer 10200 for attaching to a tag. The tag retainer 10200 may include a body 10202, which may define an opening 10204. The body 10202 may be formed from or include a polymer material or other compliant material (including combinations of materials), and may include other components or materials such as spring members, stiffeners, etc. The opening 10204 may be an opening to a partially enclosed pocket that receives a portion of a tag.

FIG. 102B is a partial cross-sectional view of the tag retainer 10200 of FIG. 102A, viewed along line 102B-102B in FIG. 102A. The opening 10204 may be defined by a wall (e.g., a circular wall) 10206 that is configured to engage a tag via a housing gap.

FIG. 102C is another partial cross-sectional view of the tag retainer 10200 of FIG. 102A, viewed along line 102B-102B in FIG. 102A, showing the tag retainer 10200 attached to the tag 300. Whereas the tag retainer 10100 is configured to attach to the tag 300 via the battery door, the tag retainer 10200 is configured to attach to the tag 300 by wrapping around the main body portion 302 of the tag 300. Thus, the partially enclosed pocket has a size (e.g., a diameter, volume, etc.) that is substantially equal to the outer part of the main body portion 302 of the tag 300, and the outer part of the main body portion 302 is substantially contained and/or enclosed in the pocket. The wall 10206 may extend into the housing gap of the tag 300 to retain the tag 300 to the tag retainer 10200. The stiffness of the material of the wall 10206 (including any stiffeners within or attached to the body 10202) may bias the wall 10206 into the housing gap to provide a secure attachment. In other cases, the wall 10206 does not extend into the housing gap, but instead securely attaches to the tag 300 due to the wall 10206 extending over a portion of the tag 300 and trapping the tag 300 in the pocket of the tag retainer 10200.

Figure 103A:
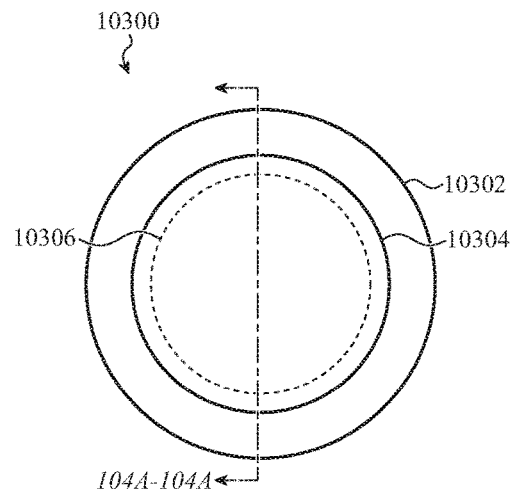
FIGS. 103A-103B depict an example wirelessly locatable tag.
Figure 103B:
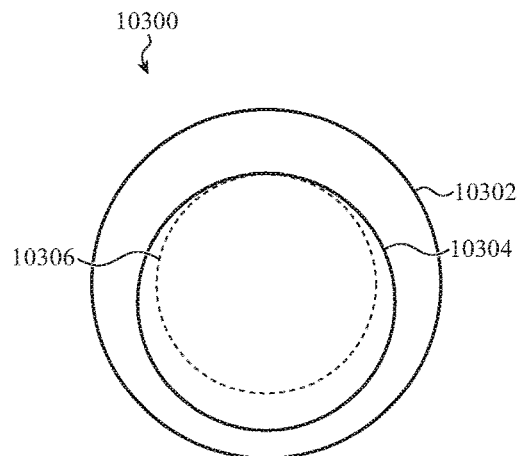

FIGS. 103A-103B illustrate another example tag 10300 with a configuration for facilitating attachment to and detachment from a tag retainer. In particular, the tag 10300 includes a main body portion 10302 (similar to the main body portion 302 of the tag 300) and a battery door 10304 (similar to the bottom housing member 304, or battery door, of the tag 300). The battery door 10304 is configured to slide, translate, or otherwise move relative to the main body portion 10302. For example, FIG. 103A illustrates the tag 10300 with the battery door 10304 in an undeflected position relative to the main body portion 10302. In this position, the battery door 10304 may be substantially centered over a shaft 10306 of the main body portion 10302. Accordingly, the battery door 10304 may overhang the shaft 10306 to define the housing gap of the tag 10300. FIG. 103B illustrates the tag 10300 with the battery door 10304 in a deflected position. In this position, at least one side of the battery door 10304 may be substantially flush with a side of the shaft 10306. The battery door 10304 may slide, translate, or otherwise move only a fixed distance relative to the main body portion 10302, and may use any suitable mechanism to facilitate the motion (e.g., friction guides, bearings, bushings, etc.). Further, while the battery door 10304 and the shaft 10306 are shown as having circular shapes, other shapes are also contemplated, including oblong shapes, ovals, rectangles, ellipses, or the like.

FIGS. 104A-104D illustrate steps of an example process for attaching the tag 10300 to a tag retainer 10400 (which may resemble the tag retainer 7600, FIG. 76A, or other tag retainers described herein). The tag retainer 10400 may be less compliant than other tag retainers, as the movement of the battery door 10304 can facilitate attachment and detachment while reducing the need for the tag retainer 10400 to deflect or deform.

Figure 104A:
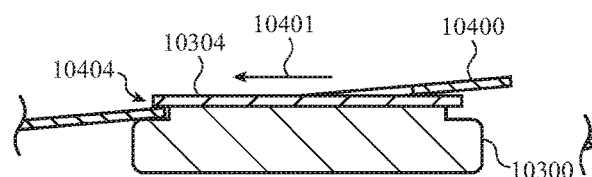
FIGS. 104A-104D depict the tag of FIGS. 103A-103B being attached to a tag retainer.
Figure 104B:
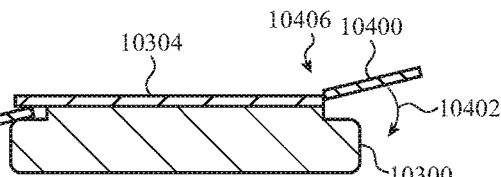
Figure 104C:
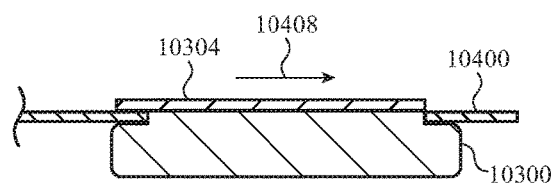
Figure 104D:
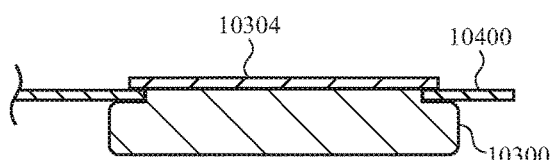

As shown in FIG. 104A, the tag retainer 10400 may be engaged with the tag 10300 at a first location 10404 while the battery door 10304 is in an undeflected position. After engaging at the location 10404, the user may slide the battery door 10304 into a deflected position (arrow 10401), which reduces the overhang of the battery door 10304 relative to the shaft 10306 at a second location 10406. This allows the tag retainer 10400 to more easily slide over the battery door 10304 and into the housing gap, as indicated by arrow 10402. FIG. 104B shows the tag retainer 10400 in place in the housing gap. Sliding the battery door 10304 back towards the undeflected position (arrow 10408, FIG. 104C) captures the tag retainer 10400 in the housing gap and retains the tag retainer 10400 to the tag 10300 (as shown in FIG. 104D).

Figure 105A:
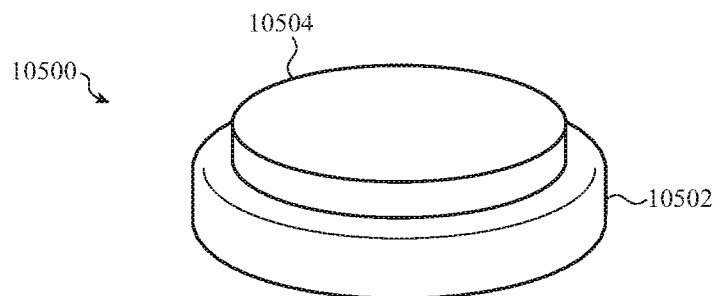
FIGS. 105A-105B depict an example wirelessly locatable tag.
Figure 105B:
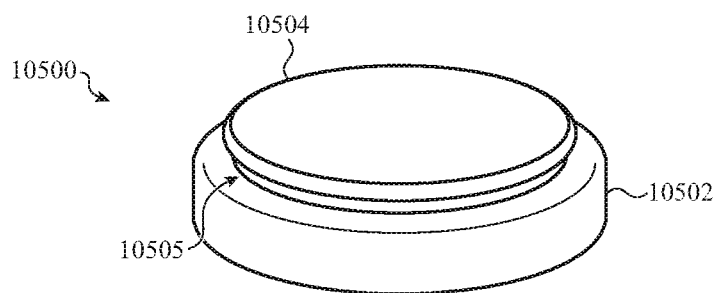

FIGS. 105A-105D illustrate another example tag 10500 with a configuration for facilitating attachment to and detachment from a tag retainer. In particular, the tag 10500 includes a main body portion 10502 (similar to the main body portion 302 of the tag 300), and a battery door 10504 that includes a bistable retraction mechanism that can be actuated to form (or remove) a housing gap. FIG. 105A shows the battery door 10504 in an extended configuration. In this configuration, the battery door 10504 does not define an undercut or lip, and thus does not define a housing gap. Rather, the extended battery door 10504 has substantially straight sides such that a tag retainer can be slid over the extended battery door 10504 without requiring the tag retainer to deform or deflect. FIG. 105B shows the battery door 10504 in a retracted configuration. In this configuration, the battery door 10504 is compressed to define a housing gap 10505 that can trap a tag retainer therein.

The battery door 10504 may include a bistable retraction mechanism and a compliant cover. The bistable retraction mechanism may operate similar to a retractable pen. For example, pressing the battery door 10504 when the bistable retraction mechanism is retracted (FIG. 105B) will result in the bistable retraction mechanism extending (FIG. 105A), and vice versa. The compliant cover may enclose internal components of the bistable retraction mechanism, such as cams, arms, plates, springs, and the like. The compliant cover may be a fabric, polymer (e.g., silicone, TPU, etc.), leather, mechanically linked rigid plates, or the like.

Figure 105C:
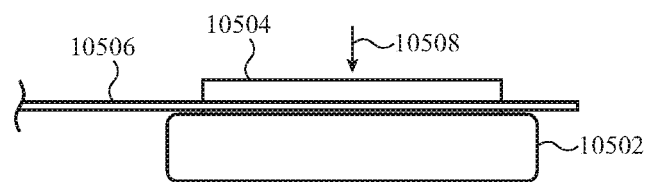
FIGS. 105C-105D depict the tag of FIGS. 105A-105B being attached to a tag retainer.
Figure 105D:
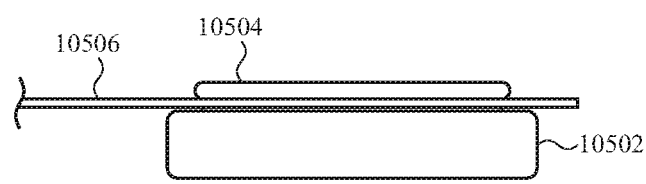

FIGS. 105C-105D illustrate how the tag 10500 may be attached to a tag retainer 10506. As shown in FIG. 105A, the battery door 10504 may be extended so that the opening of the tag retainer 10506 may be passed over the extended battery door 10504 to rest against a surface of the tag 10500 (e.g., the main body portion 10502). Once the tag retainer 10506 is in place, a force may be applied to the battery door 10504, as illustrated by arrow 10508, to force the battery door 10504 into a retracted position. FIG. 105D shows the battery door 10504 in the retracted configuration, with the tag retainer 10506 captured in the housing gap 10505 (e.g., between the battery door 10504 and the main body portion 10502). Detaching the tag retainer 10506 from the tag 10500 may be accomplished by reversing these operations.

Figure 106A:
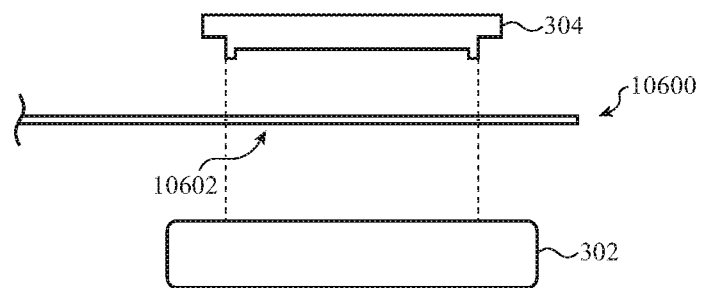
FIGS. 106A-106B depict an example wirelessly locatable tag being attached to a tag retainer.
Figure 106B:
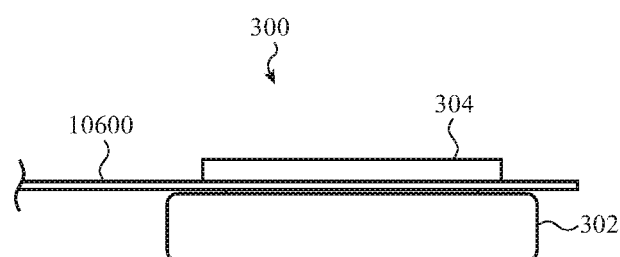

FIGS. 106A-106B illustrate another technique for attaching the tag 300 to a tag retainer 10600. The tag retainer 10600 defines an opening 10602 that is configured to receive a portion of the tag 300. More particularly, the battery door 304 of the tag 300 is separated from the main body portion 302, and the tag retainer 10600 is positioned between the battery door 304 and the main body portion 302 such that a portion of the tag 300 is in the opening 10602 and such that a portion of the tag retainer 10600 is captured between the battery door 304 and the main body portion 302 (e.g., in the housing gap of the tag 300). FIG. 106A shows an exploded view of the tag 300 in position to be attached to the retainer 10600, and FIG. 106B shows the tag 300 attached to the tag retainer 10600, with the battery door 304 attached to the main body portion 302 and the tag retainer 10600 captured in the housing gap. The tag retainer 10600 may be any suitable tag retainer, such as those described herein. Because the tag retainer 10600 (and in particular the opening 10602) does not need to expand or deform to facilitate attachment to the tag, the tag retainer 10600 may be more rigid or stiff than other tag retainers described herein. This stiffness may be accomplished by forming the tag retainer 10600 from stiffer materials (e.g., polycarbonate, metals, ABS, etc.), or incorporating stiff materials in the tag retainer 10600. For example, a closed-ring spring member, such as that shown in FIGS. 76A-76C, may be incorporated into the tag retainer 10600 around the opening 10602 and encapsulated by a compliant material that forms the rest of the tag retainer 10600. In comparison to the tag retainer 7600, however, the opening 10602 (and the diameter of the closed-ring spring member) may be smaller than the opening 7601 due to the fact that the opening 10602 does not need to fit over the battery door to attach the tag to the tag retainer. For example, the opening 10602 may have a diameter that is substantially the same size as the smallest-diameter surface of the housing gap, with only a small amount of clearance to allow for opening 10602 to accept the portion of the tag therein.

Figure 107A:
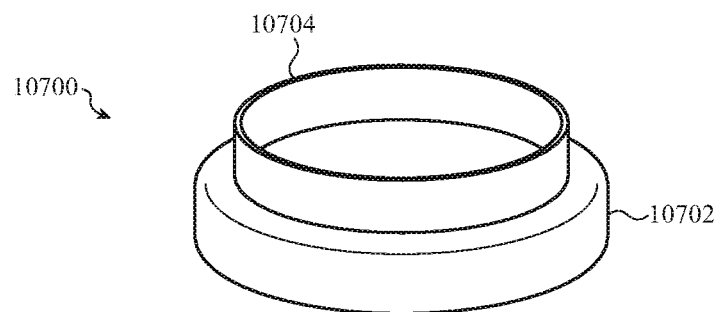
FIGS. 107A-107B depict an example wirelessly locatable tag.
Figure 107B:
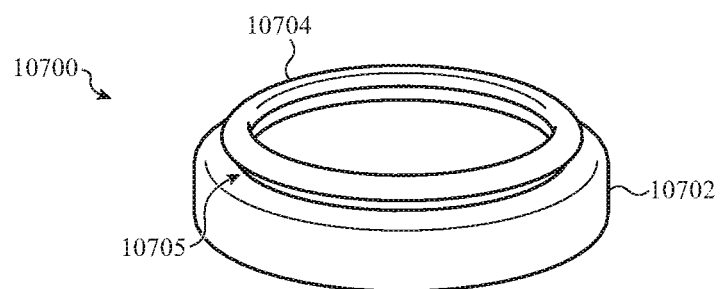

FIGS. 107A-107B illustrate another example tag 10700 with a configuration for facilitating attachment to and detachment from a tag retainer. In particular, the tag 10700 includes a main body portion 10702 (similar to the main body portion 302 of the tag 300), and a battery door that includes a bistable flange 10704 that can be manipulated to form (or remove) a housing gap. FIG. 107A shows the bistable flange 10704 in an extended configuration. In this configuration, the bistable flange 10704 does not define an undercut or lip, and thus does not define a housing gap. Rather, the extended bistable flange 10704 has substantially straight sides such that a tag retainer can be slid over the extended bistable flange 10704 without requiring the tag retainer to deform or deflect. FIG. 107B shows the bistable flange 10704 in a retracted configuration. In this configuration, the bistable flange 10704 has been forced into a retracted configuration to define a housing gap 10705 that can trap a tag retainer therein.

Figure 108A:
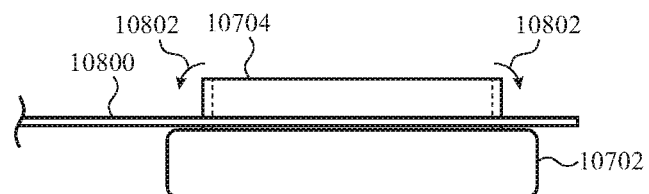
FIGS. 108A-108B depict the tag of FIGS. 107A-107B being attached to a tag retainer.
Figure 108B:
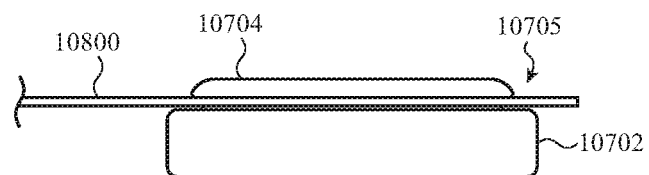

FIGS. 108A-108B illustrate how the tag 10700 may be attached to a tag retainer 10800. As shown in FIG. 108A, the bistable flange 10704 may be extended so that the opening of the tag retainer 10800 may be passed over the extended bistable flange 10704 to rest against a surface of the tag 10700 (e.g., the main body portion 10702). Once the tag retainer 10800 is in place, a force may be applied to the bistable flange 10704, as illustrated by arrows 10802, to force the bistable flange 10704 into a retracted position. FIG. 108B shows the bistable flange 10704 in the retracted configuration, with the tag retainer 10800 captured in the housing gap 10705 (e.g., between the bistable flange 10704 and the main body portion 10702). Detaching the tag retainer 10800 from the tag 10700 may be accomplished by reversing these operations.

The bistable flange 10704 may be formed from or include any suitable material. For example, the bistable flange 10704 may be formed from a polymer material such as a silicone, TPU, or the like. The bistable flange 10704 may be a single piece of material, or it may include multiple components. For example, the bistable flange 10704 may include an internal bistable member (e.g., a metal having a shape and/or material that produces a bistable configuration) with a compliant outer sheathing material (e.g., silicone, TPU, etc.). Other configurations are also contemplated.

FIGS. 109A-109D illustrate another example tag 10900 (FIG. 109A), and corresponding tag retainer 10910 (FIG. 109B) for attaching to the tag 10900. With reference to FIG. 109A, the tag 10900 includes a main body portion 10902 (similar to the main body portion 302 of the tag 300), and a battery door 10904. The tag 10900 may define channels 10906, which may be formed in the battery door 10904, that are configured to receive latch members 10916 of the tag retainer 10910 (FIG. 109B). The channels 10906 may include or define ramp segments 10920, which may be used to guide the latch members 10916 of a tag retainer out of the channels 10906 when decoupling the tag retainer 10910 from the tag 10900.

The tag 10900 may also include optional magnetic components 10908 (e.g., magnets) that are configured to magnetically attract to the latch members 10916 to help draw the latch members 10916 into the channels 10906 and retain them in the channels 10906. The tag 10900 may also include optional repelling magnetic components 10922 (e.g., magnets having an opposite polarity to the magnets 10908) that are configured to repel the latch members 10916 out of the channels 10906 when the tag retainer 10910 is rotated (such that the latch members 10916 slide along the ramp segments 10920). The combination of the ramp segments 10920 and the repelling magnetic components 10922 may provide an impetus that causes the latch members 10916 to retract back into a retracted position in the tag retainer 10910.

The tag retainer 10910, shown in FIG. 109B, includes a body 10912 (similar to the bodies of other tag retainers described herein) that defines an opening 10914 configured to receive at least a portion of the tag 10900 (e.g., the battery door 10904). The tag retainer 10910 may include latch members 10916 that can be retracted into and/or extended out from the tag retainer 10910 to engage the channels 10906 of the tag 10900, as illustrated by arrows 10918. The latch members 10916 may define ramped or contoured portions 10926 that facilitate a smooth engagement between the latch members 10916 and the ramp segments 10920 of the channels 10906 when the tag retainer 10910 is rotated (which causes the latch members 10916 to slide along the ramp segments 10920).

The latch members 10916 may be spring-loaded so that they are biased in an outward or protruding position, or they may be unbiased. In other cases, they are biased in a retracted position, and are drawn into the channels 10906 due to a magnetic attraction between the latch members 10916 and the magnetic components 10908 in the tag retainer 10910.

The latch members 10916 may be formed or include magnetic materials (e.g., a ferromagnetic material, if the magnetic components 10908 are permanent magnets) to facilitate the latch members 10916 being pulled into and retained in the channels 10906. The tag retainer 10910 may also include magnetic components 10924 (e.g., magnets) that are configured to bias the latch members 10916 into the body of the tag retainer 10910 or retain the latch members 10916 in the withdrawn or retracted position. The strength of the magnetic attraction between the latch members 10916 and the magnet components 10924 may be less than that of the attraction between the latch members 10916 and the magnetic components 10908 in the tag. In this way, the latch members 10916 may be securely retained in the channels 10906 by the magnetic components 10908 until the latch members 10916 are forced out of the channels 10906 (e.g., by the ramp segments 10920 and/or repelling magnetic components 10922), at which time the weaker magnetic attraction from the magnetic components 10924 may overcome the reduced magnetic attraction from the magnetic components 10908, thereby drawing the latch members 10916 back into the tag retainer 10910 and retaining them in the retracted position. To attach the tag 10900 to the tag retainer 10910, the tag retainer 19010 may be positioned so that the latch members 10916 are aligned with the channels 10906. In this alignment, the magnetic attraction between the latch members 10916 and the magnetic components 10908 may overcome the attraction between the latch members 10916 and the magnetic components 10924, thereby drawing the latch members 10916 into the channels to retain the tag 10900 to the tag retainer 10910.

FIG. 109C shows the tag 10900 attached to the tag retainer 10910. As shown, the latch members 10916 have extended into the channels 10906, thereby attaching the tag 10900 to the tag retainer 10910. Due to the optional spring biasing and/or the optional magnetic attraction, the latch members 10916 may be drawn into the channels 10906 as soon as the battery door 10904 is inserted into the opening 10914 of the tag retainer 10910 and the latch members 10916 are aligned with the channels 10906.

FIG. 109D shows how the latch members 10916 may be retracted into the tag retainer 10910 to detach the tag 10900 from the tag retainer 10910. For example, the tag retainer 10910 may be rotated relative to the tag 10900 (as indicated by arrow 10928 in FIG. 109C), which causes the latch members 10916 to slide along and be ejected by the ramp segments 10920 (and optionally repelled by the repelling magnetic components 10922 and further retracted by the magnetic components 10924).

Figure 110A:
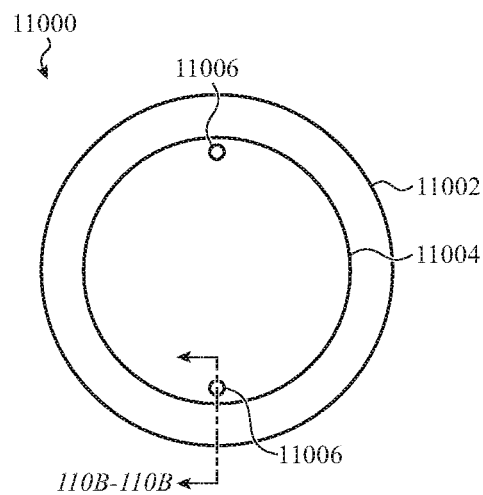
FIG. 110A-110B depict an example wirelessly locatable tag.

FIG. 110A illustrates another example tag 11000. The tag 11000 includes a main body portion 11002 (similar to the main body portion 302 of the tag 300), and a battery door 11004. The tag 11000 includes one or more accessory retention mechanisms 11006 integrated with the battery door 11004. The accessory retention mechanisms 11006 may be configured to help retain the tag 11000 to an accessory such as a tag retainer.

Figure 110B:
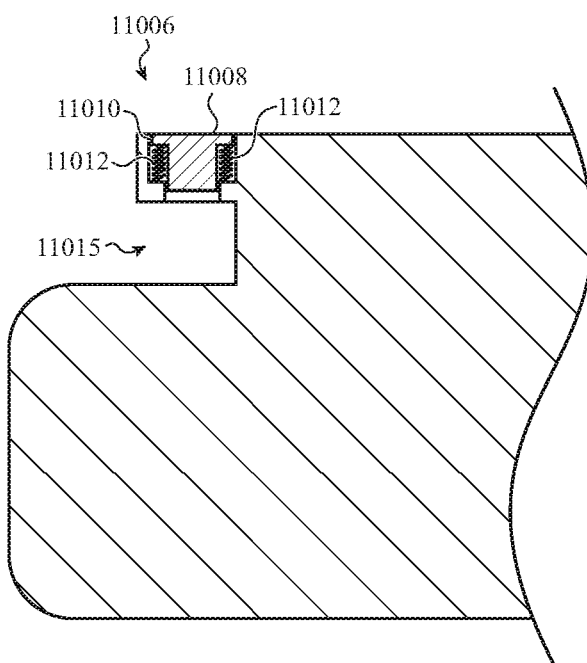

FIG. 110B is a partial cross-sectional view of the tag 11000 of FIG. 110A, viewed along line 110B-110B in FIG. 110A. FIG. 110B shows an example configuration of the accessory retention mechanisms 11006. In particular, the accessory retention mechanisms 11006 may include a plunger 11008 that is accessible to the user from the outer or exterior surface of the tag 11000, and one or more spring members 11012 biasing the plunger 11008 upwards. The accessory retention mechanisms 11006 may be situated within (and captive in) an opening 11010 in the battery door 11004, and the opening may be configured to receive therein a retention member of an accessory to help hold the accessory in place and attached to the tag 11000.

Figure 111A:
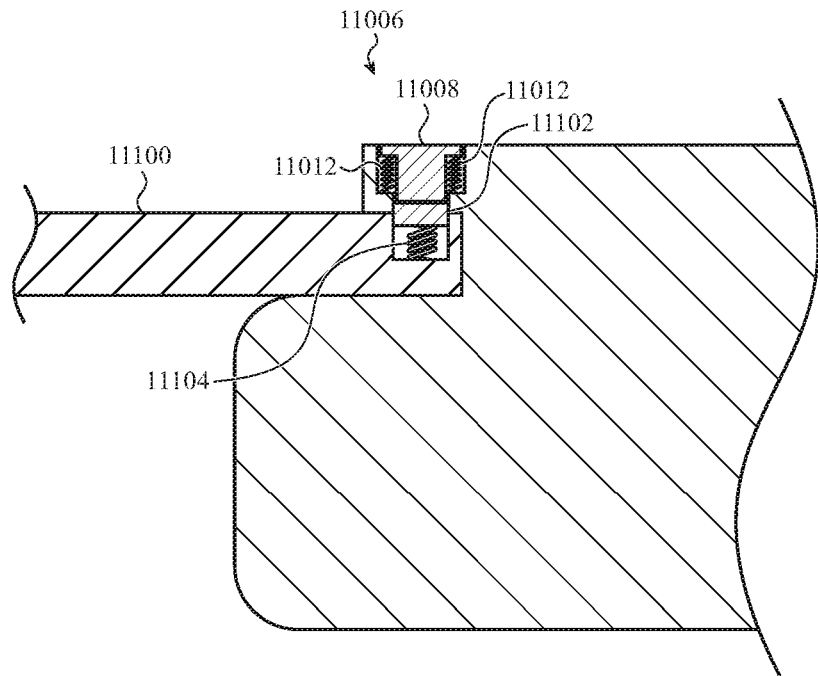
Figure 111B:
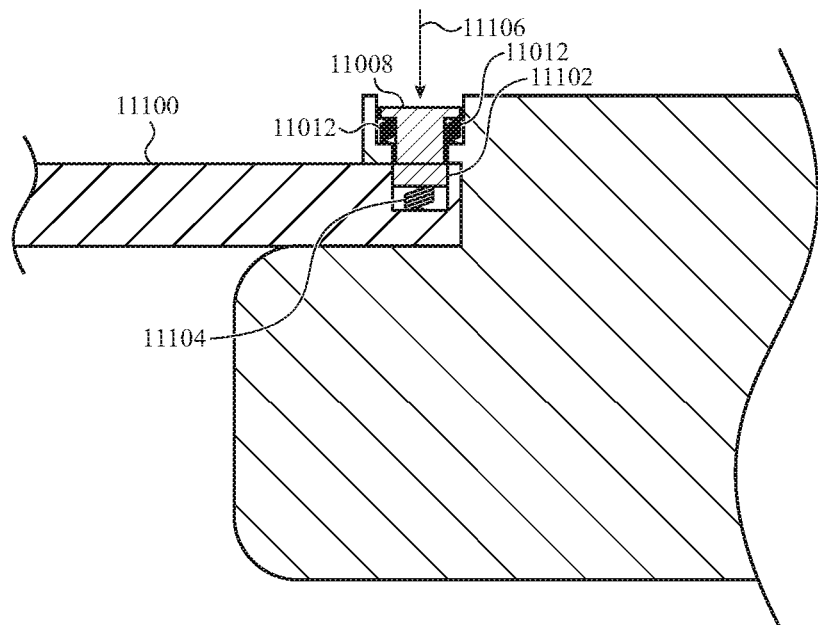

FIGS. 111A-111B illustrate partial cross-sectional views of the tag 11000 in use with an accessory 11100, which may be a tag retainer similar to others described herein. The accessory 11100 may include a retention member 11102 that is biased, by a spring member 11104, in a proud or protruding configuration (relative to adjacent portions of the accessory 11100). FIG. 111B shows the accessory 11100 attached to the tag 11000. In this configuration, the retention member 11102 is extended into the opening 11010 such that the retention member 11102 engages the opening 11010 and retains the accessory 11100 to the tag 11000.

In order to detach the accessory 11100 from the tag 11000, a user may apply a force to the plunger 11008 of the accessory retention mechanism 11006 (indicated by arrow 11106, FIG. 111B), thereby forcing the plunger 11008 against the retention member 11102 in a manner that overcomes the biasing force of the retention member 11102 and pushes the retention member 11102 out of the opening 11110. In this configuration, as shown in FIG. 111B, the accessory 11100 may be easily slid out of the housing gap 11015 to detach the accessory 11100 from the tag 11000.

The accessory 11100 may have an enclosed (e.g., circular) opening, similar to the tag retainer 7600, for example. Because the accessory retention mechanisms 11006 can retain an accessory to the tag without the accessory fully encircling the housing gap, the accessory 11100 does not necessarily require a continuous opening. For example, the accessory 11100 may be a straight strap-like accessory with a free end that is narrower than the width (e.g., diameter) of the tag 11000 and that extends into the housing gap 11015 only at a location proximate the accessory retention mechanism 11006. In some cases, an additional mechanism or retention feature is positioned on the tag 11000 on the opposite side of the accessory 11100 to retain the accessory 11100 from the underside as well.

Figure 112A:
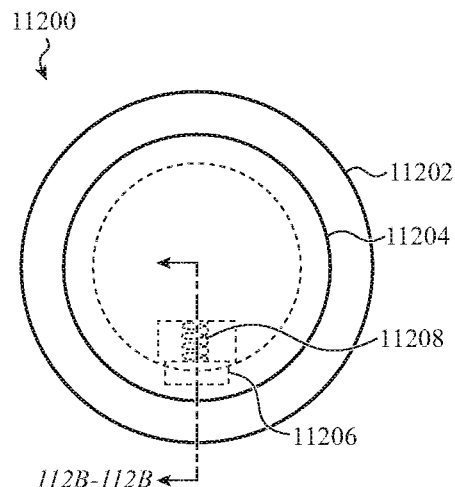
Figure 112B:
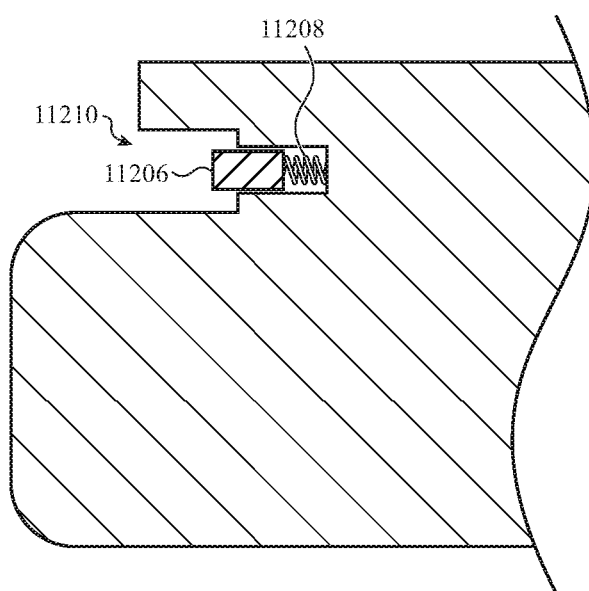

FIG. 112A illustrates another example tag 11200. The tag 11200 includes a main body portion 11202 (similar to the main body portion 302 of the tag 300), and a battery door 11204. The tag 11200 includes an accessory biasing mechanism 11206 integrated with the tag 11200. The accessory biasing mechanisms 11206 may be configured to help retain the tag 11200 to an accessory such as a tag retainer, and may help prevent the tag 11200 from moving (e.g., spinning, rattling) when attached to an accessory such as a tag retainer. The accessory biasing mechanism 11206 may be positioned in a housing gap 11210 (FIG. 112B), and may be configured to push against an accessory that is engaged with the housing gap 11210. The tag 11200 may include a spring member 11208 that biases the accessory biasing mechanism 11206 in a protruding configuration, as shown in FIG. 112B (which is a partial cross-sectional view of the tag 11200 of FIG. 112A, viewed along line 112B-112B in FIG. 112A).

Figure 113A:
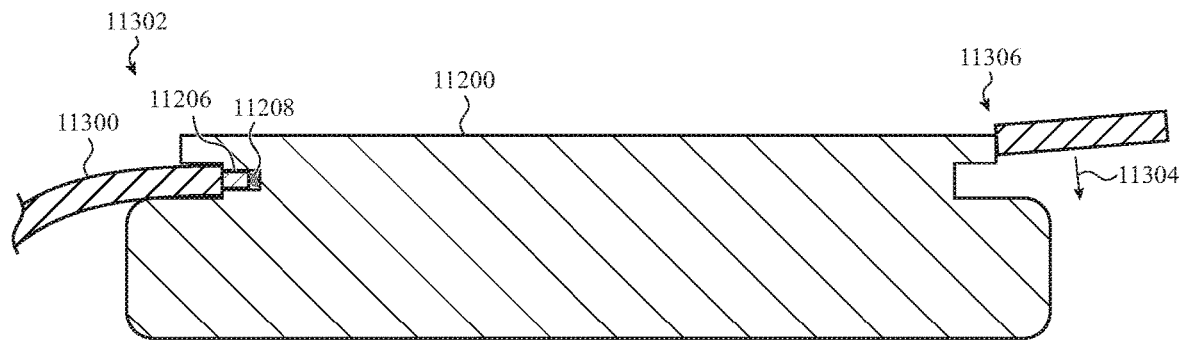
Figure 113B:
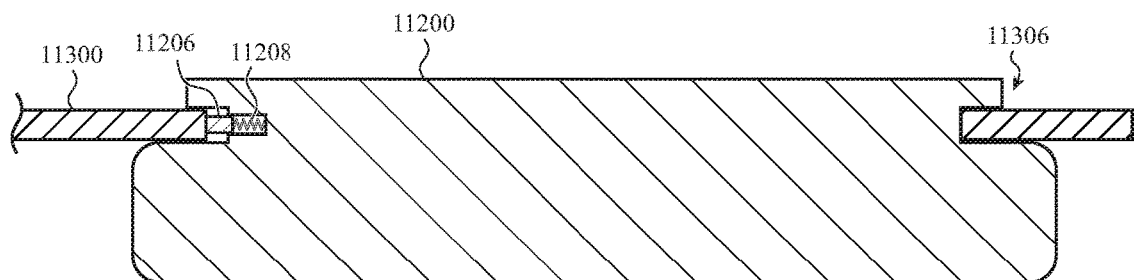

FIGS. 67A-67B illustrate the interaction of an accessory 11300 (which may be a tag retainer similar to the tag retainer 7600, or other tag retainers described herein) with the tag 11200 and the accessory biasing mechanism 11206. In particular, as the accessory 11300 is being attached to the tag 11200, the accessory may engage the tag 11200 by entering the housing gap at one side 11302 of the tag. Force from the accessory pushing against the accessory biasing mechanism 11206 may result in deflection of the accessory biasing mechanism 11206 into a recess in the tag 11200 (and may result in the accessory biasing mechanism 11206 being flush with adjacent portions of the tag 11200). The accessory 11300 may then be engaged with a second side 11306 of the tag by extending the accessory 11300 over the battery door 11204 and into the housing gap (indicated by arrow 11304). FIG. 113B shows the tag 11200 with the accessory 11300 attached and retained in the housing gap 11210. The accessory biasing mechanism 11206, forced outward by the spring member 11208, applies a force to the accessory 11300. This force may provide several advantages. For example, it may increase the engagement force between the accessory 11300 and the tag 11200 at the side opposite the accessory biasing mechanism 11206 (e.g., at the second side 11306). Further, it may increase the frictional force between the tag 11200 and the accessory 11300, thereby preventing or limiting rotation, rattling, or other motion of the tag 11200 relative to the accessory 11300.

Figure 114A:
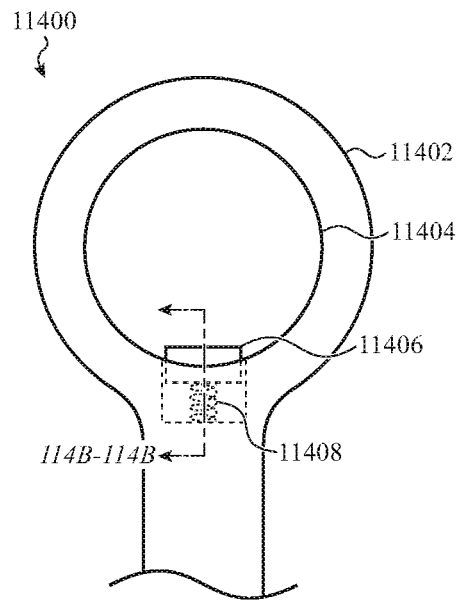

FIG. 114A illustrates another example tag retainer 11400 that may be attached to a tag. The tag retainer 11400 may include a body 11402, which may be formed from or include a polymer material or other compliant material (including combinations of materials). The tag retainer 11400 defines an opening 11404 for receiving a tag (e.g., the tag 300). The tag retainer 11400 may also include a latch member 11406 that extends into the opening 11404 and is biased outward by a spring member 11408. The latch member 11406 may be configured to be forced against a tag (e.g., the housing gap of a tag) to help retain the tag to the tag retainer 11400.

Figure 114B:
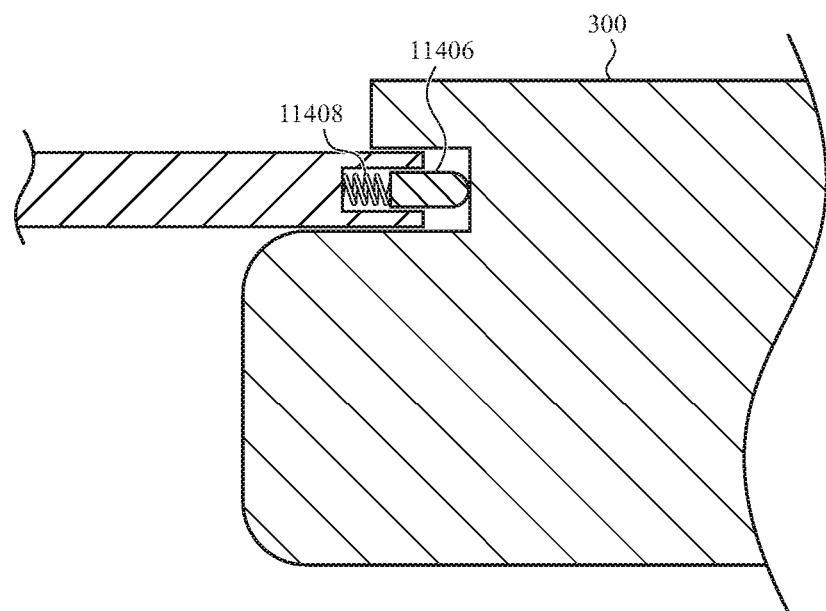

FIG. 114B is a partial cross-sectional view of the tag retainer 11400 of FIG. 114A, viewed along line 114B-114B in FIG. 114A, showing the tag retainer 11400 attached to the tag 300. As shown, the latch member 11406 is forced, by the spring member 11408, against a surface of the tag 300 within the housing gap. The force from the latch member 11406 may provide several advantages, similar to the accessory biasing mechanism described above. For example, the force from the latch member 11406 may increase the engagement force between the tag retainer 11400 and the tag 300 at the side opposite the latch member 11406, and it may increase the frictional force between the tag 300 and the tag retainer 11400, thereby preventing or limiting rotation, rattling, or other motion of the tag 300 relative to the tag retainer 11400.

The latch member 11406 and the tag 300 may have complementary shapes that allow the latch member 11406 to slide over the battery door of the tag 300 so that the tag 300 and the tag retainer 11400 can be attached and detached by a user. For example, if the tag retainer 11400 is pulled upwards (relative to the orientation shown in FIG. 114B), an interaction between the latch member 11406 and the tag 300 may force the latch member 11406 into its opening in the tag retainer 11400 to allow the tag retainer 11400 to be detached. The opposite operation may occur when the tag retainer 11400 is being attached to the tag 300.

Figure 115A:
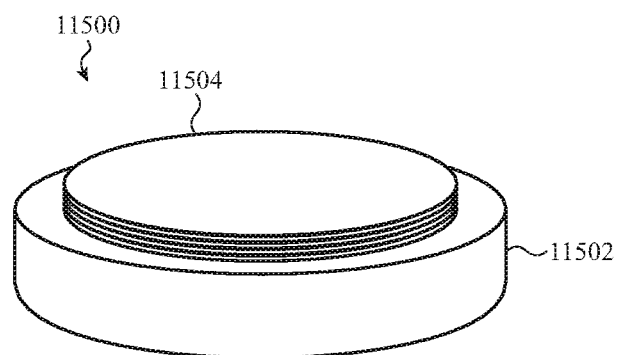

FIG. 115A illustrates an example tag 11500 that uses a threaded feature to attach to a tag retainer. The tag 11500 includes a main body portion 11502 (similar to the main body portion 302 of the tag 300), and a battery door that includes a threaded feature 11504. The threaded feature 11504 may be formed of metal, a polymer, or any other suitable material. In some cases, the threaded feature 11504 and the battery door are formed from the same unitary piece of material.

Figure 115B:
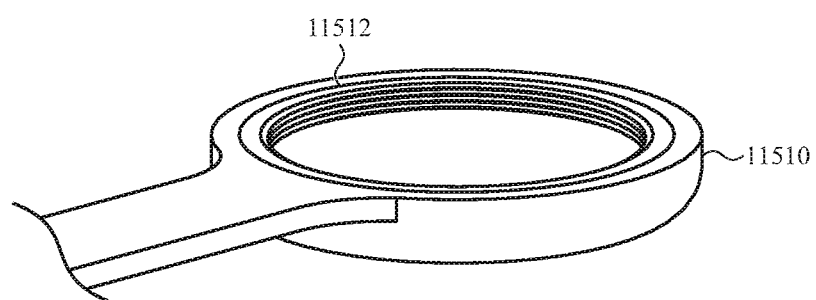
Figure 115C:
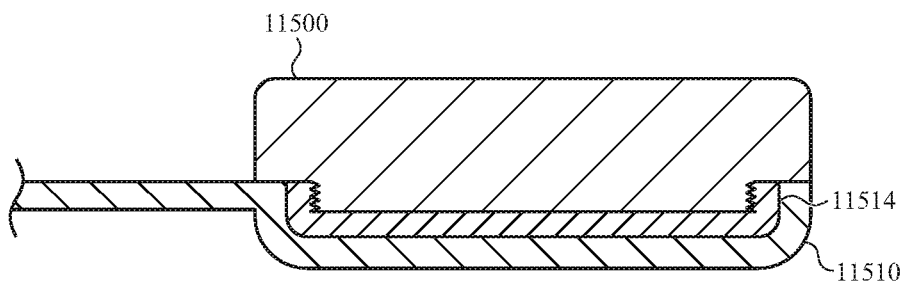

FIG. 115B illustrates an example tag retainer 11510 configured to attach to the tag 11500 by engaging the threaded feature 11504 of the tag 11500. The tag retainer 11510 may define an opening 11512 with threads that are configured to engage the threaded feature 11504 of the tag 11500. FIG. 115C is a partial cross-sectional view of the tag 11500 attached to the tag retainer 11510. In particular, the tag 11500 may be attached to or detached from the tag retainer 11510 by screwing or unscrewing the tag 11500 from the tag retainer 11510.

As shown in FIG. 115C, the tag retainer 11510 may include an insert 11514 that defines the threads. The insert 11514 may be formed of metal, a polymer, or any other suitable material or combination of materials. In some cases, the insert 11514 is stiffer than a material that surrounds the insert 11514 and/or defines the body of the tag retainer 11510. In other cases, the entire tag retainer 11510 is formed of a single piece of material and the threads are formed directly into the single piece of material.

Figure 115D:
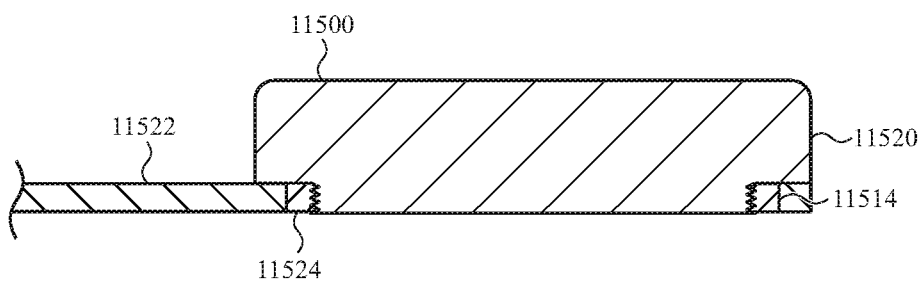

FIG. 115D illustrates an example tag 11520 and tag retainer 11522 that uses a similar threaded coupling configuration as the tag 11500 and tag retainer 11510. Whereas the tag retainer 11510 provided an enclosed recess that covered the tag 11500 (e.g., the battery door of the tag 11500), the tag retainer 11510 defines a through-hole that exposes the battery door of the tag 11520 when the tag 11520 is threaded into the threaded opening 11524 of the tag retainer 11522. In other respects, the tag 11520 and tag retainer 11522 may similar to the tag 11500 and tag retainer 11510, and for brevity those details may not be repeated here.

Figure 116A:
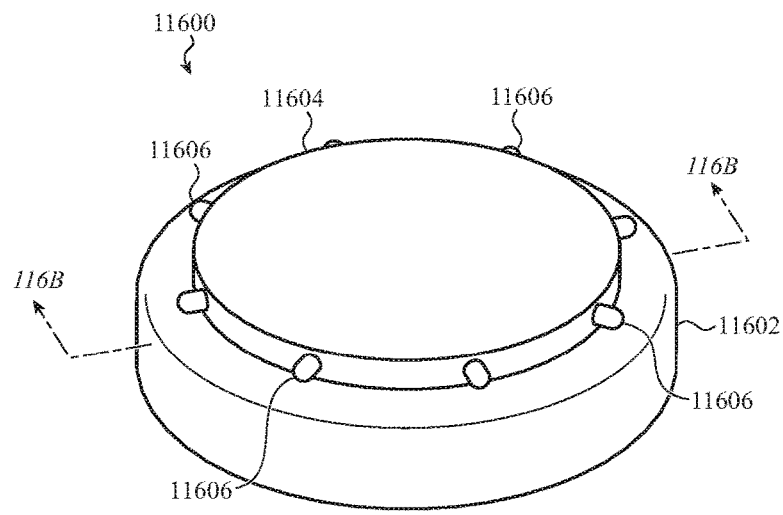

FIG. 116A illustrates an example tag 11600 that uses spring-loaded retention features to attach to an accessory such as a tag retainer. The tag 11600 includes a main body portion 11602 (similar to the main body portion 302 of the tag 300), and a battery door 11604. The battery door 11604, or any other suitable portion of the tag 11600, includes spring-loaded retention features 11606. As shown, the spring-loaded retention features 11606 are arranged about the periphery of a shaft-like portion of the battery door 11604.

Figure 116B:
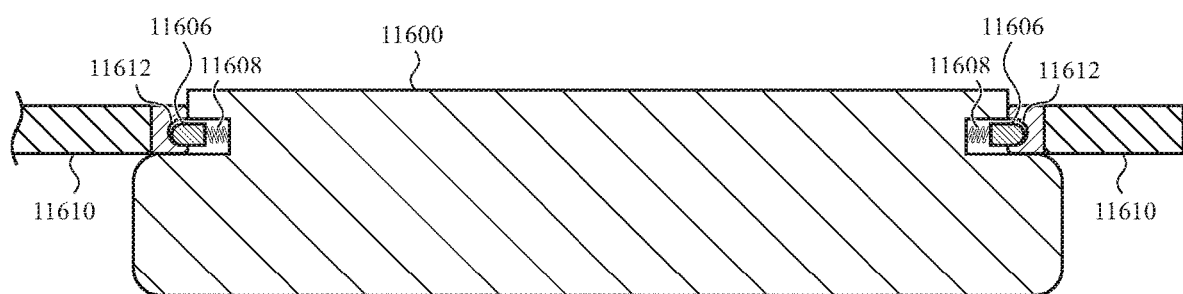

FIG. 116B is a partial cross-sectional view of the tag 11600 of FIG. 116A when attached to an accessory 11610, such as a tag retainer. The accessory 11610 may define one or more recesses 11612 that are configured to receive the spring-loaded retention features 11606. The recesses 11612 may be defined by a single continuous channel extending around the circumference of the opening of the accessory 11610. In other examples, there may be discrete recesses 11612, each configured to receive one of the spring-loaded retention features 11606. The recesses 11612 may be defined by an insert or other member that is attached to or otherwise integrated with another portion of the accessory (as shown). In other example implementations, the accessory is formed of a single piece of material and the recesses are defined in the single piece of material.

The tag 11600 may be attached to the accessory 11610 by aligning the tag 11600 with the opening in the accessory 11610 and pressing the tag 11600 and accessory 11610 together until the spring-loaded retention features 11606 slide or roll over the edge of the opening and into the recesses 11612 in the accessory 11610. The tag 11600 may be detached by reversing these operations, whereupon the spring-loaded retention features 11606 slide or roll out of the recesses 11612 to detach the tag 11600.

FIGS. 116A-116B show an example in which spring-loaded retention features are positioned on the tag and the recesses are positioned on the accessory. In other implementations, however, these positions may be reversed. For example, the spring-loaded retention features may be integrated with the accessory and the tag may define the recesses that engage the spring-loaded retention features to retain the tag and accessory together. In yet other examples, the tag and the accessory each include both recesses and spring-loaded retention features.

Figure 117A:
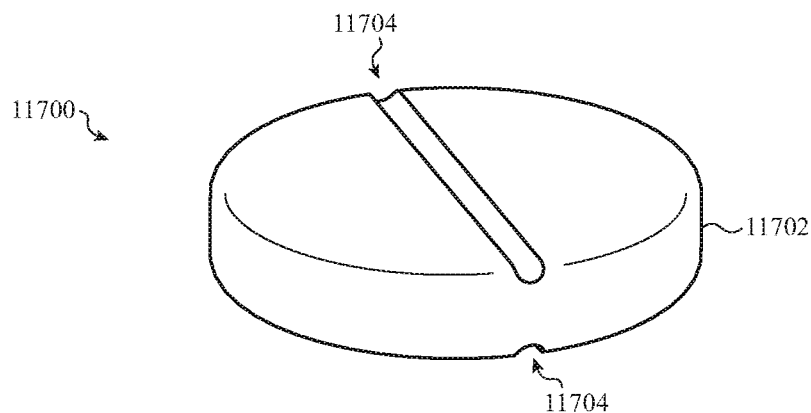

FIG. 117A illustrates an example tag 11700 having a different form factor than other tags described herein. In particular, the tag 11700 defines a body 11702 (which may include and/or be defined by any number of different housing components). The body 11702 defines two parallel channels 11704 on opposite sides of the body 11702. As shown, the channels 11704 extend along a diametrical dimension of the tag 11700, though other positions and/or orientations of the channels 11704 are also possible. In some cases, the channels 11704 are straight (as shown), while in other cases they may be curved or have any other suitable shape. The tag 11700 may be configured to attach to a tag retainer 11710 via the channels 11704, as shown in FIG. 117B.

Figure 117B:
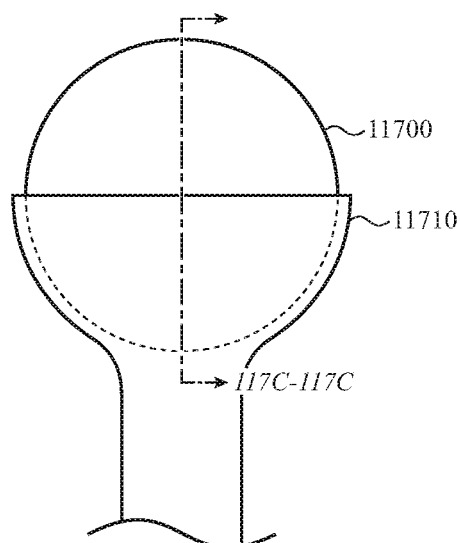
Figure 117C:
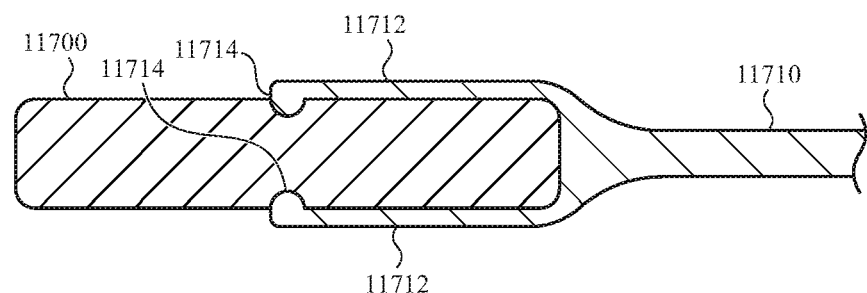

FIG. 117C is a partial cross-sectional view of the tag 11700 and tag retainer 11710 of FIG. 117B, viewed along line 117C-117C in FIG. 117B. The tag retainer 11710 includes two arms 11712 that extend around at least part of the tag 11700 so that engagement ends 11714 of the arms 11712 extend into and engage the channels 11704. The arms 11712 may be biased towards one another (e.g., with a spring member inside the tag retainer 11710) to force the engagement ends 11714 into the channels 11704 and help retain the tag 11700 to the tag retainer 11710.

Figure 118A:
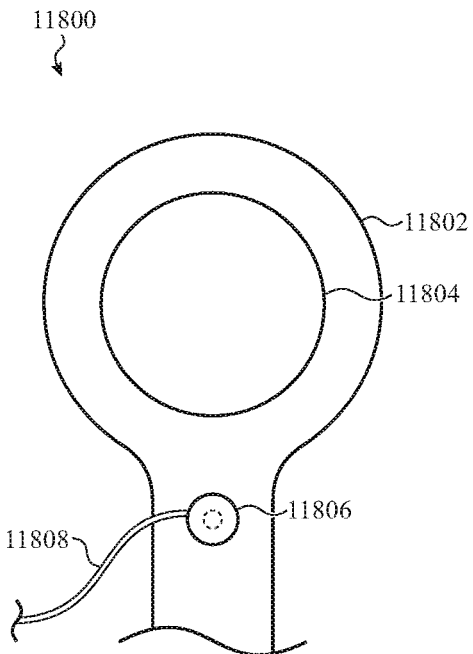
Figure 118B:
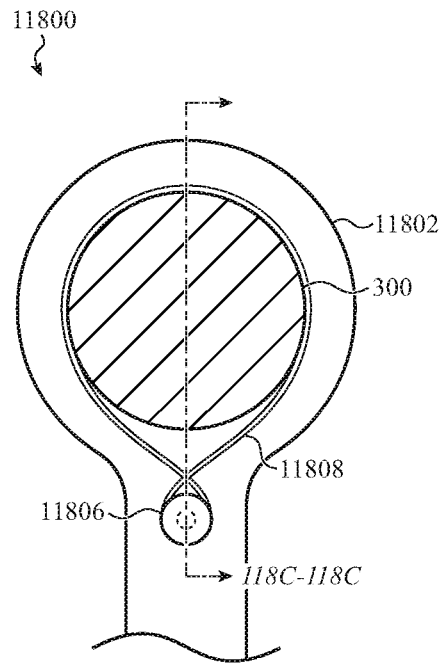
Figure 118C:
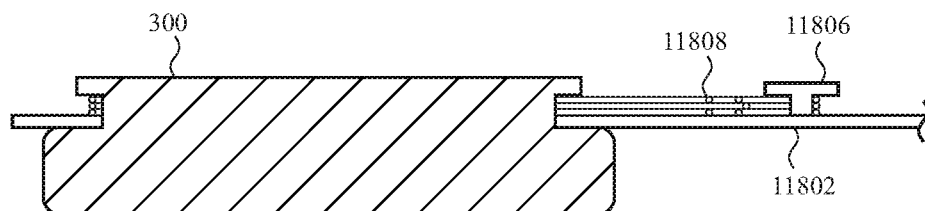

FIGS. 118A-118C illustrate an example tag retainer 11800. The tag retainer 11800 may include a body 11802, which may be formed from or include a polymer material or other compliant material (including combinations of materials), a cord retainer 11806, and a cord 11808. The body 11802 may define an opening 11804 for receiving at least a portion of a tag (e.g., the tag 300). The cord 11808 is configured to wrap around a portion of a tag to retain the tag to the tag retainer 11800.

FIG. 118B illustrates the tag retainer 11800 attached to the tag 300. In particular, the tag 300 is positioned in the opening 11804, and the cord 11808 is wrapped around the tag 300 (e.g., in a housing gap of the tag 300). The cord 11808 may also be wrapped around and secured to the cord retainer 11806. FIG. 118C is a partial cross-sectional view of the tag retainer 11800 of FIG. 118B with the tag 300 attached thereto, viewed along line 118C-118C in FIG. 118B. FIG. 118C illustrates how the cord 11808 wraps around the tag 300 (in the housing gap) and the cord retainer 11806 to retain the tag 300 to the tag retainer 11800. In particular, the size and/or location of the cord 11808 around the tag 300 and relative to the opening 11804 prevents the tag 300 from detaching by passing back through the opening 11804 (e.g., in a downward direction as oriented in FIG. 118C).

The cord retainer 11806 may have a clip, fastener, or other mechanism to which the free end of the cord 11808 may be secured after the cord 11808 is wrapped around the tag 300. The cord 11808 may be secured to the cord retainer 11806 in other ways instead of or in addition to the clip, fastener, or other mechanism. For example, the cord retainer 11806 may have a flange that defines an undercut region, and the cord 11808 may have a size and length such that the cord 11808 is compressed in the undercut region when the cord 11808 is wrapped around the tag 300 (e.g., similar to an envelope closure mechanism). As another example, the cord 11808 may be securely tied and/or knotted to the cord retainer 11806.

Figure 119A:
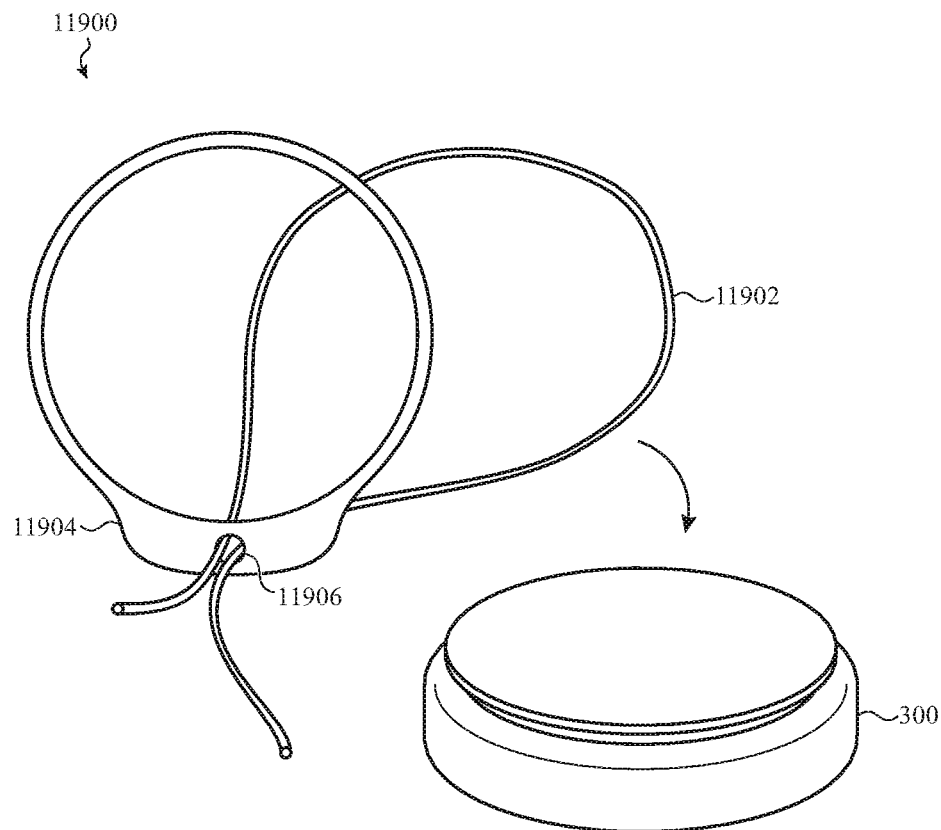
Figure 119B:
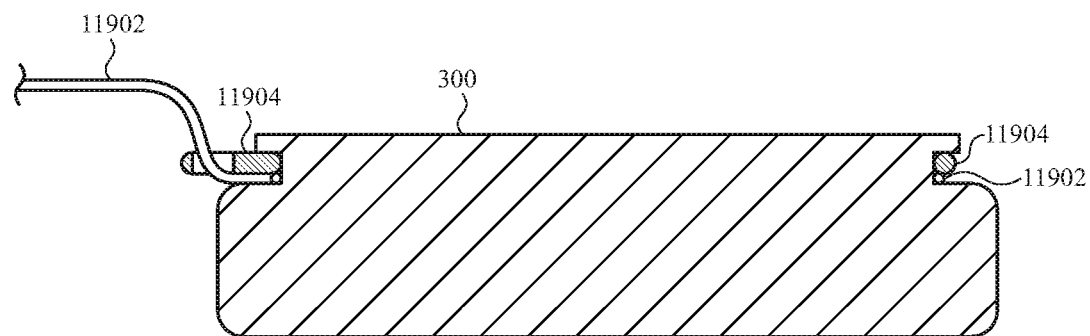

FIGS. 119A-119B illustrate another example tag retainer 11900. The tag retainer 11900 includes a cord 11902 that is configured to wrap at least partially around a tag in a housing gap, and a retaining ring 11904 that is configured to capture and retain the cord 11902 in the housing gap. The retaining ring 11904 may define an opening 11906 through which the cord 11902 may pass to assist in retaining the cord 11902 to the retaining ring 11904. The free ends of the cord 11902 may be used to attach the tag to other objects, such as by tying the free ends to the object.

FIG. 119B is a partial cross-sectional view of the tag retainer 11900 of FIG. 119A, shown attached to the tag 300. The cord 11902 may be wrapped at least partially around the tag 300 in the housing gap of the tag 300. The retaining ring 11904 may be installed in the housing gap such that it forces the cord 11902 against the tag 300 and retains the cord 11902 in the housing gap. The retaining ring 11904 and the cord 11902 may be sized such that when they are both in the housing gap, they are pressed together and against the tag 300. The resulting friction between the tag 300, the cord 11902, and the retaining ring 11904 hold the cord 11902 and retaining ring 11904 in place.

While the position of the retaining ring 11904 in the housing gap helps prevent the cord 11902 from slipping over the top of the battery door of the tag 300, the opening 11906 in the retaining ring 11904 helps prevent the cord 11902 from unwinding from around the tag 300. Without passing the cord 11902 through the opening 11906, for example, a pulling or tugging motion on the cord 11902 could pull the cord 11902 out of the housing gap despite the presence of the retaining ring 11904 in the housing gap. With the cord 11902 situated in the opening 11906, pulling or tugging forces on the free ends of the cord 11902 will not tend to pull the cord out of the housing gap. Structures or techniques other than the opening 11906 may also be used to prevent pulling forces from detaching the cord.

Figure 120A:
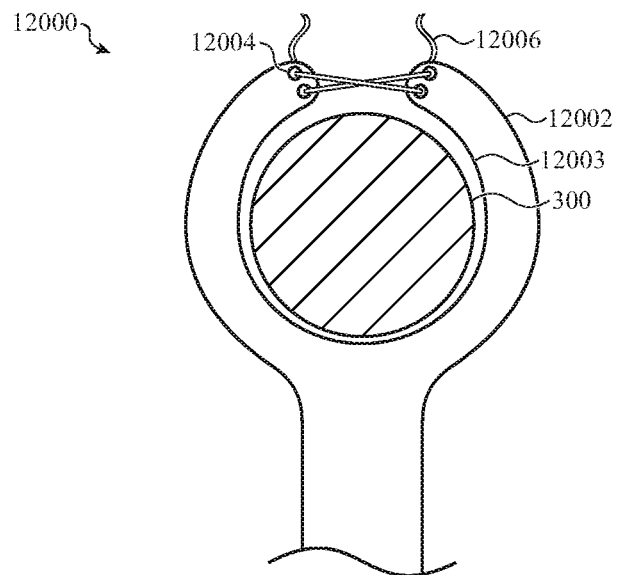
Figure 120B:
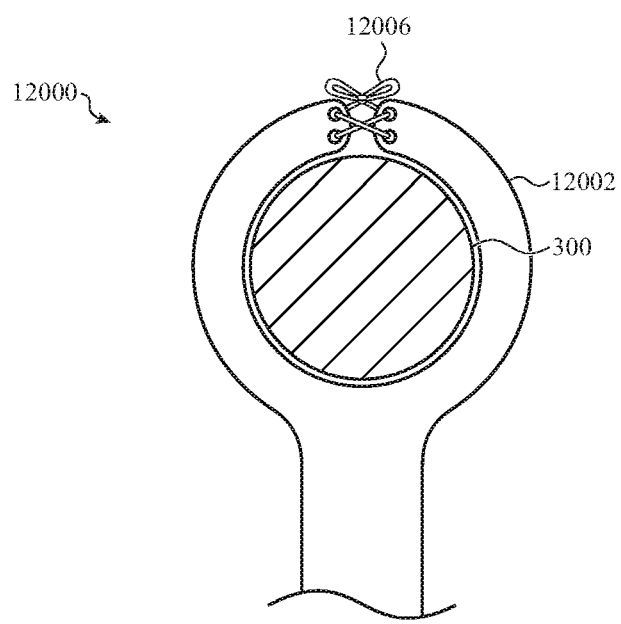

FIGS. 120A-120B illustrate another example tag retainer 12000. The tag retainer 12000 may include a body 12002, which may be formed from or include a polymer material or other compliant material (including combinations of materials). The body 12002 may define an opening 12003 for receiving the tag 300, and a cord 12006 that passes through cord openings 12004 in the body 12002. In order to attach the tag 300 to the tag retainer 12000, the cord 12006 may be untied so that the opening 12003 can be expanded and the tag 300 can be inserted into the opening 12003. To secure the tag 300, the cord 12006 may be tied together or otherwise secured, as shown in FIG. 120B, to reduce the size of the opening 12003 and hold the body 12002 in the housing gap of the tag 300. The tag 300 may be removed by untying or otherwise freeing the cord 12006 to allow the opening 12003 to expand for easy removal of the tag 300.

FIGS. 121A-121B illustrate another example tag retainer 12100, which is similar to the tag retainer 12000 except that it uses a latching mechanism to retain the free ends of the body together. In particular the tag retainer 12100 includes a body 12102, which may be formed from or include a polymer material or other compliant material (including combinations of materials). The body 12102, and in particular arms 12104 of the body 12102, define an opening 12103 for receiving the tag 300. The free ends of the arms 12104 define complementary latching features 12106. As shown in FIG. 121B, which is an end view of the tag retainer 12100, viewed along line 121B-121B in FIG. 121A, the latching features 12106 may be engaged with one another to prevent the arms 12104 from separating, thereby holding the arms 12104 together and in place in a housing gap of a tag. One or both of the arms 12104 may be biased in a position that forces the latching features 12106 into secure engagement. For example, the right-hand arm 12104-1 (FIG. 121B) may be biased upwards and to the right, as indicated by arrows 12108, 12110, respectively, relative to the left-hand arm 12104-2. This biasing configuration forces the latching mechanisms into secure engagement, thereby maintaining the arms 12104 in a closed and latched configuration to help retain the tag to the tag retainer 12100.

Many of the example tag retainers described herein are shown as having bodies with substantially uniform thicknesses (e.g., flat, plate- or sheet-like configurations). This is merely one possible configuration for the bodies, and in some cases the bodies may have different shapes and configurations, including shapes that have different thicknesses at different parts of the bodies. FIG. 122 is a partial cross-sectional view of an example tag retainer 12200 attached to the tag 300, illustrating an example of a tag retainer with a body having a varying thickness. In particular, the tag retainer 12200 defines an area 12202 of increased thickness proximate the opening that receives the tag 300 (with the greater thickness relative to another area of the tag retainer, such as a handle, strap, or the like). The area of increased thickness is configured to reduce the size of and/or access to the joint between the tag retainer 12200 and the tag 300, thereby reducing the likelihood of the tag 300 becoming detached due to snagging or other accidental contact. In some cases, the size and/or shape of the increased thickness region is configured so that the transition between the exterior surface of the tag retainer 12200 and the exterior surface of the tag 300 is a continuous curve or line (without substantial gaps, discontinuities, seams, or other areas that may snag on clothes or other objects). As shown in FIG. 122, for example, the increased thickness region defines smooth, continuous curved transitions at the top and bottom interfaces 12204, 12206 between the tag 300 and the tag retainer 12200.

While FIG. 122 shows one example tag retainer with an area of increased thickness (to reduce the possibility of accidental detachment of the tag retainer), the same and/or similar configuration may be applied to any other tag retainer described herein. In some cases, the area of increased thickness also results in the tag retainer being stiffer around the opening that receives the tag, which may further increase the strength and/or security of the attachment between the tag and the tag retainer.

The tag retainers shown in the figures are often depicted with a strap or elongated attachment portion (e.g., the attachment portion 7004, FIG. 70A, the strap 7411, FIG. 74A). This is merely one example configuration for the tag retainers, however. In some cases, a tag retainer may not include a strap or strap-like feature, and in some cases includes another type of structure to facilitate attachment of the tag retainer to another object. For example, instead of a strap, a tag retainer may have a flat, circular flange to allow the tag retainer to be adhered, sewn, fused (e.g., via laser or ultrasonic welding), or otherwise attached to another object. Further, straps may have configurations other than those shown. For example, straps may have circular or other generally non-flat configurations, and may resemble strings, cords, cables, or the like. Thus, for each of the tag retainers shown herein, it will be understood that the mechanism for attaching the tag retainer to the tag (e.g., the particular configurations of springs, body materials, stiffeners, clips, cords, and the like) may be incorporated in any type of object to facilitate tag attachment. For example, the portion of the body 10202 (FIGS. 102A-102C) that defines the opening 10204 (and receives a tag) may be incorporated directly into the material of a purse, backpack, suitcase, briefcase, or the like. In such cases, a distinct strap or other attachment feature need not be provided.

Figure 123A:
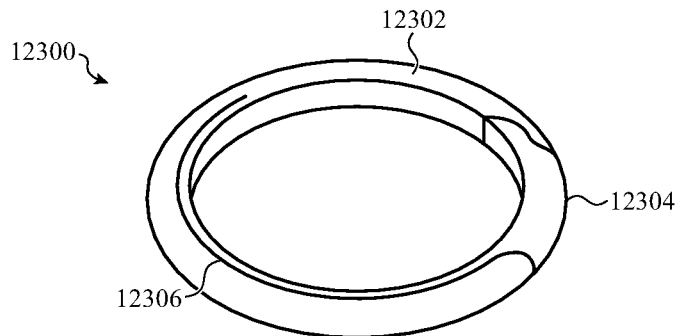
Figure 123B:
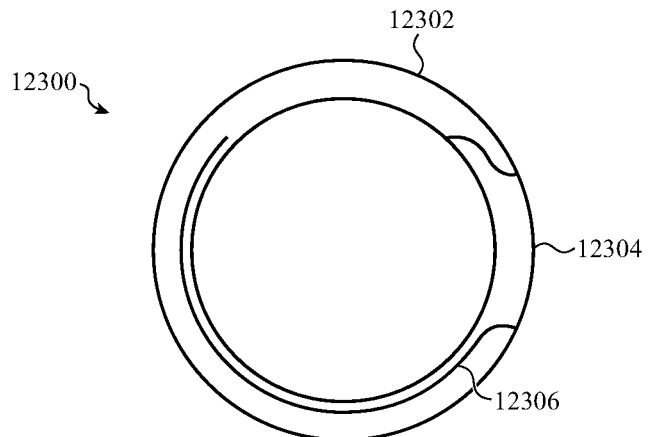
Figure 123C:
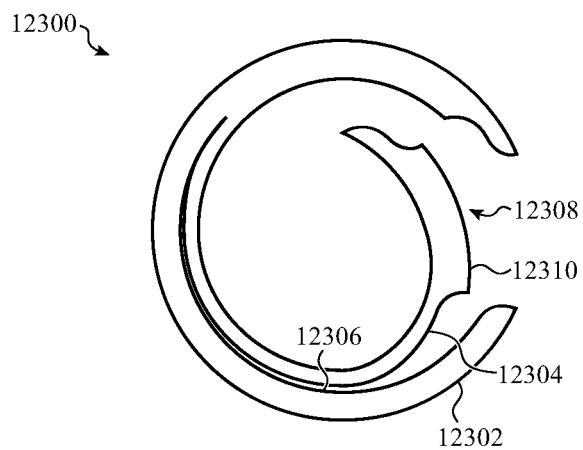

As noted above, various tag retainers described herein may be used to attach a wirelessly locatable tag to another object, such as bags, purses, keys, and so forth. In some cases, tag retainers may be provided with clips that facilitate simple and convenient attachment to such objects. FIGS. 123A-123C illustrate one such example clip 12300. For example, the clip 12300 may be attached to the attachment portion 6904 of the tag retainer 6900 (FIGS. 69A-69C) by looping the attachment portion 6904 through the central opening of the clip 12300.

The clip 12300 may be formed of a unitary piece of material, such as a single piece of metal. The clip 12300 may define an outer portion 12302 and an inner portion 12304. The outer and inner portions 12302, 12304 may be defined by forming a slit 12306 into the material of the clip 12300. The slit 12306 may be formed in any suitable manner, such as electrical discharge machining (EDM), plasma cutting, laser cutting, conventional machining or milling, or the like. The slit 12306 may define a small gap, such as equal to or less than about 200 microns, 100 microns, 50 microns, or 10 microns. The clip 12300 may be formed of any suitable material, such as metal (e.g., titanium, steel, aluminum, an alloy, etc.), polymer, carbon fiber, or the like.

The inner portion 12304 may be configured to bend or flex relative to the outer portion 12302 in response to an opening force being applied to the inner portion 12304. For example, FIG. 123C illustrates an opening force 12308 being applied to an actuation region 12310 of the inner portion 12304. The opening force 12308 causes the inner portion 12304 to flex or bend to define a gap between the inner and outer portions 12304, 12302 that allows the clip 12300 to be attached to other objects (e.g., loops on bags, holes in keys, etc.). The inner portion 12304 may be biased towards a closed position (shown in FIGS. 123A and 123B), such that when the opening force 12308 is removed, the inner portion 12304 returns to the closed position, thereby retaining the clip 12300 to other objects (and/or retaining the objects to the clip 12300).

Figure 124A:
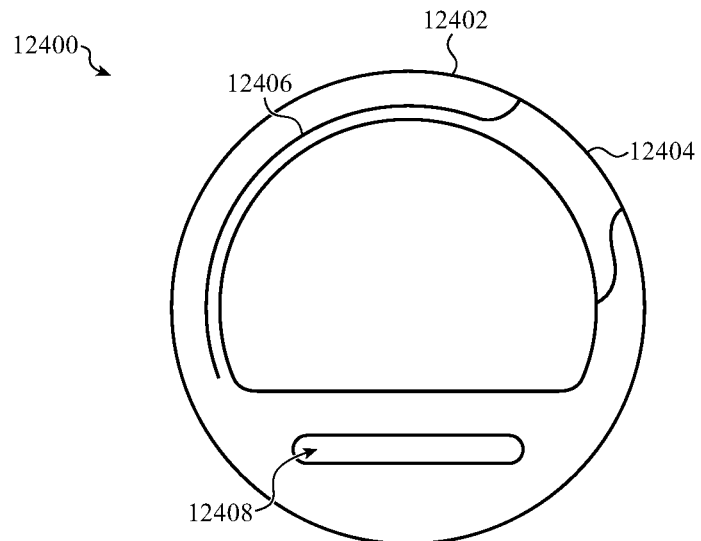
Figure 124B:
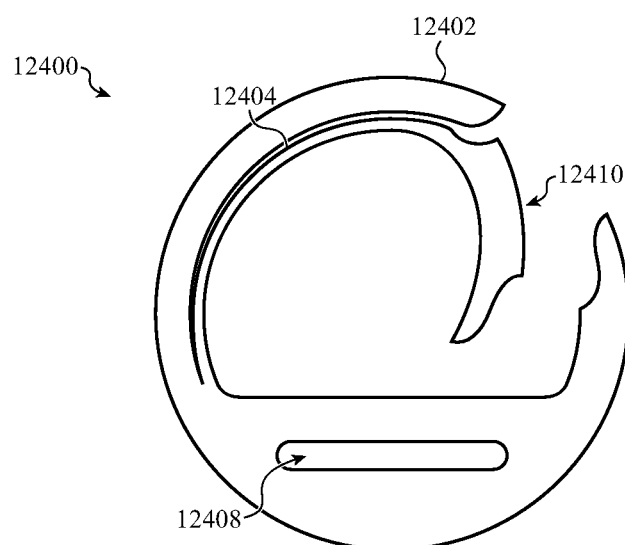

FIGS. 124A-124B illustrate another example clip 12400. The clip 12400 is similar to the clip 12300 in material, function, and manufacturing, but includes an opening 12408 for attaching to a tag retainer. For example, the attachment portion 6904 of the tag retainer 6900 (FIGS. 69A-69C) may be looped through the opening 12408 to attach the clip 12400 to the tag retainer 6900.

The clip 12400 may define an outer portion 12402 and an inner portion 12404. The outer and inner portions 12402, 12404 may be defined by forming a slit 12406 into the material of the clip 12400. The slit 12406 may be formed in any suitable manner, such as electrical discharge machining (EDM), plasma cutting, laser cutting, conventional machining or milling, or the like. The slit 12406 may define a small gap, such as equal to or less than about 200 microns, 100 microns, 50 microns, or 10 microns.

The inner portion 12404 may be configured to bend or flex relative to the outer portion 12402 in response to an opening force being applied to the inner portion 12404. For example, FIG. 124B illustrates an opening force 12410 being applied to the inner portion 12404, causing the inner portion 12404 to flex or bend to define a gap between the inner and outer portions 12404, 12402 that allows the clip 12400 to be attached to other objects (e.g., loops on bags, holes in keys, etc.). The inner portion 12404 may be biased towards a closed position (shown in FIG. 124A), such that when the opening force 12410 is removed, the inner portion 12404 returns to the closed position, thereby retaining the clip 12400 to other objects (and/or retaining the objects to the clip 12400).

Figure 125A:
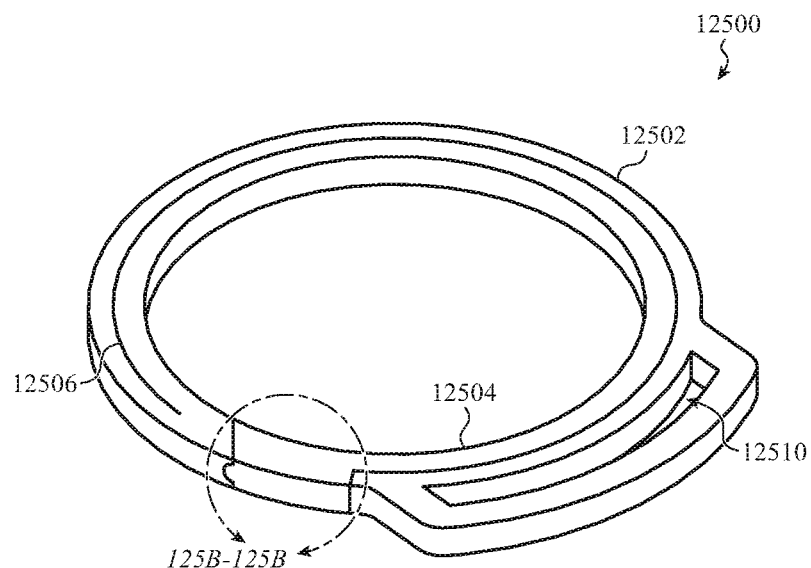
Figure 125B:
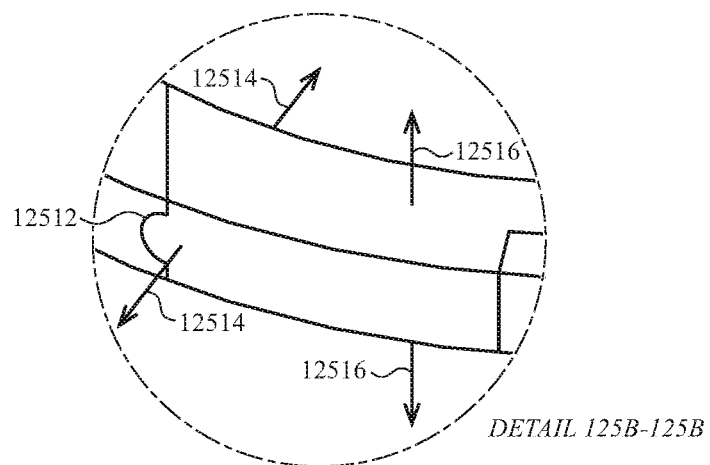

FIGS. 125A-125B illustrate another example clip 12500. The clip 12500 is similar to the clip 12400 in material, function, and manufacturing, and includes an opening 12510 for attaching to a tag retainer. For example, the attachment portion 6904 of the tag retainer 6900 (FIGS. 69A-69C) may be looped through the opening 12510 to attach the clip 12500 to the tag retainer 6900.

The clip 12500 may define an outer portion 12502 and an inner portion 12504. The outer and inner portions 12502, 12504 may be defined by forming a slit 12506 into the material of the clip 12500. The slit 12506 may be formed in any suitable manner, such as electrical discharge machining (EDM), plasma cutting, laser cutting, conventional machining or milling, or the like. The slit 12506 may define a small gap, such as equal to or less than about 200 microns, 100 microns, 50 microns, or 10 microns.

The inner portion 12504 may be configured to bend or flex relative to the outer portion 12502 in response to an opening force being applied to the inner portion 12504. The inner portion 12504 may be biased towards a closed position (shown in FIG. 125A), such that when an opening force is removed, the inner portion 12504 returns to the closed position, thereby retaining the clip 12500 to other objects (and/or retaining the objects to the clip 12500).

The clip 12500 may also define a lateral guide feature that inhibits the inner portion 12504 from deflecting laterally with respect to adjacent portions of the clip 12500. For example, FIG. 125B is a detail view of the clip 12500, showing the area 125B-125B in FIG. 125A. The clip 12500 may include a lateral guide 12512 that allows the inner portion 12504 to move inward, along the direction indicated by arrows 12514, while inhibiting out-of-plane motion along the direction indicated by arrows 12516. As shown, the lateral guide 12512 is defined by a rail protruding from an end of the inner portion 12504 and a corresponding groove formed in the surface of the clip 12500 opposite the rail. In other examples, the inner portion 12504 may include the groove and the rail may protrude from the location where the groove is shown in FIG. 125B.

Figure 126A:
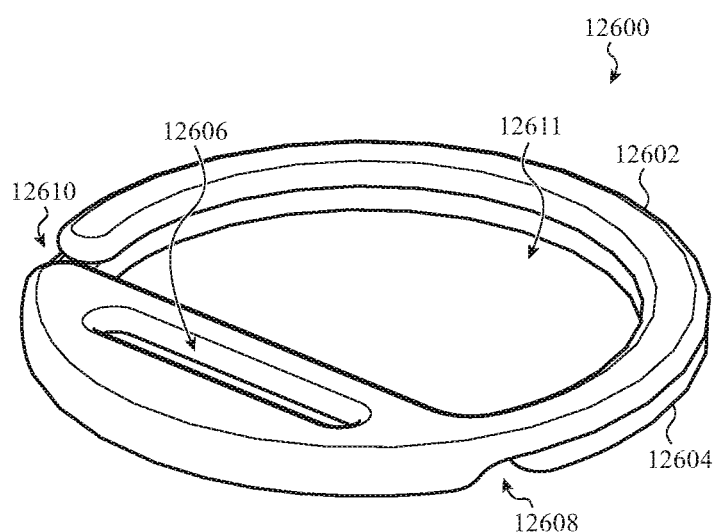
Figure 126B:
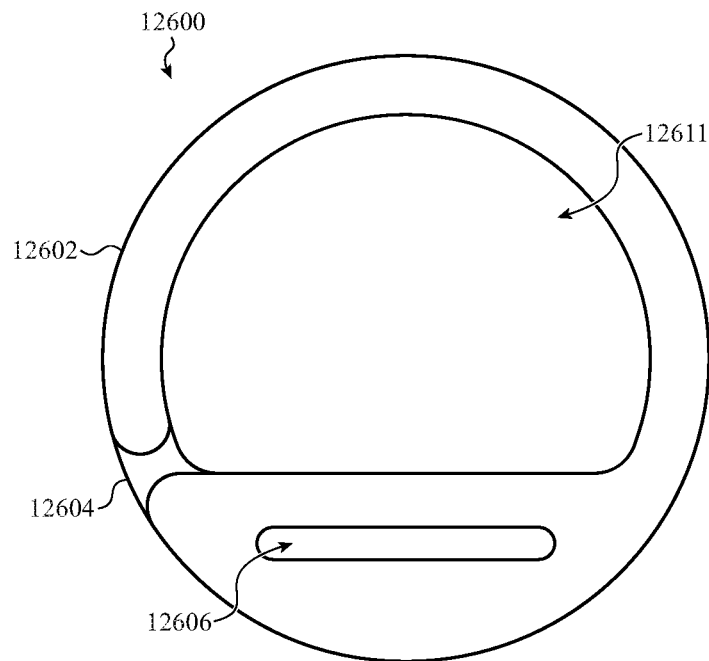
Figure 126C:
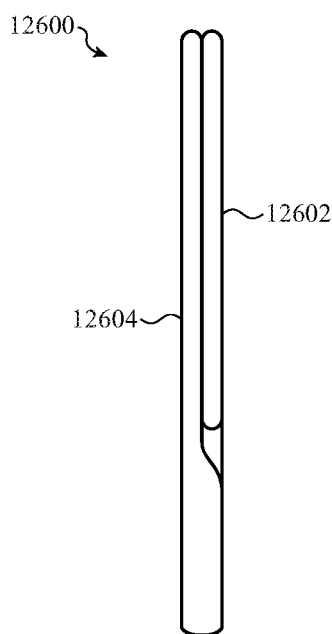

FIGS. 126A-126C illustrate perspective, front, and side views, respectively, of an example clip 12600 for attaching to a tag retainer. The clip 12600 may be formed of a unitary piece of material, such as a single piece of metal. The clip 12600 may define an opening 12606 for attaching to a tag retainer. For example, the attachment portion 6904 of the tag retainer 6900 (FIGS. 69A-69C) may be looped through the opening 12606 to attach the clip 12600 to the tag retainer 6900.

The clip 12600 may define a first ring member 12602 and a second ring member 12604, which may be biased against each other. The first and second ring members 12602, 12604 may operate in a manner similar to a split ring or key ring. For example, objects such as keys, straps, fobs, or the like may be attached to the clip 12600 by spreading the first and second ring members 12602, 12604 apart (e.g., at one of the ends 12608, 12610) and threading the object along one of the ring members until it becomes linked to the clip 12600. The clip 12600 may be formed of any suitable material, such as metal (e.g., titanium, steel, aluminum, an alloy, etc.), polymer, carbon fiber, or the like.

Figure 127A:
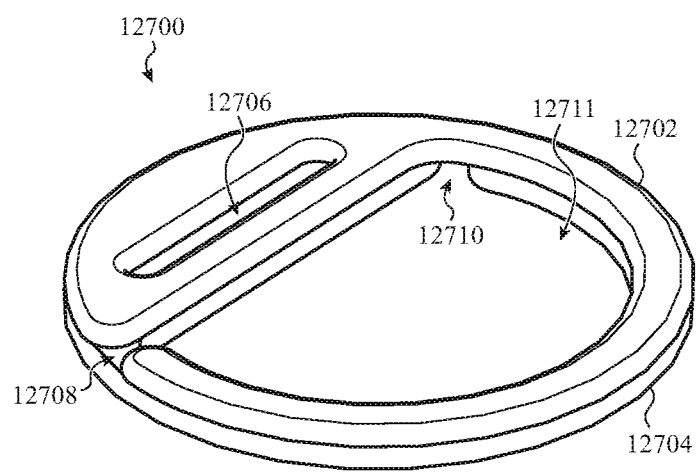
Figure 127B:
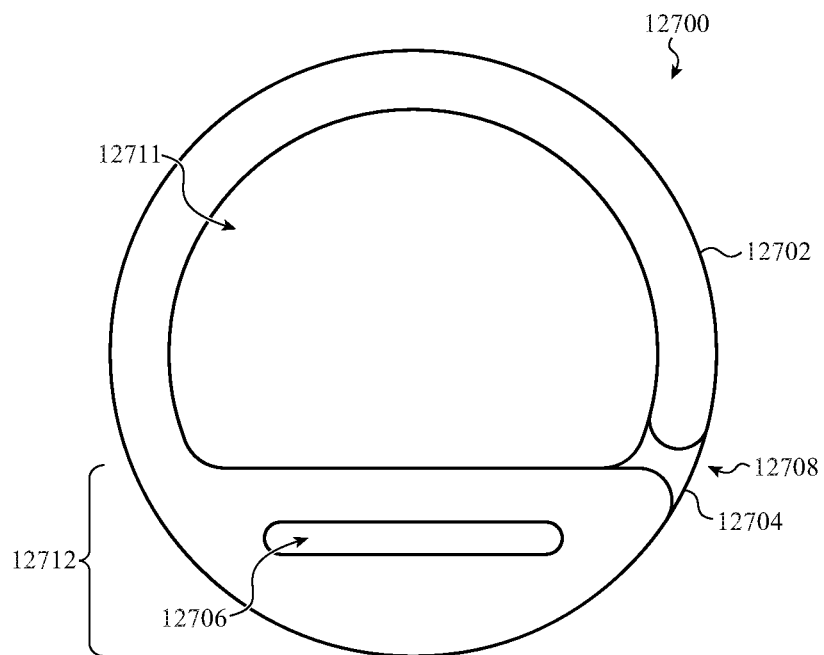
Figure 127C:
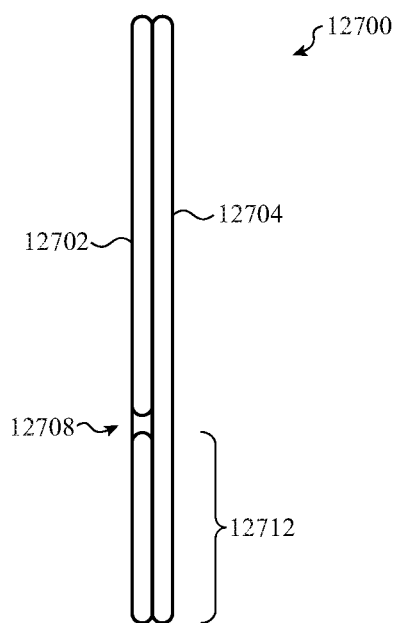

FIGS. 127A-127C illustrate perspective, front, and side views, respectively, of an example clip 12700 for attaching to a tag retainer. The clip 12700 may be similar in materials and function to the clip 12600, but instead of being a unitary piece of material, the clip 12700 may be formed by joining two members together. For example, a first member 12702 may be joined to a second member 12704 along a base region 12712. The first member 12702 may define a first opening 12708 and the second member 12704 may define a second opening 12710 to allow the clip 12700 to operate in a manner similar to a split ring or key ring, as described above with respect to the clip 12600. The clip 12700 may be formed of any suitable material, such as metal (e.g., titanium, steel, aluminum, an alloy, etc.), polymer, carbon fiber, or the like. The first and second members 12702, 12704 may be attached to one another in any suitable manner, such as via welding, soldering, brazing, adhering (e.g., with an epoxy or other adhesive), or the like.

The clip 12700 may define an opening 12706 for attaching to a tag retainer. For example, the attachment portion 6904 of the tag retainer 6900 (FIGS. 69A-69C) may be looped through the opening 12706 to attach the clip 12700 to the tag retainer 6900.

FIG. 128 illustrates a perspective view of an example ring 12800 for attaching to a tag retainer. The ring 12800 may be a unitary structure that defines a first opening 12804 and a second opening 12806. The second opening 12806 may be configured for attaching to a tag retainer. For example, the attachment portion 6904 of the tag retainer 6900 (FIGS. 69A-69C) may be looped through the second opening 12806 to attach the ring 12800 to the tag retainer 6900. The first opening 12804 may be used to attach the ring 12800 to another object. For example, a strap, clip, carabiner, zip tie, rope, Velcro strap, or any other suitable member or object may be inserted through the first opening 12804 to attach the ring 12800 to another object. The ring 12800 may be formed of any suitable material, such as metal (e.g., titanium, steel, aluminum, an alloy, etc.), polymer, carbon fiber, or the like.

As described herein, the wirelessly locatable tag may be attached to and/or held in one of a variety of accessories or tag retainers. For example, as described above with respect to FIGS. 69A-128, a lanyard, key fob, luggage tag, belt, band, or other accessory may be adapted to hold or secure the wirelessly locatable tag and facilitate attachment to another object or article. Also, as previously described with respect to some embodiments, an accessory like a lanyard may include one or more snaps or other fasteners that may be engaged to secure, retain, or couple to the wirelessly locatable tag. One or more fasteners like a snap or button may also be used to secure the lanyard or accessory to another object like a piece of luggage, article of clothing, or other personal item. For purposes of the following description, the term "snap" may be used to refer a snap assembly or snap module, which may be formed from two or more subassemblies or modules. For purposes of the following description, the term "wireless tag" may be used to refer to a wirelessly locatable tag or tag, which has been described in detail with respect to various other embodiments, herein.

FIGS. 129A-129C depict an example accessory that may include a snap or other type of fastener. In particular, FIGS. 129A-129C depict a lanyard 12900 (also referred to as a tag retainer or holder) that is configured to hold a wireless tag 12950. The wireless tag 12950 may be similar to the other wirelessly locatable tags or tags described with respect to other embodiments and examples provided herein. As previously described, it may be beneficial to attach the wireless tag 12950 to an article like a piece of luggage, a backpack, a satchel, or other personal item. The lanyard 12900 includes an attachment feature or attachment portion, specifically an attachment ring 12904, that may be made from a metal material and may be configured to be attached to a strap or other element of the personal item. The lanyard 12900 also includes a pocket 12906 (also referred to as a recess, retaining portion, or tag receptacle portion) or other tag-retaining feature that is configured to hold the wireless tag 12950 securely in the lanyard 12900, which may allow for wireless tracking of the personal item attached to the lanyard 12900 and wireless tag 12950.

As shown in FIG. 129C, the wireless tag 12950 may also be removed from the lanyard 12900 by releasing the snap 12902, which allows the pocket 12906 to be opened. As described in more detail below, the snap 12902, also referred to as a snap assembly, may be formed from two assemblies or modules (e.g., male and female assemblies) that are configured to engage each other when pressed together by the user's fingers. When the snap 12902 is closed or engaged, the snap 12902 secures elements of the lanyard 12900 together, thereby closing the pocket 12906. As described herein, the elements that are secured together or attached by the snap 12902 may be referred to generically as a first element 12910 and a second element 12912. In the present example, the first element 12910 and the second element 12912 correspond to different straps or regions of the lanyard 12900 that are secured together by the snap 12902. As shown in FIG. 129C, the snap 12902 may be separated by hand, which allows for the separation of the first element 12910 from the second element 12912 and allows for the pocket 12906 to be opened and allows the wireless tag 12950 to be removed.

FIGS. 130A-130H, 131A-131H, 132A-132C, and 133A-133B depict example fasteners that may be used for an accessory of the wireless tag (e.g., a lanyard), as described herein. In particular, the following embodiments are directed to a mechanical snap fastener that is adapted to attach two elements together using a mechanical engagement between two snap assemblies or modules. As described herein, a snap fastener may be generally referred to as a "snap" and may include two mating snap assemblies or modules, which may be referred to separately as a male module/assembly and a female module/assembly. The female and male modules/assemblies of the snap are configured to couple to one another in order to form a mechanical interlock that is secure enough to remain engaged during ordinary use. The female and male assemblies/modules of the snap may also be disengaged by hand or without the use of special tools.

Figure 130A:
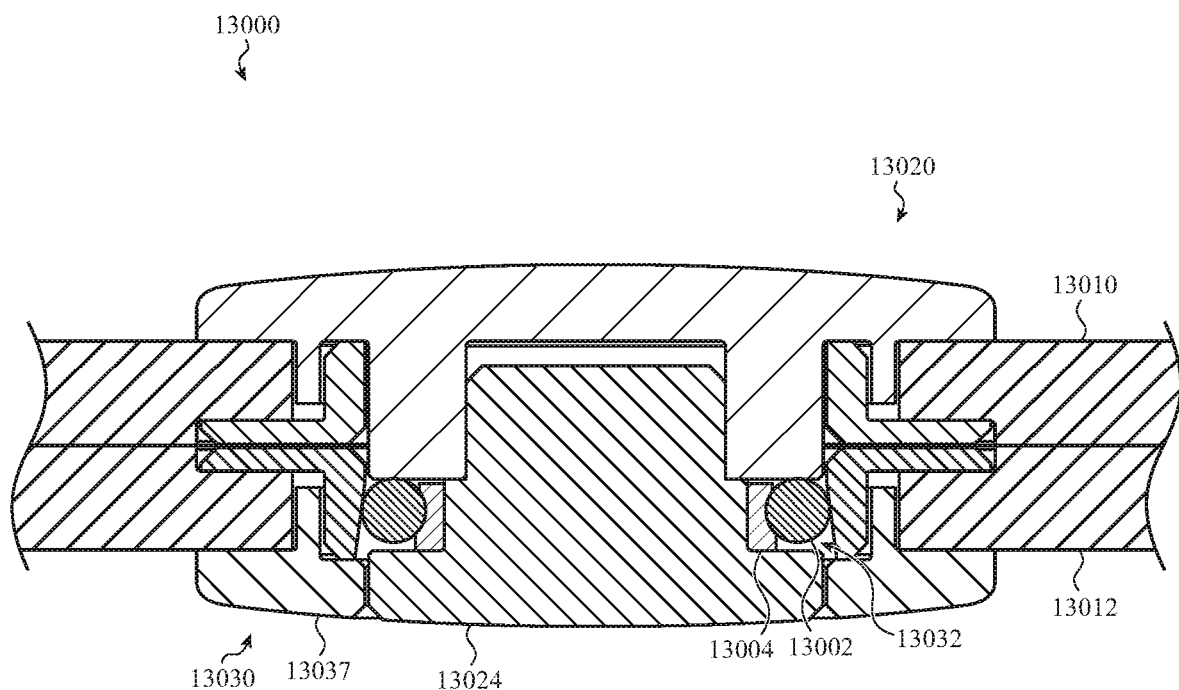
Figure 130B:
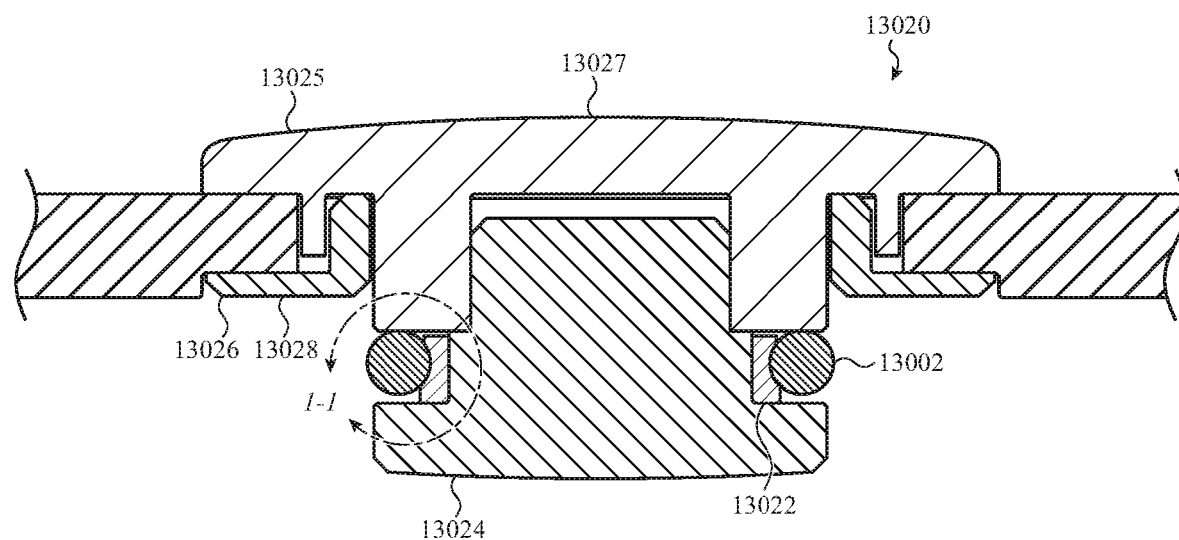
Figure 130C:
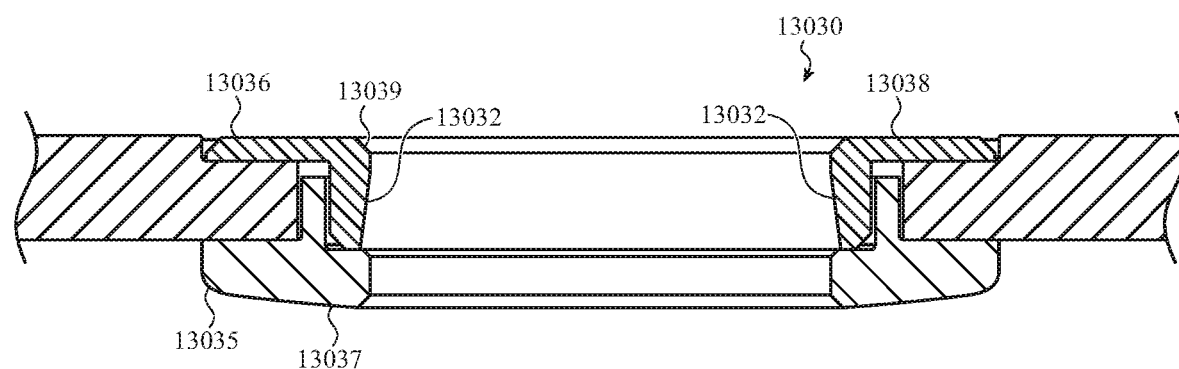

In the embodiment depicted in FIGS. 130A-130C, the snap 13000, also referred to as a snap assembly, is used to couple together two accessory elements generally referred to as a first element 13010 and a second element 13012. In some cases, the first element 13010 is a first portion of a strap and the second element 13012 is a second portion of the same strap or another strap of the accessory. In some cases, the first element 13010 and second element 13012 are separate pieces of different components that are coupled together by the snap 13000. In other cases, the first element 13010 and the second element 13012 are different portions of a common component that are coupled together by the snap 13000. Example first and second elements are also described above with respect to the lanyard 12900 of FIGS. 129A-129C having a first element 12910 and a second element 12912.

The first element 13010 and the second element 13012 may form part of an accessory that may be generally referred to as a "soft good." The soft good may be formed at least in part from a pliable or soft material that forms part of the lanyard, key fob, luggage tag, belt, band, or other accessory. The soft good may be formed from a textile, including a woven fabric or other type of cloth made from a network or matrix of fibers, whether natural or synthetic. The soft good may also be formed from a natural or synthetic sheet of a pliable material including, for example, natural rubber, urethane, polypropylene, polyethylene, nylon, silicone, fluoroelastomer, or a variety of other polymers. In some cases, the soft good may be formed from a composite material that includes multiple different materials and may also include non-pliable or rigid materials. The soft good may, for example, include one or more metal components that define clasps, rings, buckles, or other mechanical elements. In some implementations, the first element 13010 and the second element 13012 of the soft good are made from a laminate material having multiple layers that are bonded together. The outer layers may be formed from a softer material to provide comfort or a particular tactile feel and inner layers may have a higher tensile or compressive strength to improve the durability of the soft good. The inner layers may be formed from a high-strength material having a lower modulus of elasticity than the outer layers and may facilitate capture and retention of the snap 13000.

The snap 13000 of FIGS. 130A-130C is configured to provide a reliable and consistent mechanical engagement between two elements of the accessory using a mechanism that is both low profile or thin and also configured to be substantially rattle free. The design described with respect to the following embodiments may be contrasted with some traditional snap configurations, which may require significantly more space and may also include elements that may rattle or produce other potentially undesirable sounds. Traditional snaps may also not provide the desired mechanical interconnect and/or the desired tactile feel of the snap configurations that are described herein.

As described in more detail below, the snap 13000 may include a compression ring 13002 that provides a retention force to maintain engagement of the snap 13000 when closed. The design and/or integration of the compression ring 13002 may be configured to reduce potentially undesirable noise like rattles and mechanical chatter. In the present embodiment, the compression ring 13002 is at least partially constrained by one or more compliant members 13004. The compliant member 13004 may help locate the compression ring 13002 while also helping to prevent rattling or other potentially undesirable acoustic effects. The compliant member 13004 may also be used to reduce or prevent the ingress or collection of debris or other foreign matter from accumulating in the snap 13000. Additionally or alternatively, the compression ring 13002 may also be twisted or have a non-planar shape that helps to reduce potentially undesirable noise. An example of a twisted or non-planar shape is described below with respect to FIGS. 130F-130H.

The compression ring 13002 may be a metal ring having a generally circular shape and a round wire profile. The compression ring 13002, in this example, is an open-section wire loop formed from a wire member that is bent into a circular shape and having a gap between opposing ends. In some cases, the compression ring 13002 is formed from a spring steel or high-carbon steel and is formed into circular shape having an open end or section that allows for expansion and/or compression of the compression ring 13002. For purposes of the following embodiments, the term "compression rings" may be used to refer to the compression ring 13002 as it is configured to exert an outward compressive force or retention force on mating components or surfaces. However, the term "compression ring" may also be used to refer to a ring that is configured to exert an inward compressive force, retention force, or other type of force to help maintain engagement of two assemblies of the snap. Elements referred to generally as compression rings may also be referred to as expansion rings, retaining rings, or simply as rings.

FIGS. 130A-130C depict one example embodiment of a snap 13000 that is configured as a low-profile fastener that is substantially rattle free. As shown in FIGS. 130A-130B, the snap 13000 includes a male assembly 13020 having a compression ring 13002 and a compliant member 13004. As shown in FIGS. 130A-130B, the compression ring 13002 is trapped or held within groove 13022 that is formed into the male portion or protrusion component 13024. The groove 13022 may also be referred to as a recess, pocket, or retaining feature and generally includes at least one wall or surface that is configured to physically constrain the compression ring 13002. In this case, the groove 13022 is defined by three walls that generally trap or constrain the compression ring 13002. The three walls include an inner wall that extends between two opposing sidewalls. While the groove 13022 is depicted as having a substantially rectangular profile, the groove 13022 may also have a curved or rounded profile, V profile, or other type of profile shape. The groove 13022 may extend around the circumference of the male portion or protrusion component 13024, and may be referred to as a circumferential groove.

The compression ring 13002 is configured to engage with a mating feature on the female assembly or module 13030. In the example of FIGS. 130A-130C, the compression ring 13002 is configured to engage with a tapered or ramped surface 13032 defined along an inner bore of the female assembly 13030. In general, the ramped surface 13032 is angled in a manner to draw the compression ring 13002 (and the male assembly 13020) inward or toward the female assembly 13030 to help maintain the engagement between the male assembly 13020 and the female assembly 13030. In this example, the tapered or ramped surface 13032 has a draft angle that generally extends outward in a direction that is opposite to the mating male assembly 13020. While the direction of the draft angle may change depending on the implementation, the tapered or ramped surface 13032 is generally configured to exert a force on the mating assembly that draws the two assemblies of the snap 13000 together. As drawn in FIGS. 130A and 130C, the ramped surface 13032 is configured to draw the compression ring 13002 (and the male assembly 13020) downward, which pulls the first element 13010 toward the second element 13012 and maintains engagement between the two elements. The angle of the ramped surface 13032 may be specially configured, along with the spring force of the compression ring 13002, to provide the desired mechanical engagement between the two assemblies of the snap while also allowing the male and female assemblies 13020, 13030 to be disengaged by hand, as necessary. The angle of the tapered or ramped surface 13032 may range from 0.5 degrees to 2 degrees. In some cases, the angle of the ramped surface 13032 ranges from 0.5 to 5 degrees. In some cases, the angle of the ramped surface 13032 ranges from 1 to 5 degrees. In some implementations, a detent feature like a local depression or groove is used instead of or in addition to the ramped surface 13032 in order to help retain the engagement with the compression ring 13002.

As shown in FIGS. 130A-130B, a compliant member 13004 is positioned at least partially within the groove 13022 with the compression ring 13002. In this particular implementation, the compliant member 13004 is positioned along the inner wall between the compression ring 13002 and the inner wall of the groove 13022. In this position, the compliant member 13004 is able to bias the compression ring 13002 in an outward direction with respect to the groove 13022. This may help maintain consistent or uniform engagement between the compression ring 13002 and the mating surface or surfaces of the female assembly 13030 which, in this case, is the ramped surface 13032.

As shown in FIGS. 130A-130B, the compliant member 13004 may also locally deflect along an interface that contacts the compression ring 13002 to form a localized depression or groove in the compliant member 13004. The localized deflection of the compliant member 13004 helps to seat the compression ring 13002 and may help maintain the position of the compression ring 13002 within the groove 13022, which may help provide reliable or consistent insertion of the male assembly 13020 with the female assembly 13030. In particular, the compliant member 13004 may help center the compression ring 13002 with respect to the other components of the snap 13000, which may assist with reliable and consistent operation of the snap 13000. For example, the compression ring 13002 may help to maintain alignment of a central axis of the compression ring 13002 with respect to a central axis of the mating female assembly 13030. In the example snap 13000 of FIGS. 130A-130C, the compression ring 13002 provides the mechanical lead-in or guide as the male assembly 13020 is initially inserted into the female assembly 13030. In general, the larger the diameter of the compression ring 13002, the greater the lead-in and the easier it is to align the male and female assemblies 13020, 13030. However, maintaining the location of the compression ring 13002 using the compliant member 13004 allows for a smaller diameter compression ring 13002 in order to achieve the same lead-in or alignment. Using a smaller diameter compression ring 13002 may result in a lower profile or thinner snap 13000 and a more compact design. In this example, the diameter of the wire of the compression ring 13002 ranges from 0.5 mm to 1.5 mm. In some cases, the diameter of the compression ring 13002 ranges from 0.6 mm to 1.2 mm. In some cases, the diameter of the compression ring 13002 ranges from 0.6 mm to 1.0 mm. In some cases, the diameter of the compression ring 13002 ranges from 0.3 mm to 3 mm.

The compliant member 13004 may be formed from a compliant or deformable material that is soft enough to be locally deformed by the compression ring 13002 but also stiff enough to provide structural support and help constrain the compression ring 13002 within the groove 13022. The compliant member 13004 may be formed from an elastic material. In some implementations, the compliant member 13004 may be formed from a natural rubber or a synthetic or partially synthetic elastomer including, for example, silicone, neoprene Nitrile rubber, Butyl rubber, Poron, ethylene propylene (EPM) rubber, ethylene-vinyl acetate (EVA), fluorosilicone rubber, or other similar materials. In some cases, the compliant member 13004 is formed from multiple materials or has a composite construction that may include one or more polymers and/or one or more other materials.

Figures 130D, 130E:
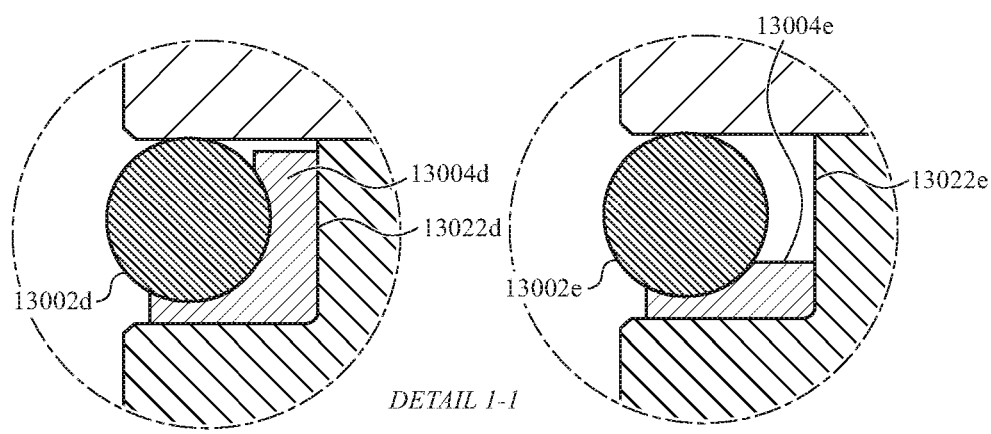

FIGS. 130D and 130E depict alternative arrangements of a compliant member with respect to a compression ring. In FIG. 130D, a compliant member 13004*d* is positioned along the rear or inner wall and one side wall of the groove 13022*d*. In this example, the compliant member 13004*d* is able to exert a force (e.g., a biasing force) that is outward and upward, as drawn in FIG. 130D. Stated another way, the compliant member 13004*d* is configured to provide a biasing force that tends to push the compression ring 13002*d* outward from the groove 13022*d* and also toward an opposing wall or side wall of the groove 13022*d*. The compliant member 13004*d* and the resulting exerted force may function in a similar manner as previously described to help constrain the compression ring 13002*d* within the groove 13022*d*. Specifically, the compliant member 13004*d* may provide a biasing force that reduces potentially undesirable noise (e.g., a rattle). Additionally, because the biasing force has a component that is transverse to a central axis of the snap 13000, the biasing force provided by the compliant member 13004*d* may tend to center the compression ring 13002*d* within the snap 13000 (e.g., maintain alignment of the central axis of the compression ring 13002*d* with respect to a central axis of the snap 13000.

In FIG. 130E, a compliant member 13004*e* is positioned along one side wall of the groove 13022*e*. In this example, the compliant member 13004*e* is able to exert a (biasing) force that is substantially parallel with a central axis of the compression ring 13002*e* (e.g., in an upward direction, as drawn in FIG. 130E). Stated another way, the compliant member 13004*e* is configured to provide a biasing force that tends to push the compression ring 13002*e* toward an opposing wall or side wall of the groove 13022*e*. The compliant member 13004*e* and the resulting exerted force may function in a similar manner as previously described to help constrain the compression ring 13002*e* within the groove 13022*e*. Similar to the previous example, the compliant member 13004*e* may apply a biasing force on the compression ring 130002*e* to reduce potentially undesirable rattles or noise. However, because the biasing force provided by the compliant member 13004*e* is substantially parallel to a central axis of the snap, the compliant member 13004*e* may not provide a biasing force component that tends to center the compression ring 13002*e* within the snap. The configurations and locations of the compliant members described in each of these embodiments are provided by way of example and are not exhaustive of all the configurations and mounting scenarios that may be used.

The snap 13000 includes various components and elements that are used to couple the snap 13000 to the accessory. As shown in FIGS. 130A-130B, male assembly 13020 includes an outer flange 13025 and an inner flange 13026 that are configured to engage and capture a respective portion of the first element 13010. The outer flange 13025 and the inner flange 13026 secure the male assembly 13020 within a respective hole formed in the first element 13010. One or both the outer flange 13025 or the inner flange 13026 may include one or more engagement features that may include one or more ribs, teeth, grooves, or protruding features that are configured to mechanically engage material of the first element 13010. The engagement features may be configured to extend into the material of the first element 13010 in order to provide a bite or anchor for the male assembly 13020. As described previously, the first element 13010 may be formed from a laminate material and may include one or more internal layers that have an improved tensile and/or compressive strength or a reduced elastic modulus, which may help maintain engagement with the outer flange 13025 and the inner flange 13026 of the male assembly 13020. In some cases, the inner materials form a bottom surface of the recess formed in the first element 13020, which may engage the one or more engagement features of the outer flange 13025 and/or the inner flange 13026.

The design of the flanges (13025, 13026, 13035, 13036) and/or the material of the first element 13010 and the second element 13012 may result in a snap 13000 that is substantially smaller than some traditional designs. In some examples, the amount of overlap between the flanges (13025, 13026, 13035, 13036) of the respective portions of the first element 13010 and the second element 13012 may be approximately half of a traditional overlap. In some cases, the overlap is less than 3 mm. In some cases, the overlap is less than 2.5 mm. In some cases, the overlap is less than 2 mm. In some cases, the overlap is approximately 1.5 mm or less.

As shown in FIGS. 130A-130B, the outer flange 13025 may be formed by an outer component 13027 that also defines an outer or exterior surface of the snap 13000. The inner flange 13026 is formed as part of an inner component 13028 that forms an inner surface of the male assembly 13020. The outer component 13027 may be directly coupled to the inner component 13028 using an adhesive, weld, press fit, threaded connection, or other structurally coupling technique. In some cases, one or more intermediate elements or components is used to couple the outer component 13027 to the inner component 13028. In this example, the protrusion component 13024 is attached to the outer component 13027 using a press or interference fit. The protrusion component 13024 may also be attached to the outer component 13027 using an adhesive, weld, threaded connection, or other attachment technique. In this example, the protrusion component 13024 and the outer component 13027 cooperate to define the groove 13022. In alternative embodiments, the groove 13022 may be formed entirely within either the protrusion component 13024 or the outer component 13027.

Similarly, as shown in FIGS. 130A and 130C, the female assembly 13030 is formed from multiple components. Specifically, the female assembly 13030 includes an outer flange 13035 and an inner flange 13036 that are configured to engage and capture a respective portion of the second element 13012. Similar to the previous example described above, the outer flange 13035 and/or the inner flange 13036 may have one or more engagement features (e.g., ribs, teeth, grooves, protruding features) that help mechanically engage the respective flange with the second element 13012. The outer flange 13035 and the inner flange 13036 secure the female assembly 13030 within a respective hole formed in the second element 13012. As shown in FIGS. 130A and 130C, the outer flange 13035 may be formed by an outer component 13037 that also defines an outer or exterior surface of the snap 13000. The inner flange 13036 is formed as part of an inner component 13038 that forms an inner surface of the female assembly 13030. The outer component 13037 may be directly coupled to the inner component 13038 using an adhesive, weld, press fit, threaded connection, or other structurally coupling technique. In some cases, one or more intermediate elements or components is used to couple the outer component 13037 to the inner component 13038.

In this example, the inner component 13038 and the outer component 13037 cooperate to define a bore or opening that receives the protrusion component 13024 of the male assembly 13020. The inner component 13038 also defines the ramped surface 13032 that is configured to engage the compression ring 13002. The inner component 13038 also includes a chamfer 13039 or lead-in feature formed along the inner surface as a lead-in to the bore or opening that receives the male assembly 13020. The chamfer 13039 is configured to engage with the leading edge of the male assembly 13020, which may also include a similar chamfer or lead-in to facilitate alignment of the two assemblies 13020, 13030 when being snapped together or coupled. The chamfer 13039 may also be configured to engage with the compression ring 13002 and compress the compression ring 13002 inward while the two assemblies 13020, 13030 are being snapped together or coupled.

As shown in FIGS. 130A-130C, an outer surface of the protrusion component 13024 is exposed along an exterior surface of the snap 13000. That is, protrusion component 13024 is configured to extend through the bore or opening defined by the female assembly 13030 to define an exterior surface of the snap 13000. Also as shown in FIG. 130A, the exposed or exterior surface of the protrusion component 13024 is substantially aligned with an exposed or exterior surface of the outer component 13037 of the female assembly 13030. In this example, the exposed or exterior surface of the protrusion component 13024 may also be described as being flush with an exposed or exterior surface of the outer component 13037 of the female assembly 13030. In some implementations, the protrusion component 13024 and the outer component 13037 of the female assembly 13030 cooperate to define a curved or non-planar profile.

The snap 13000 is also configured so that an inner surface of the first element 13010 contacts and seats against an inner surface of the second element 13012 when the male assembly 13020 is engaged with the female assembly 13030. As shown in FIG. 130A, the male assembly 13020 is separated from the female assembly 13030 by a small gap or space. This prevents contact between the two assemblies, which may also reduce rattling or other potentially undesirable effects during use. By seating the inner surfaces of the first and second elements 13010, 13012, the snap 13000 may snap together with a muted or softened feel (rather than a hard or sharp click). The small gap or space between the male assembly 13020 and the female assembly 13030 may also reduce wear between the two components and also help preserve any surface finish or surface treatment on the respective components.

The various components of the snap 13000 may be formed from a variety of materials. In some implementations, the inner components 13028, 13038 and the outer components 13027, 13037 are formed from a metal material. The metal material may be a stainless steel, carbon steel, aluminum, titanium, or other metal or metal alloy. In some implementations, the outer components 13027, 13037 or exposed surfaces of the outer components 13027, 13037 are polished to provide a smooth finish along the exterior of the snap 13100. In some cases, one or more of the components are formed from a polymer or other synthetic material. For example, one or more of the components may be partially or fully over molded with a plastic material to improve the appearance and or tactile feel of the snap 13000. In some cases, one or more of the components are formed entirely from a plastic material.

Figure 130F:
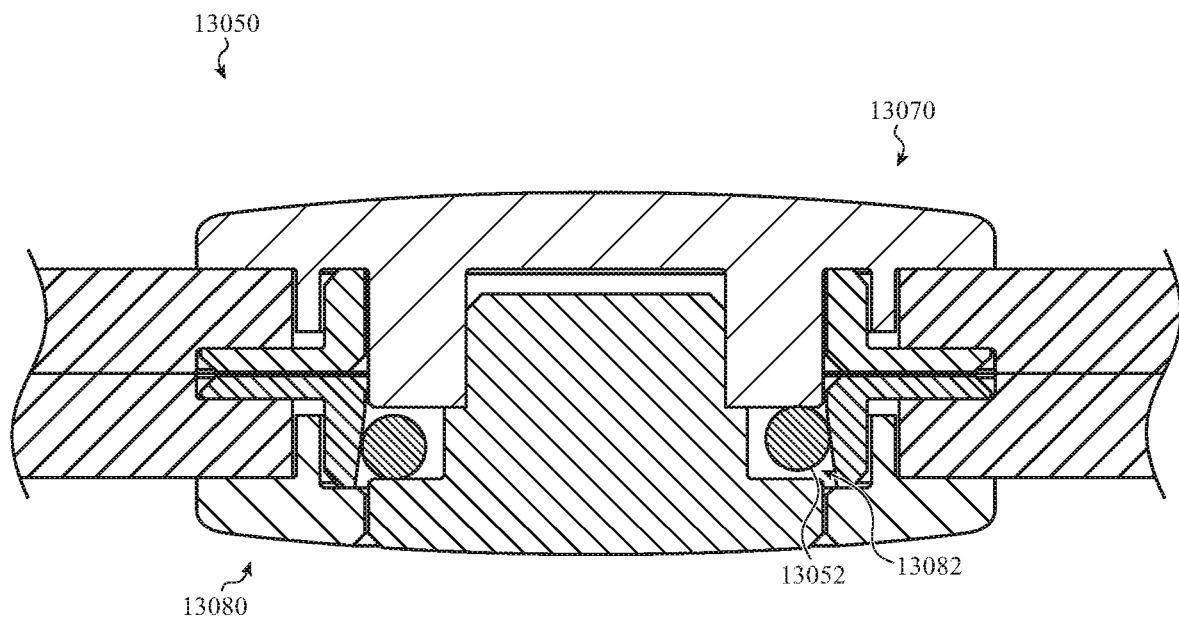
Figure 130G:
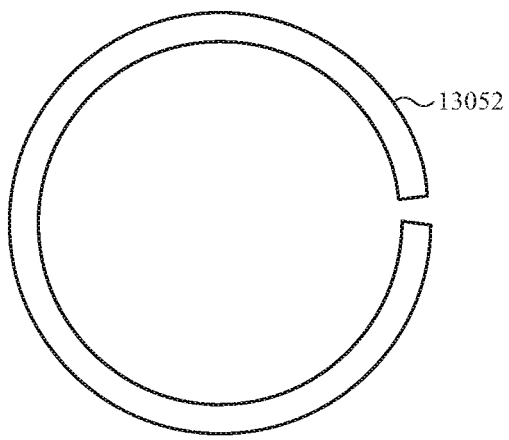
Figure 130H:
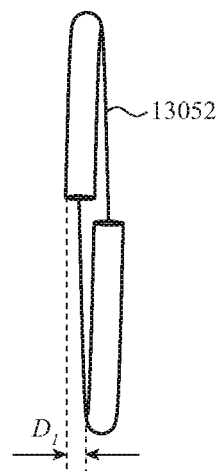

FIGS. 130F-130H depict another example snap 13050, also referred to as a snap assembly, that may be substantially rattle free. Many of the components and elements of the example snap 13050 are similar to the example snap 13000 described above, and a description of such similar elements are omitted to reduce redundancy and improve clarity. Similar to the previous example, the snap 13050 includes a male assembly 13070 that is inserted into and engaged with a female assembly 13080. Also similar to the previous example, the male assembly 13070 includes a groove 13082 that retains or captures a compression ring 13052.

In the examples of FIGS. 130F-130H, the compression ring 13052 is twisted or bent to define a non-flat or non-planar shape. Specifically, as shown in FIGS. 130G-130H the compression ring 13052 is an open-section ring or wire loop having opposing ends. The ends may be set apart by a gap and the ends of the ring, in this example, are displaced to define an offset Di. The compression ring 13052 may be described as having a partially helical shape, non-planar profile, or otherwise non-flat shape. This out-of-plane distortion or displacement helps constrain the compression ring 13052 within the groove 13082 so that the compression ring 13052 cannot move freely and cause a potentially undesirable rattle or chatter. The offset Di may be greater than the clearance between the diameter of the compression ring 13052 and the opposing walls of the groove 13082. In some cases, the offset Di is less than 0.5 mm. In some cases, the offset Di is less than 0.4 mm. In some cases, the offset Di is less than 0.3 mm. The offset Di may also be described with respect to the wire diameter of the open-section wire loop. In some cases, the offset Di ranges from 10% to 50% of the wire diameter. In some cases, the offset Di ranges from 15% to 40% of the wire diameter. In some cases, the offset Di ranges from 20% to 30% of the wire diameter. As shown in FIG. 130F, the twist or non-flat shape results in the compression ring 13052 contacting an upper wall of the groove 13082 for one portion of the groove 13082 and also contacting a lower wall of the groove 13082 for another portion of the groove 13082, which helps to constrain the compression ring 13052 along an axial direction (as defined by a central axis of the snap 13050).

The compression ring 13052 may have other non-flat or non-planar shapes that similarly constrain the compression ring 13052 within the groove 13082. For example, the compression ring 13052 may have a wavy shape, U-shape, or other non-flat shape that results in the compression ring 13052 contacting both opposing sidewalls of the groove 13082 in order to constrain the compression ring 13052 along the axial direction and reduce potential rattles or chatter. In some cases, the snaps 13000, 13050 include both a compliant member (as described above with respect to FIGS. 130A-130E) and a non-flat shape (as described with respect to FIGS. 130F-130H).

Figure 131A:
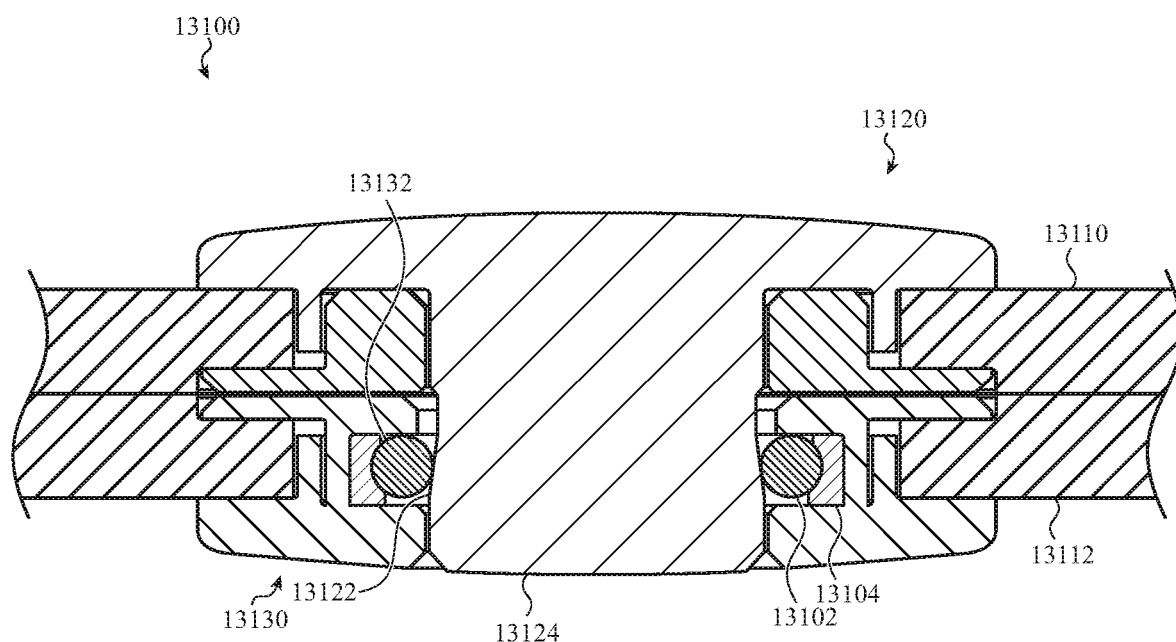

FIGS. 131A-131C depict another configuration of a snap 13100, also referred to as a snap assembly, having a low-profile and substantially rattle-free design. Many of the same or similar features described above with respect to snap 13000 also apply to the snap 13100, and a description of which are not repeated to reduce redundancy. Similar to the other embodiments described herein, the snap 13100 may be integrated with or incorporated into an accessory or soft good including, for example, a lanyard, key fob, luggage tag, belt, band, or other accessory. The snap 13100 may also be formed from similar materials and function in a similar fashion as described above with respect to FIGS. 130A-130C.

Similar to the previous example, the snap 13100 includes a male assembly 13120 and a female assembly 13130. Also similar to the previous example, the snap 13100 includes a compression ring 13102 and a compliant member 13104 that are positioned at least partially within a groove 13132. In this example, instead of a groove being formed into a protrusion component of the male assembly, the groove 13132 is formed into a component of the female assembly 13130. Also, instead of exerting an outward force, the compression ring 13102 of the snap 13100 is configured to exert a (retaining) force in an inward direction toward ramped surface 13122 that is defined along a surface of the protrusion component 13124 of the male assembly 13120. The groove 13132 may extend around the circumference of the female assembly 13130, and may be referred to as a circumferential groove.

In the example snap 13100 of FIGS. 131A-131C, the compression ring 13102 is at least partially constrained by the compliant member 13104. As shown in FIGS. 131A and 131C, the compliant member 13104 may locally deflect along an interface that contacts the compression ring 13102 to form a localized depression or groove in the compliant member 13104. The localized deflection of the compliant member 13104 helps to seat the compression ring 13102 and may help maintain the position of the compression ring 13102 within the groove 13132, which may help provide reliable or consistent insertion of the male assembly 13120 with the female assembly 13130. In particular, the compliant member 13104 may help center the compression ring 13102 with respect to the other components of the snap 13100, which may assist with reliable and consistent operation of the snap 13100. Similar to the previous example, the compression ring 13102 provides the mechanical lead-in or guide as the male assembly 13120 is initially inserted into the female assembly 13130. Maintaining the location of the compression ring 13102 and supporting the compression ring 13102 using the compliant member 13104 may allow for a smaller diameter compression ring 13102 than would ordinarily be used.

FIGS. 131D and 131E depict alternative arrangements of a compliant member with respect to a compression ring. In FIG. 131D, a compliant member 13104d is positioned along the rear or inner wall and one side wall of the groove 13132. In this example, the compliant member 13104d is able to exert a force (e.g., a biasing force) that is outward and upward, as drawn in FIG. 131D. Stated another way, the compliant member 13104d is configured to provide a biasing force that tends to push the compression ring 13102d outward from the groove 13132 and also toward an opposing wall or sidewall of the groove 13132. The compliant member 13104d and the resulting exerted force may function in a similar manner as previously described to help constrain the compression ring 13102d within the groove 13132. Specifically, the compliant member 13104d may provide a biasing force that reduces potentially undesirable noise (e.g., a rattle). Additionally, because the biasing force has a component that is transverse to a central axis of the snap, the biasing force provided by the compliant member 13104d may tend to center the compression ring 13102d within the snap.

In FIG. 131E, a compliant member 13104e is positioned along one sidewall of the groove 13132. In this example, the compliant member 13104e is able to exert a (biasing) force that is upward, as drawn in FIG. 131E. Stated another way, the compliant member 13104e is configured to provide a biasing force that tends to push the compression ring 13102e toward an opposing wall or side wall of the groove 13132. The compliant member 13104e and the resulting exerted force may function in a similar manner as previously described to help constrain the compression ring 13102e within the groove 13132. The compliant member 13104e and the resulting exerted force may function in a similar manner as previously described to help constrain the compression ring 13102e within the groove 13132. Similar to the previous example, the compliant member 13104e may apply a biasing force on the compression ring 131002e to reduce potentially undesirable rattles or noise. However, because the biasing force provided by the compliant member 13104e is approximately parallel to a central axis of the snap, the compliant member 13104e may not provide a biasing force component that tends to center the compression ring 13102e within the snap The configurations and locations of the compliant members described in each of these embodiments are provided by way of example and are not exhaustive of all the configurations and mounting scenarios that may be used.

The snap 13100 includes various components and elements that are used to couple the snap 13000 to the accessory. In particular, the snap 13100 also includes mounting flanges that couple the male and female assemblies 13120, 13130 to the respective first and second elements 13110, 13112. As shown in FIGS. 131A-131B, the male assembly 13120 includes an outer flange 13125 and an inner flange 13126 that are configured to engage and capture a respective portion of the first element 13110. The outer flange 13125 and the inner flange 13126 secure the male assembly 13120 within a respective hole formed in the first element 13110. Similar to the previous examples described above, the outer flange 13125 and/or the inner flange 13126 may have one or more engagement features (e.g., ribs, teeth, grooves, protruding features) that help mechanically engage the respective flanges with the first element 13110.

As shown in FIGS. 131A-131B, the outer flange 13125 may be formed by part of the protrusion component 13124 that also defines an outer or exterior surface of the snap 13100. The inner flange 13126 is formed as part of an inner component 13128 that forms an inner surface of the male assembly 13120. The protrusion component 13124 may be directly coupled to the inner component 13128 using an adhesive, weld, press fit, threaded connection, or other structurally coupling technique. In some cases, one or more intermediate elements or components is used to couple the protrusion component 13124 to the inner component 13128.

As shown in FIGS. 131A and 131C, the female assembly 13130 is formed from multiple components. Specifically, the female assembly 13130 includes an outer flange 13135 and an inner flange 13136 that are configured to engage and capture a respective portion of the second element 13112. The outer flange 13135 and the inner flange 13136 secure the female assembly 13130 within a respective hole formed in the second element 13112. Similar to the previous examples described above, the outer flange 13135 and/or the inner flange 13136 may have one or more engagement features (e.g., ribs, teeth, grooves, protruding features) that help mechanically engage the respective flange with the second element 13112.

As shown in FIGS. 131A and 131C, the outer flange 13135 may be formed by an outer component 13137 that also defines an outer or exterior surface of the snap 13100. The inner flange 13136 is formed as part of an inner component 13138 that forms an inner surface of the female assembly 13130. The outer component 13137 may be directly coupled to the inner component 13138 using an adhesive, weld, press fit, threaded connection, or other structurally coupling technique. In some cases, one or more intermediate elements or components is used to couple the outer component 13137 to the inner component 13138.

In this example, the inner component 13138 and the outer component 13137 cooperate to define a bore or opening that receives the protrusion component 13124 of the male assembly 13120. As shown in FIGS. 131A-131B, the protrusion component 13124 includes a chamfer 13129 that may facilitate alignment and insertion of the male assembly 13120 into the female assembly 13130. The chamfer 13139 is configured to engage with the leading edge of the female assembly 13130, which may also include a similar chamfer or lead-in to facilitate alignment of the two assemblies 13120, 13130 when being snapped together or coupled. The chamfer 13139 may also be configured to engage with the compression ring 13102 and compress the compression ring 13102 inward while the two assemblies 13120, 13130 are being snapped together or coupled.

The protrusion component 13124 also includes a ramped surface 13122, which is configured to engage with the compression ring 13102 and may help retain engagement between the male assembly 13120 into the female assembly 13130. In general, the ramped surface 13122 is angled in a manner to draw the compression ring 13102 (and the female assembly 13130) inward or toward the male assembly 13130 to help maintain the engagement between the male assembly 13120 and the female assembly 13130. In this example, the tapered or ramped surface 13122 has a draft angle that generally extends outward in a direction that is opposite to the base of the protrusion component 13124 of the male assembly 13120. While the direction of the draft angle may change depending on the implementation, the tapered or ramped surface 13122 is generally configured to exert a force on the mating assembly that draws the two assemblies of the snap 13100 together. In some implementations, a detent feature like a local depression or groove is used instead of or in addition to the ramped surface 13122 in order to help retain the engagement with the compression ring 13102

As shown in FIG. 131A, an outer surface of the protrusion component 13124 is exposed along an exterior surface of the snap 13100. That is, protrusion component 13124 is configured to extend through the bore or opening defined by the female assembly 13130 to define an exterior surface of the snap 13100. Also as shown in FIG. 131A, the exposed or exterior surface of the protrusion component 13124 is substantially aligned with an exposed or exterior surface of the outer component 13137 of the female assembly 13130. In this example, the exposed or exterior surface of the protrusion component 13124 may be described as being flush with an exposed or exterior surface of the outer component 13137 of the female assembly 13130 In some implementations, the protrusion component 13124 and the outer component 13137 of the female assembly 13130 cooperate to define a curved or non-planar profile.

The snap 13100 is also configured so that an inner surface of the first element 13110 contacts and seats against an inner surface of the second element 13112 when the male assembly 13120 is engaged with the female assembly 13130. As shown in FIG. 131A, the male assembly 13120 is separated from the female assembly 13130 by a small gap or space. This prevents contact between the two assemblies, which may also reduce rattling or other potentially undesirable effects during use. By seating the inner surfaces of the first and second elements 13110, 13112, the snap 13100 may snap together with a muted or softened feel (rather than a hard or sharp click). As described previously, the small gap or space between the male assembly 13120 and the female assembly 13130 may also reduce wear between the two components and also help preserve any surface finish or surface treatment on the respective components.

Figure 131F:
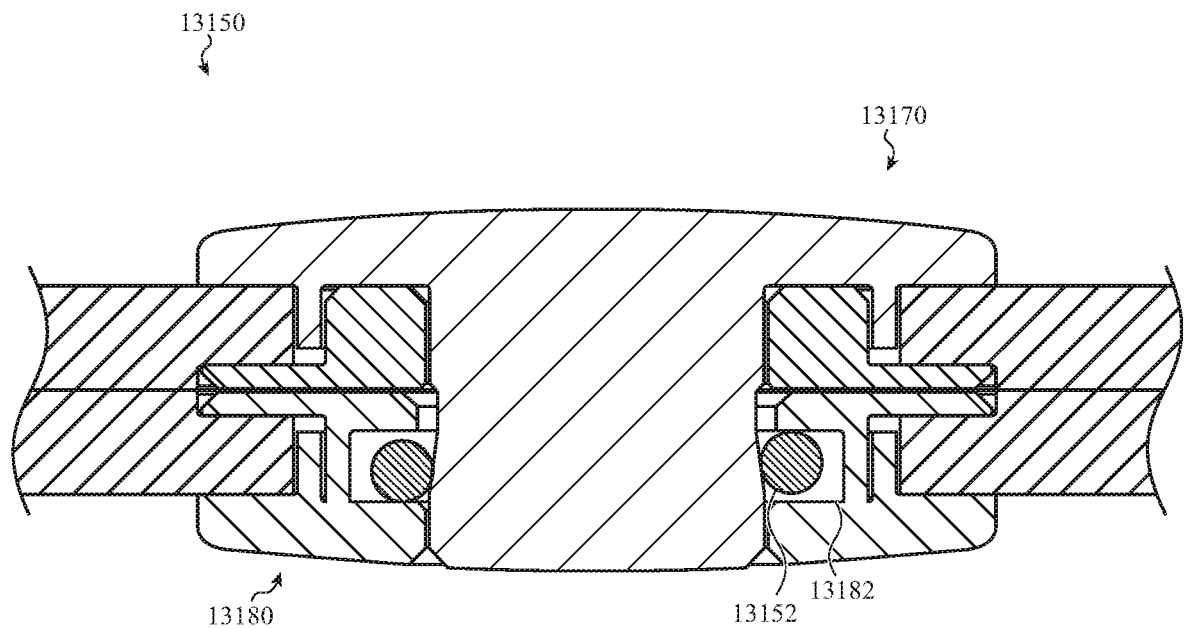
Figure 131G:
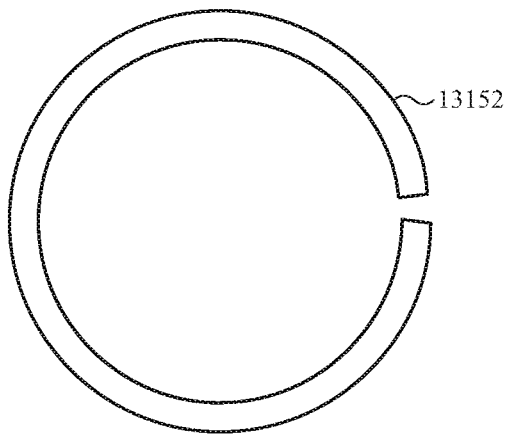
Figure 131H:
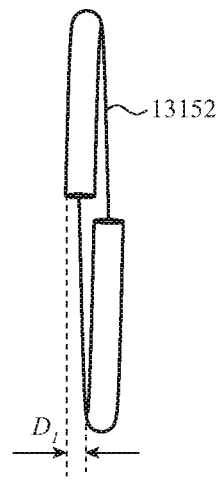

FIGS. 131F-131H depict another example snap 13150, also referred to as a snap assembly, that may be substantially rattle free. Many of the components and elements of the example snap 13150 are similar to the example snap 13100 described above, and a description of such similar elements are omitted to reduce redundancy and improve clarity. Similar to the previous example, the snap 13150 includes a male assembly 13170 that is inserted into and engaged with a female assembly 13180. Also similar to the previous example, the male assembly 13170 includes a groove 13182 that retains or captures a compression ring 13152.

In the examples of FIGS. 131F-131H, the compression ring 13152 is twisted or bent to define a non-flat or non-planar shape. Specifically, as shown in FIGS. 131G-131H, the compression ring 13152 is an open-section ring or wire loop having opposing ends. The ends may be set apart by a gap and the ends of the ring, in this example, are displaced to define an offset Di. The compression ring 13152 may be described as having a partially helical shape, non-planar profile, or otherwise non-flat shape. This out-of-plane distortion or displacement helps constrain the compression ring 13152 within the groove 13182 so that the compression ring 13152 cannot move freely and cause a potentially undesirable rattle or chatter. The offset Di may be greater than the clearance between the diameter of the compression ring 13152 and the opposing walls of the groove 13182. In some cases, the offset Di is less than 0.5 mm. In some cases, the offset Di is less than 0.4 mm. The offset Di may also be described with respect to the wire diameter of the open-section wire loop. In some cases, the offset Di ranges from 10% to 50% of the wire diameter. In some cases, the offset Di ranges from 15% to 40% of the wire diameter. In some cases, the offset Di ranges from 20% to 30% of the wire diameter. In some cases, the offset Di is less than 0.3 mm. As shown in FIG. 131F, the twist or non-flat shape results in the compression ring 13152 contacting an upper wall of the groove 13182 for one portion of the groove 13182 and also contacting a lower wall of the groove 13182 for another portion of the groove 13182, which helps to constrain the compression ring 13152 along an axial direction (as defined by a central axis of the snap 13150).

The compression ring 13152 may have other non-flat or non-planar shapes that similarly constrain the compression ring 13152 within the groove 13182. For example, the compression ring 13152 may have a wavy shape, U-shape, or other non-flat shape that results in the compression ring 13152 contacting both opposing sidewalls of the groove 13182 in order to constrain the compression ring 13152 along the axial direction and reduce potential rattles or chatter. In some cases, the snaps 13100 and 13150 include both a compliant member (as described above with respect to FIGS. 131A-131E) and a non-flat shape (as described with respect to FIGS. 131F-131H).

As described above, the snaps 13000, 13050, 13100, and 13150 of FIGS. 130A-130H and 131A-131H, also referred to as snap assemblies, may result in an overall reduced size or footprint of the snap assembly. In these examples, the overall height or thickness of the snaps (13000, 13050, 13100, and 13150) may be less than 6 mm thick. In some implementations, the overall height or thickness of the snaps (13000, 13050, 13100, and 13150) may be less than 5 mm thick. In some implementations, the overall height or thickness of the snaps (13000, 13050, 13100, and 13150) may be less than 4 mm thick. The overall diameter or profile of the snaps (13000, 13050, 13100, and 13150) may also be reduced as compared to some traditional designs. In these examples, the overall diameter of the snaps (13000, 13050, 13100, and 13150) may be less than 15 mm. In some implementations, the overall diameter of the snaps (13000, 13050, 13100, and 13150) may be less than 12 mm. In some implementations, the overall diameter of the snaps (13000, 13050, 13100, and 13150) may be less than 10 mm. Further, as described previously, the overlap between the respective snap flange and the portion of the soft good material may also be reduced as compared to some traditional snap designs. In some examples, the amount of overlap between the flange and the soft good material may be approximately half of a traditional overlap. In some cases, the overlap is less than 3 mm. In some cases, the overlap is less than 2.5 mm. In some cases, the overlap is less than 2 mm. In some cases, the overlap is approximately 1.5 mm or less.

FIGS. 132A-132C and 133A-133B depict additional snap embodiments that may be used for an accessory of a wireless tab. In particular, FIGS. 132A-132B depict an example snap 13200, also referred to as a snap assembly, having a compression ring 13202. The snap 13200 includes a single-piece or integrally formed male assembly 13220 and a single-piece or integrally formed female assembly 13230. Either or both of the male assembly 13220 and the female assembly 13230 may be formed from a stamped sheet metal member. The snap 13200 also includes partially molded end caps 13240 and 13250 that define exterior surfaces of the snap 13200 and that are attached to the male assembly 13220 and female assembly 13230 respectively. Similar to examples previously described, the snap 13200 is configured to couple a first element 13210 to a second element 13212, which may be two elements or regions of an accessory, as described previously.

As shown in FIGS. 132A-132B, the male assembly 13220 includes features that are configured to engage with the female assemble 13230 and the compression ring 13202 in a similar fashion as described above with respect to the other snap embodiments. In particular, the male assembly 13220 includes a ramped surface 13222 or other feature that is configured to engage with the compression ring 13202 when the snap 13200 is closed and the male and female assemblies 13220, 13230 are coupled. While a ramped surface 13222 is used in this example, the male assembly 13220 may also include a groove, detent, recess, or other similar feature that is configured to engage with the compression ring 13202 in order to help maintain engagement between the male and female assemblies 13220, 13230 of the snap 13200.

The snap includes a male assembly 13220 that is integrally formed as a single unitary element. The unitary element includes a protrusion portion defining the ramped surface 13222 and an inner flange 13224 that is configured to help retain the male assembly 13220 to the first element 13210. The male assembly 13220 may be stamped from a single monolithic sheet of metal and may be formed from a stainless steel, carbon steel, brass, or other material that can be formed into the geometry of the male assembly 13220 shown in FIGS. 132A-132B. In some cases the male assembly 13220 is formed from an aluminum material and may also be machined in order to form one or more of the features shown in FIGS. 132A-132B.

The male assembly 13220 is also attached to an end cap 13240, which defines an exterior cosmetic surface of the snap 13200. The male assembly 13220 may be attached to a rib 13244 of the end cap using an ultrasonic weld, laser weld, press fit, interference fit, adhesive, or other bonding technique. A cap top 13242 may be formed from a plastic material that is over molded over the rib 13244. The cap top 13242 may have a surface finish and color suitable for cosmetic and tactile requirements of the snap 13200. The cap top 13242 may also form an upper flange 13246 that helps retain the male assembly 13220 to the first element 13210. Similar to previous embodiments described herein, a portion of the first element 13210 is positioned between or sandwiched by the inner flange 13224 and the outer flange 13246 in order to retain the male assembly 13220.

The snap 13200 also includes a female assembly 13230 that is integrally formed as a single unitary element. The unitary element of the female assembly 13230 includes a recess or pocket portion that is configured to receive the protrusion of the male assembly 13220. The unitary element of the female assembly 13230 also forms an inner flange 13234 that is configured to help retain the female assembly 13230 to the second element 13212. The female assembly 13230 may be stamped from a single monolithic sheet of metal and may be formed from a stainless steel, carbon steel, brass, or other material that can be formed into the geometry of the female assembly 13230 shown in FIGS. 132A-132B. In some cases the female assembly 13230 is formed from an aluminum material and may also be machined in order to form one or more of the features shown in FIGS. 132A-132B.

The female assembly 13230 is also attached to an end cap 13250, which defines an exterior cosmetic surface of the snap 13200. The female assembly 13230 may be attached to a rib 13254 of the end cap using an ultrasonic weld, laser weld, press fit, interference fit, adhesive, or other bonding technique. A cap top 13252 may be formed from a plastic material that is over molded over the rib 13254. The cap top 13252 may have a surface finish and color suitable for cosmetic and tactile requirements of the snap 13200. The cap top 13252 may also form an upper flange 13256 that helps retain the female assembly 13230 to the second element 13212. Similar to previous embodiments described herein, a portion of the second element 13212 is positioned between or sandwiched by the inner flange 13234 and the outer flange 13256 in order to retain the female assembly 13230.

In this example, the female assembly 13230 includes a recess 13232 that receives the compression ring 13202. The recess 13232, also referred to as a groove, may be integrally formed from a bent or stamped region of the female assembly 13230. The recess 13232 may also be machined or formed using another suitable manufacturing technique. While not depicted in FIGS. 132A-132B, the snap 13200 may also include a compliant member that is also positioned within the recess 13232 and may help to locate or maintain the position of the compression ring 13202. As discussed previously, the compliant member may reduce snap rattle and, depending on the configuration, also help to center the compression ring 13202. While not depicted in FIGS. 132A-132B to reduce redundancy, any of the compliant member configurations described above with respect to FIGS. 130A-130E and 131A-131E may also be applied to snap 13200 depicted in FIGS. 132A-132B. Similarly, the compression ring 13202 may have a twisted, partially helical, non-flat, or non-planar shape that helps to reduce rattle, chatter, or other potentially undesirable noises. A description of such a compression ring is described above with respect to FIGS. 130F-130H and 131F-131H and a similar compression ring configuration may also be applied to snap 13200 depicted in FIGS. 132A-132B.

As shown in FIGS. 132A-132B, the first element 13210 and the second element 13212 include a pocket 13214, 13216, respectively. The pockets 13214, 13216 may be formed as part of a molding process or, alternatively, may be machined into the first and second elements 13210, 13212, respectively. The pockets 13214, 13216 may have a depth that is greater than the respective inner flanges 13224, 13234, which allows for the first element 13210 to seat directly on or contact the second element 13212 when the snap 13200 is engaged or closed. This may prevent contact between the male assembly 13220 and the female assembly 13230, which may help reduce undesired noises and improve the feel of the snap, when engaging the male and female assemblies 13220, 13230.

FIG. 132C depicts another example embodiment of a snap 13260, also referred to as a snap assembly. The snap 13260 of FIG. 132C is similar to the stamped snap example described above with respect to FIGS. 132A and 132B except that the snap 13260 features a protrusion component or element 13276 that extends through the female assembly 13280 and defines an external surface of the snap 13260. As shown in FIG. 132C, the protrusion component or element 13276 defines an external surface that is substantially flush or aligned with an external surface of the female assembly 13280. This may provide a desired aesthetic appearance and also improve the engagement between the male assembly 13270 and the female assembly 13280 while also maintaining a thin or low-profile form factor of the snap 13260.

Similar to the previous examples, the snap 13260 includes a male assembly 13270 that is inserted into and engaged with a female assembly 13280. A compression ring 13262 engages a ramped or tapered surface on the protrusion component or element 13276 in order to help maintain engagement between the male assembly 13270 and the female assembly 13280. Similar to the previous examples, the compression ring 13262 may be retained within a groove or recess and rattle may be reduced by using a compliant member or compression ring having a twisted or non-flat shape. A similar description of such features have been described above and are not repeated here to reduce redundancy.

As shown in FIG. 132C, the snap 13260 includes a molded cap 13272 that is insert molded over internal member 13274. The internal member 13274 may include one or more holes or other features into which the insert molded cap 13272 may flow into and provide a more robust engagement between the two components. The molded cap 13272 may define a portion of a flange that is configured to engage the soft good. Similar to the other examples described herein, the flange may include various engagement features including, for example, ribs, teeth, grooves, or protruding features that help maintain engagement between the snap 13260 and the respective portion of the soft good. The snap 13260 also includes other flanges 13284, 13286 that may also include one or more engagement features to help maintain engagement between the snap 13260 and the respective portion of the soft good.

FIGS. 133A-133B depict another embodiment of a snap 13300, also referred to as a snap assembly, that may be used in an accessory of a wireless tag. In particular, FIGS. 133A-133B depict a snap 13300 that includes a magnetic coupling rather than a compression ring engagement between the components of the snap 13300. Many of the elements and features of the snap 13300 are similar to those described above with respect to the snap 13200 of FIGS. 132A-132B. A description of some of the similar elements and features are omitted to reduce redundancy.

As shown in FIGS. 133A-133B, the snap 13300 includes a single-piece or integrally formed male assembly 13320 and a single-piece or integrally formed female assembly 13330. The snap 13300 also includes partially molded end caps 13340 and 13350 that define exterior surfaces of the snap 13300 and that are attached to the male assembly 13320 and female assembly 13330, respectively. Similar to examples previously described, the snap 13300 is configured to couple a first element 13310 to a second element 13312, which may be two elements or regions of an accessory, as described previously.

As shown in FIGS. 133A-133B, the male assembly 13320 includes an internal pocket or recess for receiving a first magnetic element 13322. In this example, the first magnetic element 13322 is positioned within the protrusion or protruding portion of the male assembly 13320. Similarly, the female assembly 13330 includes an internal pocket or recess for receiving a second magnetic element 13332 that is positioned below a surface that defines a bottom of the recess of the female assembly 13330. The first magnetic element 13322 and the second magnetic element 13332 are arranged with opposite poles facing each other such that the first and second magnetic elements 13322, 13332 are magnetically attracted to each other. As shown in FIG. 133A, the first and second magnetic elements 13322, 13332 are positioned sufficiently close that the attractive magnetic forces are sufficiently strong to maintain the engagement between the male and female assemblies 13320, 13330 of the snap 13300. In this way, the first and second magnetic elements 13322, 13332 provide the engagement force that holds the snap 13300 in the close position in order to couple the first element 13310 to the second element 13312.

The snap also includes compliant members 13324 and 13334 that are positioned behind respective magnetic elements 13322, 13332 in order to reduce rattling or other undesirable effects. As shown in FIGS. 133A-133B, the compliant member 13324 is positioned between the first magnetic element 13322 and an inner surface of the first cap 13340. The compliant member 13324 may be formed from a compressible foam or other similar material. The compliant member 13324 may be slightly compressed and exert a retaining force on the first magnetic element 13322, which may help maintain the position of the first magnetic element 13322 and prevent undesired rattling or vibration. Similarly, the other compliant member 13334 is positioned between the second magnetic element 13332 and an inner surface of the first cap 13350. The other compliant member 13334 may also be formed from a compressible material and may be slightly compressed and exert a retaining force on the second magnetic element 13332. In some implementations, the compliant members 13324, 13334 and/or the magnetic elements 13322, 13332 may be glued or adhered to an inner surface of the snap 13300 to reduce vibration or other undesirable effects.

The materials of the snap 13300 may be similar to the other example provided herein. In particular, the unitary pieces that form the male assembly 13320 and the female assembly 13330 may be a stamped stainless steel material or other metal alloy that allows for the magnetic coupling between the first and second magnetic elements 13322, 13332.

As discussed herein, the wireless tag may have a variety of features and functions that have a broad applicability and a large number of use cases. As described in more detail below with respect to FIGS. 69A-128, a wireless tag module, also referred to herein as a wireless module, may be physically integrated with an accessory of another device, also referred to herein as a base device. In particular, a wireless module may establish a wireless connection with the base device and expand the functionality of that device by allowing access to various hardware elements of the wireless module over the wireless connection. This allows aspects of the wireless tag to be integrated with the base device in order to expand the functionality of that device and provide an expanded feature set without having to modify or significantly impact the hardware of the base device.

FIGS. 134A-134C and 135A-135C depict example wireless tags or wireless modules integrated with an accessory of a base device. In particular, FIGS. 134A-134C and 135A-135C depict a wireless module that is integrated into a band accessory of a smart watch or other wrist-worn device. While the following examples are provided with respect to a wireless module that is integrated with a band accessory, the same or a similar wireless module may be integrated into another accessory, like a case, cover, lanyard, frame, docking station, and the like. Further, while the following examples are provided with respect to a watch or other wrist-worn device, many of the functions and principles described may also be applied to a variety of other base devices including, for example, a smart phone, tablet computer, digital media player, health monitoring device, laptop computing system, desktop computing system, and so on.

FIGS. 134A-134C depict an example wireless module or wireless tag that is integrated into a band of a smart watch or other wearable device. In particular, FIGS. 134A-134C depict a wireless tag, referred to herein as a wireless module 13400 that is attached or otherwise integrated with a band 13402 of a watch 13405. For ease of discussion, in the following examples, the watch 13405 includes a watch body 13404 that may be separate from the band 13402 A watch body 13404 without a band may also be referred to herein as a watch base or simply a watch. The watch 13405, as used herein, may be described as the complete electronic device that includes the watch body 13404 and the band 13402, which may in turn include the wireless module 13400. The watch body 13404 of the (smart) watch 13405, also referred to herein as a base device, includes a display 13406 for producing graphical output and various internal components including, for example, a processor, a wireless communication circuit, an input device, a battery, one or more sensors, and other electronic components. The wireless communication circuit of the watch body 13404 may be configured to transmit and receive wireless communication signals, in accordance with the embodiments described herein. The display 13406 may include a liquid crystal display (LCD) element, organic light emitting diode (OLED) display element, or other type of display element. The display 13406 may also include a touch and/or force sensor that is configured to detect a touch and/or force applied to a cover over the display 13406. In some instances, a touch-sensitive display or force-sensitive display may also be referred to as a touchscreen. As shown in FIG. 134A, the watch body 13404 may also include one or more buttons, dials, crowns, switches, or other mechanically actuated input devices. For purposes of the following description, these mechanically actuated input devices are generally referred to as a button 13408.

The watch body 13404, as an example base device, also includes a variety of other elements, components, and subsystems. A description of an example base device is provided below with respect to the electronic device 14000 of FIG. 140. In the following examples, the base device is a watch 13405 or watch body 13404 and the accessory is a band 13402. However, in other implementations, the base device may be another electronic device like a mobile phone, tablet computing device, portable media player, health monitoring device, or other type of electronic device. Likewise, in other implementations, the accessory may be a cover for the electronic device, a protective case for the electronic device, a charging station for the electronic device, or other type of accessory for the electronic device. Similar to as described below with respect to the band 13402, a wireless module 13400 may be installed or otherwise integrated with an accessory (e.g., a cover, protective case, charging station) by installing the wireless module 13400 in a hole, recess, or opening of the respective accessory. In some cases, the wireless module 13400 is integrated into the accessory through a molding technique, mechanical fastener technique, welding technique, or other integration technique.

The wireless module 13400 includes a wireless communication system, including a wireless communication circuit and antenna for wirelessly transmitting and receiving signals from a separate device. In this example, the wireless module 13400 includes a wireless communication system that is configured to operably connect or couple to the wireless communication system of the base device, which, in this case, is a smart watch 13405 or watch base 13404. The wireless link between the wireless module 13400 and the watch body 13404 may be automatically established when the band 13402 is installed or physically attached to the watch body 13404. The wireless link may be established in response to a sensor in the watch body 13404 detecting the presence of the band 13402 and/or through a manual setting provided by the user. In some cases, the wireless link may be established by determining that one or more of the respective internal sensors of the wireless module 13400 and the watch body 13404 are providing an output that indicates that the wireless module 13400 is coupled to the watch body 13404 by the band 13402. For example, accelerometer output, gyro sensor output, UWB sensing system output, GPS output, or other sensing system output may be used to determine if movement of the wireless module 13400 corresponds to movement of the watch body 13404 in a way that indicates that the devices are physically coupled.

Using the wireless communication link, sensor signals or data from the wireless module 13400 may be passed to the watch body 13404. As described herein, the sensor signals or data from the wireless module 13400 may be transmitted to the watch body 13404 as a wireless input signal, which is received by a corresponding wireless circuit of the watch body 13404. The display 13406 of the watch body 13404 may be responsive to the wireless input signal received from the wireless module 13400. By way of example, the wireless module 13400 may include a button or other input device that may be actuated in response to a user touch or finger press. As described in more detail below, the wireless module 13400 may include an electromechanical switch, capacitive touch sensor, force sensor, or other similar type of input device. In some cases, the wireless module 13400 includes an array of capacitive nodes or electrodes that are configured to determine a location of a touch, a gesture input, and/or a direction or path of a touch's movement on the surface of the wireless module 13400. The watch body 13404 may be responsive to an actuation of the input device on the wireless module 13400, which may be used to perform one or more of a variety of functions. By way of example, the watch body 13404 may be responsive to the input device in order to wake the watch body 13404, place the watch body 13404 in a sleep or hibernation mode, acknowledge receipt of an incoming message, silence an alarm or other output of the watch body 13404, initiate a payment for an electronic transaction, access a list of contacts or an address book on the watch body 13404, display a list of programs or apps running on the watch body 13404, access a previous screen or display of the graphical user interface displayed on the display 13406 of the watch body 13404, start or stop a stopwatch or other timing function of the watch 13404, initiate a running or activity tracking program or function of the watch body 13404, initiate or begin playing a song or other media for a media-player function of the watch body 13404, and/or perform another function on the watch body 13404. In some cases, the wireless module 13400 and/or the watch body 13404 may be programmable to replicate the functionality of one or more buttons 13408 of the watch body 13404. Similarly, the wireless module 13400 and/or the watch body 13404 may be programmable to replicate functionality of the touch- and/or force-sensitive surface of the display 13406 (e.g., the touchscreen). For example, an input provided to the wireless module 13400 may be used as a supplement to or replacement for a touch and/or force input on the display 13406. The wireless module 13400 may, for example, be configured to detect gesture or other dynamic touch input using a capacitive array of nodes or electrodes. The gesture and/or dynamic input may be used to replicate touch and gesture input that may be provided to the touch screen display. A touch, gesture, and/or force input to the wireless module 13400 may be used to select a graphical object displayed on the display 13406, change a display mode of the graphical user interface, actuate a virtual button displayed in the display 13406, scroll through a list of items on the display, perform a zoom function on the display, enter a passcode or signature gesture, or perform other functionality on the watch body 13404.

Using the wireless communication link, signals and/or data from the watch body 13404 may also be passed to the wireless module 13400 using a wireless input signal, wireless output signal, or other type of wireless signal. The wireless module 13400 may be responsive to such signals and/or data from the watch body 13404 and may be configured to perform one of a variety of functions or outputs in response to operations performed on the watch body 13404. In one example, the wireless module 13400 includes a haptic device or other device that is configured to produce a haptic output that is tactilely perceptible to the user. For example, the wireless module 13400 may include an electromagnetic or piezoelectric haptic engine that is configured to produce a vibration or other haptic output along an exterior surface of the wireless module 13400 that is likely to contact the user's skin. In this example, the wireless module 13400 may be configured to produce a haptic output along an inner surface of the wireless module 13400 that is likely to contact the user's wrist. The wireless module 13400 may also be configured to produce an acoustic or audio output using a speaker or other acoustic device in response to signals and/or data received from the watch body 13404. The wireless module 13400 may also include a display, light-emitting element (e.g., an LED), or other visual output device that is configured to produce a visual output in response to a signal received from the watch body 13404 and/or an internally generated command or instruction. For example, the wireless module 13400 may include a LED, array of LEDs, and/or a segmented display that is responsive to a signal received from the watch body 13404 and/or an internally generated command or instruction.

The wireless module 13400 may be responsive to activity on the watch body 13404 and produce an acoustic and/or haptic output in response to one or more of a variety of operational scenarios. For example, the wireless module 13400 may produce a haptic output, acoustic output, and/or visual output in response to: an alert or alarm initiated by the watch body 13404, a message received by the watch body 13404, or a selection of a graphical object on the display 13406 or touchscreen of the watch body 13404.

The wireless module 13400 may also be adapted to operate in concert with one or more subsystems operating on the watch body 13404. For example, the wireless module 13400 may provide a supplemental antenna or function as a wireless receiver for the watch body 13404. The wireless module 13400 may also include location-determining hardware like a global positioning system (GPS) sensor or the like and the wireless module 13400 may relay data and/or signals to the watch body 13404 to provide location information that may be used to determine the location of the user and/or supplement location-determining hardware that is incorporated into the watch body 13404. In accordance with other embodiments described herein, the wireless module 13400 may also include a wireless locating system (e.g., a UWB wireless system) that may be adapted to determine a relative and/or absolute location of the wireless module 13400 using one or more of the techniques described herein with respect to other example wirelessly locatable tags. Additionally or alternatively, the wireless module 13400 may include a wireless locating system, which may be used alone or in concert with one or more antennas of the watch body 13404 in order to improve accuracy of location-determining functionality of the watch body 13404. Similarly, the wireless module 13400 may also include one or more accelerometers, gyro sensors, magnetometers, or other sensors that may operate in coordination with one or more similar sensors incorporated into the watch body 13404 in order to improve a determination of device location, device orientation, user activity, user posture, or other similar functions. An example of the various hardware elements that may be included in the wireless module 13400 is described below with respect to FIG. 144.

As shown in FIG. 134B, the wireless module 13400 is positioned within a hole or opening 13403 of the band 13402. As shown in FIG. 134B, the wireless module 13400 includes an enclosure 13420 that is defined by an upper housing 13422 that is coupled to a lower housing 13424. The enclosure 13420 encloses a circuit assembly 13426 and a battery 13428 that is operably coupled to the circuit assembly 13426. The various components may be similar to the components described herein with respect to other wireless tag embodiments. A redundant description of the various shared components is omitted to reduce redundancy and improve clarity.

FIG. 134C depicts an example cross-sectional view of the wireless module 13400 taken along section 134C-134C of FIG. 134A. As shown in FIG. 134C, the wireless module is retained within the opening 13403 of the band 13402 by a pair of flanges. An upper flange 13440 is defined along a periphery of the upper housing 13422 and a lower flange is similarly defined along a periphery of the lower housing 13424. A portion of the band 13402 is trapped between the upper flange 13440 and the lower flange 13442 thereby retaining the wireless module 13400 within the opening 13403 of the band 13402. As shown in FIG. 134C, the opening 13403 of the band 13402 may include a counter bore on either side to help nest the respective flanges 13440, 13442 within the profile of the band 13402. In some implementations, the bottom surface defined by the lower housing 13424 is substantially aligned or coplanar with a surface of the band 13402, which may reduce the tactile perception of the wireless module 13400 by the user when the watch 13405 is being worn. In the present example, an outer surface defined by the upper housing 13422 is aligned with an outer surface of the band 13402 along a periphery of the wireless module 13400 but protrudes or is proud of the outer surface of the band 13402 along a central or middle portion that is surrounded by the periphery. This may allow the user to locate the button of the wireless module 13400 by touch or with minimal visual cues. The band 13402 may be formed from any one of a variety of materials including, for example, silicone, fluoropolymer, nylon, or another type of polymer material. In some cases, one or both of the upper housing 13422 or the lower housing 13424 may include one or more materials that are in common with the material of the band 13402 in order to provide a uniform appearance and/or tactile feel.

The lower housing 13424 and the upper housing 13422 may be formed from similar materials as other wireless tag embodiments described herein. In particular, the lower housing 13424 may be formed from a metal, polymer, and/or composite material and may include one or more latches or catches that engage a respective mating feature of the upper housing 13422. In some cases, the lower housing 13424 is configured to be removable by a user in order to replace the battery 13428 or other internal components. Various removable doors and housing components are described with respect to other embodiments herein and not repeated with respect to this example to reduce redundancy.

As shown in FIG. 134C, the wireless module 13400 includes an electromechanical switch 13430 that may be actuated with a finger press along the exterior of the enclosure 13420. In this example, the switch 13430 is a compressible tactile dome that buckles or collapses in response to an external press or force in order to close an electrical contact or produce another electrical response. The compressible tactile dome may also be referred to herein as a "tactile dome switch." In some cases, a capacitive touch sensor, a force sensor, or other type of sensor may be used to detect a press or touch of a finger. As described previously with respect to other embodiments herein, the upper housing 13422 may be configured to locally deflect or displace in response to a touch or press by a finger. In particular, an outer portion of the upper housing 13422 may be formed from a compliant or flexible material in order to allow the middle or central portion to deflect or displace in response to a touch or press. Portions of the upper housing may be formed from a silicone material, synthetic rubber, or other compliant material that allows for a deformation of the upper housing in response to a touch. In some cases, the movement of the upper housing 13422 and/or the movement of the compressible tactile dome of the switch 13430 provides a haptic or tactile output that indicates that the switch 13430 has been actuated. The haptic or tactile output may be a click or other similar tactile response. In some cases, the wireless module 13400 includes a separate haptic device that produces the haptic or tactile feedback in response to a touch or press.

In this way, the wireless module 13400 may function as a remote button or additional input device for the watch 13405. As described previously, the watch body 13404 may be responsive to an actuation of the switch 13430 and perform one or more of the functions described above. One benefit to the use of a wireless module 13400 is that additional buttons or input devices may be added to the watch body 13404, which may have limited area for additional buttons or input devices. As discussed above, the wireless module 13400 may also include one or more electronic sensors that may be used to help determine the location and/or orientation of the watch body 13404, and/or help determine a user activity or position.

The additional functionality enabled by the wireless module 13400 can be provided without having to substantially modify or alter the hardware of the watch body 13404. In the embodiment of FIGS. 134A-134C, the wireless module 13400 does not include a conductive electrical connection to the watch body 13404 and, instead, is electrically coupled to the watch body 13404 by a wireless communication link. This allows for the functionality of the wireless module 13400 to be added or removed by merely swapping the band that is attached to the watch body 13404.

In some cases, a band may include multiple wireless modules in order to provide additional user input devices and/or sensors. As depicted in FIGS. 134A-134B, the watch 13405 may include multiple wireless modules 13400, 13401 that are located along different regions of the band 13402. The additional wireless module 13401 may operate in a substantially similar way and include similar elements and components as described herein with respect to wireless module 13400. In some implementations the wireless modules 13400 and 13401 are configured differently or have different hardware arrangements. While only two wireless modules 13400, 13401 are depicted in FIGS. 134A-134B, other implementations may include more than two modules. In some cases, an array of three or more modules may be arranged along the length of the band 13402, each module configured to operate using at least some of the functionality described herein with respect to wireless module 13400.

As shown in FIG. 134C, the wireless module 13400 is electrically isolated from the watch body 13404 and includes a separate battery 13428 for a power source. The battery 13428 may be replaceable and/or rechargeable by an external power source. In the current implementation, the wireless module 13400 includes a wireless charging coil 13436 that may be configured to receive power wirelessly from an external charging coil in a separate charging dock or charging device. As described previously, the external charging coil may be configured to produce an electromagnetic field that induces a current in the charging coil 13436, which may be used to supply (wireless) power to the wireless module 13400 and charge the battery 13428.

As shown in FIG. 134C, the wireless module 13400 may also include one or more magnetic elements 13432 that may be used to secure or locate the wireless module 13400 with respect to an external charging device, which may also include a mating magnetic element that is configured to magnetically couple with the magnetic element 13432 while the wireless module 13400 is docked to the external charging device. In some instances, the protruding shape or convex profile of the upper housing 13422 may also help to locate the wireless module 13400 with respect to an external charging device. In some embodiments, the external charging device is configured to wirelessly charge both the wireless module 13400 and the watch body 13404 in a common dock that includes external wireless charging coils for both the wireless module 13400 and the watch body 13404, which may be housed or enclosed by an common dock enclosure or housing.

As shown in FIGS. 134B-134C, the wireless module includes a circuit assembly 13426 that is operably coupled to the battery 13428 and the switch 13430. The circuit assembly 13426 includes wireless communication circuitry (wireless circuitry) that is operably coupled to or includes an antenna. As described previously, the wireless communication circuitry may be configured to establish and maintain a wireless communication link with the watch body 13404. The wireless communication link may be conducted in accordance with an established wireless communication protocol including, for example, Bluetooth, BLE, WiFi, or another protocol. The wireless communication link may be established automatically based on a determination that the wireless module 13400 and band 13402 are attached to the watch body 13404.

The wireless communication circuitry may also be configured to communicate with external devices using the same protocol or another separate protocol. As described previously with respect to other wirelessly locatable tags described herein, the wireless module 13400 may have wireless communication circuitry that may be used to locate the wireless module 13400 (and thus also locate the base device—the watch 13405 or watch body 13404). In some cases, the wireless communication circuitry may be configured to generate or relay location data that may be used as part of a mesh or ad-hoc network of devices. Similar to as described above with respect to the other wirelessly locatable tag embodiments, the wireless module 13400 may be used to securely transmit location information about itself or another device using a digital key or other authentication technique. As such, the functionality of the wirelessly locatable tag, as described herein, may be added to a device by incorporating a wireless module 13400 into an accessory of the device. Because the wireless module 13400 includes a separate power supply (battery 13428) and circuit assembly 13426, the wireless module 13400 may operate independent of the base or host device while also being used to locate the base or host device (e.g., watch 13405 or watch body 13404) using one or more of the techniques described herein.

As discussed previously, the circuit assembly 13426 may also include one or more sensors including, without limitation, an accelerometer, gyro sensor, magnetometer, GPS sensor, or other similar type of sensor that may be used to track the location, orientation, and/or movement of the wireless module 13400. The circuit assembly 13426 may also include a microphone, speaker, or other audio component for producing an audio output and/or receiving an audio input. In some instances, the circuit assembly 13426 also includes one or more antennas, which may be used for wireless communication and or location using a UWB, time of flight, or other similar technique. The circuit assembly 13426 may also include one or more processors or processing units that are configured to execute instructions, software, firmware, code or other computer-executable instructions.

The circuit assembly 13426 may also include a near-field communication (NFC) circuit and antenna for wirelessly coupling to another device that is proximate to the wireless module 13400. In some cases, the NFC antenna is integrated with the wireless charging coil 13436. In some cases, the NFC antenna is a separate element or component that is electrically and/or structurally coupled with the circuit assembly 13426. In some cases, the NFC antenna is formed on or otherwise integrated into the circuit assembly 13426.

The wireless module 13400 may also include a display element and/or other visual output device. The display element may include a segmented display, LCD, OLED or other type of display element. In some cases, the circuit assembly 13426 includes one or more LEDs or other visual output devices that may provide a visual output along a surface of the wireless module 13400. The wireless modules 13400 may include one or more covers, light guides, light pipes, or other elements that enable the visual output of the display element and/or another visual output device.

As shown in FIGS. 134A-134C, the wireless module 13400 is incorporated into a band 13402 of the watch 13405. However, the wireless module 13400 may also be incorporated into another accessory or device that may be paired with the watch. The accessory or device may be manufactured by a third party and may include additional electronic components that are configured to provide a particular set of functions. The wireless module 13400 may function as the wireless connection or bridge between the third-party or external device and the base device (watch body 13404). The third party or external device may be configured to transmit signals and/or data to the wireless module 13400 using an advanced programming interface (API) or other communication protocol. Signals and/or data transmitted to the wireless module 13400 may then be passed on to the base device (watch body 13404) using the wireless communication link established between the wireless module 13400 and the base device (watch body 13404). Using the wireless module 13400 as an intermediary between devices allows accessories, third-party devices or other external devices to establish one uniform interface with the wireless module 13400. The wireless module 13400 may then be adapted to work with a range or variety of base devices without having to reprogram or reconfigure the accessory, third-party device, or other external device. For example, an accessory may access or provide signals and/or data to a first base device (e.g., a watch body 13404) using a wireless module (e.g., wireless module 13400) and also access a second base device (e.g., a phone or tablet) using another wireless module having a similar API or other protocol as the wireless module 13400.

One example implementation may involve an integration of a separate heart-rate monitor that may be worn or otherwise coupled to a user in order to track and monitor a biological function or biometric of the user, like a heart rate. The heart rate monitor may include a sensor, a processor, and a wireless communication system that has been adapted or configured to wirelessly interface with a wireless module (similar to the wireless module 13400). For purposes of this example, the heart rate monitor may be characterized as an accessory, third-party device, or an external device and may produce a signal or data that corresponds to the measured biometric (e.g., a heart rate). The signal or data (first signal or first data) may be transmitted from the heart-rate monitor to the wireless module using a first wireless communication link (which may implement a first protocol or set of APIs). The wireless module may then relay a second signal or second data (that is based on the first signal or first data) to the base device using a second wireless communication link (which may implement a second protocol or set of APIs).

The base device may display information related to the measurement of the biodata as part of a health monitoring software program or graphical user interface. Similarly, the wireless module may be used to pass signals or data from the base device to the heart rate monitor, which may include commands to initiate a measurement, stop a measurement, enter a designated power state, or other type of command or signal. Using the wireless module, the heart rate monitor may interface with a variety of base devices (e.g., a watch, a mobile phone, a tablet computing system) through a respective wireless module, without having to substantially alter a wireless interface or protocol. As a result, any base device having a suitably coupled wireless module may be used with the heart-rate monitor. A similar scheme may be used to couple a variety of external devices with a base device using a wireless module, as described herein. Example external devices include, without limitation, wireless speakers, wireless headsets, bar-code scanners, navigation systems, automobiles, home security systems, doorbell systems, thermostats, appliances, home automation systems, and the like.

FIGS. 135A-135C depict another example of a wireless tag or module that is integrated with an accessory of a device. More specifically, FIGS. 135A-135C depict another example of a wireless tag also referred to as a wireless module 13500 that is integrated with a watch band 13502 of a watch 13504. Similar to the previous example, the watch 13504 is referred to separately from the band 13502. However, the watch 13504 may also be described as including the band 13502 and, in some cases, the wireless module 13500. The smart watch or simply watch 13504, also referred to herein as a base device, includes a display 13506 for producing graphical output and various internal components including, for example, a processor, a wireless communication module, an input device, a battery, one or more sensors, and other electronic components. The display 13506 may be similar to the display 13406 described above and may include one or more display elements, a touch sensor, force sensor, and other similar elements. The watch 13504 may also include one or more buttons, dials, crowns or other input devices represented by the button 13508 depicted in FIG. 135A. The watch 13504 is an example base device and may include various components that are not expressly depicted in FIGS. 135A-135C.

The wireless module 13500 may be configured to wirelessly pair or connect to the watch 13504 in a similar fashion as described above with respect to FIGS. 134A-134C. Similar to the previous example described above, the wireless module 13500 may be used to enhance the functionality of the watch 13504 without substantially modifying or altering the hardware of the watch 13504. The wireless module 13500 may operate in a substantially similar fashion as wireless module 13400, described above. A description of the shared features and functionality is omitted from the description to reduce redundancy.

The wireless module 13500 includes many of the same components and functional elements as described above with respect to the wireless module 13400. An example of the various hardware elements that may be included in the wireless module 13500 is described below with respect to FIG. 144. However, as shown in FIG. 135B, the wireless module 13500 provides for a remote switch 13530 with may be operably and electrically coupled to the circuit assembly 13526 by a flexible circuit 13532. The flexible circuit 13532 may include an array of conductive traces that are formed on a dielectric material that may be able to be reliably flexed or bent with normal use of the band 13502. While the present example depicts a single switch 13530, an alternative embodiment may include multiple switches that may be located along the length of the band 13502.

By decoupling the switch 13530 from the other elements of the wireless module 13500, the functionality may be expanded without substantially altering the main components of the wireless module 13500. This may allow for a variety of watch band configurations having specialized or dedicated buttons that are adapted for a particular use case or functionality. For example, the wireless module 13500 may be integrated with a sports band and include multiple switches or buttons, each switch or button dedicated to a stopwatch function, fitness tracking function, or other similar sports-related function. By way of further example, the wireless module 13500 may be adapted for underwater use or for use while swimming. Due to the presence of water, the touch functionality of the touch screen display 13506 may not operate consistently or where gloves may impede the operation of a capacitive touch sensor. Key functionality or operations of the watch 13504 may be mapped to the one or more switches of the wireless module 13500 in order to allow for use when the device is wet or when a capacitive touch sensor may not be operable.

As shown in FIG. 135B, the circuit assembly 13526 may be enclosed and sealed using a set of components that together define the enclosure 13520 of the wireless module 13500. Specifically, the enclosure 13520 includes an upper housing 13522 that defines an outer or upper surface of the wireless module 13500. In this example, the upper housing 13522 includes a prong 13523 or other similar feature that may be used as a clasp or fastener for the band 13502. The prong 13523 may be configured to be inserted into and retained by a corresponding hole in a strap of the band 13502 to form a clasp or securing fastener to secure the band 13502 to the user. In this example, the prong 13523 is integrally formed with the upper housing 13522 and includes a catch or lobe at the end of the prong 13523 that is configured to engage a hole in a strap or other element of the band 13502 in order to secure the band 13502 around the wrist of a user. The enclosure also includes a lower housing 13524 that defines an inner or lower surface of the wireless module 13500. The lower housing 13524 may be removable to allow for replacement or servicing of the battery 13528. An O-ring 13562 or other type of seal may be used to form a waterproof or water-resistant seal between the lower housing 13524 and the rest of the enclosure 13520.

The enclosure 13520 also includes a central ring 13550 that is positioned between the upper housing 13522 and the lower housing 13524. The central ring 13550 may be used to mount the circuit assembly 13526 and may help secure the wireless module 13500 to the band 13502. As shown in FIG. 135B, the enclosure 13520 may include adhesive rings 13564, 13566 that form a seal between the central ring 13550 and the lower housing 13524 and the upper housing 13522, respectively. In some cases, the adhesive rings 13564, 13566 are formed from a heat-activated adhesive layer, a pressure-sensitive adhesive layer, or another type of adhesive layer or seal. In some implementations, the central ring 13550 includes threaded features that are configured to engage with either or both of the lower housing 13524 and the upper housing 13522.

FIG. 135C depicts a cross-sectional view of the wireless module 13500 along section 135C-135C of FIG. 135A. As shown in FIG. 135C, the wireless module 13500 is retained within the band 13502 by a retaining ring 13552. The retaining ring 13552 may be formed from a polymer or metal material that is inserted into a groove in an opening in the band 13502. In some cases, the band 13502 is molded around the retaining ring 13552. In other cases, the retaining ring 13552 is installed into the groove after the band 13502 has been molded or otherwise formed. As shown in FIG. 135C, the enclosure 13520 of the wireless module engages the retaining ring 13552 by an upper flange 13540 formed into the upper housing 13522 and the central ring 13550. The lower housing 13524 also includes a lower flange 13542 that is configured to seat or contact against a surface of the central ring 13550.

FIG. 135C also depicts a cross-sectional view of the switch 13530, which is positioned below a membrane, cover layer, or outer layer 13503 that defines an outer or exterior surface of the band 13502. The outer layer 13503 may be formed from a material that is similar to the main strap of the band 13502. In some cases, the outer layer 13503 is formed from silicone, fluoropolymer, nylon, or another type of polymer material. Similar to the previous example, the switch may include a tactile dome that forms an electrical switch that is closed or otherwise provides an electrical response in response to an applied force or touch, as indicated by the arrow. The tactile dome of the switch 13530 (also referred to as a "tactile dome switch") may be attached to a surface of the flexible circuit 13532, which operably and electrically couples the switch 13530 to the circuit assembly 13526.

As described herein, a wireless tag may be useful for a variety of applications. As described below with respect to FIGS. 136A-136C, 137A-137B, 138A-138B, and 139, an array of wireless tags may be used to track and/or monitor a user's posture. In general, poor posture may be a major contributor to chronic back pain and other musculoskeletal issues. As many as two thirds of adults experience lower back pain at some point in their lives and incorrect posture may be a significant cause. Lower back pain may also be a significant cause of workplace-related disabilities and may result in reduced productivity and quality of life. However, lower back pain and other musculoskeletal issues may be improved or prevented through consistent posture monitoring and posture correction. As described below with respect to FIGS. 136A-136C, 137A-137B, 138A-138B, and 139, wireless tags may be strategically positioned along a body of a user and used to monitor and correct potentially problematic posture issues to help avoid chronic physical ailments.

An array of wirelessly locatable tags (also referred to herein as "wireless tags" or simply "tags") may be positioned or fixed with respect to various regions along a user's body in order to track and monitor a user's posture. As shown in FIG. 136A, a posture-monitoring system 13601 may include an array of wireless tags 13600a-13600f that are positioned along various locations of a user's back. As previously discussed, a location of a wireless tag may be determined relative to another device using wireless location-tracking techniques including, for example, time of flight (ToF), angle of arrival (AoA), time difference of arrival (TDOA) received signal strength indication (RSSI), triangulation, synthetic aperture, and/or any other similar techniques. The wireless tag may be used to determine a relative location or distance with respect to another external device or wireless tag. The wireless tag, in some implementations, may be used to determine an absolute location or position by using a global positioning system (GPS) or other locating system that is either integrated with the wireless tag or integrated with a separate device.

As shown in FIG. 136A, a posture-monitoring system 13601 may include an electronic device 13610 and an array of wireless tags 13600a-13600f that are either directly attached to a user 13605, incorporated into an article of clothing, or otherwise coupled to the user 13605 at various positions along the user's body. The electronic device 13610 may be a mobile telephone, portable computer, tablet computer, portable music player, or other portable electronic device. The electronic device 13610 may also be attached to the user and may be a watch, a smart watch, a wrist-worn health monitoring device, or other type of wearable electronic device. The electronic device 13610 may also be a notebook or laptop computer system, a desktop computer system, health monitor device, or other type of device. An example electronic device 14300 is described below with respect to FIG. 143, a complete description which is not repeated here for electronic device 13610. In some cases, the electronic device 13610 is an appliance or other device that is fixed in a room or location. While only one electronic device 13610 is depicted in the example system, 13601 of FIG. 136A, other implementations or systems may include multiple electronic devices, which may improve the accuracy and/or reliability of the posture tracking system.

As shown in FIG. 136A, each wireless tag 13600a-13600f is positioned at a different location along the body of the user 13605. Specifically, the wireless tags 13600a and 13600b are positioned along shoulder regions of the user 13605, wireless tag 13600c is positioned along a mid-back region of the user 13605, wireless tag 13600d is positioned along a lumbar region of the user 13605, and wireless tags 13600e and 13600f are positioned along a leg (e.g., a knee region) of the user 13605. The configuration and position of the wireless tags 13600a-13600f is provided by way of an example illustration and the number and locations of the various wireless tags may vary depending on the implementation.

Each of the wireless tags 13600a-13600f is configured to use a wireless-location technology to determine a relative location with respect to one or more of the other wireless tags 13600a-13600f. In one implementation, each of the wireless tags 13600a-13600f is configured to use a respective UWB signal to determine a relative location of the respective wireless tag 13600a-13600f with respect to the electronic device 13610, also referred to herein as a base device, host device, or a reference device. As described previously, each of the wireless tags 13600a-13600f may be able to determine a relative distance to the electronic device 13610 using a time of flight (ToF), angle of arrival (AoA), time difference of arrival (TDOA) received signal strength indication (RSSI), triangulation, synthetic aperture, and/or any other similar techniques, one or more of which may be implemented using a UWB wireless system. The location and/or position information determined using each of the wireless tags 13600a-13600f may be transmitted to the electronic device 13610 as what may be referred to herein as a (wireless) locating signal. The wireless locating signal may include location data that corresponds to a distance between the respective wireless tag 13600a-13600f and the electronic device 13610 or another reference. In some cases, the wireless locating signal includes a UWB wireless pulse that is used to measure the relative distance using one or more of the aforementioned techniques. In other cases, the wireless locating signal may include locating data that includes a relative location or distance between tags or devices. In this case, the wireless locating signal may be transmitted using a wireless protocol that is different than a UWB pulse that is used to determine the relative location or distance. For example, the wireless locating data may be transmitted using a Bluetooth, WiFi, or other wireless transmission protocol.

The electronic device 13610 may be adapted to coordinate the various wireless locating signals to determine a relative location of each of the wireless tags 13600*a*-13600*f*. In some implementations, the electronic device 13610 may be able to determine an absolute location using a GPS signal or other absolute location determining technique, which may be used to determine an absolute and/or relative location of each of the wireless tags 13600*a*-13600*f*. In some implementations, a magnetometer and or accelerometer of the electronic device 13610 is used to determine a relative and/or absolute location of the wireless tags 13600*a*-13600*f*.

In some implementations, the wireless tags 13600*a*-13600*f* are configured to determine an estimated distance between each of the wireless tags 13600*a*-13600*f* without the use of an external electronic device 13610. For example, each of the wireless tags 13600*a*-13600*f* may be configured to operate as either a transmitter or a receiver in a time-of-flight or other wireless measurement scheme in order to determine a distance between a pair of wireless tags 13600*a*-13600*f*. In such embodiments, the wireless locating signal may comprise an estimate of a distance between one or more other wireless tags 13600*a*-13600*f*. In some cases, each of the wireless tags 13600*a*-13600*f* includes an accelerometer, magnetometer, or other element that is configured to determine a device orientation, which may be used to determine a relative location of each of the wireless tags 13600*a*-13600*f*. In some cases, the accelerometer, magnetometer, or other element that is configured to determine a device orientation provides additional information about the position of the user's body including torso or shoulder twist.

In some implementations, the wireless tags 13600*a*-13600*f* may be configured to use a grid or network of other wireless tags that are not attached to the user 13605 in order to determine a relative location of each of the wireless tags 13600*a*-13600*f*. Also, as suggested above, the wireless tags 13600*a*-13600*f* may be adapted to use multiple (external) electronic devices to determine a relative location. For example, three electronic devices may be used to "triangulate" multiple UWB signals and determine a relative location of each of the wireless tags 13600*a*-13600*f*.

The position and/or posture of the user 13605 may be monitored using the relative or absolute location of each of the wireless tags 13600*a*-13600*f*. The position of the user 13605 in FIG. 136A may represent a nominal or an ideal posture position. As shown in FIG. 136B, an ideal goal location of each of the wireless tags 13600*a*-13600*f* may be determined with respect to a datum or reference, here represented by the reference plane 13604 depicted in FIG. 136B. The location of the reference plane 13604, in this example, may be determined as a vertical plane that is positioned with respect to the wireless tags 13600*a*, 13600*b* located along the shoulder regions of the user 13605. A nominal position of each of the other wireless tags 13600*c*-13600*f* may be specified in terms of a reference offset or delta with respect to the reference plane 13604. The reference offset of each of the wireless tags 13600*a*-13600*f* may be determined on a user-by-user basis as each user's body is unique and the nominal, normal, or ideal position of the wireless tags 13600*a*-13600*f* may vary from user-to-user depending on muscle mass, body fat content, and other physical body features. Other techniques may also be used to determine the reference or ideal position of the wireless tags 13600*a*-13600*f* including, for example, local coordinate values with respect to a datum origin, working envelopes, or other spatial constraining techniques. Reference or ideal position data may be stored in computer-readable memory for use by the posture-measurement system 13601.

The posture monitoring system 13601 may be configured to detect a deviation or potentially problematic posture condition by measuring an actual posture, which may be measured on a regular or continuous basis and used to generate results, which may be provided to the user through a graphical user interface of the electronic device 13610. FIG. 136C depicts an example posture that deviates from the ideal posture of FIG. 136B and which may also represent a potentially problematic posture condition, which may be detected by the posture monitoring system 13601. As shown in FIG. 136C, a location of each of the wireless tags 13600*a*-13600*f* may be determined with respect to a reference plane 13604. If the positional offset of certain wireless tags 13600*a*-13600*f* falls outside of a range or exceeds a tolerance threshold, the system 13601 may determine that the user's current posture is potentially problematic or otherwise flag the posture event for the user. In some cases, the relative location of certain of the wireless tags 13600*a*-13600*f* is monitored with respect to a working envelope or other volume constraint and deviations that breach the reference working envelope or volume constraint are flagged.

The posture monitoring system 13601 may be configured to detect the user's posture using wireless locating signals received from one or more of the array of wireless tags 13600*a*-13600*f*. In the example of FIG. 136C, the posture monitoring system 13601 may be used to detect a tilted posture in which the user's torso is slumped or leaned forward. The deviation may be determined using a comparison between a current relative position and a nominal or ideal position. In this example, the measured tilt plane 13606, which may be determined using a comparison between the current position and a nominal position, may represent an angular deviation of the user's posture as determined based on the position of wireless tags 13600*a*-13600*d*. The tilt plane 13606 is provided merely to demonstrate the amount of deviation, which may be represented using any number of different techniques, depending on the implementation. A visual representation of the measured deviation including for example, the tilt plane 13606, may be provided to the user through a graphical user interface of the electronic device 13610 using another computer generated display.

Other example postures may be detected by the posture monitoring system 13601. For example, the posture monitoring system 13601 may be used to detect one or more common static postures that may be associated with chronic back pain or other health issues. Example static postures include a hollow back posture in which the lumbar region of the user's back is displaced or distorted in a direction toward the front of the user's body. Other example static postures include a flat pelvis in which the curvature of the user's lumbar region is straightened or flattened as compared to an ideal or nominal posture. Other example postures include slumped postures, military postures, rounded shoulder postures and other similar postures that may be observed through the position or curvature of the user's back from the side of the user's body. These postures may generally be referred to as bend metrics. The posture-monitoring system 13601 may also be used to detect various postures, which may be characterized by tilt or twist metrics including, for example, high or displaced shoulders, high or displaced hips, head tilts, and spinal twists including scoliosis and other spinal defects. The posture-monitoring system 13601 may also be used to detect various non-static posture defects that may be evident in a user's gait, running stride, bending motion, sitting motion, or other non-static scenarios.

The user's posture may be monitored over time and/or measured on a regular interval. If the regular interval is sufficiently small (e.g., less than about 1 second), the posture measurement may be characterized as continuous or substantially continuous. The posture measurements may be stored in a data log and used to display results to a user on a graphical user interface of the electronic device 13610 when requested. In some cases, a series or set of body measurements are used to compute an animation of an avatar or other computer-generated model. The computed avatar or other computer-generated model may be displayed on a display of the electronic device 13610.

In some cases, the body position or posture measurements are recorded in response to a determination that the user 13605 is in a static position. The static position may correspond to a standing static position, a sitting static position, a prone static position, or other static position. This determination may be made using the wireless locating signals (e.g., UWB beacon signals) a motion sensing system, accelerometers, magnetometers, or other sensors and sensing systems. If the user 13605 remains still for greater than a threshold amount of time (e.g., more than approximately 1 second), the system 13601 may determine that the user's position is at least momentarily static and a posture measurement or position measurement may be determined and stored in a log. In some cases, the one or more of the location sensors, particularly the leg sensors 13600e and 13600f are used to determine if the user 13605 is in static position, which may be used to trigger a posture measurement. In some cases, multiple posture measurements are taken and a time averaged or composite posture measurement is determined.

In some implementations, the user's position or posture is monitored by the posture-monitoring system 13601 for a minimum of 4 hours. In some cases, the user's posture is monitored by the posture-monitoring system 13601 for a minimum of 8 hours. In some cases, the user's posture is monitored by the posture-monitoring system 13601 for approximately 24 hours. In some cases, the user's posture is monitored by the posture-monitoring system 13601 for multiple days up to and including a week. In some cases, the user's posture is monitored by the posture-monitoring system 13601 for longer than a week. The user's posture may be monitored continuously or during periods in which it is predicted that the user is in a static posture. The static posture may correspond to a static condition, which may correspond to a standing, sitting, prone, sleeping, or other user position.

In some implementations, the posture-measurement system 13601 is configured to receive input from the user 13605 which may be used to indicate moments of pain or discomfort by the user 13605. In some cases, events or time periods that are associated with user pain or discomfort are used to trigger a posture measurement or flag a posture measurement that has already been taken (on a continuous or regular interval basis). The posture measurement(s) taken during an interval associated with a pain or discomfort event may be displayed to a user or medical personnel and used to identify a potentially problematic posture condition.

The posture-measurement system 13601 may be used to determine a number of different posture conditions. As shown in FIGS. 137A and 137B, a twist condition may be measured using wireless tags 13700a and 13700b. In some cases, the twist condition is determined using a relative measurement between the wireless tags 13700a and 13700b and the other wireless tags (e.g., 13600c-13600f, the electronic device 13610, or other device of FIGS. 136A-136C). As mentioned previously, the wireless tags 13700a and 13700b may also include an orientation-detecting sensor like an accelerometer, magnetometer, or other sensor, which may be used to measure a relative angular position of the respective wireless tags 13700a, 13700b and used to determine shoulder twist measurement.

While the shoulder twist depicted in FIGS. 137A and 137B is provided as an illustrative example, other example measurements may also be determined using the posture-measurement system (e.g., 13601 of FIGS. 136A-136C). The measurements may include a variety of posture or spinal characteristics, which may be generally measured as rotational degrees of freedom: twist corresponding to an amount of rotation about a vertical or longitudinal axis roughly extending along a length of the user's spine; tilt corresponding to an amount of rotation about an axis that extends from the chest to the back of the user; and bend corresponding to an amount of rotation about an axis that extends from one side of the user to the other. By way of example, the posture-measurement system 13601 may be adapted to measure neck twist, upper back twist, lower back twist, hip twist, and other similar measurements. The posture-measurement system 13601 may be adapted to measure various tilt conditions including, for example, neck tilt, upper back tilt, lower back tilt, and other similar measurements. The posture-measurement system 13601 may also be adapted to measure various bend conditions including, for example, neck bend, upper back bend, lower back bend, and other similar measurements.

The number and location of the wireless tags may vary depending on the implementation. FIG. 138A depicts one alternative arrangement of wireless tags 13800a-13800e that uses five wireless tags. As shown in FIG. 138A, the posture-measurement system 13801 includes a pair of wireless tags 13800a and 13800b that are positioned along a shoulder region of the user 13805, a wireless tag 13800d that is positioned along a mid-back region of the user 13805, and a wireless tag 13800e that is positioned along a lumbar region of the user 13805. As shown in FIG. 138A, the posture-measurement system 13801 also includes a wireless tag 13800c that is positioned along the head of the user 13805. The wireless tag 13800c may, in some cases, be integrated with a headset, eyeglass, or other head-mounted device or article worn by the user 13805.

The configuration of wireless tags 13800a-13800e depicted in FIG. 138A may be used to detect a variety of characteristics of the user's posture. For example, the wireless tags 13800a-13800e may be used to detect neck tilt, neck bend, upper back tilt, upper back bend, lower back tilt, and lower back bend. Other characteristics or measurements of the user's posture may also be measured or monitored using the wireless tags 13800a-13800e depicted in FIG. 138A including shoulder dip, shoulder twist, and other body measurements.

FIG. 138B depicts one alternative arrangement of wireless tags 13850a-13850d that uses four wireless tags. As shown in FIG. 138B, the posture-measurement system 13851 includes a wireless tag 13850b that is positioned between the shoulders of the user 13855, a wireless tag 13850c that is positioned along a mid-back region of the user 13855, and a wireless tag 13850d that is positioned along a lumbar region of the user 13855. As shown in FIG. 138B, the posture-measurement system 13851 also includes a wireless tag 13850a that is positioned along the head of the user 13855. The wireless tag 13850a may, in some cases, be integrated with a headset, eyeglass, or other head-mounted device or article worn by the user 13855.

The configuration of wireless tags 13850a-13850d depicted in FIG. 138B may be used to detect a variety of characteristics of the user's posture. For example, the wireless tags 13850a-13850d may be used to detect upper back tilt, lower back tilt. and lower back bend. Other characteristics or measurements of the user's posture may also be measured or monitored using the wireless tags 13850a-13850d depicted in FIG. 138B including shoulder dip, shoulder twist, and other body measurements. In some cases, the wireless tag 13850a that is positioned along the head of the user 13855 may be used to measure neck tilt, neck bend, upper back bend, and other body measurements.

As described herein, an array of wireless tags may be used to measure and monitor a user's posture. Similarly, an array of wireless tags may be positioned at various locations of a user's body and used to measure and monitor other user activity. Thus, the posture-monitoring systems described above may also be referred to as, more general, position-monitoring systems or simply monitoring systems. A position-monitoring system may be configured to track location data for one or more wireless tags over a period of time in order to identify an activity type. Example activity types include, for example, a weight lifting activity, a running activity, a biking activity, a sport activity (e.g., basketball, football, soccer), a yoga activity, a rowing activity, or other type of physical activity. The position-monitoring system may be configured to track location data for one or more wireless tags over a period of time in order to identify an athletic move including, for example, a bicep curl, a running step or stride, a walking step, a baseball throw, a football throw, a rowing stroke, or other type of athletic move. The position-monitoring system may be configured to count the number of athletic moves and, in some cases, estimate a calorie expenditure or activity level based, at least in part, on the number of athletic moves.

By way of further example, an array of wireless tags may be used to monitor exercise or sporting activity, which may be used to compute a health metric like calories used or power output. The wireless tags may also be used to monitor the kinematics of the user's activity like a running stride, swim stroke, baseball pitch, golf swing, or other similar kinematic motion, athletic move, or activity. In some implementations, an array of wireless tags may be used to count repetitions (reps) or other motions during an exercise or sporting activity. As mentioned above, the rep or motion count may be used to determine a more accurate estimate of calories burned or degree of exercise performed. The motion tracking information performed using the array of wireless tags may also be combined with other health-monitoring data like a heart rate or distance estimate in order to determine an estimate of a number of calories burned or a degree/amount of exercise performed.

The various wireless tags may be attached or coupled to the user by a variety of techniques. In some implementations, one or more of the wireless tags are incorporated into an article of clothing like a shirt or pants. For example, the wireless tags may be secured in one or more pockets or pouches of the clothing article that are configured to hold the respective wireless tag against the user's body in a particular location. This may require that some portion of the clothing be tightly or snugly fitted against the user's body to prevent or reduce an amount of independent movement of the wireless tag with respect to the portion of the user's body being monitored. In some cases, one or more of the wireless tags are attached to the user using an elastic band or wrap that extends around a body part of the user. For example, one or more of the wireless tags may be incorporated into a torso wrap that includes a stretchable or elastic material that extends around the torso of the user. In some implementations, one or more of the wireless tags are directly attached to the user by an adhesive or using an athletic tape.

In some implementations, one or more of the wireless tags are preprogrammed or otherwise configured to track a particular region of the user's body. For example, a wireless tag may be preprogrammed or otherwise configured to be positioned along a user's left shoulder region. Similarly, a wireless tag may be preprogrammed or otherwise configured to be positioned along a user's middle back, lumbar, leg, arm, head, or other region of the user's body. The preprogramming or configuration of the wireless tag may include a calibration or other set of coded values that may facilitate the use of the wireless tag in a particular body position. In one specific example, a wireless tag that is configured to be positioned along a user's shoulder may be adapted to measure a relative twist with respect to a complementary wireless tag that is configured to be positioned on the user's opposite shoulder.

The wireless tags described with respect to FIGS. 136A-138B may include some or all of the hardware elements and the functionality described with respect to other wirelessly locatable tags described herein. An example of the various hardware elements that may be included in the wireless tag are described below with respect to FIG. 144. In some cases, the wireless tags may be adapted to provide real-time feedback to the user regarding the user's posture or detected body position. For example, one or more of the wireless tags may be adapted to provide a haptic output, audio output, visual output, or other output signaling the user's compliance or non-compliance with a target or goal posture or body position. As described in more detail below, the wireless tags may also be used to generate an animation or computer-generated model that corresponds to the user's detected body posture or position, which may be displayed on a separated display or device.

FIG. 139 depicts an example process 13900 of using a posture-measurement system, as described herein. The process 13900 of FIG. 139 may be implemented using any one of the posture-measurement systems described above with respect to FIGS. 136A-136C, 137A-137B, and 138A-138B. The process 13900 may be implemented on an electronic device of the system, including, for example, a mobile phone, tablet computer system, watch, notebook computer system, or other device having a processor and computer memory.

In operation 13902, a user's posture is detected. As described above with respect to FIG. 136A, a posture monitoring system may include an array of wireless tags that are used to measure the relative location of various regions of a user's body. The positional measurements may be performed using a wireless time-of-flight measurement implemented using a UWB or other wireless measurement system. An orientation of one or more of the wireless tags may also be determined using the wireless measurement system, an accelerometer, a magnetometer, and/or another type of sensor. Each of the wireless tags may transmit a wireless locating signal which may be used to determine the relative position of the respective tag with respect to another wireless tag and/or a separate electronic device like a mobile phone, smart watch, or other portable electronic device. In some implementations, the separate electronic device receives a wireless locating signal from a set of wireless tags, the wireless locating signal indicating or used to measure a relative distance between the respective wireless tag and the electronic device. In some cases, the wireless locating signal indicates or is used to measure a relative distance between two wireless tags, or a wireless tag and another device or object.

In operation 13904, the system determines if the measured posture violates a condition or criteria. Similar to as described above with respect to FIGS. 136B and 136C, the posture monitoring system may be configured to detect a deviation of a user's posture with respect to an ideal or nominal posture position. The posture monitoring system may measure or detect the deviation with respect to a set of positional offsets that correspond to the relative location of the various wireless tags with respect to a datum plane or datum origin. If a positional offset exceeds a threshold or other constraint, the position may be flagged as violating the condition or criteria. The posture monitoring system may also be adapted to measure or detect the deviation using a working envelope or volumetric constraint. If one or more of the wireless tags breaches the working envelope or volumetric constraint, the position may be flagged as violating the condition or criteria.

In an alternative embodiment, the system may determine a posture condition or activity condition. For example, the system may be used to determine a static posture that is not measured relative to an ideal or nominal posture. The static posture may be analyzed to determine one or more characteristics of the posture, which may be reported or presented to the user in operation 13906. Similarly, the system may be used to monitor a series of body positions, which may correspond to an activity or athletic move. By way of example, the system may use a series of position measurements taken using the wireless tags at a series of time intervals to monitor shoulder, arm, and/or torso movement during a golf swing, a baseball swing, a tennis swing, or other similar athletic move. By way of other example, the system may use a series of measurements taken using the wireless tags over a period of time or time interval to monitor a user's hip and leg position(s) during a running stride or walking gait. The posture and/or activity that is monitored using the system may be displayed to the user in a graphical manner, as explained below with respect to operation 13906.

In operation 13906, the system signals the posture to the user. As discussed previously, an indicia of the deviation or posture event may be provided to the user. In one example, the results of the posture measurement are displayed on an electronic device through a graphical user interface or other similar technique. As discussed previously, a tilt plane or other similar reference may be displayed, which may indicate the type and degree or extent of the deviation. In some cases, an anatomical representation of the user's body is displayed and one or more of the regions of the user's body are identified as being deviated from an ideal or nominal posture. The graphical user interface may also display a description of the problem and corrective actions or other diagnostic information to the user.

In one example embodiment, an animation is generated based on location or posture information obtained using the wireless tags of the posture-monitoring system. The animation may include an avatar or other computer-generated representation of the user. The position and/or motion simulated by the avatar may correspond to a position or motion of the user that is being tracked with the wireless tags. The animation or computer-simulated avatar may be used to help diagnose or identify potential issues with a user's posture. The location information obtained from the wireless tags may also be used to generate other graphical feedback or information that is presented to the user. In one example, the location information is used to determine an amount of deviation from a nominal or ideal posture. The amount of deviation may correspond to an amount of time or number of deviations in which the user's posture exceeded a threshold with respect to the nominal or ideal posture. In some cases, the deviation or other measurement metric is displayed graphically on a histogram, bar graph, chart, or other graphical representation.

Similarly, a static posture and/or user activity may be displayed using one of a variety of graphical techniques. For example, an avatar or other computer-generated representation of the user's body may be displayed in a position that corresponds to the position and/or posture monitored using the wireless tags of the system. Similarly, an animation of an avatar or other representation of the user's body may be computed using a series of positions captured using the wireless tags over a period of time or multiple time intervals. In some cases, the animation and/or static representation of the user's activity or posture may be used to diagnose a condition, improve an athletic move, diagnose a run stride, diagnose a walking gait, or perform other further analysis. Additionally, a haptic output, audio output, and/or visual output may be provided by individual wireless tags when the user's posture or position is determined to be out of compliance and/or in compliance with a goal or target position or posture. For example, one or more of the wireless tags may produce a haptic output that is perceptible along a corresponding region of the user's body that is out of position or otherwise violates a criteria or working envelope of the goal or target position or posture, which may help the user to correct the position or posture in real time. The output provided by the wireless tags may be used as an alternative to a separate display and/or in concert with a separate display to provide feedback to the user.

As described above, wirelessly locatable tags may be used to help find and retrieve lost and/or misplaced items. For example, a user can use a smartphone or other computing device to request and receive location data of a wirelessly locatable tag via the device-location relay network. This is merely one example use case for wirelessly locatable tags, however, and because the spatial parameters (e.g., position, location, orientation) of tags can be determined with a high degree of accuracy, the tags described herein (or any device incorporating the systems and/or features of the tags) may enable myriad new or improved location-based functions and use cases. Several additional examples of applications for wirelessly locatable tags are described herein. These uses and applications may be performed by any of the tags described herein.

Using the localization features of the wirelessly locatable tags (or other devices that include tags or include the functionality of the tags), a user may be able to establish geographic and/or location-based rules for their devices. For example, a user can establish a rule that if the user's tag (which may be in the user's wallet) and phone are separated by a threshold distance, the user should be alerted. Another example rule may be that if a user's tag remains near the user's home while the user's phone is away from home (e.g., 100 feet away), the user should be alerted. Another type of geographic and/or location-based rule may help avoid false reports of lost tags. For example, a user may be able to establish locations or geographic areas in which the tag will not report itself as being "lost," so that other devices (e.g., devices not associated with the tag's owner) do not report the location of the tag.

Geographic and/or location based rules may be executed by a device other than the tag itself. For example, a user's smartphone, laptop or desktop computer, or other device may monitor the locations of a user's keys and a user's wallet (each of which may be attached to a tag), and alert the user when the threshold distance between the keys and wallet is reached. A notification may include sending a text message, email, push notification, haptic notification (via the user's phone or watch), or any other suitable notification technique. Distances between any example devices (including between tags) may be monitored (by a smartphone or other device of a user), and the user may be notified if the distance between the devices exceeds a threshold distance (or if any other distance condition is satisfied).

Notably, the localization techniques facilitated by the device-location relay network, such as using UWB signals, allow the location of a tag or other device to be determined to a high degree of accuracy (e.g., less than about three feet, less than about 1 foot, less than about 3 inches, or with even greater accuracy). Accordingly, the device-location relay network may allow a user to establish geographic and/or location-based rules that are more granular than previous techniques. For example, a user may establish a rule that they wish to be notified if their car keys have been placed in a drawer instead of on a countertop. Other types of high-resolution location-based rules and measurements are also feasible as a result of the improved location-finding accuracy.

Geographic and/or location based rules may be executed by a device that is controlled by the user (and/or in the user's possession) to help ensure security of the user's information. For example, instead of a remote server system accessing the locations of a user's tags to evaluate geographic and/or location-based rule sets, a user's phone may receive or access location reports of the user's tags, and the phone may determine when certain rules are satisfied. In some cases, a user may have multiple trusted devices that can individually or collectively evaluate the user's geographic and/or location-based rules. For example, a user's laptop computer, phone, tablet, desktop computer, home automation system, or the like, may all be authorized to access the location reports of the user's tags (or determine a location of a tag at least in part from signals received directly from a tag) and determine when a rule condition is satisfied.

In these examples, as well as others described herein, a tag's spatial parameters may be determined in various ways. For example, in some cases, any device in the device-location relay network (even those not associated with the owner of a tag) may detect a signal from a tag, determine or estimate a location of the tag, and send a location report to a server of a cloud-based service. The owner of the tag may then access those location reports at any time. In other cases, a user's own device(s) may determine the position and/or location of the user's nearby tags in real-time. Thus, for example, if a user wishes to know the location of his nearby tags, he may cause his phone (or other device) to communicate directly with the nearby tags to determine their locations, or at least their positions relative to other devices. Direct communications with a tag (e.g., using UWB to determine the position of the tag) may provide faster, real-time location information than retrieving location reports, and may enable additional use cases and features that would be less practical if all location information were served to the user's devices from a remote, cloud-based system. For ease of reference, it will be understood that both of these techniques are considered to be provided by the device-location relay network, regardless of whether a cloud-based system is accessed, or if only the user's own devices are used to determine spatial parameters of tags via local communications (direct tag-to-phone communications, for example).

Due to its high accuracy, the device-location relay network may allow accurate distance measurements between tags. For example, if two objects have tags coupled to them, the device-location relay network may determine the location of each tag (e.g., using UWB location-finding techniques described herein) and determine the distance between the objects based on the absolute locations of the tags. Measuring a distance between two objects may be used for geofencing rules that rely on relative positions or distances between two objects, as described above. For example, as described above, a user may establish a rule that he wants to receive a notification if his wallet and keys are more than ten feet apart. The device-location relay network may monitor the distance between those objects and trigger notifications when the distance condition is satisfied. As another example, speakers of a home audio system may each have attached tags (or incorporate components of a tag), and the device-location relay network may measure the distance between tags, the position of tags relative to each other, and/or the orientation of the tags (and thus the speakers) to help the user position and/or align the speakers in their home environment. As yet another example, a user may place a tag on a vehicle bumper, and another on a garage wall. The device-location relay network may determine the distance between these tags and alert the user when they are within a threshold distance (e.g., to allow the user to park their car in a consistent and safe location and avoid a collision with the garage wall). As described above, the distance between tags may be determined based on tag-to-tag communications, and the orientations of tags may be determined using magnetometers, accelerometers, or the like.

Tags may also be used to help a user track their own path of travel. For example, a user may leave tags behind as they hike, walk, or move about an environment. The device-location relay network may allow the user to use the locations of the tags (which may be supplied via other devices in the device-location relay network) to retrace their path. For example, the user's phone may display a compass-like directional indicator indicating which way to travel to reach the next tag, or it may display a map showing the locations of the tags (and an optional path defined by the tag locations). Because phones and other devices can determine the direction to a tag locally (e.g., without accessing a remote server or host system), this pathfinding technique can be used even in remote locations where cellular or other network service is unavailable.

When permitted by a user, tags may also be used to track the locations of individuals for search-and-rescue or other emergency operations. For example, a skier, hiker, cyclist, mountaineer, or other individual may attach a tag to themselves so that rescuers can find the individual in the case of an emergency such as an avalanche, blizzard, accident, or the like. Even outside of recreational uses, tags may help rescuers or other emergency personnel locate individuals who are in trouble. For example, after an earthquake, hurricane, fire, medical event, or any other time it may be advantageous for an individual to be easily located by others, the individual may selectively permit the device-location relay network to access and report his or her location to other users. More particularly, a user who has a tag on or near their person may use their phone (or other device) to report themselves to the device-location relay network as "in need of assistance" or another such designation. This may allow the device-location relay network to report the location of the user's tag to medical personnel, firefighters, police, family, or other service providers so that the user can be more easily found and assisted.

In some cases, a user may select a particular triggering event that will cause their location to become public. For example, an individual may establish a rule that if their location does not change during a thirty minute interval, then they should be reported to the device-location relay network as "in need of assistance," at which time the location reports of the user's tag (or other device) may be accessible to emergency personnel or predetermined contacts. Such rules may help ensure that a user who has become unable to manually initiate an assistance request (e.g., due to an injury during a recreational activity, a fall, a storm or fire, or the like) can still take advantage of the location-finding abilities of the device-location relay network, while also still maintaining control over their personal location information.

The device-location relay network may also be used to help map three-dimensional spaces using one or more tags or devices. For example, a user may carry a tag on their person as they go about their day, or move other devices or tags around their environment (e.g., placing their keys or phone on various surfaces or objects). The device-location relay network may securely monitor the location of the tags and, over time, construct a three-dimensional model of the user's home or work environment. More particularly, the tags' locations may be analyzed by one or more of the user's devices to predict the locations of tables, furniture, walls, and other physical objects and obstacles in the user's environment. For example, if a map of a tag's location over time shows that the tag is often at rest in a location that is about three feet above the ground, and within an area of about three feet by six feet, the user's device(s) may infer that that location corresponds to a table. In this way, a user's devices may generate a three-dimensional map of an area based on location history of one or more tags. This information may then be used, for example, to help a user locate objects, avoid obstacles, or identify patterns of behavior and/or motion. If the user then loses her wallet and uses the device-location relay network to help find it, she may be provided with an automatically generated suggestion that it may be on the "kitchen table," even if the user has never manually established or input a location of a table.

In some cases, users may manually establish the locations of physical objects in their environment by touching a tag to the object and associating that location with a particular object. For example, a user may initiate a location-learning mode (e.g., by applying an input to the tag or to another device) and then place a tag on a table. The device-location relay network may then determine the location of the tag and allow the user to associate that location with the object "table" (e.g., via an interface on the user's phone or computer). A user may perform a similar action with other objects as well, such as walls, desks, doors, beds, closets, pools, or any other suitable object. Where maps of a user's environment are generated, they may be securely stored and accessible only to the user. For example, they may be stored locally on one or more of the user's own devices, or they may be encrypted or otherwise secured and stored remotely (e.g., on a server associated with the cloud-based service).

Tags may also be used to help users locate and interact with stationary objects. For example, a tag may be placed at or near an emergency exit to a building so that, when needed, individuals can use their phone or other device to locate and navigate to the emergency exit (e.g., by showing a direction-indicating arrow on the screen of their phone or other device to guide them towards the exit). Similarly, tags may be placed at multiple locations along an exit route so that users' phones can locate the tags and guide a user along the exit route. The tags may even communicate information to the devices such as identifiers of the physical structure or object that they are associated with. For example, when a phone or tablet communicates with a tag to determine a location of the tag, the tag may send information to the phone or tablet. The information may include, for example, a name of the associated object (e.g., fire exit, fire extinguisher, defibrillator, etc.), a physical location of the object (e.g., ground floor, front hallway, etc.), or the like. Such information may be stored by the tags, and may be provided to other devices as part of a location-finding process, or it may be broadcast periodically regardless of whether the information has been explicitly requested.

FIG. 140 illustrates an example environment with objects that are associated with wirelessly locatable tags, and an example device providing a user interface that directs a user to the location of the objects. For example, FIG. 140 illustrates an example user device 14000, such as a smartphone in use in a building that has an automatic electric defibrillator (AED) 14002 and a fire extinguisher 14004. The AED 14002 and the fire extinguisher 14004 may each be associated with a respective tag. For example, a tag may be mounted on or near each object. The tags may be attached to a mounting base, such as the mounting base 6108, FIG. 61A, so that the tags can be powered indefinitely and without requiring batteries to be changed.

The device 14000 may determine the position of each object by communicating with each tag. For example, the tags may send signals using Bluetooth and/or UWB communication protocols, and the device 14000 may use techniques such as time of flight (ToF), angle of arrival (AoA), time difference of arrival (TDOA), received signal strength indication (RSSI), triangulation, synthetic aperture, and/or any other suitable technique, to determine positions of the tags relative to the device 14000. Using the detected position of the tags (and optionally spatial parameters of the device 14000 from onboard sensors such as accelerometers, magnetometers, gyroscopes, GPS systems, or the like), the device 14000 may display a directional indicator that points towards the tags. As shown in FIG. 140, the device 14000 displays, on a display such as a touchscreen display, a first directional indicator 14008 (e.g., an arrow) that points towards the AED 14002, and a second directional indicator 14010 (e.g., an arrow) that points towards the fire extinguisher. The device 14000 also displays a name (or other information) of each device, which may have been provided to the device 14000 from the tags themselves, as described above.

The objects and indicators shown in FIG. 140 are merely examples, however, and the same or similar techniques may be used to direct users to other objects as well. For example, a museum may place tags at or near exhibits to help visitors find the exhibits, stores may place tags at or near product displays to help users find products or navigate through a store, or buildings may place tags at or near entrances or along hallways to help a user navigate the building. These tags may similarly provide information about the location or object with which they are associated. For example, a tag placed near the Mona Lisa may allow a user's phone to find a distance and direction to the famous portrait, and also provide information about the portrait directly to the user's phone.

Tags in buildings and other structures may also be employed to help individuals with vision impairment navigate the buildings or structures. For example, assistive devices may determine the distance to and/or location of various tags positioned in an area, and provide outputs to a user that can help them navigate the area. As one specific example, an assistive device on the person of a user may communicate with nearby tags on walls or other obstacles to determine a distance between the device and the nearby tags. The assistive device may provide an output to the user to indicate the distance and/or direction to the tags (or to a path that avoids the tags) to help the user avoid those areas. One example output from an assistive device may be a subtle vibration with a frequency that increases as the distance between the device and the tag decreases.

In cases where tags are mounted on obstacles or walls, the tags may store offset information that indicates where a device (e.g., an assistive device, smartphone) should direct the user. Thus, instead of a tag causing a device to direct a user towards an obstacle, the tag instead causes the device to direct the user to a location or along a path that avoids the obstacle. The offset information may be sent to the user's device, which may then determine where to direct the user based on the tag's detected location, the offset, and the device's location.

Tags may also be placed along paths, trails, ski runs, or other outdoor environments to help guide users. Such tags may also facilitate or trigger the display of objects in an augmented reality environment. For example, a user can raise his or her phone to a tag on a ski run to cause a name of the ski run to be presented on the user's phone display.

Tags may also be used for augmented reality (AR) applications. In particular, because the spatial parameters of a tag can be determined with a high degree of accuracy (e.g., within a foot of the actual location, or less), a device such as a phone, tablet, head-mounted display, or the like, may use onboard sensors (e.g., magnetometers, accelerometers, inertial positioning systems, GPS) to determine how the device is oriented relative to the tag. The device may take some action or display some information to the user as a result of detecting that the device is pointed at the tag. For example, if a tag is positioned next to a light switch, a user may direct her phone camera towards the tag, which may cause her phone's display to automatically show information about the light switch, such as what light it controls. The information may be integrated into the real-time image preview shown on the user's phone, thus providing an AR interface. As another example, a tag next to the Mona Lisa may cause a description of the famous painting to appear, in a device display, next to the Mona Lisa itself. As yet another example, a user may scan a phone's camera around a room or environment, and the locations and/or descriptions of detectable tags may be indicated on the image preview (e.g., with an item description bubble and arrow pointing to the tag). In this way, the user can easily visualize the location of various different tags in an environment.

FIGS. 141A-141B illustrate an example scenario in which a user is directed to a tag using an augmented reality application. In the illustrated example, a user is attempting to locate a tag 14102 using a device 14100 (e.g., a smartphone). The tag 14102 may be attached to a set of keys, a wallet, a smartwatch, a purse, or another object, though for simplicity only the tag 14102 is illustrated in the figures.

The device 14100 may display an AR interface 14104 on a display. The AR interface may include a live preview of the environment from a camera of the device 14100. The device 14100 may determine the position and/or location of the tag 14102 using techniques described herein (e.g., using time of flight analysis on a UWB signal from the tag 14102). Based on the tag's position and the orientation of the device 14100 relative to the tag (e.g., the direction that the camera of the device 14100 is pointing relative to the position of the tag 14102), the device may determine how the device's orientation would need to be changed in order to bring the tag 14102 into the camera's field of view. The device may then display a directional indicator 14106, such as an arrow, that indicates to the user where to point or reorient the device 14100 to locate the tag 14102. FIG. 141A shows the device 14100 oriented in a direction that does not show the tag 14102. Accordingly, the AR interface 14104 shows a live preview from the device's camera, as well as the directional indicator 14106. FIG. 141B shows the device 14100 after the user has reoriented the device in accordance with the direction indicated by the directional indicator 14106. The AR interface 14104 has been updated to show the live preview of the new portion of the environment, and shows the tag 14102, as well as an updated directional indicator 14108 showing the detected position or location of the tag 14102. In some cases, a different type of graphical object may indicate the location of the tag 14102. For example, an object (e.g., a balloon, star, flashing light, or the like) may be shown hovering over or near the tag 14102. The graphical object may be displayed even when the tag 14102 is obscured or occluded, such as if the tag 14102 is in a drawer, under a stack of papers, or otherwise not visible.

The directional indicators in the AR interface 14104 may be continuously updated based on the position of the tag 14102 relative to the device 14100 (and optionally the orientation of the device 14100). Thus, for example, as the user moves and/or reorients the device 14100 while viewing the AR interface 14104, the directional indicators may be continuously updated to point the user towards one or more tags. The user may thus use the directional indicator as a compass-like guide that ultimately directs the user to the tag.

In some cases, multiple properties of a directional indicator change based on the distance to a tag. For example, the length of a displayed arrow may vary in accordance with the distance between the device 14100 and the tag 14102 (e.g., with a longer arrow indicating a greater distance), while the direction of the arrow indicates the position of the tag relative to the device 14100. Other types of information may also be displayed on the AR interface 14104, such as a numerical indicator of the distance to an object (e.g., in feet or meters), a proposed direction to move the device 14100 (e.g., up, down, left, right), or the like.

Devices other than tags, but which include the functions of a tag, may also be located and displayed to a user in an AR interface. For example, laptop computers, tablet computers, smartphones, WiFi routers, or the like, may include the same or similar components as the tag, and thus may be located by a device and incorporated into an AR interface. This may help a user find their own devices or devices with which they may want to interact. For example, a user can use a smartphone to view an AR interface that shows a live preview of the environment (through the camera). The AR interface may direct the user towards wirelessly locatable devices, and when such objects are within the live preview, show the device and a description of the device. In a specific example, the user can use the AR interface to scan or view a room to find a WiFi router so that he can approach the router to establish a connection. When the user points his or her phone camera towards the WiFi router, a graphical object may appear on the display indicating that the object is a WiFi router, and optionally provide information about the router such as an associated network name, password, wireless protocol, or the like.

Tags may also be used to facilitate augmented reality for gaming or other entertainment purposes. For example, tags may be used as game pieces. Because the devices can determine the locations of the tags with high accuracy, the devices can visually replace the tags in an augmented reality environment with computer-generated graphics. As one specific example, a game of chess may be played with each piece representing one of the chess pieces. Users may view the tags through a headset (or other device) and the headset may replace the images of the tags with animations of the chess characters, including animated battles between the characters, or the like.

As another example, tags may be attached to a user's body to allow a computer system to track the position of the tags and use position and changes in position (e.g., motion) of the tags to control an avatar that is displayed on a display (e.g., a television, head-mounted display), or the like. FIG. 142 illustrates an example user 14200 with multiple tags 14202 attached to his or her body or clothes. A computer system 14205 may determine the position and/or location of the tags 14202 (including the relative locations of each tag to each other), and use the detected spatial parameters to control the appearance and/or motion of an avatar 14206 (or other graphical object) displayed on a display 14204. The computer system 14205 may be a single device that is capable of determining the spatial parameters of the tags 14202 (using the techniques described above, such as ToF analysis of UWB signals). The computer system 14205 may be a desktop computer, gaming console, mobile phone, home automation system, or any other suitable device. In some cases, the computer system 14205 shown in FIG. 142 represents multiple devices working in concert to determine the spatial parameters and/or motions of the tags 14202. For example, multiple computers, gaming consoles, phones, tablets, or the like may cooperate to determine the spatial parameters of the tags 14202 and/or to generate or control a displayed avatar.

The application shown in FIG. 142, in which a user's body motions are tracked and used to control an avatar or other character on a display, may be used for various different applications. For example, an exercise or physical therapy program may display an example of a motion to be performed, and then monitor the actual motion of the user. The user's actual movements may be evaluated by the program to determine if they meet the displayed suggested movements, and optionally to provide additional guidance on how to perform the exercise. The user's motion may also be evaluated to count repetitions of an exercise, evaluate a user's flexibility, or the like.

A user's body motions may also be used to control an avatar in a game or augmented or virtual reality environment. For example, the user's body movements may be tracked and translated into movements of the in-game or in-environment avatar, which may in turn interact with other in-game or in-environment objects or characters.

The device-location relay network may also use the highly accurate distance- and/or position-finding functions for features that are not necessarily evident to a user. For example, a long-range wireless charging system may be able to improve its operation by having accurate position estimates of devices in its range. More particularly, a long-range wireless charging system may use highly directional, aimable electromagnetic signals to wirelessly charge devices such as phones, tablets, notebook computers, and the like. The charging system may use the device-location relay network (e.g., using a peer-to-peer communication scheme) to determine the position of a device to be charged, relative to the charging system. The charging system may then direct or aim its electromagnetic signals to that position to charge the device (e.g., using beamforming techniques). The charging system may also track a moving device with its electromagnetic signals by continuously monitoring or updating the position of the device to be charged. Similar techniques may be used for any suitable type of highly directional wireless signals (e.g., optical communications, wireless communications signals, etc.).

The accuracy of the position measurements provided by the tags and the device-location relay network may also have unique applications in sports and other recreational activities. For example, tags may be placed on a user's body to track and analyze motions to improve performance. More particularly, tags may be placed on a user's arms, back, head, legs, torso, or any other suitable location (including on sporting equipment such as golf clubs, basketballs, baseball bats, and the like). Devices may then be used to track the position of each of the tags in three-dimensional space and develop biometric models and/or animations of the user's motions. In this way, golf swings, baseball swings, basketball shots, volleyball strikes, or any other type of sports or recreation motion may be recorded for analysis and training purposes. Multiple tags may be attached to a user to track and/or record complex multi-dimensional body movements, posture, form, etc.

In some cases, tags may have feedback systems that can indicate to a user if their motion or form deviates from a target. For example, if a user bends his knees too far during a basketball shot, haptic output systems on leg-based tags may provide a haptic notification to the user indicating the deviation or error. Tags (or the systems typically provided in tags) may also be integrated into sports equipment such as golf balls (e.g., to monitor trajectory and speed, to assist in lost-ball retrieval), golf clubs, basketballs, baseballs, baseball bats, and so forth. In some cases, tags may include accelerometers, gyroscopes, or other components, which may improve or expand the biometric data captured by the tags in sporting and recreation contexts. Even outside the context of sports or recreation, tags may be used to measure users' motions for other purposes such as object tracking. For example, if a tag on a wallet is found to move along a path that is indicative of removal from a pocket, the location of that event may be recorded by the users' devices so that the user can be reminded at a later time where the wallet was removed from a pocket.

Tags may also be used to help track the locations of and the users of shared resources. For example, communities or companies may provide resources such as cars, bicycles, scooters, or other equipment (e.g., tools, computers, library books, etc.) that may be temporarily used by multiple individuals. Such resources may have tags attached to them, and the tags may facilitate the recording of who is using or has used the resource, and where the resource is located. As a specific example, a user may approach a shareable vehicle and touch his or her phone to a wirelessly locatable tag on the vehicle. The act of touching the phone to the tag may cause the NFC communications system of the tag and phone to communicate (including the tag providing a unique identifier of itself and/or the vehicle to the phone), and may initiate a checkout operation in which the user gains access to the vehicle. The location of the vehicle may be updated by the user's phone (as well as the devices of other individuals in the device-location relay network). Because the devices in the device-location relay network are able to periodically update the location of the tag, it may be possible for users to determine the locations of the shared resources. Thus, if a shared scooter is driven to another location by a first user, another user may be able to find the location of the scooter (as updated by the first user or by other devices in the device-location relay network) by accessing the location reports of the scooter. In cases where it is desirable for multiple individuals to access location reports of a tag (such as in the case of shared resources), each authorized individual may have a copy of a private key for a particular tag, or another authorization scheme may be used so that each authorized individual can access the location reports in a secure manner.

The foregoing examples of use cases for the device-location relay network are merely some example use cases, and are not limiting. Indeed, any tags may be associated with or attached to any suitable object to facilitate distance, position, location, and/or motion tracking, initiate augmented reality objects, provide navigational cues, or the like. Additional objects that may be associated with tags may include, for example, jewelry, bicycles, motorcycles, cars, scooters, vehicles, clothes, glasses, retail inventory (e.g., for theft prevention and recovery), industrial applications (e.g., for tracking products along an assembly line, for tracking materials through a supply chain, for measuring distances or tracking construction equipment or materials, etc.), musical instruments, flashlights, first aid kits, automatic electronic defibrillators, mail, packages, shoes, helmets, medicine containers, pets, animals (e.g., for studying migration, preventing poaching, etc.), and so forth.

In order to facilitate the detection of tags, devices that are capable of communicating with tags or otherwise receiving location reports of tags may include a tag-finding application or interface that shows a list of nearby tags. The list of nearby tags may include any and all tags that are associated with the user (e.g., the user's own tags) as well as any publicly accessible tags and tags that the user is authorized to see. Thus, when the user opens the tag-finding application, he or she may see a list of tags, each with an identifier of an object or location that the tag is associated with (e.g., "wallet," "car keys," "Mona Lisa," etc.). The user may then select a desired tag to get more information about the tag, such as the location of the tag, directions to the tag, a status of the tag, or the like. Users may also download or otherwise access groups of related tags. For example, a user may download or access a list of publicly accessible tags in the Guggenheim Museum, all of which may appear in the tag-finding application so that a user can view the locations and information associated with the tags.

In some cases, the location of the tags associated with or accessible by a user may be shown in a map view, allowing the user to visualize the location of the tags in a geographic environment. Or they may be shown in a "radar view," where the relative positions of the tags are shown distributed about a central point that represents the user, without displaying a geographic map. Locations may also be reported by requesting location information about a tag from a digital assistant. For example, a user may ask a voice-based digital assistant "where are my keys," which may cause the digital assistant to respond with a location of the keys (e.g., "in the kitchen" or "I'll show you on your phone").

The tag-finding application may display tags that the user's device can communicate with directly (e.g., tags that are nearby the user when the application is open), and tags that are remote from the device. In the latter cases, the location information to the tag may not be generated via direct peer-to-peer communication between the user's device and the tag, but rather may be provided from location reports that have been provided to a cloud-based system. In this way, the tag-finding application can allow a user to locate tags that are remote from the user's device. The tag-finding application may also visually or otherwise differentiate between tags that are local (e.g., in direct peer-to-peer communication with the device) and those that are remote (e.g., those that are not in direct peer-to-peer communication with the device but are associated with last-known locations and/or location reports from a cloud-based system).

The tag-finding application may also help users locate other individuals. For example, individuals may choose to allow the location of their own tags and/or devices to be viewed by others. Thus, a family attending a theme park may all choose to allow their locations to be viewed by the other members of their family. The device-location relay network allows a family member's device to access the locations of the other family members, using either direct peer-to-peer communications with the other family members' tags or devices if they are within range, or via remotely provided location reports (e.g., received from a cloud-based service).

FIG. 143 depicts an example schematic diagram of an electronic device 14300. The electronic device 14300 may represent an electronic device that determines a location of a wirelessly locatable tag, or determines the location of any other electronic device that includes the components of or provides the functionality of a wirelessly locatable tag (e.g., a receiving device 206, FIGS. 2D-2F). The electronic device 14300 as described represents a mobile phone (e.g., a smartphone), but it may also represent a laptop computer, tablet computer, desktop computer, personal digital assistant, watch (e.g., a smartwatch) or other wearable device, a wireless router or other network infrastructure device, a television, or any other suitable device.

The device 14300 includes one or more processing units 14301 that are configured to access a memory 14302 having instructions stored thereon. The instructions or computer programs may be configured to perform one or more of the operations or functions described with respect to the electronic devices described herein. For example, the instructions may be configured to control or coordinate the operation of one or more displays 14308, one or more touch sensors 14303, one or more force sensors 14305, one or more communication channels 14304, one or more audio input systems 14309, one or more audio output systems 14310, one or more positioning systems 14311, one or more sensors 14312, and/or one or more haptic feedback devices 14306.

The processing units 14301 of FIG. 143 may be implemented as any electronic device capable of processing, receiving, or transmitting data or instructions. For example, the processing units 14301 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

The memory 14302 can store electronic data that can be used by the device 14300. For example, a memory can store electrical data or content such as, for example, audio and video files, images, documents and applications, device settings and user preferences, programs, instructions, timing and control signals or data for the various modules, data structures or databases, and so on. The memory 14302 can be configured as any type of memory. By way of example only, the memory can be implemented as random access memory, read-only memory, Flash memory, removable memory, or other types of storage elements, or combinations of such devices.

The touch sensors 14303 may detect various types of touch-based inputs and generate signals or data that are able to be accessed using processor instructions. The touch sensors 14303 may use any suitable components and may rely on any suitable phenomena to detect physical inputs. For example, the touch sensors 14303 may be capacitive touch sensors, resistive touch sensors, acoustic wave sensors, or the like. The touch sensors 14303 may include any suitable components for detecting touch-based inputs and generating signals or data that are able to be accessed using processor instructions, including electrodes (e.g., electrode layers), physical components (e.g., substrates, spacing layers, structural supports, compressible elements, etc.) processors, circuitry, firmware, and the like. The touch sensors 14303 may be integrated with or otherwise configured to detect touch inputs applied to any portion of the device 14300. For example, the touch sensors 14303 may be configured to detect touch inputs applied to any portion of the device 14300 that includes a display (and may be integrated with a display). The touch sensors 14303 may operate in conjunction with the force sensors 14305 to generate signals or data in response to touch inputs. A touch sensor or force sensor that is positioned over a display surface or otherwise integrated with a display may be referred to herein as a touch-sensitive display, force-sensitive display, or touchscreen.

The force sensors 14305 may detect various types of force-based inputs and generate signals or data that are able to be accessed using processor instructions. The force sensors 14305 may use any suitable components and may rely on any suitable phenomena to detect physical inputs. For example, the force sensors 14305 may be strain-based sensors, piezoelectric-based sensors, piezoresistive-based sensors, capacitive sensors, resistive sensors, or the like. The force sensors 14305 may include any suitable components for detecting force-based inputs and generating signals or data that are able to be accessed using processor instructions, including electrodes (e.g., electrode layers), physical components (e.g., substrates, spacing layers, structural supports, compressible elements, etc.) processors, circuitry, firmware, and the like. The force sensors 14305 may be used in conjunction with various input mechanisms to detect various types of inputs. For example, the force sensors 14305 may be used to detect presses or other force inputs that satisfy a force threshold (which may represent a more forceful input than is typical for a standard "touch" input). Like the touch sensors 14303, the force sensors 14305 may be integrated with or otherwise configured to detect force inputs applied to any portion of the device 14300. For example, the force sensors 14305 may be configured to detect force inputs applied to any portion of the device 14300 that includes a display (and may be integrated with a display). The force sensors 14305 may operate in conjunction with the touch sensors 14303 to generate signals or data in response to touch- and/or force-based inputs.

The device 14300 may also include one or more haptic devices 14306. The haptic device 14306 may include one or more of a variety of haptic technologies such as, but not necessarily limited to, rotational haptic devices, linear actuators, piezoelectric devices, vibration elements, and so on. In general, the haptic device 14306 may be configured to provide punctuated and distinct feedback to a user of the device. More particularly, the haptic device 14306 may be adapted to produce a knock or tap sensation and/or a vibration sensation. Such haptic outputs may be provided in response to detection of touch and/or force inputs, and may be imparted to a user through the exterior surface of the device 14300 (e.g., via a glass or other surface that acts as a touch- and/or force-sensitive display or surface). Haptic outputs may also be provided in response to a detection that a condition of a wirelessly locatable tag has been met. For example, if a rule relating to the location of a tag is satisfied (e.g., if a tag is detected outside of a specified area or greater than a specified distance from a user or another device), the device 14300 may produce a haptic output using the haptic devices 14306.

The one or more communication channels 14304 may include one or more wireless interface(s) that are adapted to provide communication between the processing unit(s) 14301 and an external device. The one or more communication channels 14304 may include antennas, communications circuitry, firmware, software, or any other components or systems that facilitate wireless communications with other devices (e.g., with wirelessly locatable tags or devices that include such functionality). In general, the one or more communication channels 14304 may be configured to transmit and receive data and/or signals that may be interpreted by instructions executed on the processing units 14301. In some cases, the external device is part of an external communication network that is configured to exchange data with wireless devices. Generally, the wireless interface may communicate via, without limitation, radio frequency, optical, acoustic, and/or magnetic signals and may be configured to operate over a wireless interface or protocol. Example wireless interfaces include radio frequency cellular interfaces, fiber optic interfaces, acoustic interfaces, Bluetooth interfaces, infrared interfaces, USB interfaces, Wi-Fi interfaces, TCP/IP interfaces, network communications interfaces, or any conventional communication interfaces. The one or more communications channels 14304 may also include ultra-wideband interfaces, which may include any appropriate communications circuitry, instructions, and number and position of suitable UWB antennas to facilitate localization of a wirelessly locatable tag (or other device with similar functionality), as described herein.

As shown in FIG. 143, the device 14300 may include a battery 14307 that is used to store and provide power to the other components of the device 14300. The battery 14307 may be a rechargeable power supply that is configured to provide power to the device 14300.

The device 14300 may also include one or more displays 14308 configured to display graphical outputs. The displays 14308 may use any suitable display technology, including liquid crystal displays (LCD), organic light emitting diodes (OLED), active-matrix organic light-emitting diode displays (AMOLED), or the like. The displays 14308 may display information relating to the position or location of a wirelessly locatable tag, such as a graphical indicator that points to or otherwise directs a user to the location of a wirelessly locatable tag.

The device 14300 may also provide audio input functionality via one or more audio input systems 14309. The audio input systems 14309 may include microphones, transducers, or other devices that capture sound for voice calls, video calls, audio recordings, video recordings, voice commands, and the like.

The device 14300 may also provide audio output functionality via one or more audio output systems (e.g., speakers) 14310. The audio output systems 14310 may produce sound from voice calls, video calls, streaming or local audio content, streaming or local video content, or the like. The audio output systems 14310 may also provide audible outputs in response to a detection that a condition of a wirelessly locatable tag has been met.

The device 14300 may also include a positioning system 14311. The positioning system 14311 may be configured to determine the location of the device 14300. For example, the positioning system 14311 may include magnetometers, gyroscopes, accelerometers, optical sensors, cameras, global positioning system (GPS) receivers, inertial positioning systems, or the like. The positioning system 14311 may be used to determine spatial parameters of the device 14300, such as the location of the device 14300 (e.g., geographical coordinates of the device), measurements or estimates of physical movement of the device 14300, an orientation of the device 14300, or the like. The positioning system 14311 may also be used to determine spatial parameters of another device, such as a wirelessly locatable tag. The positioning system 14311 may communicate with or otherwise interact with other components of the device 14300 to perform functions relating to localization of a wirelessly locatable tag, including but not limited to the processing units 14301, memory 14302, communications channels 14304, and the like. For example, the positioning system 14311 may perform at least some of the localization processes described with respect to FIGS. 2D-2F.

The device 14300 may also include one or more additional sensors 14312 to receive inputs (e.g., from a user or another computer, device, system, network, etc.) or to detect any suitable property or parameter of the device, the environment surrounding the device, people or things interacting with the device (or nearby the device), or the like. For example, a device may include temperature sensors, biometric sensors (e.g., fingerprint sensors, photoplethysmographs, blood-oxygen sensors, blood sugar sensors, or the like), eye-tracking sensors, retinal scanners, humidity sensors, buttons, switches, lid-closure sensors, or the like.

To the extent that multiple functionalities, operations, and structures described with reference to FIG. 143 are disclosed as being part of, incorporated into, or performed by the device 14300, it should be understood that various embodiments may omit any or all such described functionalities, operations, and structures. Thus, different embodiments of the device 14300 may have some, none, or all of the various capabilities, apparatuses, physical features, modes, and operating parameters discussed herein. Further, the systems included in the device 14300 are not exclusive, and the device 14300 may include alternative or additional systems, components, modules, programs, instructions, or the like, that may be necessary or useful to perform the functions described herein.

FIG. 144 depicts an example schematic diagram of a wirelessly locatable tag 14400. The wirelessly locatable tag 14400 may represent any of the wirelessly locatable tags, wireless tags, or wireless modules described herein, and may interact with an electronic device (such as the electronic device 14300) to facilitate localization of the wirelessly locatable tag 14400. The wirelessly locatable tag 14400 as described represents a small, puck-shaped device. As noted above, however, other devices may include the components, systems, and/or modules of the wirelessly locatable tag 14400, and may provide the same or similar functionality. Accordingly, the components, systems, and/or modules (and associated programs, operations, and/or instructions) described as being included in the wirelessly locatable tag 14400 may also be included in other devices, such as mobile phones (e.g., smartphones), laptop computers, tablet computers, desktop computers, personal digital assistants, watches (e.g., smartwatches) or other wearable devices, wireless routers or other network infrastructure devices, televisions, or any other suitable devices.

The tag 14400 includes one or more processing units 14401 that are configured to access a memory 14402 having instructions stored thereon. The instructions or computer programs may be configured to perform one or more of the operations or functions described with respect to the tags described herein. For example, the instructions may be configured to control or coordinate the operation of one or more communication channels 14404, one or more audio input systems 14409, one or more input devices 14303, one or more audio output systems 14410, one or more positioning systems 14411, one or more sensors 14412, one or more haptic feedback devices 14406, and/or one or more optional displays 14408.

The processing units 14401 of FIG. 144 may be implemented as any electronic device capable of processing, receiving, or transmitting data or instructions. For example, the processing units 14401 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

The memory 14402 can store electronic data that can be used by the tag 14400. For example, a memory can store electrical data or content such as, for example, device settings and user preferences, timing and control signals or data for the various modules, data structures or databases, programs, instructions, audio and video files, images, documents and applications, and so on. The memory 14402 can be configured as any type of memory. By way of example only, the memory can be implemented as random access memory, read-only memory, Flash memory, removable memory, or other types of storage elements, or combinations of such devices.

The input devices 14403 may detect various types of inputs and generate signals or data that are able to be accessed using processor instructions. The input devices 14403 may use any suitable components and may rely on any suitable phenomena to detect physical inputs. For example, an input device 14403 may be an audio system (such as the audio system 404) that detects inputs by detecting an electrical signal (e.g., voltage, current) in a coil as a result of the coil being moved in a magnetic field. Other types of input devices 14403 may include dome switches, capacitive sensors, resistive sensors, acoustic wave sensors, strain-based sensors, piezoelectric-based sensors, piezoresistive-based sensors, or the like. Input devices 14403 may be integrated with the housing of a tag such that a deflection or deformation of the housing, as a result of a user applying an input force to the exterior housing surface, actuates the input device or otherwise produces a detectable event that causes the tag to perform an action (e.g., changing a mode of operation, changing a beacon frequency, etc.).

The input devices 14403 may include touch sensors, which may in turn include any suitable components for detecting touch-based inputs and generating signals or data that are able to be accessed using processor instructions, including electrodes (e.g., electrode layers and/or an array of capacitive electrodes), physical components (e.g., substrates, spacing layers, structural supports, compressible elements, etc.) processors, circuitry, firmware, and the like. The touch sensors may be integrated with or otherwise configured to detect touch inputs applied to any portion of the tag 14400. For example, the touch sensors may be configured to detect touch inputs applied to any portion of the tag 14400 that includes an optional display. Example touch inputs include momentary touches, taps, swipes, and other gesture and non-gesture input. The touch sensors may operate in conjunction with force sensors to generate signals or data in response to touch inputs that may correspond to a location of a touch or type of gesture provided to the input device 14403. A touch sensor or force sensor that is positioned over a display surface or otherwise integrated with a display may be referred to herein as a touch-sensitive display, force-sensitive display, or touchscreen.

The input device 14403 may also include force sensors, which may in turn detect various types of force-based inputs and generate signals or data that are able to be accessed using processor instructions. The force sensors may use any suitable components and may rely on any suitable phenomena to detect force-based inputs. For example, the force sensors may be strain-based sensors, piezoelectric-based sensors, piezoresistive-based sensors, capacitive sensors, resistive sensors, or the like. The force sensors may include any suitable components for detecting force-based inputs and generating signals or data that correspond to a degree or magnitude of the force-based input and that are able to be accessed using processor instructions, including electrodes (e.g., electrode layers), physical components (e.g., substrates, spacing layers, structural supports, compressible elements, etc.) processors, circuitry, firmware, and the like. The force sensors may be used in conjunction with various input mechanisms to detect various types of inputs. For example, the force sensors may be used to detect a finger press, object press, or other force inputs that result in a force sensor output that satisfies a force threshold (which may represent a more forceful input than is typical for a standard "touch" input). Like the touch sensors, the force sensors may be integrated with or otherwise configured to detect force inputs applied to any suitable portion of the tag 14400. For example, the force sensors may be configured to detect force inputs applied to any portion of the tag 14400 that includes an optional display (and may be integrated with a display). The force sensors may operate in conjunction with the touch sensors to generate signals or data in response to touch- and/or force-based inputs.

The tag 14400 may also provide audio output functionality via one or more audio output systems 14410. The audio output systems 14410 may include an audio system that uses a housing member as a diaphragm to produce sound, as described above. The audio output systems 14410 may also provide audible outputs in response to a detection that a condition of a wirelessly locatable tag has been met, or a signal or instruction from another device (e.g., the device 14300), or the like. The audible output may be used to indicate a status of the tag (e.g., to indicate when the tag changes modes), to help a user locate a tag (e.g., by listening for a beep or tone), or the like.

The tag 14400 may also include one or more haptic devices 14406. The haptic device 14406 may include one or more of a variety of haptic technologies such as, but not necessarily limited to, rotational haptic devices, linear actuators, piezoelectric devices, vibration elements, and so on. In general, the haptic device 14406 may be configured to provide punctuated and distinct feedback to a user of the device. More particularly, the haptic device 14406 may be adapted to produce a knock or tap sensation and/or a vibration sensation. Such haptic outputs may be provided in response to any suitable condition, such as a receipt of a wireless signal instructing the tag to produce an output (e.g., to help a user locate the tag). Haptic outputs form a haptic device 14406 may be imparted to a user through the exterior surface of the tag 14400 (e.g., via a housing member that defines an upper or top surface of the tag and also acts as a speaker diaphragm). Haptic outputs may also be provided in response to a detection that a condition of a wirelessly locatable tag has been satisfied. For example, if a rule relating to the location of a tag is satisfied (e.g., if a tag is detected outside of a specified area or greater than a specified distance from a user or another device), the tag 14400 may produce a haptic output using the haptic devices 14406. As noted above, the haptic device 14406 may be part of an audio system that uses a housing member as a speaker diaphragm. In other cases, a dedicated haptic device, such as a linear resonant actuator, piezoelectric actuator, or the like, is provided.

The one or more communication channels 14404 may include one or more wireless interface(s) that are adapted to provide communication between the processing unit(s) 14401 and an external device (e.g., the electronic device 14300). The one or more communication channels 14404 may include antennas (e.g., the antennas described with respect to FIGS. 8A-8E), communications circuitry, firmware, software, or any other components or systems that facilitate wireless communications with other devices (e.g., with devices that facilitate localization of the tag 14400, such as the device 14300). In general, the one or more communication channels 14404 may be configured to transmit and receive data and/or signals that may be interpreted by instructions executed on the processing units 14401. In some cases, the external device is part of an external communication network that is configured to exchange data with wireless devices. Generally, the wireless interface may communicate via, without limitation, radio frequency, optical, acoustic, and/or magnetic signals and may be configured to operate over a wireless interface or protocol. Example wireless interfaces include radio frequency cellular interfaces, fiber optic interfaces, acoustic interfaces, Bluetooth interfaces, infrared interfaces, USB interfaces, Wi-Fi interfaces, TCP/IP interfaces, network communications interfaces, or any conventional communication interfaces. The one or more communications channels 14404 may also include ultra-wideband interfaces, which may include any appropriate communications circuitry, instructions, and number and position of suitable UWB antennas to facilitate localization of the tag (or other tags or devices with similar functionality), as described herein. For example, the communications channels 14404 may perform at least some of the localization processes described with respect to FIGS. 2D-2F (or otherwise be used as part of the localization processes or operations). For example, UWB antennas may be operable to send wireless beacon signals to other devices to facilitate localization of the tag 14400 or of other devices.

As shown in FIG. 144, the tag 14400 may include a battery 14407 that is used to store and provide power to the other components of the tag 14400. The battery 14407 may represent the battery 514, or any other battery described above. The battery 14407 may be a button cell battery, or any other suitable type of battery. The battery 14407 may be non-rechargeable, or it may be a rechargeable battery or other power supply that is configured to provide power to the tag 14400.

The tag 14400 may also include a positioning system 14411. The positioning system 14411 may be configured to determine the location of the tag 14400. The positioning system 14411 may perform, manage, control, or otherwise facilitate localization operations such as those described with respect to FIGS. 2D-2F. The positioning system 14411 may optionally include other devices or systems, such as magnetometers, gyroscopes, accelerometers, optical sensors, cameras, global positioning system (GPS) receivers, inertial positioning systems, or the like. Such devices or systems may be used to determine spatial parameters of the tag 14400, such as the location of the tag 14400 (e.g., geographical coordinates of the device), measurements or estimates of physical movement of the tag 14400, an orientation of the tag 14400, or the like. The positioning system 14411 may also be used to determine spatial parameters of another device, such as another wirelessly locatable tag, a smartphone, or any other suitably configured device. The positioning system may communicate with or otherwise interact with other components of the tag 14400, including but not limited to the processing units 14401, memory 14402, and communications channels 14404, to perform such functions or operations.

The tag 14400 may also include one or more additional sensors 14412 to receive inputs (e.g., from a user or another computer, device, system, network, etc.) or to detect any suitable property or parameter of the device, the environment surrounding the device, people or things interacting with the device (or nearby the device), or the like. For example, a device may include temperature sensors, barometric sensors, biometric sensors (e.g., fingerprint sensors, photoplethysmographs, blood-oxygen sensors, blood sugar sensors, or the like), eye-tracking sensors, retinal scanners, humidity sensors, electric field sensors, magnetic field sensors, buttons, switches, lid-closure sensors, or the like.

The tag 14400 may optionally include one or more displays 14408 configured to display graphical outputs. (Though, as noted above, in some cases tags 14400 may be devoid of displays or other visual output devices.) The optional displays 14408 may use any suitable display technology, including liquid crystal displays (LCD), organic light emitting diodes (OLED), active-matrix organic light-emitting diode displays (AMOLED), segmented LED display, or the like. The optional displays 14408 may display information relating to the operations, modes, functions, settings, or statuses of a wirelessly locatable tag. For example, a display may display "Lost" if the tag is in a "lost" mode or state, or "Not Lost" if it is in a "not lost" mode or state. In some cases, an optional display 14400 may include indicator lights (e.g., light sources that provide a single point or pixel of light). The indicator lights may be LEDs or any other suitable light sources, and may be positioned on a tag in a location that is visible to a user, such as on (or visible along) a top exterior surface, a bottom exterior surface, a peripheral exterior surface, or any other surface. In some cases, the LED or other light source may be positioned within the housing of the tag and proximate an optically transmissive portion of the housing (e.g., a glass, crystal, or plastic housing member or window), such that the light from the LED or other light source is protected in the housing and also visible from outside the tag. The indicator lights may indicate a status of the device, such as a power state, battery charge level, operating mode, lost/not lost status, or the like. In some cases, the indicator lights may be activated in response to the tag being reported lost. For example, the indicator lights may flash (or remain steadily illuminated) to alert nearby people to the presence of the tag and its status as being lost. The indicator lights may be used for other purposes as well.

The tag 14400 may also optionally provide audio input functionality via one or more audio input systems 14409. The audio input systems 14409 may include microphones, transducers, or other devices that capture sound for recording sound content (e.g., vocal recordings to be played back by the tag), receiving voice commands for controlling operation of the tag, or the like.

To the extent that multiple functionalities, operations, and structures described with reference to FIG. 144 are disclosed as being part of, incorporated into, or performed by the tag 14400, it should be understood that various embodiments may omit any or all such described functionalities, operations, and structures. Thus, different embodiments of the tag 14400 may have some, none, or all of the various capabilities, apparatuses, physical features, modes, and operating parameters discussed herein. Further, the systems included in the tag 14400 are not exclusive, and the tag 14400 may include alternative or additional systems, components, modules, programs, instructions, or the like, that may be necessary or useful to perform the functions described herein.

As described above, one aspect of the present technology is the gathering and use of data available from specific and legitimate sources to provide the ability to track and find objects. The present disclosure contemplates that, in some instances, this gathered data may include personal information data that uniquely identifies or can be used to identify a specific person. Such personal information data can include demographic data, location-based data (e.g., locations, movements, positions, paths, etc., of a person and/or the person's belongings, devices, home environments, etc.), online identifiers, telephone numbers, email addresses, home addresses, data or records relating to a user's health or level of fitness (e.g., vital signs measurements, medication information, exercise information), date of birth, or any other personal information.

The present disclosure recognizes that the use of such personal information data, in the present technology, can be used to the benefit of users. For example, locations of a user's tags may be recorded to allow users to find their lost possessions. Further, other uses for personal information data that benefit the user are also contemplated by the present disclosure. For instance, health and fitness data may be used, in accordance with the user's preferences, to provide insights into their general wellness, or may be used as positive feedback to individuals using technology to pursue wellness goals.

The present disclosure contemplates that those entities responsible for the collection, analysis, disclosure, transfer, storage, or other use of such personal information data will comply with well-established privacy policies and/or privacy practices. In particular, such entities would be expected to implement and consistently apply privacy practices that are generally recognized as meeting or exceeding industry or governmental requirements for maintaining the privacy of users. Such information regarding the use of personal data should be prominent and easily accessible by users, and should be updated as the collection and/or use of data changes. Personal information from users should be collected for legitimate uses only. Further, such collection/sharing should occur only after receiving the consent of the users or other legitimate basis specified in applicable law. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations that may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to selectively control who can and cannot view or access the location of their tags or other location-enabled devices, and control when outside devices (e.g., devices not owned or controlled by the user) can communicate with a user's tags to provide location reports. In yet another example, users can select to limit the length of time that location information is accessible to others. In yet another example, users can configure their devices (e.g., mobile phones) not to receive, respond to, or otherwise interact with location-enabled devices such as tags. For instance, a user may configure a mobile phone to ignore instructions from tags to send location reports, display messages on behalf of the tags or the like. In addition to providing "opt in" and "opt out" options, the present disclosure contemplates providing notifications relating to the access or use of personal information. For instance, a user may be notified if another user accesses or attempts to access their location or the location of their devices or tags.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing identifiers, controlling the amount or specificity of data stored (e.g., collecting location data at city level rather than at an address level), controlling how data is stored (e.g., aggregating data across users), and/or other methods such as differential privacy.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users based on aggregated non-personal information data or a bare minimum amount of personal information, such as the content being handled only on the user's device or other non-personal information available to the content delivery services.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings. Also, when used herein to refer to positions of components, the terms above, below, over, under, left, or right (or other similar relative position terms), do not necessarily refer to an absolute position relative to an external reference, but instead refer to the relative position of components within the figure being referred to.

Objects or components that are shown or described as being at least partially embedded in or encapsulated by other objects or materials may be formed via insert molding, multi-material injection molding, or any other suitable technique. For example, in insert molding, an object may be placed into a mold, and then a moldable material may be introduced into the mold to at least partially encapsulate or at least partially embed the object in the moldable material. In multi-material injection molding, a first moldable material may be introduced into a mold (and optionally at least partially cured or hardened), followed by a second moldable material. Other techniques may also be used, such as by sewing an object into another material, positioning an object between laminate layers, or the like.

While many examples of functions and use cases are described with specific reference to a wirelessly locatable tag, it will be understood that the same function may be performed by any device that is configured to provide the functionality of the tags described herein. For example, a laptop computer or smartphone may have communications circuitry and other components that are similar to or provide the functions of a wirelessly locatable tag. Thus, any function performed or facilitated by a tag may also be performed or facilitated by a laptop. As one specific example, when a laptop computer is lost or misplaced, other devices in a device-location relay network may receive signals from the laptop (e.g., via Bluetooth, UWB) and send location reports to a server or host system.

What is claimed is:

1. A holder for an electronic tag, the electronic tag comprising a housing member, the holder comprising:
    a receptacle portion configured to at least partially surround the electronic tag, the receptacle portion comprising:
        a first pouch portion defining a first opening configured to at least partially surround an outer periphery of a battery door of the electronic tag; and
        a second pouch portion coupled to the first pouch portion and defining a second opening configured to at least partially surround a region of an exterior surface of the housing member of the electronic tag, the first pouch portion and the second pouch portion defining a third opening configured to allow the electronic tag to be positioned in the receptacle portion between the first pouch portion and the second pouch portion;
    a fastener coupled to the receptacle portion and configured to releasably secure the first opening in a closed configuration to retain the electronic tag in the receptacle portion; and
    a fastening strap configured to releasably attach the holder to an object.

2. The holder of claim 1, wherein the receptacle portion defines a cavity having a size and a shape that corresponds to a size and a shape of the electronic tag.

3. The holder of claim 2, wherein:
the cavity is defined by an inner surface of the receptacle portion; and
the inner surface contacts the electronic tag when the electronic tag is in the cavity.

4. The holder of claim 1, wherein the first and second openings are circular.

5. The holder of claim 4, wherein the first and second openings have a same diameter.

6. The holder of claim 1, wherein:
the fastener is a snap; and
the snap comprises:
   a male assembly comprising:
      a protrusion component defining a circumferential groove that extends around the protrusion component;
      a compression ring positioned within the circumferential groove;
      a compliant member positioned in the circumferential groove and configured to apply a biasing force on the compression ring; and
   a female assembly defining an opening configured to receive the protrusion component, the compression ring configured to engage a surface of the female assembly to retain an engagement between the male and female assemblies.

7. The holder of claim 1, wherein:
the fastening strap defines a strap opening at a terminal end of the fastening strap; and
the strap opening is configured to allow the receptacle portion to pass through the strap opening to form a loop in the fastening strap.

8. The holder of claim 1, wherein the first pouch portion defines a first side of the holder and the second pouch portion defines a second side of the holder opposite the first side.

9. The holder of claim 8, wherein the first opening is concentric with the second opening.

10. A holder for an electronic tag, the electronic tag comprising a housing member, the holder comprising:
   a first layer defining:
      a first portion of a receptacle portion configured to at least partially surround the electronic tag;
      a first opening extending through the first layer and configured to expose a first portion of the housing member of the electronic tag; and
      a fastening strap; and
   a second layer adjacent the first layer along an interface region and defining:
      a second portion of the receptacle portion; and
      a second opening extending through the second layer and configured to expose a second portion of the housing member of the electronic tag, the second layer attached to the first layer along a portion of the interface region, thereby defining a third opening between the first layer and the second layer; and
   a fastener comprising:
      a first fastener assembly coupled to the first layer; and
      a second fastener assembly coupled to the second layer and configured to releasably secure the third opening in a closed configuration to retain the electronic tag in the receptacle portion.

11. The holder of claim 10, wherein the third opening is configured to allow the electronic tag to be positioned in the receptacle portion.

12. The holder of claim 10, wherein the fastening strap is attached to a clip configured to releasably attach the holder to an object.

13. The holder of claim 10, wherein a terminal end of the fastening strap is secured to a base of the fastening strap to define a loop.

14. The holder of claim 13, wherein the terminal end of the fastening strap is secured to the base of the fastening strap by the first fastener assembly.

15. The holder of claim 10, wherein:
the fastening strap defines a strap opening at a terminal end of the fastening strap; and
the strap opening is configured to allow the receptacle portion to pass through the strap opening to form a loop in the fastening strap.

16. A holder for an electronic tag, the electronic tag comprising a housing member, the holder comprising:
   a receptacle portion configured to at least partially surround the electronic tag, the receptacle portion defining:
      a first opening configured to receive the electronic tag such that it can be positioned in the receptacle portion;
      a second opening aligned with a region of an exterior surface of the housing member;
   a tab extending from the receptacle portion proximate the first opening, the tab defining a third opening; and
   a strap extending from the receptacle portion proximate the first opening and configured to extend through the third opening to retain the first opening in a closed configuration.

17. The holder of claim 16, wherein the strap is configured to be removed from the third opening to allow the first opening to expand to receive the electronic tag.

18. The holder of claim 17, wherein:
the strap defines a loop at a terminal end of the strap; and
the holder further comprises a removable split ring attached to the loop.

19. The holder of claim 18, wherein a dimension of the removable split ring is larger than a dimension of the third opening, thereby preventing the terminal end of the strap from passing through the third opening when the removable split ring is attached to the loop.

20. The holder of claim 16, wherein the receptacle portion further defines a fourth opening configured to at least partially surround an outer periphery of a battery door of the electronic tag.

* * * * *